(12) United States Patent
Maor et al.

(10) Patent No.: US 10,184,131 B2
(45) Date of Patent: Jan. 22, 2019

(54) ISOLATED POLYNUCLEOTIDES EXPRESSING OR MODULATING MICRORNAS OR TARGETS OF SAME, TRANSGENIC PLANTS COMPRISING SAME AND USES THEREOF

(71) Applicant: A.B. Seeds Ltd., Lod (IL)

(72) Inventors: Rudy Maor, Rechovot (IL); Iris Nesher, Tel-Aviv (IL); Orly Noivirt-Brik, Givataim (IL); Osnat Yanai-Azulay, Rishon-LeZion (IL)

(73) Assignee: A.B. Seeds Ltd. (IL)

( * ) Notice: Subject to any disclaimer, the term of this patent is extended or adjusted under 35 U.S.C. 154(b) by 530 days.

(21) Appl. No.: 14/376,879

(22) PCT Filed: Feb. 6, 2013

(86) PCT No.: PCT/IL2013/050112
§ 371 (c)(1),
(2) Date: Aug. 6, 2014

(87) PCT Pub. No.: WO2013/118120
PCT Pub. Date: Aug. 15, 2013

(65) Prior Publication Data
US 2015/0007364 A1 Jan. 1, 2015

Related U.S. Application Data

(60) Provisional application No. 61/595,213, filed on Feb. 6, 2012.

(51) Int. Cl.
C12N 15/82 (2006.01)

(52) U.S. Cl.
CPC ..... *C12N 15/8271* (2013.01); *C12N 15/8218* (2013.01); *C12N 15/8243* (2013.01); *C12N 15/8261* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,855,237 A | 8/1989 | Morinaga et al. |
| 4,879,219 A | 11/1989 | Wands et al. |
| 4,945,050 A | 7/1990 | Sanford |
| 5,011,771 A | 4/1991 | Bellet et al. |
| 5,035,323 A | 7/1991 | Daniels et al. |
| 5,192,659 A | 3/1993 | Simons |
| 5,268,463 A | 12/1993 | Jefferson |
| 5,272,057 A | 12/1993 | Smulson et al. |
| 5,281,521 A | 1/1994 | Trojanowski et al. |
| 5,283,185 A | 2/1994 | Epand et al. |
| 5,316,931 A | 5/1994 | Donson et al. |
| 5,399,680 A | 3/1995 | Zhu et al. |
| 5,464,765 A | 11/1995 | Coffee et al. |
| 5,466,785 A | 11/1995 | de Framond |
| 5,569,597 A | 10/1996 | Grimsley et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,693,507 A | 12/1997 | Daniell et al. |
| 5,759,829 A | 6/1998 | Shewmaker et al. |
| 5,952,657 A | 9/1999 | Alexander et al. |
| 5,987,071 A | 11/1999 | Iwamatsu et al. |
| 6,656,805 B2 | 12/2003 | Kamath et al. |
| 2002/0058815 A1 | 5/2002 | Liu et al. |

(Continued)

FOREIGN PATENT DOCUMENTS

| WO | WO 87/06261 A1 | 10/1987 |
|---|---|---|
| WO | WO 93/07278 A1 | 4/1993 |

(Continued)

OTHER PUBLICATIONS

Emery et al. (Current Biology 13:1768-1774, 2003).*
Cheng et al. (Plant Mol. Biol. Rep. 28:41-48, 2010).*
International Preliminary Report on Patentability dated Aug. 21, 2014 From the International Bureau of WIPO Re. Application No. PCT/IL2013/050112.
International Search Report and the Written Opinion dated Aug. 2, 2013 From the International Searching Authority Re. Application No. PCT/IL2013/050112.
International Search Report and the Written Opinion dated Oct. 21, 2013 From the International Searching Authority Re. Application No. PCT/IL2013/050112.
Invitation to Pay Additional Fees dated May 30, 2013 From the International Searching Authority Re. Application No. PCT/IL2013/050112.

(Continued)

*Primary Examiner* — Vinod Kumar
(74) *Attorney, Agent, or Firm* — Amanda Carmany-Rampey; David Marsh; Arnold & Porter Kaye Scholer LLP

(57) ABSTRACT

Isolated polynucleotides expressing or modulating microRNAs or targets of same are provided. Also provided are transgenic plants comprising same and uses thereof in improving nitrogen use efficiency, abiotic stress tolerance, biomass, vigor or yield of a plant.

1 Claim, 3 Drawing Sheets

Specification includes a Sequence Listing.

(56) References Cited

U.S. PATENT DOCUMENTS

| | | |
|---|---|---|
| 2003/0175965 A1 | 9/2003 | Lowe et al. |
| 2003/0180955 A1 | 9/2003 | Ozasa et al. |
| 2007/0089192 A1 | 4/2007 | Huang et al. |
| 2008/0311659 A1 | 12/2008 | Huynh et al. |
| 2011/0099667 A1 | 4/2011 | Aukerman et al. |

FOREIGN PATENT DOCUMENTS

| | | | |
|---|---|---|---|
| WO | WO 99/53050 A1 | 10/1999 | |
| WO | WO 99/59029 A1 | 11/1999 | |
| WO | WO 99/61631 A1 | 12/1999 | |
| WO | WO 00/59035 A1 | 10/2000 | |
| WO | WO 02/00905 A2 | 1/2002 | |
| WO | WO 2004/081173 A2 | 9/2004 | |
| WO | WO 2011/132127 | 10/2011 | |
| WO | WO 2011132127 A1 * | 10/2011 | ......... C12N 15/8218 |
| WO | WO 2013/118120 | 8/2013 | |

OTHER PUBLICATIONS

Lindow et al. "Intragenomic Matching Reveals a Huge Potential for MiRNA-Mediated Regulation in Plants", PLoS Computational Biology, 3(11/e238): 2379-2390, Nov. 2007. Abstract.
Lindow et al. "Oeyza Sativa. Osa-MRIfI 1996-Akr. Stem-Loop Information. Stem Loop Structure Computed Using [Vienna RNA Package]", The miRNA Database [Online], 3 p., 2007.
Zhao et al. "Deep Sequencing Identifies Novel and Conserved MicroRNAs in Peanuts (*Arachis hypogaea* L.)", BMC Plant Biology, 10(3): 1-12, 2010. Abstract, p. 4-5, Table 1, 2.
Bartel, "MicroRNAs: Genomics, Biogenesis, Mechanism, and Function," *Cell*, 116:281-297 (2004).
Boutros et al., "Genome-Wide RNAi Analysis of Growth and Viability in *Drosophila* Cells," *Science*, 303:832-835 (2004).
Dietzl et al., "A genome-wide transgenic RNAi library for conditional gene inactivation in *Drosophila*," *Nature*, 448:151-156 (2007).
Kuromori et al., "A trial of phenome analysis using 4000 Ds-insertional mutants in gene-coding regions of *Arabidopsis*," *Plant Journal*, 47:640-651 (2006).
Lee et al., "A systematic RNAi screen identifies a critical role for mitochondria in C. elegans longevity," *Nature Genetics*, 33:40-48 (2002).
Ni et al., "Overexpression of gma-MIR394a confers tolerance to drought in transgenic *Arabidopsis thaliana*," *Biochem Biophys Res Commun*, 427:330-335 (2012).
Schwab et al., "Specific Effects of MicroRNAs on the Plant Transcriptome," *Developmental Cell*, 8:517-527 (2005).
Covarrubias et al., "Post-transcriptional gene regulation of salinity and drought responses by plant microRNAs," *Plant, Cell & Environment*, 33:481-489 (2010).
Ochman et al., "Genetic Applications of an Inverse Polymerase Chain Reaction," *Genetics*, 120:621-623 (1988).
Rhoades et al., "Prediction of Plant MicroRNA Targets," *Cell*, 110:513-520 (2002).
Schmutz et al., "Genome sequence of the palaeopolyploid soybean," *Nature*, 463:178-183 (2010).
Zhang, "miRU: an automated plant miRNA target prediction server," *Nucleic Acids Research*, 33:W701-W704 (2005).
Albani et al., "The Wheat Transcriptional Activator Spa: A Seed-Specific bZIP Protein That Recgnizes the GCN4-Like Motif in the Bifactorial Endosperm Box of Prolamin Genes," *The Plant Cell*, 9(2):171-184 (1997).
Altenbach et al., "Accumulation of a Brazil nut albumin in seeds of transgenic canola results in enhanced levels of seed protein methionine," *Plant Molecular Biology*, 18:235-245 (1992).
An et al., "Strong, constitutive expression of the *Arabidopsis* ACT2/ACT8 actin subclass in vegetative tissues," *The Plant Journal*, 10(1):107-121 (1996).

Anderson et al., "Nucleotide sequences of the two high-molecular-weight glutenin genes from the D-genome of a hexaploid bread wheat, *Triticum aestivum* L. cv Cheyenne," *Nucleic Acids Research*, 17(1):461-461 (1989).
Angell et al ., "Consistent gene silencing in transgenic plants expressing a replicating potato virus X RNA," *EMBO J.*, 16(12):3675-3684 (1997).
Angell et al., "Potato virus X amplicon-mediated silencing of nuclear genes," *The Plant Journal*, 20(3):357-362 (1999).
Aufsatz et al., "RNA-directed DNA methylation in *Arabidopsis*," *PNAS*, 99(4):1699-16506 (2002).
Baszczynski et al., "Isolation and nucleotide sequence of a genomic clone encoding a new *Brassica napus* napin gene," *Plant Molecular Biology*, 14:633-635 (1990).
Broin et al., "The Plastidic 2-Cysteine Peroxiredoxin Is a Target for a Thioredoxin Involved in the Protection of the Photosynthetic Apparatus against Oxidative Damage," *The Plant Cell*, 14:1417-1432 (2002).
Buchholz et al., "Cyclophilins are encoded by a small gene family in rice," *Plant Molecular Biology*, 25:837-843 (1994).
Chen et al., "Real-time quantification of microRNAs by stem-loop RT-PCR," *Nucleic Acids Research*, 33(20):e179 (2005).
Cho et al., "Inheritance of tissue-specific expression of barley hordein promoter-uidA fusions in transgenic barley plants," *Theor Appl Genet*, 98:1253-1262 (1999).
Christensen et al., "Maize polyubiquitin genes: structure, thermal perturbation of expression and transcript splicing, and promoter activity following transfer to protoplasts by electroporation," *Plant Molecular Biology*, 18:675-689 (1992).
Chuang et al., "Specific and heritable genetic interference by double-stranded RNA in *Arabidopsis*," *PNAS*, 97(9):4985-4990 (2000).
Clough et al., "Floral dip: a simplified method for *Agrobacterium*-mediated transformation of *Arabidopsis thaliana*," *The Plant Journal*, 16(6):735-743 (1998).
Colot et al., "Molecular Characterization of an active wheat LMW glutenin gene and its relation to other wheat and barley prolamin genes," *Mol Gen Genet*, 216:81-90 (1989).
Cummins et al., "cDNA sequence of a sunflower oleosin and transcript tissue specificity," *Plant Molecular Biology*, 19:873-876 (1992).
Dawson et al., "A Tobacco Mosaic Virus-Hybrid Expresses and Loses an Added Gene," *Virology*, 172:285-292 (1989).
De Pater et al., "The promoter of the rice gene GOS2 is active in various different monocot tissues and binds rice nuclear factor ASF-1," *The Plant Journal*, 2(6):837-844 (1992).
DeRose et al., "Analysis of kafirin promoter activity in transgenic tobacco seeds," *Plant Molecular Biology*, 32:1029-1035 (1996).
Desfeux et al., "Female Reproductive Tissues Are the Primary Target of *Agrobacterium*-Mediated Transformation by the *Arabidopsis* Floral-Dip Method," *Plant Physiology*, 123(3):895-904 (2000).
Ellis et al., "Tissue-specific expression of a pea legumin gene in seeds of *Nicotiana plumbaginifolia*," *Plant Molecular Biology*, 10:203-214 (1988).
French et al., "Bacterial Gene Inserted in an Engineered RNA Virus: Efficient Expression in Monocotyledonous Plant Cells," *Science*, 231(4743):1294-1297 (1986).
Gotor et al., "Analysis of three tissue-specific elements from the wheat Cab-1 enhancer," *The Plant Journal*, 3(4):509-518 (1993).
Fromm et al., "Stable transformation of maize after gene transfer by electroporation," *Nature*, 319:791-793 (1986).
Han et al., "Molecular Basis for the Recognition of Primary microRNAs by the DROSHA-DGCR8 Complex," *Cell* 125:887-901 (2006).
Helliwell et al., "Constructs and methods for high-throughput gene silencing in plants," *Methods*, 30:289-295 (2003).
Johansen et al., "Silencing on the Spot. Induction and Suppression of RNA Silencing in the *Agrobacterium*-Mediated Transient Expression System," *Plant Physiol*, 126:930-938 (2001).
Jorgensen et al., "Chalcone synthase cosuppression phenotypes in petunia flowers: comparison of sense vs. antisense constructs and single-copy vs. complex T-DNA sequences," *Plant Mol Biol*, 31(5):957-973 (1996).

(56) References Cited

OTHER PUBLICATIONS

Klee et al., "*Agrobacterium*-Mediated Plant Transformation and Its Further Applications to Plant Biology," *Ann Rev Plant Physiol*, 38:467-486 (1987).
Klein et al., "Factors Influencing Gene Delivery Into *Zea mays* Cells by High-Velocity Microprojectiles," *Nature*, 6:559-563 (1988).
Kurihara et al., "Cross-protection in *Arabidopsis* against crucifer tobamovirus Cg by an attenuated strain of the virus," *Molecular Plant Pathology*, 4(4):259-269 (2003).
Kwon et al., "Identification of a Light-Responsive Region of the Nuclear Gene Encoding of the B Subunit of Chloroplast Glyceraldehyde 3-Phosphate Dehydrogenase from *Arabidopsis thaliana*," *Plant Physiol.*, 105:357-367 (1994).
Last et al., "pEmu: an improved promoter for gene expression in cereal cells," *Theor Appl Genet*, 81:581-588 (1991).
Lepetit et al., "A plant histone gene promoter can direct both replication-dependent and -independent gene expression in transgenic plants," *Mol Gen Genet*, 231:276-285 (1992).
Matsuoka et al., "Tissue-specific light-regulated expression directed by the promoter of a $C_4$ gene, maize pyruvate, orthophosphate dikinase, in a $C_3$ plant, rice," *PNAS USA*, 90:9586-9590 (1993).
Matzke et al., "Deletion analysis of a zein gene promoter in transgenic tobacco plants," *Plant Molecular Biology*, 14:323-332 (1990).
McCabe et al., "Stable Transformation of Soybean (*Glycine max*) by Particle Acceleration," *Bio/Technology*, 6:923-926 (1988).
McElroy et al., "Isolation of an Efficient Actin Promoter for Use in Rice Transformation," *The Plant Cell*, 2:163-171 (1990).
Mena et al., "An endosperm-specific DOF protein from barley, highly conserved in wheat, binds to and activates transcription from the prolamin-box of a native B-hordein promoter in barley endosperm," *The Plant Journal*, 16(1):53-62 (1998).
Mette et al., "Transcriptional silencing and promoter methylation triggered by double-stranded RNA," *EMBO J.*, 19(19):5194-5201 (2000).
Miiller et al., "The nitrogen response of a barley C-hordein promoter is controlled by positive and negative regulation of the GCN4 and endosperm box," *The Plant Journal*, 4(2):343-355 (1993).
Murray et al., "Codon usage in plant genes," *Nucleic Acids Research*, 17(2):477-498 (1989).
Nakase et al., "Characterization of a novel bZIP protein which binds to the α-globulin promoter," *Plant Molecular Biology*, 33:513-522 (1997).
Neuhaus et al., "Transgenic rapeseed plants obtained by the microinjection of DNA into microspore-derived embryoids," *Theor Appl Genet*, 75:30-36 (1987).
Neuhaus et al., "Plant transformation by microinjection techniques," *Physiologia Plantarum*, 79(1):213-217 (1990).
Ni et al., "Strength and tissue specificity of chimeric promoters derived from the octopine and mannopine synthase genes," *The Plant Journal*, 7(4):661-676 (1995).
Nilsson et al., "The *Agrobacterium rhizogenes* rolB and rolC promoters are expressed in pericycle cells competent to serve as root initials in transgenic hybrid aspen," *Physiologia Plantarum*, 100(3):456-462 (1997).
Odell et al., "Identification of DNA sequences required for activity of the cauliflower mosaic virus 35S promoter," *Nature*, 313:810-812 (1985).
Ohta, Y. "High-efficiency transformation of maize by a mixture of pollen and exogenous DNA," *PNAS*, 83:715-719 (1986).
Opsahl-Ferstad et al., "ZmEsr, a novel endosperm-specific gene expressed in a restricted region around the maize embryo," *The Plant Journal*, 12(1):235-246 (1997).
Orozco et al., "Localization of light-inducible and tissue-specific regions of the spinach ribulose bisphosphate carboxylase/oxygenase (rubisco) activase promoter in transgenic tobacco plants," *Plant Molecular Biology*, 23:1129-1138 (1993).

Pandolfini et al., "Expression of self-complementary hairpin RNA under the control of the rolCpromoter confers systemic disease resistance to plum pox virus without preventing local infection," *BMC Biotechnology*, 3:7 (2003).
Panstruga et al., "Testing the efficiency of dsRNAi constructs in vivo: A transient expression assay based on two fluorescent proteins," *Molecular Biology Reports*, 30:135-140 (2003).
Postma-Haarsma et al., "Characterization of the KNOX class homeobox genes Oskn2 and Oskn3 identified in a collection of cDNA libraries covering the early stages of rice embryogenesis," *Plant Molecular Biology*, 39(2):257-271 (1999).
Potiykus, I., "Gene Transfer to Plants: Assessment of Published Approaches and Results," *Annu Rev Plant Physiol Plant Mol Biol*, 42:205-225 (1991).
Purcell et al. "Total Nitrogen Determination in Plant Material by Persulfate Digestion," *Agronomy Journal*, 88(1):111-113 (1996).
Quesada et al., "Genetic Architecture of NaCl Tolerance in *Arabidopsis*," *Plant Physiology*, 130:951-963 (2002).
Rafalski et al., "Developmentally regulated plant genes: the nucleotide sequence of a wheat gliadin genomic clone," *The EMBO Journal*, 3(6):1409-1415 (1984).
Rosenfeld et al., "MicroRNAs accurately identify cancer tissue origin," *Nature Biotechnology*, 26:462-469 (2008).
Russell et al., "Tissue-specific expression in transgenic maize of four endosperm promoters from maize and rice," *Transgenic Research*, 6:157-168 (1997).
Samonte et al., "Nitrogen utilization efficiency: Relationships with grain yield, grain protein, and yield-related traits in rice," *Agron J*, 98:168-176 (2006).
Sanford, J., "Biolistic plant transformation," *Physiologia Plantarum*, 79(1):206-209 (1990).
Sardana et al., "Construction and rapid testing of synthetic and modified toxin gene sequences CryIA (b&c) by expression in maize endosperm culture," *Plant Cell Reports*, 15(9):677-681 (1996).
Sato et al., "A rice homeobox gene, OSH1, is expressed before organ differentiation in a specific region during early embryogenesis," *PNAS*, 93:8117-8122 (1996).
Scofield et al., "Nucleotide Sequence of a Member of the Napin Storage Protein Family from *Brassica napus*," *J Biol. Chem.*, 262(25):12202-12208 (1987).
Shimamoto et al., "Fertile transgenic rice plants regenerated from transformed protoplasts," *Nature*, 338:274-276 (1989).
Simon et al., "Nucleotide sequence of a cDNA clone of *Brassica napus* 12S storage protein shows homology with legumin from *Pisum sativum*," *Plant Molecular Biology*, 5:191-201 (1985).
Smith et al., "Total silencing by intron-spliced hairpin RNAs," *Nature*, 407:319-320 (2000).
Sorensen et al., "Hordein promoter methylation and transcriptional activity in wild-type and mutant barley endosperm," *Mol Gen Genet*, 250:750-760 (1996).
Stålberg et al., "Disruption of an overlapping E-box/ABRE motif abolished high transcription of the napA storage-protein promoter in transgenic *Brassica napus* seeds," *Planta*, 199:515-519 (1996).
Stoutjesdijk et al., "hpRNA-Mediated Targeting of the *Arabidopsis* FAD2 Gene Gives Highly Efficient and Stable Silencing," *Plant Physiol*, 129:1723-1731 (2002).
Takaiwa et al., "A rice glutelin gene family—A major type of glutelin mRNAs can be divided into two classes," *Mol Gen Genet*, 208:15-22 (1987).
Takaiwa et al., "Nucleotide sequence of a rice glutelin gene," *FEBS Letters*, 221:43-47 (1987).
Takamatsu et al., "Expression of bacterial chloramphenicol acetyltransferase gene in tobacco plants mediated by TMV-RNA," *The EMBO Journal*, 6(2):307-311 (1987).
Takamatsu et al., "Production of encephalin in tobacco protoplasts using tobacco mosaic virus RNA vector," *FEBS Letters*, 269(1):73-76 (1990).
Toriyama et al., "Transgenic Rice Plants After Direct Gene Transfer Into Protoplasts," *Bio/Technology*, 6:1072-1074 (1988).
Twell et al., "Isolation and expression of an anther-specific gene from tomato," *Mol Gen Genet*, 217:240-245 (1989).

(56) References Cited

OTHER PUBLICATIONS

Van der Meer et al., "Promoter analysis of the chalcone synthase (chsA) gene of *Petunia hybrid*: a 67 bp promoter region directs flower-specific expression," *Plant Molecular Biology*, 15:95-109 (1990).

Vissenberg et al., "Differential Expression of AtXTH17, AtXTH18, AtXTH19, and AtXTH20 Genes in *Arabidopsis* Roots. Physiological Roles in Specification in Cell Wall Construction," *Plant Cell Physiol*, 46(1):192-200 (2005).

Yamamoto et al., "Light-responsive elements of the tobacco PSI-D gene are located both upstream and within the transcribed region," *The Plant Journal*, 12(2):255-265 (1997).

Yamamoto et al., "The Promoter of a Pine Photosynthetic Gene Allows Expression of a β-Glucuronidase Reporter Gene in Transgenic Rice Plants in a Light-Independent but Tissue-Specific Manner," *Plant Cell Physiol.*, 35(5):773-778 (1994).

Yanagisawa et al., "Metabolic engineering with Dof1 transcription factor in plants: Improved nitrogen assimilation and growth under low-nitrogen conditions," *PNAS* 101(20):7833-7838 (2004).

Yu et al., "Metabolic engineering to increase isoflavone biosynthesis in soybean seed," *Phytochemistry*, 63:753-763 (2003).

Varkonyi-Gasic et al., "Protocol: a highly sensitive RT-PCR method for detection and quantification of microRNAs," *Plant Methods*, 3:12 (2007).

Vicente-Carbajosa et al., "Barley BLZ1: a bZIP transcriptional activator that interacts with endosperm-specific gene promoters," *The Plant Journal*, 13(5):629-640 (1998).

Vodovotz, Y. "Modified microassay for serum nitrite and nitrate," *Biotechniques*, 20(3):390-392 (1996).

Wang et al., "Application of gene silencing in plants," *Current Opinion in Plant Biology*, 5:146-150 (2001).

Waterhouse et al., "Virus resistance and gene silencing in plants can be induced by simultaneous expression of sense and antisense RNA," *PNAS*, 95:13959-13964 (1998).

Waterhouse et al., "Exploring Plant Genomes by RNA-Induced Gene Silencing," *Nature Reviews—Genetics*, 4:29-38 (2003).

Wesley et al., "Construct design for efficient, effective and high-throughput gene silencing in plants," *The Plant Journal*, 27(6):581-590 (2001).

Wu et al., "Genomic Cloning of 18 kDa Oleosin and Detection of Triacylglycerols and Oleosin Isoforms in Maturing Rice and Postgerminative Seedlings," *J. Biochem*, 123:386-391 (1998).

Wu et al., "Promoters of Rice Seed Storage Protein Genes Direct Endosperm-Specific Gene Expression in Transgenic Rice," *Plant Cell Physiol*, 39(8):885-889 (1998).

Zhang et al., "Transgenic rice plants produced by electroporation-mediated plasmid uptake into protoplasts," *Plant Cell Reports*, 7:379-384 (1988).

\* cited by examiner

ISOLATED POLYNUCLEOTIDES EXPRESSING OR MODULATING MICRORNAS OR TARGETS OF SAME, TRANSGENIC PLANTS COMPRISING SAME AND USES THEREOF

RELATED APPLICATIONS

This application is a National Phase of PCT Patent Application No. PCT/IL2013/050122 having International filing date of Feb. 6, 2013, which claims the benefit of priority under 35 USC § 119(e) of U.S. Provisional Patent Application No. 61/595,213 filed on Feb. 6, 2012. The contents of the above applications are all incorporated by reference as if fully set forth herein in their entirety.

SEQUENCE LISTING STATEMENT

The ASCII file, entitled 59933SequenceListing.txt, created on Jul. 17, 2014, comprising 18,690,790 bytes, submitted concurrently with the filing of this application is incorporated herein by reference.

FIELD AND BACKGROUND OF THE INVENTION

The present invention, in some embodiments thereof, relates to isolated polynucleotides expressing or modulating microRNAs or targets of same, transgenic plants comprising same and uses thereof in improving nitrogen use efficiency, abiotic stress tolerance, biomass, vigor or yield of a plant.

Consumption of soybean for food production is increasing worldwide because of its reported beneficial health effects. Soybean is also viewed as an attractive crop for the production of biodiesel. Importantly, it has the ability to fix atmospheric nitrogen, which in turn may cut the input of nitrogen fertilizer that often accounts for the single largest energy input in agriculture.

With a growing world population, increasing demand for food, fuel and fiber, and a changing climate, agriculture faces unprecedented challenges. In general, shortage in water supply is one of the most severe global agricultural problems affecting plant growth and crop yield. Excessive efforts are made to alleviate the harmful effects of desertification of the world's arable land. Farmers are seeking advanced, biotechnology-based solutions to enable them to obtain stable high yields and give them the potential to reduce irrigation costs or to grow crops in areas where potable water is a limiting factor. It should be noted that improved abiotic stress (ABST) tolerance will confer plants with improved vigor also under non-stress conditions, resulting in crops having improved biomass and/or yield.

ABST is a collective term for numerous extreme environmental parameters such as drought, high or low salinity, high or low temperature/light, and nutrient imbalances. The major agricultural crops (corn, rice, wheat, canola and soybean) account for over half of total human caloric intake, giving their overall yield and quality vast importance. ABST causes more than 50% yield loss of the above mentioned major crops. Among the various ABSTs, drought is the major factor that limits crop productivity worldwide. Short-term conditions of reduced environmental water content typically occur during the life cycle of most crop plants. Although most plants have evolved strategies to survive these conditions, when the severity and duration of drought become too great, major alterations to the plant metabolism take place. As a result, the plant development, growth and yield profoundly diminish. Furthermore, drought is associated with increased susceptibility to various diseases. ABST-induced dehydration or osmotic stress, in the form of reduced availability of water and disruption of turgor pressure, cause irreversible cellular damage. A water-limiting environment at various plant developmental stages may activate various physiological changes.

In soybean, drought, for instance, reduces yield by approximately 40%, with the most critical period for water deprivation being the flowering stage and the period following flowering. Water deficit, salinity and low/high temperatures are stresses that cause plant cellular dehydration, due to transpiration rate that exceeds water uptake. Water use efficiency (WUE), defined as the amount of biomass accumulated per unit of water used, plays an important role in determining a plant's ability to tolerate drought stress. The higher the WUE of a plant, the higher the crop productivity and total biomass yield under drought conditions. Thus, efforts are made worldwide to increase the WUE of the most important crops and reach the best yield performance under extreme water deficiency conditions.

Studies have shown that plant adaptations to drought and other adverse environmental conditions are complex genetic traits with polygenic nature. Conventional means for crop and horticultural improvements utilize selective breeding techniques to identify plants having desirable characteristics. However, selective breeding is tedious, time consuming and has an unpredictable outcome. Furthermore, limited germplasm resources for yield improvement and incompatibility in crosses between distantly related plant species represent significant problems encountered in conventional breeding. Advances in genetic engineering have allowed mankind to modify the germplasm of plants by expression of genes-of-interest in plants. Such a technology has the capacity to generate crops or plants with improved economic, agronomic or horticultural traits. However, generation of transgenic plants expressing full-length genes is typically hampered by the selection of optimal regulatory sequences and identification of those rare transformation events that exhibit sufficient levels of gene products expression.

SUMMARY OF THE INVENTION

According to an aspect of some embodiments of the present invention there is provided a method of improving abiotic stress tolerance, nitrogen use efficiency, biomass, vigor or yield of a plant, the method comprising expressing within the plant an exogenous polynucleotide which down-regulates an activity or expression of a gene encoding an RNAi molecule having a nucleic acid sequence at least 90% identical to SEQ ID NOs: 139, 57-79, 202-219, 126-138, 140-161, 236-255, 169-173, 260-261, 3953-5114, 5117-6277, 6278, 11905-11909, 11940-11955, 11959-11961, wherein the RNAi molecule regulates abiotic stress tolerance of the plant, thereby improving abiotic stress tolerance, nitrogen use efficiency, biomass, vigor or yield of the plant.

According to an aspect of some embodiments of the present invention there is provided a method of improving abiotic stress tolerance, nitrogen use efficiency, biomass, vigor or yield of a plant, the method comprising expressing within the plant an exogenous polynucleotide having a nucleic acid sequence at least 90% identical to SEQ ID NOs: 1-56, 174-201, 80-125, 220-235, 162-168, 256-259, 262-2086, 2087-3910, 3911, 11616, 11615, 11874, 11875-11904, 11910-11939, 11956, 11957 or 11958, wherein the nucleic acid sequence is capable of regulating abiotic stress tolerance of the plant, thereby improving abiotic stress tolerance, nitrogen use efficiency, biomass, vigor or yield of the plant.

According to an aspect of some embodiments of the present invention there is provided a transgenic plant exogenously expressing a polynucleotide having a nucleic acid sequence at least 90% identical to SEQ ID NOs: SEQ ID NOs: 1-56, 174-201, 80-125, 220-235, 162-168, 256-259, 262-2086, 2087-3910, 3911, 11616, 11615, 11874, 11875-11904, 11910-11939, 11956, 11957 or 11958, wherein the nucleic acid sequence is capable of regulating abiotic stress tolerance of the plant.

According to some embodiments of the invention, the exogenous polynucleotide encodes a precursor of the nucleic acid sequence.

According to some embodiments of the invention, the precursor of the nucleic acid sequence is at least 60% identical to SEQ ID NO: 174-201, 220-235, 256-259, 2087-3910, 3911, 11910-11939, 11615, 11956, 11957 or 11958.

According to some embodiments of the invention, the precursor of the nucleic acid sequence is at least 60% identical to SEQ ID NO: 174-201, 220-235, 256-259, 2087-3910, 3911, 11875-11904, 11910-11939, 11615, 11956, 11957 or 11958.

According to some embodiments of the invention, the exogenous polynucleotide encodes a mature miRNA.

According to some embodiments of the invention, the exogenous polynucleotide is selected from the group consisting of SEQ ID NO: 1-56, 174-201, 80-125, 220-235, 162-168, 256-259, 262-2086, 2087-3910, 3911, 11616, 11615, 11874, 11875-11904, 11910-11939, 11956, 11957 or 11958.

According to an aspect of some embodiments of the present invention there is provided a nucleic acid construct comprising a nucleic acid sequence being at least 90% identical to SEQ ID NO: 139, 1-201, 202-235, 236-3910, 3911, 11616, 11615, 11874, 11875-11904, 11910-11939, 11956, 11957, 11958, 11940-11955, 11905-11909, 11959-11961, wherein the nucleic acid sequence is capable of regulating abiotic stress tolerance of a plant and wherein the nucleic acid sequence is under the regulation of a cis-acting regulatory element.

According to some embodiments of the invention, the nucleic acid sequence is selected from the group consisting of SEQ ID NOs: 1-56, 174-201, 80-125, 220-235, 162-168, 256-259, 262-2086, 2087-3910, 3911, 11616, 11615, 11874, 11875-11904, 11910-11939, 11956, 11957 or 11958.

According to some embodiments of the invention, the nucleic acid sequence is selected from the group consisting of SEQ ID NOs: 139, 57-79, 202-219, 126-138, 140-161, 236-255, 169-173, 260-261, 3953-5114, 5117-6277, 6278, 11905-11909, 11959-11961, 11940-11955.

According to an aspect of some embodiments of the present invention there is provided a transgenic plant exogenously expressing a polynucleotide which downregulates an activity or expression of a gene encoding an RNAi molecule having a nucleic acid sequence at least 90% identical to SEQ ID NOs: 139, 57-79, 202-219, 126-138, 140-161, 236-255, 169-173, 260-261, 3953-5114, 5117-6277, 6278 11905-11909, 11940-11955, 11959-11961.

According to an aspect of some embodiments of the present invention there is provided a transgenic plant exogenously expressing a polynucleotide which downregulates an activity or expression of a gene encoding an RNAi molecule having a nucleic acid sequence at least 90% identical to SEQ ID NOs: 139, 1-201, 202-235, 236-3910, 3911, 11616, 11615, 11874, 11875-11904, 11910-11939, 11956, 11957, 11958, 11905-11909, 11940-11955, 11959-11961.

According to an aspect of some embodiments of the present invention there is provided an isolated polynucleotide which downregulates an activity or expression of a gene encoding an RNAi molecule having a nucleic acid sequence selected from the group consisting of SEQ ID NOs: 139, 57-79, 202-219, 126-138, 140-161, 236-255, 169-173, 260-261, 3953-5114, 5117-6277, 6278, 11905-11909, 11940-11955, 11959-11961.

According to an aspect of some embodiments of the present invention there is provided a transgenic plant exogenously expressing a polynucleotide which downregulates an activity or expression of a gene encoding an RNAi molecule having a nucleic acid sequence at least 90% identical to SEQ ID NOs: 139, 57-79, 202-219, 126-138, 140-161, 236-255, 169-173, 260-261, 3953-5114, 5117-6277, 6278, 11905-11909, 11940-11955, 11959-11961.

According to an aspect of some embodiments of the present invention there is provided an isolated polynucleotide which downregulates an activity or expression of a gene encoding an RNAi molecule having a nucleic acid sequence selected from the group consisting of SEQ ID NOs: 139, 57-79, 202-219, 126-138, 140-161, 236-255, 169-173, 260-261, 3953-5114, 5117-6277, 6278, 11905-11909, 11940-11955, 11959-11961.

According to an aspect of some embodiments of the present invention there is provided an isolated polynucleotide which downregulates an activity or expression of a gene encoding an RNAi molecule having a nucleic acid sequence selected from the group consisting of SEQ ID NOs: 139, 1-201, 202-235, 236-3910, 3911, 3953-5114, 5117-6277, 6278, 11616, 11615, 11874, 11875-11904, 11910-11939, 11956, 11957, 11958, 11905-11909, 11940-11955, 11959-11961.

According to an aspect of some embodiments of the present invention there is provided an isolated polynucleotide which downregulates an activity or expression of a gene encoding an RNAi molecule having a nucleic acid sequence selected from the group consisting of SEQ ID NOs: 139, 1-201, 202-235, 236-3910, 3911, 11616, 11615, 11874, 11875-11904, 11910-11939, 11956, 11957, 11958, 11905-11909, 11940-11955, 11959-11961.

According to some embodiments of the invention, the polynucleotide encodes a miRNA-Resistant Target as set forth in SEQ ID NO: 11258-11359.

According to some embodiments of the invention, the polynucleotide encodes a miRNA-Resistant Target as set forth in SEQ ID NO: 11091-11257.

According to some embodiments of the invention, the isolated polynucleotide encodes a target mimic as set forth in SEQ ID NO: 11564-11613.

According to some embodiments of the invention, the polynucleotide encodes a target mimic as set forth in SEQ ID NO: 11437-11513.

According to an aspect of some embodiments of the present invention there is provided a nucleic acid construct comprising the isolated polynucleotide under the regulation of a cis-acting regulatory element.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to an aspect of some embodiments of the present invention there is provided a method of improving abiotic stress tolerance, nitrogen use efficiency, biomass, vigor or yield of a plant, the method comprising expressing within the plant an exogenous polynucleotide encoding a polypeptide having an amino acid sequence at least 80% homologous or identical to SEQ ID NOs: 9591-10364, wherein the polypeptide is capable of regulating abiotic stress tolerance of the plant, thereby improving abiotic stress tolerance, nitrogen use efficiency, biomass, vigor or yield of the plant.

According to an aspect of some embodiments of the present invention there is provided a transgenic plant exogenously expressing a polynucleotide encoding a polypeptide having an amino acid sequence at least 80% homologous or identical to SEQ ID NOs: 9591-10364, wherein the polypeptide is capable of regulating abiotic stress tolerance of the plant.

According to an aspect of some embodiments of the present invention there is provided a nucleic acid construct comprising a polynucleotide encoding a polypeptide having an amino acid sequence at least 80% homologous to SEQ ID NOs: 9591-10364, wherein the polypeptide is capable of regulating abiotic stress tolerance of the plant, and wherein the polynucleotide is under a transcriptional control of a cis-acting regulatory element.

According to some embodiments of the invention, the polynucleotide is selected from the group consisting of SEQ ID NO: 10365-10963.

According to some embodiments of the invention, the polypeptide is selected from the group consisting of SEQ ID NO: 9591-10364.

According to some embodiments of the invention, the cis-acting regulatory element comprises a promoter.

According to some embodiments of the invention, the promoter comprises a tissue-specific promoter.

According to some embodiments of the invention, the tissue-specific promoter comprises a root specific promoter.

According to some embodiments of the invention, the method further comprises growing the plant under limiting nitrogen conditions.

According to some embodiments of the invention, the method further comprises growing the plant under abiotic stress.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to some embodiments of the invention, the plant is a monocotyledon.

According to some embodiments of the invention, the plant is a dicotyledon.

According to an aspect of some embodiments of the present invention there is provided a method of improving abiotic stress tolerance, nitrogen use efficiency, biomass, vigor or yield of a plant, the method comprising expressing within the plant an exogenous polynucleotide which downregulates an activity or expression of a polypeptide having an amino acid sequence at least 80% homologous or identical to SEQ ID NOs: 6315-8129, wherein the polypeptide is capable of regulating abiotic stress tolerance of the plant, thereby improving abiotic stress tolerance, nitrogen use efficiency, biomass, vigor or yield of the plant.

According to an aspect of some embodiments of the present invention there is provided a transgenic plant exogenously expressing a polynucleotide which downregulates an activity or expression of a polypeptide having an amino acid sequence at least 80% homologous or identical to SEQ ID NOs: 6315-8129, wherein the polypeptide is capable of regulating abiotic stress tolerance of the plant.

According to an aspect of some embodiments of the present invention there is provided a nucleic acid construct comprising a polynucleotide which downregulates an activity or expression of a polypeptide having an amino acid sequence at least 80% homologous to SEQ ID NOs: 6315-8129, wherein the polypeptide is capable of regulating abiotic stress tolerance of a plant, the nucleic acid sequence being under the regulation of a cis-acting regulatory element.

According to some embodiments of the invention, the polynucleotide acts by a mechanism selected from the group consisting of sense suppression, antisense suppression, ribozyme inhibition, gene disruption.

According to some embodiments of the invention, the cis-acting regulatory element comprises a promoter.

According to some embodiments of the invention, the promoter comprises a tissue-specific promoter.

According to some embodiments of the invention, the tissue-specific promoter comprises a root specific promoter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
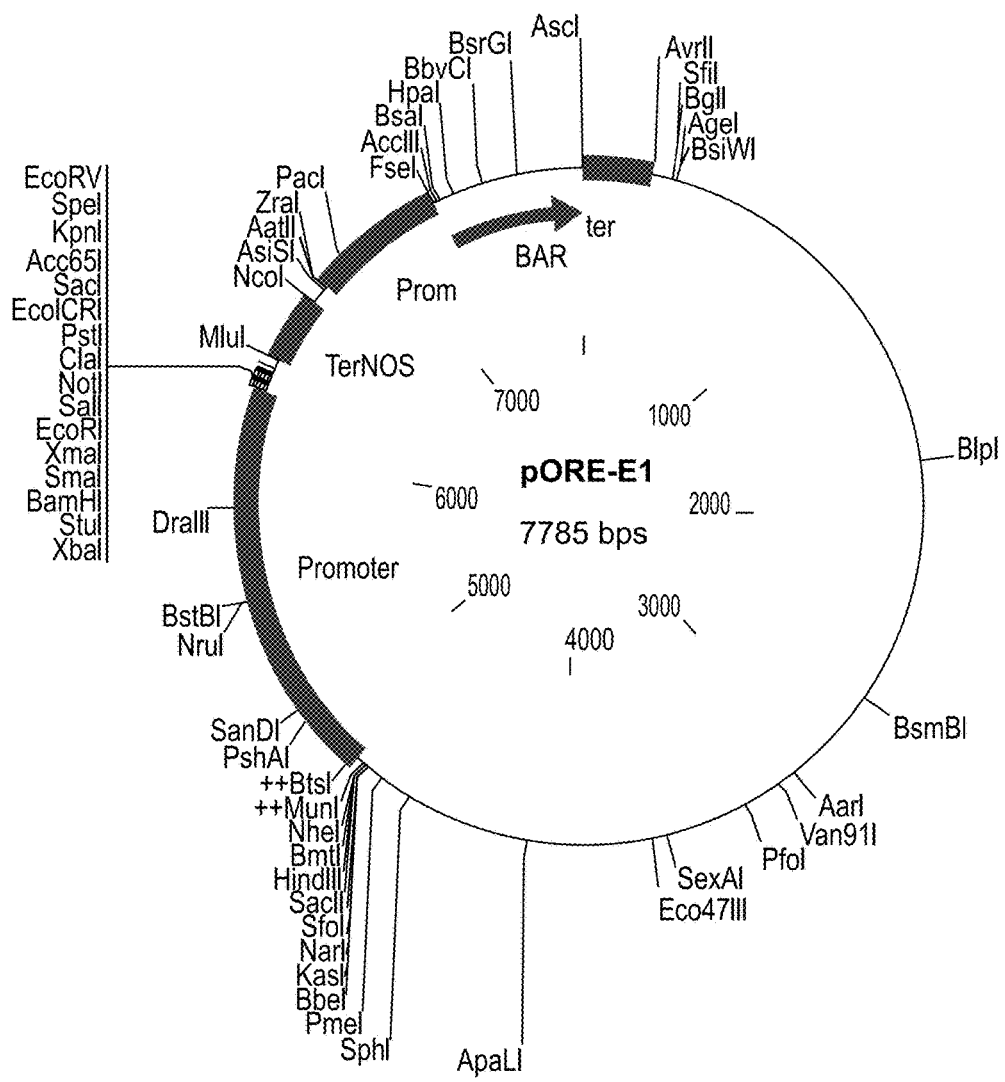
FIG. 1 is a schematic illustration of a plasmid map of the binary vector pORE-E1 used for plant transformation according to some embodiments of the invention.

The present invention, in some embodiments thereof, relates to isolated polynucleotides expressing or modulating microRNAs or targets of same, transgenic plants comprising same and uses thereof in improving nitrogen use efficiency, abiotic stress tolerance, biomass, vigor or yield of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Environmental stresses represent the most limiting factors for agricultural productivity. Apart from biotic stress caused by plant pathogens, there are a number of abiotic stresses such as extremes in temperature, drought, salinity, heavy metals and radiation which all have detrimental effects on plant growth and yield. Abiotic stresses lead to dehydration or osmotic stress through reduced availability of water for vital cellular functions and maintenance of turgor pressure. Stomata closure, reduced supply of $CO_2$ and slower rate of biochemical reactions during prolonged periods of dehydration, high light intensity, high and low temperatures lead to high production of Reactive Oxygen Intermediates (ROI) in the chloroplasts causing irreversible cellular damage and photo inhibition.

Understanding the molecular mechanism for providing protection against biotic and abiotic stresses may lead to the identification of genes associated with stress tolerance. Optimum homeostasis is always a key to living organisms for adjusted environments.

While reducing the present invention to practice, the present inventors have uncovered dsRNA sequences that are differentially expressed in soy plants grown under abiotic stress conditions including, salt stress, heat stress and drought, versus soy plants grown under optimal conditions (see Example 1 of the Examples section which follows). Following extensive experimentation and screening, the present inventors have uncovered miRNA sequences that are upregulated or downregulated in leaf samples, and suggest using same or sequences controlling same in the generation of transgenic plants having improved abiotic stress tolerance.

Each of the above mechanisms may affect water uptake as well as salt absorption and therefore embodiments of the invention further relate to enhancement of abiotic stress tolerance, nitrogen use efficiency, biomass, vigor or yield of the plant.

Example 5 of the Examples section below, validates the present results by showing that some miRs (e.g., gma-miR4376-5p, zma-miR396b-3p, aly-miR396b-3p, gma-miR156g, ma-miRf10687-akr-omolog gma-miR159d, aly-miR396b-3p, gma-miR4416a, aly-miR396a-3p, zma-miR396b-3p, gma-miR4412-3p, csi-miR162-5p, ath-miRf10279-akr) according to specific embodiment of the invention are indeed differentially expressed under abiotic stress conditions as was initially identified by microarray analysis. The present inventors were also capable of generating transgenic plants which overexpress the indicated miRs (see Example 7).

Thus, according to an aspect of the invention there is provided a method of improving abiotic stress tolerance, nitrogen use efficiency, biomass, vigor or yield of a plant, the method comprising expressing within the plant an exogenous polynucleotide having a nucleic acid sequence at least 80%, 85%, 90% or 95% identical to SEQ ID NOs: 1-56, 174-201, 80-125, 220-235, 162-168, 256-259, 262-2086, 11616, 11615, 2087-3910, 3911, 11910-11939, 11874-11904, 11956, 11957 or 11958 wherein the nucleic acid sequence is capable of regulating abiotic stress tolerance of the plant, thereby improving abiotic stress tolerance, nitrogen use efficiency, biomass, vigor or yield of the plant.

According to a specific embodiment the exogenous polynucleotide has a nucleic acid sequence at least 90% identical to SEQ ID NOs: 1-56, 174-201, 80-125, 220-235, 162-168, 256-259, 262-2086, 11616, 11615, 2087-3910, 3911, 11910-11939, 11874-11904, 11956, 11957 or 11958.

According to a specific embodiment the exogenous polynucleotide has a nucleic acid sequence at least 95% identical to SEQ ID NOs: 1-56, 174-201, 80-125, 220-235, 162-168, 256-259, 262-2086, 11616, 11615, 2087-3910, 3911, 11910-11939, 11874-11904, 11956, 11957 or 11958.

According to a specific embodiment the exogenous polynucleotide has a nucleic acid sequence as set forth in SEQ ID NOs: 1-56, 174-201, 80-125, 220-235, 162-168, 256-259, 262-2086, 11616, 11615, 2087-3910, 3911, 11910-11939, 11874-11904, 11956, 11957 or 11958.

The phrase "abiotic stress" as used herein refers to any adverse effect on metabolism, growth, viability and/or reproduction of a plant. Abiotic stress can be induced by any of suboptimal environmental growth conditions such as, for example, water deficit or drought, flooding, freezing, low or high temperature, strong winds, heavy metal toxicity, anaerobiosis, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present invention contemplates situations in which there is a single abiotic stress condition or alternatively situations in which two or more abiotic stresses occur.

According to an exemplary embodiment the abiotic stress refers to salinity.

According to another exemplary embodiment the abiotic stress refers to drought.

According to another exemplary embodiment the abiotic stress refers to a temperature stress.

As used herein the phrase "abiotic stress tolerance" refers to the ability of a plant to endure an abiotic stress without exhibiting substantial physiological or physical damage (e.g. alteration in metabolism, growth, viability and/or reproducibility of the plant).

As used herein the phrase "nitrogen use efficiency (NUE)" refers to a measure of crop production per unit of nitrogen fertilizer input. Fertilizer use efficiency (FUE) is a measure of NUE. Crop production can be measured by biomass, vigor or yield. The plant's nitrogen use efficiency is typically a result of an alteration in at least one of the uptake, spread, absorbance, accumulation, relocation (within the plant) and use of nitrogen absorbed by the plant. Improved NUE is with respect to that of a non-transgenic plant (i.e., lacking the transgene of the transgenic plant) of the same species and of the same developmental stage and grown under the same conditions.

As used herein the phrase "nitrogen-limiting conditions" refers to growth conditions which include a level (e.g., concentration) of nitrogen (e.g., ammonium or nitrate) applied which is below the level needed for optimal plant metabolism, growth, reproduction and/or viability.

As used herein the term/phrase "biomass", "biomass of a plant" or "plant biomass" refers to the amount (e.g., measured in grams of air-dry tissue) of a tissue produced from the plant in a growing season. An increase in plant biomass can be in the whole plant or in parts thereof such as aboveground (e.g. harvestable) parts, vegetative biomass, roots and/or seeds or contents thereof (e.g., oil, starch etc.).

As used herein the term/phrase "vigor", "vigor of a plant" or "plant vigor" refers to the amount (e.g., measured by weight) of tissue produced by the plant in a given time. Increased vigor could determine or affect the plant yield or the yield per growing time or growing area. In addition, early vigor (e.g. seed and/or seedling) results in improved field stand.

As used herein the term/phrase "yield", "yield of a plant" or "plant yield" refers to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

According to an exemplary embodiment the yield is measured by cellulose content, oil content, starch content and the like.

According to another exemplary embodiment the yield is measured by oil content.

According to another exemplary embodiment the yield is measured by protein content.

According to another exemplary embodiment, the yield is measured by seed number per plant or part thereof (e.g., kernel, bean).

A plant yield can be affected by various parameters including, but not limited to, plant biomass; plant vigor; plant growth rate; seed yield; seed or grain quantity; seed or grain quality; oil yield; content of oil, starch and/or protein in harvested organs (e.g., seeds or vegetative parts of the plant); number of flowers (e.g. florets) per panicle (e.g. expressed as a ratio of number of filled seeds over number of primary panicles); harvest index; number of plants grown per area; number and size of harvested organs per plant and per area; number of plants per growing area (e.g. density); number of harvested organs in field; total leaf area; carbon assimilation and carbon partitioning (e.g. the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in NUE, in tolerance to abiotic stress, in yield, in biomass or in vigor of a plant, as compared to a native or wild-type plants [i.e., plants not genetically modified to express the biomolecules (polynucleotides) of the invention, e.g., a non-transformed plant of the same species or a transformed plant transformed with a control vector, either of which being of the same developmental stage and grown under the same growth conditions as the transformed plant].

Improved plant NUE is translated in the field into either harvesting similar quantities of yield, while implementing less fertilizers, or increased yields gained by implementing the same levels of fertilizers. Thus, improved NUE or FUE has a direct effect on plant yield in the field.

The term "plant" as used herein encompasses whole plants, ancestors and progeny of the plants and plant parts, including seeds, shoots, stems, roots (including tubers), and isolated plant cells, tissues and organs. The plant may be in any form including suspension cultures, embryos, meristematic regions, callus tissue, leaves, gametophytes, sporophytes, pollen, and microspores.

As used herein the phrase "plant cell" refers to plant cells which are derived and isolated from disintegrated plant cell tissue or plant cell cultures.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present invention may comprise a particular type of a plant cell or a plurality of different types of plant cells. It should be noted that optionally plant cultures featuring a particular type of plant cell may be originally derived from a plurality of different types of such plant cells.

Any commercially or scientifically valuable plant is envisaged in accordance with some embodiments of the invention. Plants that are particularly useful in the methods of the invention include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively algae and other non-Viridiplantae can be used for the methods of the present invention.

According to some embodiments of the invention, the plant used by the method of the invention is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, sorghum, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *arabidopsis*, broccoli, cabbage, beet, *quinoa*, spinach, squash, onion, leek, tobacco, potato, sugarbeet, *papaya*, pineapple, mango, *Arabidopsis thaliana*, and also plants used in horticulture, floriculture or forestry, such as, but not limited to, poplar, fir, *eucalyptus*, pine, an ornamental plant, a perennial grass and a forage crop, coniferous plants, moss, algae, as well as other plants listed in World Wide Web (dot) nationmaster (dot) com/encyclopedia/Plantae.

According to a specific embodiment of the present invention, the plant comprises soy.

As used herein, the phrase "exogenous polynucleotide" refers to a heterologous nucleic acid sequence which may not be naturally expressed within the plant or which overexpression [i.e., expression above that found in the control non-transformed plant (e.g., wild type) grown under the same conditions and being of the same developmental stage] in the plant is desired. The exogenous polynucleotide may be introduced into the plant in a stable or transient manner, so as to produce a ribonucleic acid (RNA) molecule. It should be noted that the exogenous polynucleotide may comprise a nucleic acid sequence which is identical or partially identical (homologous) to an endogenous nucleic acid sequence of the plant.

As mentioned, the present teachings are based on the identification of miRNA sequences which regulate the tolerance of plants to abiotic stress.

According to some embodiments the exogenous polynucleotide encodes a miRNA or a precursor thereof.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence essentially complementary to the nucleotide sequence of the miRNA molecule.

Typically, a miRNA molecule is processed from a "pre-miRNA" or as used herein a precursor of a pre-miRNA molecule by proteins, such as DCL proteins, present in any plant cell and loaded onto a RISC complex where it can guide the cleavage of the target RNA molecules.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop (also referred to as "hairpin") and further comprising the nucleotide sequence of the miRNA (and its complement sequence) in the double stranded RNA stem.

According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds. Exemplary hairpin sequences are provided in Tables 1-8, below.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the miRNA molecules may be naturally occurring or synthetic.

Thus, the present teachings contemplate expressing an exogenous polynucleotide having a nucleic acid sequence at least 90%, 91%, 92%, 93%, 94%, 95%, 96%, 97%, 98% 99% or 100% identical to—NOs: 1-56, 80-125, 11874, 262-2086, 11616, (mature), provided that they regulate ABST.

Alternatively or additionally, the present teachings contemplate expressing an exogenous polynucleotide having a nucleic acid sequence at least 65%, 50%, 75%, 80%, 85%, 90%, 91%, 92%, 93%, 94%, 95%, 96%, 97%, 98% 99% or 100% identical to SEQ ID NOs: 1-56, 174-201, 80-125, 220-235, 162-168, 256-259, 262-2086, 11616, 11615, 2087-

3910, 3911, 11910-11939, 11874-11904, 11956, 11957 or 11958 (mature and precursors Tables 1, 3, 5, 7), provided that they regulate abiotic stress tolerance of the plant.

Tables 1, 3, 5 and 7 below illustrate exemplary miRNA sequences and precursors thereof which over expression are associated with modulation of abiotic stress tolerance. It is noted that Tables 1-17 below are incorporated into the specification and are considered an integral part thereof.

The present invention envisages the use of homologous and orthologous sequences of the above miRNA molecules. At the precursor level use of homologous sequences can be done to a much broader extent. Thus, in such precursor sequences the degree of homology may be lower in all those sequences not including the mature miRNA segment therein.

As used herein, the phrase "stem-loop precursor" refers to stem loop precursor RNA structure from which the miRNA can be processed.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop (also referred to as "hairpin") and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Thus, according to a specific embodiment, the exogenous polynucleotide encodes a stem-loop precursor of the nucleic acid sequence. Such a stem-loop precursor can be at least about 60%, at least about 65%, at least about 70%, at least about 75%, at least about 80%, at least about 85%, at least about 90%, at least about 95% or more identical to SEQ ID NOs: SEQ ID NO: 174-201, 220-235, 256-259, 2087-3910, 3911, 11910-11939, 11615, 11875-11904, 11956, 11957 or 11958 (homologs precursor), provided that it regulates abiotic stress tolerance.

Identity (e.g., percent identity) can be determined using any homology comparison software, including for example, the BlastN software of the National Center of Biotechnology Information (NCBI) such as by using default parameters.

Homology (e.g., percent homology, identity+similarity) can be determined using any homology comparison software, including for example, the TBLASTN software of the National Center of Biotechnology Information (NCBI) such as by using default parameters.

According to some embodiments of the invention, the term "homology" or "homologous" refers to identity of two or more nucleic acid sequences; or identity of two or more amino acid sequences.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor joining tree (Hypertext Transfer Protocol://en (dot) wikipedia (dot) org/wiki/Neighbor-joining) which helps visualizing the clustering.

As mentioned, the present inventors have also identified RNAi sequences which are down regulated under abiotic stress conditions.

Thus, according to an aspect of the invention there is provided a method of improving abiotic stress tolerance, nitrogen use efficiency, biomass, vigor or yield of a plant, the method comprising expressing within the plant an exogenous polynucleotide which downregulates an activity or expression of a gene encoding a miRNA molecule having a nucleic acid sequence at least 80%, 85% or preferably 90%, 95% or even 100% identical to the sequence selected from the group consisting of SEQ ID NOs: 57-79, 202-219, 126-161, 236-255, 169-173, 260-261, 3953-5114, 11905-11909, 11940-11955, 11959-11961, 5117-6277 or 6278 (Tables 2, 4, 6 and 8), thereby improving abiotic stress tolerance, nitrogen use efficiency, biomass, vigor or yield of a plant.

There are various approaches to down regulate miRNA sequences.

As used herein the term "down-regulation" refers to reduced activity or expression of the miRNA (at least 10%, 20%, 30%, 50%, 60%, 70%, 80%, 90% or 100% reduction in activity or expression) as compared to its activity or expression in a plant of the same species and the same developmental stage not expressing the exogenous polynucleotide.

Nucleic acid agents that down-regulate miR activity include, but are not limited to, a target mimic, a micro-RNA resistant gene and a miRNA inhibitor.

The target mimic or micro-RNA resistant target is essentially complementary to the microRNA provided that one or more of following mismatches are allowed:

(a) a mismatch between the nucleotide at the 5' end of the microRNA and the corresponding nucleotide sequence in the target mimic or micro-RNA resistant target;

(b) a mismatch between any one of the nucleotides in position 1 to position 9 of the microRNA and the corresponding nucleotide sequence in the target mimic or micro-RNA resistant target; or (c) three mismatches between any one of the nucleotides in position 12 to position 21 of the microRNA and the corresponding nucleotide sequence in the target mimic or micro-RNA resistant target provided that there are no more than two consecutive mismatches.

The target mimic RNA is essentially similar to the target RNA modified to render it resistant to miRNA induced cleavage, e.g. by modifying the sequence thereof such that a variation is introduced in the nucleotide of the target mimic sequence complementary to the nucleotides 10 or 11 of the miRNA resulting in a mismatch.

Alternatively, a microRNA-resistant target may be implemented. Thus, a silent mutation may be introduced in the microRNA binding site of the target gene so that the DNA and resulting RNA sequences are changed in a way that prevents microRNA binding, but the amino acid sequence of the protein is unchanged. Thus, a new sequence can be synthesized instead of the existing binding site, in which the DNA sequence is changed, resulting in lack of miRNA binding to its target.

Tables 14-17 below provide non-limiting examples of target mimics and target resistant sequences that can be used to down-regulate the activity of the miRs of the invention. According to a specific embodiment, the target mimic is listed in any one of the sequences of Table 7. According to a specific embodiment, the mir-resistant target sequence is listed in any one of the sequences of Table 15.

According to a specific embodiment, the target mimic or micro-RNA resistant target is linked to the promoter naturally associated with the pre-miRNA recognizing the target gene and introduced into the plant cell. In this way, the miRNA target mimic or micro-RNA resistant target RNA will be expressed under the same circumstances as the miRNA and the target mimic or micro-RNA resistant target RNA will substitute for the non-target mimic/micro-RNA resistant target RNA degraded by the miRNA induced cleavage.

Non-functional miRNA alleles or miRNA resistant target genes may also be introduced by homologous recombination to substitute the miRNA encoding alleles or miRNA sensitive target genes.

Recombinant expression is effected by cloning the nucleic acid of interest (e.g., miRNA, target gene, silencing agent etc) into a nucleic acid expression construct under the expression of a plant promoter, as further described hereinbelow.

In other embodiments of the invention, synthetic single stranded nucleic acids are used as miRNA inhibitors. A miRNA inhibitor is typically between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA.

While further reducing the present invention to practice, the present inventors have identified gene targets for the differentially expressed miRNA molecules. It is therefore contemplated, that gene targets of those miRNAs that are down regulated during stress should be overexpressed in order to confer tolerance, while gene targets of those miRNAs that are up regulated during stress should be down-regulated in the plant in order to confer tolerance.

Thus, according to an aspect of the invention there is provided a method of improving abiotic stress tolerance, nitrogen use efficiency, biomass, vigor or yield of a plant, the method comprising expressing within the plant an exogenous polynucleotide encoding a polypeptide having an amino acid sequence at least 80%, 82%, 84%, 85%, 86%, 88%, 90%, 92%, 94%, 95%, 96%, 97%, 98%, 99% or 100% homologous to SEQ ID NOs: 9591-10364 (gene targets of down regulated miRNAs, see Table 10), wherein the polypeptide is capable of regulating abiotic stress tolerance of the plant, thereby improving abiotic stress tolerance, nitrogen use efficiency, biomass, vigor or yield of the plant.

Nucleic acid sequences (also referred to herein as polynucleotides) of the polypeptides of some embodiments of the invention may be optimized for expression in a specific plant host. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Target genes which are contemplated according to the present teachings are provided in the polynucleotide sequences which comprise nucleic acid sequences as set forth in the soy polynucleotides listed in Table 10). However the present teachings also relate to orthologs or homologs at least about 60%, at least about 65%, at least about 70%, at least about 75%, at least about 80%, at least about 85%, at least about 90%, or at least about 95% or more identical or similar to SEQ ID NO: 10365-10963 (polynucleotides listed in Table 10). Parameters for determining the level of identity are provided hereinbelow.

Alternatively or additionally, target genes which are contemplated according to the present teachings are provided in the polypeptide sequences which comprise amino acid sequences as set forth in the soy polypeptides of Table 10). However the present teachings also relate to orthologs or homologs at least about 60%, at least about 65%, at least about 70%, at least about 75%, at least about 80%, at least about 85%, at least about 90%, or at least about 95% or more identical or similar to SEQ ID NO: 9591-10364 (Table 10).

As mentioned the present inventors have also identified genes which down-regulation may be done in order to improve their abiotic stress tolerance, NUE, biomass, vigor and yield.

Thus, according to an aspect of the invention there is provided a method of improving abiotic stress tolerance, nitrogen use efficiency, biomass, vigor or yield of a plant, the method comprising expressing within the plant an exogenous polynucleotide which downregulates an activity or expression of a polypeptide having an amino acid sequence at least 80%, 85%, 90%, 95%, or 100% homologous to SEQ ID NOs: 6315-8129 (polypeptides of Table 9), wherein the polypeptide is capable of regulating abiotic stress tolerance of the plant, thereby improving abiotic stress tolerance, nitrogen use efficiency, biomass, vigor or yield of the plant.

Down regulation of activity or expression is by at least 10%, 20%, 30%, 40%, 50%, 60%, 70%, 80%, 90% or even complete (100%) loss of activity or expression. Assays for measuring gene expression can be effected at the protein level (e.g., Western blot, ELISA) or at the mRNA level such as by RT-PCR.

According to a specific embodiment the amino acid sequence of the target gene is as set forth in SEQ ID NOs: 6315-8129 of Table 9.

Alternatively or additionally, the amino acid sequence of the target gene is encoded by a polynucleotide sequence as set forth in SEQ ID NOs: 8130-9590 of Table 9.

Examples of polynucleotide downregulating agents that inhibit (also referred to herein as inhibitors or nucleic acid (downregulating) agents) the expression of a target gene are given below.

1. Polynucleotide-Based Inhibition of Gene Expression.

It will be appreciated, that any of these methods when specifically referring to downregulating expression/activity of the target genes can be used, at least in part, to downregulate expression or activity of endogenous RNA molecules.

i. Sense Suppression/Cosuppression

In some embodiments of the invention, inhibition of the expression of target gene may be obtained by sense suppression or cosuppression. For cosuppression, an expression cassette is designed to express an RNA molecule corresponding to all or part of a messenger RNA encoding a target gene in the "sense" orientation. Over-expression of the RNA molecule can result in reduced expression of the native gene. Accordingly, multiple plant lines transformed with the cosuppression expression cassette are screened to identify those that show the greatest inhibition of target gene expression.

The polynucleotide used for cosuppression may correspond to all or part of the sequence encoding the target gene, all or part of the 5' and/or 3' untranslated region of a target transcript, or all or part of both the coding sequence and the untranslated regions of a transcript encoding the target gene. In some embodiments where the polynucleotide comprises all or part of the coding region for the target gene, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) Plant Cell 15:1517-1532. Cosuppression may also be used to inhibit the expression of multiple proteins in the same plant. Methods for using cosuppression to inhibit the expression of endogenous genes in plants are described in Flavell, et al., (1995) Proc. Natl. Acad. Sci. USA 91:3590-3596; Jorgensen, et al., (1996) Plant Mol. Biol. 31:957-973; Johansen and Carrington, (2001) Plant Physiol. 126:930-938; Broin, et al., (2002) Plant Cell 15:1517-1532; Stoutjesdijk, et al., (2002) Plant Physiol. 129:1723-1731; Yu, et al., (2003) Phytochemistry 63:753-763; and U.S. Pat. Nos. 5,035,323, 5,283,185 and 5,952,657; each of which is herein incorporated by reference. The efficiency of cosuppression may be increased by including a poly-dt region in the expression cassette at a position 3' to the sense sequence and 5' of the polyadenylation signal. See, US Patent Publication Number 20020058815, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,185 and 5,035,323; herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz, et al., (2002) PNAS 99(4):16499-16506; Mette, et al., (2000) EMBO J. 19(19):5194-5201)

ii. Antisense Suppression

In some embodiments of the invention, inhibition of the expression of the target gene may be obtained by antisense suppression. For antisense suppression, the expression cassette is designed to express an RNA molecule complementary to all or part of a messenger RNA encoding the target gene. Over-expression of the antisense RNA molecule can result in reduced expression of the native gene. Accordingly, multiple plant lines transformed with the antisense suppression expression cassette are screened to identify those that show the greatest inhibition of target gene expression.

The polynucleotide for use in antisense suppression may correspond to all or part of the complement of the sequence encoding the target gene, all or part of the complement of the 5' and/or 3' untranslated region of the target gene transcript, or all or part of the complement of both the coding sequence and the untranslated regions of a transcript encoding the target gene. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. Furthermore, portions of the antisense nucleotides may be used to disrupt the expression of the target gene. Generally, sequences of at least 50 nucleotides, 100 nucleotides, 200 nucleotides, 300, 500, 550 or greater may be used. Methods for using antisense suppression to inhibit the expression of endogenous genes in plants are described, for example, in Liu, et al., (2002) Plant Physiol. 129:1732-1753 and U.S. Pat. No. 5,759,829, which is herein incorporated by reference. Efficiency of antisense suppression may be increased by including a poly-dT region in the expression cassette at a position 3' to the antisense sequence and 5' of the polyadenylation signal. See, US Patent Publication Number 20020058815.

iii. Double-Stranded RNA Interference

In some embodiments of the invention, inhibition of the expression of a target gene may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of target gene expression. Methods for using dsRNA interference to inhibit the expression of endogenous plant genes are described in Waterhouse, et al., (1998) Proc. Natl. Acad. Sci. USA 95:13959-13965, Liu, et al., (2002) Plant Physiol. 129:1732-1753, and WO 99/59029, WO 99/53050, WO 99/61631, and WO 00/59035.

iv. Hairpin RNA Interference and Intron-Containing Hairpin RNA Interference

In some embodiments of the invention, inhibition of the expression of one or more target gene may be obtained by hairpin RNA (hpRNA) interference or intron-containing hairpin RNA (ihpRNA) interference. These methods are highly efficient at downregulating the expression of endogenous genes. See, Waterhouse and Helliwell, (2003) Nat. Rev. Genet. 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) Proc. Natl. Acad. Sci. USA 97:5985-5990; Stoutjesdijk, et al., (2002) Plant Physiol. 129:1723-1731; and Waterhouse and Helliwell, (2003) Nat. Rev. Genet. 5:29-38. Methods for using hpRNA interference to inhibit or silence the expression of genes are described, for example, in Chuang and Meyerowitz, (2000) Proc. Natl. Acad. Sci. USA 97:5985-5990; Stoutjesdijk, et al., (2002) Plant Physiol. 129:1723-1731; Waterhouse and Helliwell, (2003) Nat. Rev. Genet. 5:29-38; Pandolfini, et al., BMC Biotechnology 3:7, and US Patent Publication Number 20030175965; each of which is herein incorporated by reference. A transient assay for the efficiency of hpRNA constructs to silence gene expression in vivo has been described by Panstruga, et al., (2003) Mol. Biol. Rep. 30:135-150, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) Nature 507:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) Nature 507:319-320; Wesley, et al., (2001) Plant J. 27:584, 1-3, 590; Wang and Waterhouse, (2001) Curr. Opin. Plant Biol. 5:156-150; Waterhouse and Helliwell, (2003) Nat.

Rev. Genet. 5:29-38; Helliwell and Waterhouse, (2003) Methods 30:289-295, and US Patent Publication Number 20030180955, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00905, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for target gene). Methods of using amplicons to inhibit the expression of endogenous plant genes are described, for example, in Angell and Baulcombe, (1997) EMBO J. 16:3675-3685, Angell and Baulcombe, (1999) Plant J. 20:357-362, and U.S. Pat. No. 6,656,805, each of which is herein incorporated by reference.

vi. Ribozymes

In some embodiments, the polynucleotide expressed by the expression cassette of the invention is catalytic RNA or has ribozyme activity specific for the messenger RNA of target gene. Thus, the polynucleotide causes the degradation of the endogenous messenger RNA, resulting in reduced expression of the target gene. This method is described, for example, in U.S. Pat. No. 5,987,071, herein incorporated by reference.

2. Gene Disruption

In some embodiments of the present invention, the activity of a miRNA or a target gene is reduced or eliminated by disrupting the gene encoding the target polypeptide. The gene encoding the target polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced response regulator activity.

Any of the nucleic acid agents described herein (for overexpression or downregulation of either the target gene or the miRNA) can be provided to the plant as naked RNA or expressed from a nucleic acid expression construct, where it is operably linked to a regulatory sequence.

According to a specific embodiment of the invention, there is provided a nucleic acid construct comprising a nucleic acid sequence encoding a nucleic acid agent (e.g., miRNA or a precursor thereof as described herein, gene target or silencing agent), the nucleic acid sequence being under a transcriptional control of a regulatory sequence such as a tissue specific promoter.

An exemplary nucleic acid construct which can be used for plant transformation include, the pORE E2 binary vector (FIG. 1) in which the relevant nucleic acid sequence is ligated under the transcriptional control of a promoter.

A coding nucleic acid sequence is "operably linked" or "transcriptionally linked to a regulatory sequence (e.g., promoter)" if the regulatory sequence is capable of exerting a regulatory effect on the coding sequence linked thereto.

Thus, the regulatory sequence controls the transcription of the miRNA or precursor thereof, gene target or silencing agent.

The term "regulatory sequence", as used herein, means any DNA, that is involved in driving transcription and controlling (i.e., regulating) the timing and level of transcription of a given DNA sequence, such as a DNA coding for a miRNA, precursor or inhibitor of same. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin. Thus, any suitable promoter sequence can be used by the nucleic acid construct of the present invention. According to some embodiments of the invention, the promoter is a constitutive promoter, a tissue-specific promoter or an inducible promoter (e.g. an abiotic stress-inducible promoter).

Suitable constitutive promoters include, for example, hydroperoxide lyase (HPL) promoter, CaMV 35S promoter (Odell et al, Nature 313:810-812, 1985); *Arabidopsis* At6669 promoter (see PCT Publication No. WO04081173A2); *Arabidopsis* new At6669 promoter; maize Ubi 1 (Christensen et al., Plant Sol. Biol. 18:675-689, 1992); rice actin (McElroy et al., Plant Cell 2:163-171, 1990); pEMU (Last et al, Theor. Appl. Genet. 81:584, 1-3, 588, 1991); CaMV 19S (Nilsson et al, Physiol. Plant 100: 456-462, 1997); GOS2 (de Pater et al, Plant J Nov; 2(6): 837-44, 1992); ubiquitin (Christensen et al, Plant MoI. Biol. 18: 675-689, 1992); Rice cyclophilin (Bucholz et al, Plant MoI Biol. 25(5):837-43, 1994); Maize H3 histone (Lepetit et al, MoI. Gen. Genet. 231:276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608, 149; 5,608,144; 5,604,121; 5,569,597: 5,466,785; 5,399, 680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant MoI. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant MoI. Biol. 5. 191, 1985; Scofield, et al., J. Biol. Chem. 262: 12202, 1987; Baszczynski, et al., Plant MoI. Biol. 14: 633, 1990), Brazil Nut albumin (Pearson' et al., Plant MoI. Biol. 18: 235-245, 1992), legumin (Ellis, et al. Plant MoI. Biol. 10: 203-214, 1988), Glutelin (rice) (Takaiwa, et al., MoI. Gen. Genet. 208: 15-22, 1986; Takaiwa, et al., FEBS Letts. 221:43-47, 1987), Zein (Matzke et al., Plant MoI Biol, 143)323-32 1990), napA (Stalberg, et al., Planta 199: 515-519, 1996), Wheat SPA (Albanietal, Plant Cell, 9: 171-184, 1997), sunflower oleosin (Cummins, et al, Plant MoI. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3: 1409-15, 1984), Barley ltrl promoter, barley Bl, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin GIb-I (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorghum gamma-kafirin (PMB 32:1029-35, 1996); e.g., the Napin promoter], embryo specific promoters [e.g., rice OSH1 (Sato et al, Proc. Natl. Acad. Sci. USA, 93: 8117-8122), KNOX (Postma-Haarsma et al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3]. Also contemplated are root-specific promoters such as the ROOTP promoter described in Vissenberg K, et al. Plant Cell Physiol. 2005 January; 46(1):192-200.

The nucleic acid construct of some embodiments of the invention can further include an appropriate selectable marker and/or an origin of replication.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

When naked RNA or DNA is introduced into a cell, the polynucleotides may be synthesized using any method known in the art, including either enzymatic syntheses or solid-phase syntheses. These are especially useful in the case of short polynucleotide sequences with or without modifications as explained above. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

There are various methods of introducing foreign genes into both monocotyledonous and dicotyledonous plants (Potrykus, L, Annu. Rev. Plant. Physiol, Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer (e.g., T-DNA using *Agrobacterium tumefaciens* or *Agrobacterium rhizogenes*); see for example, Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

According to a specific embodiment of the present invention, the exogenous polynucleotide is introduced into the plant by infecting the plant with bacteria, such as using a floral dip transformation method (as described in further detail in Example 7, of the Examples section which follows).

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. For this reason it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261. According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Galon et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al, Virology (1989) 172: 285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat proteins which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent to the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired sequence.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it gets integrated into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference.

Regardless of the method of transformation, propagation or regeneration, the present invention also contemplates a transgenic plant exogenously expressing the polynucleotide/nucleic acid agent of the invention.

According to a specific embodiment, the transgenic plant exogenously expresses a polynucleotide having a nucleic acid sequence at least, 80%, 85%, 90%, 95% or even 100% identical to SEQ ID NOs: 1-56, 11874, 174-201, 80-125, 220-235, 162-168, 256-259, 262-2086, 2087-3910 11616, 11615, 11910-11939, 11956-11958, 11875-11904 or 3911 (Tables 1, 3, 5 and 7), wherein the nucleic acid sequence is capable of regulating abiotic stress tolerance of the plant.

According to further embodiments, the exogenous polynucleotide encodes a precursor of the nucleic acid sequence.

According to yet further embodiments, the stem-loop precursor is at least 60%, 65%, 70%, 75%, 80%, 85%, 90%, 95% or even 100% identical to SEQ ID NOs: 1-56, 11874, 174-201, 80-125, 220-235, 162-168, 256-259, 262-2086, 2087-3910 11616, 11615, 11910-11939, 11956-11958, 11875-11904 or 3911 (Tables 1, 3, 5 and 7). More specifically the exogenous polynucleotide is selected from the group consisting of SEQ ID NO: 1-56, 11874, 174-201, 80-125, 220-235, 162-168, 256-259, 262-2086, 2087-3910 11616, 11615, 11910-11939, 11956-11958, 11875-11904 or 3911 (precursor and mature sequences of unregulated Tables 1, 3, 5 and 7).

Alternatively, there is provided a transgenic plant exogenously expressing a polynucleotide which downregulates an activity or expression of a gene encoding a miRNA molecule having a nucleic acid sequence selected from the group consisting of SEQ ID NOs: 57-79, 202-219, 126-161, 236-255, 169-173, 260-261, 3953-5114, 5117-6277, 11905-11909, 11940-11955, 11959-11961 or 6278 (downregulated Tables 2, 4, 6, 8) or homologs thereof which are at least at least 80%, 85%, 90% or 95% identical to SEQ ID NOs: 57-79, 202-219, 126-161, 236-255, 169-173, 260-261, 3953-5114, 5117-6277, 11905-11909, 11940-11955, 11959-11961 or 6278 (downregulated Tables 2, 4, 6 and 8).

More specifically, the transgenic plant expresses the nucleic acid agent of Tables 14 or 16. Alternatively, the transgenic plant expresses the nucleic acid agent of Tables 15 or 17.

It will be appreciated that the present teachings also relate to nucleic acid constructs and transgenic plants expressing same which comprise a nucleic acid sequence at least 80%, 85%, 90%, 95% or even 100% identical to SEQ ID NOs: 57-79, 202-219, 126-161, 236-255, 169-173, 260-261, 3953-5114, 5117-6277, 11905-11909, 11940-11955, 11959-11961 or 6278 (Tables 2, 4, 6 and 8), wherein the nucleic acid sequence is capable of regulating abiotic stress tolerance of the plant.

Alternatively or additionally there is provided a transgenic plant exogenously expressing a polynucleotide encoding a polypeptide having an amino acid sequence at least 80%, 85%, 90%, 95% or even 100% homologous to SEQ ID NOs: 9591-10364 (polypeptides of Table 10), wherein the polypeptide is capable of regulating abiotic stress tolerance of the plant.

Alternatively or additionally there is provided a transgenic plant exogenously expressing a polynucleotide encoding a polypeptide having an amino acid sequence at least 80%, 85%, 90%, 95% or even 100% homologous to SEQ ID NOs: 6315-8129 (polypeptides of Table 9), wherein the polypeptide is capable of regulating abiotic stress tolerance of the plant.

Alternatively or additionally there is provided a transgenic plant exogenously expressing a polynucleotide which downregulates an activity or expression of a polypeptide having an amino acid sequence at least 80%, 85%, 90%, 95% or even 100% homologous to SEQ ID NOs: 6315-10963 (targets of Tables 9 and 10), wherein the polypeptide is capable of regulating abiotic stress tolerance of the plant.

Also contemplated are hybrids of the above described transgenic plants. A "hybrid plant" refers to a plant or a part thereof resulting from a cross between two parent plants, wherein one parent is a genetically engineered plant of the invention (transgenic plant expressing an exogenous miRNA sequence or a precursor thereof). Such a cross can occur naturally by, for example, sexual reproduction, or artificially by, for example, in vitro nuclear fusion. Methods of plant breeding are well-known and within the level of one of ordinary skill in the art of plant biology.

Since abiotic stress tolerance, nitrogen use efficiency as well as yield, vigor or biomass of the plant can involve multiple genes acting additively or in synergy (see, for example, in Quesda et al., Plant Physiol. 130:951-063, 2002), the invention also envisages expressing a plurality of exogenous polynucleotides in a single host plant to thereby achieve superior effect on the efficiency of nitrogen use, yield, vigor and biomass of the plant.

Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove. Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. Alternatively, the construct can include several promoter sequences each linked to a different exogenous polynucleotide sequence.

The plant cell transformed with the construct including a plurality of different exogenous polynucleotides can be regenerated into a mature plant, using the methods described hereinabove.

Alternatively, expressing a plurality of exogenous polynucleotides can be effected by introducing different nucleic acid constructs, including different exogenous polynucleotides, into a plurality of plants. The regenerated transformed plants can then be cross-bred and resultant progeny selected for superior yield or tolerance traits as described above, using conventional plant breeding techniques.

Expression of the miRNAs of the present invention or precursors thereof can be qualified using methods which are well known in the art such as those involving gene amplification e.g., PCR or RT-PCR or Northern blot or in-situ hybridization.

According to some embodiments of the invention, the plant expressing the exogenous polynucleotide(s) is grown under stress (nitrogen or abiotic) or normal conditions (e.g., biotic conditions and/or conditions with sufficient water, nutrients such as nitrogen and fertilizer). Such conditions, which depend on the plant being grown, are known to those skilled in the art of agriculture, and are further, described above.

According to some embodiments of the invention, the method further comprises growing the plant expressing the exogenous polynucleotide(s) under abiotic stress or nitrogen limiting conditions. Non-limiting examples of abiotic stress conditions include, water deprivation, drought, excess of water (e.g., flood, waterlogging), freezing, low temperature, high temperature, strong winds, heavy metal toxicity, anaerobiosis, nutrient deficiency, nutrient excess, salinity, atmospheric pollution, intense light, insufficient light, or UV irradiation, etiolation and atmospheric pollution.

Thus, the invention encompasses plants exogenously expressing the polynucleotide(s), the nucleic acid constructs of the invention.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-m situ hybridization.

The sequence information and annotations uncovered by the present teachings can be harnessed in favor of classical breeding. Thus, sub-sequence data of those polynucleotides described above, can be used as markers for marker assisted selection (MAS), in which a marker is used for indirect selection of a genetic determinant or determinants of a trait of interest (e.g., tolerance to abiotic stress). Nucleic acid data of the present teachings (DNA or RNA sequence) may contain or be linked to polymorphic sites or genetic markers on the genome such as restriction fragment length polymorphism (RFLP), microsatellites and single nucleotide polymorphism (SNP), DNA fingerprinting (DFP), amplified fragment length polymorphism (AFLP), expression level polymorphism, and any other polymorphism at the DNA or RNA sequence.

Examples of marker assisted selections include, but are not limited to, selection for a morphological trait (e.g., a gene that affects form, coloration, male sterility or resistance such as the presence or absence of awn, leaf sheath coloration, height, grain color, aroma of rice); selection for a biochemical trait (e.g., a gene that encodes a protein that can be extracted and observed; for example, isozymes and storage proteins); selection for a biological trait (e.g., pathogen races or insect biotypes based on host pathogen or host parasite interaction can be used as a marker since the genetic constitution of an organism can affect its susceptibility to pathogens or parasites).

The polynucleotides described hereinabove can be used in a wide range of economical plants, in a safe and cost effective manner.

Plant lines exogenously expressing the polynucleotide of the invention can be screened to identify those that show the greatest increase of the desired plant trait.

Thus, according to an additional embodiment of the present invention, there is provided a method of evaluating a trait of a plant, the method comprising: (a) expressing in a plant or a portion thereof the nucleic acid construct; and (b) evaluating a trait of a plant as compared to a wild type plant of the same type; thereby evaluating the trait of the plant.

Thus, the effect of the transgene (the exogenous polynucleotide) on different plant characteristics may be determined any method known to one of ordinary skill in the art.

Thus, for example, tolerance to limiting nitrogen conditions may be compared in transformed plants {i.e., expressing the transgene) compared to non-transformed (wild type) plants exposed to the same stress conditions (other stress conditions are contemplated as well, e.g. water deprivation, salt stress e.g. salinity, suboptimal temperatureosmotic stress, and the like), using the following assays.

Methods of qualifying plants as being tolerant or having improved tolerance to abiotic stress or limiting nitrogen levels are well known in the art and are further described hereinbelow.

Fertilizer use efficiency—To analyze whether the transgenic plants are more responsive to fertilizers, plants are grown in agar plates or pots with a limited amount of fertilizer, as described, for example, in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen use efficiency—To analyze whether the transgenic plants (e.g., *Arabidopsis* plants) are more responsive to nitrogen, plant are grown in 0.75-3 millimolar (mM, nitrogen deficient conditions) or 10, 6-9 mM (optimal nitrogen concentration). Plants are allowed to grow for additional 25 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen Use efficiency assay using plantlets—The assay is done according to Yanagisawa-S. et al. with minor modifications ("Metabolic engineering with Dof1 transcription factor in plants: Improved nitrogen assimilation and growth under low-nitrogen conditions" *Proc. Natl. Acad. Sci. USA* 101, 7833-7838). Briefly, transgenic plants which are grown for 7-10 days in 0.5×MS [Murashige-Skoog] supplemented with a selection agent are transferred to two nitrogen-limiting conditions: MS media in which the combined nitrogen concentration ($NH_4NO_3$ and $KNO_3$) was 0.75 mM (nitrogen deficient conditions) or 6-15 mM (optimal nitrogen concentration). Plants are allowed to grow for additional 30-40 days and then photographed, individually removed from the Agar (the shoot without the roots) and immediately weighed (fresh weight) for later statistical analysis. Constructs for which only T1 seeds are available are sown on selective media and at least 20 seedlings (each one representing an independent transformation event) are carefully transferred to the nitrogen-limiting media. For constructs for which T2 seeds are available, different transformation events are analyzed. Usually, 20 randomly selected plants from each event are transferred to the nitrogen-limiting media allowed to grow for 3-4 additional weeks and individually weighed at the end of that period. Transgenic plants are compared to control plants grown in parallel under the same conditions. Mock-transgenic plants expressing the uidA reporter gene (GUS) under the same promoter or transgenic plants carrying the same promoter but lacking a reporter gene are used as control.

Nitrogen determination—The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Tolerance to abiotic stress (e.g. tolerance to drought or salinity) can be evaluated by determining the differences in physiological and/or physical condition, including but not limited to, vigor, growth, size, or root length, or specifically, leaf color or leaf area size of the transgenic plant compared to a non-modified plant of the same species grown under the same conditions. Other techniques for evaluating tolerance to abiotic stress include, but are not limited to, measuring chlorophyll fluorescence, photosynthetic rates and gas exchange rates. Further assays for evaluating tolerance to abiotic stress are provided hereinbelow and in the Examples section which follows.

Drought tolerance assay—Soil-based drought screens are performed with plants overexpressing the polynucleotides detailed above. Seeds from control *Arabidopsis* plants, or other transgenic plants overexpressing nucleic acid of the invention are germinated and transferred to pots. Drought stress is obtained after irrigation is ceased. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as drought stress tolerant plants Salinity tolerance assay—Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution with added salt), or by culturing the plants in a hyperosmotic growth medium [e.g., 50 Murashige-Skoog medium (MS medium) with added salt]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 150 mM, 300 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of chlorosis and overall success to reach maturity and yield progeny are compared between control and transgenic plants. Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic tolerance test—Osmotic stress assays (including sodium chloride and PEG assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress experiments, the medium is supplemented for example with 50 mM, 100 mM, 200 mM NaCl or 15%, 20% or 25% PEG.

Cold stress tolerance—One way to analyze cold stress is as follows. Mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between control and transgenic plants, by measuring plant weight (wet and dry), and by comparing growth rates measured as time to flowering, plant size, yield, and the like.

Heat stress tolerance—One way to measure heat stress tolerance is by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

The biomass, vigor and yield of the plant can also be evaluated using any method known to one of ordinary skill in the art. Thus, for example, plant vigor can be calculated by the increase in growth parameters such as leaf area, fiber length, rosette diameter, plant fresh weight, oil content, seed yield and the like per time.

As mentioned, the increase of plant yield can be determined by various parameters. For example, increased yield of rice may be manifested by an increase in one or more of the following: number of plants per growing area, number of panicles per plant, number of spikelets per panicle, number of flowers per panicle, increase in the seed filling rate, increase in thousand kernel weight (1000-weight), increase oil content per seed, increase starch content per seed, among others. An increase in yield may also result in modified architecture, or may occur because of modified architecture. Similarly, increased yield of soybean may be manifested by an increase in one or more of the following: number of plants per growing area, number of pods per plant, number of seeds per pod, increase in the seed filling rate, increase in thousand seed weight (1000-weight), reduce pod shattering, increase oil content per seed, increase protein content per seed, among others. An increase in yield may also result in modified architecture, or may occur because of modified architecture.

Thus, the present invention is of high agricultural value for increasing tolerance of plants to nitrogen deficiency or abiotic stress as well as promoting the yield, biomass and vigor of commercially desired crops.

According to another embodiment of the present invention, there is provided a food or feed comprising the plants or a portion thereof of the present invention.

In a further aspect the invention, the transgenic plants of the present invention or parts thereof are comprised in a food or feed product (e.g., dry, liquid, paste). A food or feed product is any ingestible preparation containing the transgenic plants, or parts thereof, of the present invention, or preparations made from these plants. Thus, the plants or preparations are suitable for human (or animal) consumption, i.e. the transgenic plants or parts thereof are more readily digested. Feed products of the present invention further include an oil or a beverage adapted for animal consumption.

It will be appreciated that the transgenic plants, or parts thereof, of the present invention may be used directly as feed products or alternatively may be incorporated or mixed with feed products for consumption. Furthermore, the food or feed products may be processed or used as is. Exemplary feed products comprising the transgenic plants, or parts thereof, include, but are not limited to, grains, cereals, such as oats, e.g. black oats, barley, wheat, rye, sorghum, corn, vegetables, leguminous plants, especially soybeans, root vegetables and cabbage, or green forage, such as grass or hay.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differential Expression of miRNAs in Soybean Plant Under Abiotic Stress Versus Optimal Conditions Plant Material

*Glycine max* seeds (soy) were obtained from Taam-Teva shop (Israel). Plants were grown at 28° C. under a 16 hours light:8 hours dark regime.

Drought Induction

Plants were grown under standard conditions as described above until seedlings were four weeks old. Next, plants were divided into two groups: control plants were irrigated with tap water twice a week and drought-treated plants received no irrigation. The experiment continued for five days, after which plants were harvested for RNA extraction.

Salt Induction

For salinity induction, irrigation with regular water was substituted by irrigation with 300 mM NaCl solution in the stress group, for an overall of 3 irrigations for a ten-day period.

Heat Shock Induction

For induction of heat shock, the stress group plants were exposed to a high temperature (37° C.) for one hour.

Total RNA Extraction

Total RNA of leaf samples from eight biological repeats were extracted using the mirVana™ kit (Ambion, Austin, Tex.) by pooling tissues from 2-4 plants to one biological repeat. RNA analysis was performed on plant tissue samples from both experimental and control groups.

Microarray Design

Custom microarrays were manufactured by Agilent Technologies by in situ synthesis. A microarray based on Sanger version 16 was designed and consisted of a total 4602 non-redundant DNA 45-nucleotide long probes for all known plant small RNAs, with 1875 sequences (40.7%) from miRBase (http://wwwDOTmirbaseDOTorg/index-DOTshtml) and 2678 sequences (58DOT2%) from PMRD (http://bioinformaticsDOTcauDOTeduDOTcn/PMRD/), with each probe being printed in triplicate. Control and spike probes account for the remaining sequences on the microarray.

Results

Wild type soybean plants were allowed to grow at standard, optimal conditions or stress conditions for a period of time as specified above, at the end of which they were evaluated for stress tolerance. Three to four plants from each group were grouped as a biological repeat. Four to eight biological repeats were obtained for each group, and RNA was extracted from leaf tissue. The expression level of the soybean small RNAs was analyzed by high throughput microarray to identify small RNAs that were differentially expressed between the experimental groups.

Tables 1-6 below present sequences that were found to be differentially expressed in soybean grown under drought conditions (lasting five days), high salt conditions (lasting ten days) or heat shock conditions (lasting one hour), compared to optimal growth conditions. To clarify, the sequence of an up-regulated miRNA is induced under stress conditions and the sequence of a down-regulated miRNA is repressed under stress conditions.

TABLE 1

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
|---|---|---|---|---|
| ahy-miR3514-5p | AGGATTCTGTAT TAACGGTGGA (1) | ACAATAGAAGGATTCTGTATTAAC GGTGGACATGATTTATCTCGTTTTT AAAGATATCTTTGCATTTCATATG AGATTTAAAGTTTTTATTGGTAAT ATAAATCTCACATGAAATTTAAAT TTATATTTTAAAGTTAAGATAAAG TCATGTCACCGTTAATACAGAATC CTTCAATTATATTTAGTCAGGGG (174) | 5.90E-06 | 1.97 (+) |
| aly-miR831-5p | AGAAGAGGTAC AAGGAGATGAG A (2) | AAGTGCTACAAGAATGTATAGTCT TAGAGTCTCAAGAAGAGGTACAA GGAGATGAGAAGTGAATCACTGA AACAAGTGGTTCTGGTTTGTGGAT CAGTATGGTTTACCCAAAACACGT GTTTGGTGCTTCACTTCTAAACTCC TCGTACTCTTCTTGGGATTCTATGA CTTACACTTGTTGATTT (175) | 1.10E-05 | 1.88 (+) |
| aqc-miR159 | TTTGGACTGAA GGGAGCTCTA (3) | GGAGTCTTTCCAGCCCAAAACAGC TTCTTGATCTTCTTGAAAACTTCTG TTTGGACTGAAGGGAGCTCTAA (176) | 3.00E-03 | 1.51 (+) |
| ath-miR157a | TTGACAGAAGA TAGAGAGCAC (4) | GTGTTGACAGAAGATAGAGAGCA CAGATGATGAGATACAATTCGGAG CATGTTCTTTGCATCTTACTCCTTT GTGCTCTCTAGCCTTCTGTCATCAC C (177) | 1.00E-03 | 1.70 (+) |
| ath-miR159b | TTTGGATTGAAG GGAGCTCTT (5) | GGAAGAGCTCCTTGAAGTTCAATG GAGGGTTTAGCAGGGTGAAGTAA AGCTGCTAAGCTATGGATCCCATA AGCCTTATCAAATTCAATATAATT GATGATAAGGTTTTTTTTATGGAT GCCATATCTCAGGAGCTTTCACTT ACCCCTTTAATGGCTTCACTCTTCT TTGGATTGAAGGGAGCTCTTCATC TCTC (178) | 6.80E-03 | 1.63 (+) |
| ath-miR159c | TTTGGATTGAAG GGAGCTCCT (6) | GTGTAACAGAAGGAGCTCCCTTCC TCCAAAACGAAGAGGACAAGATT TGAGGAACTAAAATGCAGAATCTA AGAGTTCATGTCTTCCTCATAGAG AGTGCGCGGTGTTAAAAGCTTGAA GAAAGCACACTTTAAGGGGATTGC ACGACCTCTTAGATTCTCCCTCTTT CTCTACATATCATTCTCTTCTCTTC GTTTGGATTGAAGGGAGCTCCTTT TCTTCTTC (179) | 1.20E-03 | 1.65 (+) |
| ath-miRf10068-akr | CACCGGTGGAG GAGTGAGAG (7) | GGACTTCTCATCTTCTTTCTTAGCC GCCGGTGCTCCAGCTCCACCACCG TGTCCTCCAACATTACCGTGGCTT CCAGTTCCACCGGTGGAGGAGTGA GAGTGGGAAGTTT (11875) | 2.00E-08 | 2.09 (+) |
| ath-miRf10240-akr | ATCGAAGGAGA TGGAGGACG (8) | GATTTCTCGTCCTCCGGCAATCCTT CGAACTCATCTTCATCCCAGTAAT CGAAGGAGATGGAGGACGAAGGC TTC (11876) | 1.90E-05 | 1.90 (+) |
| ath-miRf10451-akr | AAGAAGGAGGA ACAACCTGTTG (9) | CTCTAGATCTCAACAGGTTTCCTC CTCCTTCTTTCTATTTAGCTACTTG GTTTCAATTGTTTCAAGCCTAGGT AAGCATATGTAAAAAAGAGACAA TTGAAACCAAGTAACTAAATAGAA AGAAGGAGGAACAACCTGTTGAG ATCTAGAG (11877) | 2.30E-07 | 2.19 (+) |

TABLE 1-continued

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
|---|---|---|---|---|
| ath-miRf10687-akr | TTAGCTGAAGAAGCAGAGGAG (10) | TTTGTTTGTTTAGCTGAAGAAGCAGAGGAGTCGGCATTGGGGCACAGTCACTCATCGATGCTGCAATGGGTAAGTCCTCTGCATACTTTTGCTGAGATAGGAATAGA (11878) | 3.70E-06 | 1.84 (+) |
| ath-miRf10701-akr | TGCAGTTCCTGGAGGTGGAGGA (11) | GGTGCCGCTGCAGTTCCTGGAGGTGGAGGAGGTGGTGGTGGGGCCACTGCAGCTCTTGGAGGTGGAGGCGGTGGAGGTGGAGCCGCTATAGTTGTTGGAAGTGGAGGAGGTGGCGGTGGTGGT (11879) | 1.30E-08 | 2.49 (+) |
| ath-miRf10751-akr | CTTGTGGAGAGGAAGCAAGA (12) | TTGTAATTTCTTGTGGAGAGGAAGCAAGAGGATGTGCTTGGTTGTGGAAATATAGGGCCCTTAAAATATATTCATCGTATTCACTCACATAACAAAAATTCCACAAGTAAGCACATCATCTTGCTTCCTCCACAAGAAATTACAA (11880) | 7.80E-08 | 2.10 (+) |
| ath-miRf10924-akr | TGAGGCGTATCAGGAGGTAGT (13) | TGAGGCGTATCAGGAGGTAGTGTTCTTGGTGGGACAATTTGTGTTGTATGTTTCA (11881) | 5.70E-04 | 1.73 (+) |
| ath-miRf11021-akr | GAGGTTTGCGATGAGAAAGAG (14) | GATGTTGGAGGTTTGCGATGAGAAAGAGATTGGCCGGAAGAATTATCAGCCATCAACATCGAGATTGTGAGATAATCGGAAGACCTGTAATTGTGAAGGTAACTCTTTCTCATCTGCAAATCTCAACTGTC (11882) | 1.80E-04 | 1.60 (+) |
| ath-miRf11037-akr | TCATCGGAGAAACAGAGGAGC (15) | TTGTCTCTGTTCATCGGAGAAACAGAGGAGCAAGACGTTTCAAACGGTTCTTGGCTCATAATTTGCTTCTCTGTTACCTTGGATGACAAGAAAGACAA (11883) | 1.30E-07 | 2.78 (+) |
| ath-miRf11042-akr | GGAAGAGGCAGTGCATGGGTA (16) | AGGGAGCCAGGGAAGAGGCAGTGCATGGGTAGAGACAAAACAGAGTCGTTTAATGTTTTAGTAAACTCAATCCATGCTCTGCTTGTTCCCTGTCTCTCT (11884) | 2.20E-03 | 1.56 (+) |
| ath-miRf11045-akr | TTTCTTGTGGAGGAAGCAAGAT (17) | TTGTAATTTCTTGTGGAGGAAGCAAGATGATGTGCTTACTTGTGGAATTTTTGTTATGTGAGTGAATACGATGAATATATTTTAAGGGCCCTATATTTCCACAACCAAGCACATCCTCTTGCTTCCTCTCCACAAGAAATTACAA (11885) | 8.60E-11 | 3.85 (+) |
| csi-miR3946 | TTGTAGAGAAAGAGAAGAGAGCAC (18) | ATAAAGATGATGATGACAATGAATTTTGTAGAGAAAGAGAAGAGAGCACAAACTTTTTGCTGAAAGTAGCTTTGATTCGATGTGTATCGGTTCATAGATAATGAGTTTTCAAGTCTATTTTAATAGAATACTAAAAGTTAGCTCTAAAAATC (180) | 1.80E-04 | 1.68 (+) |
| gma-miR156g | ACAGAAGATAGAGAGCACAG (19) | TGAACAATATCTTGAACAGTTTGTTGACAGAAGATAGAGAGCACAGGTGATCATACCCAAAAAAGCTTTTGTGTGTGAGCAGTTTTGTGCTCTCTACTTCTGTCAATGTACTTCTCA (181) | 2.00E-04 | 1.76 (+) |
| gma-miR157c | TGACAGAAGACTAGAGAGCAC (20) | TGACAGAAGACTAGAGAGCACAAAGGAGTGAGATGCCATTCCCTTTCATGCATTTCATCATCAGTGCTCTCTATCTTCTGTCAA (182) | 3.90E-04 | 1.58 (+) |
| gma-miR159a-3p | TTTGGATTGAAGGGAGCTCTA (21) | AATTAAAGGGGATTATGAAGTGGAGCTCCTTGAAGTCCAATTGAGGATCTTACTGGGTGAATTGAGCTGCT | 8.40E-03 | 1.59 (+) |

TABLE 1-continued

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
|---|---|---|---|---|
| | | TAGCTATGGATCCCACAGTTCTAC CCATCAATAAGTGCTTTTGTGGTA GTCTTGTGGCTTCCATATTTGGGG AGCTTCATTTGCCTTTATAGTATTA ACCTTCTTTGGATTGAAGGGAGCT CTACACCCTTCTCTTCTTTTCT (183) | | |
| iba-miR157 | TTGACAGAAGA TAGAGAGCAT (22) | TTGACAGAAGATAGAGAGCATGCT AGAAATTACATTGATAAGCTATGT GGTTCAGAGACCAATCTTCTTATG AGTTCCAATAAGGAGTTGGTTTGT CCCCCCACTGGTATTATGTCTTCA GGTTGACCCTTCACCATGAGAATC ATATGTAATTCTCCGGCGGCGCTC ATTGTGACCTGCCAATCGCCTCCG GCAACTCCTCTTAGCTTCATCAAA CTGGGCTAATTCATGAAACCTGCT GCATTGCTGACAGAAGCGCTGTTG AACTCCATTTATAAGTACT (184) | 6.40E-04 | 1.60 (+) |
| mdm-miR482a-5p | GGAATGGGCTG TTTGGGAACA (23) | GAGAAGAGGGAAAGGGAGATTGG AGCTGCTGGAAGTTTTAGGAATGG GCTGTTTGGGAACAAGGAAATTAC CACAATAATTGTCTTGTGGGGTTT CTTCCCAAGCCCGCCCATTCCTAT GATTTCCAGCTGTTCCTCCCTTTCC CTTGTCTC (185) | 1.50E-04 | 1.62 (+) |
| mtr-miR2119 | TCAAAGGGAGG TGTGGAGTAG (24) | TTTATTTTTTTTACACTAAGATACT CCCTACTTTCCTTTGATTGGAAATA AAGAGAGACAAAAAGGTAAATTT AATTTCTCTTCTTATGTCAATCAAA GGGAGGTGTGGAGTAGGGTGTAA AAAGTAAA (186) | 2.20E-07 | 2.64 (+) |
| osa-miR159e | ATTGGATTGAA GGGAGCTCCT (25) | GATGAAGAAGAAGAGCTCCCTTTC GATCCAATTCAGGAGAGGAAGTG GTAGGATGCAGCTGCCGGTTCATG GATACCTCTGGAGTGCAGGGCAAA TAGTCCTACCCTTTCATGGGTTTGC ATGACTCGGGAGATGAACCCGCCA TTGTCTTCCTCTATTGATTGGATTG AAGGGAGCTCCTCTAGCTACAT (187) | 1.40E-03 | 1.67 (+) |
| osa-miR159f | CTTGGATTGAA GGGAGCTCTA (26) | GAAGAAGAAGACGAGCTCCCTTC GATCCAATCCAGGAGAGGAAGTG GTAGGATGCAGCTGCCGGTTCATG GATACCTCTGCAGTGCATGTCGTA GGCTTGCACTTGCATGGGTTTGCA TGACCCGGGAGATGAACCCACCAT TGTCTTCCTCTTATGCTTGGATTGA AGGGAGCTCTACACCTCTCTC (188) | 5.10E-03 | 1.75 (+) |
| osa-miR1858a | GAGAGGAGGAC GGAGTGGGGC (27) | TCCCGTCATCGCTGCCGGCAAAGG GAGGGGGGTGCCGCAACAAGGA GAGGAGGACGGAGTGGGGCGAGT GGAGCGTCAAAGGGGATGTCATC GCCGCCGAATCTGCTCGTGGGACA TCCCCTTCGATGCTCCACTCGCCCC AATCCGTCCTCCTCTCCTTGTTGCG GCACCCCCTTCGCTGGCAGCGAC GACGGCCTC (189) | 3.90E-04 | 1.63 (+) |
| osa-miR1874-3p | TATGGATGGAG GTGTAACCCGA TG (28) | CCATAATCATCTATTAGTACAGTG GTGAAGACATAGGGCTACTACACC ATCCATAAGGGTTCGAATCTTCGA TGTGCCTAGATAGGGTACAGTTGG ATCCCATATGGATGGAGGTGTAAC CCGATGCCTTTTACAAATAGATGG TTATTTT (190) | 7.80E-10 | 4.36 (+) |

TABLE 1-continued

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
|---|---|---|---|---|
| osa-miR1879 | GTGTTTGGTTTA GGGATGAGGTG G (29) | TCCAACCCATCCCACCTCGTCCCC AAACCAAACACATGCACGCAAAT GGCTTGTTGAGGAATAAACATCTT GCTCCCTTGCATTCTAAACTATGA TATTCTTCAAGCATATGTGTTTGGT TTAGGGATGAGGTGGGATGGGTTA GGTCCA (191 (ATCCAACCCATCCCA CCTCGTCCCCAAACCAAACACATG CACGCAAATGGCTTGTTGAGGAAT AAACATCTTGCTCCCTTGCATTCTA AACTATGATATTCTTCAAGCATAT GTGTTTGGTTTAGGGATGAGGTGG GATGGGTTAGGTCCA (201) | 5.50E-06 | 1.91 (+) |
| osa-miRf10839-akr | CCTGTGACGTTG GTGAAGGTG (30) | CTGCGAGCCTCCAGCAGCGGCACA GGAGGAGGCCATTGCAGCTGTCAA GGACGTTGAGAAACTCGCACTTGG GCAGGAAGGGGAGCGAGGGGTCA ACAAACGGGCGGCCTTCCCCTGTG ACGTTGGTGAAGGTGTCGGAG (11886) | 1.90E-11 | 7.36 (+) |
| osa-miRf11013-akr | GGTTTGCCGGA GTTGGAGGAGA (31) | CCAGCCATCCCTCTAGAGCCGGCG AACTCCTCCCCTCCCCCCTCCCCCT TCCACTCCCACCCCACCCCACCCC GGGACCCTAACCCGTAGGGTCCTC GCCGGCGCCAGAGAAGAAGAGGT TTGCCGGAGTTGGAGGAGATGACA TGG (11887) | 7.70E-07 | 2.11 (+) |
| osa-miRf11352-akr | AGGGATTTTGG AAGGAGGTGAC A (32) | TATAATATAAGGGATTTTGGAAGG AGGTGACATATTCTAGGACTATGT ATCTGGATCCAGAGATACTAGGAT GTGTTACCTCCCTCTAAAATCCCTT ATATTATG (11888) | 1.20E-06 | 1.64 (+) |
| osa-miRf11355-akr | GGTGGAGGTGG AGCTGTGCCAA A (33) | GGTGGAGGTGGAGGTGGAGCTGT GCCAAATAGGCCCTGAGTTGTATG CACCACCAGTTCAACCCAATAGCT TAAGGGTCTGCTTGGCACAGCTCC AGCTCCACGCAGCC (11889) | 7.60E-09 | 2.57 (+) |
| osa-miRf11595-akr | CATCGGTGTTGG AGGTGGC (34) | CATCGGTGTTGGAGGTGGCGGGGA CGAGGTGCTTCTCTAGAGCGGTGC CACTACTGCCACCACCGTGGAATT GACGAGGCACAATGCCCACCTCAC CCTCCGCTGCCACTCTGCTGCCAC CGATG (11890) | 2.70E-06 | 2.10 (+) |
| osa-miRf11649-akr | AAACCGTGCAA AGGAGGTCCC (35) | TTACTTAAACCGTGCAAAGGAGGT CCCATGGCAGTATTTGCACCCGTT TTTACTAACGTGGCATCCTGTTGT ACGGTTTTTTTTGACGCAAATACT GCCATGGGACCTCTTTTGCATGGT TTGAGTAA (11891) | 1.50E-09 | 4.07 (+) |
| osa-miRf11829-akr | ACGCGGAGGAG GTGGTGTTCT (36) | GCACGCGGAGGAGGTGGTGTTCTC GCCGGAGTACGAGGAGTTCGCCGT CAGGAACGCCGCCCTCTGCGTCC (11892) | 2.80E-04 | 1.51 (+) |
| ppt-miR895 | GTAGCTTAGCG AGGTGTTGGTA (37) | GATTCATGTAATTATTGTTAACCTC TTTGTGTTCCGAGCTTTTATGATTG GTAGCTTAGCGAGGTGTTGGTATG ATACCAATCCCTGGTTTGCTTGTTC CTAATTGAGTTATGCTTGCACTCA AATCTAGGGGAGCGGTATTTTGGC TCACTCGCAATGCTTTCATGTACC CTTCCCGCATTATGAGTGCCACTT GGCTCCATGGTGTGATATATAAGT TTC (192) | 6.90E-13 | 12.97 (+) |
| psi-miR159 | CTTGGATTGAA GGGAGCTTCCA (38) | TGGAGCTCCCTTCAGTCCAACCAA AGCTTGTGCGGCGGTGGTTCAGCT | 9.90E-04 | 1.60 (+) |

TABLE 1-continued

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
|---|---|---|---|---|
| | | GCTGATTCATGCATTCGACTGCCC TGTCCGTGACTTTCCAGCAGCCTG AATCAATCAATCTATCTCCATGAC AGGATAGTGGTGTGCATGACGCAG GAGATGTATTGTCACTGGACACGC ATTCCTTGGATTGAAGGGAGCTCC A (193) | | |
| pta-miR156a | CAGAAGATAGA GAGCACATC (39) | GATGACGAAGATAGAGAGCACA TCCGCTCACATGCCGGGACTCTGC GTTTGAGGTGTATGTGGTCTCCAT GATTCTGTCATC (194) | 3.50E-04 | 1.58 (+) |
| pta-miR156b | CAGAAGATAGA GAGCACAAC (40) | GATGACAGAAGATAGAGAGCACA ACCGCTCAGATGCCGGCACTCTGC GTTTGAGGTGTATGTGCTCTCGTT GATTTTGTCATC (195) | 1.80E-04 | 1.65 (+) |
| ptc-miRf10148-akr | TGGTGCACCTG GTGGTGGAG (41) | CTAGTTCCGGAGCCCGGTGAACTT TATCACCACTTCCTGCTCCTCTTGG CAAGCTTCCAGGTGGAGGAGGTG GACGAGGTGGTCCACCAGGTGGA GGAGGTGGTGGTGGTGCACCT GGTGGTGGAGGTGG (11893) | 7.40E-06 | 2.02 (+) |
| ptc-miRf10226-akr | TCCTTTGGGGAG ATGGAGAGCTT (42) | ATGGTTGGAGAAGCTTCCGATCTC CCTCAAAGGCTTCCTCTATAATTG CCTTACATGATGGCATTAGTGGAC TCCTTTGGGGAGATGGAGAGCTTA CTCCCCAT (11894) | 1.70E-06 | 1.88 (+) |
| ptc-miRf10271-akr | TTGGATTGAAG GGAGCTCTAA (43) | GGGAGTGGAGCTCCTTGAAGTCCA ATAGAGGTTCTTGCTGGGTAGATT AAGCTGCTAAGCTATGGATCCACA GTCCTATCTATCAACCGAAGGATA GGTTTGCGGCTTGCATATCTCAGG AGCTTTATTGCCTAATGTTAGATC CCTTTTTGGATTGAAGGGAGCTCT AAACCC (11895) | 6.60E-03 | 1.65 (+) |
| ptc-miRf10300-akr | TTTGGAAAGCA AGTGAGGTG (44) | TATACATATATCTCACTTGCTTTCT CAACTATCTCACTTTTCTTTTCAGA TTTCAAAAAAACGACATCATGAGA CAGTTTGGAAAGCAAGTGAGGTGT GTGTATA (11896) | 2.70E-06 | 2.38 (+) |
| ptc-miRf10522-akr | TTGGGGAGCTG GACTCTGGA (45) | TGACGGATTCGGAGAACAGCTGTC GGTGTTGATGGTGGCTGTGGGCAG AGGACATTTCAGAATTTGGGGAGC TGGACTCTGGAGCAGTGG (11897) | 1.20E-04 | 3.58 (+) |
| ptc-miRf10619-akr | GTTGGGCTTGCT GCTGGAGGA (46) | TCTGCTTCGGGTGGCAGGTCTGGC GGTTGTAGAGGGGGCAGCGACGTT GATGATCTTCGCTCCTGTTGGTTGC CGTGGCGGTTGGGCTTGCTGCTGG AGGAAGA (11898) | 8.80E-07 | 2.47 (+) |
| ptc-miRf10985-akr | CAGAAGATAGA GAGCACTGA (47) | GTTGACAGAAGATAGAGAGCACT GACGATGAAATGCATGGAGCTTAA TTGCATCTCACTCCTTTGTGCTCTC TAGTCTTCTGTCATC (11899) | 3.20E-04 | 1.70 (+) |
| ptc-miRf11757-akr | CTTGGTGAATG GTTGGGAGGAA T (48) | TGGGACAGCTTGGTGAATGGTTGG GAGGAATGTCTTTAATGTGGTTAT GCATCAGTGAAACTCTAGTAAGAT TCTCTGTCCACTCCTCTGCATCCGG CACTTCTCTTAACCGTGCACCTGCT TTAACCA (11900) | 3.70E-07 | 1.84 (+) |
| ptc-miRf11844-akr | CCCAACTTGGA GGTGGGTGTGG (49) | GCGTCCAGACCCAACTTGGAGGTG GGTGTGGACGCGTCCAACCCCAAG TTGGGCGTGGATGCGTCCAGGCCT AATTTCGAGTTGGGCGTAGACGC (11901) | 8.30E-04 | 1.73 (+) |

TABLE 1-continued

Differentially Expressed (Up-regulated) Small RNAs in Soybean Plants Growing under Drought (5 days) versus Optimal Conditions.

| miR Name | Mature Sequence (SEQ ID NO) | Stem Loop Sequence (SEQ ID NO) | p-value | Fold-Change |
| --- | --- | --- | --- | --- |
| ptc-miRf11847-akr | GAAAGTGTGGA GAAGGTTGCC (50) | ACTTTTCTACGAAAGTGTGGAGAA GGTTGCCCCTAAAAAATCTTTTAT GGCGACTTTCTCGACATTTTGGTA GAAAAGT (11902) | 4.30E-07 | 2.28 (+) |
| ptc-miRf11855-akr | GGCAGAGCATG GATGGAGCTA (51) | CGGGGAACAGGCAGAGCATGGAT GGAGCTACTAACAGAAGTACTTGT TTTGGCTCTACCCATGCACTGCCTC TTCCCTG (11903) | 5.90E-05 | 3.96 (+) |
| sbi-miR159a | TTTGGATTGAAG GGAGCTCTG (52) | AGCGAAGCTCCTATCATTCCAATG AAGGGCCCTTTTCATGGGTGGTTC CGCTGCTCGTTCATGGTTCCCACT ATCCTATCTCATCATGTATGTGTGT ATGTACTCTAGAGGGCCCGAGAAG AGATTCATGTGGTCGTCAGTCTTT GAGATAGGCTTGTGGTTTGCATGA CCGAGGAGCTGCACCGTCCCCTTG CTGGCCGCTCTTTGGATTGAAGGG AGCTCTGCA (196) | 1.20E-02 | 1.59 (+) |
| smo-miR1103-3p | TGGAAAAAGGA GGTGCATTCTTG T (53) | GCCCATGAACAAGAGTGCACCCCC TTTCCAATCGGTTAAAGGTCTTAG GATAGTTGGAGTTTAAGCGTCCTT GGGTTTGAATAGTACTGGGCTGGG TGACCTCCCGGGAAGTCCAAATTC AGGAGCTTACATTAACCCCAAGTA TTCCAAAACGCTTAATCGATTGGA AAAAGGAGGTGCATTCTTGTTCAT AGGCCC (197) | 7.50E-10 | 3.98 (+) |
| smo-miR156b | CTGACAGAAGA TAGAGAGCAC (54) | TGGACTGCTGCTGACAGAAGATAG AGAGCACAGACGTTTGGCTGCAAG AGCGGAATCCATATCCAGCAGCTC TGCGTTCGTGCTCTCTATTCTTCTG TCATCAATCTTTCGA (198) | 2.50E-04 | 1.62 (+) |
| tae-miR2003 | CGGTTGGGCTGT ATGATGGCGA (55) | CATTCGGATTCGCCATCATACGTC CAACCGTGCATTTGATATGCATAT ATATGCATCACGAGCAACGGTTGG GCTGTATGATGGCGATACCGATTG (199) | 7.90E-05 | 2.99 (+) |
| zma-miR482-5p | TGGGAGATGAA GGAGCCTTT (11874) | AGTGGGAGATGAAGGAGCCTTGC ATCGATGTCACCGCCGGAGGAGCG CTCGCCTTCTTCGCGCACCGCCGC AATAGCCGCCCTCGGACCCCTCGC CTCGCTCTTCCTTGTTCCTCCCATT TT (11904) | 7.80E-06 | 2.19 (+) |

* NA = not available

TABLE 2

Differentially Expressed (Down-regulated) Small RNAs in Soybean Plants Growing under Drought (5 days) versus Optimal Conditions.

| miR Name | Mature Sequence (SEQ ID NO:) | Stem Loop Sequence (SEQ ID NO:) | p-Value | Fold-Change |
| --- | --- | --- | --- | --- |
| aly-miR396a-3p | GTTCAATAAAGCT GTGGGAAG (57) | TCTACGTGACCCTCTCTGTATTCTTCCACA GCTTTCTTGAACTGCAAAACTTCTTCAGAT TTGTTTTTTTTATATATATGTCTTACGCAT AAAATAGTGTTTTTGTTCACATCTCTGCTC GATTGATTTGCGGTTCAATAAAGCTGTGG GAAGATACGGACAGAGTCAAAGA (202) | 7.20E-08 | 2.93 (−) |
| aly-miR396b-3p | GCTCAAGAAAGCT GTGGGAAA (58) | GAAGAAGAAGAAGAAGATCCTGGTCATA TTTTTCCACAGCTTTCTTGAACTTTCTTTTT CATTTCCATTGTTTTTTTTTTTCTAAACCAA | 2.10E-08 | 4.25 (−) |

TABLE 2-continued

Differentially Expressed (Down-regulated) Small RNAs in Soybean Plants Growing under Drought (5 days) versus Optimal Conditions.

| miR Name | Mature Sequence (SEQ ID NO:) | Stem Loop Sequence (SEQ ID NO:) | p-Value | Fold-Change |
|---|---|---|---|---|
| | | AAAAAAAGATCTCTAAAATTTAGCATTTT GGAAACAAAGAAGAAGCTCAAGAAAGCT GTGGGAAAACATGACAATTCAGGGTTTTA CTCCATTGATTC (203) | | |
| bdi-miR2508 | ATTGAGTGCAGCG TTGATGAAC (59) | GCAAAGGCATCATTGAGTGCAGCGTTGAT GAACAGGGGCCAGGCGACCGGCGGCCGG TCCGGTTCGGTTCACCGGCGCTGCACACA GTGACGCCCTTGC (204) | 1.60E-02 | 1.73 (−) |
| ctr-miR171 | TTGAGCCGCGTCA ATATCTCC (60) | ATCGACGGTTGAAGGGGAGAGTTGTAAAA TGAAATCATCAAGGTATTGGCGCGCCTCA ATTTAAAGACGTGGTTAAATGGGCATGAT TAGCCATGTATTTTCATTGAGCCGCGTCAA TATCTCCTTAATTATTTTGTAACTCTCTCCT CTATATCCTCGCCTTCGGTATGCAGCTGCT CCTCGATACATATGAGGATTCAGAAACAG ACAAAGGCGGTAGAAGTAATCTTCATCAA TATTATTGAAGCAGGAAACATAACGGCAA GTTTTAAGACCCGTTTGGGGCATGTGGGG TCTCATTTTGATGTTAATGAAGTGAAAACT TGTATTTTCCCTCAAACATTCACTCACTCC AGGCCGGCAGGAACAAC (205) | 7.00E-04 | 1.90 (−) |
| gma-miR1507a | TCTCATTCCATACA TCGTCTGA (61) | CAGTGTTTGGCAGAGGTGTATGGAGTGAG AGAAGGGAAAGGGTATTTTCCGATTCTGT CGTTACTCTCTTCCCTCTCTCATTCCATAC ATCGTCTGACGAACGTATC (206) | 3.20E-03 | 1.61 (−) |
| gma-miR159d | AGCTGCTTAGCTAT GGATCCC (62) | GGGTGAATTGAGCTGCTTAGCTATGGATC CCACAGTTCTACCCATCAATAAGTGCTTTT GTGGTAGTCTTGTGGCTTCCATATCTGGGG AGCTTCATTTGCCT (207) | 7.30E-07 | 2.63 (−) |
| gma-miR396d | AAGAAAGCTGTGG GAGAATATGGC (63) | GGTCATGCTTTTCCACAGCTTTCTTGAACT TCTTATGCATCTTATATCTCTCCACTTCCA GCATTTTAAGCCCTAGAAGCTCAAGAAAG CTGTGGGAGAATATGGCAA (208) | 8.90E-06 | 2.12 (−) |
| gma-miR4371b | AAGTGATGACGTG GTAGACGGAGT (64) | TTGTTAGTTGCCTTTCGTTAAGTGATGACG TGGTAGACGGAGTGCCGTGTCATTATGCC TTGTCACAGACACCTCATTGCTACATCATC ACCGCTAATGATATGGCACTGACGTGTTA GTGATTGGTGTGATGACGTGACACTCTAT CTGCCACATCATCACCTAACGAAGACAA CTAACGA (209) | 2.10E-03 | 1.86 (−) |
| gma-miR4376-5p | TACGCAGGAGAGA TGACGCTGT (65) | AAGGTTTGCTACGCAGGAGAGATGACGCT GTCCCTTGCACCCATCCTAGCTTCCCTTGA GTAGGTAAGAGCAAGGCCAGCCAGCATC ATATCTCCTGCATAGTAAACCTT (210) | 6.10E-05 | 2.57 (−) |
| gma-miR4416a | ACGGGTCGCTCTCA CCTAGG (66) | CTTTGATCTGGGTGAGAGAAACGCGTATC GATGGATTGGGTTCAGTTCTGGTCTCACA CGGTTTGTTCTAACAATTTGTACTGACTGT GTTTTGATCGATACGGGTCGCTCTCACCTA GGCCAGAGTTGC (211 | 1.40E-03 | 3.07 (−) |
| gma-miR482a-3p | TCTTCCCAATTCCG CCCATTCCTA (67 | TCAGAATTTGTGGGAATGGGCTGATTGGG AAGCAATGTGTGCTGGTGCAATGCATTTA ATTTCTTCCCAATTCCGCCCATTCCTATGA TTTCTGA (212) | 1.30E-05 | 2.05 (−) |
| gma-miR482b-5p | TATGGGGGATTG GGAAGGAAT (68) | GGTATGGGGGATTGGGAAGGAATATCCA TAAGCAAAATATGCTATTTCTTCCCTACAC CTCCCATACC (213) | 3.20E-08 | 1.71 (−) |
| gso-miR169g* | TCGGCAAGTTGGC CTTGGCT (69) | AGCCAAGGAUGACUUGCCGGCAUUAGCC AAGUGAAUGAGCAUCAUAUAUAUAUA UAUAUAUAUGACUCAUGUUCUUGUCG GCAAGUUGGCCUUGGCU (11905) | 1.20E-05 | 2.46 (−) |

TABLE 2-continued

Differentially Expressed (Down-regulated) Small RNAs in Soybean Plants Growing under Drought (5 days) versus Optimal Conditions.

| miR Name | Mature Sequence (SEQ ID NO:) | Stem Loop Sequence (SEQ ID NO:) | p-Value | Fold-Change |
| --- | --- | --- | --- | --- |
| gso-miR482a | TCTTCCCTACACCT CCCATAC (70 | GGGGAAGGCATGGGTATGGGGGGATTGG GAAGGAATATCCATAAGCAAAATATGCTA TTTCTTCCCTACACCTCCCATACCACTGTT TTTCCT (214) | 1.60E-02 | 1.74 (-) |
| osa-miRf11996-akr | GTCTTATAACCTGA AACGGGGG (71) | TACTACCTCCATTTCAGGTTATAAGACTTT CTAGTGTTGCTCACATTCATATATATGTTA ATAAATTCATTAACATATAGAAAGTCTTA TAACCTGAAACGGGGGAAGTA (11906) | 2.10E-02 | 1.84 (-) |
| ppt-miR166m | TCGGACCAGGCAT CATTCCTT (72) | GCCGAGAACAGAGATTGTGTAGCTCAGCT GTAAGGAATGTGGCATGGCTCGATGCTGT TTGAGCATGTCAAGTTCAGCCTCGGACCA GGCATCATTCCTTTCATCTCAGTTACACAT TTGACATCCAGGA (215) | 2.20E-05 | 1.77 (-) |
| pta-miR166c | CCGGACCAGGCTT CATCCCAG (73) | ACCAATCGAATCCGGACCAGGCTTCATCC CAGGCATCTGGACCCAATCGACAGCAGCT CCTTTAGCCTTTGAAAGGAACTCTGTCAA GGTCTCCTCTGCTATAGACAGGAGTCCAG CGGGGCTAGCATCTCTTGGGGGATGCTGA GGTGTTGGATTATGTTGGT (216) | 8.30E-04 | 1.59 (-) |
| ptc-miR166p ptc- | TCGGACCAGGCTC CATTCCTT (74) | TAAGGTTGAGAGGAACGCTGTCTGGGTCG AGGTCATGGAGGCCATGATTATACATAAA TGGCATTATCTGATGACAGCCCAGATAAT CGATGCACCTGTCTTGAACCTAAATGATT CTCGGACCAGGCTCCATTCCTTCCAACCAT (217) | 4.70E-05 | 1.77 (-) |
| miRf11079-akr | AAGATGGAGAAGC AGGGCACGTGC (75) | GTGTGTGAGCAAGATGGAGAAGCAGGGC ACGTGCACTACTAACTCATGCACACAGAG AGGGAGACGCATTTCTTGCTGGAGTTACG AGTTACGACTCTTACCTACTATTGATTTTG TTAGCTCCAGTGAGTTAGTTATTCATGTGC CTGTCTTCCTCATCATGATCACTAC (11907) | 6.10E-04 | 1.56 (-) |
| ptc-miRf11396-akr | CAAGGCTCTGATA CCATGTCAA (76) | CTTGGTCATCAAGGCTCTGATACCATGTC AAAGAATACATATTTTGAGACCTTATCTAA CAGCTTAAGCTATTGGGTTGAGATGGTTC CTTGACATGATATCAGAGCCTTGATGACG AAG (11908) | 1.70E-05 | 1.81 (-) |
| ptc-miRf11669-akr | CAAGGCTCTGATA CCATGTT (77) | GCTTGGTCATCAAGGCTCTGATACCATGTT AAAGAACCATCTCAACCTAATACCATGTT AGAGAATAATATAAATCATATCTAGAGAC TTTACCTAACAGCTTAAGCTATTGGCCTAT TGGATTAGTATGGTTCTTTGACATGGTATC AGAGCCTTGATAACCAAGT (11909) | 2.30E-04 | 1.63 (-) |
| vvi-miR394b | TTGGCATTCTGTCC ACCTCC (78) | ACAGAGTTTATTGGCATTCTGTCCACCTCC CATCTCTTGAAAATCTCTCTTTTCTCTCTG TGGAGGTGGGCATACTGCCAACCAAGCTC TGTT (218) | 6.70E-03 | 1.55 (-) |
| zma-miR396b-3p | GTTCAATAAAGCT GTGGGAAA (79) | AGATGGCCTTCTTTGTGATCTTCCACAGCT TTCTTGAACTGCATCTCTCAGAGGAGCGG CAGCTTCAACTCCTCCACCCGCATCAGCA GGTGCATGCAGTTCAATAAAGCTGTGGGA AACTGCAGAGAGAGGCCAG (219) | 2.10E-08 | 4.76 (-) |

TABLE 3

Differentially Expressed (Up-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| ppt-miR895 | GTAGCTTAGC GAGGTGTTGG TA (80) | GATTCATGTAATTATTGTTAACCTCTTTGTG TTCCGAGCTTTTATGATTGGTAGCTTAGCGA GGTGTTGGTATGATACCAATCCCTGGTTTGC TTGTTCCTAATTGAGTTATGCTTGCACTCAA ATCTAGGGGAGCGGTATTTTGGCTCACTCG CAATGCTTTCATGTACCCTTCCCGCATTATG AGTGCCACTTGGCTCCATGGTGTGATATAT AAGTTTC (220) | 7.20E-10 | 9.36 (+) |
| ptc-miRf10300-akr | TTTGGAAAGC AAGTGAGGTG (81) | TATACATATATCTCACTTGCTTTCTCAACTA TCTCACTTTTCTTTTCAGATTTCAAAAAAAC GACATCATGAGACAGTTTGGAAAGCAAGTG AGGTGTGTGTATA (11910) | 1.40E-07 | 6.02 (+) |
| osa-miRf10839-akr | CCTGTGACGTT GGTGAAGGTG (82) | CTGCGAGCCTCCAGCAGCGGCACAGGAGGA GGCCATTGCAGCTGTCAAGGACGTTGAGAA ACTCGCACTTGGGCAGGAAGGGGAGCGAG GGGTCAACAAACGGGCGGCCTTCCCCTGTG ACGTTGGTGAAGGTGTCGGAG (11911) | 6.20E-09 | 5.21 (+) |
| smo-miR1103-3p | TGGAAAAAGG AGGTGCATTCT TGT (83) | GCCCATGAACAAGAGTGCACCCCCTTTCCA ATCGGTTAAAGGTCTTAGGATAGTTGGAGT TTAAGCGTCCTTGGGTTTGAATAGTACTGG GCTGGGTGACCTCCCGGGAAGTCCAAATTC AGGAGCTTACATTAACCCCAAGTATTCCAA AACGCTTAATCGATTGGAAAAAGGAGGTGC ATTCTTGTTCATAGGCCC (221) | 6.50E-08 | 5.20 (+) |
| osa-miRf11649-akr | AAACCGTGCA AAGGAGGTCC C (84) | TTACTTAAACCGTGCAAAGGAGGTCCCATG GCAGTATTTGCACCCGTTTTTACTAACGTGG CATCCTGTTGTACGGTTTTTTTTGACGCAAA TACTGCCATGGGACCTCTTTTGCATGGTTTG AGTAA (11912) | 9.70E-08 | 5.10 (+) |
| osa-miR1874-3p | TATGGATGGA GGTGTAACCC GATG (85) | CCATAATCATCTATTAGTACAGTGGTGAAG ACATAGGGCTACTACACCATCCATAAGGGT TCGAATCTTCGATGTGCCTAGATAGGGTAC AGTTGGATCCCATATGGATGGAGGTGTAAC CCGATGCCTTTTACAAATAGATGGTTATTTT (222) | 6.50E-09 | 4.75 (+) |
| ptc-miRf10619-akr | GTTGGGCTTGC TGCTGGAGGA (86) | TCTGCTTCGGGTGGCAGGTCTGGCGGTTGT AGAGGGGGCAGCGACGTTGATGATCTTCGC TCCTGTTGGTTGCCGTGGCGGTTGGGCTTGC TGCTGGAGGAAGA (11913) | 2.00E-08 | 3.70 (+) |
| osa-miRf10362-akr | GCTGGAGGAT GCGACGGTGC T (87) | GCCGGCTAGTACAATCGAATCCACTAGCAC CGAGGCTTGGGTCACTAGATCCCGTGGCCC TAGCCTAATTGCTGGAGGATGCGACGGTGC TTGTGAGC (11914) | 7.50E-08 | 3.48 (+) |
| ahy-miR3514-5p | AGGATTCTGT ATTAACGGTG GA (88) | ACAATAGAAGGATTCTGTATTAACGGTGGA CATGATTTATCTCGTTTTTAAAGATATCTTT GCATTTCATATGAGATTTAAAGTTTTTATTG GTAATATAAATCTCACATGAAATTTAAATTT ATATTTTAAAGTTAAGATAAAGTCATGTCA CCGTTAATACAGAATCCTTCAATTATATTTA GTCAGGGG (223) | 2.40E-08 | 3.43 (+) |
| mtr-miR2119 | TCAAAGGGAG GTGTGGAGTA G (89) | TTTATTTTTTTTACACTAAGATACTCCCTAC TTTCCTTTGATTGGAAATAAAGAGAGACAA AAAGGTAAATTTAATTTCTCTTCTTATGTCA ATCAAAGGGAGGTGTGGAGTAGGGTGTAA AAAGTAAA (224) | 2.00E-07 | 2.89 (+) |
| osa-miRf11355-akr | GGTGGAGGTG GAGCTGTGCC AAA (90) | GGTGGAGGTGGAGGTGGAGCTGTGCCAAAT AGGCCCTGAGTTGTATGCACCACCAGTTCA ACCCAATAGCTTAAGGGTCTGCTTGGCACA GCTCCAGCTCCACGCAGCC (11915) | 2.40E-07 | 2.85 (+) |

TABLE 3-continued

Differentially Expressed (Up-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| osa-miRf11595-akr | CATCGGTGTTGGAGGTGGC (91) | CATCGGTGTTGGAGGTGGCGGGGACGAGGT GCTTCTCTAGAGCGGTGCCACTACTGCCAC CACCGTGGAATTGACGAGGCACAATGCCCA CCTCACCCTCCGCTGCCACTCTGCTGCCACC GATG (11916) | 8.90E-06 | 2.77 (+) |
| ptc-miRf11844-akr | CCCAACTTGG AGGTGGGTGT GG (92) | GCGTCCAGACCCAACTTGGAGGTGGGTGTG GACGCGTCCAACCCCAAGTTGGGCGTGGAT GCGTCCAGGCCTAATTTCGAGTTGGGCGTA GACGC (11916) | 1.20E-05 | 2.75 (+) |
| ptc-miRf11847-akr | GAAAGTGTGG AGAAGGTTGC C (93) | ACTTTTCTACGAAAGTGTGGAGAAGGTTGC CCCTAAAAAATCTTTTATGGCGACTTTCTCG ACATTTTGGTAGAAAAGT (11917) | 2.50E-06 | 2.70 (+) |
| ath-miRf11045-akr | TTTCTTGTGGA GGAAGCAAGA T (94) | TTGTAATTTCTTGTGGAGGAAGCAAGATGA TGTGCTTACTTGTGGAATTTTTGTTATGTGA GTGAATACGATGAATATATTTTAAGGGCCC TATATTTCCACAACCAAGCACATCCTCTTGC TTCCTCTCCACAAGAAATTACAA (11918) | 4.40E-07 | 2.59 (+) |
| ath-miRf10702-akr | GTGGGAGGAC TCCAAGTGTG (95) | AAACATGTGGGAGGACTCCAAGTGTGGTTA TATCCTCGGTATTATCTCGATGTGAACCACA CTTGGAGTCCTCCCACATGTTT (11919) | 8.90E-07 | 2.51 (+) |
| ath-miRf10701-akr | TGCAGTTCCTG GAGGTGGAGG A (96) | GGTGCCGCTGCAGTTCCTGGAGGTGGAGGA GGTGGTGGTGGGGCCACTGCAGCTCTTGGA GGTGGAGGCGGTGGAGGTGGAGCCGCTATA GTTGTTGGAAGTGGAGGAGGTGGCGGTGGT GGT (11920) | 1.40E-06 | 2.40 (+) |
| osa-miR1869 | TGAGAACAAT AGGCATGGGA GGTA (97) | AAGGAACACCTGAGAACAATAGGCATGGG AGGTATTGGGAAAACACAGGAACATATTGT GACCCCTAATTTTAAAGGGAAATAATGGTT GAGGCTTTCCTCCATGTTCCCATGCCTAATG CTCTTAGGTGCTCTTTTT (225) | 2.20E-05 | 2.27 (+) |
| ptc-miRf10148-akr | TGGTGCACCT GGTGGTGGAG (98) | CTAGTTCCGGAGCCCGGTGAACTTTATCAC CACTTCCTGCTCCTCTTGGCAAGCTTCCAGG TGGAGGAGGTGGACGAGGTGGTCCACCAG GTGGAGGAGGTGGTGGTGGTGGTGCACCTG GTGGTGGAGGTGG (11921) | 2.80E-05 | 2.22 (+) |
| osa-miR1879 | GTGTTTGGTTT AGGGATGAGG TGG (99) | TCCAACCCATCCCACCTCGTCCCCAAACCA AACACATGCACGCAAATGGCTTGTTGAGGA ATAAACATCTTGCTCCCTTGCATTCTAAACT ATGATATTCTTCAAGCATATGTGTTTGGTTT AGGGATGAGGTGGGATGGGTTAGGTCCA (226) ATCCAACCCATCCCACCTCGTCCCCAAAC CAAACACATGCACGCAAATGGCTTGTTGAG GAATAAACATCTTGCTCCCTTGCATTCTAAA CTATGATATTCTTCAAGCATATGTGTTTGGT TTAGGGATGAGGTGGGATGGGTTAGGTCCA (235) | 5.80E-05 | 2.21 (+) |
| ath-miRf10148-akr | GGTGGTGGAA AGATCAAGAT (100) | TAGGGAATATCTTGATCTTTCCACCATCTAC AAAGAATAAAAAAAAGCTTCCAATATTAC TAGGTATTTGGTGGTGGAAAGATCAAGATA TTCCTTA (11922) | 4.90E-06 | 2.21 (+) |
| osa-miRf11013-akr | GGTTTGCCGG AGTTGGAGGA GA (101) | CCAGCCATCCCTCTAGAGCCGGCGAACTCC TCCCCTCCCCCCTCCCCCTTCCACTCCCACC CCACCCCACCCCGGGACCCTAACCCGTAGG GTCCTCGCCGGCGCCAGAGAAGAAGAGGTT TGCCGGAGTTGGAGGAGATGACATGG (11923) | 4.70E-06 | 2.21 (+) |
| ath-miRf10209-akr | ATGGTGGTAC TCGGCCAGGT GGT (102) | TCCTCGACTTCCTGGTAGAGTGGTGTGATCG AGTGATGGTCAGGTGTGGAGGTGATGATAC TCGACCAGGTGGTCAAGTGAAGTGATCAAG TGACTCTCATGGTGGTACTCGGCCAGGTGG TCGAGTGG (11924) | 8.60E-05 | 2.18 (+) |

TABLE 3-continued

Differentially Expressed (Up-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| ath-miRf10924-akr | TGAGGCGTATCAGGAGGTAGT (103) | TGAGGCGTATCAGGAGGTAGTGTTCTTGGTGGGACAATTTGTGTTGTATGTTTCA (11925) | 1.50E-04 1.90E-06 | 2.18 (+) 2.15 (+) |
| ppt-miR1220a | TTCCGGTGGTGAGGAAGATAG (104) | ACTTCTTGCACTCCTCTATCTCCCTCGGCACCTGCACAGTGATTTTCTCAATATCTTCACGTTGGTGGCCACGTTCGAACATATCCCATGCGGGCAACTCCGGCGTAGGTGTACACGGCCAGCGTTGCTTACCATCTGGAGGATACCCTTGCTCAAACCTACGACTCTGTTCCGGTGGTGAGGAAGATAGAGGAGTTCAAGAAGT (227) | | |
| osa-miRf11341-akr | CGCGCCGACGATGACGGTGGAGT (105) | CGCCGTCTCCCTCGCCGTCGCCGGCGTCGCCGGAGATGACGAGAAGACGTGCCCCGGCGCGCCGACGATGACGGTGGAGTCGGCG (11926) | 5.40E-06 | 2.12 (+) |
| osa-miRf11352-akr | AGGGATTTTGGAAGGAGGTGACA (106) | TATAATATAAGGGATTTTGGAAGGAGGTGACATATTCTAGGACTATGTATCTGGATCCAGAGATACTAGGATGTGTTACCTCCCTCTAAAATCCCTTATATTATG (11927) | 2.30E-06 | 2.11 (+) |
| osa-miR2055 | TTTCCTTGGGAAGGTGGTTTC (107) | AGAAGATGGAGGCACCAGCCCAAGGAAACACAGACATTGACACGCAATTCAAGGAGAAGATTGCGTCCTACTTTTTCCTTGGGAAGGTGGTTTCTCTTCT (228) | 7.20E-04 | 2.09 (+) |
| ath-miRf10240-akr | ATCGAAGGAGATGGAGGACG (108) | GATTTCTCGTCCTCCGGCAATCCTTCGAACTCATCTTCATCCCAGTAATCGAAGGAGATGGAGGACGAAGGCTTC (11928) | 9.80E-07 | 2.03 (+) |
| ath-miRf10068-akr | CACCGGTGGAGGAGTGAGAG (109) | GGACTTCTCATCTTCTTTCTTAGCCGCCGGTGCTCCAGCTCCACCACCGTGTCCTCCAACATTACCGTGGCTTCCAGTTCCACCGGTGGAGGAGTGAGAGTGGGAAGTTT (11929) | 6.30E-07 | 1.99 (+) |
| ghr-miR2950 | TGGTGTGCAGGGGGTGGAATA (110) | CATGGGTTTATGTTATATTCCATCTCTTGCACACTGGACTAGCCAGCTTTTTGTTGGCTTCAGCTTCAGGTTGGTGTGCAGGGGGTGGAATACATCATTGATATCATG (229) | 5.70E-06 | 1.98 (+) |
| ath-miRf10368-akr | ACTTGGGTGGTGCTGATTAT (111) | TGGTAAGTGATAATCATTACCACCCAAGCTAACATTCAAACCAAAAACCAGTTTAAGTTAACTTGGGTGGTGCTGATTATCACTTGTCG (11930) | 7.90E-04 | 1.98 (+) |
| ath-miRf10763-akr | GGTGGTGAAGAAGCATGGTT (112) | GGCGGTGGTGAAGAAGCATGGTTTGGAAATCTCACAGCCTGGATTAGAGCCATATGAAGGGCTCACATGGGAGATGACCAAGAAAAGAGACGACACTGAAGTCCACAAGTTAGAATTATATAGTGAAGTTTCTACATTATTTTCTCACCACCGCT (11931) | 9.30E-05 | 1.93 (+) |
| ptc-miRf10734-akr | CATCTAGGTGGTGGTCCAGTG (113) | TCTTACCATTGGACCACCTACTAGATGATTAAAAACTACATCATCTAACCATCTAGGTGGTGGTCCAGTGGTAAGA (11932) | 4.30E-04 | 1.92 (+) |
| osa-miRf11829-akr | ACGCGGAGGAGGTGGTGTTCT (114) | GCACGCGGAGGAGGTGGTGTTCTCGCCGGAGTACGAGGAGTTCGCCGTCAGGAACGCCGCCCTCTGCGTCC (11933) | 4.10E-05 | 1.90 (+) |
| zma-miR482-5p | TGGGAGATGAAGGAGCCTT (115) | AGTGGGAGATGAAGGAGCCTTGCATCGATGTCACCGCCGGAGGAGCGCTCGCCTTCTTCGCGCACCGCCGCAATAGCCGCCCTCGGACCCCTCGCCTCGCTCTTCCTTGTTCCTCCCATTTT (230) | 4.20E-05 | 1.88 (+) |
| osa-miR1850.1 | TGGAAAGTTGGGAGATTGGGG (116) | ATGTGATGGAGATGCGATGGAAAGTTGGGAGATTGGGGGAAGTTGTGTGTGAACTAAACGTGGATTGGGGCCCTGTTTAGTTCACATCAATCTTCCTCCAAATTCCCAACTTTTCATCACATCACAATCACAT (231) | 1.30E-05 | 1.86 (+) |

TABLE 3-continued

Differentially Expressed (Up-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| osa-miR1881 | AATGTTATTGT AGCGTGGTGG TGT (117) | AACCAAGTTAAAATGCTCATAGGTATGAAC AAGCATCAATGTTATTGTAGCGTGGTGGTG TGACCTCTGTGCACGTAAGCTTGAGGCAGC AAGTTCGACTCCTTCAAAAGGAAGATTTGT ACCGCTGGGGAAGTGCCAGAAGAAAAGAA CAAGGAAGACTTGCTAGCAGGACAAAAGG ACGGTAAACTTGGAAAAAAAAAGGTCCAG AAGAAAAGAACAAAGAAGAACTGCTTGAA GGAGTCGAACTTGCTACCTCAAGCTTGCGT GCACATAGGTCACACCACTACGCTACAATA ACGTTGATGCTTGTTCAGACCTGTGAGCATT TTAACTTGGTT (232) | 2.00E-03 | 1.76 (+) |
| ptc-miRf10226-akr | TCCTTTGGGGA GATGGAGAGC TT (118) | ATGGTTGGAGAAGCTTCCGATCTCCCTCAA AGGCTTCCTCTATAATTGCCTTACATGATGG CATTAGTGGACTCCTTTGGGGAGATGGAGA GCTTACTCCCCAT (11934) | 9.60E-05 | 1.74 (+) |
| ptc-miRf11757-akr | CTTGGTGAAT GGTTGGGAGG AAT (119) | TGGGACAGCTTGGTGAATGGTTGGGAGGAA TGTCTTTAATGTGGTTATGCATCAGTGAAAC TCTAGTAAGATTCTCTGTCCACTCCTCTGCA TCCGGCACTTCTCTTAACCGTGCACCTGCTT TAACCA (11935) | 3.90E-05 | 1.73 (+) |
| ath-miRf11021-akr | GAGGTTTGCG ATGAGAAAGA G (120) | GATGTTGGAGGTTTGCGATGAGAAAGAGAT TGGCCGGAAGAATTATCAGCCATCAACATC GAGATTGTGAGATAATCGGAAGACCTGTAA TTGTGAAGGTAACTCTTTCTCATCTGCAAAT CTCAACTGTC (11936) | 1.50E-03 | 1.66 (+) |
| ath-miRf10633-akr | TGGCGGTGGA TACTTCTTGAT CGG (121) | GTGGATACTGTTCTGGTGGAGGATACTTCA CCGGCGGATGAGGGTAAGTCTTGATCGGTG GTGGATACTTCACCGGTGGATGCTCGTATG GTGGCGGTGGATACTTCTTGATCGGTGGTG GATAC (11937) | 6.50E-04 | 1.65 (+) |
| ptc-miRf10132-akr | TTGGCGGTGA TTGAACGGAG GGT (122) | GAGAAACGCTCTAATTAATCATCGTTATGC CACGTGTCTATTTACGGATAACGCAACGCT ACTAAATCGCGAATTTTAGTTTGAGTGGAA GATCTTGGCCGTTGGATTGGCGGTGATTGA ACGGAGGGTTGATC (11938) | 1.90E-04 | 1.63 (+) |
| ptc-miRf11315-akr | CAACTTAGAG TTGGGGGTGG (123) | GCCCTTAACCAACTTAGAGTTGGGGGTGGG CACGTCATGGGTCAACCTAGGGTTGGTCTC GGACTCGCCCTTGCTCAACTTAGAGTTGGG TACGGGC (11939) | 5.20E-03 | 1.61 (+) |
| aly-miR831-5p | AGAAGAGGTA CAAGGAGATG AGA (124) | AAGTGCTACAAGAATGTATAGTCTTAGAGT CTCAAGAAGAGGTACAAGGAGATGAGAAG TGAATCACTGAAACAAGTGGTTCGGTTTG TGGATCAGTATGGTTTACCCAAAACACGTG TTTGGTGCTTCACTTCTAAACTCCTCGTACT CTTCTTGGGATTCTATGACTTACACTTGTTG ATTT (233) | 1.60E-03 | 1.61 (+) |
| csi-miR3948 | TGGAGTGGGA GTGGGAGTAG GGTG (125) | AGGAGTGTGGAGTGGGAGTGGGAGTAGGG TGTTTACTTAGACTAAATGAAAGTATGGAT TATCAATCAGAATCCTAATTATTTGTTTACT TTGTCTTGGATTGGGAGTAAATTATTTAAA TTATAATTTTATCCTTATGTACAAAATTATA A (234) | 7.10E-05 | 1.55 (+) |

TABLE 4

Differentially Expressed (Down-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| aly-miR160c-3p | GCGTACAAGGAG CCAAGCATG (126) | CATATAATAGTTTGTCGTCGTTATGCCTGGCT CCCTGTATGCCACGAGTGGATACCGATTTTGT TATAAAATCGGCTGCCGGTGGCGTACAAGGA GCCAAGCATGACCATAAGCATATG (236) | 7.60E-04 | 1.59 (-) |
| aly-miR396a-3p | GTTCAATAAAGCT GTGGGAAG (127) | TCTACGTGACCCTCTCTGTATTCTTCCACAGC TTTCTTGAACTGCAAAACTTCTTCAGATTTGT TTTTTTTATATATATGTCTTACGCATAAAATA GTGTTTTTGTTCACATCTCTGCTCGATTGATT TGCGGTTCAATAAAGCTGTGGGAAGATACGG ACAGAGTCAAAGA (237) | 1.20E-09 | 5.50 (-) |
| aly-miR396b-3p | GCTCAAGAAAGC TGTGGGAAA (128) | GAAGAAGAAGAAGAAGATCCTGGTCATATTT TTCCACAGCTTTCTTGAACTTTCTTTTTCATTT CCATTGTTTTTTTTTTCTAAACCAAAAAAAA AGATCTCTAAAATTTAGCATTTTGGAAACAA AGAAGAAGCTCAAGAAAGCTGTGGGAAAAC ATGACAATTCAGGGTTTTACTCCATTGATTC (238) | 9.00E-07 | 3.80 (-) |
| ath-miRf10197-akr | CACTCGACCAAG GGGGTCGAGTGA (129) | GGTGAAGACACTCGACCTCGTGGTCGAGTGA TGTGATCGAGTGGTGGTCAGAAGATGGAGAT GAAGTCACTCGACCAAGGGGGTCGAGTGATG TGATC (11940) | 2.90E-07 | 3.71 (-) |
| ath-miRf10239-akr | CGCCTTGCATCAA CTGAATC (130) | TCGGGCTCGGATTCGCTTGGTGCAGGTCGGG AACCAATTCGGCTGACACAGCCTCGGACTT TTAAACCTTTATTGGTTTGTGAGCAGGGATTG GATCCCGCCTTGCATCAACTGAATCGGATCC TCGA (11941) | 1.00E-03 | 2.17 (-) |
| ath-miRf10279-akr | ACTCAGCCTGGG GGTCGAGTGAT (131) | TGATGGTGATACTCGACATCCAGGTAGAGTG ATGAGGTCGAGTAGAGGTCTGGCAATGGGAT GAAGTCACTCAGCCTGGGGGTCGAGTGATGT GATCG (11942) | 7.80E-06 | 4.99 (-) |
| bna-miR2111b-5p | TAATCTGCATCCT GAGGTTTA (132) | GCACTTGATGAGGAACTGGTAATCTGCATCC TGAGGTTTAAAAATACATAGGCACATGCAAA TGTGTGTATTATAGTTTTTAATCCTCGGGATA CAGATTACCTCTTCCTTTTACTGAA (239) | 4.40E-04 | 2.55 (-) |
| bra-miR160a-3p | GCGTATGAGGAG CCATGCATA (133) | TATGTGTAGTTGTATAAGATGTGTATGCCTGG CTCCCTGTATGCCATCCTCTAAGCTCATCGAC CATTGATGACCTCCGTGAATGGCTATGAGG AGCCATGCATATTTTCATATACATTTACATAC (240) | 1.90E-04 | 1.94 (-) |
| csi-miR162-5p | TGGAGGCAGCGG TTCATCGATC (134) | AAACTGTTTACACTGATCTGTGCTGCTGATAA ATCTTAATTTTTTTTTTGAATTTTTATTTAAC AGAAAATAGAGAGAGTGAAGTCACTGGAGG CAGCGGTTCATCGATCACTTTGTGCAAATTTT GTTGTGAAAAATAACACAAAATACATGAATC GATCGATAAACCTCTGCATCCAGCGCTCACT CCAACTCTATTC (241) | 1.60E-03 | 1.95 (-) |
| gma-miR1524 | CGAGTCCGAGGA AGGAACTCC (135) | GCGACTTATTGGAGTTCATTCTTCGCACTCTC TCGGAAACCACTTGTTTCCAATCATCTAATCA GACGATAGCAGACTCAAGAAAGACGTTTCCT TCCCAGATCCTTCTAGACCATTTGCAAACCGT CTCCTTCCCCGAATCCATTCTCCAAACCCTCG ATCCTTGAGGAGCTCCACCACCGTGACGGCG CTCCGGTCTCCGCCGTCAATTGTGCCGTCGCG GTGGAGCATGAGCGTCTTCATGAGTCTGAAA GGGAATTATAGGAACTACTTTCCTGATTAGG TTATTGGAAACAAGTGGTTTCCGAGTCCGAG GAAGGAACTCCAACGCCCAAC (242) | 3.30E-03 | 1.73 (-) |
| gma-miR159d | AGCTGCTTAGCTA TGGATCCC (136) | GGGTGAATTGAGCTGCTTAGCTATGGATCCC ACAGTTCTACCCATCAATAAGTGCTTTTGTG TAGTCTTGTGGCTTCCATATCTGGGGAGCTTC ATTTGCCT (243) | 3.20E-06 | 3.24 (-) |
| gma-miR2119 | TCAAAGGGAGTT GTAGGGGAA (137) | ATACTTCATTTTTTATACTTTAATTTCCTCTAT ACCTCACTTTTATTGGAGAAAAAAGAGAATA | 2.70E-03 | 1.54 (-) |

TABLE 4-continued

Differentially Expressed (Down-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
|---|---|---|---|---|
| | | GAAAATAGTGGATTTCTCTTCTTTTTTTCAAT CAAAGGGAGTTGTAGGGGAAAGTTTAGAAA ATGGCGTGT (244) | | |
| gma-miR396d | AAGAAAGCTGTG GGAGAATATGGC (138) | GGTCATGCTTTTCCACAGCTTTCTTGAACTTC TTATGCATCTTATATCTCTCCACTTCCAGCAT TTTAAGCCCTAGAAGCTCAAGAAAGCTGTGG GAGAATATGGCAA (245) | 4.60E-08 | 2.76 (-) |
| gma-miR4412-3p | AGTGGCGTAGAT CCCCACAAC (139) | AACTGTTGCGGGTATCTTTGCCTCTGAAGGA AAGTTGTGCCTATTATTATGGCTTATTGCTTT AGTGGCGTAGATCCCCACAACAGTT (246) | 9.80E-05 | 3.03 (-) |
| gma-miR4416a | ACGGGTCGCTCTC ACCTAGG (140) | CTTTGATCTGGGTGAGAGAAACGCGTATCGA TGGATTGGGTTCAGTTCTGGTCTCACACGGTT TGTTCTAACAATTTGTACTGACTGTGTTTTGA TCGATACGGGTCGCTCTCACCTAGGCCAGAG TTGC (247) | 9.20E-06 | 4.30 (-) |
| gma-miR482b-5p | TATGGGGGGATT GGGAAGGAAT (141) | GGTATGGGGGGATTGGGAAGGAATATCCATA AGCAAAATATGCTATTTCTTCCCTACACCTCC CATACC (248) | 2.30E-10 | 2.74 (-) |
| osa-miR162a | TCGATAAACCTCT GCATCCAG (142) | GGTGATGCCTGGGCGCAGTGGTTTATCGATC CCTTCCCTGCCTTGTGGCGCTGATCCAGGAGC GGCGAATTTCTTTGAGAGGGTGTTCTTTTTTT TTCTTCCTTTTGGTCCTTGTTGCAGCCAACGA CAACGCGGGAATCGATCGATAAACCTCTGCA TCCAGTTCTCGCC (249) | 4.00E-04 | 1.52 (-) |
| osa-miR1846e | CAACGAGGAGGC CGGGACCA (143) | CGCATCCGCCAACGAGGAGGCCGGGACCACC GGATCCGGTGACTCCGGCCTCCTCGCCGGCA GATCCGG (250) | 4.30E-04 | 1.90 (-) |
| osa-miR2104 | GCGGCGAGGGGA TGCGAGCGTG (144) | ACGGGCGCTCACGGTGGCTTCGACCCTCGTC TCGGCCGCGTGCGGTAGTGCGGGAGGCATGC CGTGTGTACCGGCGGCGAGGGGATGCGAGCG TGAGTGCCTCGG (251) | 3.90E-02 | 1.51 (-) |
| osa-miRf10849-akr | TGGACTGTTTGGG GGAGCTTCT (145) | GCTGGACTGTTTGGGGGAGCTTCTGATTTTGG GAGAAACGGCTATAGCTAGAAGCTCCCCGAA ACAGGCCCAAC (11943) | 1.80E-03 | 1.52 (-) |
| osa-miRf11415-akr | GAGAGCAGGATG CAGCCAAGG (146) | GAAGAGGCAGAGAGCAGGATGCAGCCAAGG ATGACTTGCCGGCCGGCGATGGCCGACGGCG AGGTTAATTAATTGGCCGGAGACTGGCAGTC CTTCTCTGTTGATCCGGCAAGTTTGTCCTTGG CTACACCTTGCTCTCTTCTCGTC (11944) | 6.70E-03 | 1.55 (-) |
| osa-miRf11996-akr | GTCTTATAACCTG AAACGGGGG (147) | TACTACCTCCATTTCAGGTTATAAGACTTTCT AGTGTTGCTCACATTCATATATATGTTAATAA ATTCATTAACATATAGAAAGTCTTATAACCT GAAACGGGGGAAGTA (11945) | 7.20E-03 | 2.01 (-) |
| ppt-miR533b-5p | GAGCTGTCCAGG CTGTGAGGG (148) | GGAGGACCGATATGGAGAGCTGTCCAGGCTG TGAGGGGAGCACTCGTATTCTTTTGACCTTTG CTAGAAGAGGGAATACAGCGCTCTCCCTCAC AGTCTGTACAGCTCTCTGTATCTCTTCCTCT (252) | 7.90E-04 | 3.23 (-) |
| ptc-miRf10007-akr | CATTGACAGGGA AACTCACCA (149) | TTGCTGTGGTGAGTTTCCCTGTCAGTGCTCAC TACGATATTTAATGAAGAAGAAAAATAAAGC AAGAGATAAAAAAGGCATTTCCTCGATTCAG ATTTCAGGGTGCAGCATTGCATTGAGCATTG ACAGGGAAACTCACCACGGCAA (11946) | 3.90E-02 | 1.77 (-) |
| ptc-miRf10976-akr | TGGGAACGTGGC TGTGGCTA (150) | GCCCTGTTTGGGAACGTGGCTGTGGCTACAC TGATGCTTCTGGTTTGGAAATGGAGGTGCAA CTGAAGTTATGGGAACGTTCCCAAACAGGGC (11947) | 2.30E-04 | 1.81 (-) |
| ptc-miRf11018-akr | CTGCAAACCTAA GGGAGCGG (151) | CTGCAAACCTAAGGGAGCGGTTTTGCAGACC CCAAGCGCACAAGTCTGCAGACCCGCTCGCT TGGGTCTGCAG (11948) | 1.10E-02 | 1.79 (-) |

TABLE 4-continued

Differentially Expressed (Down-regulated) Small RNAs in Soybean Plants Growing under High Salt (10 days) versus Optimal Conditions.

| miR Name | Mature Sequence (SEQ ID NO:) | Stem Loop Sequence (SEQ ID NO:) | p-Value | Fold-Change |
| --- | --- | --- | --- | --- |
| ptc-miRf11079-akr | AAGATGGAGAAGCAGGGCACGTGC (152) | GTGTGTGAGCAAGATGGAGAAGCAGGGCACGTGCACTACTAACTCATGCACACAGAGAGGGAGACGCATTTCTTGCTGGAGTTACGAGTTACGACTCTTACCTACTATTGATTTTGTTAGCTCCAGTGAGTTAGTTATTCATGTGCCTGTCTTCCTCATCATGATCACTAC (11949) | 2.30E-05 | 2.43 (-) |
| ptc-miRf11324-akr | CTTGTCGCAGGAGAGATGGCGCT (153) | TTGGGGGTTTCTTGTCGCAGGAGAGATGGCGCTAGCTAACCATGGTCATATCATATATATCATATGGCAAGTATTACTTGCTCTTTGTATGTATCAGCTGTAAAGATAGCTCAGCTAAAGCCATCCTCCTGCGACTGGACACCCTGCAA (11950) | 5.90E-05 | 1.73 (-) |
| ptc-miRf11396-akr | CAAGGCTCTGATACCATGTCAA (154) | CTTGGTCATCAAGGCTCTGATACCATGTCAAAGAATCATATTTTGAGACCTTATCTAACAGCTTAAGCTATTGGGTTGAGATGGTTCCTTGACATGATATCAGAGCCTTGATGACGAAG (11951) | 4.10E-04 | 1.51 (-) |
| ptc-miRf11953-akr | GTAATCTGCATCCTGAGGTT (155) | AGGATTGGGTAATCTGCATCCTGAGGTTTGGATCACCACATGTTTTGATCTAGTCCTTGGGTTGCAGATTACCTCTTCCT (11952) | 1.90E-04 | 2.74 (-) |
| ptc-miRf12069-akr | GGAGGGGCTGCAAGACCCAAG (156) | CTTGGGCCAGGAGGGGCTGCAAGACCCAAGTGACTTGGGTCTGCGCTCTTGCCACACCCAAGCAACTTGGGTCAGACGCCCTTCCAAGCCCCAAG (11953) | 3.90E-07 | 3.81 (-) |
| ptc-miRf12389-akr | GTCGACCTGGCGAGTCAACCGGG (157) | TGAGTCGACCTGGCGAGTCAACCGGGTTTGATTGTTTTTTTATCCTTGCTAGTCTTTCACCTTACTAGGACCGGTCCAGCCACCGGGTTAATCGAGTCCCGGGTTGACTTGCTGGGCCGTCTGG (11954) | 1.00E-02 | 1.75 (-) |
| vvi-miR2111-5p | TAATCTGCATCCTGAGGTCTA (158) | GCAATATTGGGTCAGGATCGGGTAATCTGCATCCTGAGGTCTAGATAAGTATATCTCCGTTGCAGCTAGTCCTCTGGTTGCAGATTACTTCTTCCTCACTGCCAATGC (253) | 3.10E-04 | 2.82 (-) |
| zma-miR167u | TGAAGCTGCCACATGATCTG (159) | TGAAGCTGCCACATGATCTGATGACGCAGAGTCATGCATATGCATTGCATCCAGCAAGCTCCATGCGTGCGTGCATGGCCGAATGGCCGAAGAGACTAGCTAGTCCATCTCTCCAAGGCCATCCACGTGTGAGAATTCAATTCCTCGTGGATCAGATCAGGCTGTTGTTGACAACTGCATGCCGCACCTGCACTACAGCAACCCAAGGCATAGGTAGCTAGCTAGGTTTCGGTGGTCAGATCAGATCAGGCTGGCAGCTTCA (254) | 2.20E-05 | 1.57 (-) |
| zma-miR396b-3p | GTTCAATAAAGCTGTGGGAAA (160) | AGATGGCCTTCTTTGTGATCTTCCACAGCTTTCTTGAACTGCATCTCTCAGAGGAGCGGCAGCTTCAACTCCTCCACCCGCATCAGCAGGTGCATGCAGTTCAATAAAGCTGTGGGAAACTGCAGAGAGAGGCCAG (255) | 7.90E-09 | 6.05 (-) |
| zma-miR398a-5p | GGGGCGAACTGAGAACACATG (161) | GGGGGCGAACUGAGAACACAUGAGAAUAAUGAGAUGAGAUUGCUCGCCUCGCGGUACGGUUCGUGCUGGCCUGGACCACCGUCGUCGCCGUUCAUCUUGUACGCAUAAUAAUGCUGCAUGUGUUCUCAGGUCGCCCCCGC (11955) | 3.00E-04 | 1.89 (-) |

TABLE 5

Differentially Expressed (Up-regulated) Small RNAs in Soybean Plants Growing under Heat Shock (1 hour) versus Optimal Conditions.

| miR Name | Mature Sequence (SEQ ID NO:) | Stem Loop Sequence (SEQ ID NO:) | p-Value | Fold-Change |
|---|---|---|---|---|
| aly-miR831-5p | AGAAGAGGTACAAGGAGATGAGA (162) | AAGTGCTACAAGAATGTATAGTCTTAGAG TCTCAAGAAGAGGTACAAGGAGATGAGA AGTGAATCACTGAAACAAGTGGTTCTGGT TTGTGGATCAGTATGGTTTACCCAAAACA CGTGTTTGGTGCTTCACTTCTAAACTCCTC GTACTCTTCTTGGGATTCTATGACTTACAC TTGTTGATTT (256) | 4.20E-05 | 1.73 (+) |
| ath-miRf10687-akr | TTAGCTGAAGAAGCAGAGGAG (163) | TTTGTTTGTTTAGCTGAAGAAGCAGAGGA GTCGGCATTGGGGCACAGTCACTCATCGA TGCTGCAATGGGTAAGTCCTCTGCATACTT TTGCTGAGATAGGAATAGA (11956) | 2.10E-05 | 1.76 (+) |
| ath-miRf11021-akr | GAGGTTTGCGATGAGAAAGAG (164) | GATGTTGGAGGTTTGCGATGAGAAAGAGA TTGGCCGGAAGAATTATCAGCCATCAACA TCGAGATTGTGAGATAATCGGAAGACCTG TAATTGTGAAGGTAACTCTTTCTCATCTGC AAATCTCAACTGTC (11957) | 2.10E-07 | 1.82 (+) |
| far-miR1134 | CGACAACAACAACAAGAAGAAGAG (165) | ACGGCAATCCCAGCTTCAACGGGCCGGTG CCAGGCGTGCCTCCCGGCGATGCCCATCG GTCGCCGACGCCTCCTAGCACGCCAGCTG GCTCACAAGGTGTCTCTCCCGGCGGCGAC AACAACAACAAGAAGAAGAGATCAGGTC TGGTGCTGGCTACTACCATCCCGGTCTCA GTCAGTGTGGTGGCGCTCATCTCGCTGGG TGCCGTGCTGCTCTTCCGCAAGAAAAACA ACGGGTCCG (257) | 2.80E-04 | 1.63 (+) |
| osa-miRf10105-akr | TTGGCCTCGTCGAAGAAGGAGA (166) | TCTCGTTCTTGGAGAGGCCCTTGCCGACCT TGGCGATGCGCTTGCCGGCCCTGGACCAG CGGGACGCCGCGGTCTCCTGCTTGGCCTC GTCGAAGAAGGAGA (11958) | 1.90E-06 | 2.01 (+) |
| pab-miR3711 | TGGCGCTAGAAGGAGGGCCT (167) | AAATGGCGCTAGAAGGAGGGCCTGAAAA TTATTAATGGCACGAGGCAGTCGTAAGAC TCCTCCACCACCCAACCACTCACCTATAGT GAAAAGAAGTCATTAAAATGATAACATCA CCCCTCAAATAGAACCA (258) | 6.60E-05 | 1.68 (+) |
| zma-miR482-5p | TGGGAGATGAAGGAGCCTT (168) | AGTGGGAGATGAAGGAGCCTTGCATCGAT GTCACCGCCGGAGGAGCGCTCGCCTTCTT CGCGCACCGCCGCAATAGCCGCCCTCGGA CCCCTCGCCTCGCTCTTCCTTGTTCCTCCC ATTTT (259) | 8.20E-07 | 2.05 (+) |

TABLE 6

Differentially Expressed (Down-regulated) Small RNAs in Soybean Plants Growing under Heat Shock (1 hour) versus Optimal Conditions.

| miR Name | Mature Sequence (SEQ ID NO:) | Stem Loop Sequence (SEQ ID NO:) | p-Value | Fold-Change |
|---|---|---|---|---|
| ath-miRf10279-akr | ACTCAGCCTGGGGGTCGAGTGAT (169) | TGATGGTGATACTCGACATCCAGGTAGA GTGATGAGGTCGAGTAGAGGTCTGGCAA TGGGATGAAGTCACTCAGCCTGGGGGTC GAGTGATGTGATCG (11959) | 1.30E-02 | 2.56 (−) |
| csi-miR162-5p | TGGAGGCAGCGGTTCATCGATC (170) | AAACTGTTTACACTGATCTGTGCTGCTG ATAAATCTTAATTTTTTTTTTTGAATTTTT ATTTAACAGAAAATAGAGAGAGTGAAG TCACTGGAGGCAGCGGTTCATCGATCAC TTTGTGCAAATTTTGTTGTGAAAAATAA CACAAAATACATGAATCGATCGATAAAC CTCTGCATCCAGCGCTCACTCCAACTCTA TTC (260) | 4.10E-05 | 1.71 (−) |

TABLE 6-continued

Differentially Expressed (Down-regulated) Small RNAs in Soybean Plants Growing under Heat Shock (1 hour) versus Optimal Conditions.

| miR Name | Mature Sequence (SEQ ID NO:) | Stem Loop Sequence (SEQ ID NO:) | p-Value | Fold-Change |
| --- | --- | --- | --- | --- |
| gma-miR4412-3p | AGTGGCGTAGATC CCCACAAC (171) | AACTGTTGCGGGTATCTTTGCCTCTGAA GGAAAGTTGTGCCTATTATTATGGCTTAT TGCTTTAGTGGCGTAGATCCCCACAACA GTT (261) | 1.60E-05 | 1.81 (−) |
| osa-miRf10151-akr | TGGCTATATTTTGG GACGGAG (172) | GTATACTACCTCCGTCCCAAAATATAGC CACTTTTAGATTCATAAACAAAAGTGGC TATATTTTGGGACGGAGGGAGTATAT (11960) | 3.60E-03 | 2.06 (−) |
| ptc-miRf12069-akr | GGAGGGGCTGCAA GACCCAAG (173) | CTTGGGCCAGGAGGGGCTGCAAGACCCA AGTGACTTGGGTCTGCGCTCTTGCCACA CCCAAGCAACTTGGGTCAGACGCCCTTC CAAGCCCCAAG (11961) | 1.90E-03 | 2.03 (−) |

Example 2

Identification of Homologous and Orthologous Sequences of Differential Small RNAs Associated with Enhanced Abiotic Stress Tolerance The miRNA sequences of the invention that were either down- or up-regulated under abiotic stress conditions were examined for homologous and orthologous sequences using the miRBase database (http://wwwDOTmirbaseDOTorg/) and the Plant MicroRNA Database (PMRD, http://bioinformaticsDOTcauDOTeduDOTcn/PMRD). The mature miRNA sequences that are homologous or orthologous to the soy miRNAs listed in Tables 1-6 above, were found using miRNA public databases, having at least 75% identity of the entire mature miRNA length of the original soy sequence listed in Tables 1-6 and are summarized in Tables 7-8 below.

TABLE 7

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
| --- | --- | --- | --- | --- |
| far-miR1134 | tae-miR1134 | CAACAACAACAAGAAG AAGAAGAT (262) | 0.88 | 2087 |
| mtr-miR2119 | gma-miR2119 | TCAAAGGGAGTTGTAG GGGAA (263) | 0.76 | 2088 |
|  | pvu-miR2119 | TCAAAGGGAGTTGTAG GGGAA (264) | 0.76 | 2089 |
| ppt-miR1220a | ppt-miR1220b | TTCCGGTGGTGAGGAAG ATAG (265) | 1 | 2090 |
| aqc-miR159 | acb-miR159 | TTGGACTGAAGGGAGCT CCCT (266) | 0.86 | 2091 |
|  | aha-miR159 | TTGGACTGAAGGGAGCT CCCT (267) | 0.86 | 2092 |
|  | ahi-miR159 | TTGGACTGAAGGGAGCT CCCT (268) | 0.86 | 2093 |
|  | ahy-miR159 | TTTGGATTGAAGGGAGC TCTA (269) | 0.95 | 2094 |
|  | aly-miR159a | TTTGGATTGAAGGGAGC TCTA (270) | 0.95 | 2095 |
|  | aly-miR159b | TTTGGATTGAAGGGAGC TCTT (271) | 0.9 | 2096 |
|  | aly-miR159c | TTTGGATTGAAGGGAGC TCCT (272) | 0.86 | 2097 |
|  | ape-miR159 | TTGGACTGAAGGGAGCT CCCT (273) | 0.86 | 2098 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ath-miR159a | TTTGGATTGAAGGGAGCTCTA (274) | 0.95 | 2099 |
| | ath-miR159b | TTTGGATTGAAGGGAGCTCTT (275) | 0.9 | 2100 |
| | ath-miR159c | TTTGGATTGAAGGGAGCTCCT (276) | 0.86 | 2101 |
| | bdi-miR159 | CTTGGATTGAAGGGAGCTCT (277) | 0.86 | 2102 |
| | bna-miR159 | TTTGGATTGAAGGGAGCTCTA (278) | 0.95 | 2103 |
| | bra-miR159a | TTTGGATTGAAGGGAGCTCTA (279) | 0.95 | 2104 |
| | bvl-miR159 | TTGGACTGAAGGGAGCTCCCT (280) | 0.86 | 2105 |
| | cmi-miR159 | TTGGACTGAAGGGAGCTCCCT (281) | 0.86 | 2106 |
| | cor-miR159 | TTGGACTGAAGGGAGCTCCCT (282) | 0.86 | 2107 |
| | crb-miR159 | TTGGACTGAAGGGAGCTCCCT (283) | 0.86 | 2108 |
| | csi-miR159 | TTTGGATTGAAGGGAGCTCTA (284) | 0.95 | 2109 |
| | dso-miR159 | TTGGACTGAAGGGAGCTCCCT (285) | 0.86 | 2110 |
| | ech-miR159 | TTGGACTGAAGGGAGCTCCCT (286) | 0.86 | 2111 |
| | fal-miR159 | TTGGACTGAAGGGAGCTCCCT (287) | 0.86 | 2112 |
| | far-miR159 | TTTGGATTGAAGGGAGCTCTG (288) | 0.9 | 2113 |
| | gma-miR159a-3p | TTTGGATTGAAGGGAGCTCTA (289) | 0.95 | 2114 |
| | gma-miR159b | ATTGGAGTGAAGGGAGCTCCA (290) | 0.86 | 2115 |
| | gma-miR159c | ATTGGAGTGAAGGGAGCTCCG (291) | 0.81 | 2116 |
| | hvu-miR159a | TTTGGATTGAAGGGAGCTCTG (292) | 0.9 | 2117 |
| | hvu-miR159b | TTTGGATTGAAGGGAGCTCTG (293) | 0.9 | 2118 |
| | hvv-miR159a | TTTGGATTGAAGGGAGCTCTG (294) | 0.9 | 2119 |
| | hvv-miR159b | TTTGGATTGAAGGGAGCTCTG (295) | 0.9 | 2120 |
| | ltu-miR159 | TTTGGATTGAAGGGAGCTCTA (296) | 0.95 | 2121 |
| | mma-miR159 | TTGGACTGAAGGGAGCTCCCT (297) | 0.86 | 2122 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | mtr-miR159a | TTTGGATTGAAGGGAGCTCTA (298) | 0.95 | 2123 |
| | mtr-miR159b | ATTGAATTGAAGGGAGCAACT (299) | 0.67 | 2124 |
| | mtr-miR159c | TTTGGATTGAAGGGAGCTCTA (300) | 0.95 | 2125 |
| | nof-miR159 | TTGGACTGAAGGGAGCTCCCT (301) | 0.86 | 2126 |
| | oru-miR159 | TTTGGATTGAAGGGAGCTCTG (302) | 0.9 | 2127 |
| | osa-miR159a | TTTGGATTGAAGGGAGCTCTG (303) | 0.9 | 2128 |
| | osa-miR159a.1 | TTTGGATTGAAGGGAGCTCTG (304) | 0.9 | 2129 |
| | osa-miR159b | TTTGGATTGAAGGGAGCTCTG (305) | 0.9 | 2130 |
| | osa-miR159c | ATTGGATTGAAGGGAGCTCCA (306) | 0.86 | 2131 |
| | osa-miR159d | ATTGGATTGAAGGGAGCTCCG (307) | 0.81 | 2132 |
| | osa-miR159e | ATTGGATTGAAGGGAGCTCCT (308) | 0.81 | 2133 |
| | osa-miR159f | CTTGGATTGAAGGGAGCTCTA (309) | 0.9 | 2134 |
| | osa-miR159m | TTTGGATTGAAGGGAGCTCTG (310) | 0.9 | 2135 |
| | pgl-miR159 | TTTGGATTGAAGGGAGCTCTG (311) | 0.9 | 2136 |
| | psi-miR159 | CTTGGATTGAAGGGAGCTCCA (312) | 0.86 | 2137 |
| | pta-miR159a | TTGGATTGAAGGGAGCTCCA (313) | 0.86 | 2138 |
| | pta-miR159b | TTGGATTGAAGAGAGCTCCC (314) | 0.76 | 2139 |
| | pta-miR159c | CTTGGATTGAAGGGAGCTCCC (315) | 0.81 | 2140 |
| | ptc-miR159a | TTTGGATTGAAGGGAGCTCTA (316) | 0.95 | 2141 |
| | ptc-miR159b | TTTGGATTGAAGGGAGCTCTA (317) | 0.95 | 2142 |
| | ptc-miR159c | TTTGGATTGAAGGGAGCTCTA (318) | 0.95 | 2143 |
| | ptc-miR159d | CTTGGATTGAAGGGAGCTCCT (319) | 0.81 | 2144 |
| | ptc-miR159e | CTTGGGGTGAAGGGAGCTCCT (320) | 0.76 | 2145 |
| | ptc-miR159f | ATTGGAGTGAAGGGAGCTCGA (321) | 0.86 | 2146 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | pvu-miR159 | TTTGGATTGAAGGGAGCTCTA (322) | 0.95 | 2147 |
| | pvu-miR159a.1 | TTTGGATTGAAGGGAGCTCTA (323) | 0.95 | 2148 |
| | rco-miR159 | TTTGGATTGAAGGGAGCTCTA (324) | 0.95 | 2149 |
| | rin-miR159 | TTGGACTGAAGGGAGCTCCCT (325) | 0.86 | 2150 |
| | sar-miR159 | TTTGGATTGAAGGGAGCTCTG (326) | 0.9 | 2151 |
| | sbi-miR159a | TTTGGATTGAAGGGAGCTCTG (327) | 0.9 | 2152 |
| | sbi-miR159b | CTTGGATTGAAGGGAGCTCCT (328) | 0.81 | 2153 |
| | sly-miR159 | TTTGGATTGAAGGGAGCTCTA (329) | 0.95 | 2154 |
| | smo-miR159 | CTTGGATTGAAGGGAGCTCCC (330) | 0.81 | 2155 |
| | sof-miR159a | TTTGGATTGAAGGGAGCTCTG (331) | 0.9 | 2156 |
| | sof-miR159b | TTTGGATTGAAGGGAGCTCTG (332) | 0.9 | 2157 |
| | sof-miR159c | CTTGGATTGAAGGGAGCTCCT (333) | 0.81 | 2158 |
| | sof-miR159d | TTTGGATTGAAGGGAGCTCTG (334) | 0.9 | 2159 |
| | sof-miR159e | TTTGGATTGAAAGGAGCTCTT (335) | 0.86 | 2160 |
| | spr-miR159 | TTTGGATTGAAGGGAGCTCTG (336) | 0.9 | 2161 |
| | ssp-miR159a | TTTGGATTGAAGGGAGCTCTG (337) | 0.9 | 2162 |
| | svi-miR159 | TTGGACTGAAGGGAGCTCCCT (338) | 0.86 | 2163 |
| | tae-miR159a | TTTGGATTGAAGGGAGCTCTG (339) | 0.9 | 2164 |
| | tae-miR159b | TTTGGATTGAAGGGAGCTCTG (340) | 0.9 | 2165 |
| | tar-miR159 | TTGGACTGAAGGGAGCTCCCT (341) | 0.86 | 2166 |
| | vvi-miR159a | CTTGGAGTGAAGGGAGCTCTC (342) | 0.86 | 2167 |
| | vvi-miR159b | CTTGGAGTGAAGGGAGCTCTC (343) | 0.86 | 2168 |
| | vvi-miR159c | TTTGGATTGAAGGGAGCTCTA (344) | 0.95 | 2169 |
| | zma-miR159a | TTTGGATTGAAGGGAGCTCTG (345) | 0.9 | 2170 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR159b | TTTGGATTGAAGGGAGCTCTG (346) | 0.9 | 2171 |
| | zma-miR159c | CTTGGATTGAAGGGAGCTCCT (347) | 0.81 | 2172 |
| | zma-miR159d | CTTGGATTGAAGGGAGCTCCT (348) | 0.81 | 2173 |
| | zma-miR159e | ATTGGTTTGAAGGGAGCTCCA (349) | 0.81 | 2174 |
| | zma-miR159f | TTTGGATTGAAGGGAGCTCTG (350) | 0.9 | 2175 |
| | zma-miR159g | TTTGGAGTGAAGGGAGTTCTG (351) | 0.86 | 2176 |
| | zma-miR159h | TTTGGAGTGAAGGGAGCTCTG (352) | 0.9 | 2177 |
| | zma-miR159i | TTTGGAGTGAAGGGAGCTCTG (353) | 0.9 | 2178 |
| | zma-miR159j | TTTGGATTGAAGGGAGCTCTG (354) | 0.9 | 2179 |
| | zma-miR159k | TTTGGATTGAAGGGAGCTCTG (355) | 0.9 | 2180 |
| | zma-miR159m | TTTGGATTGAAGGGAGCTCTG (356) | 0.9 | 2181 |
| ath-miR159b | acb-miR159 | TTGGACTGAAGGGAGCTCCCT (357) | 0.81 | 2182 |
| | aha-miR159 | TTGGACTGAAGGGAGCTCCCT (358) | 0.81 | 2183 |
| | ahi-miR159 | TTGGACTGAAGGGAGCTCCCT (359) | 0.81 | 2184 |
| | ahy-miR159 | TTTGGATTGAAGGGAGCTCTA (360) | 0.95 | 2185 |
| | aly-miR159a | TTTGGATTGAAGGGAGCTCTA (361) | 0.95 | 2186 |
| | aly-miR159b | TTTGGATTGAAGGGAGCTCTT (362) | 1 | 2187 |
| | aly-miR159c | TTTGGATTGAAGGGAGCTCCT (363) | 0.95 | 2188 |
| | ape-miR159 | TTGGACTGAAGGGAGCTCCCT (364) | 0.81 | 2189 |
| | aqc-miR159 | TTTGGACTGAAGGGAGCTCTA (365) | 0.9 | 2190 |
| | ath-miR159a | TTTGGATTGAAGGGAGCTCTA (366) | 0.95 | 2191 |
| | ath-miR159c | TTTGGATTGAAGGGAGCTCCT (367) | 0.95 | 2192 |
| | bdi-miR159 | CTTGGATTGAAGGGAGCTCT (368) | 0.9 | 2193 |
| | bna-miR159 | TTTGGATTGAAGGGAGCTCTA (369) | 0.95 | 2194 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | bra-miR159a | TTTGGATTGAAGGGAGCTCTA (370) | 0.95 | 2195 |
| | byl-miR159 | TTGGACTGAAGGGAGCTCCCT (371) | 0.81 | 2196 |
| | cmi-miR159 | TTGGACTGAAGGGAGCTCCCT (372) | 0.81 | 2197 |
| | cor-miR159 | TTGGACTGAAGGGAGCTCCCT (373) | 0.81 | 2198 |
| | crb-miR159 | TTGGACTGAAGGGAGCTCCCT (374) | 0.81 | 2199 |
| | csi-miR159 | TTTGGATTGAAGGGAGCTCTA (375) | 0.95 | 2200 |
| | dso-miR159 | TTGGACTGAAGGGAGCTCCCT (376) | 0.81 | 2201 |
| | ech-miR159 | TTGGACTGAAGGGAGCTCCCT (377) | 0.81 | 2202 |
| | fal-miR159 | TTGGACTGAAGGGAGCTCCCT (378) | 0.81 | 2203 |
| | far-miR159 | TTTGGATTGAAGGGAGCTCTG (379) | 0.95 | 2204 |
| | gma-miR159a-3p | TTTGGATTGAAGGGAGCTCTA (380) | 0.95 | 2205 |
| | gma-miR159b | ATTGGAGTGAAGGGAGCTCCA (381) | 0.81 | 2206 |
| | gma-miR159c | ATTGGAGTGAAGGGAGCTCCG (382) | 0.81 | 2207 |
| | hvu-miR159a | TTTGGATTGAAGGGAGCTCTG (383) | 0.95 | 2208 |
| | hvu-miR159b | TTTGGATTGAAGGGAGCTCTG (384) | 0.95 | 2209 |
| | hvv-miR159a | TTTGGATTGAAGGGAGCTCTG (385) | 0.95 | 2210 |
| | hvv-miR159b | TTTGGATTGAAGGGAGCTCTG (386) | 0.95 | 2211 |
| | ltu-miR159 | TTTGGATTGAAGGGAGCTCTA (387) | 0.95 | 2212 |
| | mma-miR159 | TTGGACTGAAGGGAGCTCCCT (388) | 0.81 | 2213 |
| | mtr-miR159a | TTTGGATTGAAGGGAGCTCTA (389) | 0.95 | 2214 |
| | mtr-miR159b | ATTGAATTGAAGGGAGCAACT (390) | 0.76 | 2215 |
| | mtr-miR159c | TTTGGATTGAAGGGAGCTCTA (391) | 0.95 | 2216 |
| | nof-miR159 | TTGGACTGAAGGGAGCTCCCT (392) | 0.81 | 2217 |
| | oru-miR159 | TTTGGATTGAAGGGAGCTCTG (393) | 0.95 | 2218 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | osa-miR159a | TTTGGATTGAAGGGAGCTCTG (394) | 0.95 | 2219 |
| | osa-miR159a.1 | TTTGGATTGAAGGGAGCTCTG (395) | 0.95 | 2220 |
| | osa-miR159b | TTTGGATTGAAGGGAGCTCTG (396) | 0.95 | 2221 |
| | osa-miR159c | ATTGGATTGAAGGGAGCTCCA (397) | 0.86 | 2222 |
| | osa-miR159d | ATTGGATTGAAGGGAGCTCCG (398) | 0.86 | 2223 |
| | osa-miR159e | ATTGGATTGAAGGGAGCTCCT (399) | 0.9 | 2224 |
| | osa-miR159f | CTTGGATTGAAGGGAGCTCTA (400) | 0.9 | 2225 |
| | osa-miR159m | TTTGGATTGAAGGGAGCTCTG (401) | 0.95 | 2226 |
| | pgl-miR159 | TTTGGATTGAAGGGAGCTCTG (402) | 0.95 | 2227 |
| | psi-miR159 | CTTGGATTGAAGGGAGCTCCA (403) | 0.86 | 2228 |
| | pta-miR159a | TTGGATTGAAGGGAGCTCCA (404) | 0.86 | 2229 |
| | pta-miR159b | TTGGATTGAAGAGAGCTCCC (405) | 0.81 | 2230 |
| | pta-miR159c | CTTGGATTGAAGGGAGCTCCC (406) | 0.86 | 2231 |
| | ptc-miR159a | TTTGGATTGAAGGGAGCTCTA (407) | 0.95 | 2232 |
| | ptc-miR159b | TTTGGATTGAAGGGAGCTCTA (408) | 0.95 | 2233 |
| | ptc-miR159c | TTTGGATTGAAGGGAGCTCTA (409) | 0.95 | 2234 |
| | ptc-miR159d | CTTGGATTGAAGGGAGCTCCT (410) | 0.9 | 2235 |
| | ptc-miR159e | CTTGGGGTGAAGGGAGCTCCT (411) | 0.81 | 2236 |
| | ptc-miR159f | ATTGGAGTGAAGGGAGCTCGA (412) | 0.81 | 2237 |
| | pvu-miR159 | TTTGGATTGAAGGGAGCTCTA (413) | 0.95 | 2238 |
| | pvu-miR159a.1 | TTTGGATTGAAGGGAGCTCTA (414) | 0.95 | 2239 |
| | rco-miR159 | TTTGGATTGAAGGGAGCTCTA (415) | 0.95 | 2240 |
| | rin-miR159 | TTGGACTGAAGGGAGCTCCCT (416) | 0.81 | 2241 |
| | sar-miR159 | TTTGGATTGAAGGGAGCTCTG (417) | 0.95 | 2242 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sbi-miR159a | TTTGGATTGAAGGGAGCTCTG (418) | 0.95 | 2243 |
| | sbi-miR159b | CTTGGATTGAAGGGAGCTCCT (419) | 0.9 | 2244 |
| | sly-miR159 | TTTGGATTGAAGGGAGCTCTA (420) | 0.95 | 2245 |
| | smo-miR159 | CTTGGATTGAAGGGAGCTCCC (421) | 0.86 | 2246 |
| | sof-miR159a | TTTGGATTGAAGGGAGCTCTG (422) | 0.95 | 2247 |
| | sof-miR159b | TTTGGATTGAAGGGAGCTCTG (423) | 0.95 | 2248 |
| | sof-miR159c | CTTGGATTGAAGGGAGCTCCT (424) | 0.9 | 2249 |
| | sof-miR159d | TTTGGATTGAAGGGAGCTCTG (425) | 0.95 | 2250 |
| | sof-miR159e | TTTGGATTGAAAGGAGCTCTT (426) | 0.95 | 2251 |
| | spr-miR159 | TTTGGATTGAAGGGAGCTCTG (427) | 0.95 | 2252 |
| | ssp-miR159a | TTTGGATTGAAGGGAGCTCTG (428) | 0.95 | 2253 |
| | svi-miR159 | TTGGACTGAAGGGAGCTCCCT (429) | 0.81 | 2254 |
| | tae-miR159a | TTTGGATTGAAGGGAGCTCTG (430) | 0.95 | 2255 |
| | tae-miR159b | TTTGGATTGAAGGGAGCTCTG (431) | 0.95 | 2256 |
| | tar-miR159 | TTGGACTGAAGGGAGCTCCCT (432) | 0.81 | 2257 |
| | vvi-miR159a | CTTGGAGTGAAGGGAGCTCTC (433) | 0.86 | 2258 |
| | vvi-miR159b | CTTGGAGTGAAGGGAGCTCTC (434) | 0.86 | 2259 |
| | vvi-miR159c | TTTGGATTGAAGGGAGCTCTA (435) | 0.95 | 2260 |
| | zma-miR159a | TTTGGATTGAAGGGAGCTCTG (436) | 0.95 | 2261 |
| | zma-miR159b | TTTGGATTGAAGGGAGCTCTG (437) | 0.95 | 2262 |
| | zma-miR159c | CTTGGATTGAAGGGAGCTCCT (438) | 0.9 | 2263 |
| | zma-miR159d | CTTGGATTGAAGGGAGCTCCT (439) | 0.9 | 2264 |
| | zma-miR159e | ATTGGTTTGAAGGGAGCTCCA (440) | 0.81 | 2265 |
| | zma-miR159f | TTTGGATTGAAGGGAGCTCTG (441) | 0.95 | 2266 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR159g | TTTGGAGTGAAGGGAGTTCTG (442) | 0.86 | 2267 |
| | zma-miR159h | TTTGGAGTGAAGGGAGCTCTG (443) | 0.9 | 2268 |
| | zma-miR159i | TTTGGAGTGAAGGGAGCTCTG (444) | 0.9 | 2269 |
| | zma-miR159j | TTTGGATTGAAGGGAGCTCTG (445) | 0.95 | 2270 |
| | zma-miR159k | TTTGGATTGAAGGGAGCTCTG (446) | 0.95 | 2271 |
| | zma-miR159m | TTTGGATTGAAGGGAGCTCTG (447) | 0.95 | 2272 |
| ath-miR159c | acb-miR159 | TTGGACTGAAGGGAGCTCCCT (448) | 0.86 | 2273 |
| | aha-miR159 | TTGGACTGAAGGGAGCTCCCT (449) | 0.86 | 2274 |
| | ahi-miR159 | TTGGACTGAAGGGAGCTCCCT (450) | 0.86 | 2275 |
| | ahy-miR159 | TTTGGATTGAAGGGAGCTCTA (451) | 0.9 | 2276 |
| | aly-miR159a | TTTGGATTGAAGGGAGCTCTA (452) | 0.9 | 2277 |
| | aly-miR159b | TTTGGATTGAAGGGAGCTCTT (453) | 0.95 | 2278 |
| | aly-miR159c | TTTGGATTGAAGGGAGCTCCT (454) | 1 | 2279 |
| | ape-miR159 | TTGGACTGAAGGGAGCTCCCT (455) | 0.86 | 2280 |
| | aqc-miR159 | TTTGGACTGAAGGGAGCTCTA (456) | 0.86 | 2281 |
| | ath-miR159a | TTTGGATTGAAGGGAGCTCTA (457) | 0.9 | 2282 |
| | ath-miR159b | TTTGGATTGAAGGGAGCTCTT (458) | 0.95 | 2283 |
| | bdi-miR159 | CTTGGATTGAAGGGAGCTCT (459) | 0.86 | 2284 |
| | bna-miR159 | TTTGGATTGAAGGGAGCTCTA (460) | 0.9 | 2285 |
| | bra-miR159a | TTTGGATTGAAGGGAGCTCTA (461) | 0.9 | 2286 |
| | byl-miR159 | TTGGACTGAAGGGAGCTCCCT (462) | 0.86 | 2287 |
| | cmi-miR159 | TTGGACTGAAGGGAGCTCCCT (463) | 0.86 | 2288 |
| | cor-miR159 | TTGGACTGAAGGGAGCTCCCT (464) | 0.86 | 2289 |
| | crb-miR159 | TTGGACTGAAGGGAGCTCCCT (465) | 0.86 | 2290 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | csi-miR159 | TTTGGATTGAAGGGAGCTCTA (466) | 0.9 | 2291 |
| | dso-miR159 | TTGGACTGAAGGGAGCTCCCT (467) | 0.86 | 2292 |
| | ech-miR159 | TTGGACTGAAGGGAGCTCCCT (468) | 0.86 | 2293 |
| | fal-miR159 | TTGGACTGAAGGGAGCTCCCT (469) | 0.86 | 2294 |
| | far-miR159 | TTTGGATTGAAGGGAGCTCTG (470) | 0.9 | 2295 |
| | gma-miR159a-3p | TTTGGATTGAAGGGAGCTCTA (471) | 0.9 | 2296 |
| | gma-miR159b | ATTGGAGTGAAGGGAGCTCCA (472) | 0.86 | 2297 |
| | gma-miR159c | ATTGGAGTGAAGGGAGCTCCG (473) | 0.86 | 2298 |
| | hvu-miR159a | TTTGGATTGAAGGGAGCTCTG (474) | 0.9 | 2299 |
| | hvu-miR159b | TTTGGATTGAAGGGAGCTCTG (475) | 0.9 | 2300 |
| | hvv-miR159a | TTTGGATTGAAGGGAGCTCTG (476) | 0.9 | 2301 |
| | hvv-miR159b | TTTGGATTGAAGGGAGCTCTG (477) | 0.9 | 2302 |
| | ltu-miR159 | TTTGGATTGAAGGGAGCTCTA (478) | 0.9 | 2303 |
| | mma-miR159 | TTGGACTGAAGGGAGCTCCCT (479) | 0.86 | 2304 |
| | mtr-miR159a | TTTGGATTGAAGGGAGCTCTA (480) | 0.9 | 2305 |
| | mtr-miR159b | ATTGAATTGAAGGGAGCAACT (481) | 0.81 | 2306 |
| | mtr-miR159c | TTTGGATTGAAGGGAGCTCTA (482) | 0.9 | 2307 |
| | nof-miR159 | TTGGACTGAAGGGAGCTCCCT (483) | 0.86 | 2308 |
| | oru-miR159 | TTTGGATTGAAGGGAGCTCTG (484) | 0.9 | 2309 |
| | osa-miR159a | TTTGGATTGAAGGGAGCTCTG (485) | 0.9 | 2310 |
| | osa-miR159a.1 | TTTGGATTGAAGGGAGCTCTG (486) | 0.9 | 2311 |
| | osa-miR159b | TTTGGATTGAAGGGAGCTCTG (487) | 0.9 | 2312 |
| | osa-miR159c | ATTGGATTGAAGGGAGCTCCA (488) | 0.9 | 2313 |
| | osa-miR159d | ATTGGATTGAAGGGAGCTCCG (489) | 0.9 | 2314 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | osa-miR159e | ATTGGATTGAAGGGAGCTCCT (490) | 0.95 | 2315 |
| | osa-miR159f | CTTGGATTGAAGGGAGCTCTA (491) | 0.86 | 2316 |
| | osa-miR159m | TTTGGATTGAAGGGAGCTCTG (492) | 0.9 | 2317 |
| | pgl-miR159 | TTTGGATTGAAGGGAGCTCTG (493) | 0.9 | 2318 |
| | psi-miR159 | CTTGGATTGAAGGGAGCTCCA (494) | 0.9 | 2319 |
| | pta-miR159a | TTGGATTGAAGGGAGCTCCA (495) | 0.9 | 2320 |
| | pta-miR159b | TTGGATTGAAGAGAGCTCCC (496) | 0.86 | 2321 |
| | pta-miR159c | CTTGGATTGAAGGGAGCTCCC (497) | 0.9 | 2322 |
| | ptc-miR159a | TTTGGATTGAAGGGAGCTCTA (498) | 0.9 | 2323 |
| | ptc-miR159b | TTTGGATTGAAGGGAGCTCTA (499) | 0.9 | 2324 |
| | ptc-miR159c | TTTGGATTGAAGGGAGCTCTA (500) | 0.9 | 2325 |
| | ptc-miR159d | CTTGGATTGAAGGGAGCTCCT (501) | 0.95 | 2326 |
| | ptc-miR159e | CTTGGGGTGAAGGGAGCTCCT (502) | 0.86 | 2327 |
| | ptc-miR159f | ATTGGAGTGAAGGGAGCTCGA (503) | 0.81 | 2328 |
| | pvu-miR159 | TTTGGATTGAAGGGAGCTCTA (504) | 0.9 | 2329 |
| | pvu-miR159a.1 | TTTGGATTGAAGGGAGCTCTA (505) | 0.9 | 2330 |
| | rco-miR159 | TTTGGATTGAAGGGAGCTCTA (506) | 0.9 | 2331 |
| | rin-miR159 | TTGGACTGAAGGGAGCTCCCT (507) | 0.86 | 2332 |
| | sar-miR159 | TTTGGATTGAAGGGAGCTCTG (508) | 0.9 | 2333 |
| | sbi-miR159a | TTTGGATTGAAGGGAGCTCTG (509) | 0.9 | 2334 |
| | sbi-miR159b | CTTGGATTGAAGGGAGCTCCT (510) | 0.95 | 2335 |
| | sly-miR159 | TTTGGATTGAAGGGAGCTCTA (511) | 0.9 | 2336 |
| | smo-miR159 | CTTGGATTGAAGGGAGCTCCC (512) | 0.9 | 2337 |
| | sof-miR159a | TTTGGATTGAAGGGAGCTCTG (513) | 0.9 | 2338 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sof-miR159b | TTTGGATTGAAGGGAGCTCTG (514) | 0.9 | 2339 |
| | sof-miR159c | CTTGGATTGAAGGGAGCTCCT (515) | 0.95 | 2340 |
| | sof-miR159d | TTTGGATTGAAGGGAGCTCTG (516) | 0.9 | 2341 |
| | sof-miR159e | TTTGGATTGAAAGGAGCTCTT (517) | 0.9 | 2342 |
| | spr-miR159 | TTTGGATTGAAGGGAGCTCTG (518) | 0.9 | 2343 |
| | ssp-miR159a | TTTGGATTGAAGGGAGCTCTG (519) | 0.9 | 2344 |
| | svi-miR159 | TTGGACTGAAGGGAGCTCCCT (520) | 0.86 | 2345 |
| | tae-miR159a | TTTGGATTGAAGGGAGCTCTG (521) | 0.9 | 2346 |
| | tae-miR159b | TTTGGATTGAAGGGAGCTCTG (522) | 0.9 | 2347 |
| | tar-miR159 | TTGGACTGAAGGGAGCTCCCT (523) | 0.86 | 2348 |
| | vvi-miR159a | CTTGGAGTGAAGGGAGCTCTC (524) | 0.81 | 2349 |
| | vvi-miR159b | CTTGGAGTGAAGGGAGCTCTC (525) | 0.81 | 2350 |
| | vvi-miR159c | TTTGGATTGAAGGGAGCTCTA (526) | 0.9 | 2351 |
| | zma-miR159a | TTTGGATTGAAGGGAGCTCTG (527) | 0.9 | 2352 |
| | zma-miR159b | TTTGGATTGAAGGGAGCTCTG (528) | 0.9 | 2353 |
| | zma-miR159c | CTTGGATTGAAGGGAGCTCCT (529) | 0.95 | 2354 |
| | zma-miR159d | CTTGGATTGAAGGGAGCTCCT (530) | 0.95 | 2355 |
| | zma-miR159e | ATTGGTTTGAAGGGAGCTCCA (531) | 0.86 | 2356 |
| | zma-miR159f | TTTGGATTGAAGGGAGCTCTG (532) | 0.9 | 2357 |
| | zma-miR159g | TTTGGAGTGAAGGGAGTTCTG (533) | 0.81 | 2358 |
| | zma-miR159h | TTTGGAGTGAAGGGAGCTCTG (534) | 0.86 | 2359 |
| | zma-miR159i | TTTGGAGTGAAGGGAGCTCTG (535) | 0.86 | 2360 |
| | zma-miR159j | TTTGGATTGAAGGGAGCTCTG (536) | 0.9 | 2361 |
| | zma-miR159k | TTTGGATTGAAGGGAGCTCTG (537) | 0.9 | 2362 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR159m | TTTGGATTGAAGGGAGCTCTG (538) | 0.9 | 2363 |
| ath-miRf10687-akr | gma-miRf10687-akr-homolog | TTAGCCGCAGAGGCAGAGGAG (11616) | 0.86 | 11615 |
| ghr-miR2950 | vvi-miR2950* | TGGTGTGCACGGGATGGAATA (539) | 0.9 | 2364 |
| gma-miR156g | ahy-miR156a | TGACAGAAGAGAGAGAGCAC (540) | 0.85 | 2365 |
| | ahy-miR156b-5p | TTGACAGAAGATAGAGAGCAC (541) | 0.9 | 2366 |
| | ahy-miR156c | TTGACAGAAGAGAGAGAGCAC (542) | 0.85 | 2367 |
| | aly-miR156a | TGACAGAAGAGAGTGAGCAC (543) | 0.8 | 2368 |
| | aly-miR156b | TGACAGAAGAGAGTGAGCAC (544) | 0.8 | 2369 |
| | aly-miR156c | TGACAGAAGAGAGTGAGCAC (545) | 0.8 | 2370 |
| | aly-miR156d | TGACAGAAGAGAGTGAGCAC (546) | 0.8 | 2371 |
| | aly-miR156e | TGACAGAAGAGAGTGAGCAC (547) | 0.8 | 2372 |
| | aly-miR156f | TGACAGAAGAGAGTGAGCAC (548) | 0.8 | 2373 |
| | aly-miR156g | CGACAGAAGAGAGTGAGCAC (549) | 0.8 | 2374 |
| | aly-miR156h | TGACAGAAGAAAGAGAGCAC (550) | 0.85 | 2375 |
| | aqc-miR156a | TGACAGAAGATAGAGAGCAC (551) | 0.9 | 2376 |
| | aqc-miR156b | TGACAGAAGATAGAGAGCAC (552) | 0.9 | 2377 |
| | ath-miR156a | TGACAGAAGAGAGTGAGCAC (553) | 0.8 | 2378 |
| | ath-miR156b | TGACAGAAGAGAGTGAGCAC (554) | 0.8 | 2379 |
| | ath-miR156c | TGACAGAAGAGAGTGAGCAC (555) | 0.8 | 2380 |
| | ath-miR156d | TGACAGAAGAGAGTGAGCAC (556) | 0.8 | 2381 |
| | ath-miR156e | TGACAGAAGAGAGTGAGCAC (557) | 0.8 | 2382 |
| | ath-miR156f | TGACAGAAGAGAGTGAGCAC (558) | 0.8 | 2383 |
| | ath-miR156g | CGACAGAAGAGAGTGAGCAC (559) | 0.8 | 2384 |
| | ath-miR156h | TGACAGAAGAAAGAGAGCAC (560) | 0.85 | 2385 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | bdi-miR156 | TGACAGAAGAGAGAGA GCACA (561) | 0.9 | 2386 |
| | bdi-miR156b | TGACAGAAGAGAGTGA GCAC (562) | 0.8 | 2387 |
| | bdi-miR156c | TGACAGAAGAGAGTGA GCAC (563) | 0.8 | 2388 |
| | bdi-miR156d | TGACAGAAGAGAGTGA GCAC (564) | 0.8 | 2389 |
| | bna-miR156a | TGACAGAAGAGAGTGA GCACA (565) | 0.85 | 2390 |
| | bna-miR156b | TTGACAGAAGATAGAG AGCAC (566) | 0.9 | 2391 |
| | bna-miR156c | TTGACAGAAGATAGAG AGCAC (567) | 0.9 | 2392 |
| | csi-miR156 | TGACAGAAGAGAGTGA GCAC (568) | 0.8 | 2393 |
| | ctr-miR156 | TGACAGAAGAGAGTGA GCAC (569) | 0.8 | 2394 |
| | far-miR156a | TGACAGAAGAGAGAGA GCACA (570) | 0.9 | 2395 |
| | far-miR156b | TTGACAGAAGAGAGAG AGCAC (571) | 0.85 | 2396 |
| | ghr-miR156a | TGACAGAAGAGAGTGA GCAC (572) | 0.8 | 2397 |
| | ghr-miR156b | TGACAGAAGAGAGTGA GCAC (573) | 0.8 | 2398 |
| | ghr-miR156c | TGTCAGAAGAGAGTGA GCAC (574) | 0.75 | 2399 |
| | ghr-miR156d | TGACAGAAGAGAGTGA GCAC (575) | 0.8 | 2400 |
| | gma-miR156a | TGACAGAAGAGAGTGA GCAC (576) | 0.8 | 2401 |
| | gma-miR156b | TGACAGAAGAGAGAGA GCACA (577) | 0.9 | 2402 |
| | gma-miR156c | TTGACAGAAGATAGAG AGCAC (578) | 0.9 | 2403 |
| | gma-miR156d | TTGACAGAAGATAGAG AGCAC (579) | 0.9 | 2404 |
| | gma-miR156e | TTGACAGAAGATAGAG AGCAC (580) | 0.9 | 2405 |
| | gma-miR156f | TTGACAGAAGAGAGAG AGCACA (581) | 0.9 | 2406 |
| | hvu-miR156 | TGACAGAAGAGAGTGA GCACA (582) | 0.85 | 2407 |
| | mtr-miR156 | TGACAGAAGAGAGAGA GCACA (583) | 0.9 | 2408 |
| | mtr-miR156b | TGACAGAAGAGAGTGA GCAC (584) | 0.8 | 2409 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | mtr-miR156c | TGACAGAAGAGAGTGAGCAC (585) | 0.8 | 2410 |
| | mtr-miR156d | TGACAGAAGAGAGTGAGCAC (586) | 0.8 | 2411 |
| | mtr-miR156e | TTGACAGAAGATAGAGAGCAC (587) | 0.9 | 2412 |
| | mtr-miR156f | TTGACAGAAGATAGAGAGCAC (588) | 0.9 | 2413 |
| | mtr-miR156g | TTGACAGAAGATAGAGGGCAC (589) | 0.85 | 2414 |
| | mtr-miR156h | TTGACAGAAGATAGAGAGCAC (590) | 0.9 | 2415 |
| | mtr-miR156i | TGACAGAAGAGAGTGAGCAC (591) | 0.8 | 2416 |
| | osa-miR156a | TGACAGAAGAGAGTGAGCAC (592) | 0.8 | 2417 |
| | osa-miR156b | TGACAGAAGAGAGTGAGCAC (593) | 0.8 | 2418 |
| | osa-miR156c | TGACAGAAGAGAGTGAGCAC (594) | 0.8 | 2419 |
| | osa-miR156d | TGACAGAAGAGAGTGAGCAC (595) | 0.8 | 2420 |
| | osa-miR156e | TGACAGAAGAGAGTGAGCAC (596) | 0.8 | 2421 |
| | osa-miR156f | TGACAGAAGAGAGTGAGCAC (597) | 0.8 | 2422 |
| | osa-miR156g | TGACAGAAGAGAGTGAGCAC (598) | 0.8 | 2423 |
| | osa-miR156h | TGACAGAAGAGAGTGAGCAC (599) | 0.8 | 2424 |
| | osa-miR156i | TGACAGAAGAGAGTGAGCAC (600) | 0.8 | 2425 |
| | osa-miR156j | TGACAGAAGAGAGTGAGCAC (601) | 0.8 | 2426 |
| | osa-miR156k | TGACAGAAGAGAGAGAGCACA (602) | 0.9 | 2427 |
| | osa-miR156l | CGACAGAAGAGAGTGAGCATA (603) | 0.8 | 2428 |
| | ppt-miR156a | TGACAGAAGAGAGTGAGCAC (604) | 0.8 | 2429 |
| | ppt-miR156b | TGACAGAAGAGAGTGAGCAC (605) | 0.8 | 2430 |
| | ppt-miR156c | TGACAGAAGAGAGTGAGCAC (606) | 0.8 | 2431 |
| | pta-miR156a | CAGAAGATAGAGAGCACATC (607) | 0.9 | 2432 |
| | pta-miR156b | CAGAAGATAGAGAGCACAAC (608) | 0.9 | 2433 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ptc-miR156a | TGACAGAAGAGAGTGAGCAC (609) | 0.8 | 2434 |
| | ptc-miR156b | TGACAGAAGAGAGTGAGCAC (610) | 0.8 | 2435 |
| | ptc-miR156c | TGACAGAAGAGAGTGAGCAC (611) | 0.8 | 2436 |
| | ptc-miR156d | TGACAGAAGAGAGTGAGCAC (612) | 0.8 | 2437 |
| | ptc-miR156e | TGACAGAAGAGAGTGAGCAC (613) | 0.8 | 2438 |
| | ptc-miR156f | TGACAGAAGAGAGTGAGCAC (614) | 0.8 | 2439 |
| | ptc-miR156g | TTGACAGAAGATAGAGAGCAC (615) | 0.9 | 2440 |
| | ptc-miR156h | TTGACAGAAGATAGAGAGCAC (616) | 0.9 | 2441 |
| | ptc-miR156i | TTGACAGAAGATAGAGAGCAC (617) | 0.9 | 2442 |
| | ptc-miR156j | TTGACAGAAGATAGAGAGCAC (618) | 0.9 | 2443 |
| | ptc-miR156k | TGACAGAAGAGAGGGAGCAC (619) | 0.8 | 2444 |
| | rco-miR156a | TGACAGAAGAGAGTGAGCACA (620) | 0.85 | 2445 |
| | rco-miR156b | TGACAGAAGAGAGTGAGCACA (621) | 0.85 | 2446 |
| | rco-miR156c | TGACAGAAGAGAGTGAGCACA (622) | 0.85 | 2447 |
| | rco-miR156d | TGACAGAAGAGAGTGAGCACA (623) | 0.85 | 2448 |
| | rco-miR156e | TGACAGAAGAGAGAGAGCACA (624) | 0.9 | 2449 |
| | rco-miR156f | TTGACAGAAGATAGAGAGCAC (625) | 0.9 | 2450 |
| | rco-miR156g | TTGACAGAAGATAGAGAGCAC (626) | 0.9 | 2451 |
| | rco-miR156h | TTGACAGAAGATAGAGAGCAC (627) | 0.9 | 2452 |
| | sbi-miR156a | TGACAGAAGAGAGTGAGCAC (628) | 0.8 | 2453 |
| | sbi-miR156b | TGACAGAAGAGAGTGAGCAC (629) | 0.8 | 2454 |
| | sbi-miR156c | TGACAGAAGAGAGTGAGCAC (630) | 0.8 | 2455 |
| | sbi-miR156d | TGACAGAAGAGAGAGAGCACA (631) | 0.9 | 2456 |
| | sbi-miR156e | TGACAGAAGAGAGAGCGAGCAC (632) | 0.8 | 2457 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sbi-miR156f | TGACAGAAGAGAGTGAGCAC (633) | 0.8 | 2458 |
| | sbi-miR156g | TGACAGAAGAGAGTGAGCAC (634) | 0.8 | 2459 |
| | sbi-miR156h | TGACAGAAGAGAGTGAGCAC (635) | 0.8 | 2460 |
| | sbi-miR156i | TGACAGAAGAGAGTGAGCAC (636) | 0.8 | 2461 |
| | sly-miR156a | TTGACAGAAGATAGAGAGCAC (637) | 0.9 | 2462 |
| | sly-miR156b | TTGACAGAAGATAGAGAGCAC (638) | 0.9 | 2463 |
| | sly-miR156c | TTGACAGAAGATAGAGAGCAC (639) | 0.9 | 2464 |
| | smo-miR156a | CGACAGAAGAGAGTGAGCAC (640) | 0.8 | 2465 |
| | smo-miR156b | CTGACAGAAGATAGAGAGCAC (641) | 0.9 | 2466 |
| | smo-miR156c | TTGACAGAAGAAAGAGAGCAC (642) | 0.85 | 2467 |
| | smo-miR156d | TTGACAGAAGACAGGGAGCAC (643) | 0.8 | 2468 |
| | sof-miR156 | TGACAGAAGAGAGTGAGCAC (644) | 0.8 | 2469 |
| | ssp-miR156 | TGACAGAAGAGAGTGAGCACA (645) | 0.85 | 2470 |
| | tae-miR156 | TGACAGAAGAGAGTGAGCACA (646) | 0.85 | 2471 |
| | tcc-miR156a | TGACAGAAGAGAGAGAGCACA (647) | 0.9 | 2472 |
| | tcc-miR156b | TGACAGAAGAGAGTGAGCAC (648) | 0.8 | 2473 |
| | tcc-miR156c | TGACAGAAGAGAGTGAGCAC (649) | 0.8 | 2474 |
| | tcc-miR156d | TGACAGAAGAGAGTGAGCAC (650) | 0.8 | 2475 |
| | tcc-miR156e | TTGACAGAAGATAGAGAGCAC (651) | 0.9 | 2476 |
| | tcc-miR156f | TTGACAGAAGATAGAGAGCAC (652) | 0.9 | 2477 |
| | tcc-miR156g | TGACAGAAGAGAGTGAGCAC (653) | 0.8 | 2478 |
| | vvi-miR156a | TGACAGAAGAGAGGGAGCAC (654) | 0.8 | 2479 |
| | vvi-miR156b | TGACAGAAGAGAGTGAGCAC (655) | 0.8 | 2480 |
| | vvi-miR156c | TGACAGAAGAGAGTGAGCAC (656) | 0.8 | 2481 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | vvi-miR156d | TGACAGAAGAGAGTGAGCAC (657) | 0.8 | 2482 |
| | vvi-miR156e | TGACAGAGGAGAGTGAGCAC (658) | 0.75 | 2483 |
| | vvi-miR156f | TTGACAGAAGATAGAGAGCAC (659) | 0.9 | 2484 |
| | vvi-miR156g | TTGACAGAAGATAGAGAGCAC (660) | 0.9 | 2485 |
| | vvi-miR156h | TGACAGAAGAGAGAGAGCAT (661) | 0.8 | 2486 |
| | vvi-miR156i | TTGACAGAAGATAGAGAGCAC (662) | 0.9 | 2487 |
| | zma-miR156a | TGACAGAAGAGAGTGAGCAC (663) | 0.8 | 2488 |
| | zma-miR156b | TGACAGAAGAGAGTGAGCAC (664) | 0.8 | 2489 |
| | zma-miR156c | TGACAGAAGAGAGTGAGCAC (665) | 0.8 | 2490 |
| | zma-miR156d | TGACAGAAGAGAGTGAGCAC (666) | 0.8 | 2491 |
| | zma-miR156e | TGACAGAAGAGAGTGAGCAC (667) | 0.8 | 2492 |
| | zma-miR156f | TGACAGAAGAGAGTGAGCAC (668) | 0.8 | 2493 |
| | zma-miR156g | TGACAGAAGAGAGTGAGCAC (669) | 0.8 | 2494 |
| | zma-miR156h | TGACAGAAGAGAGTGAGCAC (670) | 0.8 | 2495 |
| | zma-miR156i | TGACAGAAGAGAGTGAGCAC (671) | 0.8 | 2496 |
| | zma-miR156j | TGACAGAAGAGAGAGAGCACA (672) | 0.9 | 2497 |
| | zma-miR156k | TGACAGAAGAGAGCGAGCAC (673) | 0.8 | 2498 |
| | zma-miR156l | TGACAGAAGAGAGTGAGCAC (674) | 0.8 | 2499 |
| gma-miR157c | ahy-miR157a-5p | TTGACAGAAGATAGAGAGCAC (675) | 0.95 | 2500 |
| | ahy-miR157k | TTGACAGAAGAGAGAGAGCAC (676) | 0.9 | 2501 |
| | aly-miR157a | TTGACAGAAGATAGAGAGCAC (677) | 0.95 | 2502 |
| | aly-miR157b | TTGACAGAAGATAGAGAGCAC (678) | 0.95 | 2503 |
| | aly-miR157c | TTGACAGAAGATAGAGAGCAC (679) | 0.95 | 2504 |
| | aly-miR157d | TGACAGAAGATAGAGAGCAC (680) | 0.95 | 2505 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ath-miR157a | TTGACAGAAGATAGAGAGCAC (681) | 0.95 | 2506 |
| | ath-miR157b | TTGACAGAAGATAGAGAGCAC (682) | 0.95 | 2507 |
| | ath-miR157c | TTGACAGAAGATAGAGAGCAC (683) | 0.95 | 2508 |
| | ath-miR157d | TGACAGAAGATAGAGAGCAC (684) | 0.95 | 2509 |
| | ath-miR157m | TTGACAGAAGAGAGAGAGCAC (685) | 0.9 | 2510 |
| | bol-miR157a | TTGACAGAAGATAGAGAGCAC (686) | 0.95 | 2511 |
| | bra-miR157a | TTGACAGAAGATAGAGAGCAC (687) | 0.95 | 2512 |
| | can-miR157 | TTGACAGAAGAGAGAGAGCAC (688) | 0.9 | 2513 |
| | ghr-miR157 | ATGACAGAAGAGAGAGAGCAC (689) | 0.9 | 2514 |
| | gma-miR157r | TTGACAGAAGAGAGAGAGCAC (690) | 0.9 | 2515 |
| | gra-miR157a | TTGACAGAAGATAGAGAGCAC (691) | 0.95 | 2516 |
| | gra-miR157b | TTGACAGAAGATAGAGAGCAC (692) | 0.95 | 2517 |
| | gra-miR157c | TTGACAGAAGAGAGAGAGCAC (693) | 0.9 | 2518 |
| | gra-miR157d | TTGACAGAAGAGAGAGAGCAC (694) | 0.9 | 2519 |
| | han-miR157a | TTGACAGAAGATAGAGAGCAC (695) | 0.95 | 2520 |
| | han-miR157b | TTGACAGAAGAGAGAGAGCAC (696) | 0.9 | 2521 |
| | iba-miR157 | TTGACAGAAGATAGAGAGCAT (697) | 0.9 | 2522 |
| | ini-miR157a | TTGACAGAAGATAGAGAGCAT (698) | 0.9 | 2523 |
| | ini-miR157b | TTGACAGAAGATAGAGAGCAT (699) | 0.9 | 2524 |
| | lja-miR157a | TTGACAGAAGATAGAGAGCAC (700) | 0.95 | 2525 |
| | lja-miR157b | TTGACAGAAGAGAGAGAGCAC (701) | 0.9 | 2526 |
| | lja-miR157c | TTGACAGAAGATAGAGAGCAT (702) | 0.9 | 2527 |
| | lsa-miR157 | TTGACAGAAGAGAGAGAGCAC (703) | 0.9 | 2528 |
| | mtr-miR157 | TTGACAGAAGATAGAGGGCAC (704) | 0.9 | 2529 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | nad-miR157a | TTGACAGAAGACAGAGAGCAC (705) | 0.95 | 2530 |
| | nad-miR157b | TTGACAGAAGACAGAGAGCAC (706) | 0.95 | 2531 |
| | nad-miR157c | TTGACAGAAGACAGAGAGCAC (707) | 0.95 | 2532 |
| | nbe-miR157a | TTGACAGAAGAGAGAGAGCAC (708) | 0.9 | 2533 |
| | nbe-miR157b | TTGACAGAAGAGAGAGAGCAC (709) | 0.9 | 2534 |
| | nta-miR157 | TTGACAGAAGATAGAGAGCAC (710) | 0.95 | 2535 |
| | pam-miR157 | TTGACAGAAGAGAGAGAGCAC (711) | 0.9 | 2536 |
| | par-miR157 | TTGACAGAAGAGAGAGAGCAC (712) | 0.9 | 2537 |
| | pco-miR157 | TTGACAGAAGATAGAGAGCAT (713) | 0.9 | 2538 |
| | pts-miR157 | TTGACAGAAGAGAGAGAGCAC (714) | 0.9 | 2539 |
| | sbi-miR157 | TTGACAGAAGAGAGAGTGAGCAC (715) | 0.86 | 2540 |
| | sin-miR157 | TTGACAGAAGAGAGAGAGCAC (716) | 0.9 | 2541 |
| | sly-miR157a | TTGACAGAAGATAGAGAGCAT (717) | 0.9 | 2542 |
| | sly-miR157b | TTGACAGAAGATAGAGAGCAT (718) | 0.9 | 2543 |
| | sly-miR157c | TTGACAGAAGATAGAGAGCAT (719) | 0.9 | 2544 |
| | stu-miR157a | TTGACAGAAGATAGAGAGCAC (720) | 0.95 | 2545 |
| | stu-miR157b | TTGACAGAAGAGAGAGAGCAC (721) | 0.9 | 2546 |
| | stu-miR157c | TTGACAGAAGAGAGAGAGCAC (722) | 0.9 | 2547 |
| | zel-miR157 | TTGACAGAAGAGAGAGAGCAC (723) | 0.9 | 2548 |
| | zma-miR157m | TTGACAGAAGAGAGAGAGCAC (724) | 0.9 | 2549 |
| iba-miR157 | ahy-miR157a-5p | TTGACAGAAGATAGAGAGCAC (725) | 0.95 | 2550 |
| | ahy-miR157k | TTGACAGAAGAGAGAGAGCAC (726) | 0.9 | 2551 |
| | aly-miR157a | TTGACAGAAGATAGAGAGCAC (727) | 0.95 | 2552 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | aly-miR157b | TTGACAGAAGATAGAGAGCAC (728) | 0.95 | 2553 |
| | aly-miR157c | TTGACAGAAGATAGAGAGCAC (729) | 0.95 | 2554 |
| | aly-miR157d | TGACAGAAGATAGAGAGCAC (730) | 0.9 | 2555 |
| | ath-miR157a | TTGACAGAAGATAGAGAGCAC (731) | 0.95 | 2556 |
| | ath-miR157b | TTGACAGAAGATAGAGAGCAC (732) | 0.95 | 2557 |
| | ath-miR157c | TTGACAGAAGATAGAGAGCAC (733) | 0.95 | 2558 |
| | ath-miR157d | TGACAGAAGATAGAGAGCAC (734) | 0.9 | 2559 |
| | ath-miR157m | TTGACAGAAGAGAGAGAGCAC (735) | 0.9 | 2560 |
| | bol-miR157a | TTGACAGAAGATAGAGAGCAC (736) | 0.95 | 2561 |
| | bra-miR157a | TTGACAGAAGATAGAGAGCAC (737) | 0.95 | 2562 |
| | can-miR157 | TTGACAGAAGAGAGAGAGCAC (738) | 0.9 | 2563 |
| | ghr-miR157 | ATGACAGAAGAGAGAGAGCAC (739) | 0.86 | 2564 |
| | gma-miR157c | TGACAGAAGACTAGAGAGCAC (740) | 0.9 | 2565 |
| | gma-miR157r | TTGACAGAAGAGAGAGAGCAC (741) | 0.9 | 2566 |
| | gra-miR157a | TTGACAGAAGATAGAGAGCAC (742) | 0.95 | 2567 |
| | gra-miR157b | TTGACAGAAGATAGAGAGCAC (743) | 0.95 | 2568 |
| | gra-miR157c | TTGACAGAAGAGAGAGAGCAC (744) | 0.9 | 2569 |
| | gra-miR157d | TTGACAGAAGAGAGAGAGCAC (745) | 0.9 | 2570 |
| | han-miR157a | TTGACAGAAGATAGAGAGCAC (746) | 0.95 | 2571 |
| | han-miR157b | TTGACAGAAGAGAGAGAGCAC (747) | 0.9 | 2572 |
| | ini-miR157a | TTGACAGAAGATAGAGAGCAT (748) | 1 | 2573 |
| | ini-miR157b | TTGACAGAAGATAGAGAGCAT (749) | 1 | 2574 |
| | lja-miR157a | TTGACAGAAGATAGAGAGCAC (750) | 0.95 | 2575 |
| | lja-miR157b | TTGACAGAAGAGAGAGAGCAC (751) | 0.9 | 2576 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | lja-miR157c | TTGACAGAAGATAGAGAGCAT (752) | 1 | 2577 |
| | lsa-miR157 | TTGACAGAAGAGAGAGAGCAC (753) | 0.9 | 2578 |
| | mtr-miR157 | TTGACAGAAGATAGAGGGCAC (754) | 0.9 | 2579 |
| | nad-miR157a | TTGACAGAAGACAGAGAGCAC (755) | 0.9 | 2580 |
| | nad-miR157b | TTGACAGAAGACAGAGAGCAC (756) | 0.9 | 2581 |
| | nad-miR157c | TTGACAGAAGACAGAGAGCAC (757) | 0.9 | 2582 |
| | nbe-miR157a | TTGACAGAAGAGAGAGAGCAC (758) | 0.9 | 2583 |
| | nbe-miR157b | TTGACAGAAGAGAGAGAGCAC (759) | 0.9 | 2584 |
| | nta-miR157 | TTGACAGAAGATAGAGAGCAC (760) | 0.95 | 2585 |
| | pam-miR157 | TTGACAGAAGAGAGAGAGCAC (761) | 0.9 | 2586 |
| | par-miR157 | TTGACAGAAGAGAGAGAGCAC (762) | 0.9 | 2587 |
| | pco-miR157 | TTGACAGAAGATAGAGAGCAT (763) | 1 | 2588 |
| | pts-miR157 | TTGACAGAAGAGAGAGAGCAC (764) | 0.9 | 2589 |
| | sbi-miR157 | TTGACAGAAGAGAGTGAGCAC (765) | 0.86 | 2590 |
| | sin-miR157 | TTGACAGAAGAGAGAGAGCAC (766) | 0.9 | 2591 |
| | sly-miR157a | TTGACAGAAGATAGAGAGCAT (767) | 1 | 2592 |
| | sly-miR157b | TTGACAGAAGATAGAGAGCAT (768) | 1 | 2593 |
| | sly-miR157c | TTGACAGAAGATAGAGAGCAT (769) | 1 | 2594 |
| | stu-miR157a | TTGACAGAAGATAGAGAGCAC (770) | 0.95 | 2595 |
| | stu-miR157b | TTGACAGAAGAGAGAGAGCAC (771) | 0.9 | 2596 |
| | stu-miR157c | TTGACAGAAGAGAGAGAGCAC (772) | 0.9 | 2597 |
| | zel-miR157 | TTGACAGAAGAGAGAGAGCAC (773) | 0.9 | 2598 |
| | zma-miR157m | TTGACAGAAGAGAGAGAGCAC (774) | 0.9 | 2599 |
| mdm-miR482a-5p | gma-miR482b-5p | TATGGGGGGATTGGGAAGGAAT (775) | 0.62 | 2600 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | mdo-miR482* | GGAATGGGCTGTTTGGGAACA (776) | 1 | 2601 |
| | pvu-miR482* | GGAATGGGCTGATTGGGAAGCA (777) | 0.95 | 2602 |
| osa-miR159e | acb-miR159 | TTGGACTGAAGGGAGCTCCCT (778) | 0.86 | 2603 |
| | aha-miR159 | TTGGACTGAAGGGAGCTCCCT (779) | 0.86 | 2604 |
| | ahi-miR159 | TTGGACTGAAGGGAGCTCCCT (780) | 0.86 | 2605 |
| | ahy-miR159 | TTTGGATTGAAGGGAGCTCTA (781) | 0.86 | 2606 |
| | aly-miR159a | TTTGGATTGAAGGGAGCTCTA (782) | 0.86 | 2607 |
| | aly-miR159b | TTTGGATTGAAGGGAGCTCTT (783) | 0.9 | 2608 |
| | aly-miR159c | TTTGGATTGAAGGGAGCTCCT (784) | 0.95 | 2609 |
| | ape-miR159 | TTGGACTGAAGGGAGCTCCCT (785) | 0.86 | 2610 |
| | aqc-miR159 | TTTGGACTGAAGGGAGCTCTA (786) | 0.81 | 2611 |
| | ath-miR159a | TTTGGATTGAAGGGAGCTCTA (787) | 0.86 | 2612 |
| | ath-miR159b | TTTGGATTGAAGGGAGCTCTT (788) | 0.9 | 2613 |
| | ath-miR159c | TTTGGATTGAAGGGAGCTCCT (789) | 0.95 | 2614 |
| | bdi-miR159 | CTTGGATTGAAGGGAGCTCT (790) | 0.86 | 2615 |
| | bna-miR159 | TTTGGATTGAAGGGAGCTCTA (791) | 0.86 | 2616 |
| | bra-miR159a | TTTGGATTGAAGGGAGCTCTA (792) | 0.86 | 2617 |
| | bvl-miR159 | TTGGACTGAAGGGAGCTCCCT (793) | 0.86 | 2618 |
| | cmi-miR159 | TTGGACTGAAGGGAGCTCCCT (794) | 0.86 | 2619 |
| | cor-miR159 | TTGGACTGAAGGGAGCTCCCT (795) | 0.86 | 2620 |
| | crb-miR159 | TTGGACTGAAGGGAGCTCCCT (796) | 0.86 | 2621 |
| | csi-miR159 | TTTGGATTGAAGGGAGCTCTA (797) | 0.86 | 2622 |
| | dso-miR159 | TTGGACTGAAGGGAGCTCCCT (798) | 0.86 | 2623 |
| | ech-miR159 | TTGGACTGAAGGGAGCTCCCT (799) | 0.86 | 2624 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | fal-miR159 | TTGGACTGAAGGGAGCTCCCT (800) | 0.86 | 2625 |
| | far-miR159 | TTTGGATTGAAGGGAGCTCTG (801) | 0.86 | 2626 |
| | gma-miR159a-3p | TTTGGATTGAAGGGAGCTCTA (802) | 0.86 | 2627 |
| | gma-miR159b | ATTGGAGTGAAGGGAGCTCCA (803) | 0.9 | 2628 |
| | gma-miR159c | ATTGGAGTGAAGGGAGCTCCG (804) | 0.9 | 2629 |
| | hvu-miR159a | TTTGGATTGAAGGGAGCTCTG (805) | 0.86 | 2630 |
| | hvu-miR159b | TTTGGATTGAAGGGAGCTCTG (806) | 0.86 | 2631 |
| | hvv-miR159a | TTTGGATTGAAGGGAGCTCTG (807) | 0.86 | 2632 |
| | hvv-miR159b | TTTGGATTGAAGGGAGCTCTG (808) | 0.86 | 2633 |
| | ltu-miR159 | TTTGGATTGAAGGGAGCTCTA (809) | 0.86 | 2634 |
| | mma-miR159 | TTGGACTGAAGGGAGCTCCCT (810) | 0.86 | 2635 |
| | mtr-miR159a | TTTGGATTGAAGGGAGCTCTA (811) | 0.86 | 2636 |
| | mtr-miR159b | ATTGAATTGAAGGGAGCAACT (812) | 0.86 | 2637 |
| | mtr-miR159c | TTTGGATTGAAGGGAGCTCTA (813) | 0.86 | 2638 |
| | nof-miR159 | TTGGACTGAAGGGAGCTCCCT (814) | 0.86 | 2639 |
| | oru-miR159 | TTTGGATTGAAGGGAGCTCTG (815) | 0.86 | 2640 |
| | osa-miR159a | TTTGGATTGAAGGGAGCTCTG (816) | 0.86 | 2641 |
| | osa-miR159a.1 | TTTGGATTGAAGGGAGCTCTG (817) | 0.86 | 2642 |
| | osa-miR159b | TTTGGATTGAAGGGAGCTCTG (818) | 0.86 | 2643 |
| | osa-miR159c | ATTGGATTGAAGGGAGCTCCA (819) | 0.95 | 2644 |
| | osa-miR159d | ATTGGATTGAAGGGAGCTCCG (820) | 0.95 | 2645 |
| | osa-miR159f | CTTGGATTGAAGGGAGCTCTA (821) | 0.86 | 2646 |
| | osa-miR159m | TTTGGATTGAAGGGAGCTCTG (822) | 0.86 | 2647 |
| | pgl-miR159 | TTTGGATTGAAGGGAGCTCTG (823) | 0.86 | 2648 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | psi-miR159 | CTTGGATTGAAGGGAGCTCCA (824) | 0.9 | 2649 |
| | pta-miR159a | TTGGATTGAAGGGAGCTCCA (825) | 0.9 | 2650 |
| | pta-miR159b | TTGGATTGAAGAGAGCTCCC (826) | 0.86 | 2651 |
| | pta-miR159c | CTTGGATTGAAGGGAGCTCCC (827) | 0.9 | 2652 |
| | ptc-miR159a | TTTGGATTGAAGGGAGCTCTA (828) | 0.86 | 2653 |
| | ptc-miR159b | TTTGGATTGAAGGGAGCTCTA (829) | 0.86 | 2654 |
| | ptc-miR159c | TTTGGATTGAAGGGAGCTCTA (830) | 0.86 | 2655 |
| | ptc-miR159d | CTTGGATTGAAGGGAGCTCCT (831) | 0.95 | 2656 |
| | ptc-miR159e | CTTGGGGTGAAGGGAGCTCCT (832) | 0.86 | 2657 |
| | ptc-miR159f | ATTGGAGTGAAGGGAGCTCGA (833) | 0.86 | 2658 |
| | pvu-miR159 | TTTGGATTGAAGGGAGCTCTA (834) | 0.86 | 2659 |
| | pvu-miR159.2 | CTTCCATATCTGGGAGCTTC (835) | 0.62 | 2660 |
| | pvu-miR159a.1 | TTTGGATTGAAGGGAGCTCTA (836) | 0.86 | 2661 |
| | pvu-miR159a.2 | CTTCCATATCTGGGAGCTTC (837) | 0.62 | 2662 |
| | rco-miR159 | TTTGGATTGAAGGGAGCTCTA (838) | 0.86 | 2663 |
| | rin-miR159 | TTGGACTGAAGGGAGCTCCCT (839) | 0.86 | 2664 |
| | sar-miR159 | TTTGGATTGAAGGGAGCTCTG (840) | 0.86 | 2665 |
| | sbi-miR159a | TTTGGATTGAAGGGAGCTCTG (841) | 0.86 | 2666 |
| | sbi-miR159b | CTTGGATTGAAGGGAGCTCCT (842) | 0.95 | 2667 |
| | sly-miR159 | TTTGGATTGAAGGGAGCTCTA (843) | 0.86 | 2668 |
| | smo-miR159 | CTTGGATTGAAGGGAGCTCCC (844) | 0.9 | 2669 |
| | sof-miR159a | TTTGGATTGAAGGGAGCTCTG (845) | 0.86 | 2670 |
| | sof-miR159b | TTTGGATTGAAGGGAGCTCTG (846) | 0.86 | 2671 |
| | sof-miR159c | CTTGGATTGAAGGGAGCTCCT (847) | 0.95 | 2672 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sof-miR159d | TTTGGATTGAAGGGAGCTCTG (848) | 0.86 | 2673 |
| | sof-miR159e | TTTGGATTGAAAGGAGCTCTT (849) | 0.86 | 2674 |
| | spr-miR159 | TTTGGATTGAAGGGAGCTCTG (850) | 0.86 | 2675 |
| | ssp-miR159a | TTTGGATTGAAGGGAGCTCTG (851) | 0.86 | 2676 |
| | svi-miR159 | TTGGACTGAAGGGAGCTCCCT (852) | 0.86 | 2677 |
| | tae-miR159a | TTTGGATTGAAGGGAGCTCTG (853) | 0.86 | 2678 |
| | tae-miR159b | TTTGGATTGAAGGGAGCTCTG (854) | 0.86 | 2679 |
| | tar-miR159 | TTGGACTGAAGGGAGCTCCCT (855) | 0.86 | 2680 |
| | vvi-miR159a | CTTGGAGTGAAGGGAGCTCTC (856) | 0.81 | 2681 |
| | vvi-miR159b | CTTGGAGTGAAGGGAGCTCTC (857) | 0.81 | 2682 |
| | vvi-miR159c | TTTGGATTGAAGGGAGCTCTA (858) | 0.86 | 2683 |
| | zma-miR159a | TTTGGATTGAAGGGAGCTCTG (859) | 0.86 | 2684 |
| | zma-miR159b | TTTGGATTGAAGGGAGCTCTG (860) | 0.86 | 2685 |
| | zma-miR159c | CTTGGATTGAAGGGAGCTCCT (861) | 0.95 | 2686 |
| | zma-miR159d | CTTGGATTGAAGGGAGCTCCT (862) | 0.95 | 2687 |
| | zma-miR159e | ATTGGTTTGAAGGGAGCTCCA (863) | 0.9 | 2688 |
| | zma-miR159f | TTTGGATTGAAGGGAGCTCTG (864) | 0.86 | 2689 |
| | zma-miR159g | TTTGGAGTGAAGGGAGTTCTG (865) | 0.76 | 2690 |
| | zma-miR159h | TTTGGAGTGAAGGGAGCTCTG (866) | 0.81 | 2691 |
| | zma-miR159i | TTTGGAGTGAAGGGAGCTCTG (867) | 0.81 | 2692 |
| | zma-miR159j | TTTGGATTGAAGGGAGCTCTG (868) | 0.86 | 2693 |
| | zma-miR159k | TTTGGATTGAAGGGAGCTCTG (869) | 0.86 | 2694 |
| | zma-miR159m | TTTGGATTGAAGGGAGCTCTG (870) | 0.86 | 2695 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| osa-miR159f | acb-miR159 | TTGGACTGAAGGGAGCTCCCT (871) | 0.81 | 2696 |
| | aha-miR159 | TTGGACTGAAGGGAGCTCCCT (872) | 0.81 | 2697 |
| | ahi-miR159 | TTGGACTGAAGGGAGCTCCCT (873) | 0.81 | 2698 |
| | ahy-miR159 | TTTGGATTGAAGGGAGCTCTA (874) | 0.95 | 2699 |
| | aly-miR159a | TTTGGATTGAAGGGAGCTCTA (875) | 0.95 | 2700 |
| | aly-miR159b | TTTGGATTGAAGGGAGCTCTT (876) | 0.9 | 2701 |
| | aly-miR159c | TTTGGATTGAAGGGAGCTCCT (877) | 0.86 | 2702 |
| | ape-miR159 | TTGGACTGAAGGGAGCTCCCT (878) | 0.81 | 2703 |
| | aqc-miR159 | TTTGGACTGAAGGGAGCTCTA (879) | 0.9 | 2704 |
| | ath-miR159a | TTTGGATTGAAGGGAGCTCTA (880) | 0.95 | 2705 |
| | ath-miR159b | TTTGGATTGAAGGGAGCTCTT (881) | 0.9 | 2706 |
| | ath-miR159c | TTTGGATTGAAGGGAGCTCCT (882) | 0.86 | 2707 |
| | bdi-miR159 | CTTGGATTGAAGGGAGCTCT (883) | 0.95 | 2708 |
| | bna-miR159 | TTTGGATTGAAGGGAGCTCTA (884) | 0.95 | 2709 |
| | bra-miR159a | TTTGGATTGAAGGGAGCTCTA (885) | 0.95 | 2710 |
| | bvl-miR159 | TTGGACTGAAGGGAGCTCCCT (886) | 0.81 | 2711 |
| | cmi-miR159 | TTGGACTGAAGGGAGCTCCCT (887) | 0.81 | 2712 |
| | cor-miR159 | TTGGACTGAAGGGAGCTCCCT (888) | 0.81 | 2713 |
| | crb-miR159 | TTGGACTGAAGGGAGCTCCCT (889) | 0.81 | 2714 |
| | csi-miR159 | TTTGGATTGAAGGGAGCTCTA (890) | 0.95 | 2715 |
| | dso-miR159 | TTGGACTGAAGGGAGCTCCCT (891) | 0.81 | 2716 |
| | ech-miR159 | TTGGACTGAAGGGAGCTCCCT (892) | 0.81 | 2717 |
| | fal-miR159 | TTGGACTGAAGGGAGCTCCCT (893) | 0.81 | 2718 |
| | far-miR159 | TTTGGATTGAAGGGAGCTCTG (894) | 0.9 | 2719 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | gma-miR159a-3p | TTTGGATTGAAGGGAGCTCTA (895) | 0.95 | 2720 |
| | gma-miR159b | ATTGGAGTGAAGGGAGCTCCA (896) | 0.86 | 2721 |
| | gma-miR159c | ATTGGAGTGAAGGGAGCTCCG (897) | 0.81 | 2722 |
| | hvu-miR159a | TTTGGATTGAAGGGAGCTCTG (898) | 0.9 | 2723 |
| | hvu-miR159b | TTTGGATTGAAGGGAGCTCTG (899) | 0.9 | 2724 |
| | hvv-miR159a | TTTGGATTGAAGGGAGCTCTG (900) | 0.9 | 2725 |
| | hvv-miR159b | TTTGGATTGAAGGGAGCTCTG (901) | 0.9 | 2726 |
| | ltu-miR159 | TTTGGATTGAAGGGAGCTCTA (902) | 0.95 | 2727 |
| | mma-miR159 | TTGGACTGAAGGGAGCTCCCT (903) | 0.81 | 2728 |
| | mtr-miR159a | TTTGGATTGAAGGGAGCTCTA (904) | 0.95 | 2729 |
| | mtr-miR159b | ATTGAATTGAAGGGAGCAACT (905) | 0.71 | 2730 |
| | mtr-miR159c | TTTGGATTGAAGGGAGCTCTA (906) | 0.95 | 2731 |
| | nof-miR159 | TTGGACTGAAGGGAGCTCCCT (907) | 0.81 | 2732 |
| | oru-miR159 | TTTGGATTGAAGGGAGCTCTG (908) | 0.9 | 2733 |
| | osa-miR159a | TTTGGATTGAAGGGAGCTCTG (909) | 0.9 | 2734 |
| | osa-miR159a.1 | TTTGGATTGAAGGGAGCTCTG (910) | 0.9 | 2735 |
| | osa-miR159b | TTTGGATTGAAGGGAGCTCTG (911) | 0.9 | 2736 |
| | osa-miR159c | ATTGGATTGAAGGGAGCTCCA (912) | 0.9 | 2737 |
| | osa-miR159d | ATTGGATTGAAGGGAGCTCCG (913) | 0.86 | 2738 |
| | osa-miR159e | ATTGGATTGAAGGGAGCTCCT (914) | 0.86 | 2739 |
| | osa-miR159m | TTTGGATTGAAGGGAGCTCTG (915) | 0.9 | 2740 |
| | pgl-miR159 | TTTGGATTGAAGGGAGCTCTG (916) | 0.9 | 2741 |
| | psi-miR159 | CTTGGATTGAAGGGAGCTCCA (917) | 0.95 | 2742 |
| | pta-miR159a | TTGGATTGAAGGGAGCTCCA (918) | 0.9 | 2743 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | pta-miR159b | TTGGATTGAAGAGAGCTCCC (919) | 0.81 | 2744 |
| | pta-miR159c | CTTGGATTGAAGGGAGCTCCC (920) | 0.9 | 2745 |
| | ptc-miR159a | TTTGGATTGAAGGGAGCTCTA (921) | 0.95 | 2746 |
| | ptc-miR159b | TTTGGATTGAAGGGAGCTCTA (922) | 0.95 | 2747 |
| | ptc-miR159c | TTTGGATTGAAGGGAGCTCTA (923) | 0.95 | 2748 |
| | ptc-miR159d | CTTGGATTGAAGGGAGCTCCT (924) | 0.9 | 2749 |
| | ptc-miR159e | CTTGGGGTGAAGGGAGCTCCT (925) | 0.81 | 2750 |
| | ptc-miR159f | ATTGGAGTGAAGGGAGCTCGA (926) | 0.86 | 2751 |
| | pvu-miR159 | TTTGGATTGAAGGGAGCTCTA (927) | 0.95 | 2752 |
| | pvu-miR159.2 | CTTCCATATCTGGGAGCTTC (928) | 0.62 | 2753 |
| | pvu-miR159a.1 | TTTGGATTGAAGGGAGCTCTA (929) | 0.95 | 2754 |
| | pvu-miR159a.2 | CTTCCATATCTGGGAGCTTC (930) | 0.62 | 2755 |
| | rco-miR159 | TTTGGATTGAAGGGAGCTCTA (931) | 0.95 | 2756 |
| | rin-miR159 | TTGGACTGAAGGGAGCTCCCT (932) | 0.81 | 2757 |
| | sar-miR159 | TTTGGATTGAAGGGAGCTCTG (933) | 0.9 | 2758 |
| | sbi-miR159a | TTTGGATTGAAGGGAGCTCTG (934) | 0.9 | 2759 |
| | sbi-miR159b | CTTGGATTGAAGGGAGCTCCT (935) | 0.9 | 2760 |
| | sly-miR159 | TTTGGATTGAAGGGAGCTCTA (936) | 0.95 | 2761 |
| | smo-miR159 | CTTGGATTGAAGGGAGCTCCC (937) | 0.9 | 2762 |
| | sof-miR159a | TTTGGATTGAAGGGAGCTCTG (938) | 0.9 | 2763 |
| | sof-miR159b | TTTGGATTGAAGGGAGCTCTG (939) | 0.9 | 2764 |
| | sof-miR159c | CTTGGATTGAAGGGAGCTCCT (940) | 0.9 | 2765 |
| | sof-miR159d | TTTGGATTGAAGGGAGCTCTG (941) | 0.9 | 2766 |
| | sof-miR159e | TTTGGATTGAAAGGAGCTCTT (942) | 0.86 | 2767 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | spr-miR159 | TTTGGATTGAAGGGAGCTCTG (943) | 0.9 | 2768 |
| | ssp-miR159a | TTTGGATTGAAGGGAGCTCTG (944) | 0.9 | 2769 |
| | svi-miR159 | TTGGACTGAAGGGAGCTCCCT (945) | 0.81 | 2770 |
| | tae-miR159a | TTTGGATTGAAGGGAGCTCTG (946) | 0.9 | 2771 |
| | tae-miR159b | TTTGGATTGAAGGGAGCTCTG (947) | 0.9 | 2772 |
| | tar-miR159 | TTGGACTGAAGGGAGCTCCCT (948) | 0.81 | 2773 |
| | vvi-miR159a | CTTGGAGTGAAGGGAGCTCTC (949) | 0.9 | 2774 |
| | vvi-miR159b | CTTGGAGTGAAGGGAGCTCTC (950) | 0.9 | 2775 |
| | vvi-miR159c | TTTGGATTGAAGGGAGCTCTA (951) | 0.95 | 2776 |
| | zma-miR159a | TTTGGATTGAAGGGAGCTCTG (952) | 0.9 | 2777 |
| | zma-miR159b | TTTGGATTGAAGGGAGCTCTG (953) | 0.9 | 2778 |
| | zma-miR159c | CTTGGATTGAAGGGAGCTCCT (954) | 0.9 | 2779 |
| | zma-miR159d | CTTGGATTGAAGGGAGCTCCT (955) | 0.9 | 2780 |
| | zma-miR159e | ATTGGTTTGAAGGGAGCTCCA (956) | 0.86 | 2781 |
| | zma-miR159f | TTTGGATTGAAGGGAGCTCTG (957) | 0.9 | 2782 |
| | zma-miR159g | TTTGGAGTGAAGGGAGTTCTG (958) | 0.81 | 2783 |
| | zma-miR159h | TTTGGAGTGAAGGGAGCTCTG (959) | 0.86 | 2784 |
| | zma-miR159i | TTTGGAGTGAAGGGAGCTCTG (960) | 0.86 | 2785 |
| | zma-miR159j | TTTGGATTGAAGGGAGCTCTG (961) | 0.9 | 2786 |
| | zma-miR159k | TTTGGATTGAAGGGAGCTCTG (962) | 0.9 | 2787 |
| | zma-miR159m | TTTGGATTGAAGGGAGCTCTG (963) | 0.9 | 2788 |
| osa-miR1858a | osa-miR1858b | GAGAGGAGGACGGAGTGGGGC (964) | 1 | 2789 |
| psi-miR159 | acb-miR159 | TTGGACTGAAGGGAGCTCCCT (965) | 0.86 | 2790 |
| | aha-miR159 | TTGGACTGAAGGGAGCTCCCT (966) | 0.86 | 2791 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ahi-miR159 | TTGGACTGAAGGGAGCTCCCT (967) | 0.86 | 2792 |
| | ahy-miR159 | TTTGGATTGAAGGGAGCTCTA (968) | 0.9 | 2793 |
| | aly-miR159a | TTTGGATTGAAGGGAGCTCTA (969) | 0.9 | 2794 |
| | aly-miR159b | TTTGGATTGAAGGGAGCTCTT (970) | 0.86 | 2795 |
| | aly-miR159c | TTTGGATTGAAGGGAGCTCCT (971) | 0.9 | 2796 |
| | ape-miR159 | TTGGACTGAAGGGAGCTCCCT (972) | 0.86 | 2797 |
| | aqc-miR159 | TTTGGACTGAAGGGAGCTCTA (973) | 0.86 | 2798 |
| | ath-miR159a | TTTGGATTGAAGGGAGCTCTA (974) | 0.9 | 2799 |
| | ath-miR159b | TTTGGATTGAAGGGAGCTCTT (975) | 0.86 | 2800 |
| | ath-miR159c | TTTGGATTGAAGGGAGCTCCT (976) | 0.9 | 2801 |
| | bdi-miR159 | CTTGGATTGAAGGGAGCTCT (977) | 0.9 | 2802 |
| | bna-miR159 | TTTGGATTGAAGGGAGCTCTA (978) | 0.9 | 2803 |
| | bra-miR159a | TTTGGATTGAAGGGAGCTCTA (979) | 0.9 | 2804 |
| | bvl-miR159 | TTGGACTGAAGGGAGCTCCCT (980) | 0.86 | 2805 |
| | cmi-miR159 | TTGGACTGAAGGGAGCTCCCT (981) | 0.86 | 2806 |
| | cor-miR159 | TTGGACTGAAGGGAGCTCCCT (982) | 0.86 | 2807 |
| | crb-miR159 | TTGGACTGAAGGGAGCTCCCT (983) | 0.86 | 2808 |
| | csi-miR159 | TTTGGATTGAAGGGAGCTCTA (984) | 0.9 | 2809 |
| | dso-miR159 | TTGGACTGAAGGGAGCTCCCT (985) | 0.86 | 2810 |
| | ech-miR159 | TTGGACTGAAGGGAGCTCCCT (986) | 0.86 | 2811 |
| | fal-miR159 | TTGGACTGAAGGGAGCTCCCT (987) | 0.86 | 2812 |
| | far-miR159 | TTTGGATTGAAGGGAGCTCTG (988) | 0.86 | 2813 |
| | gma-miR159a-3p | TTTGGATTGAAGGGAGCTCTA (989) | 0.9 | 2814 |
| | gma-miR159b | ATTGGAGTGAAGGGAGCTCCA (990) | 0.9 | 2815 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | gma-miR159c | ATTGGAGTGAAGGGAGCTCCG (991) | 0.86 | 2816 |
| | hvu-miR159a | TTTGGATTGAAGGGAGCTCTG (992) | 0.86 | 2817 |
| | hvu-miR159b | TTTGGATTGAAGGGAGCTCTG (993) | 0.86 | 2818 |
| | hvv-miR159a | TTTGGATTGAAGGGAGCTCTG (994) | 0.86 | 2819 |
| | hvv-miR159b | TTTGGATTGAAGGGAGCTCTG (995) | 0.86 | 2820 |
| | ltu-miR159 | TTTGGATTGAAGGGAGCTCTA (996) | 0.9 | 2821 |
| | mma-miR159 | TTGGACTGAAGGGAGCTCCCT (997) | 0.86 | 2822 |
| | mtr-miR159a | TTTGGATTGAAGGGAGCTCTA (998) | 0.9 | 2823 |
| | mtr-miR159b | ATTGAATTGAAGGGAGCAACT (999) | 0.76 | 2824 |
| | mtr-miR159c | TTTGGATTGAAGGGAGCTCTA (1000) | 0.9 | 2825 |
| | nof-miR159 | TTGGACTGAAGGGAGCTCCCT (1001) | 0.86 | 2826 |
| | oru-miR159 | TTTGGATTGAAGGGAGCTCTG (1002) | 0.86 | 2827 |
| | osa-miR159a | TTTGGATTGAAGGGAGCTCTG (1003) | 0.86 | 2828 |
| | osa-miR159a.1 | TTTGGATTGAAGGGAGCTCTG (1004) | 0.86 | 2829 |
| | osa-miR159a.2 | TTGCATGCCCCAGGAGCTGCA (1005) | 0.62 | 2830 |
| | osa-miR159b | TTTGGATTGAAGGGAGCTCTG (1006) | 0.86 | 2831 |
| | osa-miR159c | ATTGGATTGAAGGGAGCTCCA (1007) | 0.95 | 2832 |
| | osa-miR159d | ATTGGATTGAAGGGAGCTCCG (1008) | 0.9 | 2833 |
| | osa-miR159e | ATTGGATTGAAGGGAGCTCCT (1009) | 0.9 | 2834 |
| | osa-miR159f | CTTGGATTGAAGGGAGCTCTA (1010) | 0.95 | 2835 |
| | osa-miR159m | TTTGGATTGAAGGGAGCTCTG (1011) | 0.86 | 2836 |
| | pgl-miR159 | TTTGGATTGAAGGGAGCTCTG (1012) | 0.86 | 2837 |
| | pta-miR159a | TTGGATTGAAGGGAGCTCCA (1013) | 0.95 | 2838 |
| | pta-miR159b | TTGGATTGAAGAGAGCTCCC (1014) | 0.86 | 2839 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | pta-miR159c | CTTGGATTGAAGGGAGC TCCC (1015) | 0.95 | 2840 |
| | ptc-miR159a | TTTGGATTGAAGGGAGC TCTA (1016) | 0.9 | 2841 |
| | ptc-miR159b | TTTGGATTGAAGGGAGC TCTA (1017) | 0.9 | 2842 |
| | ptc-miR159c | TTTGGATTGAAGGGAGC TCTA (1018) | 0.9 | 2843 |
| | ptc-miR159d | CTTGGATTGAAGGGAGC TCCT (1019) | 0.95 | 2844 |
| | ptc-miR159e | CTTGGGGTGAAGGGAG CTCCT (1020) | 0.86 | 2845 |
| | ptc-miR159f | ATTGGAGTGAAGGGAG CTCGA (1021) | 0.86 | 2846 |
| | pvu-miR159 | TTTGGATTGAAGGGAGC TCTA (1022) | 0.9 | 2847 |
| | pvu-miR159.2 | CTTCCATATCTGGGGAG CTTC (1023) | 0.67 | 2848 |
| | pvu-miR159a.1 | TTTGGATTGAAGGGAGC TCTA (1024) | 0.9 | 2849 |
| | pvu-miR159a.2 | CTTCCATATCTGGGGAG CTTC (1025) | 0.67 | 2850 |
| | rco-miR159 | TTTGGATTGAAGGGAGC TCTA (1026) | 0.9 | 2851 |
| | rin-miR159 | TTGGACTGAAGGGAGCT CCCT (1027) | 0.86 | 2852 |
| | sar-miR159 | TTTGGATTGAAGGGAGC TCTG (1028) | 0.86 | 2853 |
| | sbi-miR159a | TTTGGATTGAAGGGAGC TCTG (1029) | 0.86 | 2854 |
| | sbi-miR159b | CTTGGATTGAAGGGAGC TCCT (1030) | 0.95 | 2855 |
| | sly-miR159 | TTTGGATTGAAGGGAGC TCTA (1031) | 0.9 | 2856 |
| | smo-miR159 | CTTGGATTGAAGGGAGC TCCC (1032) | 0.95 | 2857 |
| | sof-miR159a | TTTGGATTGAAGGGAGC TCTG (1033) | 0.86 | 2858 |
| | sof-miR159b | TTTGGATTGAAGGGAGC TCTG (1034) | 0.86 | 2859 |
| | sof-miR159c | CTTGGATTGAAGGGAGC TCCT (1035) | 0.95 | 2860 |
| | sof-miR159d | TTTGGATTGAAGGGAGC TCTG (1036) | 0.86 | 2861 |
| | sof-miR159e | TTTGGATTGAAAGGAGC TCTT (1037) | 0.81 | 2862 |
| | spr-miR159 | TTTGGATTGAAGGGAGC TCTG (1038) | 0.86 | 2863 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
| --- | --- | --- | --- | --- |
| | ssp-miR159a | TTTGGATTGAAGGGAGCTCTG (1039) | 0.86 | 2864 |
| | svi-miR159 | TTGGACTGAAGGGAGCTCCCT (1040) | 0.86 | 2865 |
| | tae-miR159a | TTTGGATTGAAGGGAGCTCTG (1041) | 0.86 | 2866 |
| | tae-miR159b | TTTGGATTGAAGGGAGCTCTG (1042) | 0.86 | 2867 |
| | tar-miR159 | TTGGACTGAAGGGAGCTCCCT (1043) | 0.86 | 2868 |
| | vvi-miR159a | CTTGGAGTGAAGGGAGCTCTC (1044) | 0.86 | 2869 |
| | vvi-miR159b | CTTGGAGTGAAGGGAGCTCTC (1045) | 0.86 | 2870 |
| | vvi-miR159c | TTTGGATTGAAGGGAGCTCTA (1046) | 0.9 | 2871 |
| | zma-miR159a | TTTGGATTGAAGGGAGCTCTG (1047) | 0.86 | 2872 |
| | zma-miR159b | TTTGGATTGAAGGGAGCTCTG (1048) | 0.86 | 2873 |
| | zma-miR159c | CTTGGATTGAAGGGAGCTCCT (1049) | 0.95 | 2874 |
| | zma-miR159d | CTTGGATTGAAGGGAGCTCCT (1050) | 0.95 | 2875 |
| | zma-miR159e | ATTGGTTTGAAGGGAGCTCCA (1051) | 0.9 | 2876 |
| | zma-miR159f | TTTGGATTGAAGGGAGCTCTG (1052) | 0.86 | 2877 |
| | zma-miR159g | TTTGGAGTGAAGGGAGTTCTG (1053) | 0.76 | 2878 |
| | zma-miR159h | TTTGGAGTGAAGGGAGCTCTG (1054) | 0.81 | 2879 |
| | zma-miR159i | TTTGGAGTGAAGGGAGCTCTG (1055) | 0.81 | 2880 |
| | zma-miR159j | TTTGGATTGAAGGGAGCTCTG (1056) | 0.86 | 2881 |
| | zma-miR159k | TTTGGATTGAAGGGAGCTCTG (1057) | 0.86 | 2882 |
| | zma-miR159m | TTTGGATTGAAGGGAGCTCTG (1058) | 0.86 | 2883 |
| pta-miR156a | ahy-miR156a | TGACAGAAGAGAGAGCAC (1059) | 0.8 | 2884 |
| | ahy-miR156b-5p | TTGACAGAAGATAGAGAGCAC (1060) | 0.85 | 2885 |
| | ahy-miR156c | TTGACAGAAGAGAGAGCAC (1061) | 0.8 | 2886 |
| | aly-miR156a | TGACAGAAGAGAGTGAGCAC (1062) | 0.75 | 2887 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | aly-miR156b | TGACAGAAGAGAGTGAGCAC (1063) | 0.75 | 2888 |
| | aly-miR156c | TGACAGAAGAGAGTGAGCAC (1064) | 0.75 | 2889 |
| | aly-miR156d | TGACAGAAGAGAGTGAGCAC (1065) | 0.75 | 2890 |
| | aly-miR156e | TGACAGAAGAGAGTGAGCAC (1066) | 0.75 | 2891 |
| | aly-miR156f | TGACAGAAGAGAGTGAGCAC (1067) | 0.75 | 2892 |
| | aly-miR156g | CGACAGAAGAGAGTGAGCAC (1068) | 0.75 | 2893 |
| | aly-miR156h | TGACAGAAGAAAGAGAGCAC (1069) | 0.8 | 2894 |
| | aqc-miR156a | TGACAGAAGATAGAGAGCAC (1070) | 0.85 | 2895 |
| | aqc-miR156b | TGACAGAAGATAGAGAGCAC (1071) | 0.85 | 2896 |
| | ath-miR156a | TGACAGAAGAGAGTGAGCAC (1072) | 0.75 | 2897 |
| | ath-miR156b | TGACAGAAGAGAGTGAGCAC (1073) | 0.75 | 2898 |
| | ath-miR156c | TGACAGAAGAGAGTGAGCAC (1074) | 0.75 | 2899 |
| | ath-miR156d | TGACAGAAGAGAGTGAGCAC (1075) | 0.75 | 2900 |
| | ath-miR156e | TGACAGAAGAGAGTGAGCAC (1076) | 0.75 | 2901 |
| | ath-miR156f | TGACAGAAGAGAGTGAGCAC (1077) | 0.75 | 2902 |
| | ath-miR156g | CGACAGAAGAGAGTGAGCAC (1078) | 0.75 | 2903 |
| | ath-miR156h | TGACAGAAGAAAGAGAGCAC (1079) | 0.8 | 2904 |
| | ath-miR156m | TGACAGAAGAGAGAGAGCAC (1080) | 0.8 | 2905 |
| | ath-miR156o | TGACAGAAGAGAGAGAGCAC (1081) | 0.8 | 2906 |
| | ath-miR156p | TGACAGAAGAGAGAGAGCAC (1082) | 0.8 | 2907 |
| | ath-miR156q | TGACAGAAGAGAGAGAGCAC (1083) | 0.8 | 2908 |
| | ath-miR156r | TGACAGAAGAGAGAGAGCAC (1084) | 0.8 | 2909 |
| | ath-miR156s | TGACAGAAGAGAGAGAGCAC (1085) | 0.8 | 2910 |
| | bdi-miR156 | TGACAGAAGAGAGAGAGCACA (1086) | 0.85 | 2911 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | bdi-miR156b | TGACAGAAGAGAGTGAGCAC (1087) | 0.75 | 2912 |
| | bdi-miR156c | TGACAGAAGAGAGTGAGCAC (1088) | 0.75 | 2913 |
| | bdi-miR156d | TGACAGAAGAGAGTGAGCAC (1089) | 0.75 | 2914 |
| | bna-miR156a | TGACAGAAGAGAGTGAGCACA (1090) | 0.8 | 2915 |
| | bna-miR156b | TTGACAGAAGATAGAGAGCAC (1091) | 0.85 | 2916 |
| | bna-miR156c | TTGACAGAAGATAGAGAGCAC (1092) | 0.85 | 2917 |
| | can-miR156a | TGACAGAAGAGAGAGAGCAC (1093) | 0.8 | 2918 |
| | can-miR156b | TGACAGAAGAGAGGGAGCAC (1094) | 0.75 | 2919 |
| | cpt-miR156a | TGACAGAAGAGAGTGAGCAC (1095) | 0.75 | 2920 |
| | cpt-miR156b | TGACAGAAGAGAGAGAGCAC (1096) | 0.8 | 2921 |
| | cru-miR156 | TGACAGAAGAGAGAGAGCAC (1097) | 0.8 | 2922 |
| | csi-miR156 | TGACAGAAGAGAGTGAGCAC (1098) | 0.75 | 2923 |
| | csi-miR156a | TGACAGAAGAGAGAGAGCAC (1099) | 0.8 | 2924 |
| | csi-miR156b | TGACAGAAGAGAGAGAGCAC (1100) | 0.8 | 2925 |
| | ctr-miR156 | TGACAGAAGAGAGTGAGCAC (1101) | 0.75 | 2926 |
| | eca-miR156 | TGACAGAAGAGAGAGAGCAC (1102) | 0.8 | 2927 |
| | far-miR156a | TGACAGAAGAGAGAGAGCACA (1103) | 0.85 | 2928 |
| | far-miR156b | TTGACAGAAGAGAGAGAGCAC (1104) | 0.8 | 2929 |
| | ghr-miR156a | TGACAGAAGAGAGTGAGCAC (1105) | 0.75 | 2930 |
| | ghr-miR156b | TGACAGAAGAGAGTGAGCAC (1106) | 0.75 | 2931 |
| | ghr-miR156c | TGTCAGAAGAGAGTGAGCAC (1107) | 0.75 | 2932 |
| | ghr-miR156d | TGACAGAAGAGAGTGAGCAC (1108) | 0.75 | 2933 |
| | gma-miR156a | TGACAGAAGAGAGTGAGCAC (1109) | 0.75 | 2934 |
| | gma-miR156b | TGACAGAAGAGAGAGAGCACA (1110) | 0.85 | 2935 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | gma-miR156c | TTGACAGAAGATAGAGAGCAC (1111) | 0.85 | 2936 |
| | gma-miR156d | TTGACAGAAGATAGAGAGCAC (1112) | 0.85 | 2937 |
| | gma-miR156e | TTGACAGAAGATAGAGAGCAC (1113) | 0.85 | 2938 |
| | gma-miR156f | TTGACAGAAGAGAGAGAGCACA (1114) | 0.85 | 2939 |
| | gma-miR156g | ACAGAAGATAGAGAGCACAG (1115) | 0.9 | 2940 |
| | gma-miR156h | TGACAGAAGAGAGAGAGCAC (1116) | 0.8 | 2941 |
| | gma-miR156i | TGACAGAAGAGAGAGAGCAC (1117) | 0.8 | 2942 |
| | han-miR156 | TGACAGAAGAGAGAGAGCAC (1118) | 0.8 | 2943 |
| | hvs-miR156 | TGACAGAAGAGAGAGAGCAC (1119) | 0.8 | 2944 |
| | hvu-miR156 | TGACAGAAGAGAGTGAGCACA (1120) | 0.8 | 2945 |
| | hvv-miR156a | TGACAGAAGAGAGTGAGCAC (1121) | 0.75 | 2946 |
| | hvv-miR156b | TGACAGAAGAGAGAGAGCAC (1122) | 0.8 | 2947 |
| | hvv-miR156c | TGACAGAAGAGAGAGAGCAC (1123) | 0.8 | 2948 |
| | hvv-miR156d | TGACAGAAGAGAGAGAGCAC (1124) | 0.8 | 2949 |
| | lja-miR156 | TGACAGAAGAGAGAGAGCAC (1125) | 0.8 | 2950 |
| | lsa-miR156 | TGACAGAAGAGAGAGAGCAC (1126) | 0.8 | 2951 |
| | mdo-miR156a | TGACAGAAGAGAGAGAGCAC (1127) | 0.8 | 2952 |
| | mdo-miR156b | TGACAGAAGAGAGAGAGCAC (1128) | 0.8 | 2953 |
| | mtr-miR156 | TGACAGAAGAGAGAGAGCACA (1129) | 0.85 | 2954 |
| | mtr-miR156b | TGACAGAAGAGAGTGAGCAC (1130) | 0.75 | 2955 |
| | mtr-miR156c | TGACAGAAGAGAGTGAGCAC (1131) | 0.75 | 2956 |
| | mtr-miR156d | TGACAGAAGAGAGTGAGCAC (1132) | 0.75 | 2957 |
| | mtr-miR156e | TTGACAGAAGATAGAGAGCAC (1133) | 0.85 | 2958 |
| | mtr-miR156f | TTGACAGAAGATAGAGAGCAC (1134) | 0.85 | 2959 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | mtr-miR156g | TTGACAGAAGATAGAGGGCAC (1135) | 0.8 | 2960 |
| | mtr-miR156h | TTGACAGAAGATAGAGAGCAC (1136) | 0.85 | 2961 |
| | mtr-miR156i | TGACAGAAGAGAGTGAGCAC (1137) | 0.75 | 2962 |
| | nbe-miR156a | TGACAGAAGAGAGAGAGCAC (1138) | 0.8 | 2963 |
| | nbe-miR156b | TGACAGAAGAGAGAGAGCAC (1139) | 0.8 | 2964 |
| | oru-miR156 | TGACAGAAGAGAGTGAGCAC (1140) | 0.75 | 2965 |
| | osa-miR156a | TGACAGAAGAGAGTGAGCAC (1141) | 0.75 | 2966 |
| | osa-miR156b | TGACAGAAGAGAGTGAGCAC (1142) | 0.75 | 2967 |
| | osa-miR156c | TGACAGAAGAGAGTGAGCAC (1143) | 0.75 | 2968 |
| | osa-miR156d | TGACAGAAGAGAGTGAGCAC (1144) | 0.75 | 2969 |
| | osa-miR156e | TGACAGAAGAGAGTGAGCAC (1145) | 0.75 | 2970 |
| | osa-miR156f | TGACAGAAGAGAGTGAGCAC (1146) | 0.75 | 2971 |
| | osa-miR156g | TGACAGAAGAGAGTGAGCAC (1147) | 0.75 | 2972 |
| | osa-miR156h | TGACAGAAGAGAGTGAGCAC (1148) | 0.75 | 2973 |
| | osa-miR156i | TGACAGAAGAGAGTGAGCAC (1149) | 0.75 | 2974 |
| | osa-miR156j | TGACAGAAGAGAGTGAGCAC (1150) | 0.75 | 2975 |
| | osa-miR156k | TGACAGAAGAGAGAGAGCACA (1151) | 0.85 | 2976 |
| | osa-miR156l | CGACAGAAGAGAGTGAGCATA (1152) | 0.75 | 2977 |
| | osa-miR156m | TGACAGAAGAGAGTGAGCAC (1153) | 0.75 | 2978 |
| | osa-miR156n | TGACAGAAGAGAGTGAGCAC (1154) | 0.75 | 2979 |
| | osa-miR156o | TGACAGAAGAGAGTGAGCAT (1155) | 0.7 | 2980 |
| | osa-miR156p | TGACAGAAGAGAGTGAGCTC (1156) | 0.7 | 2981 |
| | osa-miR156q | TGACAGAACAGAGTGAGCAC (1157) | 0.7 | 2982 |
| | osa-miR156r | TGACAGAAGAGAGAGAGCAC (1158) | 0.8 | 2983 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | par-miR156 | TGACAGAAGAGAGAGAGCAC (1159) | 0.8 | 2984 |
| | ppd-miR156 | TGACAGAAGAGAGAGAGCAC (1160) | 0.8 | 2985 |
| | ppr-miR156 | TGACAGAAGAGAGTGAGCAC (1161) | 0.75 | 2986 |
| | ppt-miR156a | TGACAGAAGAGAGTGAGCAC (1162) | 0.75 | 2987 |
| | ppt-miR156b | TGACAGAAGAGAGTGAGCAC (1163) | 0.75 | 2988 |
| | ppt-miR156c | TGACAGAAGAGAGTGAGCAC (1164) | 0.75 | 2989 |
| | pta-miR156b | CAGAAGATAGAGAGCACAAC (1165) | 0.95 | 2990 |
| | ptc-miR156a | TGACAGAAGAGAGTGAGCAC (1166) | 0.75 | 2991 |
| | ptc-miR156b | TGACAGAAGAGAGTGAGCAC (1167) | 0.75 | 2992 |
| | ptc-miR156c | TGACAGAAGAGAGTGAGCAC (1168) | 0.75 | 2993 |
| | ptc-miR156d | TGACAGAAGAGAGTGAGCAC (1169) | 0.75 | 2994 |
| | ptc-miR156e | TGACAGAAGAGAGTGAGCAC (1170) | 0.75 | 2995 |
| | ptc-miR156f | TGACAGAAGAGAGTGAGCAC (1171) | 0.75 | 2996 |
| | ptc-miR156g | TTGACAGAAGATAGAGAGCAC (1172) | 0.85 | 2997 |
| | ptc-miR156h | TTGACAGAAGATAGAGAGCAC (1173) | 0.85 | 2998 |
| | ptc-miR156i | TTGACAGAAGATAGAGAGCAC (1174) | 0.85 | 2999 |
| | ptc-miR156j | TTGACAGAAGATAGAGAGCAC (1175) | 0.85 | 3000 |
| | ptc-miR156k | TGACAGAAGAGAGGGAGCAC (1176) | 0.75 | 3001 |
| | ptr-miR156 | TGACAGAAGAGAGAGAGCAC (1177) | 0.8 | 3002 |
| | pts-miR156a | TGACAGAAGAGAGTGAGCGC (1178) | 0.7 | 3003 |
| | pts-miR156b | TGACAGAAGAGAGAGAGCAC (1179) | 0.8 | 3004 |
| | pts-miR156c | TGACAGAAGAGAGAGAGCAC (1180) | 0.8 | 3005 |
| | rco-miR156a | TGACAGAAGAGAGTGAGCACA (1181) | 0.8 | 3006 |
| | rco-miR156b | TGACAGAAGAGAGTGAGCACA (1182) | 0.8 | 3007 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | rco-miR156c | TGACAGAAGAGAGTGAGCACA (1183) | 0.8 | 3008 |
| | rco-miR156d | TGACAGAAGAGAGTGAGCACA (1184) | 0.8 | 3009 |
| | rco-miR156e | TGACAGAAGAGAGAGAGCACA (1185) | 0.85 | 3010 |
| | rco-miR156f | TTGACAGAAGATAGAGAGCAC (1186) | 0.85 | 3011 |
| | rco-miR156g | TTGACAGAAGATAGAGAGCAC (1187) | 0.85 | 3012 |
| | rco-miR156h | TTGACAGAAGATAGAGAGCAC (1188) | 0.85 | 3013 |
| | sbi-miR156a | TGACAGAAGAGAGTGAGCAC (1189) | 0.75 | 3014 |
| | sbi-miR156b | TGACAGAAGAGAGTGAGCAC (1190) | 0.75 | 3015 |
| | sbi-miR156c | TGACAGAAGAGAGTGAGCAC (1191) | 0.75 | 3016 |
| | sbi-miR156d | TGACAGAAGAGAGAGAGCACA (1192) | 0.85 | 3017 |
| | sbi-miR156e | TGACAGAAGAGAGCGAGCAC (1193) | 0.75 | 3018 |
| | sbi-miR156f | TGACAGAAGAGAGTGAGCAC (1194) | 0.75 | 3019 |
| | sbi-miR156g | TGACAGAAGAGAGTGAGCAC (1195) | 0.75 | 3020 |
| | sbi-miR156h | TGACAGAAGAGAGTGAGCAC (1196) | 0.75 | 3021 |
| | sbi-miR156i | TGACAGAAGAGAGTGAGCAC (1197) | 0.75 | 3022 |
| | sin-miR156 | TGACAGAAGAGAGAGAGCAC (1198) | 0.8 | 3023 |
| | sly-miR156a | TTGACAGAAGATAGAGAGCAC (1199) | 0.85 | 3024 |
| | sly-miR156b | TTGACAGAAGATAGAGAGCAC (1200) | 0.85 | 3025 |
| | sly-miR156c | TTGACAGAAGATAGAGAGCAC (1201) | 0.85 | 3026 |
| | smo-miR156a | CGACAGAAGAGAGTGAGCAC (1202) | 0.75 | 3027 |
| | smo-miR156b | CTGACAGAAGATAGAGAGCAC (1203) | 0.85 | 3028 |
| | smo-miR156c | TTGACAGAAGAAAGAGAGCAC (1204) | 0.8 | 3029 |
| | smo-miR156d | TTGACAGAAGACAGGGAGCAC (1205) | 0.75 | 3030 |
| | sof-miR156 | TGACAGAAGAGAGTGAGCAC (1206) | 0.75 | 3031 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sof-miR156c | TGACAGAAGAGAGAGCAC (1207) | 0.8 | 3032 |
| | sof-miR156d | TGACAGAAGAGAGAGCAC (1208) | 0.8 | 3033 |
| | sof-miR156e | TGACAGAAGAGAGAGCAC (1209) | 0.8 | 3034 |
| | sof-miR156f | TGACAGAAGAGAGAGCAC (1210) | 0.8 | 3035 |
| | sof-miR156g | TGACAGAAGAGAGAGCAC (1211) | 0.8 | 3036 |
| | sof-miR156h | TGACAGAAGAGAGAGCAC (1212) | 0.8 | 3037 |
| | sof-miR156u | TGACAGAAGAGAGAGCAC (1213) | 0.8 | 3038 |
| | spr-miR156 | TGACAGAAGAGAGAGCAC (1214) | 0.8 | 3039 |
| | ssp-miR156 | TGACAGAAGAGAGTGAGCACA (1215) | 0.8 | 3040 |
| | stu-miR156a | TGACAGAAGAGAGTGAGCAC (1216) | 0.75 | 3041 |
| | stu-miR156b | TGACAGAAGAGAGAGCAC (1217) | 0.8 | 3042 |
| | stu-miR156c | TGACAGAAGAGAGAGCAC (1218) | 0.8 | 3043 |
| | stu-miR156d | TGACAGAAGAGAGAGCAC (1219) | 0.8 | 3044 |
| | stu-miR156e | TGACAGAAGAGAGAGCAC (1220) | 0.8 | 3045 |
| | tae-miR156 | TGACAGAAGAGAGTGAGCACA (1221) | 0.8 | 3046 |
| | tae-miR156a | TGACAGAAGAGAGAGCAC (1222) | 0.8 | 3047 |
| | tae-miR156b | TGACAGAAGAGAGAGCAC (1223) | 0.8 | 3048 |
| | tcc-miR156a | TGACAGAAGAGAGAGAGCACA (1224) | 0.85 | 3049 |
| | tcc-miR156b | TGACAGAAGAGAGTGAGCAC (1225) | 0.75 | 3050 |
| | tcc-miR156c | TGACAGAAGAGAGTGAGCAC (1226) | 0.75 | 3051 |
| | tcc-miR156d | TGACAGAAGAGAGTGAGCAC (1227) | 0.75 | 3052 |
| | tcc-miR156e | TTGACAGAAGATAGAGAGCAC (1228) | 0.85 | 3053 |
| | tcc-miR156f | TTGACAGAAGATAGAGAGCAC (1229) | 0.85 | 3054 |
| | tcc-miR156g | TGACAGAAGAGAGTGAGCAC (1230) | 0.75 | 3055 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | tre-miR156 | TGACAGAAGAGAGTGAGCAC (1231) | 0.75 | 3056 |
| | vvi-miR156a | TGACAGAAGAGAGGGAGCAC (1232) | 0.75 | 3057 |
| | vvi-miR156b | TGACAGAAGAGAGTGAGCAC (1233) | 0.75 | 3058 |
| | vvi-miR156c | TGACAGAAGAGAGTGAGCAC (1234) | 0.75 | 3059 |
| | vvi-miR156d | TGACAGAAGAGAGTGAGCAC (1235) | 0.75 | 3060 |
| | vvi-miR156e | TGACAGAGGAGAGTGAGCAC (1236) | 0.7 | 3061 |
| | vvi-miR156f | TTGACAGAAGATAGAGAGCAC (1237) | 0.85 | 3062 |
| | vvi-miR156g | TTGACAGAAGATAGAGAGCAC (1238) | 0.85 | 3063 |
| | vvi-miR156h | TGACAGAAGAGAGAGAGCAT (1239) | 0.75 | 3064 |
| | vvi-miR156i | TTGACAGAAGATAGAGAGCAC (1240) | 0.85 | 3065 |
| | zel-miR156 | TGACAGAAGAGAGAGAGCAC (1241) | 0.8 | 3066 |
| | zma-miR156a | TGACAGAAGAGAGTGAGCAC (1242) | 0.75 | 3067 |
| | zma-miR156b | TGACAGAAGAGAGTGAGCAC (1243) | 0.75 | 3068 |
| | zma-miR156c | TGACAGAAGAGAGTGAGCAC (1244) | 0.75 | 3069 |
| | zma-miR156d | TGACAGAAGAGAGTGAGCAC (1245) | 0.75 | 3070 |
| | zma-miR156e | TGACAGAAGAGAGTGAGCAC (1246) | 0.75 | 3071 |
| | zma-miR156f | TGACAGAAGAGAGTGAGCAC (1247) | 0.75 | 3072 |
| | zma-miR156g | TGACAGAAGAGAGTGAGCAC (1248) | 0.75 | 3073 |
| | zma-miR156h | TGACAGAAGAGAGTGAGCAC (1249) | 0.75 | 3074 |
| | zma-miR156i | TGACAGAAGAGAGTGAGCAC (1250) | 0.75 | 3075 |
| | zma-miR156j | TGACAGAAGAGAGAGAGCACA (1251) | 0.85 | 3076 |
| | zma-miR156k | TGACAGAAGAGAGCGAGCAC (1252) | 0.75 | 3077 |
| | zma-miR156l | TGACAGAAGAGAGTGAGCAC (1253) | 0.75 | 3078 |
| | zma-miR156m | TGACAGAAGAGAGTGAGCAC (1254) | 0.75 | 3079 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR156n | TGACAGAAGAGAGTGAGCAC (1255) | 0.75 | 3080 |
| | zma-miR156o | TGACAGAAGAGAGTGAGCAC (1256) | 0.75 | 3081 |
| | zma-miR156p | TGACAGAAGAGAGAGAGCAC (1257) | 0.8 | 3082 |
| | zma-miR156q | TGACAGAAGAGAGAGAGCAC (1258) | 0.8 | 3083 |
| | zma-miR156r | TGACAGAAGAGAGTGGGCAC (1259) | 0.7 | 3084 |
| pta-miR156b | ahy-miR156a | TGACAGAAGAGAGAGAGCAC (1260) | 0.8 | 3085 |
| | ahy-miR156b-5p | TTGACAGAAGATAGAGAGCAC (1261) | 0.85 | 3086 |
| | ahy-miR156c | TTGACAGAAGAGAGAGAGCAC (1262) | 0.8 | 3087 |
| | aly-miR156a | TGACAGAAGAGAGTGAGCAC (1263) | 0.75 | 3088 |
| | aly-miR156b | TGACAGAAGAGAGTGAGCAC (1264) | 0.75 | 3089 |
| | aly-miR156c | TGACAGAAGAGAGTGAGCAC (1265) | 0.75 | 3090 |
| | aly-miR156d | TGACAGAAGAGAGTGAGCAC (1266) | 0.75 | 3091 |
| | aly-miR156e | TGACAGAAGAGAGTGAGCAC (1267) | 0.75 | 3092 |
| | aly-miR156f | TGACAGAAGAGAGTGAGCAC (1268) | 0.75 | 3093 |
| | aly-miR156g | CGACAGAAGAGAGTGAGCAC (1269) | 0.75 | 3094 |
| | aly-miR156h | TGACAGAAGAAAGAGAGCAC (1270) | 0.8 | 3095 |
| | aqc-miR156a | TGACAGAAGATAGAGAGCAC (1271) | 0.85 | 3096 |
| | aqc-miR156b | TGACAGAAGATAGAGAGCAC (1272) | 0.85 | 3097 |
| | ath-miR156a | TGACAGAAGAGAGTGAGCAC (1273) | 0.75 | 3098 |
| | ath-miR156b | TGACAGAAGAGAGTGAGCAC (1274) | 0.75 | 3099 |
| | ath-miR156c | TGACAGAAGAGAGTGAGCAC (1275) | 0.75 | 3100 |
| | ath-miR156d | TGACAGAAGAGAGTGAGCAC (1276) | 0.75 | 3101 |
| | ath-miR156e | TGACAGAAGAGAGTGAGCAC (1277) | 0.75 | 3102 |
| | ath-miR156f | TGACAGAAGAGAGTGAGCAC (1278) | 0.75 | 3103 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ath-miR156g | CGACAGAAGAGAGTGAGCAC (1279) | 0.75 | 3104 |
| | ath-miR156h | TGACAGAAGAAAGAGAGCAC (1280) | 0.8 | 3105 |
| | ath-miR156m | TGACAGAAGAGAGAGAGCAC (1281) | 0.8 | 3106 |
| | ath-miR156o | TGACAGAAGAGAGAGAGCAC (1282) | 0.8 | 3107 |
| | ath-miR156p | TGACAGAAGAGAGAGAGCAC (1283) | 0.8 | 3108 |
| | ath-miR156q | TGACAGAAGAGAGAGAGCAC (1284) | 0.8 | 3109 |
| | ath-miR156r | TGACAGAAGAGAGAGAGCAC (1285) | 0.8 | 3110 |
| | ath-miR156s | TGACAGAAGAGAGAGAGCAC (1286) | 0.8 | 3111 |
| | bdi-miR156 | TGACAGAAGAGAGAGAGCACA (1287) | 0.85 | 3112 |
| | bdi-miR156b | TGACAGAAGAGAGTGAGCAC (1288) | 0.75 | 3113 |
| | bdi-miR156c | TGACAGAAGAGAGTGAGCAC (1289) | 0.75 | 3114 |
| | bdi-miR156d | TGACAGAAGAGAGTGAGCAC (1290) | 0.75 | 3115 |
| | bna-miR156a | TGACAGAAGAGAGTGAGCACA (1291) | 0.8 | 3116 |
| | bna-miR156b | TTGACAGAAGATAGAGAGCAC (1292) | 0.85 | 3117 |
| | bna-miR156c | TTGACAGAAGATAGAGAGCAC (1293) | 0.85 | 3118 |
| | can-miR156a | TGACAGAAGAGAGAGAGCAC (1294) | 0.8 | 3119 |
| | can-miR156b | TGACAGAAGAGAGGGAGCAC (1295) | 0.75 | 3120 |
| | cpt-miR156a | TGACAGAAGAGAGTGAGCAC (1296) | 0.75 | 3121 |
| | cpt-miR156b | TGACAGAAGAGAGAGAGCAC (1297) | 0.8 | 3122 |
| | cru-miR156 | TGACAGAAGAGAGAGAGCAC (1298) | 0.8 | 3123 |
| | csi-miR156 | TGACAGAAGAGAGTGAGCAC (1299) | 0.75 | 3124 |
| | csi-miR156a | TGACAGAAGAGAGAGAGCAC (1300) | 0.8 | 3125 |
| | csi-miR156b | TGACAGAAGAGAGAGAGCAC (1301) | 0.8 | 3126 |
| | ctr-miR156 | TGACAGAAGAGAGTGAGCAC (1302) | 0.75 | 3127 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | eca-miR156 | TGACAGAAGAGAGAGA GCAC (1303) | 0.8 | 3128 |
| | far-miR156a | TGACAGAAGAGAGAGA GCACA (1304) | 0.85 | 3129 |
| | far-miR156b | TTGACAGAAGAGAGAG AGCAC (1305) | 0.8 | 3130 |
| | ghr-miR156a | TGACAGAAGAGAGTGA GCAC (1306) | 0.75 | 3131 |
| | ghr-miR156b | TGACAGAAGAGAGTGA GCAC (1307) | 0.75 | 3132 |
| | ghr-miR156c | TGTCAGAAGAGAGTGA GCAC (1308) | 0.75 | 3133 |
| | ghr-miR156d | TGACAGAAGAGAGTGA GCAC (1309) | 0.75 | 3134 |
| | gma-miR156a | TGACAGAAGAGAGTGA GCAC (1310) | 0.75 | 3135 |
| | gma-miR156b | TGACAGAAGAGAGAGA GCACA (1311) | 0.85 | 3136 |
| | gma-miR156c | TTGACAGAAGATAGAG AGCAC (1312) | 0.85 | 3137 |
| | gma-miR156d | TTGACAGAAGATAGAG AGCAC (1313) | 0.85 | 3138 |
| | gma-miR156e | TTGACAGAAGATAGAG AGCAC (1314) | 0.85 | 3139 |
| | gma-miR156f | TTGACAGAAGAGAGAG AGCACA (1315) | 0.85 | 3140 |
| | gma-miR156g | ACAGAAGATAGAGAGC ACAG (1316) | 0.9 | 3141 |
| | gma-miR156h | TGACAGAAGAGAGAGA GCAC (1317) | 0.8 | 3142 |
| | gma-miR156i | TGACAGAAGAGAGAGA GCAC (1318) | 0.8 | 3143 |
| | han-miR156 | TGACAGAAGAGAGAGA GCAC (1319) | 0.8 | 3144 |
| | hvs-miR156 | TGACAGAAGAGAGAGA GCAC (1320) | 0.8 | 3145 |
| | hvu-miR156 | TGACAGAAGAGAGTGA GCACA (1321) | 0.8 | 3146 |
| | hvv-miR156a | TGACAGAAGAGAGTGA GCAC (1322) | 0.75 | 3147 |
| | hvv-miR156b | TGACAGAAGAGAGAGA GCAC (1323) | 0.8 | 3148 |
| | hvv-miR156c | TGACAGAAGAGAGAGA GCAC (1324) | 0.8 | 3149 |
| | hvv-miR156d | TGACAGAAGAGAGAGA GCAC (1325) | 0.8 | 3150 |
| | lja-miR156 | TGACAGAAGAGAGAGA GCAC (1326) | 0.8 | 3151 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
| --- | --- | --- | --- | --- |
| | lsa-miR156 | TGACAGAAGAGAGAGCAC (1327) | 0.8 | 3152 |
| | mdo-miR156a | TGACAGAAGAGAGAGCAC (1328) | 0.8 | 3153 |
| | mdo-miR156b | TGACAGAAGAGAGAGCAC (1329) | 0.8 | 3154 |
| | mtr-miR156 | TGACAGAAGAGAGAGCACA (1330) | 0.85 | 3155 |
| | mtr-miR156b | TGACAGAAGAGAGTGAGCAC (1331) | 0.75 | 3156 |
| | mtr-miR156c | TGACAGAAGAGAGTGAGCAC (1332) | 0.75 | 3157 |
| | mtr-miR156d | TGACAGAAGAGAGTGAGCAC (1333) | 0.75 | 3158 |
| | mtr-miR156e | TTGACAGAAGATAGAGAGCAC (1334) | 0.85 | 3159 |
| | mtr-miR156f | TTGACAGAAGATAGAGAGCAC (1335) | 0.85 | 3160 |
| | mtr-miR156g | TTGACAGAAGATAGAGGGCAC (1336) | 0.8 | 3161 |
| | mtr-miR156h | TTGACAGAAGATAGAGAGCAC (1337) | 0.85 | 3162 |
| | mtr-miR156i | TGACAGAAGAGAGTGAGCAC (1338) | 0.75 | 3163 |
| | nbe-miR156a | TGACAGAAGAGAGAGCAC (1339) | 0.8 | 3164 |
| | nbe-miR156b | TGACAGAAGAGAGAGCAC (1340) | 0.8 | 3165 |
| | oru-miR156 | TGACAGAAGAGAGTGAGCAC (1341) | 0.75 | 3166 |
| | osa-miR156a | TGACAGAAGAGAGTGAGCAC (1342) | 0.75 | 3167 |
| | osa-miR156b | TGACAGAAGAGAGTGAGCAC (1343) | 0.75 | 3168 |
| | osa-miR156c | TGACAGAAGAGAGTGAGCAC (1344) | 0.75 | 3169 |
| | osa-miR156d | TGACAGAAGAGAGTGAGCAC (1345) | 0.75 | 3170 |
| | osa-miR156e | TGACAGAAGAGAGTGAGCAC (1346) | 0.75 | 3171 |
| | osa-miR156f | TGACAGAAGAGAGTGAGCAC (1347) | 0.75 | 3172 |
| | osa-miR156g | TGACAGAAGAGAGTGAGCAC (1348) | 0.75 | 3173 |
| | osa-miR156h | TGACAGAAGAGAGTGAGCAC (1349) | 0.75 | 3174 |
| | osa-miR156i | TGACAGAAGAGAGTGAGCAC (1350) | 0.75 | 3175 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | osa-miR156j | TGACAGAAGAGAGTGA GCAC (1351) | 0.75 | 3176 |
| | osa-miR156k | TGACAGAAGAGAGAGA GCACA (1352) | 0.85 | 3177 |
| | osa-miR156l | CGACAGAAGAGAGTGA GCATA (1353) | 0.75 | 3178 |
| | osa-miR156m | TGACAGAAGAGAGTGA GCAC (1354) | 0.75 | 3179 |
| | osa-miR156n | TGACAGAAGAGAGTGA GCAC (1355) | 0.75 | 3180 |
| | osa-miR156o | TGACAGAAGAGAGTGA GCAT (1356) | 0.7 | 3181 |
| | osa-miR156p | TGACAGAAGAGAGTGA GCTC (1357) | 0.7 | 3182 |
| | osa-miR156q | TGACAGAACAGAGTGA GCAC (1358) | 0.7 | 3183 |
| | osa-miR156r | TGACAGAAGAGAGAGA GCAC (1359) | 0.8 | 3184 |
| | par-miR156 | TGACAGAAGAGAGAGA GCAC (1360) | 0.8 | 3185 |
| | ppd-miR156 | TGACAGAAGAGAGAGA GCAC (1361) | 0.8 | 3186 |
| | ppr-miR156 | TGACAGAAGAGAGTGA GCAC (1362) | 0.75 | 3187 |
| | ppt-miR156a | TGACAGAAGAGAGTGA GCAC (1363) | 0.75 | 3188 |
| | ppt-miR156b | TGACAGAAGAGAGTGA GCAC (1364) | 0.75 | 3189 |
| | ppt-miR156c | TGACAGAAGAGAGTGA GCAC (1365) | 0.75 | 3190 |
| | pta-miR156a | CAGAAGATAGAGAGCA CATC (1366) | 0.95 | 3191 |
| | ptc-miR156a | TGACAGAAGAGAGTGA GCAC (1367) | 0.75 | 3192 |
| | ptc-miR156b | TGACAGAAGAGAGTGA GCAC (1368) | 0.75 | 3193 |
| | ptc-miR156c | TGACAGAAGAGAGTGA GCAC (1369) | 0.75 | 3194 |
| | ptc-miR156d | TGACAGAAGAGAGTGA GCAC (1370) | 0.75 | 3195 |
| | ptc-miR156e | TGACAGAAGAGAGTGA GCAC (1371) | 0.75 | 3196 |
| | ptc-miR156f | TGACAGAAGAGAGTGA GCAC (1372) | 0.75 | 3197 |
| | ptc-miR156g | TTGACAGAAGATAGAG AGCAC (1373) | 0.85 | 3198 |
| | ptc-miR156h | TTGACAGAAGATAGAG AGCAC (1374) | 0.85 | 3199 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ptc-miR156i | TTGACAGAAGATAGAGAGCAC (1375) | 0.85 | 3200 |
| | ptc-miR156j | TTGACAGAAGATAGAGAGCAC (1376) | 0.85 | 3201 |
| | ptc-miR156k | TGACAGAAGAGAGGGAGCAC (1377) | 0.75 | 3202 |
| | ptr-miR156 | TGACAGAAGAGAGAGAGCAC (1378) | 0.8 | 3203 |
| | pts-miR156a | TGACAGAAGAGAGAGTGAGCGC (1379) | 0.7 | 3204 |
| | pts-miR156b | TGACAGAAGAGAGAGAGCAC (1380) | 0.8 | 3205 |
| | pts-miR156c | TGACAGAAGAGAGAGAGCAC (1381) | 0.8 | 3206 |
| | rco-miR156a | TGACAGAAGAGAGTGAGCACA (1382) | 0.8 | 3207 |
| | rco-miR156b | TGACAGAAGAGAGTGAGCACA (1383) | 0.8 | 3208 |
| | rco-miR156c | TGACAGAAGAGAGTGAGCACA (1384) | 0.8 | 3209 |
| | rco-miR156d | TGACAGAAGAGAGTGAGCACA (1385) | 0.8 | 3210 |
| | rco-miR156e | TGACAGAAGAGAGAGAGCACA (1386) | 0.85 | 3211 |
| | rco-miR156f | TTGACAGAAGATAGAGAGCAC (1387) | 0.85 | 3212 |
| | rco-miR156g | TTGACAGAAGATAGAGAGCAC (1388) | 0.85 | 3213 |
| | rco-miR156h | TTGACAGAAGATAGAGAGCAC (1389) | 0.85 | 3214 |
| | sbi-miR156a | TGACAGAAGAGAGTGAGCAC (1390) | 0.75 | 3215 |
| | sbi-miR156b | TGACAGAAGAGAGTGAGCAC (1391) | 0.75 | 3216 |
| | sbi-miR156c | TGACAGAAGAGAGTGAGCAC (1392) | 0.75 | 3217 |
| | sbi-miR156d | TGACAGAAGAGAGAGAGCACA (1393) | 0.85 | 3218 |
| | sbi-miR156e | TGACAGAAGAGAGCGAGCAC (1394) | 0.75 | 3219 |
| | sbi-miR156f | TGACAGAAGAGAGTGAGCAC (1395) | 0.75 | 3220 |
| | sbi-miR156g | TGACAGAAGAGAGTGAGCAC (1396) | 0.75 | 3221 |
| | sbi-miR156h | TGACAGAAGAGAGTGAGCAC (1397) | 0.75 | 3222 |
| | sbi-miR156i | TGACAGAAGAGAGTGAGCAC (1398) | 0.75 | 3223 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sin-miR156 | TGACAGAAGAGAGAGCAC (1399) | 0.8 | 3224 |
| | sly-miR156a | TTGACAGAAGATAGAGAGCAC (1400) | 0.85 | 3225 |
| | sly-miR156b | TTGACAGAAGATAGAGAGCAC (1401) | 0.85 | 3226 |
| | sly-miR156c | TTGACAGAAGATAGAGAGCAC (1402) | 0.85 | 3227 |
| | smo-miR156a | CGACAGAAGAGAGTGAGCAC (1403) | 0.75 | 3228 |
| | smo-miR156b | CTGACAGAAGATAGAGAGCAC (1404) | 0.85 | 3229 |
| | smo-miR156c | TTGACAGAAGAAAGAGAGCAC (1405) | 0.8 | 3230 |
| | smo-miR156d | TTGACAGAAGACAGGGAGCAC (1406) | 0.75 | 3231 |
| | sof-miR156 | TGACAGAAGAGAGTGAGCAC (1407) | 0.75 | 3232 |
| | sof-miR156c | TGACAGAAGAGAGAGAGCAC (1408) | 0.8 | 3233 |
| | sof-miR156d | TGACAGAAGAGAGAGAGCAC (1409) | 0.8 | 3234 |
| | sof-miR156e | TGACAGAAGAGAGAGAGCAC (1410) | 0.8 | 3235 |
| | sof-miR156f | TGACAGAAGAGAGAGAGCAC (1411) | 0.8 | 3236 |
| | sof-miR156g | TGACAGAAGAGAGAGAGCAC (1412) | 0.8 | 3237 |
| | sof-miR156h | TGACAGAAGAGAGAGAGCAC (1413) | 0.8 | 3238 |
| | sof-miR156u | TGACAGAAGAGAGAGAGCAC (1414) | 0.8 | 3239 |
| | spr-miR156 | TGACAGAAGAGAGAGAGCAC (1415) | 0.8 | 3240 |
| | ssp-miR156 | TGACAGAAGAGAGTGAGCACA (1416) | 0.8 | 3241 |
| | stu-miR156a | TGACAGAAGAGAGTGAGCAC (1417) | 0.75 | 3242 |
| | stu-miR156b | TGACAGAAGAGAGAGAGCAC (1418) | 0.8 | 3243 |
| | stu-miR156c | TGACAGAAGAGAGAGAGCAC (1419) | 0.8 | 3244 |
| | stu-miR156d | TGACAGAAGAGAGAGAGCAC (1420) | 0.8 | 3245 |
| | stu-miR156e | TGACAGAAGAGAGAGAGCAC (1421) | 0.8 | 3246 |
| | tae-miR156 | TGACAGAAGAGAGTGAGCACA (1422) | 0.8 | 3247 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | tae-miR156a | TGACAGAAGAGAGAGA GCAC (1423) | 0.8 | 3248 |
| | tae-miR156b | TGACAGAAGAGAGAGA GCAC (1424) | 0.8 | 3249 |
| | tcc-miR156a | TGACAGAAGAGAGAGA GCACA (1425) | 0.85 | 3250 |
| | tcc-miR156b | TGACAGAAGAGAGTGA GCAC (1426) | 0.75 | 3251 |
| | tcc-miR156c | TGACAGAAGAGAGTGA GCAC (1427) | 0.75 | 3252 |
| | tcc-miR156d | TGACAGAAGAGAGTGA GCAC (1428) | 0.75 | 3253 |
| | tcc-miR156e | TTGACAGAAGATAGAG AGCAC (1429) | 0.85 | 3254 |
| | tcc-miR156f | TTGACAGAAGATAGAG AGCAC (1430) | 0.85 | 3255 |
| | tcc-miR156g | TGACAGAAGAGAGTGA GCAC (1431) | 0.75 | 3256 |
| | tre-miR156 | TGACAGAAGAGAGTGA GCAC (1432) | 0.75 | 3257 |
| | vvi-miR156a | TGACAGAAGAGAGGGA GCAC (1433) | 0.75 | 3258 |
| | vvi-miR156b | TGACAGAAGAGAGTGA GCAC (1434) | 0.75 | 3259 |
| | vvi-miR156c | TGACAGAAGAGAGTGA GCAC (1435) | 0.75 | 3260 |
| | vvi-miR156d | TGACAGAAGAGAGTGA GCAC (1436) | 0.75 | 3261 |
| | vvi-miR156e | TGACAGAGGAGAGTGA GCAC (1437) | 0.7 | 3262 |
| | vvi-miR156f | TTGACAGAAGATAGAG AGCAC (1438) | 0.85 | 3263 |
| | vvi-miR156g | TTGACAGAAGATAGAG AGCAC (1439) | 0.85 | 3264 |
| | vvi-miR156h | TGACAGAAGAGAGAGA GCAT (1440) | 0.75 | 3265 |
| | vvi-miR156i | TTGACAGAAGATAGAG AGCAC (1441) | 0.85 | 3266 |
| | zel-miR156 | TGACAGAAGAGAGAGA GCAC (1442) | 0.8 | 3267 |
| | zma-miR156a | TGACAGAAGAGAGTGA GCAC (1443) | 0.75 | 3268 |
| | zma-miR156b | TGACAGAAGAGAGTGA GCAC (1444) | 0.75 | 3269 |
| | zma-miR156c | TGACAGAAGAGAGTGA GCAC (1445) | 0.75 | 3270 |
| | zma-miR156d | TGACAGAAGAGAGTGA GCAC (1446) | 0.75 | 3271 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR156e | TGACAGAAGAGAGTGA GCAC (1447) | 0.75 | 3272 |
| | zma-miR156f | TGACAGAAGAGAGTGA GCAC (1448) | 0.75 | 3273 |
| | zma-miR156g | TGACAGAAGAGAGTGA GCAC (1449) | 0.75 | 3274 |
| | zma-miR156h | TGACAGAAGAGAGTGA GCAC (1450) | 0.75 | 3275 |
| | zma-miR156i | TGACAGAAGAGAGTGA GCAC (1451) | 0.75 | 3276 |
| | zma-miR156j | TGACAGAAGAGAGAGA GCACA (1452) | 0.85 | 3277 |
| | zma-miR156k | TGACAGAAGAGAGCGA GCAC (1453) | 0.75 | 3278 |
| | zma-miR156l | TGACAGAAGAGAGTGA GCAC (1454) | 0.75 | 3279 |
| | zma-miR156m | TGACAGAAGAGAGTGA GCAC (1455) | 0.75 | 3280 |
| | zma-miR156n | TGACAGAAGAGAGTGA GCAC (1456) | 0.75 | 3281 |
| | zma-miR156o | TGACAGAAGAGAGTGA GCAC (1457) | 0.75 | 3282 |
| | zma-miR156p | TGACAGAAGAGAGAGA GCAC (1458) | 0.8 | 3283 |
| | zma-miR156q | TGACAGAAGAGAGAGA GCAC (1459) | 0.8 | 3284 |
| | zma-miR156r | TGACAGAAGAGAGTGG GCAC (1460) | 0.7 | 3285 |
| ptc-miRf10271-akr | ahy-miR159 | TTTGGATTGAAGGGAGC TCTA (1461) | 0.95 | 3286 |
| | aly-miR159a | TTTGGATTGAAGGGAGC TCTA (1462) | 0.95 | 3287 |
| | aly-miR159b | TTTGGATTGAAGGGAGC TCTT (1463) | 0.9 | 3288 |
| | aqc-miR159 | TTTGGACTGAAGGGAGC TCTA (1464) | 0.9 | 3289 |
| | ath-miR159a | TTTGGATTGAAGGGAGC TCTA (1465) | 0.95 | 3290 |
| | ath-miR159b | TTTGGATTGAAGGGAGC TCTT (1466) | 0.9 | 3291 |
| | bdi-miR159 | CTTGGATTGAAGGGAGC TCT (1467) | 0.9 | 3292 |
| | bna-miR159 | TTTGGATTGAAGGGAGC TCTA (1468) | 0.95 | 3293 |
| | bra-miR159a | TTTGGATTGAAGGGAGC TCTA (1469) | 0.95 | 3294 |
| | csi-miR159 | TTTGGATTGAAGGGAGC TCTA (1470) | 0.95 | 3295 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | far-miR159 | TTTGGATTGAAGGGAGCTCTG (1471) | 0.9 | 3296 |
| | gma-miR159a-3p | TTTGGATTGAAGGGAGCTCTA (1472) | 0.95 | 3297 |
| | hvu-miR159a | TTTGGATTGAAGGGAGCTCTG (1473) | 0.9 | 3298 |
| | hvu-miR159b | TTTGGATTGAAGGGAGCTCTG (1474) | 0.9 | 3299 |
| | mtr-miR159a | TTTGGATTGAAGGGAGCTCTA (1475) | 0.95 | 3300 |
| | osa-miR159a.1 | TTTGGATTGAAGGGAGCTCTG (1476) | 0.9 | 3301 |
| | osa-miR159b | TTTGGATTGAAGGGAGCTCTG (1477) | 0.9 | 3302 |
| | osa-miR159c | ATTGGATTGAAGGGAGCTCCA (1478) | 0.9 | 3303 |
| | osa-miR159f | CTTGGATTGAAGGGAGCTCTA (1479) | 0.95 | 3304 |
| | pta-miR159a | TTGGATTGAAGGGAGCTCCA (1480) | 0.9 | 3305 |
| | ptc-miR159a | TTTGGATTGAAGGGAGCTCTA (1481) | 0.95 | 3306 |
| | ptc-miR159b | TTTGGATTGAAGGGAGCTCTA (1482) | 0.95 | 3307 |
| | ptc-miR159c | TTTGGATTGAAGGGAGCTCTA (1483) | 0.95 | 3308 |
| | pvu-miR159a.1 | TTTGGATTGAAGGGAGCTCTA (1484) | 0.95 | 3309 |
| | rco-miR159 | TTTGGATTGAAGGGAGCTCTA (1485) | 0.95 | 3310 |
| | sbi-miR159a | TTTGGATTGAAGGGAGCTCTG (1486) | 0.9 | 3311 |
| | sly-miR159 | TTTGGATTGAAGGGAGCTCTA (1487) | 0.95 | 3312 |
| | sof-miR159a | TTTGGATTGAAGGGAGCTCTG (1488) | 0.9 | 3313 |
| | sof-miR159b | TTTGGATTGAAGGGAGCTCTG (1489) | 0.9 | 3314 |
| | sof-miR159d | TTTGGATTGAAGGGAGCTCTG (1490) | 0.9 | 3315 |
| | ssp-miR159a | TTTGGATTGAAGGGAGCTCTG (1491) | 0.9 | 3316 |
| | tae-miR159a | TTTGGATTGAAGGGAGCTCTG (1492) | 0.9 | 3317 |
| | tae-miR159b | TTTGGATTGAAGGGAGCTCTG (1493) | 0.9 | 3318 |
| | vvi-miR159c | TTTGGATTGAAGGGAGCTCTA (1494) | 0.95 | 3319 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR159a | TTTGGATTGAAGGGAGCTCTG (1495) | 0.9 | 3320 |
| | zma-miR159b | TTTGGATTGAAGGGAGCTCTG (1496) | 0.9 | 3321 |
| | zma-miR159f | TTTGGATTGAAGGGAGCTCTG (1497) | 0.9 | 3322 |
| | zma-miR159j | TTTGGATTGAAGGGAGCTCTG (1498) | 0.9 | 3323 |
| | zma-miR159k | TTTGGATTGAAGGGAGCTCTG (1499) | 0.9 | 3324 |
| ptc-miRf10985-akr | gma-miR156g | ACAGAAGATAGAGAGCACAG (1500) | 0.9 | 3325 |
| ath-miR157a | ahy-miR156a | TGACAGAAGAGAGAGAGCAC (1501) | 0.9 | 3326 |
| | ahy-miR156b-5p | TTGACAGAAGATAGAGAGCAC (1502) | 1 | 3327 |
| | ahy-miR156c | TTGACAGAAGAGAGAGAGCAC (1503) | 0.95 | 3328 |
| | aly-miR156a | TGACAGAAGAGAGTGAGCAC (1504) | 0.86 | 3329 |
| | aly-miR156b | TGACAGAAGAGAGTGAGCAC (1505) | 0.86 | 3330 |
| | aly-miR156c | TGACAGAAGAGAGTGAGCAC (1506) | 0.86 | 3331 |
| | aly-miR156d | TGACAGAAGAGAGTGAGCAC (1507) | 0.86 | 3332 |
| | aly-miR156e | TGACAGAAGAGAGTGAGCAC (1508) | 0.86 | 3333 |
| | aly-miR156f | TGACAGAAGAGAGTGAGCAC (1509) | 0.86 | 3334 |
| | aly-miR156g | CGACAGAAGAGAGTGAGCAC (1510) | 0.81 | 3335 |
| | aly-miR156h | TGACAGAAGAAAGAGAGCAC (1511) | 0.9 | 3336 |
| | aqc-miR156a | TGACAGAAGATAGAGAGCAC (1512) | 0.95 | 3337 |
| | aqc-miR156b | TGACAGAAGATAGAGAGCAC (1513) | 0.95 | 3338 |
| | ath-miR156a | TGACAGAAGAGAGTGAGCAC (1514) | 0.86 | 3339 |
| | ath-miR156b | TGACAGAAGAGAGTGAGCAC (1515) | 0.86 | 3340 |
| | ath-miR156c | TGACAGAAGAGAGTGAGCAC (1516) | 0.86 | 3341 |
| | ath-miR156d | TGACAGAAGAGAGTGAGCAC (1517) | 0.86 | 3342 |
| | ath-miR156e | TGACAGAAGAGAGTGAGCAC (1518) | 0.86 | 3343 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ath-miR156f | TGACAGAAGAGAGTGAGCAC (1519) | 0.86 | 3344 |
| | ath-miR156g | CGACAGAAGAGAGTGAGCAC (1520) | 0.81 | 3345 |
| | ath-miR156h | TGACAGAAGAAAGAGAGCAC (1521) | 0.9 | 3346 |
| | ath-miR156m | TGACAGAAGAGAGAGAGCAC (1522) | 0.9 | 3347 |
| | ath-miR156o | TGACAGAAGAGAGAGAGCAC (1523) | 0.9 | 3348 |
| | ath-miR156p | TGACAGAAGAGAGAGAGCAC (1524) | 0.9 | 3349 |
| | ath-miR156q | TGACAGAAGAGAGAGAGCAC (1525) | 0.9 | 3350 |
| | ath-miR156r | TGACAGAAGAGAGAGAGCAC (1526) | 0.9 | 3351 |
| | ath-miR156s | TGACAGAAGAGAGAGAGCAC (1527) | 0.9 | 3352 |
| | bdi-miR156 | TGACAGAAGAGAGAGAGCACA (1528) | 0.9 | 3353 |
| | bdi-miR156b | TGACAGAAGAGAGTGAGCAC (1529) | 0.86 | 3354 |
| | bdi-miR156c | TGACAGAAGAGAGTGAGCAC (1530) | 0.86 | 3355 |
| | bdi-miR156d | TGACAGAAGAGAGTGAGCAC (1531) | 0.86 | 3356 |
| | bna-miR156a | TGACAGAAGAGAGTGAGCACA (1532) | 0.86 | 3357 |
| | bna-miR156b | TTGACAGAAGATAGAGAGCAC (1533) | 1 | 3358 |
| | bna-miR156c | TTGACAGAAGATAGAGAGCAC (1534) | 1 | 3359 |
| | can-miR156a | TGACAGAAGAGAGAGAGCAC (1535) | 0.9 | 3360 |
| | can-miR156b | TGACAGAAGAGAGGGAGCAC (1536) | 0.86 | 3361 |
| | cpt-miR156a | TGACAGAAGAGAGTGAGCAC (1537) | 0.86 | 3362 |
| | cpt-miR156b | TGACAGAAGAGAGAGAGCAC (1538) | 0.9 | 3363 |
| | cru-miR156 | TGACAGAAGAGAGAGAGCAC (1539) | 0.9 | 3364 |
| | csi-miR156 | TGACAGAAGAGAGTGAGCAC (1540) | 0.86 | 3365 |
| | csi-miR156a | TGACAGAAGAGAGAGAGCAC (1541) | 0.9 | 3366 |
| | csi-miR156b | TGACAGAAGAGAGAGAGCAC (1542) | 0.9 | 3367 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ctr-miR156 | TGACAGAAGAGAGTGAGCAC (1543) | 0.86 | 3368 |
| | eca-miR156 | TGACAGAAGAGAGAGAGCAC (1544) | 0.9 | 3369 |
| | far-miR156a | TGACAGAAGAGAGAGAGCACA (1545) | 0.9 | 3370 |
| | far-miR156b | TTGACAGAAGAGAGAGAGCAC (1546) | 0.95 | 3371 |
| | ghr-miR156a | TGACAGAAGAGAGTGAGCAC (1547) | 0.86 | 3372 |
| | ghr-miR156b | TGACAGAAGAGAGTGAGCAC (1548) | 0.86 | 3373 |
| | ghr-miR156c | TGTCAGAAGAGAGTGAGCAC (1549) | 0.81 | 3374 |
| | ghr-miR156d | TGACAGAAGAGAGTGAGCAC (1550) | 0.86 | 3375 |
| | gma-miR156a | TGACAGAAGAGAGTGAGCAC (1551) | 0.86 | 3376 |
| | gma-miR156b | TGACAGAAGAGAGAGAGCACA (1552) | 0.9 | 3377 |
| | gma-miR156c | TTGACAGAAGATAGAGAGCAC (1553) | 1 | 3378 |
| | gma-miR156d | TTGACAGAAGATAGAGAGCAC (1554) | 1 | 3379 |
| | gma-miR156e | TTGACAGAAGATAGAGAGCAC (1555) | 1 | 3380 |
| | gma-miR156f | TTGACAGAAGAGAGAGAGCACA (1556) | 0.95 | 3381 |
| | gma-miR156g | ACAGAAGATAGAGAGCACAG (1557) | 0.86 | 3382 |
| | gma-miR156h | TGACAGAAGAGAGAGAGCAC (1558) | 0.9 | 3383 |
| | gma-miR156i | TGACAGAAGAGAGAGAGCAC (1559) | 0.9 | 3384 |
| | han-miR156 | TGACAGAAGAGAGAGAGCAC (1560) | 0.9 | 3385 |
| | hvs-miR156 | TGACAGAAGAGAGAGAGCAC (1561) | 0.9 | 3386 |
| | hvu-miR156 | TGACAGAAGAGAGTGAGCACA (1562) | 0.86 | 3387 |
| | hvv-miR156a | TGACAGAAGAGAGTGAGCAC (1563) | 0.86 | 3388 |
| | hvv-miR156b | TGACAGAAGAGAGAGAGCAC (1564) | 0.9 | 3389 |
| | hvv-miR156c | TGACAGAAGAGAGAGAGCAC (1565) | 0.9 | 3390 |
| | hvv-miR156d | TGACAGAAGAGAGAGAGCAC (1566) | 0.9 | 3391 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | lja-miR156 | TGACAGAAGAGAGAGA GCAC (1567) | 0.9 | 3392 |
| | lsa-miR156 | TGACAGAAGAGAGAGA GCAC (1568) | 0.9 | 3393 |
| | mdo-miR156a | TGACAGAAGAGAGAGA GCAC (1569) | 0.9 | 3394 |
| | mdo-miR156b | TGACAGAAGAGAGAGA GCAC (1570) | 0.9 | 3395 |
| | mtr-miR156 | TGACAGAAGAGAGAGA GCACA (1571) | 0.9 | 3396 |
| | mtr-miR156b | TGACAGAAGAGAGTGA GCAC (1572) | 0.86 | 3397 |
| | mtr-miR156c | TGACAGAAGAGAGTGA GCAC (1573) | 0.86 | 3398 |
| | mtr-miR156d | TGACAGAAGAGAGTGA GCAC (1574) | 0.86 | 3399 |
| | mtr-miR156e | TTGACAGAAGATAGAG AGCAC (1575) | 1 | 3400 |
| | mtr-miR156f | TTGACAGAAGATAGAG AGCAC (1576) | 1 | 3401 |
| | mtr-miR156g | TTGACAGAAGATAGAG GGCAC (1577) | 0.95 | 3402 |
| | mtr-miR156h | TTGACAGAAGATAGAG AGCAC (1578) | 1 | 3403 |
| | mtr-miR156i | TGACAGAAGAGAGTGA GCAC (1579) | 0.86 | 3404 |
| | nbe-miR156a | TGACAGAAGAGAGAGA GCAC (1580) | 0.9 | 3405 |
| | nbe-miR156b | TGACAGAAGAGAGAGA GCAC (1581) | 0.9 | 3406 |
| | oru-miR156 | TGACAGAAGAGAGTGA GCAC (1582) | 0.86 | 3407 |
| | osa-miR156a | TGACAGAAGAGAGTGA GCAC (1583) | 0.86 | 3408 |
| | osa-miR156b | TGACAGAAGAGAGTGA GCAC (1584) | 0.86 | 3409 |
| | osa-miR156c | TGACAGAAGAGAGTGA GCAC (1585) | 0.86 | 3410 |
| | osa-miR156d | TGACAGAAGAGAGTGA GCAC (1586) | 0.86 | 3411 |
| | osa-miR156e | TGACAGAAGAGAGTGA GCAC (1587) | 0.86 | 3412 |
| | osa-miR156f | TGACAGAAGAGAGTGA GCAC (1588) | 0.86 | 3413 |
| | osa-miR156g | TGACAGAAGAGAGTGA GCAC (1589) | 0.86 | 3414 |
| | osa-miR156h | TGACAGAAGAGAGTGA GCAC (1590) | 0.86 | 3415 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | osa-miR156i | TGACAGAAGAGAGTGAGCAC (1591) | 0.86 | 3416 |
| | osa-miR156j | TGACAGAAGAGAGTGAGCAC (1592) | 0.86 | 3417 |
| | osa-miR156k | TGACAGAAGAGAGAGAGCACA (1593) | 0.9 | 3418 |
| | osa-miR156l | CGACAGAAGAGAGTGAGCATA (1594) | 0.76 | 3419 |
| | osa-miR156m | TGACAGAAGAGAGTGAGCAC (1595) | 0.86 | 3420 |
| | osa-miR156n | TGACAGAAGAGAGTGAGCAC (1596) | 0.86 | 3421 |
| | osa-miR156o | TGACAGAAGAGAGTGAGCAT (1597) | 0.81 | 3422 |
| | osa-miR156p | TGACAGAAGAGAGTGAGCTC (1598) | 0.81 | 3423 |
| | osa-miR156q | TGACAGAACAGAGTGAGCAC (1599) | 0.81 | 3424 |
| | osa-miR156r | TGACAGAAGAGAGAGAGCAC (1600) | 0.9 | 3425 |
| | par-miR156 | TGACAGAAGAGAGAGAGCAC (1601) | 0.9 | 3426 |
| | pga-miR156a | GATCCTAGAGCCCTTGAGCC (1602) | 0.38 | 3427 |
| | ppd-miR156 | TGACAGAAGAGAGAGAGCAC (1603) | 0.9 | 3428 |
| | ppr-miR156 | TGACAGAAGAGAGTGAGCAC (1604) | 0.86 | 3429 |
| | ppt-miR156a | TGACAGAAGAGAGTGAGCAC (1605) | 0.86 | 3430 |
| | ppt-miR156b | TGACAGAAGAGAGTGAGCAC (1606) | 0.86 | 3431 |
| | ppt-miR156c | TGACAGAAGAGAGTGAGCAC (1607) | 0.86 | 3432 |
| | pta-miR156a | CAGAAGATAGAGAGCACATC (1608) | 0.81 | 3433 |
| | pta-miR156b | CAGAAGATAGAGAGCACAAC (1609) | 0.81 | 3434 |
| | ptc-miR156a | TGACAGAAGAGAGTGAGCAC (1610) | 0.86 | 3435 |
| | ptc-miR156b | TGACAGAAGAGAGTGAGCAC (1611) | 0.86 | 3436 |
| | ptc-miR156c | TGACAGAAGAGAGTGAGCAC (1612) | 0.86 | 3437 |
| | ptc-miR156d | TGACAGAAGAGAGTGAGCAC (1613) | 0.86 | 3438 |
| | ptc-miR156e | TGACAGAAGAGAGTGAGCAC (1614) | 0.86 | 3439 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ptc-miR156f | TGACAGAAGAGAGTGA GCAC (1615) | 0.86 | 3440 |
| | ptc-miR156g | TTGACAGAAGATAGAG AGCAC (1616) | 1 | 3441 |
| | ptc-miR156h | TTGACAGAAGATAGAG AGCAC (1617) | 1 | 3442 |
| | ptc-miR156i | TTGACAGAAGATAGAG AGCAC (1618) | 1 | 3443 |
| | ptc-miR156j | TTGACAGAAGATAGAG AGCAC (1619) | 1 | 3444 |
| | ptc-miR156k | TGACAGAAGAGAGGGA GCAC (1620) | 0.86 | 3445 |
| | ptr-miR156 | TGACAGAAGAGAGAGA GCAC (1621) | 0.9 | 3446 |
| | pts-miR156a | TGACAGAAGAGAGTGA GCGC (1622) | 0.81 | 3447 |
| | pts-miR156b | TGACAGAAGAGAGAGA GCAC (1623) | 0.9 | 3448 |
| | pts-miR156c | TGACAGAAGAGAGAGA GCAC (1624) | 0.9 | 3449 |
| | rco-miR156a | TGACAGAAGAGAGTGA GCACA (1625) | 0.86 | 3450 |
| | rco-miR156b | TGACAGAAGAGAGTGA GCACA (1626) | 0.86 | 3451 |
| | rco-miR156c | TGACAGAAGAGAGTGA GCACA (1627) | 0.86 | 3452 |
| | rco-miR156d | TGACAGAAGAGAGTGA GCACA (1628) | 0.86 | 3453 |
| | rco-miR156e | TGACAGAAGAGAGAGA GCACA (1629) | 0.9 | 3454 |
| | rco-miR156f | TTGACAGAAGATAGAG AGCAC (1630) | 1 | 3455 |
| | rco-miR156g | TTGACAGAAGATAGAG AGCAC (1631) | 1 | 3456 |
| | rco-miR156h | TTGACAGAAGATAGAG AGCAC (1632) | 1 | 3457 |
| | sbi-miR156a | TGACAGAAGAGAGTGA GCAC (1633) | 0.86 | 3458 |
| | sbi-miR156b | TGACAGAAGAGAGTGA GCAC (1634) | 0.86 | 3459 |
| | sbi-miR156c | TGACAGAAGAGAGTGA GCAC (1635) | 0.86 | 3460 |
| | sbi-miR156d | TGACAGAAGAGAGAGA GCACA (1636) | 0.9 | 3461 |
| | sbi-miR156e | TGACAGAAGAGAGCGA GCAC (1637) | 0.86 | 3462 |
| | sbi-miR156f | TGACAGAAGAGAGTGA GCAC (1638) | 0.86 | 3463 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sbi-miR156g | TGACAGAAGAGAGTGAGCAC (1639) | 0.86 | 3464 |
| | sbi-miR156h | TGACAGAAGAGAGTGAGCAC (1640) | 0.86 | 3465 |
| | sbi-miR156i | TGACAGAAGAGAGTGAGCAC (1641) | 0.86 | 3466 |
| | sin-miR156 | TGACAGAAGAGAGAGAGCAC (1642) | 0.9 | 3467 |
| | sly-miR156a | TTGACAGAAGATAGAGAGCAC (1643) | 1 | 3468 |
| | sly-miR156b | TTGACAGAAGATAGAGAGCAC (1644) | 1 | 3469 |
| | sly-miR156c | TTGACAGAAGATAGAGAGCAC (1645) | 1 | 3470 |
| | smo-miR156a | CGACAGAAGAGAGTGAGCAC (1646) | 0.81 | 3471 |
| | smo-miR156b | CTGACAGAAGATAGAGAGCAC (1647) | 0.95 | 3472 |
| | smo-miR156c | TTGACAGAAGAAAGAGAGCAC (1648) | 0.95 | 3473 |
| | smo-miR156d | TTGACAGAAGACAGGGAGCAC (1649) | 0.9 | 3474 |
| | sof-miR156 | TGACAGAAGAGAGTGAGCAC (1650) | 0.86 | 3475 |
| | sof-miR156c | TGACAGAAGAGAGAGAGCAC (1651) | 0.9 | 3476 |
| | sof-miR156d | TGACAGAAGAGAGAGAGCAC (1652) | 0.9 | 3477 |
| | sof-miR156e | TGACAGAAGAGAGAGAGCAC (1653) | 0.9 | 3478 |
| | sof-miR156f | TGACAGAAGAGAGAGAGCAC (1654) | 0.9 | 3479 |
| | sof-miR156g | TGACAGAAGAGAGAGAGCAC (1655) | 0.9 | 3480 |
| | sof-miR156h | TGACAGAAGAGAGAGAGCAC (1656) | 0.9 | 3481 |
| | sof-miR156u | TGACAGAAGAGAGAGAGCAC (1657) | 0.9 | 3482 |
| | spr-miR156 | TGACAGAAGAGAGAGAGCAC (1658) | 0.9 | 3483 |
| | ssp-miR156 | TGACAGAAGAGAGTGAGCACA (1659) | 0.86 | 3484 |
| | stu-miR156a | TGACAGAAGAGAGTGAGCAC (1660) | 0.86 | 3485 |
| | stu-miR156b | TGACAGAAGAGAGAGAGCAC (1661) | 0.9 | 3486 |
| | stu-miR156c | TGACAGAAGAGAGAGAGCAC (1662) | 0.9 | 3487 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | stu-miR156d | TGACAGAAGAGAGAGA GCAC (1663) | 0.9 | 3488 |
| | stu-miR156e | TGACAGAAGAGAGAGA GCAC (1664) | 0.9 | 3489 |
| | tae-miR156 | TGACAGAAGAGAGTGA GCACA (1665) | 0.86 | 3490 |
| | tae-miR156a | TGACAGAAGAGAGAGA GCAC (1666) | 0.9 | 3491 |
| | tae-miR156b | TGACAGAAGAGAGAGA GCAC (1667) | 0.9 | 3492 |
| | tcc-miR156a | TGACAGAAGAGAGAGA GCACA (1668) | 0.9 | 3493 |
| | tcc-miR156b | TGACAGAAGAGAGTGA GCAC (1669) | 0.86 | 3494 |
| | tcc-miR156c | TGACAGAAGAGAGTGA GCAC (1670) | 0.86 | 3495 |
| | tcc-miR156d | TGACAGAAGAGAGTGA GCAC (1671) | 0.86 | 3496 |
| | tcc-miR156e | TTGACAGAAGATAGAG AGCAC (1672) | 1 | 3497 |
| | tcc-miR156f | TTGACAGAAGATAGAG AGCAC (1673) | 1 | 3498 |
| | tcc-miR156g | TGACAGAAGAGAGTGA GCAC (1674) | 0.86 | 3499 |
| | tre-miR156 | TGACAGAAGAGAGTGA GCAC (1675) | 0.86 | 3500 |
| | vvi-miR156a | TGACAGAAGAGAGGGA GCAC (1676) | 0.86 | 3501 |
| | vvi-miR156b | TGACAGAAGAGAGTGA GCAC (1677) | 0.86 | 3502 |
| | vvi-miR156c | TGACAGAAGAGAGTGA GCAC (1678) | 0.86 | 3503 |
| | vvi-miR156d | TGACAGAAGAGAGTGA GCAC (1679) | 0.86 | 3504 |
| | vvi-miR156e | TGACAGAGGAGAGTGA GCAC (1680) | 0.81 | 3505 |
| | vvi-miR156f | TTGACAGAAGATAGAG AGCAC (1681) | 1 | 3506 |
| | vvi-miR156g | TTGACAGAAGATAGAG AGCAC (1682) | 1 | 3507 |
| | vvi-miR156h | TGACAGAAGAGAGAGA GCAT (1683) | 0.86 | 3508 |
| | vvi-miR156i | TTGACAGAAGATAGAG AGCAC (1684) | 1 | 3509 |
| | zel-miR156 | TGACAGAAGAGAGAGA GCAC (1685) | 0.9 | 3510 |
| | zma-miR156a | TGACAGAAGAGAGTGA GCAC (1686) | 0.86 | 3511 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR156b | TGACAGAAGAGAGTGAGCAC (1687) | 0.86 | 3512 |
| | zma-miR156c | TGACAGAAGAGAGTGAGCAC (1688) | 0.86 | 3513 |
| | zma-miR156d | TGACAGAAGAGAGTGAGCAC (1689) | 0.86 | 3514 |
| | zma-miR156e | TGACAGAAGAGAGTGAGCAC (1690) | 0.86 | 3515 |
| | zma-miR156f | TGACAGAAGAGAGTGAGCAC (1691) | 0.86 | 3516 |
| | zma-miR156g | TGACAGAAGAGAGTGAGCAC (1692) | 0.86 | 3517 |
| | zma-miR156h | TGACAGAAGAGAGTGAGCAC (1693) | 0.86 | 3518 |
| | zma-miR156i | TGACAGAAGAGAGTGAGCAC (1694) | 0.86 | 3519 |
| | zma-miR156j | TGACAGAAGAGAGAGAGCACA (1695) | 0.9 | 3520 |
| | zma-miR156k | TGACAGAAGAGAGCGAGCAC (1696) | 0.86 | 3521 |
| | zma-miR156l | TGACAGAAGAGAGTGAGCAC (1697) | 0.86 | 3522 |
| | zma-miR156m | TGACAGAAGAGAGTGAGCAC (1698) | 0.86 | 3523 |
| | zma-miR156n | TGACAGAAGAGAGTGAGCAC (1699) | 0.86 | 3524 |
| | zma-miR156o | TGACAGAAGAGAGTGAGCAC (1700) | 0.86 | 3525 |
| | zma-miR156p | TGACAGAAGAGAGAGAGCAC (1701) | 0.9 | 3526 |
| | zma-miR156q | TGACAGAAGAGAGAGAGCAC (1702) | 0.9 | 3527 |
| | zma-miR156r | TGACAGAAGAGAGTGGGCAC (1703) | 0.81 | 3528 |
| smo-miR156b | ahy-miR156a | TGACAGAAGAGAGAGAGCAC (1704) | 0.9 | 3529 |
| | ahy-miR156b-5p | TTGACAGAAGATAGAGAGCAC (1705) | 0.95 | 3530 |
| | ahy-miR156c | TTGACAGAAGAGAGAGAGCAC (1706) | 0.9 | 3531 |
| | aly-miR156a | TGACAGAAGAGAGTGAGCAC (1707) | 0.86 | 3532 |
| | aly-miR156b | TGACAGAAGAGAGTGAGCAC (1708) | 0.86 | 3533 |
| | aly-miR156c | TGACAGAAGAGAGTGAGCAC (1709) | 0.86 | 3534 |
| | aly-miR156d | TGACAGAAGAGAGTGAGCAC (1710) | 0.86 | 3535 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | aly-miR156e | TGACAGAAGAGAGTGAGCAC (1711) | 0.86 | 3536 |
| | aly-miR156f | TGACAGAAGAGAGTGAGCAC (1712) | 0.86 | 3537 |
| | aly-miR156g | CGACAGAAGAGAGTGAGCAC (1713) | 0.81 | 3538 |
| | aly-miR156h | TGACAGAAGAAAGAGAGCAC (1714) | 0.9 | 3539 |
| | aqc-miR156a | TGACAGAAGATAGAGAGCAC (1715) | 0.95 | 3540 |
| | aqc-miR156b | TGACAGAAGATAGAGAGCAC (1716) | 0.95 | 3541 |
| | ath-miR156a | TGACAGAAGAGAGTGAGCAC (1717) | 0.86 | 3542 |
| | ath-miR156b | TGACAGAAGAGAGTGAGCAC (1718) | 0.86 | 3543 |
| | ath-miR156c | TGACAGAAGAGAGTGAGCAC (1719) | 0.86 | 3544 |
| | ath-miR156d | TGACAGAAGAGAGTGAGCAC (1720) | 0.86 | 3545 |
| | ath-miR156e | TGACAGAAGAGAGTGAGCAC (1721) | 0.86 | 3546 |
| | ath-miR156f | TGACAGAAGAGAGTGAGCAC (1722) | 0.86 | 3547 |
| | ath-miR156g | CGACAGAAGAGAGTGAGCAC (1723) | 0.81 | 3548 |
| | ath-miR156h | TGACAGAAGAAAGAGAGCAC (1724) | 0.9 | 3549 |
| | ath-miR156m | TGACAGAAGAGAGAGAGCAC (1725) | 0.9 | 3550 |
| | ath-miR156o | TGACAGAAGAGAGAGAGCAC (1726) | 0.9 | 3551 |
| | ath-miR156p | TGACAGAAGAGAGAGAGCAC (1727) | 0.9 | 3552 |
| | ath-miR156q | TGACAGAAGAGAGAGAGCAC (1728) | 0.9 | 3553 |
| | ath-miR156r | TGACAGAAGAGAGAGAGCAC (1729) | 0.9 | 3554 |
| | ath-miR156s | TGACAGAAGAGAGAGAGCAC (1730) | 0.9 | 3555 |
| | bdi-miR156 | TGACAGAAGAGAGAGAGCACA (1731) | 0.9 | 3556 |
| | bdi-miR156b | TGACAGAAGAGAGTGAGCAC (1732) | 0.86 | 3557 |
| | bdi-miR156c | TGACAGAAGAGAGTGAGCAC (1733) | 0.86 | 3558 |
| | bdi-miR156d | TGACAGAAGAGAGTGAGCAC (1734) | 0.86 | 3559 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | bna-miR156a | TGACAGAAGAGAGTGAGCACA (1735) | 0.86 | 3560 |
| | bna-miR156b | TTGACAGAAGATAGAGAGCAC (1736) | 0.95 | 3561 |
| | bna-miR156c | TTGACAGAAGATAGAGAGCAC (1737) | 0.95 | 3562 |
| | can-miR156a | TGACAGAAGAGAGAGAGCAC (1738) | 0.9 | 3563 |
| | can-miR156b | TGACAGAAGAGAGGGAGCAC (1739) | 0.86 | 3564 |
| | cpt-miR156a | TGACAGAAGAGAGTGAGCAC (1740) | 0.86 | 3565 |
| | cpt-miR156b | TGACAGAAGAGAGAGAGCAC (1741) | 0.9 | 3566 |
| | cru-miR156 | TGACAGAAGAGAGAGAGCAC (1742) | 0.9 | 3567 |
| | csi-miR156 | TGACAGAAGAGAGTGAGCAC (1743) | 0.86 | 3568 |
| | csi-miR156a | TGACAGAAGAGAGAGAGCAC (1744) | 0.9 | 3569 |
| | csi-miR156b | TGACAGAAGAGAGAGAGCAC (1745) | 0.9 | 3570 |
| | ctr-miR156 | TGACAGAAGAGAGTGAGCAC (1746) | 0.86 | 3571 |
| | eca-miR156 | TGACAGAAGAGAGAGAGCAC (1747) | 0.9 | 3572 |
| | far-miR156a | TGACAGAAGAGAGAGAGCACA (1748) | 0.9 | 3573 |
| | far-miR156b | TTGACAGAAGAGAGAGAGCAC (1749) | 0.9 | 3574 |
| | ghr-miR156a | TGACAGAAGAGAGTGAGCAC (1750) | 0.86 | 3575 |
| | ghr-miR156b | TGACAGAAGAGAGTGAGCAC (1751) | 0.86 | 3576 |
| | ghr-miR156c | TGTCAGAAGAGAGTGAGCAC (1752) | 0.81 | 3577 |
| | ghr-miR156d | TGACAGAAGAGAGTGAGCAC (1753) | 0.86 | 3578 |
| | gma-miR156a | TGACAGAAGAGAGTGAGCAC (1754) | 0.86 | 3579 |
| | gma-miR156b | TGACAGAAGAGAGAGAGCACA (1755) | 0.9 | 3580 |
| | gma-miR156c | TTGACAGAAGATAGAGAGCAC (1756) | 0.95 | 3581 |
| | gma-miR156d | TTGACAGAAGATAGAGAGCAC (1757) | 0.95 | 3582 |
| | gma-miR156e | TTGACAGAAGATAGAGAGCAC (1758) | 0.95 | 3583 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | gma-miR156f | TTGACAGAAGAGAGAG AGCACA (1759) | 0.9 | 3584 |
| | gma-miR156g | ACAGAAGATAGAGAGC ACAG (1760) | 0.86 | 3585 |
| | gma-miR156h | TGACAGAAGAGAGAGA GCAC (1761) | 0.9 | 3586 |
| | gma-miR156i | TGACAGAAGAGAGAGA GCAC (1762) | 0.9 | 3587 |
| | han-miR156 | TGACAGAAGAGAGAGA GCAC (1763) | 0.9 | 3588 |
| | hvs-miR156 | TGACAGAAGAGAGAGA GCAC (1764) | 0.9 | 3589 |
| | hvu-miR156 | TGACAGAAGAGAGTGA GCACA (1765) | 0.86 | 3590 |
| | hvv-miR156a | TGACAGAAGAGAGTGA GCACA (1766) | 0.86 | 3591 |
| | hvv-miR156b | TGACAGAAGAGAGAGA GCAC (1767) | 0.9 | 3592 |
| | hvv-miR156c | TGACAGAAGAGAGAGA GCAC (1768) | 0.9 | 3593 |
| | hvv-miR156d | TGACAGAAGAGAGAGA GCAC (1769) | 0.9 | 3594 |
| | lja-miR156 | TGACAGAAGAGAGAGA GCAC (1770) | 0.9 | 3595 |
| | lsa-miR156 | TGACAGAAGAGAGAGA GCAC (1771) | 0.9 | 3596 |
| | mdo-miR156a | TGACAGAAGAGAGAGA GCAC (1772) | 0.9 | 3597 |
| | mdo-miR156b | TGACAGAAGAGAGAGA GCAC (1773) | 0.9 | 3598 |
| | mtr-miR156 | TGACAGAAGAGAGAGA GCACA (1774) | 0.9 | 3599 |
| | mtr-miR156b | TGACAGAAGAGAGTGA GCAC (1775) | 0.86 | 3600 |
| | mtr-miR156c | TGACAGAAGAGAGTGA GCAC (1776) | 0.86 | 3601 |
| | mtr-miR156d | TGACAGAAGAGAGTGA GCAC (1777) | 0.86 | 3602 |
| | mtr-miR156e | TTGACAGAAGATAGAG AGCAC (1778) | 0.95 | 3603 |
| | mtr-miR156f | TTGACAGAAGATAGAG AGCAC (1779) | 0.95 | 3604 |
| | mtr-miR156g | TTGACAGAAGATAGAG GGCAC (1780) | 0.9 | 3605 |
| | mtr-miR156h | TTGACAGAAGATAGAG AGCAC (1781) | 0.95 | 3606 |
| | mtr-miR156i | TGACAGAAGAGAGTGA GCAC (1782) | 0.86 | 3607 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | nbe-miR156a | TGACAGAAGAGAGAGCAC (1783) | 0.9 | 3608 |
| | nbe-miR156b | TGACAGAAGAGAGAGCAC (1784) | 0.9 | 3609 |
| | oru-miR156 | TGACAGAAGAGAGTGAGCAC (1785) | 0.86 | 3610 |
| | osa-miR156a | TGACAGAAGAGAGTGAGCAC (1786) | 0.86 | 3611 |
| | osa-miR156b | TGACAGAAGAGAGTGAGCAC (1787) | 0.86 | 3612 |
| | osa-miR156c | TGACAGAAGAGAGTGAGCAC (1788) | 0.86 | 3613 |
| | osa-miR156d | TGACAGAAGAGAGTGAGCAC (1789) | 0.86 | 3614 |
| | osa-miR156e | TGACAGAAGAGAGTGAGCAC (1790) | 0.86 | 3615 |
| | osa-miR156f | TGACAGAAGAGAGTGAGCAC (1791) | 0.86 | 3616 |
| | osa-miR156g | TGACAGAAGAGAGTGAGCAC (1792) | 0.86 | 3617 |
| | osa-miR156h | TGACAGAAGAGAGTGAGCAC (1793) | 0.86 | 3618 |
| | osa-miR156i | TGACAGAAGAGAGTGAGCAC (1794) | 0.86 | 3619 |
| | osa-miR156j | TGACAGAAGAGAGTGAGCAC (1795) | 0.86 | 3620 |
| | osa-miR156k | TGACAGAAGAGAGAGAGCACA (1796) | 0.9 | 3621 |
| | osa-miR156l | CGACAGAAGAGAGTGAGCATA (1797) | 0.76 | 3622 |
| | osa-miR156m | TGACAGAAGAGAGTGAGCAC (1798) | 0.86 | 3623 |
| | osa-miR156n | TGACAGAAGAGAGTGAGCAC (1799) | 0.86 | 3624 |
| | osa-miR156o | TGACAGAAGAGAGTGAGCAT (1800) | 0.81 | 3625 |
| | osa-miR156p | TGACAGAAGAGAGTGAGCTC (1801) | 0.81 | 3626 |
| | osa-miR156q | TGACAGAACAGAGTGAGCAC (1802) | 0.81 | 3627 |
| | osa-miR156r | TGACAGAAGAGAGAGAGCAC (1803) | 0.9 | 3628 |
| | par-miR156 | TGACAGAAGAGAGAGAGCAC (1804) | 0.9 | 3629 |
| | ppd-miR156 | TGACAGAAGAGAGAGAGCAC (1805) | 0.9 | 3630 |
| | ppr-miR156 | TGACAGAAGAGAGTGAGCAC (1806) | 0.86 | 3631 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
| --- | --- | --- | --- | --- |
| | ppt-miR156a | TGACAGAAGAGAGTGAGCAC (1807) | 0.86 | 3632 |
| | ppt-miR156b | TGACAGAAGAGAGTGAGCAC (1808) | 0.86 | 3633 |
| | ppt-miR156c | TGACAGAAGAGAGTGAGCAC (1809) | 0.86 | 3634 |
| | pta-miR156a | CAGAAGATAGAGAGCACATC (1810) | 0.81 | 3635 |
| | pta-miR156b | CAGAAGATAGAGAGCACAAC (1811) | 0.81 | 3636 |
| | ptc-miR156a | TGACAGAAGAGAGTGAGCAC (1812) | 0.86 | 3637 |
| | ptc-miR156b | TGACAGAAGAGAGTGAGCAC (1813) | 0.86 | 3638 |
| | ptc-miR156c | TGACAGAAGAGAGTGAGCAC (1814) | 0.86 | 3639 |
| | ptc-miR156d | TGACAGAAGAGAGTGAGCAC (1815) | 0.86 | 3640 |
| | ptc-miR156e | TGACAGAAGAGAGTGAGCAC (1816) | 0.86 | 3641 |
| | ptc-miR156f | TGACAGAAGAGAGTGAGCAC (1817) | 0.86 | 3642 |
| | ptc-miR156g | TTGACAGAAGATAGAGAGCAC (1818) | 0.95 | 3643 |
| | ptc-miR156h | TTGACAGAAGATAGAGAGCAC (1819) | 0.95 | 3644 |
| | ptc-miR156i | TTGACAGAAGATAGAGAGCAC (1820) | 0.95 | 3645 |
| | ptc-miR156j | TTGACAGAAGATAGAGAGCAC (1821) | 0.95 | 3646 |
| | ptc-miR156k | TGACAGAAGAGAGGGAGCAC (1822) | 0.86 | 3647 |
| | ptr-miR156 | TGACAGAAGAGAGAGAGCAC (1823) | 0.9 | 3648 |
| | pts-miR156a | TGACAGAAGAGAGTGAGCGC (1824) | 0.81 | 3649 |
| | pts-miR156b | TGACAGAAGAGAGAGAGCAC (1825) | 0.9 | 3650 |
| | pts-miR156c | TGACAGAAGAGAGAGAGCAC (1826) | 0.9 | 3651 |
| | rco-miR156a | TGACAGAAGAGAGTGAGCACA (1827) | 0.86 | 3652 |
| | rco-miR156b | TGACAGAAGAGAGTGAGCACA (1828) | 0.86 | 3653 |
| | rco-miR156c | TGACAGAAGAGAGTGAGCACA (1829) | 0.86 | 3654 |
| | rco-miR156d | TGACAGAAGAGAGTGAGCACA (1830) | 0.86 | 3655 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | rco-miR156e | TGACAGAAGAGAGAGA GCACA (1831) | 0.9 | 3656 |
| | rco-miR156f | TTGACAGAAGATAGAG AGCAC (1832) | 0.95 | 3657 |
| | rco-miR156g | TTGACAGAAGATAGAG AGCAC (1833) | 0.95 | 3658 |
| | rco-miR156h | TTGACAGAAGATAGAG AGCAC (1834) | 0.95 | 3659 |
| | sbi-miR156a | TGACAGAAGAGAGTGA GCAC (1835) | 0.86 | 3660 |
| | sbi-miR156b | TGACAGAAGAGAGTGA GCAC (1836) | 0.86 | 3661 |
| | sbi-miR156c | TGACAGAAGAGAGTGA GCAC (1837) | 0.86 | 3662 |
| | sbi-miR156d | TGACAGAAGAGAGAGA GCACA (1838) | 0.9 | 3663 |
| | sbi-miR156e | TGACAGAAGAGAGCGA GCAC (1839) | 0.86 | 3664 |
| | sbi-miR156f | TGACAGAAGAGAGTGA GCAC (1840) | 0.86 | 3665 |
| | sbi-miR156g | TGACAGAAGAGAGTGA GCAC (1841) | 0.86 | 3666 |
| | sbi-miR156h | TGACAGAAGAGAGTGA GCAC (1842) | 0.86 | 3667 |
| | sbi-miR156i | TGACAGAAGAGAGTGA GCAC (1843) | 0.86 | 3668 |
| | sin-miR156 | TGACAGAAGAGAGAGA GCAC (1844) | 0.9 | 3669 |
| | sly-miR156a | TTGACAGAAGATAGAG AGCAC (1845) | 0.95 | 3670 |
| | sly-miR156b | TTGACAGAAGATAGAG AGCAC (1846) | 0.95 | 3671 |
| | sly-miR156c | TTGACAGAAGATAGAG AGCAC (1847) | 0.95 | 3672 |
| | smo-miR156a | CGACAGAAGAGAGTGA GCAC (1848) | 0.81 | 3673 |
| | smo-miR156c | TTGACAGAAGAAAGAG AGCAC (1849) | 0.9 | 3674 |
| | smo-miR156d | TTGACAGAAGACAGGG AGCAC (1850) | 0.86 | 3675 |
| | sof-miR156 | TGACAGAAGAGAGTGA GCAC (1851) | 0.86 | 3676 |
| | sof-miR156c | TGACAGAAGAGAGAGA GCAC (1852) | 0.9 | 3677 |
| | sof-miR156d | TGACAGAAGAGAGAGA GCAC (1853) | 0.9 | 3678 |
| | sof-miR156e | TGACAGAAGAGAGAGA GCAC (1854) | 0.9 | 3679 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | sof-miR156f | TGACAGAAGAGAGAGA GCAC (1855) | 0.9 | 3680 |
| | sof-miR156g | TGACAGAAGAGAGAGA GCAC (1856) | 0.9 | 3681 |
| | sof-miR156h | TGACAGAAGAGAGAGA GCAC (1857) | 0.9 | 3682 |
| | sof-miR156u | TGACAGAAGAGAGAGA GCAC (1858) | 0.9 | 3683 |
| | spr-miR156 | TGACAGAAGAGAGAGA GCAC (1859) | 0.9 | 3684 |
| | ssp-miR156 | TGACAGAAGAGAGTGA GCACA (1860) | 0.86 | 3685 |
| | stu-miR156a | TGACAGAAGAGAGTGA GCAC (1861) | 0.86 | 3686 |
| | stu-miR156b | TGACAGAAGAGAGAGA GCAC (1862) | 0.9 | 3687 |
| | stu-miR156c | TGACAGAAGAGAGAGA GCAC (1863) | 0.9 | 3688 |
| | stu-miR156d | TGACAGAAGAGAGAGA GCAC (1864) | 0.9 | 3689 |
| | stu-miR156e | TGACAGAAGAGAGAGA GCAC (1865) | 0.9 | 3690 |
| | tae-miR156 | TGACAGAAGAGAGTGA GCACA (1866) | 0.86 | 3691 |
| | tae-miR156a | TGACAGAAGAGAGAGA GCAC (1867) | 0.9 | 3692 |
| | tae-miR156b | TGACAGAAGAGAGAGA GCAC (1868) | 0.9 | 3693 |
| | tcc-miR156a | TGACAGAAGAGAGAGA GCACA (1869) | 0.9 | 3694 |
| | tcc-miR156b | TGACAGAAGAGAGTGA GCAC (1870) | 0.86 | 3695 |
| | tcc-miR156c | TGACAGAAGAGAGTGA GCAC (1871) | 0.86 | 3696 |
| | tcc-miR156d | TGACAGAAGAGAGTGA GCAC (1872) | 0.86 | 3697 |
| | tcc-miR156e | TTGACAGAAGATAGAG AGCAC (1873) | 0.95 | 3698 |
| | tcc-miR156f | TTGACAGAAGATAGAG AGCAC (1874) | 0.95 | 3699 |
| | tcc-miR156g | TGACAGAAGAGAGTGA GCAC (1875) | 0.86 | 3700 |
| | tre-miR156 | TGACAGAAGAGAGTGA GCAC (1876) | 0.86 | 3701 |
| | vvi-miR156a | TGACAGAAGAGAGGGA GCAC (1877) | 0.86 | 3702 |
| | vvi-miR156b | TGACAGAAGAGAGTGA GCAC (1878) | 0.86 | 3703 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
| --- | --- | --- | --- | --- |
| | vvi-miR156c | TGACAGAAGAGAGTGAGCAC (1879) | 0.86 | 3704 |
| | vvi-miR156d | TGACAGAAGAGAGTGAGCAC (1880) | 0.86 | 3705 |
| | vvi-miR156e | TGACAGAGGAGAGTGAGCAC (1881) | 0.81 | 3706 |
| | vvi-miR156f | TTGACAGAAGATAGAGAGCAC (1882) | 0.95 | 3707 |
| | vvi-miR156g | TTGACAGAAGATAGAGAGCAC (1883) | 0.95 | 3708 |
| | vvi-miR156h | TGACAGAAGAGAGAGAGCAT (1884) | 0.86 | 3709 |
| | vvi-miR156i | TTGACAGAAGATAGAGAGCAC (1885) | 0.95 | 3710 |
| | zel-miR156 | TGACAGAAGAGAGAGAGCAC (1886) | 0.9 | 3711 |
| | zma-miR156a | TGACAGAAGAGAGTGAGCAC (1887) | 0.86 | 3712 |
| | zma-miR156b | TGACAGAAGAGAGTGAGCAC (1888) | 0.86 | 3713 |
| | zma-miR156c | TGACAGAAGAGAGTGAGCAC (1889) | 0.86 | 3714 |
| | zma-miR156d | TGACAGAAGAGAGTGAGCAC (1890) | 0.86 | 3715 |
| | zma-miR156e | TGACAGAAGAGAGTGAGCAC (1891) | 0.86 | 3716 |
| | zma-miR156f | TGACAGAAGAGAGTGAGCAC (1892) | 0.86 | 3717 |
| | zma-miR156g | TGACAGAAGAGAGTGAGCAC (1893) | 0.86 | 3718 |
| | zma-miR156h | TGACAGAAGAGAGTGAGCAC (1894) | 0.86 | 3719 |
| | zma-miR156i | TGACAGAAGAGAGTGAGCAC (1895) | 0.86 | 3720 |
| | zma-miR156j | TGACAGAAGAGAGAGAGCACA (1896) | 0.9 | 3721 |
| | zma-miR156k | TGACAGAAGAGAGCGAGCAC (1897) | 0.86 | 3722 |
| | zma-miR156l | TGACAGAAGAGAGTGAGCAC (1898) | 0.86 | 3723 |
| | zma-miR156m | TGACAGAAGAGAGTGAGCAC (1899) | 0.86 | 3724 |
| | zma-miR156n | TGACAGAAGAGAGTGAGCAC (1900) | 0.86 | 3725 |
| | zma-miR156o | TGACAGAAGAGAGTGAGCAC (1901) | 0.86 | 3726 |
| | zma-miR156p | TGACAGAAGAGAGAGAGCAC (1902) | 0.9 | 3727 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | zma-miR156q | TGACAGAAGAGAGAGA GCAC (1903) | 0.9 | 3728 |
| | zma-miR156r | TGACAGAAGAGAGTGG GCAC (1904) | 0.81 | 3729 |
| gma-miR159a-3p | acb-miR159 | TTGGACTGAAGGGAGCT CCCT (1905) | 0.81 | 3730 |
| | aha-miR159 | TTGGACTGAAGGGAGCT CCCT (1906) | 0.81 | 3731 |
| | ahi-miR159 | TTGGACTGAAGGGAGCT CCCT (1907) | 0.81 | 3732 |
| | ahy-miR159 | TTTGGATTGAAGGGAGC TCTA (1908) | 1 | 3733 |
| | aly-miR159a | TTTGGATTGAAGGGAGC TCTA (1909) | 1 | 3734 |
| | aly-miR159b | TTTGGATTGAAGGGAGC TCTT (1910) | 0.95 | 3735 |
| | aly-miR159c | TTTGGATTGAAGGGAGC TCCT (1911) | 0.9 | 3736 |
| | ape-miR159 | TTGGACTGAAGGGAGCT CCCT (1912) | 0.81 | 3737 |
| | aqc-miR159 | TTTGGACTGAAGGGAGC TCTA (1913) | 0.95 | 3738 |
| | ath-miR159a | TTTGGATTGAAGGGAGC TCTA (1914) | 1 | 3739 |
| | ath-miR159b | TTTGGATTGAAGGGAGC TCTT (1915) | 0.95 | 3740 |
| | ath-miR159c | TTTGGATTGAAGGGAGC TCCT (1916) | 0.9 | 3741 |
| | bdi-miR159 | CTTGGATTGAAGGGAGC TCT (1917) | 0.9 | 3742 |
| | bna-miR159 | TTTGGATTGAAGGGAGC TCTA (1918) | 1 | 3743 |
| | bra-miR159a | TTTGGATTGAAGGGAGC TCTA (1919) | 1 | 3744 |
| | bvl-miR159 | TTGGACTGAAGGGAGCT CCCT (1920) | 0.81 | 3745 |
| | cmi-miR159 | TTGGACTGAAGGGAGCT CCCT (1921) | 0.81 | 3746 |
| | cor-miR159 | TTGGACTGAAGGGAGCT CCCT (1922) | 0.81 | 3747 |
| | crb-miR159 | TTGGACTGAAGGGAGCT CCCT (1923) | 0.81 | 3748 |
| | csi-miR159 | TTTGGATTGAAGGGAGC TCTA (1924) | 1 | 3749 |
| | dso-miR159 | TTGGACTGAAGGGAGCT CCCT (1925) | 0.81 | 3750 |
| | ech-miR159 | TTGGACTGAAGGGAGCT CCCT (1926) | 0.81 | 3751 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | fal-miR159 | TTGGACTGAAGGGAGCTCCCT (1927) | 0.81 | 3752 |
| | far-miR159 | TTTGGATTGAAGGGAGCTCTG (1928) | 0.95 | 3753 |
| | gma-miR159b | ATTGGAGTGAAGGGAGCTCCA (1929) | 0.86 | 3754 |
| | gma-miR159c | ATTGGAGTGAAGGGAGCTCCG (1930) | 0.81 | 3755 |
| | hvu-miR159a | TTTGGATTGAAGGGAGCTCTG (1931) | 0.95 | 3756 |
| | hvu-miR159b | TTTGGATTGAAGGGAGCTCTG (1932) | 0.95 | 3757 |
| | hvv-miR159a | TTTGGATTGAAGGGAGCTCTG (1933) | 0.95 | 3758 |
| | hvv-miR159b | TTTGGATTGAAGGGAGCTCTG (1934) | 0.95 | 3759 |
| | ltu-miR159 | TTTGGATTGAAGGGAGCTCTA (1935) | 1 | 3760 |
| | mma-miR159 | TTGGACTGAAGGGAGCTCCCT (1936) | 0.81 | 3761 |
| | mtr-miR159a | TTTGGATTGAAGGGAGCTCTA (1937) | 1 | 3762 |
| | mtr-miR159b | ATTGAATTGAAGGGAGCAACT (1938) | 0.71 | 3763 |
| | mtr-miR159c | TTTGGATTGAAGGGAGCTCTA (1939) | 1 | 3764 |
| | nof-miR159 | TTGGACTGAAGGGAGCTCCCT (1940) | 0.81 | 3765 |
| | oru-miR159 | TTTGGATTGAAGGGAGCTCTG (1941) | 0.95 | 3766 |
| | osa-miR159a | TTTGGATTGAAGGGAGCTCTG (1942) | 0.95 | 3767 |
| | osa-miR159a.1 | TTTGGATTGAAGGGAGCTCTG (1943) | 0.95 | 3768 |
| | osa-miR159b | TTTGGATTGAAGGGAGCTCTG (1944) | 0.95 | 3769 |
| | osa-miR159c | ATTGGATTGAAGGGAGCTCCA (1945) | 0.9 | 3770 |
| | osa-miR159d | ATTGGATTGAAGGGAGCTCCG (1946) | 0.86 | 3771 |
| | osa-miR159e | ATTGGATTGAAGGGAGCTCCT (1947) | 0.86 | 3772 |
| | osa-miR159f | CTTGGATTGAAGGGAGCTCTA (1948) | 0.95 | 3773 |
| | osa-miR159m | TTTGGATTGAAGGGAGCTCTG (1949) | 0.95 | 3774 |
| | pgl-miR159 | TTTGGATTGAAGGGAGCTCTG (1950) | 0.95 | 3775 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | psi-miR159 | CTTGGATTGAAGGGAGCTCCA (1951) | 0.9 | 3776 |
| | pta-miR159a | TTGGATTGAAGGGAGCTCCA (1952) | 0.9 | 3777 |
| | pta-miR159b | TTGGATTGAAGAGAGCTCCC (1953) | 0.81 | 3778 |
| | pta-miR159c | CTTGGATTGAAGGGAGCTCCC (1954) | 0.86 | 3779 |
| | ptc-miR159a | TTTGGATTGAAGGGAGCTCTA (1955) | 1 | 3780 |
| | ptc-miR159b | TTTGGATTGAAGGGAGCTCTA (1956) | 1 | 3781 |
| | ptc-miR159c | TTTGGATTGAAGGGAGCTCTA (1957) | 1 | 3782 |
| | ptc-miR159d | CTTGGATTGAAGGGAGCTCCT (1958) | 0.86 | 3783 |
| | ptc-miR159e | CTTGGGGTGAAGGGAGCTCCT (1959) | 0.76 | 3784 |
| | ptc-miR159f | ATTGGAGTGAAGGGAGCTCGA (1960) | 0.86 | 3785 |
| | pvu-miR159 | TTTGGATTGAAGGGAGCTCTA (1961) | 1 | 3786 |
| | pvu-miR159a.1 | TTTGGATTGAAGGGAGCTCTA (1962) | 1 | 3787 |
| | rco-miR159 | TTTGGATTGAAGGGAGCTCTA (1963) | 1 | 3788 |
| | rin-miR159 | TTGGACTGAAGGGAGCTCCCT (1964) | 0.81 | 3789 |
| | sar-miR159 | TTTGGATTGAAGGGAGCTCTG (1965) | 0.95 | 3790 |
| | sbi-miR159a | TTTGGATTGAAGGGAGCTCTG (1966) | 0.95 | 3791 |
| | sbi-miR159b | CTTGGATTGAAGGGAGCTCCT (1967) | 0.86 | 3792 |
| | sly-miR159 | TTTGGATTGAAGGGAGCTCTA (1968) | 1 | 3793 |
| | smo-miR159 | CTTGGATTGAAGGGAGCTCCC (1969) | 0.86 | 3794 |
| | sof-miR159a | TTTGGATTGAAGGGAGCTCTG (1970) | 0.95 | 3795 |
| | sof-miR159b | TTTGGATTGAAGGGAGCTCTG (1971) | 0.95 | 3796 |
| | sof-miR159c | CTTGGATTGAAGGGAGCTCCT (1972) | 0.86 | 3797 |
| | sof-miR159d | TTTGGATTGAAGGGAGCTCTG (1973) | 0.95 | 3798 |
| | sof-miR159e | TTTGGATTGAAAGGAGCTCTT (1974) | 0.9 | 3799 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | spr-miR159 | TTTGGATTGAAGGGAGCTCTG (1975) | 0.95 | 3800 |
| | ssp-miR159a | TTTGGATTGAAG)GGAGCTCTG (1976 | 0.95 | 3801 |
| | svi-miR159 | TTGGACTGAAG)GGAGCTCCCT (1977 | 0.81 | 3802 |
| | tae-miR159a | TTTGGATTGAAGGGAGCTCTG (1978) | 0.95 | 3803 |
| | tae-miR159b | TTTGGATTGAAGGGAGCTCTG (1979) | 0.95 | 3804 |
| | tar-miR159 | TTGGACTGAAGGGAGCTCCCT (1980) | 0.81 | 3805 |
| | vvi-miR159a | CTTGGAGTGAAGGGAGCTCTC (1981) | 0.86 | 3806 |
| | vvi-miR159b | CTTGGAGTGAAGGGAGCTCTC (1982) | 0.86 | 3807 |
| | vvi-miR159c | TTTGGATTGAAGGGAGCTCTA (1983) | 1 | 3808 |
| | zma-miR159a | TTTGGATTGAAGGGAGCTCTG (1984) | 0.95 | 3809 |
| | zma-miR159b | TTTGGATTGAAGGGAGCTCTG (1985) | 0.95 | 3810 |
| | zma-miR159c | CTTGGATTGAAGGGAGCTCCT (1986) | 0.86 | 3811 |
| | zma-miR159d | CTTGGATTGAAGGGAGCTCCT (1987) | 0.86 | 3812 |
| | zma-miR159e | ATTGGTTTGAAGGGAGCTCCA (1988) | 0.86 | 3813 |
| | zma-miR159f | TTTGGATTGAAGGGAGCTCTG (1989) | 0.95 | 3814 |
| | zma-miR159g | TTTGGAGTGAAGGGAGTTCTG (1990) | 0.86 | 3815 |
| | zma-miR159h | TTTGGAGTGAAGGGAGCTCTG (1991) | 0.9 | 3816 |
| | zma-miR159i | TTTGGAGTGAAGGGAGCTCTG (1992) | 0.9 | 3817 |
| | zma-miR159j | TTTGGATTGAAGGGAGCTCTG (1993) | 0.95 | 3818 |
| | zma-miR159k | TTTGGATTGAAGGGAGCTCTG (1994) | 0.95 | 3819 |
| | zma-miR159m | TTTGGATTGAAGGGAGCTCTG (1995) | 0.95 | 3820 |
| sbi-miR159a | acb-miR159 | TTGGACTGAAGGGAGCTCCCT (1996) | 0.81 | 3821 |
| | aha-miR159 | TTGGACTGAAGGGAGCTCCCT (1997) | 0.81 | 3822 |
| | ahi-miR159 | TTGGACTGAAGGGAGCTCCCT (1998) | 0.81 | 3823 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ahy-miR159 | TTTGGATTGAAGGGAGCTCTA (1999) | 0.95 | 3824 |
| | aly-miR159a | TTTGGATTGAAGGGAGCTCTA (2000) | 0.95 | 3825 |
| | aly-miR159b | TTTGGATTGAAGGGAGCTCTT (2001) | 0.95 | 3826 |
| | aly-miR159c | TTTGGATTGAAGGGAGCTCCT (2002) | 0.9 | 3827 |
| | ape-miR159 | TTGGACTGAAGGGAGCTCCCT (2003) | 0.81 | 3828 |
| | aqc-miR159 | TTTGGACTGAAGGGAGCTCTA (2004) | 0.9 | 3829 |
| | ath-miR159a | TTTGGATTGAAGGGAGCTCTA (2005) | 0.95 | 3830 |
| | ath-miR159b | TTTGGATTGAAGGGAGCTCTT (2006) | 0.95 | 3831 |
| | ath-miR159c | TTTGGATTGAAGGGAGCTCCT (2007) | 0.9 | 3832 |
| | bdi-miR159 | CTTGGATTGAAGGGAGCTCT (2008) | 0.9 | 3833 |
| | bna-miR159 | TTTGGATTGAAGGGAGCTCTA (2009) | 0.95 | 3834 |
| | bra-miR159a | TTTGGATTGAAGGGAGCTCTA (2010) | 0.95 | 3835 |
| | bvl-miR159 | TTGGACTGAAGGGAGCTCCCT (2011) | 0.81 | 3836 |
| | cmi-miR159 | TTGGACTGAAGGGAGCTCCCT (2012) | 0.81 | 3837 |
| | cor-miR159 | TTGGACTGAAGGGAGCTCCCT (2013) | 0.81 | 3838 |
| | crb-miR159 | TTGGACTGAAGGGAGCTCCCT (2014) | 0.81 | 3839 |
| | csi-miR159 | TTTGGATTGAAGGGAGCTCTA (2015) | 0.95 | 3840 |
| | dso-miR159 | TTGGACTGAAGGGAGCTCCCT (2016) | 0.81 | 3841 |
| | ech-miR159 | TTGGACTGAAGGGAGCTCCCT (2017) | 0.81 | 3842 |
| | fal-miR159 | TTGGACTGAAGGGAGCTCCCT (2018) | 0.81 | 3843 |
| | far-miR159 | TTTGGATTGAAGGGAGCTCTG (2019) | 1 | 3844 |
| | gma-miR159a-3p | TTTGGATTGAAGGGAGCTCTA (2020) | 0.95 | 3845 |
| | gma-miR159b | ATTGGAGTGAAGGGAGCTCCA (2021) | 0.81 | 3846 |
| | gma-miR159c | ATTGGAGTGAAGGGAGCTCCG (2022) | 0.86 | 3847 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | hvu-miR159a | TTTGGATTGAAGGGAGCTCTG (2023) | 1 | 3848 |
| | hvu-miR159b | TTTGGATTGAAGGGAGCTCTG (2024) | 1 | 3849 |
| | hvv-miR159a | TTTGGATTGAAGGGAGCTCTG (2025) | 1 | 3850 |
| | hvv-miR159b | TTTGGATTGAAGGGAGCTCTG (2026) | 1 | 3851 |
| | ltu-miR159 | TTTGGATTGAAGGGAGCTCTA (2027) | 0.95 | 3852 |
| | mma-miR159 | TTGGACTGAAGGGAGCTCCCT (2028) | 0.81 | 3853 |
| | mtr-miR159a | TTTGGATTGAAGGGAGCTCTA (2029) | 0.95 | 3854 |
| | mtr-miR159b | ATTGAATTGAAGGGAGCAACT (2030) | 0.71 | 3855 |
| | mtr-miR159c | TTTGGATTGAAGGGAGCTCTA (2031) | 0.95 | 3856 |
| | nof-miR159 | TTGGACTGAAGGGAGCTCCCT (2032) | 0.81 | 3857 |
| | oru-miR159 | TTTGGATTGAAGGGAGCTCTG (2033) | 1 | 3858 |
| | osa-miR159a | TTTGGATTGAAGGGAGCTCTG (2034) | 1 | 3859 |
| | osa-miR159a.1 | TTTGGATTGAAGGGAGCTCTG (2035) | 1 | 3860 |
| | osa-miR159b | TTTGGATTGAAGGGAGCTCTG (2036) | 1 | 3861 |
| | osa-miR159c | ATTGGATTGAAGGGAGCTCCA (2037) | 0.86 | 3862 |
| | osa-miR159d | ATTGGATTGAAGGGAGCTCCG (2038) | 0.9 | 3863 |
| | osa-miR159e | ATTGGATTGAAGGGAGCTCCT (2039) | 0.86 | 3864 |
| | osa-miR159f | CTTGGATTGAAGGGAGCTCTA (2040) | 0.9 | 3865 |
| | osa-miR159m | TTTGGATTGAAGGGAGCTCTG (2041) | 1 | 3866 |
| | pgl-miR159 | TTTGGATTGAAGGGAGCTCTG (2042) | 1 | 3867 |
| | psi-miR159 | CTTGGATTGAAGGGAGCTCCA (2043) | 0.86 | 3868 |
| | pta-miR159a | TTGGATTGAAGGGAGCTCCA (2044) | 0.86 | 3869 |
| | pta-miR159b | TTGGATTGAAGAGAGCTCCC (2045) | 0.81 | 3870 |
| | pta-miR159c | CTTGGATTGAAGGGAGCTCCC (2046) | 0.86 | 3871 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | ptc-miR159a | TTTGGATTGAAGGGAGCTCTA (2047) | 0.95 | 3872 |
| | ptc-miR159b | TTTGGATTGAAGGGAGCTCTA (2048) | 0.95 | 3873 |
| | ptc-miR159c | TTTGGATTGAAGGGAGCTCTA (2049) | 0.95 | 3874 |
| | ptc-miR159d | CTTGGATTGAAGGGAGCTCCT (2050) | 0.86 | 3875 |
| | ptc-miR159e | CTTGGGGTGAAGGGAGCTCCT (2051) | 0.76 | 3876 |
| | ptc-miR159f | ATTGGAGTGAAGGGAGCTCGA (2052) | 0.81 | 3877 |
| | pvu-miR159 | TTTGGATTGAAGGGAGCTCTA (2053) | 0.95 | 3878 |
| | pvu-miR159a.1 | TTTGGATTGAAGGGAGCTCTA (2054) | 0.95 | 3879 |
| | rco-miR159 | TTTGGATTGAAGGGAGCTCTA (2055) | 0.95 | 3880 |
| | rin-miR159 | TTGGACTGAAGGGAGCTCCCT (2056) | 0.81 | 3881 |
| | sar-miR159 | TTTGGATTGAAGGGAGCTCTG (2057) | 1 | 3882 |
| | sbi-miR159b | CTTGGATTGAAGGGAGCTCCT (2058) | 0.86 | 3883 |
| | sly-miR159 | TTTGGATTGAAGGGAGCTCTA (2059) | 0.95 | 3884 |
| | smo-miR159 | CTTGGATTGAAGGGAGCTCCC (2060) | 0.86 | 3885 |
| | sof-miR159a | TTTGGATTGAAGGGAGCTCTG (2061) | 1 | 3886 |
| | sof-miR159b | TTTGGATTGAAGGGAGCTCTG (2062) | 1 | 3887 |
| | sof-miR159c | CTTGGATTGAAGGGAGCTCCT (2063) | 0.86 | 3888 |
| | sof-miR159d | TTTGGATTGAAGGGAGCTCTG (2064) | 1 | 3889 |
| | sof-miR159e | TTTGGATTGAAAGGAGCTCTT (2065) | 0.9 | 3890 |
| | spr-miR159 | TTTGGATTGAAGGGAGCTCTG (2066) | 1 | 3891 |
| | ssp-miR159a | TTTGGATTGAAGGGAGCTCTG (2067) | 1 | 3892 |
| | svi-miR159 | TTGGACTGAAGGGAGCTCCCT (2068) | 0.81 | 3893 |
| | tae-miR159a | TTTGGATTGAAGGGAGCTCTG (2069) | 1 | 3894 |
| | tae-miR159b | TTTGGATTGAAGGGAGCTCTG (2070) | 1 | 3895 |

TABLE 7-continued

Summary of Homologs (Orthologs to Small RNAs which are up-regulated in Abiotic Stress in Soybean Plants.

| Mir Name | Homolog Name | Homolog Sequence (SEQ ID NO:) | % Identity | Homolog stem-loop sequence (SEQ ID NO:) |
|---|---|---|---|---|
| | tar-miR159 | TTGGACTGAAGGGAGCTCCCT (2071) | 0.81 | 3896 |
| | vvi-miR159a | CTTGGAGTGAAGGGAGCTCTC (2072) | 0.86 | 3897 |
| | vvi-miR159b | CTTGGAGTGAAGGGAGCTCTC (2073) | 0.86 | 3898 |
| | vvi-miR159c | TTTGGATTGAAGGGAGCTCTA (2074) | 0.95 | 3899 |
| | zma-miR159a | TTTGGATTGAAGGGAGCTCTG (2075) | 1 | 3900 |
| | zma-miR159b | TTTGGATTGAAGGGAGCTCTG (2076) | 1 | 3901 |
| | zma-miR159c | CTTGGATTGAAGGGAGCTCCT (2077) | 0.86 | 3902 |
| | zma-miR159d | CTTGGATTGAAGGGAGCTCCT (2078) | 0.86 | 3903 |
| | zma-miR159e | ATTGGTTTGAAGGGAGCTCCA (2079) | 0.81 | 3904 |
| | zma-miR159f | TTTGGATTGAAGGGAGCTCTG (2080) | 1 | 3905 |
| | zma-miR159g | TTTGGAGTGAAGGGAGTTCTG (2081) | 0.9 | 3906 |
| | zma-miR159h | TTTGGAGTGAAGGGAGCTCTG (2082) | 0.95 | 3907 |
| | zma-miR159i | TTTGGAGTGAAGGGAGCTCTG (2083) | 0.95 | 3908 |
| | zma-miR159j | TTTGGATTGAAGGGAGCTCTG (2084) | 1 | 3909 |
| | zma-miR159k | TTTGGATTGAAGGGAGCTCTG (2085) | 1 | 3910 |
| | zma-miR159m | TTTGGATTGAAGGGAGCTCTG (2086) | 1 | 3911 |

TABLE 8

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| aly-miR396a-3p | aly-miR396b-3p | GCTCAAGAAAGCTGTGGGAAA (3953) | 0.86 | 5117 |
| | csi-miR396c | TTCAAGAAATCTGTGGGAAG (3954) | 0.86 | 5118 |
| | gma-miR396d | AAGAAAGCTGTGGGAGAATATGGC (3955) | 0.67 | 5119 |
| | osa-miR396e* | GTTCAAGAAAGCCCATGGAAA (3956) | 0.71 | 5120 |
| | osa-miR396e-3p | ATGGTTCAAGAAAGCCCATGGAAA (3957) | 0.71 | 5121 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | osa-miR396f* | GTTCAAGAAAGTCCTTGGAAA (3958) | 0.71 | 5122 |
| | osa-miR396f-3p | ATAGTTCAAGAAAGTCCTTGGAAA (3959) | 0.71 | 5123 |
| | zma-miR396a* | GTTCAATAAAGCTGTGGGAAA (3960) | 0.95 | 5124 |
| | zma-miR396b-3p | GTTCAATAAAGCTGTGGGAAA (3961) | 0.95 | 5125 |
| | zma-miR396e* | GGTCAAGAAAGCCGTGGGAAG (3962) | 0.86 | 5126 |
| | zma-miR396f* | GGTCAAGAAAGCTGTGGGAAG (3963) | 0.9 | 5127 |
| | zma-miR396g* | GTTCAAGAAAGCTGTGGAAGA (3964) | 0.81 | 5128 |
| aly-miR396b-3p | aly-miR396a-3p | GTTCAATAAAGCTGTGGGAAG (3965) | 0.86 | 5129 |
| | csi-miR396c | TTCAAGAAATCTGTGGGAAG (3966) | 0.81 | 5130 |
| | gma-miR396d | AAGAAAGCTGTGGGAGAATATGGC (3967) | 0.76 | 5131 |
| | osa-miR396e* | GTTCAAGAAAGCCCATGGAAA (3968) | 0.76 | 5132 |
| | osa-miR396e-3p | ATGGTTCAAGAAAGCCCATGGAAA (3969) | 0.76 | 5133 |
| | osa-miR396f* | GTTCAAGAAAGTCCTTGGAAA (3970) | 0.76 | 5134 |
| | osa-miR396f-3p | ATAGTTCAAGAAAGTCCTTGGAAA (3971) | 0.76 | 5135 |
| | zma-miR396a* | GTTCAATAAAGCTGTGGGAAA (3972) | 0.9 | 5136 |
| | zma-miR396b-3p | GTTCAATAAAGCTGTGGGAAA (3973) | 0.9 | 5137 |
| | zma-miR396e* | GGTCAAGAAAGCCGTGGGAAG (3974) | 0.86 | 5138 |
| | zma-miR396f* | GGTCAAGAAAGCTGTGGGAAG (3975) | 0.9 | 5139 |
| | zma-miR396g* | GTTCAAGAAAGCTGTGGAAGA (3976) | 0.86 | 5140 |
| ath-miRf10239-akr | aly-miR168a* | CCCGCCTTGCATCAACTGAAT (3977) | 0.95 | 5141 |
| bna-miR2111b-5p | aly-miR2111a | TAATCTGCATCCTGAGGTTTA (3978) | 1 | 5142 |
| | aly-miR2111b | TAATCTGCATCCTGAGGTTTA (3979) | 1 | 5143 |
| | ath-miR2111a | TAATCTGCATCCTGAGGTTTA (3980) | 1 | 5144 |
| | ath-miR2111b | TAATCTGCATCCTGAGGTTTA (3981) | 1 | 5145 |
| | bna-miR2111a | TAATCTGCATCCTGAGGTTTA (3982) | 1 | 5146 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | bra-miR2111a | TAATCTGCATCCTGAGGTTTA (3983) | 1 | 5147 |
| | bra-miR2111b | TAATCTGCATCCTGAGGTTTA (3984) | 1 | 5148 |
| | lja-miR2111 | TAATCTGCATCCTGAGGTTTA (3985) | 1 | 5149 |
| | mtr-miR2111a | TAATCTGCATCCTGAGGTTTA (3986) | 1 | 5150 |
| | mtr-miR2111b | TAATCTGCATCCTGAGGTTTA (3987) | 1 | 5151 |
| | mtr-miR2111c | TAATCTGCATCCTGAGGTTTA (3988) | 1 | 5152 |
| | mtr-miR2111d | TAATCTGCATCCTGAGGTTTA (3989) | 1 | 5153 |
| | mtr-miR2111e | TAATCTGCATCCTGAGGTTTA (3990) | 1 | 5154 |
| | mtr-miR2111f | TAATCTGCATCCTGAGGTTTA (3991) | 1 | 5155 |
| | mtr-miR2111h | TAATCTGCATCCTGAGGTTTA (3992) | 1 | 5156 |
| | mtr-miR2111i | TAATCTGCATCCTGAGGTTTA (3993) | 1 | 5157 |
| | mtr-miR2111j | TAATCTGCATCCTGAGGTTTA (3994) | 1 | 5158 |
| | mtr-miR2111k | TAATCTGCATCCTGAGGTTTA (3995) | 1 | 5159 |
| | mtr-miR2111l | TAATCTGCATCCTGAGGTTTA (3996) | 1 | 5160 |
| | mtr-miR2111m | TAATCTGCATCCTGAGGTTTA (3997) | 1 | 5161 |
| | mtr-miR2111n | TAATCTGCATCCTGAGGTTTA (3998) | 1 | 5162 |
| | mtr-miR2111o | TAATCTGCATCCTGAGGTTTA (3999) | 1 | 5163 |
| | mtr-miR2111p | TAATCTGCATCCTGAGGTTTA (4000) | 1 | 5164 |
| | mtr-miR2111q | TAATCTGCATCCTGAGGTTTA (4001) | 1 | 5165 |
| | mtr-miR2111r | TAATCTGCATCCTGAGGTTTA (4002) | 1 | 5166 |
| | mtr-miR2111s | TAATCTGCATCCTGAGGTTTA (4003) | 1 | 5167 |
| | tcc-miR2111 | TAATCTGCATCCTGAGGTTTA (4004) | 1 | 5168 |
| | vvi-miR2111-5p | TAATCTGCATCCTGAGGTCTA (4005) | 0.95 | 5169 |
| csi-miR162-5p | aly-miR162a* | GGAGGCAGCGGTTCATCGATC (4006) | 0.95 | 5170 |
| | aly-miR162b* | GGAGGCAGCGGTTCATCGATC (4007) | 0.95 | 5171 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR162* | GGGCGCAGTGGTTTATCGATC (4008) | 0.77 | 5172 |
| gma-miR396d | aly-miR396b-3p | GCTCAAGAAAGCTGTGGGAAA (4009) | 0.67 | 5173 |
| | zma-miR396a* | GTTCAATAAAGCTGTGGGAAA (4010) | 0.63 | 5174 |
| | zma-miR396b-3p | GTTCAATAAAGCTGTGGGAAA (4011) | 0.63 | 5175 |
| | zma-miR396f* | GGTCAAGAAAGCTGTGGGAAG (4012) | 0.63 | 5176 |
| | zma-miR396g* | GTTCAAGAAAGCTGTGGAAGA (4013) | 0.67 | 5177 |
| gma-miR482a-3p | aqc-miR482a | TCTTGCCGACTCCTCCCATACC (4014) | 0.71 | 5178 |
| | aqc-miR482b | TCTTGCCGACTCCTCCCATACC (4015) | 0.71 | 5179 |
| | aqc-miR482c | TCTTGCCGACTCCTCCCATACC (4016) | 0.71 | 5180 |
| | csi-miR482a | TCTTCCCTATGCCTCCCATTCC (4017) | 0.79 | 5181 |
| | csi-miR482b | TCTTGCCCACCCCTCCCATTCC (4018) | 0.71 | 5182 |
| | csi-miR482c | TTCCCTAGTCCCCCTATTCCTA (4019) | 0.75 | 5183 |
| | ghr-miR482a | TCTTTCCTACTCCTCCCATACC (4020) | 0.71 | 5184 |
| | ghr-miR482b | TCTTGCCTACTCCACCCATGCC (4021) | 0.71 | 5185 |
| | gma-miR482 | TCTTCCCAATTCCGCCCATTCCTA (4022) | 1 | 5186 |
| | gra-miR482 | TCTTTCCAATTCCTCCCATTCC (4023) | 0.83 | 5187 |
| | gso-miR482a | TCTTCCCTACACCTCCCATAC (4024) | 0.67 | 5188 |
| | gso-miR482b | TCTTCCCTACACCTCCCATAC (4025) | 0.67 | 5189 |
| | mdm-miR482 | TCTTCCCAAGCCCGCCCATTCC (4026) | 0.83 | 5190 |
| | mdo-miR482 | TCTTCCCAAGCCCGCCCATTCC (4027) | 0.83 | 5191 |
| | pab-miR482a | TCTTCCCTACTCCTCCCATTCC (4028) | 0.79 | 5192 |
| | pab-miR482b | TCTTCCCTATTCCTCCCATTCC (4029) | 0.83 | 5193 |
| | pab-miR482c | TCTTTCCTACTCCTCCCATTCC (4030) | 0.75 | 5194 |
| | pta-miR482a | TCTTCCCTACTCCTCCCATTCC (4031) | 0.79 | 5195 |
| | pta-miR482b | TCTTCCCTACTCCTCCCATTCC (4032) | 0.79 | 5196 |
| | pta-miR482c | TCTTCCCTATTCCTCCCATT (4033) | 0.75 | 5197 |
| | pta-miR482d | TCCTCCCTACTCCTCCCATT (4034) | 0.67 | 5198 |
| | ptc-miR482.2 | TCTTGCCTACTCCTCCCATT (4035) | 0.67 | 5199 |
| | pvu-miR482 | TCTTCCCAATTCCGCCCATTCC (4036) | 0.92 | 5200 |
| | sly-miR482 | TTTCCAATTCCACCCATTCCTA (4037) | 0.83 | 5201 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | vvi-miR482 | TCTTTCCTACTCCTCCCATTCC (4038) | 0.75 | 5202 |
| | zma-miR482 | TCTTCCTTGTTCCTCCCATT (4039) | 0.67 | 5203 |
| gma-miR482b-5p | pvu-miR482* | GGAATGGGCTGATTGGGAAGCA (4040) | 0.73 | 5204 |
| gso-miR169g* | aly-miR169a* | GGCAAGTTGTCCTTGGCTACA (4041) | 0.85 | 5205 |
| | aly-miR169b* | GGCAAGTTGTCCTTCGGCTACA (4042) | 0.85 | 5206 |
| | aly-miR169c* | GGCAAGTCATCTCTGGCTATG (4043) | 0.65 | 5207 |
| | aly-miR169d* | GCAAGTTGACCTTGGCTCTGT (4044) | 0.8 | 5208 |
| | aly-miR169e* | GCAAGTTGACCTTGGCTCTGT (4045) | 0.8 | 5209 |
| | aly-miR169f* | GCAAGTTGACCTTGGCTCTGC (4046) | 0.8 | 5210 |
| | aly-miR169g* | GCAAGTTGACCTTGGCTCTGT (4047) | 0.8 | 5211 |
| | aly-miR169h | TAGCCAAGGATGACTTGCCTG (4048) | 0.65 | 5212 |
| | aly-miR169h* | GGCAGTCTCCTTGGCTATT (4049) | 0.65 | 5213 |
| | aly-miR169i | TAGCCAAGGATGACTTGCCTG (4050) | 0.65 | 5214 |
| | aly-miR169i* | GGCAGTCTCCTTGGATATC (4051) | 0.6 | 5215 |
| | aly-miR169j | TAGCCAAGGATGACTTGCCTG (4052) | 0.65 | 5216 |
| | aly-miR169j* | GGCAGTCTCCTTGGCTATC (4053) | 0.65 | 5217 |
| | aly-miR169k | TAGCCAAGGATGACTTGCCTG (4054) | 0.65 | 5218 |
| | aly-miR169k* | GGCAGTCTCCTTGGCTATC (4055) | 0.65 | 5219 |
| | aly-miR169l | TAGCCAAGGATGACTTGCCTG (4056) | 0.65 | 5220 |
| | aly-miR169l* | GGCAGTCTCCTTGGCTATC (4057) | 0.65 | 5221 |
| | aly-miR169m | TAGCCAAGGATGACTTGCCTG (4058) | 0.65 | 5222 |
| | aly-miR169m* | GGCAGTCTTCTTGGCTATC (4059) | 0.6 | 5223 |
| | aly-miR169n | TAGCCAAAGATGACTTGCCTG (4060) | 0.6 | 5224 |
| | aly-miR169n* | GGCAGTCTCTTTGGCTATC (4061) | 0.6 | 5225 |
| | aqc-miR169a | TAGCCAAGGATGACTTGCCTA (4062) | 0.65 | 5226 |
| | aqc-miR169b | TAGCCAAGGATGACTTGCCTG (4063) | 0.65 | 5227 |
| | ath-miR169g* | TCCGGCAAGTTGACCTTGGCT (4064) | 0.9 | 5228 |
| | ath-miR169h | TAGCCAAGGATGACTTGCCTG (4065) | 0.65 | 5229 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ath-miR169i | TAGCCAAGGATGACTTGCCTG (4066) | 0.65 | 5230 |
| | ath-miR169j | TAGCCAAGGATGACTTGCCTG (4067) | 0.65 | 5231 |
| | ath-miR169k | TAGCCAAGGATGACTTGCCTG (4068) | 0.65 | 5232 |
| | ath-miR169l | TAGCCAAGGATGACTTGCCTG (4069) | 0.65 | 5233 |
| | ath-miR169m | TAGCCAAGGATGACTTGCCTG (4070) | 0.65 | 5234 |
| | ath-miR169n | TAGCCAAGGATGACTTGCCTG (4071) | 0.65 | 5235 |
| | bdi-miR169b | TAGCCAAGGATGACTTGCCGG (4072) | 0.6 | 5236 |
| | bdi-miR169d | TAGCCAAGAATGACTTGCCTA (4073) | 0.65 | 5237 |
| | bdi-miR169e | TAGCCAAGGATGACTTGCCTG (4074) | 0.65 | 5238 |
| | bdi-miR169g | TAGCCAAGGATGACTTGCCTG (4075) | 0.65 | 5239 |
| | bdi-miR169h | TAGCCAAGGATGACTTGCCTA (4076) | 0.65 | 5240 |
| | bdi-miR169i | CCAGCCAAGAATGGCTTGCCTA (4077) | 0.6 | 5241 |
| | bdi-miR169j | TAGCCAGGAATGGCTTGCCTA (4078) | 0.6 | 5242 |
| | bdi-miR169k | TAGCCAAGGATGATTTGCCTGT (4079) | 0.6 | 5243 |
| | bna-miR169c | TAGCCAAGGATGACTTGCCTA (4080) | 0.65 | 5244 |
| | bna-miR169d | TAGCCAAGGATGACTTGCCTA (4081) | 0.65 | 5245 |
| | bna-miR169e | TAGCCAAGGATGACTTGCCTA (4082) | 0.65 | 5246 |
| | bna-miR169f | TAGCCAAGGATGACTTGCCTA (4083) | 0.65 | 5247 |
| | bna-miR169g | TAGCCAAGGATGACTTGCCTGC (4084) | 0.65 | 5248 |
| | bna-miR169h | TAGCCAAGGATGACTTGCCTGC (4085) | 0.65 | 5249 |
| | bna-miR169i | TAGCCAAGGATGACTTGCCTGC (4086) | 0.65 | 5250 |
| | bna-miR169j | TAGCCAAGGATGACTTGCCTGC (4087) | 0.65 | 5251 |
| | bna-miR169k | TAGCCAAGGATGACTTGCCTGC (4088) | 0.65 | 5252 |
| | bna-miR169l | TAGCCAAGGATGACTTGCCTGC (4089) | 0.65 | 5253 |
| | far-miR169 | TAGCCAAGGATGACTTGCCTA (4090) | 0.65 | 5254 |
| | ghb-miR169a | TAGCCAAGGATGACTTGCCTG (4091) | 0.65 | 5255 |
| | ghr-miR169 | ACGCCAAGGATGTCTTGCGTC (4092) | 0.6 | 5256 |
| | mtr-miR169f | AAGCCAAGGATGACTTGCCTA (4093) | 0.6 | 5257 |
| | osa-miR169e | TAGCCAAGGATGACTTGCCGG (4094) | 0.6 | 5258 |
| | osa-miR169f | TAGCCAAGGATGACTTGCCTA (4095) | 0.65 | 5259 |
| | osa-miR169g | TAGCCAAGGATGACTTGCCTA (4096) | 0.65 | 5260 |
| | osa-miR169h | TAGCCAAGGATGACTTGCCTG (4097) | 0.65 | 5261 |
| | osa-miR169i | TAGCCAAGGATGACTTGCCTG (4098) | 0.65 | 5262 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | osa-miR169j | TAGCCAAGGATGACTTGCCTG (4099) | 0.65 | 5263 |
| | osa-miR169k | TAGCCAAGGATGACTTGCCTG (4100) | 0.65 | 5264 |
| | osa-miR169l | TAGCCAAGGATGACTTGCCTG (4101) | 0.65 | 5265 |
| | osa-miR169m | TAGCCAAGGATGACTTGCCTG (4102) | 0.65 | 5266 |
| | osa-miR169n | TAGCCAAGAATGACTTGCCTA (4103) | 0.65 | 5267 |
| | osa-miR169o | TAGCCAAGAATGACTTGCCTA (4104) | 0.65 | 5268 |
| | ptc-miR169ab | TAGCCAAGGACGACTTGCCCA (4105) | 0.6 | 5269 |
| | ptc-miR169ac | TAGCCAAGGACGACTTGCCCA (4106) | 0.6 | 5270 |
| | ptc-miR169ad | TAGCCAAGGACGACTTGCCCA (4107) | 0.6 | 5271 |
| | ptc-miR169ae | TAGCCAAGGACGACTTGCCCA (4108) | 0.6 | 5272 |
| | ptc-miR169af | TAGCCAAGGACGACTTGCCCA (4109) | 0.6 | 5273 |
| | ptc-miR169i | TAGCCAAGGATGACTTGCCTG (4110) | 0.65 | 5274 |
| | ptc-miR169j | TAGCCAAGGATGACTTGCCTG (4111) | 0.65 | 5275 |
| | ptc-miR169k | TAGCCAAGGATGACTTGCCTG (4112) | 0.65 | 5276 |
| | ptc-miR169l | TAGCCAAGGATGACTTGCCTG (4113) | 0.65 | 5277 |
| | ptc-miR169m | TAGCCAAGGATGACTTGCCTG (4114) | 0.65 | 5278 |
| | ptc-miR169o | AAGCCAAGGATGACTTGCCTG (4115) | 0.6 | 5279 |
| | ptc-miR169p | AAGCCAAGGATGACTTGCCTG (4116) | 0.6 | 5280 |
| | ptc-miR169q | TAGCCAAGGACGACTTGCCTG (4117) | 0.65 | 5281 |
| | ptc-miR169r | TAGCCAAGGATGACTTGCCTA (4118) | 0.65 | 5282 |
| | ptc-miR169s | TCAGCCAAGGATGACTTGCCG (4119) | 0.65 | 5283 |
| | ptc-miR169u | TAGCCAAGGACGACTTGCCTA (4120) | 0.65 | 5284 |
| | ptc-miR169v | TAGCCAAGGATGACTTGCCCA (4121) | 0.6 | 5285 |
| | ptc-miR169w | TAGCCAAGGATGACTTGCCCA (4122) | 0.6 | 5286 |
| | sbi-miR169c | TAGCCAAGGATGACTTGCCTA (4123) | 0.65 | 5287 |
| | sbi-miR169d | TAGCCAAGGATGACTTGCCTA (4124) | 0.65 | 5288 |
| | sbi-miR169e | TAGCCAAGGATGACTTGCCGG (4125) | 0.6 | 5289 |
| | sbi-miR169f | TAGCCAAGGATGACTTGCCTG (4126) | 0.65 | 5290 |
| | sbi-miR169g | TAGCCAAGGATGACTTGCCTG (4127) | 0.65 | 5291 |
| | sbi-miR169h | TAGCCAAGGATGACTTGCCTA (4128) | 0.65 | 5292 |
| | sbi-miR169i | TAGCCAAGAATGACTTGCCTA (4129) | 0.65 | 5293 |
| | sbi-miR169j | TAGCCAAGGATGACTTGCCGG (4130) | 0.6 | 5294 |
| | sbi-miR169l | TAGCCAAGGATGACTTGCCTG (4131) | 0.65 | 5295 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | sbi-miR169m | TAGCCAAGGATGACTTGCCTA (4132) | 0.65 | 5296 |
| | sbi-miR169n | TAGCCAAGGATGACTTGCCTA (4133) | 0.65 | 5297 |
| | sbi-miR169o | TAGCCAAGGATGATTTGCCTG (4134) | 0.6 | 5298 |
| | sbi-miR169p | TAGCCAAGAATGGCTTGCCTA (4135) | 0.65 | 5299 |
| | sbi-miR169q | TAGCCAAGAATGGCTTGCCTA (4136) | 0.65 | 5300 |
| | sly-miR169b | TAGCCAAGGATGACTTGCCTG (4137) | 0.65 | 5301 |
| | sly-miR169d | TAGCCAAGGATGACTTGCCTA (4138) | 0.65 | 5302 |
| | sof-miR169 | TAGCCAAGGATGACTTGCCGG (4139) | 0.6 | 5303 |
| | ssp-miR169 | TAGCCAAGGATGACTTGCCGG (4140) | 0.6 | 5304 |
| | tcc-miR169d | TAGCCAAGGATGACTTGCCTA (4141) | 0.65 | 5305 |
| | tcc-miR169f | AAGCCAAGAATGACTTGCCTG (4142) | 0.6 | 5306 |
| | tcc-miR169g | TAGCCAGGGATGACTTGCCTA (4143) | 0.6 | 5307 |
| | tcc-miR169h | TAGCCAAGGATGACTTGCCTG (4144) | 0.65 | 5308 |
| | tcc-miR169i | TAGCCAAGGATGAGTTGCCTG (4145) | 0.6 | 5309 |
| | tcc-miR169j | TAGCCAAGGATGACTTGCCTG (4146) | 0.65 | 5310 |
| | vvi-miR169e | TAGCCAAGGATGACTTGCCTGC (4147) | 0.65 | 5311 |
| | vvi-miR169x | TAGCCAAGGATGACTTGCCTA (4148) | 0.65 | 5312 |
| | vvi-miR169y | TAGCGAAGGATGACTTGCCTA (4149) | 0.6 | 5313 |
| | zma-miR169a* | GGCAAGTTGTTCTTGGCTACA (4150) | 0.8 | 5314 |
| | zma-miR169b* | GGCAAGTTGTTCTTGGCTACA (4151) | 0.8 | 5315 |
| | zma-miR169c* | GGCAAGTCTGTCCTTGGCTACA (4152) | 0.85 | 5316 |
| | zma-miR169f | TAGCCAAGGATGACTTGCCTA (4153) | 0.65 | 5317 |
| | zma-miR169f* | GGCATGTCTTCCTTGGCTACT (4154) | 0.7 | 5318 |
| | zma-miR169g | TAGCCAAGGATGACTTGCCTA (4155) | 0.65 | 5319 |
| | zma-miR169h | TAGCCAAGGATGACTTGCCTA (4156) | 0.65 | 5320 |
| | zma-miR169i | TAGCCAAGGATGACTTGCCTG (4157) | 0.65 | 5321 |
| | zma-miR169i* | GGCAGTCTCCTTGGCTAG (4158) | 0.65 | 5322 |
| | zma-miR169j | TAGCCAAGGATGACTTGCCTG (4159) | 0.65 | 5323 |
| | zma-miR169j* | GGCAGTCTCCTTGGCTAG (4160) | 0.65 | 5324 |
| | zma-miR169k | TAGCCAAGGATGACTTGCCTG (4161) | 0.65 | 5325 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR169k* | GGCAGTCTCCTTGGCTAG (4162) | 0.65 | 5326 |
| | zma-miR169m | TAGCCAAGAATGGCTTGCCTA (4163) | 0.65 | 5327 |
| | zma-miR169n | TAGCCAAGAATGGCTTGCCTA (4164) | 0.65 | 5328 |
| | zma-miR169n* | GGCAGGCCTTCTTGGCTAAG (4165) | 0.6 | 5329 |
| | zma-miR169o | TAGCCAAGAATGACTTGCCTA (4166) | 0.65 | 5330 |
| | zma-miR169o* | GGCAGGTCTTCTTGGCTAGC (4167) | 0.65 | 5331 |
| | zma-miR169p | TAGCCAAGGATGACTTGCCGG (4168) | 0.6 | 5332 |
| | zma-miR169p* | GGCAAGTCATCTGGGGCTACG (4169) | 0.6 | 5333 |
| | zma-miR169q | TAGCCAAGAATGGCTTGCCTA (4170) | 0.65 | 5334 |
| | zma-miR169r* | GGCAAGTTGTCCTTGGCTACA (4171) | 0.85 | 5335 |
| ppt-miR533b-5p | ppt-miR533a* | GAGCTGGCCAGGCTGTGAGGG (4172) | 0.95 | 5336 |
| ptc-miRf11953-akr | aly-miR2111a | TAATCTGCATCCTGAGGTTTA (4173) | 0.95 | 5337 |
| | aly-miR2111b | TAATCTGCATCCTGAGGTTTA (4174) | 0.95 | 5338 |
| | ath-miR2111a | TAATCTGCATCCTGAGGTTTA (4175) | 0.95 | 5339 |
| | ath-miR2111b | TAATCTGCATCCTGAGGTTTA (4176) | 0.95 | 5340 |
| | bna-miR2111a | TAATCTGCATCCTGAGGTTTA (4177) | 0.95 | 5341 |
| | bna-miR2111b-5p | TAATCTGCATCCTGAGGTTTA (4178) | 0.95 | 5342 |
| | bra-miR2111a | TAATCTGCATCCTGAGGTTTA (4179) | 0.95 | 5343 |
| | bra-miR2111b | TAATCTGCATCCTGAGGTTTA (4180) | 0.95 | 5344 |
| | lja-miR2111 | TAATCTGCATCCTGAGGTTTA (4181) | 0.95 | 5345 |
| | mtr-miR2111a | TAATCTGCATCCTGAGGTTTA (4182) | 0.95 | 5346 |
| | mtr-miR2111b | TAATCTGCATCCTGAGGTTTA (4183) | 0.95 | 5347 |
| | mtr-miR2111c | TAATCTGCATCCTGAGGTTTA (4184) | 0.95 | 5348 |
| | mtr-miR2111d | TAATCTGCATCCTGAGGTTTA (4185) | 0.95 | 5349 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
| --- | --- | --- | --- | --- |
| | mtr-miR2111e | TAATCTGCATCCTGAGGTTTA (4186) | 0.95 | 5350 |
| | mtr-miR2111f | TAATCTGCATCCTGAGGTTTA (4187) | 0.95 | 5351 |
| | mtr-miR2111h | TAATCTGCATCCTGAGGTTTA (4188) | 0.95 | 5352 |
| | mtr-miR2111i | TAATCTGCATCCTGAGGTTTA (4189) | 0.95 | 5353 |
| | mtr-miR2111j | TAATCTGCATCCTGAGGTTTA (4190) | 0.95 | 5354 |
| | mtr-miR2111k | TAATCTGCATCCTGAGGTTTA (4191) | 0.95 | 5355 |
| | mtr-miR2111l | TAATCTGCATCCTGAGGTTTA (4192) | 0.95 | 5356 |
| | mtr-miR2111m | TAATCTGCATCCTGAGGTTTA (4193) | 0.95 | 5357 |
| | mtr-miR2111n | TAATCTGCATCCTGAGGTTTA (4194) | 0.95 | 5358 |
| | mtr-miR2111o | TAATCTGCATCCTGAGGTTTA (4195) | 0.95 | 5359 |
| | mtr-miR2111p | TAATCTGCATCCTGAGGTTTA (4196) | 0.95 | 5360 |
| | mtr-miR2111q | TAATCTGCATCCTGAGGTTTA (4197) | 0.95 | 5361 |
| | mtr-miR2111r | TAATCTGCATCCTGAGGTTTA (4198) | 0.95 | 5362 |
| | mtr-miR2111s | TAATCTGCATCCTGAGGTTTA (4199) | 0.95 | 5363 |
| | tcc-miR2111 | TAATCTGCATCCTGAGGTTTA (4200) | 0.95 | 5364 |
| | vvi-miR2111-5p | TAATCTGCATCCTGAGGTCTA (4201) | 0.9 | 5365 |
| vvi-miR2111-5p | aly-miR2111a | TAATCTGCATCCTGAGGTTTA (4202) | 0.95 | 5366 |
| | aly-miR2111b | TAATCTGCATCCTGAGGTTTA (4203) | 0.95 | 5367 |
| | ath-miR2111a | TAATCTGCATCCTGAGGTTTA (4204) | 0.95 | 5368 |
| | ath-miR2111b | TAATCTGCATCCTGAGGTTTA (4205) | 0.95 | 5369 |
| | bna-miR2111a | TAATCTGCATCCTGAGGTTTA (4206) | 0.95 | 5370 |
| | bna-miR2111b-5p | TAATCTGCATCCTGAGGTTTA (4207) | 0.95 | 5371 |
| | bra-miR2111a | TAATCTGCATCCTGAGGTTTA (4208) | 0.95 | 5372 |
| | bra-miR2111b | TAATCTGCATCCTGAGGTTTA (4209) | 0.95 | 5373 |
| | lja-miR2111 | TAATCTGCATCCTGAGGTTTA (4210) | 0.95 | 5374 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | mtr-miR2111a | TAATCTGCATCCTGAGGTTTA (4211) | 0.95 | 5375 |
| | mtr-miR2111b | TAATCTGCATCCTGAGGTTTA (4212) | 0.95 | 5376 |
| | mtr-miR2111c | TAATCTGCATCCTGAGGTTTA (4213) | 0.95 | 5377 |
| | mtr-miR2111d | TAATCTGCATCCTGAGGTTTA (4214) | 0.95 | 5378 |
| | mtr-miR2111e | TAATCTGCATCCTGAGGTTTA (4215) | 0.95 | 5379 |
| | mtr-miR2111f | TAATCTGCATCCTGAGGTTTA (4216) | 0.95 | 5380 |
| | mtr-miR2111h | TAATCTGCATCCTGAGGTTTA (4217) | 0.95 | 5381 |
| | mtr-miR2111i | TAATCTGCATCCTGAGGTTTA (4218) | 0.95 | 5382 |
| | mtr-miR2111j | TAATCTGCATCCTGAGGTTTA (4219) | 0.95 | 5383 |
| | mtr-miR2111k | TAATCTGCATCCTGAGGTTTA (4220) | 0.95 | 5384 |
| | mtr-miR2111l | TAATCTGCATCCTGAGGTTTA (4221) | 0.95 | 5385 |
| | mtr-miR2111m | TAATCTGCATCCTGAGGTTTA (4222) | 0.95 | 5386 |
| | mtr-miR2111n | TAATCTGCATCCTGAGGTTTA (4223) | 0.95 | 5387 |
| | mtr-miR2111o | TAATCTGCATCCTGAGGTTTA (4224) | 0.95 | 5388 |
| | mtr-miR2111p | TAATCTGCATCCTGAGGTTTA (4225) | 0.95 | 5389 |
| | mtr-miR2111q | TAATCTGCATCCTGAGGTTTA (4226) | 0.95 | 5390 |
| | mtr-miR2111r | TAATCTGCATCCTGAGGTTTA (4227) | 0.95 | 5391 |
| | mtr-miR2111s | TAATCTGCATCCTGAGGTTTA (4228) | 0.95 | 5392 |
| | tcc-miR2111 | TAATCTGCATCCTGAGGTTTA (4229) | 0.95 | 5393 |
| zma-miR396b-3p | aly-miR396a-3p | GTTCAATAAAGCTGTGGGAAG (4230) | 0.95 | 5394 |
| | aly-miR396b-3p | GCTCAAGAAAGCTGTGGGAAA (4231) | 0.9 | 5395 |
| | csi-miR396c | TTCAAGAAATCTGTGGGAAG (4232) | 0.81 | 5396 |
| | gma-miR396d | AAGAAAGCTGTGGGAGAATATGGC (4233) | 0.71 | 5397 |
| | osa-miR396e* | GTTCAAGAAAGCCCATGGAAA (4234) | 0.76 | 5398 |
| | osa-miR396e-3p | ATGGTTCAAGAAAGCCCATGGAAA (4235) | 0.76 | 5399 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | osa-miR396f* | GTTCAAGAAAGTCCTTGGAAA (4236) | 0.76 | 5400 |
| | osa-miR396f-3p | ATAGTTCAAGAAAGTCCTTGGAAA (4237) | 0.76 | 5401 |
| | zma-miR396a* | GTTCAATAAAGCTGTGGGAAA (4238) | 1 | 5402 |
| | zma-miR396e* | GGTCAAGAAAGCCGTGGGAAG (4239) | 0.81 | 5403 |
| | zma-miR396f* | GGTCAAGAAAGCTGTGGGAAG (4240) | 0.86 | 5404 |
| | zma-miR396g* | GTTCAAGAAAGCTGTGGAAGA (4241) | 0.86 | 5405 |
| ctr-miR171 | aly-miR171a | TGATTGAGCCGCGCCAATATC (4242) | 0.81 | 5406 |
| | aly-miR171b | TTGAGCCGTGCCAATATCACG (4243) | 0.81 | 5407 |
| | aly-miR171c | TTGAGCCGTGCCAATATCACG (4244) | 0.81 | 5408 |
| | aqc-miR171a | TGATTGAGCCGTGCCAATATC (4245) | 0.76 | 5409 |
| | aqc-miR171b | TGATTGAGCCGTGCCAATATC (4246) | 0.76 | 5410 |
| | aqc-miR171c | TAATTGAACCGCACTAATATC (4247) | 0.67 | 5411 |
| | aqc-miR171d | TGATTGAGCCGTGCCAATATC (4248) | 0.76 | 5412 |
| | aqc-miR171e | TGAATGAACCGAGCCAACATC (4249) | 0.62 | 5413 |
| | aqc-miR171f | TAATTGAGCCGTGCCAATATC (4250) | 0.76 | 5414 |
| | ath-miR171a | TGATTGAGCCGCGCCAATATC (4251) | 0.81 | 5415 |
| | ath-miR171b | TTGAGCCGTGCCAATATCACG (4252) | 0.81 | 5416 |
| | ath-miR171c | TTGAGCCGTGCCAATATCACG (4253) | 0.81 | 5417 |
| | bdi-miR171a | TGATTGAGCCGCGCCAATATC (4254) | 0.81 | 5418 |
| | bdi-miR171b | TGATTGAGCCGTGCCAATATC (4255) | 0.76 | 5419 |
| | bdi-miR171c | TGATTGAGCCGTGCCAATATC (4256) | 0.76 | 5420 |
| | bdi-miR171d | TGATTGAGCCGTGCCAATATC (4257) | 0.76 | 5421 |
| | bna-miR171a | TTGAGCCGTGCCAATATCACG (4258) | 0.81 | 5422 |
| | bna-miR171b | TTGAGCCGTGCCAATATCACG (4259) | 0.81 | 5423 |
| | bna-miR171c | TTGAGCCGTGCCAATATCACG (4260) | 0.81 | 5424 |
| | bna-miR171d | TTGAGCCGTGCCAATATCACG (4261) | 0.81 | 5425 |
| | bna-miR171e | TTGAGCCGTGCCAATATCACG (4262) | 0.81 | 5426 |
| | bna-miR171f | TGATTGAGCCGCGCCAATATC (4263) | 0.81 | 5427 |
| | bna-miR171g | TGATTGAGCCGCGCCAATATCT (4264) | 0.86 | 5428 |
| | bol-miR171a | TTGAGCCGTGCCAATATCACG (4265) | 0.81 | 5429 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | bra-miR171a | TTGAGCCGTGCCAATATCACG (4266) | 0.81 | 5430 |
| | bra-miR171b | TTGAGCCGTGCCAATATCACG (4267) | 0.81 | 5431 |
| | bra-miR171c | TTGAGCCGTGCCAATATCACG (4268) | 0.81 | 5432 |
| | bra-miR171d | TTGAGCCGTGCCAATATCACG (4269) | 0.81 | 5433 |
| | bra-miR171e | TGATTGAGCCGCGCCAATATC (4270) | 0.81 | 5434 |
| | ccl-miR171 | TGATTGAGCCGCGCCAATATC (4271) | 0.81 | 5435 |
| | crt-miR171 | TGATTGAGCCGTGCCAATATC (4272) | 0.76 | 5436 |
| | csi-miR171a | TTGAGCCGCGCCAATATCAC (4273) | 0.86 | 5437 |
| | csi-miR171b | CGAGCCGAATCAATATCACTC (4274) | 0.71 | 5438 |
| | ctr-miR171 | TTGAGCCGCGTCAATATCTCC (4275) | 1 | 5439 |
| | far-miR171 | TGATTGAGCCGTGCCAATATC (4276) | 0.76 | 5440 |
| | gma-miR171a | TGAGCCGTGCCAATATCACGA (4277) | 0.76 | 5441 |
| | gma-miR171b-3p | CGAGCCGAATCAATATCACTC (4278) | 0.71 | 5442 |
| | hvu-miR171 | TGATTGAGCCGTGCCAATATC (4279) | 0.76 | 5443 |
| | mtr-miR171 | TGATTGAGTCGTGCCAATATC (4280) | 0.71 | 5444 |
| | mtr-miR171b | TGATTGAGCCGCGTCAATATC (4281) | 0.86 | 5445 |
| | mtr-miR171c | TGATTGAGCCGTGCCAATATT (4282) | 0.71 | 5446 |
| | mtr-miR171d | TGATTGAGCCGTGCCAATATC (4283) | 0.76 | 5447 |
| | mtr-miR171e | AGATTGAGCCGCGCCAATATC (4284) | 0.81 | 5448 |
| | mtr-miR171f | TTGAGCCGTGCCAATATCACG (4285) | 0.81 | 5449 |
| | mtr-miR171g | TGATTGAGCCGTGCCAATATC (4286) | 0.76 | 5450 |
| | osa-miR171a | TGATTGAGCCGCGCCAATATC (4287) | 0.81 | 5451 |
| | osa-miR171b | TGATTGAGCCGTGCCAATATC (4288) | 0.76 | 5452 |
| | osa-miR171c | TGATTGAGCCGTGCCAATATC (4289) | 0.76 | 5453 |
| | osa-miR171d | TGATTGAGCCGTGCCAATATC (4290) | 0.76 | 5454 |
| | osa-miR171e | TGATTGAGCCGTGCCAATATC (4291) | 0.76 | 5455 |
| | osa-miR171f | TGATTGAGCCGTGCCAATATC (4292) | 0.76 | 5456 |
| | osa-miR171g | GAGGTGAGCCGAGCCAATATC (4293) | 0.71 | 5457 |
| | osa-miR171h | GTGAGCCGAACCAATATCACT (4294) | 0.71 | 5458 |
| | osa-miR171i | GGATTGAGCCGCGTCAATATC (4295) | 0.86 | 5459 |
| | ppt-miR171a | TGAGCCGCGCCAATATCACAT (4296) | 0.81 | 5460 |
| | ppt-miR171b | TTGAGCCGCGCCAATATCACA (4297) | 0.86 | 5461 |
| | pta-miR171 | TGATTGAGACGAGTCCATATC (4298) | 0.71 | 5462 |
| | ptc-miR171a | TTGAGCCGTGCCAATATCACG (4299) | 0.81 | 5463 |
| | ptc-miR171b | TTGAGCCGTGCCAATATCACG (4300) | 0.81 | 5464 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ptc-miR171c | AGATTGAGCCGCGCCAATATC (4301) | 0.81 | 5465 |
| | ptc-miR171d | AGATTGAGCCGCGCCAATATC (4302) | 0.81 | 5466 |
| | ptc-miR171e | TGATTGAGCCGTGCCAATATC (4303) | 0.76 | 5467 |
| | ptc-miR171f | TGATTGAGCCGTGCCAATATC (4304) | 0.76 | 5468 |
| | ptc-miR171g | TGATTGAGCCGTGCCAATATC (4305) | 0.76 | 5469 |
| | ptc-miR171h | TGATTGAGCCGTGCCAATATC (4306) | 0.76 | 5470 |
| | ptc-miR171i | TGATTGAGCCGTGCCAATATC (4307) | 0.76 | 5471 |
| | ptc-miR171j | GGATTGAGCCGCGCCAATACT (4308) | 0.71 | 5472 |
| | ptc-miR171k | GGATTGAGCCGCGCCAATATC (4309) | 0.81 | 5473 |
| | ptc-miR171l | CGAGCCGAATCAATATCACT (4310) | 0.71 | 5474 |
| | ptc-miR171m | CGAGCCGAATCAATATCACT (4311) | 0.71 | 5475 |
| | ptc-miR171n | CGAGCCGAATCAATATCACT (4312) | 0.71 | 5476 |
| | rco-miR171a | TTGAGCCGTGCCAATATCACG (4313) | 0.81 | 5477 |
| | rco-miR171b | TTGAGCCGTGCCAATATCACG (4314) | 0.81 | 5478 |
| | rco-miR171c | TGATTGAGCCGTGCCAATATC (4315) | 0.76 | 5479 |
| | rco-miR171d | TGATTGAGCCGTGCCAATATC (4316) | 0.76 | 5480 |
| | rco-miR171e | TGATTGAGCCGTGCCAATATC (4317) | 0.76 | 5481 |
| | rco-miR171f | TGATTGAGCCGTGCCAATATC (4318) | 0.76 | 5482 |
| | rco-miR171g | AGATTGAGCCGCGCCAATATC (4319) | 0.81 | 5483 |
| | sbi-miR171a | TGATTGAGCCGTGCCAATATC (4320) | 0.76 | 5484 |
| | sbi-miR171b | TGATTGAGCCGTGCCAATATC (4321) | 0.76 | 5485 |
| | sbi-miR171c | GAGGTGAGCCGAGCCAATATC (4322) | 0.71 | 5486 |
| | sbi-miR171d | TGATTGAGCCGTGCCAATATC (4323) | 0.76 | 5487 |
| | sbi-miR171e | GTGAGCCGAACCAATATCACT (4324) | 0.71 | 5488 |
| | sbi-miR171f | ATGAGCCGAACCAATATCACT (4325) | 0.71 | 5489 |
| | sbi-miR171g | TGATTGAGCCGCGCCAATATC (4326) | 0.81 | 5490 |
| | sbi-miR171h | GGATTGAGCCGCGTCAATATC (4327) | 0.86 | 5491 |
| | sbi-miR171i | TGATTGAGCCGTGCCAATATC (4328) | 0.76 | 5492 |
| | sbi-miR171j | TGATTGAGCCGCGCCAATATC (4329) | 0.81 | 5493 |
| | sbi-miR171k | TGATTGAGCCGTGCCAATATC (4330) | 0.76 | 5494 |
| | sly-miR171a | TGATTGAGCCGTGCCAATATC (4331) | 0.76 | 5495 |
| | sly-miR171b | TTGAGCCGTGCCAATATCACG (4332) | 0.81 | 5496 |
| | sly-miR171d | TTGAGCCGCGCCAATATCAC (4333) | 0.86 | 5497 |
| | smo-miR171a | TTGAGCCGTGCCAATATCACT (4334) | 0.81 | 5498 |
| | smo-miR171b | TGAGCCGTGCCAATATCACAT (4335) | 0.76 | 5499 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | smo-miR171c | TTGAGTCGCGCCAATATCATG (4336) | 0.76 | 5500 |
| | smo-miR171d | TGAGCCGCGCCAATATCACAT (4337) | 0.81 | 5501 |
| | tae-miR171a | TGATTGAGCCGTGCCAATATC (4338) | 0.76 | 5502 |
| | tae-miR171b | TTGAGCCGTGCCAATATCACG (4339) | 0.81 | 5503 |
| | tcc-miR171a | TGATTGAGCCGCGCCAATATC (4340) | 0.81 | 5504 |
| | tcc-miR171b | AGATTGAGCCGCGCCAATATC (4341) | 0.81 | 5505 |
| | tcc-miR171c | AGATTGAGCCGCGCCAATATC (4342) | 0.81 | 5506 |
| | tcc-miR171d | TGATTGAGCCGTGCCAATATC (4343) | 0.76 | 5507 |
| | tcc-miR171e | TGATTGAGCCGTGCCAATATC (4344) | 0.76 | 5508 |
| | tcc-miR171f | TGATTGAGCCGTGCCAATATC (4345) | 0.76 | 5509 |
| | tcc-miR171g | TGATTGAGCCGTGCCAATATC (4346) | 0.76 | 5510 |
| | tcc-miR171h | TGATTGAGCCGTGCCAATATC (4347) | 0.76 | 5511 |
| | vvi-miR171a | TGATTGAGCCGTGCCAATATC (4348) | 0.76 | 5512 |
| | vvi-miR171b | TGATTGAGCCGCGTCAATATC (4349) | 0.86 | 5513 |
| | vvi-miR171c | TGATTGAGCCGTGCCAATATC (4350) | 0.76 | 5514 |
| | vvi-miR171d | TGATTGAGCCGTGCCAATATC (4351) | 0.76 | 5515 |
| | vvi-miR171e | TGATTGAGCCGCGCCAATATC (4352) | 0.81 | 5516 |
| | vvi-miR171f | TTGAGCCGCGCCAATATCACT (4353) | 0.86 | 5517 |
| | vvi-miR171g | TTGAGCCGAACCAATATCACC (4354) | 0.81 | 5518 |
| | vvi-miR171h | TGGTTGAGCCGCGCCAATATC (4355) | 0.81 | 5519 |
| | vvi-miR171i | TGATTGAGCCGTGCCAATATC (4356) | 0.76 | 5520 |
| | zma-miR171a | TGATTGAGCCGCGCCAATAT (4357) | 0.76 | 5521 |
| | zma-miR171b | TTGAGCCGTGCCAATATCAC (4358) | 0.81 | 5522 |
| | zma-miR171c | TGACTGAGCCGTGCCAATATC (4359) | 0.71 | 5523 |
| | zma-miR171d | TGATTGAGCCGTGCCAATATC (4360) | 0.76 | 5524 |
| | zma-miR171e | TGATTGAGCCGTGCCAATATC (4361) | 0.76 | 5525 |
| | zma-miR171f | TTGAGCCGTGCCAATATCACA (4362) | 0.81 | 5526 |
| | zma-miR171g | GAGGTGAGCCGAGCCAATATC (4363) | 0.71 | 5527 |
| | zma-miR171h | GTGAGCCGAACCAATATCACT (4364) | 0.71 | 5528 |
| | zma-miR171i | TGATTGAGCCGTGCCAATATC (4365) | 0.76 | 5529 |
| | zma-miR171j | TGATTGAGCCGTGCCAATATC (4366) | 0.76 | 5530 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR171k | GTGAGCCGAACCAATATCACT (4367) | 0.71 | 5531 |
| | zma-miR171l | GGATTGAGCCGCGTCAATATC (4368) | 0.86 | 5532 |
| | zma-miR171m | GGATTGAGCCGCGTCAATATC (4369) | 0.86 | 5533 |
| | zma-miR171n | TGATTGAGCCGCGCCAATATC (4370) | 0.81 | 5534 |
| aly-miR160c-3p | ahy-miR160-3p | GCATGAAGGGAGTCACGCAGG (4371) | 0.67 | 5535 |
| | aly-miR160a* | GCGTATGAGGAGCCATGCATA (4372) | 0.81 | 5536 |
| | aly-miR160b* | GCGTACAGAGTAGTCAAGCATG (4373) | 0.86 | 5537 |
| | bra-miR160a-3p | GCGTATGAGGAGCCATGCATA (4374) | 0.81 | 5538 |
| | zma-miR160a* | GCGTGCAAGGGGCCAAGCATG (4375) | 0.9 | 5539 |
| | zma-miR160b* | GCGTGCAAGGAGCCAAGCATG (4376) | 0.95 | 5540 |
| | zma-miR160c* | GCGTGCATGGTGCCAAGCATA (4377) | 0.81 | 5541 |
| | zma-miR160d* | GCGTGCGTGGAGCCAAGCATG (4378) | 0.86 | 5542 |
| | zma-miR160f* | GCGTGCGAGGTGCCAGGCATG (4379) | 0.81 | 5543 |
| | zma-miR160g* | GCGTGCAAGGAGCCAAGCATG (4380) | 0.95 | 5544 |
| bra-miR160a-3p | aly-miR160a* | GCGTATGAGGAGCCATGCATA (4381) | 1 | 5545 |
| | aly-miR160b* | GCGTACAGAGTAGTCAAGCATG (4382) | 0.76 | 5546 |
| | aly-miR160c-3p | GCGTACAAGGAGCCAAGCATG (4383) | 0.81 | 5547 |
| | zma-miR160a* | GCGTGCAAGGGGCCAAGCATG (4384) | 0.71 | 5548 |
| | zma-miR160b* | GCGTGCAAGGAGCCAAGCATG (4385) | 0.76 | 5549 |
| | zma-miR160c* | GCGTGCATGGTGCCAAGCATA (4386) | 0.71 | 5550 |
| | zma-miR160d* | GCGTGCGTGGAGCCAAGCATG (4387) | 0.76 | 5551 |
| | zma-miR160f* | GCGTGCGAGGTGCCAGGCATG (4388) | 0.76 | 5552 |
| | zma-miR160g* | GCGTGCAAGGAGCCAAGCATG (4389) | 0.76 | 5553 |
| gma-miR1507a | ahy-miR1507 | CCTCGTTCCATACATCATCTA (4390) | 0.77 | 5554 |
| | gma-miR1507b | TCTCATTCCATACATCGTCTG (4391) | 0.95 | 5555 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | gso-miR1507a | TCTCATTCCATACATCGTCTGA (4392) | 1 | 5556 |
| | gso-miR1507b | TCTCATTCCATACATCGTCTGA (4393) | 1 | 5557 |
| | mtr-miR1507 | CCTCGTTCCATACATCATCTAG (4394) | 0.77 | 5558 |
| | vun-miR1507a | TCTCATTCCATACATCGTCTG (4395) | 0.95 | 5559 |
| | vun-miR1507b | TCTCATTCCATACATCGTCTG (4396) | 0.95 | 5560 |
| gma-miR4371b | gma-miR4371a | AAGTGATGACATGACAAGCGAAGT (4397) | 0.75 | 5561 |
| gso-miR482a | aqc-miR482a | TCTTGCCGACTCCTCCCATACC (4398) | 0.86 | 5562 |
| | aqc-miR482b | TCTTGCCGACTCCTCCCATACC (4399) | 0.86 | 5563 |
| | aqc-miR482c | TCTTGCCGACTCCTCCCATACC (4400) | 0.86 | 5564 |
| | csi-miR482a | TCTTCCCTATGCCTCCCATTCC (4401) | 0.86 | 5565 |
| | csi-miR482b | TCTTGCCCACCCCTCCCATTCC (4402) | 0.81 | 5566 |
| | csi-miR482c | TTCCCTAGTCCCCCTATTCCTA (4403) | 0.67 | 5567 |
| | ghr-miR482a | TCTTTCCTACTCCTCCCATACC (4404) | 0.9 | 5568 |
| | ghr-miR482b | TCTTGCCTACTCCACCCATGCC (4405) | 0.81 | 5569 |
| | gma-miR482 | TCTTCCCAATTCCGCCCATTCCTA (4406) | 0.76 | 5570 |
| | gma-miR482a-3p | TCTTCCCAATTCCGCCCATTCCTA (4407) | 0.76 | 5571 |
| | gra-miR482 | TCTTTCCAATTCCTCCCATTCC (4408) | 0.76 | 5572 |
| | gso-miR482b | TCTTCCCTACACCTCCCATAC (4409) | 1 | 5573 |
| | mdm-miR482 | TCTTCCCAAGCCCGCCCATTCC (4410) | 0.76 | 5574 |
| | mdo-miR482 | TCTTCCCAAGCCCGCCCATTCC (4411) | 0.76 | 5575 |
| | pab-miR482a | TCTTCCCTACTCCTCCCATTCC (4412) | 0.9 | 5576 |
| | pab-miR482b | TCTTCCCTATTCCTCCCATTCC (4413) | 0.86 | 5577 |
| | pab-miR482c | TCTTTCCTACTCCTCCCATTCC (4414) | 0.86 | 5578 |
| | pta-miR482a | TCTTCCCTACTCCTCCCATTCC (4415) | 0.9 | 5579 |
| | pta-miR482b | TCTTCCCTACTCCTCCCATTCC (4416) | 0.9 | 5580 |
| | pta-miR482c | TCTTCCCTATTCCTCCCATT (4417) | 0.81 | 5581 |
| | pta-miR482d | TCCTCCCTACTCCTCCCATT (4418) | 0.81 | 5582 |
| | ptc-miR482.1 | CCTACTCCTCCCATTCC (4419) | 0.67 | 5583 |
| | ptc-miR482.2 | TCTTGCCTACTCCTCCCATT (4420) | 0.81 | 5584 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | pvu-miR482 | TCTTCCCAATTCCGCCCATTCC (4421) | 0.76 | 5585 |
| | sly-miR482 | TTTCCAATTCCACCCATTCCTA (4422) | 0.62 | 5586 |
| | vvi-miR482 | TCTTTCCTACTCCTCCCATTCC (4423) | 0.86 | 5587 |
| | zma-miR482 | TCTTCCTTGTTCCTCCCATT (4424) | 0.71 | 5588 |
| osa-miR1846e | osa-miR1846a-5p | AGTGAGGAGGCCGGGGCCGCT (4425) | 0.75 | 5589 |
| | osa-miR1846b-5p | AGTGAGGAGGCCGGGGCCGCT (4426) | 0.75 | 5590 |
| | osa-miR1846c-5p | AGTGAGGAGGCCGGGGCCGCT (4427) | 0.75 | 5591 |
| ppt-miR166m | aly-miR166a | TCGGACCAGGCTTCATTCCCC (4428) | 0.86 | 5592 |
| | aly-miR166b | TCGGACCAGGCTTCATTCCCC (4429) | 0.86 | 5593 |
| | aly-miR166c | TCGGACCAGGCTTCATTCCCC (4430) | 0.86 | 5594 |
| | aly-miR166d | TCGGACCAGGCTTCATTCCCC (4431) | 0.86 | 5595 |
| | aly-miR166e | TCGGACCAGGCTTCATTCCCC (4432) | 0.86 | 5596 |
| | aly-miR166f | TCGGACCAGGCTTCATTCCCC (4433) | 0.86 | 5597 |
| | aly-miR166g | TCGGACCAGGCTTCATTCCCC (4434) | 0.86 | 5598 |
| | aqc-miR166a | TCGGACCAGGCTTCATTCCTC (4435) | 0.9 | 5599 |
| | aqc-miR166b | TCGGACCAGGCTTCATTCCCC (4436) | 0.86 | 5600 |
| | aqc-miR166c | TCGGACCAGGCTTCATTCCT (4437) | 0.9 | 5601 |
| | aqc-miR166d | TCGGACCAGGCTTCATTCCTC (4438) | 0.9 | 5602 |
| | aqc-miR166e | TCGGACCAGGCTTCATTCCCC (4439) | 0.86 | 5603 |
| | ath-miR166a | TCGGACCAGGCTTCATTCCCC (4440) | 0.86 | 5604 |
| | ath-miR166b | TCGGACCAGGCTTCATTCCCC (4441) | 0.86 | 5605 |
| | ath-miR166c | TCGGACCAGGCTTCATTCCCC (4442) | 0.86 | 5606 |
| | ath-miR166d | TCGGACCAGGCTTCATTCCCC (4443) | 0.86 | 5607 |
| | ath-miR166e | TCGGACCAGGCTTCATTCCCC (4444) | 0.86 | 5608 |
| | ath-miR166f | TCGGACCAGGCTTCATTCCCC (4445) | 0.86 | 5609 |
| | ath-miR166g | TCGGACCAGGCTTCATTCCCC (4446) | 0.86 | 5610 |
| | bdi-miR166 | TCGGACCAGGCTTCATTCCCC (4447) | 0.86 | 5611 |
| | bdi-miR166a | TCGGACCAGGCTTCATTCCCC (4448) | 0.86 | 5612 |
| | bdi-miR166b | TCGGACCAGGCTTCATTCCCC (4449) | 0.86 | 5613 |
| | bdi-miR166c | TCGGACCAGGCTTCATTCCCC (4450) | 0.86 | 5614 |
| | bdi-miR166d | TCGGACCAGGCTTCATTCCCC (4451) | 0.86 | 5615 |
| | bdi-miR166e | CTCGGACCAGGCTTCATTCCC (4452) | 0.86 | 5616 |
| | bdi-miR166f | TCTCGGACCAGGCTTCATTCC (4453) | 0.86 | 5617 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | bna-miR166a | TCGGACCAGGCTTCATTCCCC (4454) | 0.86 | 5618 |
| | bna-miR166b | TCGGACCAGGCTTCATTCCCC (4455) | 0.86 | 5619 |
| | bna-miR166c | TCGGACCAGGCTTCATTCCCC (4456) | 0.86 | 5620 |
| | bna-miR166d | TCGGACCAGGCTTCATTCCCC (4457) | 0.86 | 5621 |
| | cpt-miR166 | TCGGACCAGGCTTCATTCCC (4458) | 0.86 | 5622 |
| | crt-miR166a | TCGGACCAGGCTTCATTCCCGT (4459) | 0.86 | 5623 |
| | crt-miR166b | TCGGACCAGGCTTCATTCCCTT (4460) | 0.9 | 5624 |
| | csi-miR166 | TCGGACCAGGCTTCATTCCCC (4461) | 0.86 | 5625 |
| | csi-miR166a | TCGGACCAGGCTTCATTCCCCC (4462) | 0.86 | 5626 |
| | csi-miR166b | TCGGACCAGGCTTCATTCCCGT (4463) | 0.86 | 5627 |
| | csi-miR166c | TCGGACCAGGCTTCATTCCC (4464) | 0.86 | 5628 |
| | csi-miR166d | TCGGACCAGGCTTCATTCCCT (4465) | 0.9 | 5629 |
| | csi-miR166e | TCGGACCAGGCTTCATTCCCC (4466) | 0.86 | 5630 |
| | ctr-miR166 | TCGGACCAGGCTTCATTCCCCC (4467) | 0.86 | 5631 |
| | far-miR166 | CCGGACCAGGCTTCATCCCAG (4468) | 0.76 | 5632 |
| | flm-miR166 | TCGGACCAGGCTTCATCCCCC (4469) | 0.81 | 5633 |
| | ghr-miR166a | TCGGACCAGGCTTCATTCCCC (4470) | 0.86 | 5634 |
| | ghr-miR166b | TCGGACCAGGCTTCATTCCCC (4471) | 0.86 | 5635 |
| | gma-miR166a | TCGGACCAGGCTTCATTCCCC (4472) | 0.86 | 5636 |
| | gma-miR166b | TCGGACCAGGCTTCATTCCCC (4473) | 0.86 | 5637 |
| | gma-miR166n | TCGGACCAGGCTTCATTCCCC (4474) | 0.86 | 5638 |
| | gma-miR166o | TCGGACCAGGCTTCATTCCCC (4475) | 0.86 | 5639 |
| | gma-miR166q | TCGGACCAGGCTTCATTCCCG (4476) | 0.86 | 5640 |
| | gma-miR166r | TCGGACCAGGCTTCATTCCCT (4477) | 0.9 | 5641 |
| | hvu-miR166 | TCGGACCAGGCTTCATTCCCC (4478) | 0.86 | 5642 |
| | hvu-miR166b | TCGGACCAGGCTTCATTCCCC (4479) | 0.86 | 5643 |
| | hvu-miR166c | TCGGACCAGGCTTCATTCCCC (4480) | 0.86 | 5644 |
| | hvv-miR166 | TCGGACCAGGCTTCATTCCCC (4481) | 0.86 | 5645 |
| | ini-miR166 | TCGGACCAGGCTTCATTCCTC (4482) | 0.9 | 5646 |
| | mtr-miR166 | TCGGACCAGGCTTCATTCCCC (4483) | 0.86 | 5647 |
| | mtr-miR166b | TCGGACCAGGCTTCATTCCTA (4484) (TCGGACCAGGCTTCATTCCCC (5115) | 0.9 | 5648 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | mtr-miR166c | TCGGACCAGGCTTCATTCCTC (4485) | 0.9 | 5649 |
| | mtr-miR166d | TCGGGCCAGGCTTCATCCCCC (4486) | 0.76 | 5650 |
| | mtr-miR166e | TCGGACCAGGCTTCATTCCCC (4487) | 0.86 | 5651 |
| | mtr-miR166f | TCGGACCAGGCTTCATTCCTC (4488) | 0.9 | 5652 |
| | mtr-miR166g | TCGGACCAGGCTTCATTCCCC (4489) | 0.86 | 5653 |
| | mtr-miR166h | TCGGACCAGGCTTCATTCCCC (4490) | 0.86 | 5654 |
| | nsy-miR166 | TCGGACCAGGCTTCATTCCCC (4491) | 0.86 | 5655 |
| | osa-miR166a | TCGGACCAGGCTTCATTCCCC (4492) | 0.86 | 5656 |
| | osa-miR166b | TCGGACCAGGCTTCATTCCCC (4493) | 0.86 | 5657 |
| | osa-miR166c | TCGGACCAGGCTTCATTCCCC (4494) | 0.86 | 5658 |
| | osa-miR166d | TCGGACCAGGCTTCATTCCCC (4495) | 0.86 | 5659 |
| | osa-miR166e | TCGAACCAGGCTTCATTCCCC (4496) | 0.81 | 5660 |
| | osa-miR166f | TCGGACCAGGCTTCATTCCCC (4497) | 0.86 | 5661 |
| | osa-miR166g | TCGGACCAGGCTTCATTCCTC (4498) | 0.9 | 5662 |
| | osa-miR166h | TCGGACCAGGCTTCATTCCTC (4499) | 0.9 | 5663 |
| | osa-miR166i | TCGGATCAGGCTTCATTCCTC (4500) | 0.86 | 5664 |
| | osa-miR166j | TCGGATCAGGCTTCATTCCTC (4501) | 0.86 | 5665 |
| | osa-miR166k | TCGGACCAGGCTTCAATCCCT (4502) | 0.86 | 5666 |
| | osa-miR166l | TCGGACCAGGCTTCAATCCCT (4503) | 0.86 | 5667 |
| | osa-miR166m | TCGGACCAGGCTTCATTCCCT (4504) | 0.9 | 5668 |
| | osa-miR166n | TCGGACCAGGCTTCATTCCCC (4505) | 0.86 | 5669 |
| | pab-miR166a | TCGGACCAGGCTTCATTCCTC (4506) | 0.9 | 5670 |
| | pab-miR166b | TCGGACCAGGCTTCATTCCTT (4507) | 0.95 | 5671 |
| | pga-miR166 | TCGGACCAGGCTTCATTCCTT (4508) | 0.95 | 5672 |
| | ppt-miR166a | TCGGACCAGGCTTCATTCCCC (4509) | 0.86 | 5673 |
| | ppt-miR166b | TCGGACCAGGCTTCATTCCCC (4510) | 0.86 | 5674 |
| | ppt-miR166c | TCGGACCAGGCTTCATTCCCC (4511) | 0.86 | 5675 |
| | ppt-miR166d | TCGGACCAGGCTTCATTCCCC (4512) | 0.86 | 5676 |
| | ppt-miR166e | TCGGACCAGGCTTCATTCCCC (4513) | 0.86 | 5677 |
| | ppt-miR166f | TCGGACCAGGCTTCATTCCCC (4514) | 0.86 | 5678 |
| | ppt-miR166g | TCGGACCAGGCTTCATTCCCC (4515) | 0.86 | 5679 |
| | ppt-miR166h | TCGGACCAGGCTTCATTCCCC (4516) | 0.86 | 5680 |
| | ppt-miR166i | TCGGACCAGGCTTCATTCCCC (4517) | 0.86 | 5681 |
| | ppt-miR166j | TCCGGACCAGGCTTCATTCCC (4518) | 0.81 | 5682 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ppt-miR166k | TCCGGACCAGGCTTCATTCCCC (4519) | 0.81 | 5683 |
| | ppt-miR166l | TCCGGACCAGGCTTCATTCCCC (4520) | 0.81 | 5684 |
| | pta-miR166a | TCGGACCAGGCTTCATTCCCC (4521) | 0.86 | 5685 |
| | pta-miR166b | TCGGACCAGGCTTCATTCCCC (4522) | 0.86 | 5686 |
| | pta-miR166c | CCGGACCAGGCTTCATCCCAG (4523) | 0.76 | 5687 |
| | ptc-miR166a | TCGGACCAGGCTTCATTCCCC (4524) | 0.86 | 5688 |
| | ptc-miR166b | TCGGACCAGGCTTCATTCCCC (4525) | 0.86 | 5689 |
| | ptc-miR166c | TCGGACCAGGCTTCATTCCCC (4526) | 0.86 | 5690 |
| | ptc-miR166d | TCGGACCAGGCTTCATTCCCC (4527) | 0.86 | 5691 |
| | ptc-miR166e | TCGGACCAGGCTTCATTCCCC (4528) | 0.86 | 5692 |
| | ptc-miR166f | TCGGACCAGGCTTCATTCCCC (4529) | 0.86 | 5693 |
| | ptc-miR166g | TCGGACCAGGCTTCATTCCCC (4530) | 0.86 | 5694 |
| | ptc-miR166h | TCGGACCAGGCTTCATTCCCC (4531) | 0.86 | 5695 |
| | ptc-miR166i | TCGGACCAGGCTTCATTCCCC (4532) | 0.86 | 5696 |
| | ptc-miR166j | TCGGACCAGGCTTCATTCCCC (4533) | 0.86 | 5697 |
| | ptc-miR166k | TCGGACCAGGCTTCATTCCCC (4534) | 0.86 | 5698 |
| | ptc-miR166l | TCGGACCAGGCTTCATTCCCC (4535) | 0.86 | 5699 |
| | ptc-miR166m | TCGGACCAGGCTTCATTCCCC (4536) | 0.86 | 5700 |
| | ptc-miR166n | TCGGACCAGGCTTCATTCCTT (4537) | 0.95 | 5701 |
| | ptc-miR166o | TCGGACCAGGCTTCATTCCTT (4538) | 0.95 | 5702 |
| | ptc-miR166p | TCGGACCAGGCTCCATTCCTT (4539) | 0.9 | 5703 |
| | ptc-miR166q | TCGGACCAGGCTTCATTCCTT (4540) | 0.95 | 5704 |
| | pvu-miR166 | TCGGACCAGGCTTCATTCCCC (4541) | 0.86 | 5705 |
| | pvu-miR166a | TCGGACCAGGCTTCATTCCCC (4542) | 0.86 | 5706 |
| | rco-miR166a | TCGGACCAGGCTTCATTCCCC (4543) | 0.86 | 5707 |
| | rco-miR166b | TCGGACCAGGCTTCATTCCCC (4544) | 0.86 | 5708 |
| | rco-miR166c | TCGGACCAGGCTTCATTCCCC (4545) | 0.86 | 5709 |
| | rco-miR166d | TCGGACCAGGCTTCATTCCCC (4546) | 0.86 | 5710 |
| | rco-miR166e | TCGGACCAGGCTTCATTCCCC (4547) | 0.86 | 5711 |
| | sbi-miR166a | TCGGACCAGGCTTCATTCCC (4548) | 0.86 | 5712 |
| | sbi-miR166b | TCGGACCAGGCTTCATTCCC (4549) | 0.86 | 5713 |
| | sbi-miR166c | TCGGACCAGGCTTCATTCCC (4550) | 0.86 | 5714 |
| | sbi-miR166d | TCGGACCAGGCTTCATTCCC (4551) | 0.86 | 5715 |
| | sbi-miR166e | TCGGACCAGGCTTCAATCCCT (4552) | 0.86 | 5716 |
| | sbi-miR166f | TCGGACCAGGCTTCATTCCTC (4553) | 0.9 | 5717 |
| | sbi-miR166g | TCGGACCAGGCTTCAATCCCT (4554) | 0.86 | 5718 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | sbi-miR166h | TCGGACCAGGCTTCATTCCC (4555) | 0.86 | 5719 |
| | sbi-miR166i | TCGGACCAGGCTTCATTCCC (4556) | 0.86 | 5720 |
| | sbi-miR166j | TCGGACCAGGCTTCATTCCC (4557) | 0.86 | 5721 |
| | sbi-miR166k | TCGGACCAGGCTTCATTCCT (4558) | 0.9 | 5722 |
| | sly-miR166a | TCGGACCAGGCTTCATTCCCC (4559) | 0.86 | 5723 |
| | sly-miR166b | TCGGACCAGGCTTCATTCCCC (4560) | 0.86 | 5724 |
| | smo-miR166a | TCGGACCAGGCTTCATTCCCC (4561) | 0.86 | 5725 |
| | smo-miR166b | TCGGACCAGGCTTCATTCCCC (4562) | 0.86 | 5726 |
| | smo-miR166c | TCGGACCAGGCTTCATTCCCC (4563) | 0.86 | 5727 |
| | sof-miR166 | TCGGACCAGGCTTCATTCCCC (4564) | 0.86 | 5728 |
| | tae-miR166 | CCGGACCAGGCTTCATTCCCA (4565) | 0.81 | 5729 |
| | tcc-miR166a | TCGGACCAGGCTTCATTCCCC (4566) | 0.86 | 5730 |
| | tcc-miR166b | TCGGACCAGGCTTCATTCCC (4567) | 0.86 | 5731 |
| | tcc-miR166c | TCGGACCAGGCTTCATTCCTC (4568) | 0.9 | 5732 |
| | tcc-miR166d | TCGGACCAGGCTTCATTCCCC (4569) | 0.86 | 5733 |
| | vvi-miR166a | TCGGACCAGGCTTCATTCC (4570) | 0.86 | 5734 |
| | vvi-miR166b | TCGGACCAGGCTTCATTCC (4571) | 0.86 | 5735 |
| | vvi-miR166c | TCGGACCAGGCTTCATTCCCC (4572) | 0.86 | 5736 |
| | vvi-miR166d | TCGGACCAGGCTTCATTCCCC (4573) | 0.86 | 5737 |
| | vvi-miR166e | TCGGACCAGGCTTCATTCCCC (4574) | 0.86 | 5738 |
| | vvi-miR166f | TCGGACCAGGCTTCATTCCCC (4575) | 0.86 | 5739 |
| | vvi-miR166g | TCGGACCAGGCTTCATTCCCC (4576) | 0.86 | 5740 |
| | vvi-miR166h | TCGGACCAGGCTTCATTCCCC (4577) | 0.86 | 5741 |
| | zma-miR166a | TCGGACCAGGCTTCATTCCCC (4578) | 0.86 | 5742 |
| | zma-miR166b | TCGGACCAGGCTTCATTCCC (4579) | 0.86 | 5743 |
| | zma-miR166c | TCGGACCAGGCTTCATTCCC (4580) | 0.86 | 5744 |
| | zma-miR166d | TCGGACCAGGCTTCATTCCC (4581) | 0.86 | 5745 |
| | zma-miR166e | TCGGACCAGGCTTCATTCCC (4582) | 0.86 | 5746 |
| | zma-miR166f | TCGGACCAGGCTTCATTCCC (4583) | 0.86 | 5747 |
| | zma-miR166g | TCGGACCAGGCTTCATTCCC (4584) | 0.86 | 5748 |
| | zma-miR166h | TCGGACCAGGCTTCATTCCC (4585) | 0.86 | 5749 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR166i | TCGGACCAGGCTTCATTCCCC (4586) | 0.86 | 5750 |
| | zma-miR166j | TCGGACCAGGCTTCAATCCCT (4587) | 0.86 | 5751 |
| | zma-miR166k | TCGGACCAGGCTTCAATCCCT (4588) | 0.86 | 5752 |
| | zma-miR166l | TCGGACCAGGCTTCATTCCTC (4589) | 0.9 | 5753 |
| | zma-miR166m | TCGGACCAGGCTTCATTCCTC (4590) | 0.9 | 5754 |
| | zma-miR166n | TCGGACCAGGCTTCAATCCCT (4591) | 0.86 | 5755 |
| | zma-miR166o | TCGGACCAGGCTTCATTCCCC (4592) | 0.86 | 5756 |
| | zma-miR166p | TCGGACCAGGCTTCATTCCCC (4593) | 0.86 | 5757 |
| | zma-miR166q | TCGGACCAGGCTTCATTCCCC (4594) | 0.86 | 5758 |
| | zma-miR166r | TCGGACCAGGCTTCATTCCCC (4595) | 0.86 | 5759 |
| | zma-miR166s | TCGGACCAGGCTTCATTCCCC (4596) | 0.86 | 5760 |
| | zma-miR166t | TCGGACCAGGCTTCATTCCCC (4597) | 0.86 | 5761 |
| | zma-miR166u | TCGGACCACGCTTCATTCCCC (4598) | 0.81 | 5762 |
| pta-miR166c | aly-miR166a | TCGGACCAGGCTTCATTCCCC (4599) | 0.81 | 5763 |
| | aly-miR166b | TCGGACCAGGCTTCATTCCCC (4600) | 0.81 | 5764 |
| | aly-miR166c | TCGGACCAGGCTTCATTCCCC (4601) | 0.81 | 5765 |
| | aly-miR166d | TCGGACCAGGCTTCATTCCCC (4602) | 0.81 | 5766 |
| | aly-miR166e | TCGGACCAGGCTTCATTCCCC (4603) | 0.81 | 5767 |
| | aly-miR166f | TCGGACCAGGCTTCATTCCCC (4604) | 0.81 | 5768 |
| | aly-miR166g | TCGGACCAGGCTTCATTCCCC (4605) | 0.81 | 5769 |
| | aqc-miR166a | TCGGACCAGGCTTCATTCCTC (4606) | 0.81 | 5770 |
| | aqc-miR166b | TCGGACCAGGCTTCATTCCCC (4607) | 0.81 | 5771 |
| | aqc-miR166c | TCGGACCAGGCTTCATTCCT (4608) | 0.81 | 5772 |
| | aqc-miR166d | TCGGACCAGGCTTCATTCCTC (4609) | 0.81 | 5773 |
| | aqc-miR166e | TCGGACCAGGCTTCATTCCCC (4610) | 0.81 | 5774 |
| | ath-miR166a | TCGGACCAGGCTTCATTCCCC (4611) | 0.81 | 5775 |
| | ath-miR166b | TCGGACCAGGCTTCATTCCCC (4612) | 0.81 | 5776 |
| | ath-miR166c | TCGGACCAGGCTTCATTCCCC (4613) | 0.81 | 5777 |
| | ath-miR166d | TCGGACCAGGCTTCATTCCCC (4614) | 0.81 | 5778 |
| | ath-miR166e | TCGGACCAGGCTTCATTCCCC (4615) | 0.81 | 5779 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ath-miR166f | TCGGACCAGGCTTCATTCCCC (4616) | 0.81 | 5780 |
| | ath-miR166g | TCGGACCAGGCTTCATTCCCC (4617) | 0.81 | 5781 |
| | bdi-miR166 | TCGGACCAGGCTTCATTCCCC (4618) | 0.81 | 5782 |
| | bdi-miR166a | TCGGACCAGGCTTCATTCCCC (4619) | 0.81 | 5783 |
| | bdi-miR166b | TCGGACCAGGCTTCATTCCCC (4620) | 0.81 | 5784 |
| | bdi-miR166c | TCGGACCAGGCTTCATTCCCC (4621) | 0.81 | 5785 |
| | bdi-miR166d | TCGGACCAGGCTTCATTCCCC (4622) | 0.81 | 5786 |
| | bdi-miR166e | CTCGGACCAGGCTTCATTCCC (4623) | 0.81 | 5787 |
| | bdi-miR166f | TCTCGGACCAGGCTTCATTCC (4624) | 0.81 | 5788 |
| | bna-miR166a | TCGGACCAGGCTTCATTCCCC (4625) | 0.81 | 5789 |
| | bna-miR166b | TCGGACCAGGCTTCATTCCCC (4626) | 0.81 | 5790 |
| | bna-miR166c | TCGGACCAGGCTTCATTCCCC (4627) | 0.81 | 5791 |
| | bna-miR166d | TCGGACCAGGCTTCATTCCCC (4628) | 0.81 | 5792 |
| | cpt-miR166 | TCGGACCAGGCTTCATTCCC (4629) | 0.81 | 5793 |
| | crt-miR166a | TCGGACCAGGCTTCATTCCCGT (4630) | 0.86 | 5794 |
| | crt-miR166b | TCGGACCAGGCTTCATTCCCTT (4631) | 0.81 | 5795 |
| | csi-miR166 | TCGGACCAGGCTTCATTCCCC (4632) | 0.81 | 5796 |
| | csi-miR166a | TCGGACCAGGCTTCATTCCCCC (4633) | 0.81 | 5797 |
| | csi-miR166b | TCGGACCAGGCTTCATTCCCGT (4634) | 0.86 | 5798 |
| | csi-miR166c | TCGGACCAGGCTTCATTCCC (4635) | 0.81 | 5799 |
| | csi-miR166d | TCGGACCAGGCTTCATTCCCT (4636) | 0.81 | 5800 |
| | csi-miR166e | TCGGACCAGGCTTCATTCCCC (4637) | 0.81 | 5801 |
| | ctr-miR166 | TCGGACCAGGCTTCATTCCCCC (4638) | 0.81 | 5802 |
| | far-miR166 | CCGGACCAGGCTTCATCCCAG (4639) | 1 | 5803 |
| | flm-miR166 | TCGGACCAGGCTTCATCCCCC (4640) | 0.86 | 5804 |
| | ghr-miR166a | TCGGACCAGGCTTCATTCCCC (4641) | 0.81 | 5805 |
| | ghr-miR166b | TCGGACCAGGCTTCATTCCCC (4642) | 0.81 | 5806 |
| | gma-miR166a | TCGGACCAGGCTTCATTCCCC (4643) | 0.81 | 5807 |
| | gma-miR166b | TCGGACCAGGCTTCATTCCCC (4644) | 0.81 | 5808 |
| | gma-miR166n | TCGGACCAGGCTTCATTCCCC (4645) | 0.81 | 5809 |
| | gma-miR166o | TCGGACCAGGCTTCATTCCCC (4646) | 0.81 | 5810 |
| | gma-miR166q | TCGGACCAGGCTTCATTCCCG (4647) | 0.86 | 5811 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | gma-miR166r | TCGGACCAGGCTTCATTCCCT (4648) | 0.81 | 5812 |
| | hvu-miR166 | TCGGACCAGGCTTCATTCCCC (4649) | 0.81 | 5813 |
| | hvu-miR166b | TCGGACCAGGCTTCATTCCCC (4650) | 0.81 | 5814 |
| | hvu-miR166c | TCGGACCAGGCTTCATTCCCC (4651) | 0.81 | 5815 |
| | hvv-miR166 | TCGGACCAGGCTTCATTCCCC (4652) | 0.81 | 5816 |
| | ini-miR166 | TCGGACCAGGCTTCATTCCTC (4653) | 0.81 | 5817 |
| | mtr-miR166 | TCGGACCAGGCTTCATTCCCC (4654) | 0.81 | 5818 |
| | mtr-miR166b | TCGGACCAGGCTTCATTCCTA (4655) | 0.81 | 5819 |
| | mtr-miR166c | TCGGACCAGGCTTCATTCCTC (4656) | 0.81 | 5820 |
| | mtr-miR166d | TCGGGCCAGGCTTCATCCCCC (4657) | 0.81 | 5821 |
| | mtr-miR166e | TCGGACCAGGCTTCATTCCCC (4658) | 0.81 | 5822 |
| | mtr-miR166f | TCGGACCAGGCTTCATTCCTC (4659) | 0.81 | 5823 |
| | mtr-miR166g | TCGGACCAGGCTTCATTCCCC (4660) | 0.81 | 5824 |
| | mtr-miR166h | TCGGACCAGGCTTCATTCCCC (4661) | 0.81 | 5825 |
| | nsy-miR166 | TCGGACCAGGCTTCATTCCCC (4662) | 0.81 | 5826 |
| | osa-miR166a | TCGGACCAGGCTTCATTCCCC (4663) | 0.81 | 5827 |
| | osa-miR166b | TCGGACCAGGCTTCATTCCCC (4664) | 0.81 | 5828 |
| | osa-miR166c | TCGGACCAGGCTTCATTCCCC (4665) | 0.81 | 5829 |
| | osa-miR166d | TCGGACCAGGCTTCATTCCCC (4666) | 0.81 | 5830 |
| | osa-miR166e | TCGAACCAGGCTTCATTCCCC (4667) | 0.76 | 5831 |
| | osa-miR166f | TCGGACCAGGCTTCATTCCCC (4668) | 0.81 | 5832 |
| | osa-miR166g | TCGGACCAGGCTTCATTCCTC (4669) | 0.81 | 5833 |
| | osa-miR166h | TCGGACCAGGCTTCATTCCTC (4670) | 0.81 | 5834 |
| | osa-miR166i | TCGGATCAGGCTTCATTCCTC (4671) | 0.76 | 5835 |
| | osa-miR166j | TCGGATCAGGCTTCATTCCTC (4672) | 0.76 | 5836 |
| | osa-miR166k | TCGGACCAGGCTTCAATCCCT (4673) | 0.76 | 5837 |
| | osa-miR166l | TCGGACCAGGCTTCAATCCCT (4674) | 0.76 | 5838 |
| | osa-miR166m | TCGGACCAGGCTTCATTCCCT (4675) | 0.81 | 5839 |
| | osa-miR166n | TCGGACCAGGCTTCATTCCCC (4676) | 0.81 | 5840 |
| | pab-miR166a | TCGGACCAGGCTTCATTCCTC (4677) | 0.81 | 5841 |
| | pab-miR166b | TCGGACCAGGCTTCATTCCTT (4678) | 0.81 | 5842 |
| | pga-miR166 | TCGGACCAGGCTTCATTCCTT (4679) | 0.81 | 5843 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ppt-miR166a | TCGGACCAGGCTTCATTCCCC (4680) | 0.81 | 5844 |
| | ppt-miR166b | TCGGACCAGGCTTCATTCCCC (4681) | 0.81 | 5845 |
| | ppt-miR166c | TCGGACCAGGCTTCATTCCCC (4682) | 0.81 | 5846 |
| | ppt-miR166d | TCGGACCAGGCTTCATTCCCC (4683) | 0.81 | 5847 |
| | ppt-miR166e | TCGGACCAGGCTTCATTCCCC (4684) | 0.81 | 5848 |
| | ppt-miR166f | TCGGACCAGGCTTCATTCCCC (4685) | 0.81 | 5849 |
| | ppt-miR166g | TCGGACCAGGCTTCATTCCCC (4686) | 0.81 | 5850 |
| | ppt-miR166h | TCGGACCAGGCTTCATTCCCC (4687) | 0.81 | 5851 |
| | ppt-miR166i | TCGGACCAGGCTTCATTCCCC (4688) | 0.81 | 5852 |
| | ppt-miR166j | TCCGGACCAGGCTTCATTCCC (4689) | 0.86 | 5853 |
| | ppt-miR166k | TCCGGACCAGGCTTCATTCCC (4690) | 0.86 | 5854 |
| | ppt-miR166l | TCCGGACCAGGCTTCATTCCC (4691) | 0.86 | 5855 |
| | ppt-miR166m | TCGGACCAGGCATCATTCCTT (4692) | 0.76 | 5856 |
| | pta-miR166a | TCGGACCAGGCTTCATTCCCC (4693) | 0.81 | 5857 |
| | pta-miR166b | TCGGACCAGGCTTCATTCCCC (4694) | 0.81 | 5858 |
| | ptc-miR166a | TCGGACCAGGCTTCATTCCCC (4695) | 0.81 | 5859 |
| | ptc-miR166b | TCGGACCAGGCTTCATTCCCC (4696) | 0.81 | 5860 |
| | ptc-miR166c | TCGGACCAGGCTTCATTCCCC (4697) | 0.81 | 5861 |
| | ptc-miR166d | TCGGACCAGGCTTCATTCCCC (4698) | 0.81 | 5862 |
| | ptc-miR166e | TCGGACCAGGCTTCATTCCCC (4699) | 0.81 | 5863 |
| | ptc-miR166f | TCGGACCAGGCTTCATTCCCC (4700) | 0.81 | 5864 |
| | ptc-miR166g | TCGGACCAGGCTTCATTCCCC (4701) | 0.81 | 5865 |
| | ptc-miR166h | TCGGACCAGGCTTCATTCCCC (4702) | 0.81 | 5866 |
| | ptc-miR166i | TCGGACCAGGCTTCATTCCCC (4703) | 0.81 | 5867 |
| | ptc-miR166j | TCGGACCAGGCTTCATTCCCC (4704) | 0.81 | 5868 |
| | ptc-miR166k | TCGGACCAGGCTTCATTCCCC (4705) | 0.81 | 5869 |
| | ptc-miR166l | TCGGACCAGGCTTCATTCCCC (4706) | 0.81 | 5870 |
| | ptc-miR166m | TCGGACCAGGCTTCATTCCCC (4707) | 0.81 | 5871 |
| | ptc-miR166n | TCGGACCAGGCTTCATTCCTT (4708) | 0.81 | 5872 |
| | ptc-miR166o | TCGGACCAGGCTTCATTCCTT (4709) | 0.81 | 5873 |
| | ptc-miR166p | TCGGACCAGGCTCCATTCCTT (4710) | 0.76 | 5874 |
| | ptc-miR166q | TCGGACCAGGCTTCATTCCTT (4711) | 0.81 | 5875 |
| | pvu-miR166 | TCGGACCAGGCTTCATTCCCC (4712) | 0.81 | 5876 |
| | pvu-miR166a | TCGGACCAGGCTTCATTCCCC (4713) | 0.81 | 5877 |
| | rco-miR166a | TCGGACCAGGCTTCATTCCCC (4714) | 0.81 | 5878 |
| | rco-miR166b | TCGGACCAGGCTTCATTCCCC (4715) | 0.81 | 5879 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | rco-miR166c | TCGGACCAGGCTTCATTCCCC (4716) | 0.81 | 5880 |
| | rco-miR166d | TCGGACCAGGCTTCATTCCCC (4717) | 0.81 | 5881 |
| | rco-miR166e | TCGGACCAGGCTTCATTCCCC (4718) | 0.81 | 5882 |
| | sbi-miR166a | TCGGACCAGGCTTCATTCCC (4719) | 0.81 | 5883 |
| | sbi-miR166b | TCGGACCAGGCTTCATTCCC (4720) | 0.81 | 5884 |
| | sbi-miR166c | TCGGACCAGGCTTCATTCCC (4721) | 0.81 | 5885 |
| | sbi-miR166d | TCGGACCAGGCTTCATTCCC (4722) | 0.81 | 5886 |
| | sbi-miR166e | TCGGACCAGGCTTCAATCCCT (4723) | 0.76 | 5887 |
| | sbi-miR166f | TCGGACCAGGCTTCATTCCTC (4724) | 0.81 | 5888 |
| | sbi-miR166g | TCGGACCAGGCTTCAATCCCT (4725) | 0.76 | 5889 |
| | sbi-miR166h | TCGGACCAGGCTTCATTCCC (4726) | 0.81 | 5890 |
| | sbi-miR166i | TCGGACCAGGCTTCATTCCC (4727) | 0.81 | 5891 |
| | sbi-miR166j | TCGGACCAGGCTTCATTCCC (4728) | 0.81 | 5892 |
| | sbi-miR166k | TCGGACCAGGCTTCATTCCT (4729) | 0.81 | 5893 |
| | sly-miR166a | TCGGACCAGGCTTCATTCCCC (4730) | 0.81 | 5894 |
| | sly-miR166b | TCGGACCAGGCTTCATTCCCC (4731) | 0.81 | 5895 |
| | smo-miR166a | TCGGACCAGGCTTCATTCCCC (4732) | 0.81 | 5896 |
| | smo-miR166b | TCGGACCAGGCTTCATTCCCC (4733) | 0.81 | 5897 |
| | smo-miR166c | TCGGACCAGGCTTCATTCCCC (4734) | 0.81 | 5898 |
| | sof-miR166 | TCGGACCAGGCTTCATTCCCC (4735) | 0.81 | 5899 |
| | tae-miR166 | CCGGACCAGGCTTCATTCCCA (4736) | 0.86 | 5900 |
| | tcc-miR166a | TCGGACCAGGCTTCATTCCCC (4737) | 0.81 | 5901 |
| | tcc-miR166b | TCGGACCAGGCTTCATTCCC (4738) | 0.81 | 5902 |
| | tcc-miR166c | TCGGACCAGGCTTCATTCCTC (4739) | 0.81 | 5903 |
| | tcc-miR166d | TCGGACCAGGCTTCATTCCCC (4740) | 0.81 | 5904 |
| | vvi-miR166a | TCGGACCAGGCTTCATTCC (4741) | 0.81 | 5905 |
| | vvi-miR166b | TCGGACCAGGCTTCATTCC (4742) | 0.81 | 5906 |
| | vvi-miR166c | TCGGACCAGGCTTCATTCCCC (4743) | 0.81 | 5907 |
| | vvi-miR166d | TCGGACCAGGCTTCATTCCCC (4744) | 0.81 | 5908 |
| | vvi-miR166e | TCGGACCAGGCTTCATTCCCC (4745) | 0.81 | 5909 |
| | vvi-miR166f | TCGGACCAGGCTTCATTCCCC (4746) | 0.81 | 5910 |
| | vvi-miR166g | TCGGACCAGGCTTCATTCCCC (4747) | 0.81 | 5911 |
| | vvi-miR166h | TCGGACCAGGCTTCATTCCCC (4748) | 0.81 | 5912 |
| | zma-miR166a | TCGGACCAGGCTTCATTCCCC (4749) | 0.81 | 5913 |
| | zma-miR166b | TCGGACCAGGCTTCATTCCC (4750) | 0.81 | 5914 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR166c | TCGGACCAGGCTTCATTCCC (4751) | 0.81 | 5915 |
| | zma-miR166d | TCGGACCAGGCTTCATTCCC (4752) | 0.81 | 5916 |
| | zma-miR166e | TCGGACCAGGCTTCATTCCC (4753) | 0.81 | 5917 |
| | zma-miR166f | TCGGACCAGGCTTCATTCCC (4754) | 0.81 | 5918 |
| | zma-miR166g | TCGGACCAGGCTTCATTCCC (4755) | 0.81 | 5919 |
| | zma-miR166h | TCGGACCAGGCTTCATTCCC (4756) | 0.81 | 5920 |
| | zma-miR166i | TCGGACCAGGCTTCATTCCC (4757) | 0.81 | 5921 |
| | zma-miR166j | TCGGACCAGGCTTCAATCCCT (4758) | 0.76 | 5922 |
| | zma-miR166k | TCGGACCAGGCTTCAATCCCT (4759) | 0.76 | 5923 |
| | zma-miR166l | TCGGACCAGGCTTCATTCCTC (4760) | 0.81 | 5924 |
| | zma-miR166m | TCGGACCAGGCTTCATTCCTC (4761) | 0.81 | 5925 |
| | zma-miR166n | TCGGACCAGGCTTCAATCCCT (4762) | 0.76 | 5926 |
| | zma-miR166o | TCGGACCAGGCTTCATTCCCC (4763) | 0.81 | 5927 |
| | zma-miR166p | TCGGACCAGGCTTCATTCCCC (4764) | 0.81 | 5928 |
| | zma-miR166q | TCGGACCAGGCTTCATTCCCC (4765) | 0.81 | 5929 |
| | zma-miR166r | TCGGACCAGGCTTCATTCCCC (4766) | 0.81 | 5930 |
| | zma-miR166s | TCGGACCAGGCTTCATTCCCC (4767) | 0.81 | 5931 |
| | zma-miR166t | TCGGACCAGGCTTCATTCCCC (4768) | 0.81 | 5932 |
| | zma-miR166u | TCGGACCACGCTTCATTCCCC (4769) | 0.76 | 5933 |
| ptc-miR166p | aly-miR166a | TCGGACCAGGCTTCATTCCCC (4770) | 0.86 | 5934 |
| | aly-miR166b | TCGGACCAGGCTTCATTCCCC (4771) | 0.86 | 5935 |
| | aly-miR166c | TCGGACCAGGCTTCATTCCCC (4772) | 0.86 | 5936 |
| | aly-miR166d | TCGGACCAGGCTTCATTCCCC (4773) | 0.86 | 5937 |
| | aly-miR166e | TCGGACCAGGCTTCATTCCCC (4774) | 0.86 | 5938 |
| | aly-miR166f | TCGGACCAGGCTTCATTCCCC (4775) | 0.86 | 5939 |
| | aly-miR166g | TCGGACCAGGCTTCATTCCCC (4776) | 0.86 | 5940 |
| | aqc-miR166a | TCGGACCAGGCTTCATTCCTC (4777) | 0.9 | 5941 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | aqc-miR166b | TCGGACCAGGCTTCATTCCCC (4778) | 0.86 | 5942 |
| | aqc-miR166c | TCGGACCAGGCTTCATTCCT (4779) | 0.9 | 5943 |
| | aqc-miR166d | TCGGACCAGGCTTCATTCCTC (4780) | 0.9 | 5944 |
| | aqc-miR166e | TCGGACCAGGCTTCATTCCCC (4781) | 0.86 | 5945 |
| | ath-miR166a | TCGGACCAGGCTTCATTCCCC (4782) | 0.86 | 5946 |
| | ath-miR166b | TCGGACCAGGCTTCATTCCCC (4783) | 0.86 | 5947 |
| | ath-miR166c | TCGGACCAGGCTTCATTCCCC (4784) | 0.86 | 5948 |
| | ath-miR166d | TCGGACCAGGCTTCATTCCCC (4785) | 0.86 | 5949 |
| | ath-miR166e | TCGGACCAGGCTTCATTCCCC (4786) | 0.86 | 5950 |
| | ath-miR166f | TCGGACCAGGCTTCATTCCCC (4787) | 0.86 | 5951 |
| | ath-miR166g | TCGGACCAGGCTTCATTCCCC (4788) | 0.86 | 5952 |
| | bdi-miR166 | TCGGACCAGGCTTCATTCCCC (4789) | 0.86 | 5953 |
| | bdi-miR166a | TCGGACCAGGCTTCATTCCCC (4790) | 0.86 | 5954 |
| | bdi-miR166b | TCGGACCAGGCTTCATTCCCC (4791) | 0.86 | 5955 |
| | bdi-miR166c | TCGGACCAGGCTTCATTCCCC (4792) | 0.86 | 5956 |
| | bdi-miR166d | TCGGACCAGGCTTCATTCCCC (4793) | 0.86 | 5957 |
| | bdi-miR166e | CTCGGACCAGGCTTCATTCCC (4794) | 0.86 | 5958 |
| | bdi-miR166f | TCTCGGACCAGGCTTCATTCC (4795) | 0.86 | 5959 |
| | bna-miR166a | TCGGACCAGGCTTCATTCCCC (4796) | 0.86 | 5960 |
| | bna-miR166b | TCGGACCAGGCTTCATTCCCC (4797) | 0.86 | 5961 |
| | bna-miR166c | TCGGACCAGGCTTCATTCCCC (4798) | 0.86 | 5962 |
| | bna-miR166d | TCGGACCAGGCTTCATTCCCC (4799) | 0.86 | 5963 |
| | cpt-miR166 | TCGGACCAGGCTTCATTCCC (4800) | 0.86 | 5964 |
| | crt-miR166a | TCGGACCAGGCTTCATTCCCGT (4801) | 0.86 | 5965 |
| | crt-miR166b | TCGGACCAGGCTTCATTCCCTT (4802) | 0.9 | 5966 |
| | csi-miR166 | TCGGACCAGGCTTCATTCCCC (4803) | 0.86 | 5967 |
| | csi-miR166a | TCGGACCAGGCTTCATTCCCCC (4804) | 0.86 | 5968 |
| | csi-miR166b | TCGGACCAGGCTTCATTCCCGT (4805) | 0.86 | 5969 |
| | csi-miR166c | TCGGACCAGGCTTCATTCCC (4806) | 0.86 | 5970 |
| | csi-miR166d | TCGGACCAGGCTTCATTCCCT (4807) | 0.9 | 5971 |
| | csi-miR166e | TCGGACCAGGCTTCATTCCCC (4808) | 0.86 | 5972 |
| | ctr-miR166 | TCGGACCAGGCTTCATTCCCCC (4809) | 0.86 | 5973 |
| | far-miR166 | CCGGACCAGGCTTCATCCCAG (4810) | 0.76 | 5974 |
| | flm-miR166 | TCGGACCAGGCTTCATCCCCC (4811) | 0.81 | 5975 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ghr-miR166a | TCGGACCAGGCTTCATTCCCC (4812) | 0.86 | 5976 |
| | ghr-miR166b | TCGGACCAGGCTTCATTCCCC (4813) | 0.86 | 5977 |
| | gma-miR166a | TCGGACCAGGCTTCATTCCCC (4814) | 0.86 | 5978 |
| | gma-miR166b | TCGGACCAGGCTTCATTCCCC (4815) | 0.86 | 5979 |
| | gma-miR166n | TCGGACCAGGCTTCATTCCCC (4816) | 0.86 | 5980 |
| | gma-miR166o | TCGGACCAGGCTTCATTCCCC (4817) | 0.86 | 5981 |
| | gma-miR166q | TCGGACCAGGCTTCATTCCCG (4818) | 0.86 | 5982 |
| | gma-miR166r | TCGGACCAGGCTTCATTCCCT (4819) | 0.9 | 5983 |
| | hvu-miR166 | TCGGACCAGGCTTCATTCCCC (4820) | 0.86 | 5984 |
| | hvu-miR166b | TCGGACCAGGCTTCATTCCCC (4821) | 0.86 | 5985 |
| | hvu-miR166c | TCGGACCAGGCTTCATTCCCC (4822) | 0.86 | 5986 |
| | hvv-miR166 | TCGGACCAGGCTTCATTCCCC (4823) | 0.86 | 5987 |
| | ini-miR166 | TCGGACCAGGCTTCATTCCTC (4824) | 0.9 | 5988 |
| | mtr-miR166 | TCGGACCAGGCTTCATTCCCC (4825) | 0.86 | 5989 |
| | mtr-miR166b | TCGGACCAGGCTTCATTCCTA (4826) (TCGGACCAGGCTTCATTCCCC (5116) | 0.9 | 5990 |
| | mtr-miR166c | TCGGACCAGGCTTCATTCCTC (4827) | 0.9 | 5991 |
| | mtr-miR166d | TCGGGCCAGGCTTCATCCCCC (4828) | 0.76 | 5992 |
| | mtr-miR166e | TCGGACCAGGCTTCATTCCCC (4829) | 0.86 | 5993 |
| | mtr-miR166f | TCGGACCAGGCTTCATTCCTC (4830) | 0.9 | 5994 |
| | mtr-miR166g | TCGGACCAGGCTTCATTCCCC (4831) | 0.86 | 5995 |
| | mtr-miR166h | TCGGACCAGGCTTCATTCCCC (4832) | 0.86 | 5996 |
| | nsy-miR166 | TCGGACCAGGCTTCATTCCCC (4833) | 0.86 | 5997 |
| | osa-miR166a | TCGGACCAGGCTTCATTCCCC (4834) | 0.86 | 5998 |
| | osa-miR166b | TCGGACCAGGCTTCATTCCCC (4835) | 0.86 | 5999 |
| | osa-miR166c | TCGGACCAGGCTTCATTCCCC (4836) | 0.86 | 6000 |
| | osa-miR166d | TCGGACCAGGCTTCATTCCCC (4837) | 0.86 | 6001 |
| | osa-miR166e | TCGAACCAGGCTTCATTCCCC (4838) | 0.81 | 6002 |
| | osa-miR166f | TCGGACCAGGCTTCATTCCCC (4839) | 0.86 | 6003 |
| | osa-miR166g | TCGGACCAGGCTTCATTCCTC (4840) | 0.9 | 6004 |
| | osa-miR166h | TCGGACCAGGCTTCATTCCTC (4841) | 0.9 | 6005 |
| | osa-miR166i | TCGGATCAGGCTTCATTCCTC (4842) | 0.86 | 6006 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
| --- | --- | --- | --- | --- |
| | osa-miR166j | TCGGATCAGGCTTCATTCCTC (4843) | 0.86 | 6007 |
| | osa-miR166k | TCGGACCAGGCTTCAATCCCT (4844) | 0.86 | 6008 |
| | osa-miR166l | TCGGACCAGGCTTCAATCCCT (4845) | 0.86 | 6009 |
| | osa-miR166m | TCGGACCAGGCTTCATTCCCT (4846) | 0.9 | 6010 |
| | osa-miR166n | TCGGACCAGGCTTCATTCCCC (4847) | 0.86 | 6011 |
| | pab-miR166a | TCGGACCAGGCTTCATTCCTC (4848) | 0.9 | 6012 |
| | pab-miR166b | TCGGACCAGGCTTCATTCCTT (4849) | 0.95 | 6013 |
| | pga-miR166 | TCGGACCAGGCTTCATTCCTT (4850) | 0.95 | 6014 |
| | ppt-miR166a | TCGGACCAGGCTTCATTCCCC (4851) | 0.86 | 6015 |
| | ppt-miR166b | TCGGACCAGGCTTCATTCCCC (4852) | 0.86 | 6016 |
| | ppt-miR166c | TCGGACCAGGCTTCATTCCCC (4853) | 0.86 | 6017 |
| | ppt-miR166d | TCGGACCAGGCTTCATTCCCC (4854) | 0.86 | 6018 |
| | ppt-miR166e | TCGGACCAGGCTTCATTCCCC (4855) | 0.86 | 6019 |
| | ppt-miR166f | TCGGACCAGGCTTCATTCCCC (4856) | 0.86 | 6020 |
| | ppt-miR166g | TCGGACCAGGCTTCATTCCCC (4857) | 0.86 | 6021 |
| | ppt-miR166h | TCGGACCAGGCTTCATTCCCC (4858) | 0.86 | 6022 |
| | ppt-miR166i | TCGGACCAGGCTTCATTCCCC (4859) | 0.86 | 6023 |
| | ppt-miR166j | TCCGGACCAGGCTTCATTCCC (4860) | 0.81 | 6024 |
| | ppt-miR166k | TCCGGACCAGGCTTCATTCCC (4861) | 0.81 | 6025 |
| | ppt-miR166l | TCCGGACCAGGCTTCATTCCC (4862) | 0.81 | 6026 |
| | ppt-miR166m | TCGGACCAGGCATCATTCCTT (4863) | 0.9 | 6027 |
| | pta-miR166a | TCGGACCAGGCTTCATTCCCC (4864) | 0.86 | 6028 |
| | pta-miR166b | TCGGACCAGGCTTCATTCCCC (4865) | 0.86 | 6029 |
| | pta-miR166c | CCGGACCAGGCTTCATCCCAG (4866) | 0.76 | 6030 |
| | ptc-miR166a | TCGGACCAGGCTTCATTCCCC (4867) | 0.86 | 6031 |
| | ptc-miR166b | TCGGACCAGGCTTCATTCCCC (4868) | 0.86 | 6032 |
| | ptc-miR166c | TCGGACCAGGCTTCATTCCCC (4869) | 0.86 | 6033 |
| | ptc-miR166d | TCGGACCAGGCTTCATTCCCC (4870) | 0.86 | 6034 |
| | ptc-miR166e | TCGGACCAGGCTTCATTCCCC (4871) | 0.86 | 6035 |
| | ptc-miR166f | TCGGACCAGGCTTCATTCCCC (4872) | 0.86 | 6036 |
| | ptc-miR166g | TCGGACCAGGCTTCATTCCCC (4873) | 0.86 | 6037 |
| | ptc-miR166h | TCGGACCAGGCTTCATTCCCC (4874) | 0.86 | 6038 |
| | ptc-miR166i | TCGGACCAGGCTTCATTCCCC (4875) | 0.86 | 6039 |
| | ptc-miR166j | TCGGACCAGGCTTCATTCCCC (4876) | 0.86 | 6040 |
| | ptc-miR166k | TCGGACCAGGCTTCATTCCCC (4877) | 0.86 | 6041 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ptc-miR166l | TCGGACCAGGCTTCATTCCCC (4878) | 0.86 | 6042 |
| | ptc-miR166m | TCGGACCAGGCTTCATTCCCC (4879) | 0.86 | 6043 |
| | ptc-miR166n | TCGGACCAGGCTTCATTCCTT (4880) | 0.95 | 6044 |
| | ptc-miR166o | TCGGACCAGGCTTCATTCCTT (4881) | 0.95 | 6045 |
| | ptc-miR166q | TCGGACCAGGCTTCATTCCTT (4882) | 0.95 | 6046 |
| | pvu-miR166 | TCGGACCAGGCTTCATTCCCC (4883) | 0.86 | 6047 |
| | pvu-miR166a | TCGGACCAGGCTTCATTCCCC (4884) | 0.86 | 6048 |
| | rco-miR166a | TCGGACCAGGCTTCATTCCCC (4885) | 0.86 | 6049 |
| | rco-miR166b | TCGGACCAGGCTTCATTCCCC (4886) | 0.86 | 6050 |
| | rco-miR166c | TCGGACCAGGCTTCATTCCCC (4887) | 0.86 | 6051 |
| | rco-miR166d | TCGGACCAGGCTTCATTCCCC (4888) | 0.86 | 6052 |
| | rco-miR166e | TCGGACCAGGCTTCATTCCCC (4889) | 0.86 | 6053 |
| | sbi-miR166a | TCGGACCAGGCTTCATTCCC (4890) | 0.86 | 6054 |
| | sbi-miR166b | TCGGACCAGGCTTCATTCCC (4891) | 0.86 | 6055 |
| | sbi-miR166c | TCGGACCAGGCTTCATTCCC (4892) | 0.86 | 6056 |
| | sbi-miR166d | TCGGACCAGGCTTCATTCCC (4893) | 0.86 | 6057 |
| | sbi-miR166e | TCGGACCAGGCTTCAATCCCT (4894) | 0.86 | 6058 |
| | sbi-miR166f | TCGGACCAGGCTTCATTCCTC (4895) | 0.9 | 6059 |
| | sbi-miR166g | TCGGACCAGGCTTCAATCCCT (4896) | 0.86 | 6060 |
| | sbi-miR166h | TCGGACCAGGCTTCATTCCC (4897) | 0.86 | 6061 |
| | sbi-miR166i | TCGGACCAGGCTTCATTCCC (4898) | 0.86 | 6062 |
| | sbi-miR166j | TCGGACCAGGCTTCATTCCC (4899) | 0.86 | 6063 |
| | sbi-miR166k | TCGGACCAGGCTTCATTCCT (4900) | 0.9 | 6064 |
| | sly-miR166a | TCGGACCAGGCTTCATTCCCC (4901) | 0.86 | 6065 |
| | sly-miR166b | TCGGACCAGGCTTCATTCCCC (4902) | 0.86 | 6066 |
| | smo-miR166a | TCGGACCAGGCTTCATTCCCC (4903) | 0.86 | 6067 |
| | smo-miR166b | TCGGACCAGGCTTCATTCCCC (4904) | 0.86 | 6068 |
| | smo-miR166c | TCGGACCAGGCTTCATTCCCC (4905) | 0.86 | 6069 |
| | sof-miR166 | TCGGACCAGGCTTCATTCCCC (4906) | 0.86 | 6070 |
| | tae-miR166 | CCGGACCAGGCTTCATTCCCA (4907) | 0.81 | 6071 |
| | tcc-miR166a | TCGGACCAGGCTTCATTCCCC (4908) | 0.86 | 6072 |
| | tcc-miR166b | TCGGACCAGGCTTCATTCCC (4909) | 0.86 | 6073 |
| | tcc-miR166c | TCGGACCAGGCTTCATTCCTC (4910) | 0.9 | 6074 |
| | tcc-miR166d | TCGGACCAGGCTTCATTCCCC (4911) | 0.86 | 6075 |
| | vvi-miR166a | TCGGACCAGGCTTCATTCC (4912) | 0.86 | 6076 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | vvi-miR166b | TCGGACCAGGCTTCATTCC (4913) | 0.86 | 6077 |
| | vvi-miR166c | TCGGACCAGGCTTCATTCCCC (4914) | 0.86 | 6078 |
| | vvi-miR166d | TCGGACCAGGCTTCATTCCCC (4915) | 0.86 | 6079 |
| | vvi-miR166e | TCGGACCAGGCTTCATTCCCC (4916) | 0.86 | 6080 |
| | vvi-miR166f | TCGGACCAGGCTTCATTCCCC (4917) | 0.86 | 6081 |
| | vvi-miR166g | TCGGACCAGGCTTCATTCCCC (4918) | 0.86 | 6082 |
| | vvi-miR166h | TCGGACCAGGCTTCATTCCCC (4919) | 0.86 | 6083 |
| | zma-miR166a | TCGGACCAGGCTTCATTCCCC (4920) | 0.86 | 6084 |
| | zma-miR166b | TCGGACCAGGCTTCATTCCC (4921) | 0.86 | 6085 |
| | zma-miR166c | TCGGACCAGGCTTCATTCCC (4922) | 0.86 | 6086 |
| | zma-miR166d | TCGGACCAGGCTTCATTCCC (4923) | 0.86 | 6087 |
| | zma-miR166e | TCGGACCAGGCTTCATTCCC (4924) | 0.86 | 6088 |
| | zma-miR166f | TCGGACCAGGCTTCATTCCC (4925) | 0.86 | 6089 |
| | zma-miR166g | TCGGACCAGGCTTCATTCCC (4926) | 0.86 | 6090 |
| | zma-miR166h | TCGGACCAGGCTTCATTCCC (4927) | 0.86 | 6091 |
| | zma-miR166i | TCGGACCAGGCTTCATTCCC (4928) | 0.86 | 6092 |
| | zma-miR166j | TCGGACCAGGCTTCAATCCCT (4929) | 0.86 | 6093 |
| | zma-miR166k | TCGGACCAGGCTTCAATCCCT (4930) | 0.86 | 6094 |
| | zma-miR166l | TCGGACCAGGCTTCATTCCTC (4931) | 0.9 | 6095 |
| | zma-miR166m | TCGGACCAGGCTTCATTCCTC (4932) | 0.9 | 6096 |
| | zma-miR166n | TCGGACCAGGCTTCAATCCCT (4933) | 0.86 | 6097 |
| | zma-miR166o | TCGGACCAGGCTTCATTCCCC (4934) | 0.86 | 6098 |
| | zma-miR166p | TCGGACCAGGCTTCATTCCCC (4935) | 0.86 | 6099 |
| | zma-miR166q | TCGGACCAGGCTTCATTCCCC (4936) | 0.86 | 6100 |
| | zma-miR166r | TCGGACCAGGCTTCATTCCCC (4937) | 0.86 | 6101 |
| | zma-miR166s | TCGGACCAGGCTTCATTCCCC (4938) | 0.86 | 6102 |
| | zma-miR166t | TCGGACCAGGCTTCATTCCCC (4939) | 0.86 | 6103 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR166u | TCGGACCACGCTTCATTCCCC (4940) | 0.81 | 6104 |
| vvi-miR394b | ahy-miR394 | TTGGCATTCTGTCCACCTCC (4941) | 1 | 6105 |
| | aly-miR394a | TTGGCATTCTGTCCACCTCC (4942) | 1 | 6106 |
| | aly-miR394b | TTGGCATTCTGTCCACCTCC (4943) | 1 | 6107 |
| | ath-miR394a | TTGGCATTCTGTCCACCTCC (4944) | 1 | 6108 |
| | ath-miR394b | TTGGCATTCTGTCCACCTCC (4945) | 1 | 6109 |
| | bdi-miR394 | TTGGCATTCTGTCCACCTCC (4946) | 1 | 6110 |
| | csi-miR394 | TTGGCATTCTGTCCACCTCC (4947) | 1 | 6111 |
| | ghr-miR394 | TTGGCATTCTGTCCACCTCC (4948) | 1 | 6112 |
| | ghr-miR394a | TTGGCATTCTGTCCACCTCC (4949) | 1 | 6113 |
| | ghr-miR394b | TTGGCATTCTGTCCACCTCC (4950) | 1 | 6114 |
| | gma-miR394b | AGGTGGGCATACTGTCAACT (4951) | 0.65 | 6115 |
| | osa-miR394 | TTGGCATTCTGTCCACCTCC (4952) | 1 | 6116 |
| | ptc-miR394a-5p | TTGGCATTCTGTCCACCTCC (4953) | 1 | 6117 |
| | ptc-miR394b-5p | TTGGCATTCTGTCCACCTCC (4954) | 1 | 6118 |
| | sbi-miR394a | TTGGCATTCTGTCCACCTCC (4955) | 1 | 6119 |
| | sbi-miR394b | TTGGCATTCTGTCCACCTCC (4956) | 1 | 6120 |
| | tcc-miR394a | TTGGCATTCTGTCCACCTCC (4957) | 1 | 6121 |
| | tcc-miR394b | TTGGCATTCTGTCCACCTCC (4958) | 1 | 6122 |
| | vvi-miR394a | TTGGCATTCTGTCCACCTCCAT (4959) | 1 | 6123 |
| | vvi-miR394c | TTGGCATTCTGTCCACCTCCAT (4960) | 1 | 6124 |
| | zma-miR394a | TTGGCATTCTGTCCACCTCC (4961) | 1 | 6125 |
| | zma-miR394b | TTGGCATTCTGTCCACCTCC (4962) | 1 | 6126 |
| zma-miR167u | ahy-miR167-5p | TGAAGCTGCCAGCATGATCTT (4963) | 0.95 | 6127 |
| | aly-miR167a | TGAAGCTGCCAGCATGATCTA (4964) | 0.95 | 6128 |
| | aly-miR167b | TGAAGCTGCCAGCATGATCTA (4965) | 0.95 | 6129 |
| | aly-miR167b* | GGTCATGCTCTGACAGCCTCACT (4966) | 0.5 | 6130 |
| | aly-miR167c | TAAGCTGCCAGCATGATCTTG (4967) | 0.85 | 6131 |
| | aly-miR167d | TGAAGCTGCCAGCATGATCTGG (4968) | 1 | 6132 |
| | aqc-miR167 | TCAAGCTGCCAGCATGATCTA (4969) | 0.9 | 6133 |
| | ath-miR167a | TGAAGCTGCCAGCATGATCTA (4970) | 0.95 | 6134 |
| | ath-miR167b | TGAAGCTGCCAGCATGATCTA (4971) | 0.95 | 6135 |
| | ath-miR167c | TAAGCTGCCAGCATGATCTTG (4972) | 0.85 | 6136 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | ath-miR167d | TGAAGCTGCCAGCATGATCTGG (4973) | 1 | 6137 |
| | ath-miR167m | TGAAGCTGCCAGCATGATCTG (4974) | 1 | 6138 |
| | bdi-miR167 | TGAAGCTGCCAGCATGATCTA (4975) | 0.95 | 6139 |
| | bdi-miR167a | TGAAGCTGCCAGCATGATCTA (4976) | 0.95 | 6140 |
| | bdi-miR167b | TGAAGCTGCCAGCATGATCTA (4977) | 0.95 | 6141 |
| | bdi-miR167c | TGAAGCTGCCAGCATGATCTGA (4978) | 1 | 6142 |
| | bdi-miR167d | TGAAGCTGCCAGCATGATCTGA (4979) | 1 | 6143 |
| | bna-miR167a | TGAAGCTGCCAGCATGATCTAA (4980) | 0.95 | 6144 |
| | bna-miR167b | TGAAGCTGCCAGCATGATCTAA (4981) | 0.95 | 6145 |
| | bna-miR167c | TGAAGCTGCCAGCATGATCTA (4982) | 0.95 | 6146 |
| | bra-miR167a | TGAAGCTGCCAGCATGATCTA (4983) | 0.95 | 6147 |
| | bra-miR167b | TGAAGCTGCCAGCATGATCTA (4984) | 0.95 | 6148 |
| | bra-miR167c | TGAAGCTGCCAGCATGATCTA (4985) | 0.95 | 6149 |
| | bra-miR167d | TGAAGCTGCCAGCATGATCTA (4986) | 0.95 | 6150 |
| | ccl-miR167a | TGAAGCTGCCAGCATGATCTGA (4987) | 1 | 6151 |
| | ccl-miR167b | TGAAGCTGCCAGCATGATCTGA (4988) | 1 | 6152 |
| | cle-miR167 | TGAAGCTGCCAGCATGATCTG (4989) | 1 | 6153 |
| | csi-miR167a | TGAAGCTGCCAGCATGATCTG (4990) | 1 | 6154 |
| | csi-miR167b | TGAAGCTGCCAGCATGATCTT (4991) | 0.95 | 6155 |
| | csi-miR167c | TGAAGCTGCCAGCATGATCTG (4992) | 1 | 6156 |
| | ctr-miR167 | TGAAGCTGCCAGCATGATCTGA (4993) | 1 | 6157 |
| | ghr-miR167 | TGAAGCTGCCAGCATGATCTA (4994) | 0.95 | 6158 |
| | gma-miR167a | TGAAGCTGCCAGCATGATCTA (4995) | 0.95 | 6159 |
| | gma-miR167b | TGAAGCTGCCAGCATGATCTA (4996) | 0.95 | 6160 |
| | gma-miR167c | TGAAGCTGCCAGCATGATCTG (4997) | 1 | 6161 |
| | gma-miR167d | TGAAGCTGCCAGCATGATCTA (4998) | 0.95 | 6162 |
| | gma-miR167e | TGAAGCTGCCAGCATGATCTT (4999) | 0.95 | 6163 |
| | gma-miR167f | TGAAGCTGCCAGCATGATCTT (5000) | 0.95 | 6164 |
| | gma-miR167g | TGAAGCTGCCAGCATGATCTGA (5001) | 1 | 6165 |
| | gma-miR167n | TGAAGCTGCCAGCATGATCT (5002) | 0.95 | 6166 |
| | gma-miR167o | TGAAGCTGCCAGCATGATCTG (5003) | 1 | 6167 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | gso-miR167a | TGAAGCTGCCAGCATGATCTG (5004) | 1 | 6168 |
| | ini-miR167 | TGAAGCTGCCAGCATGATCTG (5005) | 1 | 6169 |
| | lja-miR167 | TGAAGCTGCCAGCATGATCTG (5006) | 1 | 6170 |
| | mtr-miR167 | TGAAGCTGCCAGCATGATCTA (5007) | 0.95 | 6171 |
| | osa-miR167a | TGAAGCTGCCAGCATGATCTA (5008) | 0.95 | 6172 |
| | osa-miR167a* | ATCATGCATGACAGCCTCATTT (5009) | 0.65 | 6173 |
| | osa-miR167b | TGAAGCTGCCAGCATGATCTA (5010) | 0.95 | 6174 |
| | osa-miR167c | TGAAGCTGCCAGCATGATCTA (5011) | 0.95 | 6175 |
| | osa-miR167d | TGAAGCTGCCAGCATGATCTG (5012) | 1 | 6176 |
| | osa-miR167e | TGAAGCTGCCAGCATGATCTG (5013) | 1 | 6177 |
| | osa-miR167f | TGAAGCTGCCAGCATGATCTG (5014) | 1 | 6178 |
| | osa-miR167g | TGAAGCTGCCAGCATGATCTG (5015) | 1 | 6179 |
| | osa-miR167h | TGAAGCTGCCAGCATGATCTG (5016) | 1 | 6180 |
| | osa-miR167i | TGAAGCTGCCAGCATGATCTG (5017) | 1 | 6181 |
| | osa-miR167j | TGAAGCTGCCAGCATGATCTG (5018) | 1 | 6182 |
| | osa-miR167m | TGAAGCTGCCAGCATGATCTG (5019) | 1 | 6183 |
| | osa-miR167n | TGAAGCTGCCAGCATGATCTG (5020) | 1 | 6184 |
| | pco-miR167 | TGAAGCTGCCAGCATGATCTT (5021) | 0.95 | 6185 |
| | ppl-miR167a | TGAAGCTGCCAGCATGATCTA (5022) | 0.95 | 6186 |
| | ppl-miR167b | TGAAGCTGCCAGCATGATCTG (5023) | 1 | 6187 |
| | ppt-miR167 | GGAAGCTGCCAGCATGATCCT (5024) | 0.85 | 6188 |
| | ptc-miR167a | TGAAGCTGCCAGCATGATCTA (5025) | 0.95 | 6189 |
| | ptc-miR167b | TGAAGCTGCCAGCATGATCTA (5026) | 0.95 | 6190 |
| | ptc-miR167c | TGAAGCTGCCAGCATGATCTA (5027) | 0.95 | 6191 |
| | ptc-miR167d | TGAAGCTGCCAGCATGATCTA (5028) | 0.95 | 6192 |
| | ptc-miR167e | TGAAGCTGCCAGCATGATCTG (5029) | 1 | 6193 |
| | ptc-miR167f | TGAAGCTGCCAGCATGATCTT (5030) | 0.95 | 6194 |
| | ptc-miR167g | TGAAGCTGCCAGCATGATCTT (5031) | 0.95 | 6195 |
| | ptc-miR167h | TGAAGCTGCCAACATGATCTG (5032) | 1 | 6196 |
| | pts-miR167 | TGAAGCTGCCAGCATGATCTG (5033) | 1 | 6197 |
| | rco-miR167a | TGAAGCTGCCAGCATGATCTA (5034) | 0.95 | 6198 |
| | rco-miR167b | TGAAGCTGCCAGCATGATCTA (5035) | 0.95 | 6199 |
| | rco-miR167c | TGAAGCTGCCAGCATGATCTGG (5036) | 1 | 6200 |
| | sbi-miR167a | TGAAGCTGCCAGCATGATCTA (5037) | 0.95 | 6201 |
| | sbi-miR167b | TGAAGCTGCCAGCATGATCTA (5038) | 0.95 | 6202 |
| | sbi-miR167c | TGAAGCTGCCAGCATGATCTG (5039) | 1 | 6203 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | sbi-miR167d | TGAAGCTGCCAGCATGATCTG (5040) | 1 | 6204 |
| | sbi-miR167e | TGAAGCTGCCAGCATGATCTG (5041) | 1 | 6205 |
| | sbi-miR167f | TGAAGCTGCCAGCATGATCTG (5042) | 1 | 6206 |
| | sbi-miR167g | TGAAGCTGCCAGCATGATCTG (5043) | 1 | 6207 |
| | sbi-miR167h | TGAAGCTGCCAGCATGATCTG (5044) | 1 | 6208 |
| | sbi-miR167i | TGAAGCTGCCAGCATGATCTA (5045) | 0.95 | 6209 |
| | sly-miR167 | TGAAGCTGCCAGCATGATCTA (5046) | 0.95 | 6210 |
| | sof-miR167a | TGAAGCTGCCAGCATGATCTG (5047) | 1 | 6211 |
| | sof-miR167b | TGAAGCTGCCAGCATGATCTG (5048) | 1 | 6212 |
| | ssp-miR167 | TGAAGCTGCCAGCATGATCTG (5049) | 1 | 6213 |
| | ssp-miR167b | TGAAGCTGCCAGCATGATCTG (5050) | 1 | 6214 |
| | tae-miR167 | TGAAGCTGCCAGCATGATCTA (5051) | 0.95 | 6215 |
| | tae-miR167b | TGAAGCTGACAGCATGATCTA (5052) | 0.9 | 6216 |
| | tcc-miR167a | TGAAGCTGCCAGCATGATCTA (5053) | 0.95 | 6217 |
| | tcc-miR167b | TGAAGCTGCCAGCATGATCTA (5054) | 0.95 | 6218 |
| | tcc-miR167c | TGAAGCTGCCAGCATGATCTT (5055) | 0.95 | 6219 |
| | vvi-miR167a | TGAAGCTGCCAGCATGATCTG (5056) | 1 | 6220 |
| | vvi-miR167b | TGAAGCTGCCAGCATGATCTA (5057) | 0.95 | 6221 |
| | vvi-miR167c | TGAAGCTGCCAGCATGATCTC (5058) | 0.95 | 6222 |
| | vvi-miR167d | TGAAGCTGCCAGCATGATCTA (5059) | 0.95 | 6223 |
| | vvi-miR167e | TGAAGCTGCCAGCATGATCTA (5060) | 0.95 | 6224 |
| | zma-miR167a | TGAAGCTGCCAGCATGATCTA (5061) | 0.95 | 6225 |
| | zma-miR167b | TGAAGCTGCCAGCATGATCTA (5062) | 0.95 | 6226 |
| | zma-miR167b* | GATCATGCTGTGACAGTTTCACT (5063) | 0.55 | 6227 |
| | zma-miR167c | TGAAGCTGCCAGCATGATCTA (5064) | 0.95 | 6228 |
| | zma-miR167d | TGAAGCTGCCAGCATGATCTA (5065) | 0.95 | 6229 |
| | zma-miR167e | TGAAGCTGCCAGCATGATCTG (5066) | 1 | 6230 |
| | zma-miR167f | TGAAGCTGCCAGCATGATCTG (5067) | 1 | 6231 |
| | zma-miR167g | TGAAGCTGCCAGCATGATCTG (5068) | 1 | 6232 |
| | zma-miR167h | TGAAGCTGCCAGCATGATCTG (5069) | 1 | 6233 |
| | zma-miR167i | TGAAGCTGCCAGCATGATCTG (5070) | 1 | 6234 |
| | zma-miR167j | TGAAGCTGCCAGCATGATCTG (5071) | 1 | 6235 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | zma-miR167k | TGAAGCTGCCAGCATGATCTG (5072) | 1 | 6236 |
| | zma-miR167l | TGAAGCTGCCAGCATGATCTG (5073) | 1 | 6237 |
| | zma-miR167m | TGAAGCTGCCAGCATGATCTG (5074) | 1 | 6238 |
| | zma-miR167n | TGAAGCTGCCAGCATGATCTA (5075) | 0.95 | 6239 |
| | zma-miR167o | TGAAGCTGCCAGCATGATCTA (5076) | 0.95 | 6240 |
| | zma-miR167p | TGAAGCTGCCAGCATGATCTA (5077) | 0.95 | 6241 |
| | zma-miR167q | TGAAGCTGCCAGCATGATCTA (5078) | 0.95 | 6242 |
| | zma-miR167r | TGAAGCTGCCAGCATGATCTA (5079) | 0.95 | 6243 |
| | zma-miR167s | TGAAGCTGCCAGCATGATCTA (5080) | 0.95 | 6244 |
| | zma-miR167t | TGAAGCTGCCAGCATGATCTA (5081) | 0.95 | 6245 |
| gma-miR2119 | mtr-miR2119 | TCAAAGGGAGGTGTGGAGTAG (5082) | 0.76 | 6246 |
| | pvu-miR2119 | TCAAAGGGAGTTGTAGGGGAA (5083) | 1 | 6247 |
| osa-miR162a | aly-miR162a | TCGATAAACCTCTGCATCCAG (5084) | 1 | 6248 |
| | aly-miR162b | TCGATAAACCTCTGCATCCAG (5085) | 1 | 6249 |
| | ath-miR162a | TCGATAAACCTCTGCATCCAG (5086) | 1 | 6250 |
| | ath-miR162b | TCGATAAACCTCTGCATCCAG (5087) | 1 | 6251 |
| | bdi-miR162 | TCGATAAACCTCTGCATCCGG (5088) | 0.95 | 6252 |
| | cpa-miR162a | TCGATAAACCTCTGCATCCAG (5089) | 1 | 6253 |
| | csi-miR162 | TCGATAAACCTCTGCATCCAG (5090) | 1 | 6254 |
| | csi-miR162.5 | TCGATAAACCTCTGCATCCAG (5091) | 1 | 6255 |
| | ghr-miR162a | TCGATAAACCTCTGCATCCAG (5092) | 1 | 6256 |
| | gma-miR162 | TCGATAAACCTCTGCATCCA (5093) | 0.95 | 6257 |
| | gma-miR162a | TCGATAAACCTCTGCATCCAG (5094) | 1 | 6258 |
| | gma-miR162m | TCGATAAACCTCTGCATCCAG (5095) | 1 | 6259 |
| | llu-miR162 | TCGATAAACCTCTGCATCCAG (5096) | 1 | 6260 |
| | lsa-miR162 | TCGATAAACCTCTGCATCCAG (5097) | 1 | 6261 |
| | mdo-miR162 | TCGATAAACCTTTGCATCCAG (5098) | 0.95 | 6262 |
| | mtr-miR162 | TCGATAAACCTCTGCATCCAG (5099) | 1 | 6263 |
| | mtr-miR162b | TCGATAAACCTCTGCATCCA (5100) | 0.95 | 6264 |

TABLE 8-continued

Summary of Homologs (Orthologs to Small RNAs which are down-regulated in Abiotic Stress in Soybean Plants.

| Mir Name | Homolog Name | Homolog Sequence (SEQ ID NO:) | % Identity | Homolog Stem-loop Sequence |
|---|---|---|---|---|
| | mtr-miR162c | TCGATGAACCGCTGCATCCAG (5101) | 0.9 | 6265 |
| | mtr-miR162d | TCGATAAACCTCTGCATCCAG (5102) | 1 | 6266 |
| | osa-miR162b | TCGATAAGCCTCTGCATCCAG (5103) | 0.95 | 6267 |
| | osa-miR162m | TCGATAAGCCTCTGCATCCAG (5104) | 0.95 | 6268 |
| | ptc-miR162a | TCGATAAACCTCTGCATCCAG (5105) | 1 | 6269 |
| | ptc-miR162b | TCGATAAACCTCTGCATCCAG (5106) | 1 | 6270 |
| | ptc-miR162c | TCGATAAACCTCTGCATCCAG (5107) | 1 | 6271 |
| | rco-miR162 | TCGATAAACCTCTGCATCCAG (5108) | 1 | 6272 |
| | sbi-miR162 | TCGATAAACCTCTGCATCCAG (5109) | 1 | 6273 |
| | sly-miR162 | TCGATAAACCTCTGCATCCAG (5110) | 1 | 6274 |
| | tcc-miR162 | TCGATAAACCTCTGCATCCAG (5111) | 1 | 6275 |
| | vvi-miR162 | TCGATAAACCTCTGCATCCAG (5112) | 1 | 6276 |
| | zma-miR162 | TCGATAAACCTCTGCATCCA (5113) | 0.95 | 6277 |
| | zma-miR162b | TCGATAAACCTCTGCATCCAG (5114) | 1 | 6278 |

Example 3

Identification of miRNAs Associated with Abiotic Stress and Target Prediction Using Bioinformatics Tools Small RNAs that are potentially associated with improved abiotic or biotic stress tolerance can be identified by proprietary computational algorithms that analyze RNA expression profiles alongside publicly available gene and protein databases. A high throughput screening is performed on microarrays loaded with miRNAs that were found to be differential under multiple stress and optimal environmental conditions and in different plant tissues. The initial trait-associated miRNAs are later validated by quantitative Real Time PCR (qRT-PCR).

Target prediction—homologous or orthologous genes to the genes of interest in soybean and/or *arabidopsis* are found through a proprietary tool that analyzes publicly available genomic as well as expression and gene annotation databases from multiple plant species. Homologous and orthologous protein and nucleotide sequences of target genes of the small RNA sequences of the invention, were found using BLAST having at least 70% identity on at least 60% of the entire master gene length, and are summarized in Tables 9-10 below.

TABLE 9

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| aqc-miR159 | 305-325 | XP_003551790 | 356567161 | 1 | *Glycine max* | 6315 | 8130 |
| | 334-354 | XP_003554567 | 356572827 | 1 | *Glycine max* | 6316 | 8131 |
| | | XP_003521605 | 356505654 | 0.9723 | *Glycine max* | 6317 | 8132 |
| | | XP_003521606 | 356505656 | 0.9723 | *Glycine max* | 6318 | 8133 |
| | | XP_003626013 | 357511448 | 0.8949 | *Medicago truncatula* | 6319 | 8134 |
| | | XP_002272575 | 225437676 | 0.8423 | *Vitis vinifera* | 6320 | 8135 |
| | | CBI37003 | 270254427 | 0.8409 | *Vitis vinifera* | 6321 | 8136 |
| | | XP_002515224 | 255761086 | 0.8382 | *Ricinus communis* | 6322 | |
| | | CAN71135 | 147786943 | 0.8354 | *Vitis vinifera* | 6323 | 8137 |
| | | XP_002301535 | 255761085 | 0.8313 | *Populus trichocarpa* | 6324 | |
| | | ADF30190 | 294713705 | 0.8119 | *Brassica napus* | 6325 | 8138 |
| | 124-144 | XP_003543825 | 356550908 | 1 | *Glycine max* | 6326 | 8139 |
| | 752-772 | XP_003543825 | 356550908 | 1 | *Glycine max* | 6327 | 8140 |
| | | XP_003556814 | 356577399 | 0.813 | *Glycine max* | 6328 | 8141 |
| | 360-380 | XP_003549039 | 356561539 | 1 | *Glycine max* | 6329 | 8142 |
| | | XP_003533180 | 356529191 | 0.8282 | *Glycine max* | 6330 | 8143 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 614-634 | XP_003541563 | 356546291 | 1 | Glycine max | 6331 | 8144 |
| | | XP_003545791 | 356554924 | 0.805 | Glycine max | 6332 | 8145 |
| | 905-925 | XP_003556814 | 356577399 | 1 | Glycine max | 6333 | 8146 |
| | | XP_003543825 | 356550908 | 0.8659 | Glycine max | 6334 | 8147 |
| | 141-161 | XP_003518351 | 356499037 | 1 | Glycine max | 6335 | 8148 |
| | 2016-2036 | XP_003538988 | 356541033 | 1 | Glycine max | 6336 | 8149 |
| | | XP_003607189 | 357473808 | 0.7407 | Medicago truncatula | 6337 | 8150 |
| | | XP_003604038 | 357467506 | 0.7035 | Medicago truncatula | 6338 | 8151 |
| | 839-859 | XP_003526354 | 356515330 | 1 | Glycine max | 6339 | 8152 |
| | | XP_003523913 | 356510372 | 0.9333 | Glycine max | 6340 | 8153 |
| | 842-862 | XP_003523913 | 356510372 | 1 | Glycine max | 6341 | 8154 |
| | | XP_003526354 | 356515330 | 0.9333 | Glycine max | 6342 | 8155 |
| | 926-946 | XP_003545791 | 356554924 | 1 | Glycine max | 6343 | 8156 |
| | | XP_003541563 | 356546291 | 0.8662 | Glycine max | 6344 | 8157 |
| ath-miR159b | 334-354 | XP_003554567 | 356572827 | 1 | Glycine max | 6345 | 8158 |
| | | XP_003521605 | 356505654 | 0.9723 | Glycine max | 6346 | 8159 |
| | | XP_003521606 | 356505656 | 0.9723 | Glycine max | 6347 | 8160 |
| | | XP_003626013 | 357511448 | 0.8949 | Medicago truncatula | 6348 | 8161 |
| | | XP_002272575 | 225437676 | 0.8423 | Vitis vinifera | 6349 | 8162 |
| | | CBI37003 | 270254427 | 0.8409 | Vitis vinifera | 6350 | 8163 |
| | | XP_002515224 | 255761086 | 0.8382 | Ricinus communis | 6351 | |
| | | CAN71135 | 147786943 | 0.8354 | Vitis vinifera | 6352 | 8164 |
| | | XP_002301535 | 255761085 | 0.8313 | Populus trichocarpa | 6353 | |
| | | ADF30190 | 294713705 | 0.8119 | Brassica napus | 6354 | 8165 |
| | 405-425 | XP_003542140 | 356547479 | 1 | Glycine max | 6355 | 8166 |
| | | XP_003546908 | 356557204 | 0.8696 | Glycine max | 6356 | 8167 |
| | 305-325 | XP_003541823 | 356546825 | 1 | Glycine max | 6357 | 8168 |
| | 124-144 | XP_003543825 | 356550908 | 1 | Glycine max | 6358 | 8169 |
| | | XP_003556814 | 356577399 | 0.813 | Glycine max | 6359 | 8170 |
| | 839-859 | XP_003526354 | 356515330 | 1 | Glycine max | 6360 | 8171 |
| | | XP_003523913 | 356510372 | 0.9333 | Glycine max | 6361 | 8172 |
| | 2079-2099 | XP_003538988 | 356541033 | 1 | Glycine max | 6362 | 8173 |
| | | XP_003607189 | 357473808 | 0.7407 | Medicago truncatula | 6363 | 8174 |
| | | XP_003604038 | 357467506 | 0.7035 | Medicago truncatula | 6364 | 8175 |
| | 614-634 | XP_003541563 | 356546291 | 1 | Glycine max | 6365 | 8176 |
| | | XP_003545791 | 356554924 | 0.805 | Glycine max | 6366 | 8177 |
| | 905-925 | XP_003556814 | 356577399 | 1 | Glycine max | 6367 | 8178 |
| | | XP_003543825 | 356550908 | 0.8659 | Glycine max | 6368 | 8179 |
| | 926-946 | XP_003545791 | 356554924 | 1 | Glycine max | 6369 | 8180 |
| | | XP_003541563 | 356546291 | 0.8662 | Glycine max | 6370 | 8181 |
| | 842-862 | XP_003523913 | 356510372 | 1 | Glycine max | 6371 | 8182 |
| | | XP_003526354 | 356515330 | 0.9333 | Glycine max | 6372 | 8183 |
| ath-miR159c | 251-271 | NP_001236122 | 351727005 | 1 | Glycine max | 6373 | 8184 |
| | | ACU21384 | 255642238 | 0.7676 | Glycine max | 6374 | 8185 |
| | 46-66 | XP_003519140 | 356500640 | 1 | Glycine max | 6375 | 8186 |
| | | XP_003549552 | 356562588 | 0.8757 | Glycine max | 6376 | 8187 |
| | | XP_003610353 | 357480134 | 0.9006 | Medicago truncatula | 6377 | 8188 |
| | 817-837 | XP_003525997 | 356514606 | 1 | Glycine max | 6378 | 8189 |
| | | XP_003540066 | 356543230 | 0.8441 | Glycine max | 6379 | 8190 |
| | 289-309 | XP_003518627 | 356499601 | 1 | Glycine max | 6380 | 8191 |
| | | XP_003542153 | 356547506 | 0.9478 | Glycine max | 6381 | 8192 |
| | | ADN33938 | 307136081 | 0.7937 | Cucumis melo subsp. melo | 6382 | 8193 |
| | | XP_002518919 | 255761086 | 0.7755 | Ricinus communis | 6383 | |
| | | XP_002279642 | 225426567 | 0.7755 | Vitis vinifera | 6384 | 8194 |
| | | XP_002870592 | 297853636 | 0.7664 | Arabidopsis lyrata subsp. lyrata | 6385 | |
| | | NP_199024 | 30693991 | 0.7642 | Arabidopsis thaliana | 6386 | 8195 |
| | | AAM63843 | 21405504 | 0.7596 | Arabidopsis thaliana | 6387 | 8196 |
| | | XP_002299422 | 255761085 | 0.7528 | Populus trichocarpa | 6388 | |
| | | XP_002303695 | 255761085 | 0.7574 | Populus trichocarpa | 6389 | |
| | 124-144 | XP_003543825 | 356550908 | 1 | Glycine max | 6390 | 8197 |
| | | XP_003556814 | 356577399 | 0.813 | Glycine max | 6391 | 8198 |
| | 461-481 | XP_003542153 | 356547506 | 1 | Glycine max | 6392 | 8199 |
| | | XP_003518627 | 356499601 | 0.9436 | Glycine max | 6393 | 8200 |
| | 1162-1182 | XP_003531162 | 356525093 | 1 | Glycine max | 6394 | 8201 |
| | | XP_003524148 | 356510852 | 0.7692 | Glycine max | 6395 | 8202 |
| | 839-859 | XP_003526354 | 356515330 | 1 | Glycine max | 6396 | 8203 |
| | | XP_003523913 | 356510372 | 0.9333 | Glycine max | 6397 | 8204 |
| | 495-515 | XP_003524148 | 356510852 | 1 | Glycine max | 6398 | 8205 |
| | | XP_003531162 | 356525093 | 0.7762 | Glycine max | 6399 | 8206 |
| | 949-969 | XP_003547199 | 356557800 | 1 | Glycine max | 6400 | 8207 |
| | | XP_003541668 | 356546507 | 0.8748 | Glycine max | 6401 | 8208 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 614-634 | XP_003541563 | 356546291 | 1 | Glycine max | 6402 | 8209 |
| | | XP_003545791 | 356554924 | 0.805 | Glycine max | 6403 | 8210 |
| | 905-925 | XP_003556814 | 356577399 | 1 | Glycine max | 6404 | 8211 |
| | | XP_003543825 | 356550908 | 0.8659 | Glycine max | 6405 | 8212 |
| | 2016-2036 | XP_003538988 | 356541033 | 1 | Glycine max | 6406 | 8213 |
| | | XP_003607189 | 357473808 | 0.7407 | Medicago truncatula | 6407 | 8214 |
| | | XP_003604038 | 357467506 | 0.7035 | Medicago truncatula | 6408 | 8215 |
| | 1330-1350 | XP_003541668 | 356546507 | 1 | Glycine max | 6409 | 8216 |
| | | XP_003547199 | 356557800 | 0.8383 | Glycine max | 6410 | 8217 |
| | 842-862 | XP_003523913 | 356510372 | 1 | Glycine max | 6411 | 8218 |
| | | XP_003526354 | 356515330 | 0.9333 | Glycine max | 6412 | 8219 |
| | 926-946 | XP_003545791 | 356554924 | 1 | Glycine max | 6413 | 8220 |
| | | XP_003541563 | 356546291 | 0.8662 | Glycine max | 6414 | 8221 |
| ath-miRf10240-akr | 288-307 | AES96257 | 357486022 | 1 | Medicago truncatula | 6415 | 8222 |
| | | XP_003613299 | 357486022 | 1 | Medicago truncatula | 6416 | 8223 |
| | | XP_003517816 | 356497943 | 0.9446 | Glycine max | 6417 | 8224 |
| | | XP_003519545 | 356501464 | 0.9418 | Glycine max | 6418 | 8225 |
| | | XP_003517817 | 356497945 | 0.9446 | Glycine max | 6419 | 8226 |
| | | XP_003530656 | 356524070 | 0.8809 | Glycine max | 6420 | 8227 |
| | | XP_003551180 | 356565911 | 0.8753 | Glycine max | 6421 | 8228 |
| | | XP_002531401 | 255761086 | 0.8421 | Ricinus communis | 6422 | |
| | | XP_003628672 | 357516766 | 0.8504 | Medicago truncatula | 6423 | 8229 |
| | | XP_002266222 | 225424743 | 0.8393 | Vitis vinifera | 6424 | 8230 |
| | | CAN76955 | 147776916 | 0.8338 | Vitis vinifera | 6425 | 8231 |
| | 1503-1522 | XP_003547951 | 356559326 | 1 | Glycine max | 6426 | 8232 |
| | | ACU23369 | 255645751 | 0.998 | Glycine max | 6427 | 8233 |
| | | XP_003547950 | 356559324 | 0.8408 | Glycine max | 6428 | 8234 |
| | | ACU18289 | 255635883 | 0.8388 | Glycine max | 6429 | 8235 |
| | | XP_003629354 | 357518130 | 0.7531 | Medicago truncatula | 6430 | 8236 |
| | | XP_002531509 | 255761086 | 0.7204 | Ricinus communis | 6431 | |
| | | ABK95760 | 118487875 | 0.7245 | Populus trichocarpa | 6432 | 8237 |
| | | XP_003612122 | 357483670 | 0.7327 | Medicago truncatula | 6433 | 8238 |
| | | XP_002333330 | 255761085 | 0.7122 | Populus trichocarpa | 6434 | |
| | | XP_002310843 | 255761085 | 0.702 | Populus trichocarpa | 6435 | |
| | 115-134 | AES78100 | 357503186 | 1 | Medicago truncatula | 6436 | 8239 |
| | | XP_003621882 | 357503186 | 1 | Medicago truncatula | 6437 | 8240 |
| | 95-114 | AET03830 | 357518130 | 1 | Medicago truncatula | 6438 | 8241 |
| | | XP_003547951 | 356559326 | 0.811 | Glycine max | 6439 | 8242 |
| | 487-506 | NP_001238238 | 351721588 | 1 | Glycine max | 6440 | 8243 |
| | | NP_001237618 | 351725834 | 0.9947 | Glycine max | 6441 | 8244 |
| | | ACU16478 | 255632239 | 0.9679 | Glycine max | 6442 | 8245 |
| | | XP_003519150 | 356500660 | 0.7968 | Glycine max | 6443 | 8246 |
| | 149-168 | XP_003531007 | 356524781 | 1 | Glycine max | 6444 | 8247 |
| | | XP_003528405 | 356519488 | 0.9391 | Glycine max | 6445 | 8248 |
| | | XP_003608343 | 357476114 | 0.8746 | Medicago truncatula | 6446 | 8249 |
| | | XP_002264303 | 225429239 | 0.7885 | Vitis vinifera | 6447 | 8250 |
| | | CBI35448 | 270252044 | 0.7885 | Vitis vinifera | 6448 | |
| | | XP_002518318 | 255761086 | 0.767 | Ricinus communis | 6449 | |
| | | NP_201251 | 145359643 | 0.7742 | Arabidopsis thaliana | 6450 | 8251 |
| | | XP_002866616 | 297853636 | 0.7778 | Arabidopsis lyrata subsp. lyrata | 6451 | |
| | | ABK95206 | 118486740 | 0.7527 | Populus trichocarpa | 6452 | 8252 |
| | | XP_002313210 | 255761085 | 0.7491 | Populus trichocarpa | 6453 | |
| | 214-233 | XP_003525932 | 356514476 | 1 | Glycine max | 6454 | 8253 |
| | 700-719 | XP_003523287 | 356509093 | 1 | Glycine max | 6455 | 8254 |
| | | XP_003526789 | 356516210 | 0.9406 | Glycine max | 6456 | 8255 |
| | | XP_003518282 | 356498893 | 0.7406 | Glycine max | 6457 | 8256 |
| | | XP_003544853 | 356553012 | 0.7406 | Glycine max | 6458 | 8257 |
| ath-miRf10368-akr | 587-606 | XP_003543893 | 356551052 | 1 | Glycine max | 6459 | 8258 |
| | | XP_003554723 | 356573142 | 0.9659 | Glycine max | 6460 | 8259 |
| | | ACJ85427 | 357496652 | 0.8447 | Medicago truncatula | 6461 | 8260 |
| | | XP_003531841 | 356526470 | 0.8333 | Glycine max | 6462 | 8261 |
| | | XP_003552550 | 356568703 | 0.8106 | Glycine max | 6463 | 8262 |
| | | XP_002284521 | 225457306 | 0.7765 | Vitis vinifera | 6464 | 8263 |
| | | XP_002323884 | 255761085 | 0.7765 | Populus trichocarpa | 6465 | |
| | | XP_002284184 | 225452935 | 0.7803 | Vitis vinifera | 6466 | 8264 |
| | | XP_002306045 | 255761085 | 0.7424 | Populus trichocarpa | 6467 | |
| | | XP_002526069 | 255761086 | 0.7424 | Ricinus communis | 6468 | |
| | 456-475 | XP_003539013 | 356541084 | 1 | Glycine max | 6469 | 8265 |
| | | XP_003540676 | 356544475 | 0.8768 | Glycine max | 6470 | 8266 |
| | | XP_003539012 | 356541082 | 0.7183 | Glycine max | 6471 | 8267 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 685-704 | NP_001235161 | 351721419 | 1 | Glycine max | 6472 | 8268 |
| | | XP_003548144 | 356559717 | 0.9705 | Glycine max | 6473 | 8269 |
| | | XP_003548143 | 356559715 | 0.7785 | Glycine max | 6474 | 8270 |
| | | BAB86923 | 19911192 | 0.711 | Vigna angularis | 6475 | 8271 |
| | 685-704 | NP_001235161 | 351721419 | 1 | Glycine max | 6476 | 8272 |
| | 3330-3349 | XP_003551446 | 356566453 | 1 | Glycine max | 6477 | |
| | 347-366 | XP_003540896 | 356544921 | 1 | Glycine max | 6478 | 8273 |
| | | XP_003533477 | 356529802 | 0.7278 | Glycine max | 6479 | 8274 |
| | | XP_003607171 | 357473772 | 0.8086 | Medicago truncatula | 6480 | 8275 |
| | | XP_002533189 | 255761086 | 0.7412 | Ricinus communis | 6481 | |
| | | XP_002279051 | 225428040 | 0.7305 | Vitis vinifera | 6482 | 8276 |
| | | XP_003522637 | 356507769 | 0.7466 | Glycine max | 6483 | 8277 |
| | | XP_003526942 | 356516520 | 0.7035 | Glycine max | 6484 | 8278 |
| | 88-107 | XP_002533189 | 255761086 | 1 | Ricinus communis | 6485 | |
| | | XP_003540896 | 356544921 | 0.7035 | Glycine max | 6486 | 8279 |
| | | XP_002270345 | 225457886 | 0.7008 | Vitis vinifera | 6487 | 8280 |
| | 589-608 | XP_003518505 | 356499351 | 1 | Glycine max | 6488 | 8281 |
| | 75-94 | XP_002312957 | 255761085 | 1 | Populus trichocarpa | 6489 | |
| | | XP_002306186 | 255761085 | 0.9181 | Populus trichocarpa | 6490 | |
| | | CAN67732 | 147790359 | 0.8836 | Vitis vinifera | 6491 | 8282 |
| | 682-701 | XP_003556840 | 356577453 | 1 | Glycine max | 6492 | 8283 |
| | | XP_003519003 | 356500365 | 0.7261 | Glycine max | 6493 | 8284 |
| | | XP_003542320 | 356547854 | 0.7261 | Glycine max | 6494 | 8285 |
| | 220-239 | XP_003527967 | 356518600 | 1 | Glycine max | 6495 | 8286 |
| | | XP_003523399 | 356509321 | 0.7599 | Glycine max | 6496 | 8287 |
| | 1834-1853 | XP_003539709 | 356542508 | 1 | Glycine max | 6497 | 8288 |
| | | XP_003538207 | 356539441 | 0.9136 | Glycine max | 6498 | 8289 |
| | | XP_003606389 | 357472208 | 0.8066 | Medicago truncatula | 6499 | 8290 |
| | | NP_001238028 | 351722912 | 0.7617 | Glycine max | 6500 | 8291 |
| | | XP_003543464 | 356550174 | 0.7375 | Glycine max | 6501 | 8292 |
| | | XP_003539710 | 356542510 | 0.8394 | Glycine max | 6502 | 8293 |
| | | XP_002530284 | 255761086 | 0.7081 | Ricinus communis | 6503 | |
| | 0-19 | AES82704 | 357512394 | 1 | Medicago truncatula | 6504 | |
| | | XP_003521781 | 356506009 | 0.8339 | Glycine max | 6505 | |
| | | CBI28651 | 270241399 | 0.747 | Vitis vinifera | 6506 | |
| | | XP_002267871 | 225430630 | 0.7263 | Vitis vinifera | 6507 | |
| | | XP_003553769 | 356571203 | 0.8332 | Glycine max | 6508 | |
| | 1104-1123 | XP_003518991 | 356500340 | 1 | Glycine max | 6509 | 8294 |
| | | XP_003535145 | 356533178 | 0.8841 | Glycine max | 6510 | 8295 |
| | | XP_003535146 | 356533180 | 0.8509 | Glycine max | 6511 | 8296 |
| | 439-458 | XP_003526441 | 356515505 | 1 | Glycine max | 6512 | 8297 |
| | | XP_003522648 | 356507791 | 0.9351 | Glycine max | 6513 | 8298 |
| | | XP_003522647 | 356507789 | 0.8643 | Glycine max | 6514 | 8299 |
| | | XP_002284618 | 225430104 | 0.7935 | Vitis vinifera | 6515 | 8300 |
| | | XP_003526440 | 356515503 | 0.8525 | Glycine max | 6516 | 8301 |
| | | XP_002284775 | 225445329 | 0.7788 | Vitis vinifera | 6517 | 8302 |
| | | XP_002515572 | 255761086 | 0.7699 | Ricinus communis | 6518 | |
| | | AES73734 | 357466396 | 0.7876 | Medicago truncatula | 6519 | 8303 |
| | 1245-1264 | NP_001238286 | 351722970 | 1 | Glycine max | 6520 | 8304 |
| | | BAG72094 | 207367147 | 0.9584 | Glycine max | 6521 | 8305 |
| | | ACE79196 | 190586158 | 0.9558 | Glycine max | 6522 | 8306 |
| | | ACE79197 | 190586160 | 0.9019 | Glycine max | 6523 | 8307 |
| | | XP_003555766 | 356575272 | 0.8983 | Glycine max | 6524 | 8308 |
| | | P93673 | | 0.8453 | Lathyrus sativus | 6525 | |
| | | P15001 | | 0.8453 | Pisum sativum | 6526 | |
| | | AES61525 | 357441992 | 0.8426 | Medicago truncatula | 6527 | 8309 |
| | | XP_002278610 | 225450404 | 0.7772 | Vitis vinifera | 6528 | 8310 |
| | | ACC60969 | 183239021 | 0.7763 | Vitis riparia | 6529 | |
| | 177-196 | XP_002306186 | 255761085 | 1 | Populus trichocarpa | 6530 | |
| | | XP_002312957 | 255761085 | 0.7553 | Populus trichocarpa | 6531 | |
| | 439-458 | XP_003522648 | 356507791 | 1 | Glycine max | 6532 | 8311 |
| | | XP_003526441 | 356515505 | 0.9351 | Glycine max | 6533 | 8312 |
| | | NP_189078 | 42565156 | 0.7168 | Arabidopsis thaliana | 6534 | 8313 |
| | 200-219 | XP_003597608 | 357454654 | 1 | Medicago truncatula | 6535 | 8314 |
| | | ABN08398 | 357454654 | 1 | Medicago truncatula | 6536 | 8315 |
| | | XP_003546676 | 356556729 | 0.8954 | Glycine max | 6537 | 8316 |
| | | XP_003543598 | 356550445 | 0.8942 | Glycine max | 6538 | 8317 |
| | | XP_003531618 | 356526020 | 0.8609 | Glycine max | 6539 | 8318 |
| | | XP_003529875 | 356522481 | 0.8537 | Glycine max | 6540 | 8319 |
| | | CAA07236 | 316995680 | 0.849 | Cicer arietinum | 6541 | 8320 |
| | | ABK96254 | 118488889 | 0.8121 | Populus trichocarpa × Populus deltoides | 6542 | 8321 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | CAC44500 | 14970838 | 0.8157 | *Fragaria × ananassa* | 6543 | 8322 |
| | | XP_002327432 | 255761085 | 0.8109 | *Populus trichocarpa* | 6544 | |
| | | ABV32545 | 157313303 | 0.824 | *Prunus persica* | 6545 | 8323 |
| | 20-39 | XP_003538511 | 356540064 | 1 | *Glycine max* | 6546 | |
| | | XP_003540789 | 356544707 | 0.9546 | *Glycine max* | 6547 | |
| | | AES88424 | 357471884 | 0.8454 | *Medicago truncatula* | 6548 | |
| | | XP_002328167 | 255761085 | 0.78 | *Populus trichocarpa* | 6549 | |
| | | XP_002529065 | 255761086 | 0.7791 | *Ricinus communis* | 6550 | |
| | | XP_002269920 | 225436294 | 0.7732 | *Vitis vinifera* | 6551 | |
| | 1726-1745 | XP_003538207 | 356539441 | 1 | *Glycine max* | 6552 | 8324 |
| | | XP_003539709 | 356542508 | 0.901 | *Glycine max* | 6553 | 8325 |
| | | AES88586 | 357472208 | 0.8038 | *Medicago truncatula* | 6554 | 8326 |
| | | XP_003538208 | 356539443 | 0.8362 | *Glycine max* | 6555 | 8327 |
| ath-miRf10763-akr | 137-156 | XP_003540953 | 356545038 | 1 | *Glycine max* | 6556 | 8328 |
| | | XP_003537828 | 356538677 | 0.9174 | *Glycine max* | 6557 | 8329 |
| | 246-265 | ACU17625 | 255634523 | 1 | *Glycine max* | 6558 | 8330 |
| | | XP_003520499 | 356503402 | 0.9227 | *Glycine max* | 6559 | 8331 |
| | | XP_003554133 | 356571948 | 0.8886 | *Glycine max* | 6560 | 8332 |
| | 448-467 | XP_003555015 | 356573740 | 1 | *Glycine max* | 6561 | 8333 |
| | 145-164 | XP_002267145 | 225438252 | 1 | *Vitis vinifera* | 6562 | 8334 |
| | | XP_003517356 | 356497006 | 0.8121 | *Glycine max* | 6563 | 8335 |
| | | XP_003539260 | 356541595 | 0.8166 | *Glycine max* | 6564 | 8336 |
| | | XP_003611551 | 357482528 | 0.7919 | *Medicago truncatula* | 6565 | 8337 |
| | | NP_566927 | 42565786 | 0.7696 | *Arabidopsis thaliana* | 6566 | 8338 |
| | | XP_002877705 | 297853636 | 0.774 | *Arabidopsis lyrata* subsp. *lyrata* | 6567 | |
| | | XP_002285420 | 225458889 | 0.8076 | *Vitis vinifera* | 6568 | 8339 |
| | | AAM61258 | 21403407 | 0.7673 | *Arabidopsis thaliana* | 6569 | 8340 |
| | | NP_201393 | 30698164 | 0.7405 | *Arabidopsis thaliana* | 6570 | 8341 |
| | | AAL32554 | 17064799 | 0.7383 | *Arabidopsis thaliana* | 6571 | 8342 |
| | 523-542 | XP_003524815 | 356512212 | 1 | *Glycine max* | 6572 | 8343 |
| | | | 356528136 | 0.981 | *Glycine max* | 6573 | |
| | 136-155 | XP_003520083 | 356502552 | 1 | *Glycine max* | 6574 | 8344 |
| | | XP_003517797 | 356497905 | 0.8522 | *Glycine max* | 6575 | 8345 |
| | 993-1012 | AET34792 | 356650815 | 1 | *Pisum sativum* | 6576 | 8346 |
| | | AET34790 | 356650811 | 0.9979 | *Pisum sativum* | 6577 | 8347 |
| | | AET34786 | 356650803 | 0.9358 | *Medicago truncatula* | 6578 | 8348 |
| | | XP_003625012 | 357509446 | 0.9337 | *Medicago truncatula* | 6579 | 8349 |
| | | AET34796 | 356650823 | 0.8654 | *Glycine max* | 6580 | 8350 |
| | | XP_003521136 | 356504705 | 0.8551 | *Glycine max* | 6581 | 8351 |
| | | AEM62768 | 343794555 | 0.8778 | *Lotus japonicus* | 6582 | 8352 |
| | | XP_002275980 | 225441316 | 0.8282 | *Vitis vinifera* | 6583 | 8353 |
| | | CAN80112 | 147852377 | 0.8282 | *Vitis vinifera* | 6584 | 8354 |
| | | XP_002308905 | 255761085 | 0.824 | *Populus trichocarpa* | 6585 | |
| | 223-242 | XP_003520499 | 356503402 | 1 | *Glycine max* | 6586 | 8355 |
| | | ACU17625 | 255634523 | 0.9878 | *Glycine max* | 6587 | 8356 |
| | 217-236 | XP_003526336 | 356515293 | 1 | *Glycine max* | 6588 | 8357 |
| | | XP_003540834 | 356544797 | 0.7611 | *Glycine max* | 6589 | 8358 |
| | 241-260 | XP_003519685 | 356501746 | 1 | *Glycine max* | 6590 | 8359 |
| | | ACU23918 | 255646896 | 0.9948 | *Glycine max* | 6591 | 8360 |
| | | XP_003545065 | 356553441 | 0.8093 | *Glycine max* | 6592 | 8361 |
| | 26-45 | CBI33098 | 270247736 | 1 | *Vitis vinifera* | 6593 | 8362 |
| | 237-256 | AAF73257 | 8132346 | 1 | *Pisum sativum* | 6594 | 8363 |
| | | XP_003523778 | 356510099 | 0.9489 | *Glycine max* | 6595 | 8364 |
| | | XP_003527981 | 356518628 | 0.9382 | *Glycine max* | 6596 | 8365 |
| | | CAN70091 | 123701299 | 0.8817 | *Vitis vinifera* | 6597 | 8366 |
| | | Q40517 | | 0.8817 | *Nicotiana tabacum* | 6598 | |
| | | NP_001233761 | 350539780 | 0.8737 | *Solanum lycopersicum* | 6599 | 8367 |
| | | Q40884 | | 0.8737 | *Petunia × hybrida* | 6600 | |
| | | XP_002302017 | 255761085 | 0.871 | *Populus trichocarpa* | 6601 | |
| | | XP_002510434 | 255761086 | 0.8737 | *Ricinus communis* | 6602 | |
| | 360-379 | XP_003539534 | 356542151 | 1 | *Glycine max* | 6603 | 8368 |
| | | XP_003543335 | 356549913 | 0.8571 | *Glycine max* | 6604 | 8369 |
| | 26-45 | XP_003601902 | 357463240 | 1 | *Medicago truncatula* | 6605 | 8370 |
| | | XP_003538598 | 356540240 | 0.8571 | *Glycine max* | 6606 | 8371 |
| | | XP_003551994 | 356567575 | 0.8521 | *Glycine max* | 6607 | 8372 |
| | | XP_003531333 | 356525440 | 0.8045 | *Glycine max* | 6608 | 8373 |
| | | XP_003525038 | 356512665 | 0.797 | *Glycine max* | 6609 | 8374 |
| | | XP_002530039 | 255761086 | 0.7845 | *Ricinus communis* | 6610 | |
| | | XP_002314593 | 255761085 | 0.7694 | *Populus trichocarpa* | 6611 | |
| | | XP_002282407 | 225424658 | 0.7669 | *Vitis vinifera* | 6612 | 8375 |
| | | XP_002311761 | 255761085 | 0.7669 | *Populus trichocarpa* | 6613 | |
| | | CBI16790 | 270228074 | 0.7569 | *Vitis vinifera* | 6614 | |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 502-521 | NP_001234991 | 351723886 | 1 | Glycine max | 6615 | 8376 |
| | | XP_003552315 | 356568227 | 0.9954 | Glycine max | 6616 | 8377 |
| | | XP_003543429 | 356550102 | 0.9815 | Glycine max | 6617 | 8378 |
| | | NP_001236946 | 351721215 | 0.9769 | Glycine max | 6618 | 8379 |
| | | XP_003596822 | 357453090 | 0.9444 | Medicago truncatula | 6619 | 8380 |
| | | XP_003611340 | 357482108 | 0.9444 | Medicago truncatula | 6620 | 8381 |
| | | XP_003600923 | 357461282 | 0.9444 | Medicago truncatula | 6621 | 8382 |
| | | NP_001237030 | 351723638 | 0.9306 | Glycine max | 6622 | 8383 |
| | | ACG24758 | 195605855 | 0.875 | Zea mays | 6623 | 8384 |
| | | ACG33436 | 195623211 | 0.875 | Zea mays | 6624 | 8385 |
| | 129-148 | ACU17625 | 255634523 | 1 | Glycine max | 6625 | 8386 |
| | 290-309 | XP_003548849 | 356561151 | 1 | Glycine max | 6626 | 8387 |
| | | XP_003519868 | 356502117 | 0.8445 | Glycine max | 6627 | 8388 |
| | | XP_003629318 | 357518058 | 0.7456 | Medicago truncatula | 6628 | 8389 |
| | 237-256 | XP_003527981 | 356518628 | 1 | Glycine max | 6629 | 8390 |
| | | AAF73257 | 8132346 | 0.9407 | Pisum sativum | 6630 | 8391 |
| | | ABA00652 | 74231015 | 0.8814 | Gossypium hirsutum | 6631 | 8392 |
| | 37-56 | XP_003547100 | 356557592 | 1 | Glycine max | 6632 | 8393 |
| | | XP_003541782 | 356546742 | 0.862 | Glycine max | 6633 | 8394 |
| | | XP_003593272 | 357445988 | 0.7085 | Medicago truncatula | 6634 | 8395 |
| | 248-267 | ACU23918 | 255646896 | 1 | Glycine max | 6635 | 8396 |
| | | XP_003519685 | 356501746 | 0.9948 | Glycine max | 6636 | 8397 |
| ath-miRf11042-akr | 757-777 | XP_003629993 | 357519408 | 1 | Medicago truncatula | 6637 | 8398 |
| | | ACJ84083 | 217071445 | 0.9917 | Medicago truncatula | 6638 | 8399 |
| | | NP_001235375 | 351727608 | 0.8595 | Glycine max | 6639 | 8400 |
| | | NP_001237170 | 351727706 | 0.8264 | Glycine max | 6640 | 8401 |
| | | CAA10134 | 3860332 | 0.8347 | Cicer arietinum | 6641 | 8402 |
| | | XP_002298184 | 255761085 | 0.719 | Populus trichocarpa | 6642 | |
| | | NP_001237531 | 351723330 | 0.7107 | Glycine max | 6643 | 8403 |
| | | XP_003523409 | 356509341 | 0.7107 | Glycine max | 6644 | 8404 |
| | | | 357519363 | 1 | Medicago truncatula | 6645 | |
| | 361-381 | XP_003592180 | 357443804 | 1 | Medicago truncatula | 6646 | 8405 |
| | | XP_003556131 | 356576015 | 0.7984 | Glycine max | 6647 | 8406 |
| | | XP_003535589 | 356534086 | 0.8 | Glycine max | 6648 | 8407 |
| | | XP_002329680 | 255761085 | 0.777 | Populus trichocarpa | 6649 | |
| | | XP_002276766 | 225464654 | 0.7475 | Vitis vinifera | 6650 | 8408 |
| | | CBI22616 | 270233919 | 0.7213 | Vitis vinifera | 6651 | 8409 |
| | 1042-1062 | XP_003616507 | 357492436 | 1 | Medicago truncatula | 6652 | 8410 |
| | | XP_003518398 | 356499134 | 0.8512 | Glycine max | 6653 | 8411 |
| | | XP_003545247 | 356553814 | 0.8492 | Glycine max | 6654 | 8412 |
| | | XP_003537472 | 356537955 | 0.7738 | Glycine max | 6655 | 8413 |
| | | XP_003552860 | 356569339 | 0.7718 | Glycine max | 6656 | 8414 |
| | | XP_002524242 | 255761086 | 0.7321 | Ricinus communis | 6657 | |
| | | XP_002277622 | 225449359 | 0.7063 | Vitis vinifera | 6658 | 8415 |
| | 520-540 | XP_003534554 | 356531980 | 1 | Glycine max | 6659 | |
| | | XP_003552402 | 356568406 | 0.9572 | Glycine max | 6660 | |
| | | XP_003548671 | 356560791 | 0.7736 | Glycine max | 6661 | |
| | | XP_003528847 | 356520393 | 0.7732 | Glycine max | 6662 | |
| | | XP_003623999 | 357507420 | 0.7898 | Medicago truncatula | 6663 | |
| | | XP_003627563 | 357514548 | 0.7385 | Medicago truncatula | 6664 | |
| | | XP_002276245 | 225454279 | 0.7367 | Vitis vinifera | 6665 | |
| | | XP_002511882 | 255761086 | 0.7349 | Ricinus communis | 6666 | |
| | | CAN74059 | 147789689 | 0.7228 | Vitis vinifera | 6667 | |
| | 1412-1432 | XP_003556131 | 356576015 | 1 | Glycine max | 6668 | 8416 |
| | | XP_003592180 | 357443804 | 0.8203 | Medicago truncatula | 6669 | 8417 |
| csi-miR3948 | 43-66 | XP_003547789 | 356558998 | 1 | Glycine max | 6670 | 8418 |
| | | XP_003531955 | 356526700 | 0.9164 | Glycine max | 6671 | 8419 |
| | | ACU23577 | 255646183 | 0.9078 | Glycine max | 6672 | 8420 |
| | 209-232 | XP_003540784 | 356544697 | 1 | Glycine max | 6673 | 8421 |
| | | XP_003539180 | 356541429 | 0.8869 | Glycine max | 6674 | 8422 |
| | 40-63 | XP_003556473 | 356576709 | 1 | Glycine max | 6675 | 8423 |
| | | XP_003535369 | 356533638 | 0.8958 | Glycine max | 6676 | 8424 |
| | 47-70 | XP_003527776 | 356518214 | 1 | Glycine max | 6677 | 8425 |
| | 77-100 | XP_003550061 | 356563623 | 1 | Glycine max | 6678 | 8426 |
| | | XP_003525811 | 356514233 | 0.9621 | Glycine max | 6679 | 8427 |
| | | XP_002310135 | 255761085 | 0.7098 | Populus trichocarpa | 6680 | |
| | | XP_002523601 | 255761086 | 0.7035 | Ricinus communis | 6681 | |
| | 173-196 | XP_003525811 | 356514233 | 1 | Glycine max | 6682 | 8428 |
| | | XP_003550061 | 356563623 | 0.9591 | Glycine max | 6683 | 8429 |
| | 208-231 | XP_003542594 | 356548408 | 1 | Glycine max | 6684 | 8430 |
| | | XP_003537062 | 356537086 | 0.7495 | Glycine max | 6685 | 8431 |
| | 179-202 | XP_003539180 | 356541429 | 1 | Glycine max | 6686 | 8432 |
| | | XP_003540784 | 356544697 | 0.8923 | Glycine max | 6687 | 8433 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 209-232 | BAD18437 | 47077005 | 1 | Homo sapiens | 6688 | 8434 |
| | | XP_003522605 | 356507705 | 1 | Glycine max | 6689 | 8435 |
| | | XP_003526400 | 356515423 | 0.9316 | Glycine max | 6690 | 8436 |
| | 232-255 | XP_003537062 | 356537086 | 1 | Glycine max | 6691 | 8437 |
| | | XP_003542594 | 356548408 | 0.7416 | Glycine max | 6692 | 8438 |
| ghr-miR2950 | 37-57 | XP_003518096 | 356498514 | 1 | Glycine max | 6693 | 8439 |
| | | XP_003537196 | 356537360 | 0.9379 | Glycine max | 6694 | 8440 |
| | | XP_003516696 | 356495666 | 0.7495 | Glycine max | 6695 | 8441 |
| | 909-929 | XP_003529456 | 356521627 | 1 | Glycine max | 6696 | 8442 |
| | | XP_003556690 | 356577148 | 0.8891 | Glycine max | 6697 | 8443 |
| | | XP_003601600 | 357462636 | 0.8073 | Medicago truncatula | 6698 | 8444 |
| | | XP_003601595 | 357462626 | 0.8073 | Medicago truncatula | 6699 | 8445 |
| | | XP_003601599 | 357462634 | 0.8073 | Medicago truncatula | 6700 | 8446 |
| | | XP_003601596 | 357462628 | 0.8036 | Medicago truncatula | 6701 | 8447 |
| | | XP_003607816 | 357475060 | 0.7764 | Medicago truncatula | 6702 | 8448 |
| | | XP_003601601 | 357462638 | 0.7982 | Medicago truncatula | 6703 | 8449 |
| | | XP_003538519 | 356540080 | 0.7436 | Glycine max | 6704 | 8450 |
| | | XP_002303974 | 255761085 | 0.7491 | Populus trichocarpa | 6705 | |
| | 1446-1466 | BAG68945 | 197209811 | 1 | Lotus japonicus | 6706 | 8451 |
| | | XP_003549436 | 356562352 | 0.881 | Glycine max | 6707 | 8452 |
| | | AAC09468 | 6503252 | 0.8541 | Pisum sativum | 6708 | 8453 |
| | | XP_003541616 | 356546403 | 0.8824 | Glycine max | 6709 | 8454 |
| | | XP_003610109 | 357479646 | 0.8598 | Medicago truncatula | 6710 | 8455 |
| | | XP_002270732 | 225446043 | 0.8116 | Vitis vinifera | 6711 | 8456 |
| | | ACN54324 | 224551851 | 0.7805 | Gossypium hirsutum | 6712 | 8457 |
| | | AAK15261 | 13183565 | 0.7748 | Populus trichocarpa × Populus deltoides | 6713 | 8458 |
| | | CBI17838 | 270228824 | 0.7734 | Vitis vinifera | 6714 | |
| | | XP_002324469 | 255761085 | 0.7677 | Populus trichocarpa | 6715 | |
| | 177-197 | XP_003554852 | 356573405 | 1 | Glycine max | 6716 | 8459 |
| | | XP_003543493 | 356550234 | 0.8998 | Glycine max | 6717 | 8460 |
| | 461-481 | XP_003536297 | 356535528 | 1 | Glycine max | 6718 | 8461 |
| | | XP_003556292 | 356576342 | 0.9205 | Glycine max | 6719 | 8462 |
| | 238-258 | XP_003518581 | 356499506 | 1 | Glycine max | 6720 | 8463 |
| | | XP_003618091 | 357495604 | 0.7113 | Medicago truncatula | 6721 | 8464 |
| gma-miR156g | 75-94 | XP_003520455 | 356503312 | 1 | Glycine max | 6722 | 8465 |
| | | XP_003530170 | 356523079 | 0.848 | Glycine max | 6723 | 8466 |
| | 371-390 | XP_003553428 | 356570509 | 1 | Glycine max | 6724 | 8467 |
| | | XP_003520534 | 356503475 | 0.9081 | Glycine max | 6725 | 8468 |
| | 759-778 | XP_003520534 | 356503475 | 1 | Glycine max | 6726 | 8469 |
| | | XP_003553428 | 356570509 | 0.9081 | Glycine max | 6727 | 8470 |
| | 108-127 | XP_003553944 | 356571558 | 1 | Glycine max | 6728 | 8471 |
| | | XP_003549130 | 356561725 | 0.9452 | Glycine max | 6729 | 8472 |
| | 237-256 | XP_003551188 | 356565928 | 1 | Glycine max | 6730 | 8473 |
| | | XP_003538544 | 356540131 | 0.9106 | Glycine max | 6731 | 8474 |
| | | ACU18328 | 255635963 | 0.9083 | Glycine max | 6732 | 8475 |
| | | XP_003601767 | 357462970 | 0.7064 | Medicago truncatula | 6733 | 8476 |
| | 36-55 | AAM12880 | 20149261 | 1 | Helianthus annuus | 6734 | 8477 |
| | | CBI28152 | 270240501 | 0.991 | Vitis vinifera | 6735 | |
| | | XP_002284967 | 225430201 | 0.991 | Vitis vinifera | 6736 | 8478 |
| | | CBI21000 | 270231236 | 0.991 | Vitis vinifera | 6737 | |
| | | CBI36254 | 270253379 | 0.9819 | Vitis vinifera | 6738 | 8479 |
| | | NP_200330 | 145359269 | 0.9864 | Arabidopsis thaliana | 6739 | 8480 |
| | | XP_003522628 | 356507751 | 0.9819 | Glycine max | 6740 | 8481 |
| | | AEM97804 | 344189954 | 0.9864 | Dimocarpus longan | 6741 | 8482 |
| | | XP_002864382 | 297853636 | 0.9864 | Arabidopsis lyrata subsp. lyrata | 6742 | |
| | | XP_002285307 | 225442824 | 0.9819 | Vitis vinifera | 6743 | 8483 |
| | 1020-1039 | XP_003532399 | 356527605 | 1 | Glycine max | 6744 | 8484 |
| | | XP_003525415 | 356513426 | 0.8914 | Glycine max | 6745 | 8485 |
| | 114-133 | ACU18105 | 255635506 | 1 | Glycine max | 6746 | 8486 |
| | 756-775 | XP_003518080 | 356498481 | 1 | Glycine max | 6747 | 8487 |
| | | XP_003551421 | 356566402 | 0.8408 | Glycine max | 6748 | 8488 |
| | 118-137 | XP_003549130 | 356561725 | 1 | Glycine max | 6749 | 8489 |
| | | XP_003553944 | 356571558 | 0.9452 | Glycine max | 6750 | 8490 |
| | 662-681 | XP_003550514 | 356564545 | 1 | Glycine max | 6751 | 8491 |
| | | XP_003528668 | 356520027 | 0.9389 | Glycine max | 6752 | 8492 |
| | | XP_003541638 | 356546447 | 0.8242 | Glycine max | 6753 | 8493 |
| | | XP_003547234 | 356557871 | 0.808 | Glycine max | 6754 | 8494 |
| | | XP_003594096 | 357447640 | 0.803 | Medicago truncatula | 6755 | 8495 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002279739 | 225432499 | 0.7382 | Vitis vinifera | 6756 | 8496 |
| | | CAN70618 | 147801938 | 0.7406 | Vitis vinifera | 6757 | 8497 |
| | | XP_002314424 | 255761085 | 0.7406 | Populus trichocarpa | 6758 | |
| | | XP_002516799 | 255761086 | 0.7219 | Ricinus communis | 6759 | |
| | | XP_002312735 | 255761085 | 0.7157 | Populus trichocarpa | 6760 | |
| | 691-710 | XP_003525415 | 356513426 | 1 | Glycine max | 6761 | 8498 |
| | | XP_003532399 | 356527605 | 0.9051 | Glycine max | 6762 | 8499 |
| | 114-133 | XP_003538544 | 356540131 | 1 | Glycine max | 6763 | 8500 |
| | | XP_003551188 | 356565928 | 0.9097 | Glycine max | 6764 | 8501 |
| | 1068-1087 | XP_003525436 | 356513468 | 1 | Glycine max | 6765 | 8502 |
| | | XP_003550708 | 356564947 | 0.9204 | Glycine max | 6766 | 8503 |
| | | XP_003522278 | 356507037 | 0.7595 | Glycine max | 6767 | 8504 |
| | 999-1018 | XP_003550708 | 356564947 | 1 | Glycine max | 6768 | 8505 |
| | | XP_003525436 | 356513468 | 0.9373 | Glycine max | 6769 | 8506 |
| | 1098-1117 | XP_003520128 | 356502644 | 1 | Glycine max | 6770 | 8507 |
| | | XP_003517860 | 356498034 | 0.9129 | Glycine max | 6771 | 8508 |
| | 179-198 | XP_003523155 | 356508826 | 1 | Glycine max | 6772 | 8509 |
| | 711-730 | XP_003551421 | 356566402 | 1 | Glycine max | 6773 | 8510 |
| | | XP_003518080 | 356498481 | 0.7962 | Glycine max | 6774 | 8511 |
| gma-miR157c | 164-183 | XP_003549130 | 356561725 | 1 | Glycine max | 6775 | 8512 |
| | | XP_003553944 | 356571558 | 0.9452 | Glycine max | 6776 | 8513 |
| | 593-612 | NP_001236309 | 351724988 | 1 | Glycine max | 6777 | 8514 |
| | | XP_003529339 | 356521389 | 0.838 | Glycine max | 6778 | 8515 |
| gma-miR159a-3p | 305-325 | XP_003551790 | 356567161 | 1 | Glycine max | 6779 | 8516 |
| | 305-325 | XP_003541823 | 356546825 | 1 | Glycine max | 6780 | 8517 |
| | 124-144 | XP_003543825 | 356550908 | 1 | Glycine max | 6781 | 8518 |
| | | XP_003556814 | 356577399 | 0.813 | Glycine max | 6782 | 8519 |
| | 405-425 | XP_003542140 | 356547479 | 1 | Glycine max | 6783 | 8520 |
| | | XP_003546908 | 356557204 | 0.8696 | Glycine max | 6784 | 8521 |
| | 305-325 | XP_003541823 | 356546825 | 1 | Glycine max | 6785 | 8522 |
| | 124-144 | XP_003543825 | 356550908 | 1 | Glycine max | 6786 | 8523 |
| | 839-859 | XP_003526354 | 356515330 | 1 | Glycine max | 6787 | 8524 |
| | | XP_003523913 | 356510372 | 0.9333 | Glycine max | 6788 | 8525 |
| | 73-93 | XP_003535315 | 356533526 | 1 | Glycine max | 6789 | 8526 |
| | | XP_003555178 | 356574075 | 0.9462 | Glycine max | 6790 | 8527 |
| | | XP_003591226 | 357441896 | 0.7849 | Medicago truncatula | 6791 | 8528 |
| | | XP_002512536 | 255761086 | 0.7465 | Ricinus communis | 6792 | |
| | | CBI39621 | 270257428 | 0.7465 | Vitis vinifera | 6793 | 8529 |
| | | CAP59645 | 163913883 | 0.7558 | Vitis vinifera | 6794 | 8530 |
| | | XP_002277312 | 225450534 | 0.7496 | Vitis vinifera | 6795 | 8531 |
| | | XP_002280462 | 225432056 | 0.7404 | Vitis vinifera | 6796 | 8532 |
| | | CAP59646 | 163913885 | 0.7512 | Vitis vinifera | 6797 | 8533 |
| | | CAN63178 | 123711273 | 0.7373 | Vitis vinifera | 6798 | 8534 |
| | 614-634 | XP_003541563 | 356546291 | 1 | Glycine max | 6799 | 8535 |
| | | XP_003545791 | 356554924 | 0.805 | Glycine max | 6800 | 8536 |
| | 905-925 | XP_003556814 | 356577399 | 1 | Glycine max | 6801 | 8537 |
| | | XP_003543825 | 356550908 | 0.8659 | Glycine max | 6802 | 8538 |
| | 2016-2036 | XP_003538988 | 356541033 | 1 | Glycine max | 6803 | 8539 |
| | | XP_003607189 | 357473808 | 0.7407 | Medicago truncatula | 6804 | 8540 |
| | | XP_003604038 | 357467506 | 0.7035 | Medicago truncatula | 6805 | 8541 |
| | 926-946 | XP_003545791 | 356554924 | 1 | Glycine max | 6806 | 8542 |
| | | XP_003541563 | 356546291 | 0.8662 | Glycine max | 6807 | 8543 |
| | 842-862 | XP_003523913 | 356510372 | 1 | Glycine max | 6808 | 8544 |
| | | XP_003526354 | 356515330 | 0.9333 | Glycine max | 6809 | 8545 |
| iba-miR157 | 164-184 | XP_003549130 | 356561725 | 1 | Glycine max | 6810 | 8546 |
| | | XP_003553944 | 356571558 | 0.9452 | Glycine max | 6811 | 8547 |
| | 238-258 | XP_003551188 | 356565928 | 1 | Glycine max | 6812 | 8548 |
| | | XP_003538544 | 356540131 | 0.9106 | Glycine max | 6813 | 8549 |
| | | ACU18328 | 255635963 | 0.9083 | Glycine max | 6814 | 8550 |
| | | XP_003601767 | 357462970 | 0.7064 | Medicago truncatula | 6815 | 8551 |
| | 1129-1149 | XP_003525415 | 356513426 | 1 | Glycine max | 6816 | 8552 |
| | | XP_003532399 | 356527605 | 0.9051 | Glycine max | 6817 | 8553 |
| | 898-918 | XP_003540473 | 356544059 | 1 | Glycine max | 6818 | 8554 |
| | | XP_003543233 | 356549706 | 0.9305 | Glycine max | 6819 | 8555 |
| | | ACU24116 | 255647298 | 0.9251 | Glycine max | 6820 | 8556 |
| | 118-138 | XP_003525436 | 356513468 | 1 | Glycine max | 6821 | 8557 |
| | | XP_003550708 | 356564947 | 0.9204 | Glycine max | 6822 | 8558 |
| | | XP_003522278 | 356507037 | 0.7595 | Glycine max | 6823 | 8559 |
| | 77-97 | XP_003520455 | 356503312 | 1 | Glycine max | 6824 | 8560 |
| | | XP_003530170 | 356523079 | 0.848 | Glycine max | 6825 | 8561 |
| | 498-518 | XP_003553428 | 356570509 | 1 | Glycine max | 6826 | 8562 |
| | | XP_003520534 | 356503475 | 0.9081 | Glycine max | 6827 | 8563 |
| | 50-70 | XP_003550708 | 356564947 | 1 | Glycine max | 6828 | 8564 |
| | | XP_003525436 | 356513468 | 0.9373 | Glycine max | 6829 | 8565 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 170-190 | XP_003538544 | 356540131 | 1 | Glycine max | 6830 | 8566 |
| | | XP_003551188 | 356565928 | 0.9097 | Glycine max | 6831 | 8567 |
| | 593-613 | NP_001236309 | 351724988 | 1 | Glycine max | 6832 | 8568 |
| | | XP_003529339 | 356521389 | 0.838 | Glycine max | 6833 | 8569 |
| | 144-164 | XP_002275728 | 225446415 | 1 | Vitis vinifera | 6834 | 8570 |
| | | AAY16440 | 62856978 | 0.7396 | Betula platyphylla | 6835 | 8571 |
| | 112-132 | XP_003522278 | 356507037 | 1 | Glycine max | 6836 | 8572 |
| | 396-416 | XP_003520128 | 356502644 | 1 | Glycine max | 6837 | 8573 |
| | | XP_003517860 | 356498034 | 0.9129 | Glycine max | 6838 | 8574 |
| | 181-201 | XP_003523155 | 356508826 | 1 | Glycine max | 6839 | 8575 |
| | 77-97 | XP_003520455 | 356503312 | 1 | Glycine max | 6840 | 8576 |
| | 373-393 | XP_003553428 | 356570509 | 1 | Glycine max | 6841 | 8577 |
| | 761-781 | XP_003520534 | 356503475 | 1 | Glycine max | 6842 | 8578 |
| | | XP_003553428 | 356570509 | 0.9081 | Glycine max | 6843 | 8579 |
| | 110-130 | XP_003553944 | 356571558 | 1 | Glycine max | 6844 | 8580 |
| | 239-259 | XP_003551188 | 356565928 | 1 | Glycine max | 6845 | 8581 |
| | 1022-1042 | XP_003532399 | 356527605 | 1 | Glycine max | 6846 | 8582 |
| | | XP_003525415 | 356513426 | 0.8914 | Glycine max | 6847 | 8583 |
| | 593-613 | NP_001236309 | 351724988 | 1 | Glycine max | 6848 | 8584 |
| | 116-136 | ACU18105 | 255635506 | 1 | Glycine max | 6849 | 8585 |
| | 758-778 | XP_003518080 | 356498481 | 1 | Glycine max | 6850 | 8586 |
| | | XP_003551421 | 356566402 | 0.8408 | Glycine max | 6851 | 8587 |
| | 120-140 | XP_003549130 | 356561725 | 1 | Glycine max | 6852 | 8588 |
| | 693-713 | XP_003525415 | 356513426 | 1 | Glycine max | 6853 | 8589 |
| | 656-676 | XP_003517558 | 356497418 | 1 | Glycine max | 6854 | 8590 |
| | | XP_003537666 | 356538348 | 0.9182 | Glycine max | 6855 | 8591 |
| | | XP_003539001 | 356541059 | 0.7453 | Glycine max | 6856 | 8592 |
| | | XP_003540042 | 356543182 | 0.7421 | Glycine max | 6857 | 8593 |
| | 116-136 | XP_003538544 | 356540131 | 1 | Glycine max | 6858 | 8594 |
| | 1070-1090 | XP_003525436 | 356513468 | 1 | Glycine max | 6859 | 8595 |
| | 404-424 | XP_003526029 | 356514674 | 1 | Glycine max | 6860 | 8596 |
| | | XP_003540122 | 356543345 | 0.8919 | Glycine max | 6861 | 8597 |
| | 1100-1120 | XP_003520128 | 356502644 | 1 | Glycine max | 6862 | 8598 |
| | 1001-1021 | XP_003550708 | 356564947 | 1 | Glycine max | 6863 | 8599 |
| | 243-263 | XP_003540122 | 356543345 | 1 | Glycine max | 6864 | 8600 |
| | | XP_003526029 | 356514674 | 0.8684 | Glycine max | 6865 | 8601 |
| | 555-575 | XP_003524444 | 356511459 | 1 | Glycine max | 6866 | 8602 |
| | | XP_003533073 | 356528975 | 0.7951 | Glycine max | 6867 | 8603 |
| | 181-201 | XP_003523155 | 356508826 | 1 | Glycine max | 6868 | 8604 |
| | 713-733 | XP_003551421 | 356566402 | 1 | Glycine max | 6869 | 8605 |
| | | XP_003518080 | 356498481 | 0.7962 | Glycine max | 6870 | 8606 |
| mdm-miR482a-5p | 517-537 | XP_003528897 | 356520494 | 1 | Glycine max | 6871 | 8607 |
| | | ACU19201 | 255637757 | 0.988 | Glycine max | 6872 | 8608 |
| | | XP_003529981 | 356522693 | 0.7784 | Glycine max | 6873 | 8609 |
| | | XP_003521936 | 356506325 | 0.7695 | Glycine max | 6874 | 8610 |
| | 626-646 | XP_003554327 | 356572340 | 1 | Glycine max | 6875 | 8611 |
| | | XP_003521338 | 356505115 | 0.984 | Glycine max | 6876 | 8612 |
| | | XP_003554326 | 356572338 | 1 | Glycine max | 6877 | 8613 |
| | | XP_003521337 | 356505113 | 0.984 | Glycine max | 6878 | 8614 |
| | | AES81717 | 357510420 | 0.869 | Medicago truncatula | 6879 | 8615 |
| | | ACJ84304 | 217071887 | 0.8658 | Medicago truncatula | 6880 | 8616 |
| | | ABN05708 | 46063642 | 0.8594 | Medicago truncatula | 6881 | 8617 |
| | | AES84650 | 339649035 | 0.8339 | Medicago truncatula | 6882 | 8618 |
| | | XP_003542462 | 356548141 | 0.8115 | Glycine max | 6883 | 8619 |
| | | XP_003542461 | 356548139 | 0.8115 | Glycine max | 6884 | 8620 |
| | 204-224 | XP_003625987 | 357511396 | 1 | Medicago truncatula | 6885 | 8621 |
| | | AES82205 | 357511396 | 1 | Medicago truncatula | 6886 | 8622 |
| | | XP_003520757 | 356503939 | 0.8043 | Glycine max | 6887 | 8623 |
| | | XP_003554555 | 356572802 | 0.802 | Glycine max | 6888 | 8624 |
| | 175-195 | XP_003554555 | 356572802 | 1 | Glycine max | 6889 | 8625 |
| | | XP_002271147 | 225437597 | 0.7397 | Vitis vinifera | 6890 | 8626 |
| | | XP_002515261 | 255761086 | 0.7188 | Ricinus communis | 6891 | |
| | 716-736 | XP_003539613 | 356542313 | 1 | Glycine max | 6892 | 8627 |
| | | XP_003543221 | 356549682 | 0.8767 | Glycine max | 6893 | 8628 |
| | 778-798 | XP_003625499 | 357510420 | 1 | Medicago truncatula | 6894 | 8629 |
| | | XP_003554327 | 356572340 | 0.8395 | Glycine max | 6895 | 8630 |
| | | XP_003537175 | 356537316 | 0.8056 | Glycine max | 6896 | 8631 |
| osa-miR159e | 500-520 | XP_003541668 | 356546507 | 1 | Glycine max | 6897 | 8632 |
| | | XP_003547199 | 356557800 | 0.8383 | Glycine max | 6898 | 8633 |
| | 495-515 | XP_003524148 | 356510852 | 1 | Glycine max | 6899 | 8634 |
| | | XP_003531162 | 356525093 | 0.7762 | Glycine max | 6900 | 8635 |
| | 26-46 | XP_003547199 | 356557800 | 1 | Glycine max | 6901 | 8636 |
| | 124-144 | XP_003543825 | 356550908 | 1 | Glycine max | 6902 | 8637 |
| | | XP_003556814 | 356577399 | 0.813 | Glycine max | 6903 | 8638 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 817-837 | XP_003525997 | 356514606 | 1 | *Glycine max* | 6904 | 8639 |
| | | XP_003540066 | 356543230 | 0.8441 | *Glycine max* | 6905 | 8640 |
| | 289-309 | XP_003518627 | 356499601 | 1 | *Glycine max* | 6906 | 8641 |
| | | XP_003542153 | 356547506 | 0.9478 | *Glycine max* | 6907 | 8642 |
| | | ADN33938 | 307136081 | 0.7937 | *Cucumis melo* subsp. *melo* | 6908 | 8643 |
| | | XP_002518919 | 255761086 | 0.7755 | *Ricinus communis* | 6909 | |
| | | XP_002279642 | 225426567 | 0.7755 | *Vitis vinifera* | 6910 | 8644 |
| | | XP_002870592 | 297853636 | 0.7664 | *Arabidopsis lyrata* subsp. *lyrata* | 6911 | |
| | | NP_199024 | 30693991 | 0.7642 | *Arabidopsis thaliana* | 6912 | 8645 |
| | | AAM63843 | 21405504 | 0.7596 | *Arabidopsis thaliana* | 6913 | 8646 |
| | | XP_002299422 | 255761085 | 0.7528 | *Populus trichocarpa* | 6914 | |
| | | XP_002303695 | 255761085 | 0.7574 | *Populus trichocarpa* | 6915 | |
| | 124-144 | XP_003543825 | 356550908 | 1 | *Glycine max* | 6916 | 8647 |
| | 461-481 | XP_003542153 | 356547506 | 1 | *Glycine max* | 6917 | 8648 |
| | | XP_003518627 | 356499601 | 0.9436 | *Glycine max* | 6918 | 8649 |
| | 1162-1182 | XP_003531162 | 356525093 | 1 | *Glycine max* | 6919 | 8650 |
| | | XP_003524148 | 356510852 | 0.7692 | *Glycine max* | 6920 | 8651 |
| | 839-859 | XP_003526354 | 356515330 | 1 | *Glycine max* | 6921 | 8652 |
| | | XP_003523913 | 356510372 | 0.9333 | *Glycine max* | 6922 | 8653 |
| | 495-515 | XP_003524148 | 356510852 | 1 | *Glycine max* | 6923 | 8654 |
| | 949-969 | XP_003547199 | 356557800 | 1 | *Glycine max* | 6924 | 8655 |
| | 614-634 | XP_003541563 | 356546291 | 1 | *Glycine max* | 6925 | 8656 |
| | | XP_003545791 | 356554924 | 0.805 | *Glycine max* | 6926 | 8657 |
| | 905-925 | XP_003556814 | 356577399 | 1 | *Glycine max* | 6927 | 8658 |
| | | XP_003543825 | 356550908 | 0.8659 | *Glycine max* | 6928 | 8659 |
| | 2016-2036 | XP_003538988 | 356541033 | 1 | *Glycine max* | 6929 | 8660 |
| | | XP_003607189 | 357473808 | 0.7407 | *Medicago truncatula* | 6930 | 8661 |
| | | XP_003604038 | 357467506 | 0.7035 | *Medicago truncatula* | 6931 | 8662 |
| | 1330-1350 | XP_003541668 | 356546507 | 1 | *Glycine max* | 6932 | 8663 |
| | 842-862 | XP_003523913 | 356510372 | 1 | *Glycine max* | 6933 | 8664 |
| | | XP_003526354 | 356515330 | 0.9333 | *Glycine max* | 6934 | 8665 |
| | 926-946 | XP_003545791 | 356554924 | 1 | *Glycine max* | 6935 | 8666 |
| | | XP_003541563 | 356546291 | 0.8662 | *Glycine max* | 6936 | 8667 |
| osa-miR159f | 124-144 | XP_003543825 | 356550908 | 1 | *Glycine max* | 6937 | 8668 |
| | | XP_003556814 | 356577399 | 0.813 | *Glycine max* | 6938 | 8669 |
| | 305-325 | XP_003541823 | 356546825 | 1 | *Glycine max* | 6939 | 8670 |
| | 124-144 | XP_003543825 | 356550908 | 1 | *Glycine max* | 6940 | 8671 |
| | 839-859 | XP_003526354 | 356515330 | 1 | *Glycine max* | 6941 | 8672 |
| | | XP_003523913 | 356510372 | 0.9333 | *Glycine max* | 6942 | 8673 |
| | 614-634 | XP_003541563 | 356546291 | 1 | *Glycine max* | 6943 | 8674 |
| | | XP_003545791 | 356554924 | 0.805 | *Glycine max* | 6944 | 8675 |
| | 905-925 | XP_003556814 | 356577399 | 1 | *Glycine max* | 6945 | 8676 |
| | 2016-2036 | XP_003538988 | 356541033 | 1 | *Glycine max* | 6946 | 8677 |
| | | XP_003607189 | 357473808 | 0.7407 | *Medicago truncatula* | 6947 | 8678 |
| | | XP_003604038 | 357467506 | 0.7035 | *Medicago truncatula* | 6948 | 8679 |
| | 842-862 | XP_003523913 | 356510372 | 1 | *Glycine max* | 6949 | 8680 |
| | | XP_003526354 | 356515330 | 0.9333 | *Glycine max* | 6950 | 8681 |
| | 926-946 | XP_003545791 | 356554924 | 1 | *Glycine max* | 6951 | 8682 |
| | | XP_003541563 | 356546291 | 0.8662 | *Glycine max* | 6952 | 8683 |
| osa-miR1850.1 | 796-816 | ABC49719 | 84028520 | 1 | *Arachis hypogaea* | 6953 | 8684 |
| | | NP_001236448 | 351734389 | 0.9568 | *Glycine max* | 6954 | 8685 |
| | | XP_003535034 | 356532953 | 0.9496 | *Glycine max* | 6955 | 8686 |
| | | XP_003594440 | 357448328 | 0.8993 | *Medicago truncatula* | 6956 | 8687 |
| | | ACJ84098 | 217071475 | 0.8921 | *Medicago truncatula* | 6957 | 8688 |
| | | XP_003629907 | 357519236 | 0.8705 | *Medicago truncatula* | 6958 | 8689 |
| | | ABD63906 | 89212811 | 0.8921 | *Gossypium hirsutum* | 6959 | 8690 |
| | | ABD66505 | 89276296 | 0.8849 | *Gossypium hirsutum* | 6960 | 8691 |
| | | ADN34239 | 307136431 | 0.8633 | *Cucumis melo* subsp. *melo* | 6961 | 8692 |
| | | ABD66508 | 89276302 | 0.8849 | *Gossypium hirsutum* | 6962 | 8693 |
| | 746-766 | XP_003535034 | 356532953 | 1 | *Glycine max* | 6963 | 8694 |
| | | CAJ38384 | 106879600 | 0.8849 | *Plantago major* | 6964 | 8695 |
| | | XP_002299887 | 255761085 | 0.9065 | *Populus trichocarpa* | 6965 | |
| | 17-37 | XP_003534041 | 356530948 | 1 | *Glycine max* | 6966 | 8696 |
| | 117-137 | XP_003524950 | 356512486 | 1 | *Glycine max* | 6967 | 8697 |
| | 243-263 | XP_003548988 | 356561437 | 1 | *Glycine max* | 6968 | 8698 |
| | | XP_003548995 | 356561451 | 0.7944 | *Glycine max* | 6969 | 8699 |
| | | XP_003548992 | 356561445 | 0.728 | *Glycine max* | 6970 | 8700 |
| | | XP_003548994 | 356561449 | 0.7846 | *Glycine max* | 6971 | 8701 |
| | | XP_003548993 | 356561447 | 0.921 | *Glycine max* | 6972 | 8702 |
| | | XP_003548986 | 356561433 | 0.8079 | *Glycine max* | 6973 | 8703 |
| | | XP_003548991 | 356561443 | 0.807 | *Glycine max* | 6974 | 8704 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_003617757 | 357494936 | 0.8241 | *Medicago truncatula* | 6975 | 8705 |
| | | XP_003616414 | 357492250 | 0.7971 | *Medicago truncatula* | 6976 | 8706 |
| | 53-73 | XP_003552127 | 356567847 | 1 | *Glycine max* | 6977 | 8707 |
| | | XP_003532277 | 356527355 | 0.9545 | *Glycine max* | 6978 | 8708 |
| | | ADB79567 | 284156655 | 0.7995 | *Arachis hypogaea* | 6979 | 8709 |
| | | XP_002262721 | 225470104 | 0.7433 | *Vitis vinifera* | 6980 | 8710 |
| | | ABX82799 | 296916970 | 0.7219 | *Jatropha curcas* | 6981 | 8711 |
| | | XP_002532744 | 255761086 | 0.7166 | *Ricinus communis* | 6982 | |
| | | XP_002863277 | 297853636 | 0.7112 | *Arabidopsis lyrata* subsp. *lyrata* | 6983 | |
| | | AAC49002 | 595956 | 0.7059 | *Brassica rapa* | 6984 | 8712 |
| | 141-161 | XP_003555849 | 356575439 | 1 | *Glycine max* | 6985 | 8713 |
| | | XP_003592693 | 357444830 | 0.8289 | *Medicago truncatula* | 6986 | 8714 |
| | | XP_002529805 | 255761086 | 0.7425 | *Ricinus communis* | 6987 | |
| | | XP_002306206 | 255761085 | 0.7331 | *Populus trichocarpa* | 6988 | |
| | | XP_002264823 | 225467465 | 0.7221 | *Vitis vinifera* | 6989 | 8715 |
| | | XP_002278507 | 225428128 | 0.719 | *Vitis vinifera* | 6990 | 8716 |
| | | XP_002312937 | 255761085 | 0.7159 | *Populus trichocarpa* | 6991 | |
| | 2940-2960 | XP_003550417 | 356564348 | 1 | *Glycine max* | 6992 | 8717 |
| | | XP_003523561 | 356509653 | 0.7407 | *Glycine max* | 6993 | 8718 |
| | | XP_003523562 | 356509655 | 0.7323 | *Glycine max* | 6994 | 8719 |
| osa-miR1858a | 90-110 | XP_003520359 | 356503118 | 1 | *Glycine max* | 6995 | 8720 |
| | | XP_003547751 | 356558921 | 0.94 | *Glycine max* | 6996 | 8721 |
| | | AES83637 | 339648991 | 0.7389 | *Medicago truncatula* | 6997 | |
| | | XP_003522288 | 356507057 | 0.7176 | *Glycine max* | 6998 | 8722 |
| | | XP_003604071 | 357467572 | 0.706 | *Medicago truncatula* | 6999 | 8723 |
| | 24-44 | XP_003553781 | 356571227 | 1 | *Glycine max* | 7000 | 8724 |
| | | NP_001235053 | 351725668 | 0.8396 | *Glycine max* | 7001 | 8725 |
| | | BAF49302 | 133874197 | 0.7167 | *Clitoria ternatea* | 7002 | 8726 |
| | 364-384 | XP_003554024 | 356571724 | 1 | *Glycine max* | 7003 | 8727 |
| | | XP_003554025 | 356571726 | 0.9937 | *Glycine max* | 7004 | 8728 |
| | | XP_003548728 | 356560906 | 0.9669 | *Glycine max* | 7005 | 8729 |
| | | XP_003624635 | 357508692 | 0.8873 | *Medicago truncatula* | 7006 | 8730 |
| | | XP_002285720 | 225435753 | 0.8202 | *Vitis vinifera* | 7007 | 8731 |
| | | XP_002281591 | 225441588 | 0.8229 | *Vitis vinifera* | 7008 | 8732 |
| | | XP_003531251 | 356525273 | 0.8157 | *Glycine max* | 7009 | 8733 |
| | | XP_002304857 | 255761085 | 0.797 | *Populus trichocarpa* | 7010 | |
| | | XP_002299105 | 255761085 | 0.7898 | *Populus trichocarpa* | 7011 | |
| | | XP_003629733 | 357518888 | 0.7987 | *Medicago truncatula* | 7012 | 8734 |
| | 345-365 | XP_003548728 | 356560906 | 1 | *Glycine max* | 7013 | 8735 |
| | | XP_003554024 | 356571724 | 0.9704 | *Glycine max* | 7014 | 8736 |
| | 24-44 | XP_003553781 | 356571227 | 1 | *Glycine max* | 7015 | 8737 |
| | 56-76 | XP_003521247 | 356504932 | 1 | *Glycine max* | 7016 | 8738 |
| | | XP_003554255 | 356572193 | 0.9395 | *Glycine max* | 7017 | 8739 |
| | | XP_002520726 | 255761086 | 0.7893 | *Ricinus communis* | 7018 | |
| | | XP_002278267 | 225437025 | 0.8136 | *Vitis vinifera* | 7019 | 8740 |
| | | XP_002307588 | 255761085 | 0.7966 | *Populus trichocarpa* | 7020 | |
| | | XP_002892149 | 297853636 | 0.7215 | *Arabidopsis lyrata* subsp. *lyrata* | 7021 | |
| | | NP_563676 | 30678481 | 0.7361 | *Arabidopsis thaliana* | 7022 | 8741 |
| | 360-380 | NP_001237118 | 351726189 | 1 | *Glycine max* | 7023 | 8742 |
| | | XP_003556230 | 356576216 | 0.9243 | *Glycine max* | 7024 | 8743 |
| | | XP_002529571 | 255761086 | 0.7775 | *Ricinus communis* | 7025 | |
| | | XP_002315301 | 255761085 | 0.7706 | *Populus trichocarpa* | 7026 | |
| | | XP_002275232 | 225449067 | 0.7752 | *Vitis vinifera* | 7027 | 8744 |
| | | XP_002312018 | 255761085 | 0.7569 | *Populus trichocarpa* | 7028 | |
| | | ACM45079 | 222136858 | 0.7729 | *Vitis vinifera* | 7029 | 8745 |
| | | XP_002894135 | 297853636 | 0.7729 | *Arabidopsis lyrata* subsp. *lyrata* | 7030 | |
| | | ABA54870 | 76782199 | 0.7638 | *Fagus sylvatica* | 7031 | 8746 |
| | | CAN73646 | 123693264 | 0.7706 | *Vitis vinifera* | 7032 | |
| | 277-297 | XP_003591923 | 357443290 | 1 | *Medicago truncatula* | 7033 | 8747 |
| | 180-200 | XP_003524517 | 356511610 | 1 | *Glycine max* | 7034 | 8748 |
| | | XP_003549799 | 356563090 | 0.9173 | *Glycine max* | 7035 | 8749 |
| | 564-584 | NP_001235053 | 351725668 | 1 | *Glycine max* | 7036 | 8750 |
| | | XP_003553781 | 356571227 | 0.8319 | *Glycine max* | 7037 | 8751 |
| | | XP_003626556 | 357512534 | 0.7059 | *Medicago truncatula* | 7038 | 8752 |
| | | ACJ85806 | 217074891 | 0.7017 | *Medicago truncatula* | 7039 | 8753 |
| | 369-389 | XP_003530234 | 356523208 | 1 | *Glycine max* | 7040 | 8754 |
| | | XP_003551508 | 356566578 | 0.9298 | *Glycine max* | 7041 | 8755 |
| | 188-208 | XP_002529571 | 255761086 | 1 | *Ricinus communis* | 7042 | |
| | | NP_564534 | 145336530 | 0.8046 | *Arabidopsis thaliana* | 7043 | 8756 |
| | | AAG50662 | 12321108 | 0.8023 | *Arabidopsis thaliana* | 7044 | 8757 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 378-398 | XP_003551508 | 356566578 | 1 | Glycine max | 7045 | 8758 |
| | | XP_003530234 | 356523208 | 0.8745 | Glycine max | 7046 | 8759 |
| | 231-251 | XP_003528545 | 356519775 | 1 | Glycine max | 7047 | 8760 |
| | | XP_003556667 | 356577102 | 0.9204 | Glycine max | 7048 | 8761 |
| | | XP_003607899 | 357475226 | 0.7898 | Medicago truncatula | 7049 | 8762 |
| | 156-176 | XP_003547641 | 356558699 | 1 | Glycine max | 7050 | 8763 |
| | | XP_003548802 | 356561057 | 0.9768 | Glycine max | 7051 | 8764 |
| | 141-161 | XP_003543554 | 356550357 | 1 | Glycine max | 7052 | 8765 |
| | | XP_003554155 | 356571993 | 0.932 | Glycine max | 7053 | 8766 |
| | 180-200 | XP_003549799 | 356563090 | 1 | Glycine max | 7054 | 8767 |
| | | XP_003524517 | 356511610 | 0.9176 | Glycine max | 7055 | 8768 |
| | 192-212 | XP_003531267 | 356525308 | 1 | Glycine max | 7056 | 8769 |
| | | XP_003624841 | 357509104 | 0.7936 | Medicago truncatula | 7057 | 8770 |
| | | XP_003522101 | 356506673 | 0.7277 | Glycine max | 7058 | 8771 |
| | 132-152 | XP_003556667 | 356577102 | 1 | Glycine max | 7059 | 8772 |
| | | XP_003528545 | 356519775 | 0.9129 | Glycine max | 7060 | 8773 |
| psi-miR159 | 124-144 | XP_003543825 | 356550908 | 1 | Glycine max | 7061 | 8774 |
| | | XP_003556814 | 356577399 | 0.813 | Glycine max | 7062 | 8775 |
| | 289-309 | XP_003518627 | 356499601 | 1 | Glycine max | 7063 | 8776 |
| | | XP_003542153 | 356547506 | 0.9478 | Glycine max | 7064 | 8777 |
| | | ADN33938 | 307136081 | 0.7937 | Cucumis melo subsp. melo | 7065 | 8778 |
| | | XP_002518919 | 255761086 | 0.7755 | Ricinus communis | 7066 | |
| | | XP_002279642 | 225426567 | 0.7755 | Vitis vinifera | 7067 | 8779 |
| | | XP_002870592 | 297853636 | 0.7664 | Arabidopsis lyrata subsp. lyrata | 7068 | |
| | | NP_199024 | 30693991 | 0.7642 | Arabidopsis thaliana | 7069 | 8780 |
| | | AAM63843 | 21405504 | 0.7596 | Arabidopsis thaliana | 7070 | 8781 |
| | | XP_002299422 | 255761085 | 0.7528 | Populus trichocarpa | 7071 | |
| | | XP_002303695 | 255761085 | 0.7574 | Populus trichocarpa | 7072 | |
| | 124-144 | XP_003543825 | 356550908 | 1 | Glycine max | 7073 | 8782 |
| | 461-481 | XP_003542153 | 356547506 | 1 | Glycine max | 7074 | 8783 |
| | | XP_003518627 | 356499601 | 0.9436 | Glycine max | 7075 | 8784 |
| | 839-859 | XP_003526354 | 356515330 | 1 | Glycine max | 7076 | 8785 |
| | | XP_003523913 | 356510372 | 0.9333 | Glycine max | 7077 | 8786 |
| | 614-634 | XP_003541563 | 356546291 | 1 | Glycine max | 7078 | 8787 |
| | | XP_003545791 | 356554924 | 0.805 | Glycine max | 7079 | 8788 |
| | 905-925 | XP_003556814 | 356577399 | 1 | Glycine max | 7080 | 8789 |
| | 19-39 | NP_001236539 | 351724240 | 1 | Glycine max | 7081 | 8790 |
| | | NP_001237767 | 351722762 | 0.9915 | Glycine max | 7082 | 8791 |
| | | NP_001237736 | 351721871 | 0.7778 | Glycine max | 7083 | 8792 |
| | | BAF50740 | 139005586 | 0.7436 | Apios americana | 7084 | 8793 |
| | | XP_003623947 | 357507316 | 0.7094 | Medicago truncatula | 7085 | 8794 |
| | 2016-2036 | XP_003538988 | 356541033 | 1 | Glycine max | 7086 | 8795 |
| | | XP_003607189 | 357473808 | 0.7407 | Medicago truncatula | 7087 | 8796 |
| | | XP_003604038 | 357467506 | 0.7035 | Medicago truncatula | 7088 | 8797 |
| | 926-946 | XP_003545791 | 356554924 | 1 | Glycine max | 7089 | 8798 |
| | | XP_003541563 | 356546291 | 0.8662 | Glycine max | 7090 | 8799 |
| | 842-862 | XP_003523913 | 356510372 | 1 | Glycine max | 7091 | 8800 |
| | | XP_003526354 | 356515330 | 0.9333 | Glycine max | 7092 | 8801 |
| pta-miR156a | 161-180 | XP_003549130 | 356561725 | 1 | Glycine max | 7093 | 8802 |
| | | XP_003553944 | 356571558 | 0.9452 | Glycine max | 7094 | 8803 |
| | 106-125 | XP_003520455 | 356503312 | 1 | Glycine max | 7095 | 8804 |
| | | XP_003530170 | 356523079 | 0.848 | Glycine max | 7096 | 8805 |
| | 115-134 | XP_003525436 | 356513468 | 1 | Glycine max | 7097 | 8806 |
| | | XP_003550708 | 356564947 | 0.9204 | Glycine max | 7098 | 8807 |
| | | XP_003522278 | 356507037 | 0.7595 | Glycine max | 7099 | 8808 |
| | 47-66 | XP_003550708 | 356564947 | 1 | Glycine max | 7100 | 8809 |
| | | XP_003525436 | 356513468 | 0.9373 | Glycine max | 7101 | 8810 |
| | 495-514 | XP_003553428 | 356570509 | 1 | Glycine max | 7102 | 8811 |
| | | XP_003520534 | 356503475 | 0.9081 | Glycine max | 7103 | 8812 |
| | 303-322 | XP_003530747 | 356524258 | 1 | Glycine max | 7104 | |
| | | XP_003553084 | 356569799 | 0.9116 | Glycine max | 7105 | |
| | 393-412 | XP_003520128 | 356502644 | 1 | Glycine max | 7106 | 8813 |
| | | XP_003517860 | 356498034 | 0.9129 | Glycine max | 7107 | 8814 |
| | 109-128 | XP_003522278 | 356507037 | 1 | Glycine max | 7108 | 8815 |
| | 178-197 | XP_003523155 | 356508826 | 1 | Glycine max | 7109 | 8816 |
| | 755-774 | XP_003518080 | 356498481 | 1 | Glycine max | 7110 | 8817 |
| | | XP_003551421 | 356566402 | 0.8408 | Glycine max | 7111 | 8818 |
| | 117-136 | XP_003549130 | 356561725 | 1 | Glycine max | 7112 | 8819 |
| | 734-753 | XP_003553428 | 356570509 | 1 | Glycine max | 7113 | 8820 |
| | 815-834 | XP_003553944 | 356571558 | 1 | Glycine max | 7114 | 8821 |
| | 121-140 | ACU18105 | 255635506 | 1 | Glycine max | 7115 | 8822 |
| | 1067-1086 | XP_003525436 | 356513468 | 1 | Glycine max | 7116 | 8823 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 106-125 | XP_003520455 | 356503312 | 1 | *Glycine max* | 7117 | 8824 |
| | 1097-1116 | XP_003520128 | 356502644 | 1 | *Glycine max* | 7118 | 8825 |
| | 998-1017 | XP_003550708 | 356564947 | 1 | *Glycine max* | 7119 | 8826 |
| | 178-197 | XP_003523155 | 356508826 | 1 | *Glycine max* | 7120 | 8827 |
| | 590-609 | NP_001236309 | 351724988 | 1 | *Glycine max* | 7121 | 8828 |
| | | XP_003529339 | 356521389 | 0.838 | *Glycine max* | 7122 | 8829 |
| | 710-729 | XP_003551421 | 356566402 | 1 | *Glycine max* | 7123 | 8830 |
| | | XP_003518080 | 356498481 | 0.7962 | *Glycine max* | 7124 | 8831 |
| pta-miR156b | 161-180 | XP_003549130 | 356561725 | 1 | *Glycine max* | 7125 | 8832 |
| | | XP_003553944 | 356571558 | 0.9452 | *Glycine max* | 7126 | 8833 |
| | 320-339 | XP_003531511 | 356525799 | 1 | *Glycine max* | 7127 | 8834 |
| | | XP_003546792 | 356556969 | 0.7324 | *Glycine max* | 7128 | 8835 |
| | 115-134 | XP_003525436 | 356513468 | 1 | *Glycine max* | 7129 | 8836 |
| | | XP_003550708 | 356564947 | 0.9204 | *Glycine max* | 7130 | 8837 |
| | | XP_003522278 | 356507037 | 0.7595 | *Glycine max* | 7131 | 8838 |
| | 106-125 | XP_003520455 | 356503312 | 1 | *Glycine max* | 7132 | 8839 |
| | | XP_003530170 | 356523079 | 0.848 | *Glycine max* | 7133 | 8840 |
| | 47-66 | XP_003550708 | 356564947 | 1 | *Glycine max* | 7134 | 8841 |
| | | XP_003525436 | 356513468 | 0.9373 | *Glycine max* | 7135 | 8842 |
| | 495-514 | XP_003553428 | 356570509 | 1 | *Glycine max* | 7136 | 8843 |
| | | XP_003520534 | 356503475 | 0.9081 | *Glycine max* | 7137 | 8844 |
| | 396-415 | ABW03160 | 157922334 | 1 | *Pisum sativum* | 7138 | 8845 |
| | | XP_003546545 | 356556463 | 0.9946 | lipoamide | 7139 | 8846 |
| | | ACU19644 | 255638677 | 0.9919 | *Glycine max* | 7140 | 8847 |
| | | XP_003533815 | 356530492 | 0.9621 | lipoamide | 7141 | 8848 |
| | | CAG14980 | 45720177 | 0.8916 | *Cicer arietinum* | 7142 | 8849 |
| | | ABW03161 | 157922336 | 0.8862 | *Pisum sativum* | 7143 | 8850 |
| | | XP_003595440 | 357450326 | 0.878 | *Medicago truncatula* | 7144 | 8851 |
| | | XP_002314330 | 255761085 | 0.8699 | *Populus trichocarpa* | 7145 | |
| | | XP_003621874 | 357503170 | 0.8564 | *Medicago truncatula* | 7146 | 8852 |
| | | XP_002267959 | 225432170 | 0.8618 | *Vitis vinifera* | 7147 | 8853 |
| | 1563-1582 | XP_002526256 | 255761086 | 1 | *Ricinus communis* | 7148 | |
| | | XP_002318437 | 255761085 | 0.9495 | *Populus trichocarpa* | 7149 | |
| | | XP_002276600 | 225455335 | 0.946 | *Vitis vinifera* | 7150 | 8854 |
| | | CBI23029 | 270234399 | 0.946 | *Vitis vinifera* | 7151 | 8855 |
| | | XP_002515853 | 255761086 | 0.9414 | *Ricinus communis* | 7152 | |
| | | XP_003530452 | 356523654 | 0.8886 | *Glycine max* | 7153 | 8856 |
| | | XP_003525330 | 356513256 | 0.884 | *Glycine max* | 7154 | 8857 |
| | | XP_002864245 | 297853636 | 0.8794 | *Arabidopsis lyrata* subsp. *lyrata* | 7155 | |
| | | NP_200160 | 42568511 | 0.876 | *Arabidopsis thaliana* | 7156 | 8858 |
| | | BAJ93177 | 326526000 | 0.8324 | *Hordeum vulgare* subsp. *vulgare* | 7157 | 8859 |
| | 393-412 | XP_003520128 | 356502644 | 1 | *Glycine max* | 7158 | 8860 |
| | | XP_003517860 | 356498034 | 0.9129 | *Glycine max* | 7159 | 8861 |
| | 109-128 | XP_003522278 | 356507037 | 1 | *Glycine max* | 7160 | 8862 |
| | 178-197 | XP_003523155 | 356508826 | 1 | *Glycine max* | 7161 | 8863 |
| | 203-222 | XP_003551276 | 356566105 | 1 | *Glycine max* | 7162 | 8864 |
| | | XP_003538548 | 356540139 | 0.9368 | *Glycine max* | 7163 | 8865 |
| | | XP_003601783 | 357463002 | 0.8103 | *Medicago truncatula* | 7164 | 8866 |
| | | XP_003524894 | 356512372 | 0.7615 | *Glycine max* | 7165 | 8867 |
| | | XP_003531195 | 356525159 | 0.7759 | *Glycine max* | 7166 | 8868 |
| | | XP_002514915 | 255761086 | 0.7557 | *Ricinus communis* | 7167 | |
| | | XP_002297844 | 255761085 | 0.7471 | *Populus trichocarpa* | 7168 | |
| | | XP_002304680 | 255761085 | 0.7414 | *Populus trichocarpa* | 7169 | |
| | | XP_002271442 | 225425417 | 0.7098 | *Vitis vinifera* | 7170 | 8869 |
| | 74-93 | XP_003520455 | 356503312 | 1 | *Glycine max* | 7171 | 8870 |
| | 370-389 | XP_003553428 | 356570509 | 1 | *Glycine max* | 7172 | 8871 |
| | 758-777 | XP_003520534 | 356503475 | 1 | *Glycine max* | 7173 | 8872 |
| | | XP_003553428 | 356570509 | 0.9081 | *Glycine max* | 7174 | 8873 |
| | 107-126 | XP_003553944 | 356571558 | 1 | *Glycine max* | 7175 | 8874 |
| | 35-54 | AAM12880 | 20149261 | 1 | *Helianthus annuus* | 7176 | 8875 |
| | | CBI28152 | 270240501 | 0.991 | *Vitis vinifera* | 7177 | |
| | | XP_002284967 | 225430201 | 0.991 | *Vitis vinifera* | 7178 | 8876 |
| | | CBI21000 | 270231236 | 0.991 | *Vitis vinifera* | 7179 | |
| | | CBI36254 | 270253379 | 0.9819 | *Vitis vinifera* | 7180 | 8877 |
| | | NP_200330 | 145359269 | 0.9864 | *Arabidopsis thaliana* | 7181 | 8878 |
| | | XP_003522628 | 356507751 | 0.9819 | *Glycine max* | 7182 | 8879 |
| | | AEM97804 | 344189954 | 0.9864 | *Dimocarpus longan* | 7183 | 8880 |
| | | XP_002864382 | 297853636 | 0.9864 | *Arabidopsis lyrata* subsp. *lyrata* | 7184 | |
| | | XP_002285307 | 225442824 | 0.9819 | *Vitis vinifera* | 7185 | 8881 |
| | 1019-1038 | XP_003532399 | 356527605 | 1 | *Glycine max* | 7186 | 8882 |
| | | XP_003525415 | 356513426 | 0.8914 | *Glycine max* | 7187 | 8883 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 113-132 | ACU18105 | 255635506 | 1 | Glycine max | 7188 | 8884 |
| | 755-774 | XP_003518080 | 356498481 | 1 | Glycine max | 7189 | 8885 |
| | | XP_003551421 | 356566402 | 0.8408 | Glycine max | 7190 | 8886 |
| | 117-136 | XP_003549130 | 356561725 | 1 | Glycine max | 7191 | 8887 |
| | 690-709 | XP_003525415 | 356513426 | 1 | Glycine max | 7192 | 8888 |
| | | XP_003532399 | 356527605 | 0.9051 | Glycine max | 7193 | 8889 |
| | 1067-1086 | XP_003525436 | 356513468 | 1 | Glycine max | 7194 | 8890 |
| | 1097-1116 | XP_003520128 | 356502644 | 1 | Glycine max | 7195 | 8891 |
| | 998-1017 | XP_003550708 | 356564947 | 1 | Glycine max | 7196 | 8892 |
| | 178-197 | XP_003523155 | 356508826 | 1 | Glycine max | 7197 | 8893 |
| | 467-486 | XP_003610314 | 357480056 | 1 | Medicago truncatula | 7198 | 8894 |
| | | XP_003549541 | 356562566 | 0.8796 | Glycine max | 7199 | 8895 |
| | | XP_003519149 | 356500658 | 0.8728 | Glycine max | 7200 | 8896 |
| | | XP_003540100 | 356543299 | 0.8605 | Glycine max | 7201 | 8897 |
| | | XP_002278464 | 225445858 | 0.8098 | Vitis vinifera | 7202 | 8898 |
| | | XP_002529385 | 255761086 | 0.8167 | Ricinus communis | 7203 | |
| | | XP_002325129 | 255761085 | 0.7852 | Populus trichocarpa | 7204 | |
| | | NP_851209 | 42570605 | 0.762 | Arabidopsis thaliana | 7205 | 8899 |
| | | XP_002864540 | 297853636 | 0.7579 | Arabidopsis lyrata subsp. lyrata | 7206 | |
| | | NP_974953 | 42573713 | 0.7565 | Arabidopsis thaliana | 7207 | 8900 |
| | 710-729 | XP_003551421 | 356566402 | 1 | Glycine max | 7208 | 8901 |
| | | XP_003518080 | 356498481 | 0.7962 | Glycine max | 7209 | 8902 |
| ptc-miRf10226-akr | 312-334 | XP_003547131 | 356557655 | 1 | Glycine max | 7210 | 8903 |
| | | XP_003541752 | 356546681 | 0.9148 | Glycine max | 7211 | 8904 |
| | 247-269 | XP_003542817 | 356548860 | 1 | Glycine max | 7212 | 8905 |
| | | XP_003546711 | 356556804 | 0.9141 | Glycine max | 7213 | 8906 |
| | | AET02361 | 357515192 | 0.7607 | Medicago truncatula | 7214 | 8907 |
| | 131-153 | XP_003523607 | | 1 | Glycine max | 7215 | |
| | | XP_003525906 | | 0.9439 | Glycine max | 7216 | |
| | 106-128 | XP_003549610 | 356562705 | 1 | Glycine max | 7217 | 8908 |
| | | XP_003529657 | 356522038 | 0.8762 | Glycine max | 7218 | 8909 |
| | 161-183 | XP_003525906 | 356514424 | 1 | Glycine max | 7219 | 8910 |
| | | XP_003523607 | 356509746 | 0.9381 | Glycine max | 7220 | 8911 |
| ptc-miRf10271-akr | 123-143 | XP_003543825 | 356550908 | 1 | Glycine max | 7221 | 8912 |
| | | XP_003556814 | 356577399 | 0.813 | Glycine max | 7222 | 8913 |
| | 423-443 | XP_002325684 | 255761085 | 1 | Populus trichocarpa | 7223 | |
| | | XP_002319934 | 255761085 | 0.9342 | Populus trichocarpa | 7224 | |
| | | ACU14088 | 255627486 | 0.8202 | Glycine max | 7225 | 8914 |
| | | XP_003543368 | 356549979 | 0.8114 | Glycine max | 7226 | 8915 |
| | | NP_001237648 | 351726723 | 0.7982 | Glycine max | 7227 | 8916 |
| | | ACU20677 | 255640786 | 0.7807 | Glycine max | 7228 | 8917 |
| | | XP_002284361 | 225461286 | 0.7719 | Vitis vinifera | 7229 | 8918 |
| | | ADU05416 | 315364829 | 0.7851 | Citrullus lanatus | 7230 | 8919 |
| | | XP_002265183 | 225465748 | 0.75 | Vitis vinifera | 7231 | 8920 |
| | | XP_002513246 | 255761086 | 0.807 | Ricinus communis | 7232 | |
| | 544-564 | ACU20677 | 255640786 | 1 | Glycine max | 7233 | 8921 |
| | | P26291 | | 0.7099 | Pisum sativum | 7234 | |
| | | XP_003597086 | 357453610 | 0.7023 | Medicago truncatula | 7235 | 8922 |
| | 304-324 | XP_003541823 | 356546825 | 1 | Glycine max | 7236 | 8923 |
| | 288-308 | XP_003518627 | 356499601 | 1 | Glycine max | 7237 | 8924 |
| | | XP_003542153 | 356547506 | 0.9478 | Glycine max | 7238 | 8925 |
| | | ADN33938 | 307136081 | 0.7937 | Cucumis melo subsp. melo | 7239 | 8926 |
| | | XP_002518919 | 255761086 | 0.7755 | Ricinus communis | 7240 | |
| | | XP_002279642 | 225426567 | 0.7755 | Vitis vinifera | 7241 | 8927 |
| | | XP_002870592 | 297853636 | 0.7664 | Arabidopsis lyrata subsp. lyrata | 7242 | |
| | | NP_199024 | 30693991 | 0.7642 | Arabidopsis thaliana | 7243 | 8928 |
| | | AAM63843 | 21405504 | 0.7596 | Arabidopsis thaliana | 7244 | 8929 |
| | | XP_002299422 | 255761085 | 0.7528 | Populus trichocarpa | 7245 | |
| | | XP_002303695 | 255761085 | 0.7574 | Populus trichocarpa | 7246 | |
| | 123-143 | XP_003543825 | 356550908 | 1 | Glycine max | 7247 | 8930 |
| | 460-480 | XP_003542153 | 356547506 | 1 | Glycine max | 7248 | 8931 |
| | | XP_003518627 | 356499601 | 0.9436 | Glycine max | 7249 | 8932 |
| | 838-858 | XP_003526354 | 356515330 | 1 | Glycine max | 7250 | 8933 |
| | | XP_003523913 | 356510372 | 0.9333 | Glycine max | 7251 | 8934 |
| | 72-92 | XP_003535315 | 356533526 | 1 | Glycine max | 7252 | 8935 |
| | | XP_003555178 | 356574075 | 0.9462 | Glycine max | 7253 | 8936 |
| | | XP_003591226 | 357441896 | 0.7849 | Medicago truncatula | 7254 | 8937 |
| | | XP_002512536 | 255761086 | 0.7465 | Ricinus communis | 7255 | |
| | | CBI39621 | 270257428 | 0.7465 | Vitis vinifera | 7256 | 8938 |
| | | CAP59645 | 163913883 | 0.7558 | Vitis vinifera | 7257 | 8939 |
| | | XP_002277312 | 225450534 | 0.7496 | Vitis vinifera | 7258 | 8940 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002280462 | 225432056 | 0.7404 | *Vitis vinifera* | 7259 | 8941 |
| | | CAP59646 | 163913885 | 0.7512 | *Vitis vinifera* | 7260 | 8942 |
| | | CAN63178 | 123711273 | 0.7373 | *Vitis vinifera* | 7261 | 8943 |
| | 157-177 | XP_003594856 | 357449158 | 1 | *Medicago truncatula* | 7262 | 8944 |
| | | XP_003533661 | 356530178 | 0.913 | *Glycine max* | 7263 | 8945 |
| | | ACU18911 | 255637160 | 0.9091 | *Glycine max* | 7264 | 8946 |
| | | ACU19698 | 255638787 | 0.9051 | *Glycine max* | 7265 | 8947 |
| | | XP_002273965 | 225423594 | 0.83 | *Vitis vinifera* | 7266 | 8948 |
| | | NP_001058303 | 115469407 | 0.7984 | *Oryza sativa* Japonica Group | 7267 | 8949 |
| | | XP_002528147 | 255761086 | 0.8063 | *Ricinus communis* | 7268 | |
| | | AEL99129 | 343172851 | 0.8142 | *Silene latifolia* | 7269 | 8950 |
| | | AEL99130 | 343172853 | 0.8103 | *Silene latifolia* | 7270 | 8951 |
| | | XP_002438809 | 255761094 | 0.7787 | *Sorghum bicolor* | 7271 | |
| | 613-633 | XP_003541563 | 356546291 | 1 | *Glycine max* | 7272 | 8952 |
| | | XP_003545791 | 356554924 | 0.805 | *Glycine max* | 7273 | 8953 |
| | 904-924 | XP_003556814 | 356577399 | 1 | *Glycine max* | 7274 | 8954 |
| | 2015-2035 | XP_003538988 | 356541033 | 1 | *Glycine max* | 7275 | 8955 |
| | | XP_003607189 | 357473808 | 0.7407 | *Medicago truncatula* | 7276 | 8956 |
| | | XP_003604038 | 357467506 | 0.7035 | *Medicago truncatula* | 7277 | 8957 |
| | 841-861 | XP_003523913 | 356510372 | 1 | *Glycine max* | 7278 | 8958 |
| | | XP_003526354 | 356515330 | 0.9333 | *Glycine max* | 7279 | 8959 |
| | 925-945 | XP_003545791 | 356554924 | 1 | *Glycine max* | 7280 | 8960 |
| | | XP_003541563 | 356546291 | 0.8662 | *Glycine max* | 7281 | 8961 |
| ptc-miRf10734-akr | 371-391 | XP_003518621 | 356499589 | 1 | *Glycine max* | 7282 | 8962 |
| | | XP_003529232 | 356521172 | 0.9575 | *Glycine max* | 7283 | 8963 |
| | | ABI48270 | 113911567 | 0.8826 | *Lotus japonicus* | 7284 | 8964 |
| | | XP_003525213 | 356513021 | 0.8512 | *Glycine max* | 7285 | 8965 |
| | | XP_003530935 | 356524637 | 0.8502 | *Glycine max* | 7286 | 8966 |
| | | XP_003631014 | 357521450 | 0.836 | *Medicago truncatula* | 7287 | 8967 |
| | | XP_002285117 | 225424439 | 0.8117 | *Vitis vinifera* | 7288 | 8968 |
| | | ACE63259 | 190148352 | 0.8067 | *Betula pendula* | 7289 | 8969 |
| | | ABI48271 | 113911569 | 0.8259 | *Lotus japonicus* | 7290 | 8970 |
| | | XP_002314765 | 255761085 | 0.7783 | *Populus trichocarpa* | 7291 | |
| | 1151-1171 | XP_003520774 | 356503973 | 1 | *Glycine max* | 7292 | 8971 |
| | 1761-1781 | XP_003523576 | 356509683 | 1 | *Glycine max* | 7293 | |
| | | XP_003527692 | 356518039 | 0.8899 | *Glycine max* | 7294 | |
| | 1929-1949 | XP_003527692 | 356518039 | 1 | *Glycine max* | 7295 | |
| | | XP_003523576 | 356509683 | 0.8906 | *Glycine max* | 7296 | |
| | 1230-1250 | XP_003538849 | 356540752 | 1 | *Glycine max* | 7297 | 8972 |
| | | XP_003520774 | 356503973 | 0.7213 | *Glycine max* | 7298 | 8973 |
| ptc-miRf10985-akr | 161-180 | XP_003549130 | 356561725 | 1 | *Glycine max* | 7299 | 8974 |
| | | XP_003553944 | 356571558 | 0.9452 | *Glycine max* | 7300 | 8975 |
| | 1659-1678 | AAF67341 | 7682676 | 1 | *Vigna radiata* | 7301 | 8976 |
| | | ACF22882 | 193850556 | 0.9362 | *Glycine max* | 7302 | |
| | | XP_003546457 | 356556285 | 0.9334 | *Glycine max* | 7303 | 8977 |
| | | XP_003550633 | 356564793 | 0.8239 | *Glycine max* | 7304 | 8978 |
| | | CAA09457 | 3641864 | 0.8017 | *Cicer arietinum* | 7305 | 8979 |
| | | CAA06309 | 14274980 | 0.7961 | *Cicer arietinum* | 7306 | 8980 |
| | | CAA09467 | 3860419 | 0.8058 | *Lupinus angustifolius* | 7307 | 8981 |
| | | XP_002514108 | 255761086 | 0.7878 | *Ricinus communis* | 7308 | |
| | | XP_003595162 | 357449770 | 0.7906 | *Medicago truncatula* | 7309 | 8982 |
| | | XP_002308268 | 255761085 | 0.7684 | *Populus trichocarpa* | 7310 | |
| | 235-254 | BAF31130 | 114213453 | 1 | *Vicia faba* | 7311 | 8983 |
| | | P48488 | | 0.9751 | *Medicago sativa* subsp. × *varia* | 7312 | |
| | | ACJ84258 | 217071795 | 0.972 | *Medicago truncatula* | 7313 | 8984 |
| | | XP_003532976 | 356528780 | 0.9346 | *Glycine max* | 7314 | 8985 |
| | | XP_003525372 | 356513340 | 0.9283 | *Glycine max* | 7315 | 8986 |
| | | ACU20069 | 255639548 | 0.9252 | *Glycine max* | 7316 | 8987 |
| | | XP_002509868 | 255761086 | 0.9034 | *Ricinus communis* | 7317 | |
| | | XP_002298008 | 255761085 | 0.8972 | *Populus trichocarpa* | 7318 | |
| | | XP_002277816 | 225426133 | 0.9034 | *Vitis vinifera* | 7319 | 8988 |
| | | NP_176587 | 145337150 | 0.8442 | *Arabidopsis thaliana* | 7320 | 8989 |
| | 235-254 | XP_003551188 | 356565928 | 1 | *Glycine max* | 7321 | 8990 |
| | | XP_003538544 | 356540131 | 0.9106 | *Glycine max* | 7322 | 8991 |
| | | ACU18328 | 255635963 | 0.9083 | *Glycine max* | 7323 | 8992 |
| | | XP_003601767 | 357462970 | 0.7064 | *Medicago truncatula* | 7324 | 8993 |
| | 495-514 | XP_003553428 | 356570509 | 1 | *Glycine max* | 7325 | 8994 |
| | | XP_003520534 | 356503475 | 0.9081 | *Glycine max* | 7326 | 8995 |
| | 51-70 | XP_003545057 | 356553424 | 1 | *Glycine max* | 7327 | 8996 |
| | | XP_003519693 | 356501762 | 0.9036 | *Glycine max* | 7328 | 8997 |
| | | XP_002312804 | 255761085 | 0.7267 | *Populus trichocarpa* | 7329 | |
| | | XP_002279611 | 225428277 | 0.7199 | *Vitis vinifera* | 7330 | 8998 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 167-186 | XP_003538544 | 356540131 | 1 | Glycine max | 7331 | 8999 |
| | | XP_003551188 | 356565928 | 0.9097 | Glycine max | 7332 | 9000 |
| | 109-128 | XP_003522278 | 356507037 | 1 | Glycine max | 7333 | 9001 |
| | | XP_003525436 | 356513468 | 0.7319 | Glycine max | 7334 | 9002 |
| | | XP_003550708 | 356564947 | 0.7072 | Glycine max | 7335 | 9003 |
| | 393-412 | XP_003520128 | 356502644 | 1 | Glycine max | 7336 | 9004 |
| | | XP_003517860 | 356498034 | 0.9129 | Glycine max | 7337 | 9005 |
| | 217-236 | AES84797 | 339649045 | 1 | Medicago truncatula | 7338 | 9006 |
| | | XP_003518611 | 356499568 | 0.8041 | Glycine max | 7339 | 9007 |
| | | XP_003529219 | 356521146 | 0.7947 | Glycine max | 7340 | 9008 |
| | | XP_003525231 | 356513057 | 0.7665 | Glycine max | 7341 | 9009 |
| | | XP_003630941 | 357521304 | 0.7834 | Medicago truncatula | 7342 | 9010 |
| | | XP_003530877 | 356524520 | 0.7552 | Glycine max | 7343 | 9011 |
| | | XP_002525995 | 255761086 | 0.7269 | Ricinus communis | 7344 | |
| | | XP_002315857 | 255761085 | 0.7213 | Populus trichocarpa | 7345 | |
| | | ABK94575 | 118485436 | 0.7213 | Populus trichocarpa | 7346 | 9012 |
| | | XP_002311530 | 255761085 | 0.7175 | Populus trichocarpa | 7347 | |
| | 398-417 | XP_003588450 | 357436348 | 1 | Medicago truncatula | 7348 | 9013 |
| | | XP_003526513 | 356515652 | 0.8496 | Glycine max | 7349 | 9014 |
| | | XP_003522729 | 356507956 | 0.8453 | Glycine max | 7350 | 9015 |
| | | XP_003603665 | 357466760 | 0.839 | Medicago truncatula | 7351 | 9016 |
| | | ACU21356 | 255642182 | 0.8432 | Glycine max | 7352 | 9017 |
| | | XP_003550117 | 356563738 | 0.8305 | Glycine max | 7353 | 9018 |
| | | CAD92450 | 31455392 | 0.7479 | Brassica napus | 7354 | 9019 |
| | | ADB92670 | 284519839 | 0.75 | Populus tremula × Populus alba | 7355 | 9020 |
| | | XP_002510013 | 255761086 | 0.7373 | Ricinus communis | 7356 | |
| | | XP_002301129 | 255761085 | 0.7373 | Populus trichocarpa | 7357 | |
| | 370-389 | XP_003553428 | 356570509 | 1 | Glycine max | 7358 | 9021 |
| | 758-777 | XP_003520534 | 356503475 | 1 | Glycine max | 7359 | 9022 |
| | | XP_003553428 | 356570509 | 0.9081 | Glycine max | 7360 | 9023 |
| | 236-255 | XP_003551188 | 356565928 | 1 | Glycine max | 7361 | 9024 |
| | 35-54 | AAM12880 | 20149261 | 1 | Helianthus annuus | 7362 | 9025 |
| | | CBI28152 | 270240501 | 0.991 | Vitis vinifera | 7363 | |
| | | XP_002284967 | 225430201 | 0.991 | Vitis vinifera | 7364 | 9026 |
| | | CBI21000 | 270231236 | 0.991 | Vitis vinifera | 7365 | |
| | | CBI36254 | 270253379 | 0.9819 | Vitis vinifera | 7366 | 9027 |
| | | NP_200330 | 145359269 | 0.9864 | Arabidopsis thaliana | 7367 | 9028 |
| | | XP_003522628 | 356507751 | 0.9819 | Glycine max | 7368 | 9029 |
| | | AEM97804 | 344189954 | 0.9864 | Dimocarpus longan | 7369 | 9030 |
| | | XP_002864382 | 297853636 | 0.9864 | Arabidopsis lyrata subsp. lyrata | 7370 | |
| | | XP_002285307 | 225442824 | 0.9819 | Vitis vinifera | 7371 | 9031 |
| | 755-774 | XP_003518080 | 356498481 | 1 | Glycine max | 7372 | 9032 |
| | | XP_003551421 | 356566402 | 0.8408 | Glycine max | 7373 | 9033 |
| | 56-75 | XP_003522398 | 356507283 | 1 | Glycine max | 7374 | 9034 |
| | | XP_003526192 | 356515005 | 0.9095 | Glycine max | 7375 | 9035 |
| | | XP_003526191 | 356515003 | 0.9128 | Glycine max | 7376 | 9036 |
| | | XP_003527777 | 356518217 | 0.7966 | Glycine max | 7377 | 9037 |
| | 113-132 | XP_003538544 | 356540131 | 1 | Glycine max | 7378 | 9038 |
| | 1097-1116 | XP_003520128 | 356502644 | 1 | Glycine max | 7379 | 9039 |
| | 1482-1501 | XP_003546504 | 356556379 | 1 | Glycine max | 7380 | 9040 |
| | | XP_003550617 | 356564761 | 0.7923 | Glycine max | 7381 | 9041 |
| | | XP_003542359 | 356547932 | 0.7889 | Glycine max | 7382 | 9042 |
| | | XP_002279041 | 225444747 | 0.7337 | Vitis vinifera | 7383 | 9043 |
| | | XP_002870435 | 297853636 | 0.7119 | Arabidopsis lyrata subsp. lyrata | 7384 | |
| | | XP_002516284 | 255761086 | 0.7102 | Ricinus communis | 7385 | |
| | | NP_568528 | 22327353 | 0.7018 | Arabidopsis thaliana | 7386 | 9044 |
| | | XP_002326282 | 255761085 | 0.7002 | Populus trichocarpa | 7387 | |
| ptc-miRf11315-akr | 264-283 | XP_003518840 | 356500034 | 1 | Glycine max | 7388 | 9045 |
| | | XP_003529395 | 356521503 | 0.9171 | Glycine max | 7389 | 9046 |
| | | XP_003607985 | 357475398 | 0.8275 | Medicago truncatula | 7390 | 9047 |
| | | XP_002518769 | 255761086 | 0.7579 | Ricinus communis | 7391 | |
| | | XP_002313117 | 255761085 | 0.7496 | Populus trichocarpa | 7392 | |
| | | AAQ90244 | 37223341 | 0.7446 | Solanum lycopersicum | 7393 | 9048 |
| | | NP_001234399 | 350534489 | 0.7446 | Solanum lycopersicum | 7394 | 9049 |
| | | NP_188555 | 30685246 | 0.7247 | Arabidopsis thaliana | 7395 | 9050 |
| | | XP_002883169 | 297853636 | 0.7164 | Arabidopsis lyrata subsp. lyrata | 7396 | |
| | | CBI32416 | 270245997 | 0.7313 | Vitis vinifera | 7397 | 9051 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 324-343 | XP_003550774 | 356565082 | 1 | Glycine max | 7398 | 9052 |
| | | XP_003525472 | 356513541 | 0.8489 | Glycine max | 7399 | 9053 |
| | 324-343 | XP_003550774 | 356565082 | 1 | Glycine max | 7400 | 9054 |
| | 680-699 | XP_003554964 | 356573636 | 1 | Glycine max | 7401 | 9055 |
| ptc-miRf11757-akr | 404-426 | XP_003612685 | 357484794 | 1 | Medicago truncatula | 7402 | 9056 |
| | | XP_003516858 | 356495999 | 0.8914 | Glycine max | 7403 | 9057 |
| | | XP_003534304 | 356531476 | 0.8801 | Glycine max | 7404 | 9058 |
| | | BAH03477 | 218744535 | 0.8015 | Nicotiana tabacum | 7405 | 9059 |
| | | XP_002519001 | 255761086 | 0.824 | Ricinus communis | 7406 | |
| | | XP_002303454 | 255761085 | 0.8127 | Populus trichocarpa | 7407 | |
| | | ABK93338 | 118482845 | 0.8052 | Populus trichocarpa | 7408 | 9060 |
| | | XP_002326571 | 255761085 | 0.8015 | Populus trichocarpa | 7409 | |
| | | XP_002274060 | 225427054 | 0.764 | Vitis vinifera | 7410 | 9061 |
| | | XP_002890966 | 297853636 | 0.7603 | Arabidopsis lyrata subsp. lyrata | 7411 | |
| ath-miR157a | 164-184 | XP_003549130 | 356561725 | 1 | Glycine max | 7412 | 9062 |
| | | XP_003553944 | 356571558 | 0.9452 | Glycine max | 7413 | 9063 |
| | 238-258 | XP_003551188 | 356565928 | 1 | Glycine max | 7414 | 9064 |
| | | XP_003538544 | 356540131 | 0.9106 | Glycine max | 7415 | 9065 |
| | | ACU18328 | 255635963 | 0.9083 | Glycine max | 7416 | 9066 |
| | | XP_003601767 | 357462970 | 0.7064 | Medicago truncatula | 7417 | 9067 |
| | 1129-1149 | XP_003525415 | 356513426 | 1 | Glycine max | 7418 | 9068 |
| | | XP_003532399 | 356527605 | 0.9051 | Glycine max | 7419 | 9069 |
| | 898-918 | XP_003540473 | 356544059 | 1 | Glycine max | 7420 | 9070 |
| | | XP_003543233 | 356549706 | 0.9305 | Glycine max | 7421 | 9071 |
| | | ACU24116 | 255647298 | 0.9251 | Glycine max | 7422 | 9072 |
| | 118-138 | XP_003525436 | 356513468 | 1 | Glycine max | 7423 | 9073 |
| | | XP_003550708 | 356564947 | 0.9204 | Glycine max | 7424 | 9074 |
| | | XP_003522278 | 356507037 | 0.7595 | Glycine max | 7425 | 9075 |
| | 77-97 | XP_003520455 | 356503312 | 1 | Glycine max | 7426 | 9076 |
| | | XP_003530170 | 356523079 | 0.848 | Glycine max | 7427 | 9077 |
| | 498-518 | XP_003553428 | 356570509 | 1 | Glycine max | 7428 | 9078 |
| | | XP_003520534 | 356503475 | 0.9081 | Glycine max | 7429 | 9079 |
| | 50-70 | XP_003550708 | 356564947 | 1 | Glycine max | 7430 | 9080 |
| | | XP_003525436 | 356513468 | 0.9373 | Glycine max | 7431 | 9081 |
| | 854-875 | XP_003555667 | 356575073 | 1 | Glycine max | 7432 | 9082 |
| | 170-190 | XP_003538544 | 356540131 | 1 | Glycine max | 7433 | 9083 |
| | | XP_003551188 | 356565928 | 0.9097 | Glycine max | 7434 | 9084 |
| | 593-613 | NP_001236309 | 351724988 | 1 | Glycine max | 7435 | 9085 |
| | | XP_003529339 | 356521389 | 0.838 | Glycine max | 7436 | 9086 |
| | 144-164 | XP_002275728 | 225446415 | 1 | Vitis vinifera | 7437 | 9087 |
| | | AAY16440 | 62856978 | 0.7396 | Betula platyphylla | 7438 | 9088 |
| | 112-132 | XP_003522278 | 356507037 | 1 | Glycine max | 7439 | 9089 |
| | 396-416 | XP_003520128 | 356502644 | 1 | Glycine max | 7440 | 9090 |
| | | XP_003517860 | 356498034 | 0.9129 | Glycine max | 7441 | 9091 |
| | 181-201 | XP_003523155 | 356508826 | 1 | Glycine max | 7442 | 9092 |
| | 593-613 | NP_001236309 | 351724988 | 1 | Glycine max | 7443 | 9093 |
| | 116-136 | ACU18105 | 255635506 | 1 | Glycine max | 7444 | 9094 |
| | 758-778 | XP_003518080 | 356498481 | 1 | Glycine max | 7445 | 9095 |
| | | XP_003551421 | 356566402 | 0.8408 | Glycine max | 7446 | 9096 |
| | 120-140 | XP_003549130 | 356561725 | 1 | Glycine max | 7447 | |
| | 693-713 | XP_003525415 | 356513426 | 1 | Glycine max | 7448 | 9097 |
| | 737-757 | XP_003553428 | 356570509 | 1 | Glycine max | 7449 | 9098 |
| | 116-136 | XP_003538544 | 356540131 | 1 | Glycine max | 7450 | 9099 |
| | 818-838 | XP_003553944 | 356571558 | 1 | Glycine max | 7451 | 9100 |
| | 238-258 | XP_003551188 | 356565928 | 1 | Glycine max | 7452 | 9101 |
| | 1070-1090 | XP_003525436 | 356513468 | 1 | Glycine max | 7453 | 9102 |
| | 109-129 | XP_003520455 | 356503312 | 1 | Glycine max | 7454 | 9103 |
| | 404-424 | XP_003526029 | 356514674 | 1 | Glycine max | 7455 | 9104 |
| | | XP_003540122 | 356543345 | 0.8919 | Glycine max | 7456 | 9105 |
| | 181-201 | XP_003523155 | 356508826 | 1 | Glycine max | 7457 | 9106 |
| | 713-733 | XP_003551421 | 356566402 | 1 | Glycine max | 7458 | 9107 |
| | | XP_003518080 | 356498481 | 0.7962 | Glycine max | 7459 | 9108 |
| sbi-miR159a | 305-325 | XP_003541823 | 356546825 | 1 | Glycine max | 7460 | 9109 |
| | 305-325 | XP_003541823 | 356546825 | 1 | Glycine max | 7461 | 9110 |
| | 289-309 | XP_003518627 | 356499601 | 1 | Glycine max | 7462 | 9111 |
| | | XP_003542153 | 356547506 | 0.9478 | Glycine max | 7463 | 9112 |
| | | ADN33938 | 307136081 | 0.7937 | Cucumis melo subsp. melo | 7464 | 9113 |
| | | XP_002518919 | 255761086 | 0.7755 | Ricinus communis | 7465 | |
| | | XP_002279642 | 225426567 | 0.7755 | Vitis vinifera | 7466 | 9114 |
| | | XP_002870592 | 297853636 | 0.7664 | Arabidopsis lyrata subsp. lyrata | 7467 | |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | NP_199024 | 30693991 | 0.7642 | Arabidopsis thaliana | 7468 | 9115 |
| | | AAM63843 | 21405504 | 0.7596 | Arabidopsis thaliana | 7469 | 9116 |
| | | XP_002299422 | 255761085 | 0.7528 | Populus trichocarpa | 7470 | |
| | | XP_002303695 | 255761085 | 0.7574 | Populus trichocarpa | 7471 | |
| | 124-144 | XP_003543825 | 356550908 | 1 | Glycine max | 7472 | 9117 |
| | | XP_003556814 | 356577399 | 0.813 | Glycine max | 7473 | 9118 |
| | 461-481 | XP_003542153 | 356547506 | 1 | Glycine max | 7474 | 9119 |
| | | XP_003518627 | 356499601 | 0.9436 | Glycine max | 7475 | 9120 |
| | 839-859 | XP_003526354 | 356515330 | 1 | Glycine max | 7476 | 9121 |
| | | XP_003523913 | 356510372 | 0.9333 | Glycine max | 7477 | 9122 |
| | 73-93 | XP_003535315 | 356533526 | 1 | Glycine max | 7478 | 9123 |
| | | XP_003555178 | 356574075 | 0.9462 | Glycine max | 7479 | 9124 |
| | | XP_003591226 | 357441896 | 0.7849 | Medicago truncatula | 7480 | 9125 |
| | | XP_002512536 | 255761086 | 0.7465 | Ricinus communis | 7481 | |
| | | CBI39621 | 270257428 | 0.7465 | Vitis vinifera | 7482 | 9126 |
| | | CAP59645 | 163913883 | 0.7558 | Vitis vinifera | 7483 | 9127 |
| | | XP_002277312 | 225450534 | 0.7496 | Vitis vinifera | 7484 | 9128 |
| | | XP_002280462 | 225432056 | 0.7404 | Vitis vinifera | 7485 | 9129 |
| | | CAP59646 | 163913885 | 0.7512 | Vitis vinifera | 7486 | 9130 |
| | | CAN63178 | 123711273 | 0.7373 | Vitis vinifera | 7487 | 9131 |
| | 614-634 | XP_003541563 | 356546291 | 1 | Glycine max | 7488 | 9132 |
| | | XP_003545791 | 356554924 | 0.805 | Glycine max | 7489 | 9133 |
| | 905-925 | XP_003556814 | 356577399 | 1 | Glycine max | 7490 | 9134 |
| | | XP_003543825 | 356550908 | 0.8659 | Glycine max | 7491 | 9135 |
| smo-miR156b | 164-184 | XP_003549130 | 356561725 | 1 | Glycine max | 7492 | 9136 |
| | | XP_003553944 | 356571558 | 0.9452 | Glycine max | 7493 | 9137 |
| | 238-258 | XP_003551188 | 356565928 | 1 | Glycine max | 7494 | 9138 |
| | | XP_003538544 | 356540131 | 0.9106 | Glycine max | 7495 | 9139 |
| | | ACU18328 | 255635963 | 0.9083 | Glycine max | 7496 | 9140 |
| | | XP_003601767 | 357462970 | 0.7064 | Medicago truncatula | 7497 | 9141 |
| | 1129-1149 | XP_003525415 | 356513426 | 1 | Glycine max | 7498 | 9142 |
| | | XP_003532399 | 356527605 | 0.9051 | Glycine max | 7499 | 9143 |
| | 118-138 | XP_003525436 | 356513468 | 1 | Glycine max | 7500 | 9144 |
| | | XP_003550708 | 356564947 | 0.9204 | Glycine max | 7501 | 9145 |
| | | XP_003522278 | 356507037 | 0.7595 | Glycine max | 7502 | 9146 |
| | 77-97 | XP_003520455 | 356503312 | 1 | Glycine max | 7503 | 9147 |
| | | XP_003530170 | 356523079 | 0.848 | Glycine max | 7504 | 9148 |
| | 50-70 | XP_003550708 | 356564947 | 1 | Glycine max | 7505 | 9149 |
| | | XP_003525436 | 356513468 | 0.9373 | Glycine max | 7506 | 9150 |
| | 498-518 | XP_003553428 | 356570509 | 1 | Glycine max | 7507 | 9151 |
| | | XP_003520534 | 356503475 | 0.9081 | Glycine max | 7508 | 9152 |
| | 170-190 | XP_003538544 | 356540131 | 1 | Glycine max | 7509 | 9153 |
| | | XP_003551188 | 356565928 | 0.9097 | Glycine max | 7510 | 9154 |
| | 593-613 | NP_001236309 | 351724988 | 1 | Glycine max | 7511 | 9155 |
| | | XP_003529339 | 356521389 | 0.838 | Glycine max | 7512 | 9156 |
| | 475-495 | XP_003528960 | 356520620 | 1 | Glycine max | 7513 | 9157 |
| | | NP_001235425 | 351721650 | 0.9279 | Glycine max | 7514 | 9158 |
| | 144-164 | XP_002275728 | 225446415 | 1 | Vitis vinifera | 7515 | 9159 |
| | | AAY16440 | 62856978 | 0.7396 | Betula platyphylla | 7516 | 9160 |
| | 112-132 | XP_003522278 | 356507037 | 1 | Glycine max | 7517 | 9161 |
| | 396-416 | XP_003520128 | 356502644 | 1 | Glycine max | 7518 | 9162 |
| | | XP_003517860 | 356498034 | 0.9129 | Glycine max | 7519 | 9163 |
| | 243-263 | XP_003540122 | 356543345 | 1 | Glycine max | 7520 | 9164 |
| | | XP_003526029 | 356514674 | 0.8684 | Glycine max | 7521 | 9165 |
| | 181-201 | XP_003523155 | 356508826 | 1 | Glycine max | 7522 | 9166 |
| | 77-97 | XP_003520455 | 356503312 | 1 | Glycine max | 7523 | 9167 |
| | 373-393 | XP_003553428 | 356570509 | 1 | Glycine max | 7524 | 9168 |
| | 761-781 | XP_003520534 | 356503475 | 1 | Glycine max | 7525 | 9169 |
| | | XP_003553428 | 356570509 | 0.9081 | Glycine max | 7526 | 9170 |
| | 110-130 | XP_003553944 | 356571558 | 1 | Glycine max | 7527 | 9171 |
| | 239-259 | XP_003551188 | 356565928 | 1 | Glycine max | 7528 | 9172 |
| | 1022-1042 | XP_003532399 | 356527605 | 1 | Glycine max | 7529 | 9173 |
| | | XP_003525415 | 356513426 | 0.8914 | Glycine max | 7530 | 9174 |
| | 593-613 | NP_001236309 | 351724988 | 1 | Glycine max | 7531 | 9175 |
| | 116-136 | ACU18105 | 255635506 | 1 | Glycine max | 7532 | 9176 |
| | 758-778 | XP_003518080 | 356498481 | 1 | Glycine max | 7533 | 9177 |
| | | XP_003551421 | 356566402 | 0.8408 | Glycine max | 7534 | 9178 |
| | 1231-1251 | XP_003525415 | 356513426 | 1 | Glycine max | 7535 | 9179 |
| | 20-40 | XP_003549130 | 356561725 | 1 | Glycine max | 7536 | 9180 |
| | 1070-1090 | XP_003525436 | 356513468 | 1 | Glycine max | 7537 | 9181 |
| | 404-424 | XP_003526029 | 356514674 | 1 | Glycine max | 7538 | 9182 |
| | | XP_003540122 | 356543345 | 0.8919 | Glycine max | 7539 | 9183 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 185-205 | XP_003538544 | 356540131 | 1 | *Glycine max* | 7540 | 9184 |
| | 713-733 | XP_003551421 | 356566402 | 1 | *Glycine max* | 7541 | 9185 |
| | | XP_003518080 | 356498481 | 0.7962 | *Glycine max* | 7542 | 9186 |
| osa-miRf10839-akr | 32-52 | AAM97011 | 22531013 | 1 | *Arabidopsis thaliana* | 7543 | 9187 |
| | | NP_563815 | 145335272 | 0.9929 | *Arabidopsis thaliana* | 7544 | 9188 |
| | | XP_002892455 | 297853636 | 0.9786 | *Arabidopsis lyrata* subsp. *lyrata* | 7545 | |
| | | BAJ33638 | 312281544 | 0.9429 | *Thellungiella halophila* | 7546 | 9189 |
| | | XP_002523852 | 255761086 | 0.7714 | *Ricinus communis* | 7547 | |
| | | AEL99169 | 343172931 | 0.75 | *Silene latifolia* | 7548 | 9190 |
| | | XP_002313603 | 255761085 | 0.7429 | *Populus trichocarpa* | 7549 | |
| | | ACJ86143 | 217075565 | 0.7214 | *Medicago truncatula* | 7550 | 9191 |
| | | ADI45844 | 297525844 | 0.7429 | *Silene vulgaris* | 7551 | 9192 |
| | | XP_002328107 | 255761085 | 0.75 | *Populus trichocarpa* | 7552 | |
| ptc-miRf10300-akr | 35-54 | ACJ37435 | 212717187 | 1 | *Glycine max* | 7553 | 9193 |
| | | ACU23160 | 255645326 | 0.9948 | *Glycine max* | 7554 | 9194 |
| | | ACJ37436 | 212717189 | 0.933 | *Glycine max* | 7555 | 9195 |
| | 537-556 | NP_001235206 | 351722714 | 1 | *Glycine max* | 7556 | 9196 |
| | | NP_001236569 | 351725110 | 0.9581 | *Glycine max* | 7557 | 9197 |
| | | XP_002866588 | 297853636 | 0.7126 | *Arabidopsis lyrata* subsp. *lyrata* | 7558 | |
| | | XP_002309915 | 255761085 | 0.7665 | *Populus trichocarpa* | 7559 | |
| | | NP_201209 | 145359627 | 0.7066 | *Arabidopsis thaliana* | 7560 | 9198 |
| | | ABK96256 | 118488893 | 0.7605 | *Populus trichocarpa* x *Populus deltoides* | 7561 | 9199 |
| | | XP_002526638 | 255761086 | 0.7485 | *Ricinus communis* | 7562 | |
| | | XP_002306249 | 255761085 | 0.7784 | *Populus trichocarpa* | 7563 | |
| | | 2WSC_N | | 0.7844 | *Phaseolus vulgaris* | 7564 | |
| | | BAJ33864 | 312281996 | 0.7066 | *Thellungiella halophila* | 7565 | 9200 |
| | 39-58 | XP_002283864 | 225429937 | 1 | *Vitis vinifera* | 7566 | 9201 |
| ptc-miRf10619-akr | 318-339 | BAG09382 | 167961874 | 1 | *Glycine max* | 7567 | 9202 |
| | | NP_001238412 | 351726609 | 0.9838 | *Glycine max* | 7568 | 9203 |
| | | ACU19205 | 255637765 | 0.9704 | *Glycine max* | 7569 | 9204 |
| | | CAN67413 | 123711204 | 0.9272 | *Vitis vinifera* | 7570 | 9205 |
| | | ACD93720 | 223987377 | 0.903 | *Mikania micrantha* | 7571 | 9206 |
| | | XP_002862992 | 297853636 | 0.9191 | *Arabidopsis lyrata* subsp. *lyrata* | 7572 | |
| | | XP_002277249 | 225462095 | 0.9299 | *Vitis vinifera* | 7573 | 9207 |
| | | XP_002317470 | 255761085 | 0.9218 | *Populus trichocarpa* | 7574 | |
| | | 1803516A | | 0.9191 | *Lens culinaris* | 7575 | |
| | | XP_002519658 | 255761086 | 0.9084 | *Ricinus communis* | 7576 | |
| | 32-53 | ACU18791 | 255636916 | 1 | *Glycine max* | 7577 | 9208 |
| | 1512-1532 | ACQ44234 | 228485370 | 1 | *Glycine max* | 7578 | 9209 |
| | 55-75 | XP_002512977 | 255761086 | 1 | *Ricinus communis* | 7579 | |
| ptc-miRf11847-akr | 418-438 | ACU17540 | 255634349 | 1 | *Glycine max* | 7580 | 9210 |
| ath-miRf10701-akr | 293-314 | ACU18306 | 255635917 | 1 | *Glycine max* | 7581 | 9211 |
| | 918-939 | NP_001237102 | 351725712 | 1 | *Glycine max* | 7582 | 9212 |
| | | XP_002284425 | 225445231 | 0.7562 | *Vitis vinifera* | 7583 | 9213 |
| | 348-369 | NP_001236604 | 351726125 | 1 | *Glycine max* | 7584 | 9214 |
| | 1178-1199 | ACU21144 | 255641746 | 1 | *Glycine max* | 7585 | 9215 |
| | | XP_002277008 | 225444658 | 0.7859 | *Vitis vinifera* | 7586 | 9216 |
| | | XP_002276983 | 225444660 | 0.7859 | *Vitis vinifera* | 7587 | 9217 |
| | | CAB75429 | 6996559 | 0.7204 | *Nicotiana plumbaginifolia* | 7588 | 9218 |
| | | XP_002331184 | 255761085 | 0.733 | *Populus trichocarpa* | 7589 | |
| | | XP_002529199 | 255761086 | 0.7355 | *Ricinus communis* | 7590 | |
| | | XP_002516242 | 255761086 | 0.7179 | *Ricinus communis* | 7591 | |
| | | XP_002270823 | 225442060 | 0.7254 | *Vitis vinifera* | 7592 | 9219 |
| | | CBI35841 | 270253379 | 0.7179 | *Vitis vinifera* | 7593 | |
| | | CAN65009 | 147797980 | 0.7229 | *Vitis vinifera* | 7594 | 9220 |
| osa-miRf11595-akr | 321-339 | ABB02162 | 77744234 | 1 | *Medicago sativa* | 7595 | 9221 |
| | | ABB02161 | 77744232 | 0.975 | *Medicago sativa* | 7596 | 9222 |
| | | ACJ85732 | 217074743 | 0.9711 | *Medicago truncatula* | 7597 | 9223 |
| | | AEO21428 | 346229108 | 0.8227 | *Glycine max* | 7598 | 9224 |
| | | ABC59101 | 84514184 | 0.8073 | *Medicago truncatula* | 7599 | 9225 |
| | | ABC68398 | 85001688 | 0.7842 | *Glycine max* | 7600 | 9226 |
| | | ABS53040 | 153869430 | 0.8073 | *Leucaena leucocephala* | 7601 | 9227 |
| | | AAT39511 | 47933889 | 0.7553 | *Camptotheca acuminata* | 7602 | 9228 |
| | | XP_002327769 | 255761085 | 0.7572 | *Populus trichocarpa* | 7603 | |
| | | XP_002327770 | 255761085 | 0.7437 | *Populus trichocarpa* | 7604 | |
| | 107-125 | NP_001236740 | 351722666 | 1 | *Glycine max* | 7605 | 9229 |
| | 56-74 | CAE02645 | 34495198 | 1 | *Lotus japonicus* | 7606 | 9230 |
| | | CAA65585 | 2347053 | 0.7513 | *Vitis vinifera* | 7607 | 9231 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | AAP36992 | 46371994 | 0.753 | Cucumis sativus | 7608 | 9232 |
| | | BAE71301 | 84468435 | 0.7598 | Trifolium pratense | 7609 | 9233 |
| | | XP_002269030 | 225427781 | 0.7445 | Vitis vinifera | 7610 | 9234 |
| | | BAE71251 | 84468335 | 0.7581 | Trifolium pratense | 7611 | 9235 |
| | | BAG68575 | 195976672 | 0.7496 | Prunus persica | 7612 | 9236 |
| | | BAD06581 | 40645471 | 0.7394 | Nicotiana tabacum | 7613 | 9237 |
| | | CAN65288 | 147782233 | 0.7291 | Vitis vinifera | 7614 | 9238 |
| | | CAB64599 | 6646839 | 0.7359 | Datura stramonium | 7615 | 9239 |
| | 311-329 | ACU18654 | 255636632 | 1 | Glycine max | 7616 | 9240 |
| | 515-533 | NP_001235161 | 351721419 | 1 | Glycine max | 7617 | 9241 |
| | | BAB86923 | 19911192 | 0.711 | Vigna angularis | 7618 | 9242 |
| | 22-40 | NP_001237655 | 351726929 | 1 | Glycine max | 7619 | 9243 |
| | 421-439 | ACU22898 | 255644792 | 1 | Glycine max | 7620 | 9244 |
| osa-miRf11013-akr | 407-428 | NP_001237033 | 351723724 | 1 | Glycine max | 7621 | 9245 |
| | 32-53 | ABY84658 | 166203235 | 1 | Glycine max | 7622 | 9246 |
| | | NP_001236902 | 351727360 | 0.9715 | Glycine max | 7623 | 9247 |
| | | AAL32033 | 18158618 | 0.7967 | Retama raetam | 7624 | 9248 |
| | 597-618 | ACU23333 | 255645678 | 1 | Glycine max | 7625 | 9249 |
| | 29-50 | NP_001236902 | 351727360 | 1 | Glycine max | 7626 | 9250 |
| | | ABY84658 | 166203235 | 0.9696 | Glycine max | 7627 | 9251 |
| ptc-miRf10148-akr | 679-698 | NP_001238384 | 351725780 | 1 | Glycine max | 7628 | 9252 |
| | 547-566 | XP_002283799 | 225435835 | 1 | Vitis vinifera | 7629 | 9253 |
| | | CAN72395 | 147774368 | 0.9606 | Vitis vinifera | 7630 | |
| | | ACU20767 | 255640974 | 0.9462 | Glycine max | 7631 | 9254 |
| | | XP_002304844 | 255761085 | 1.0896 | Populus trichocarpa | 7632 | |
| | | CBI16575 | 270227042 | 0.9176 | Vitis vinifera | 7633 | |
| | | XP_002523383 | 255761086 | 0.8746 | Ricinus communis | 7634 | |
| | | XP_002299088 | 255761085 | 0.8853 | Populus trichocarpa | 7635 | |
| | | NP_850182 | 42570348 | 0.81 | Arabidopsis thaliana | 7636 | 9255 |
| | | NP_565736 | 42569548 | 0.8065 | Arabidopsis thaliana | 7637 | 9256 |
| | | XP_002862885 | 297853636 | 0.8029 | Arabidopsis lyrata subsp. lyrata | 7638 | |
| | 135-154 | ACU17996 | 255635284 | 1 | Glycine max | 7639 | 9257 |
| | | ACU23482 | 255645988 | 0.8725 | Glycine max | 7640 | 9258 |
| | | XP_002307595 | 255761085 | 0.8406 | Populus trichocarpa | 7641 | |
| | | XP_002524761 | 255761086 | 0.8319 | Ricinus communis | 7642 | |
| | | XP_002300832 | 255761085 | 0.8261 | Populus trichocarpa | 7643 | |
| | | XP_002279156 | 225437057 | 0.8029 | Vitis vinifera | 7644 | 9259 |
| | | XP_002878504 | 297853636 | 0.7072 | Arabidopsis lyrata subsp. lyrata | 7645 | |
| | 141-160 | XP_002283799 | 225435835 | 1 | Vitis vinifera | 7646 | 9260 |
| | 367-386 | ACU17970 | 255635230 | 1 | Glycine max | 7647 | 9261 |
| | | ACU18145 | 255635589 | 0.9494 | Glycine max | 7648 | 9262 |
| | | XP_002510492 | 255761086 | 0.7946 | Ricinus communis | 7649 | |
| | | XP_002278539 | 225458064 | 0.7798 | Vitis vinifera | 7650 | 9263 |
| | | XP_002306908 | 255761085 | 0.7619 | Populus trichocarpa | 7651 | |
| | | ABL10371 | 118723367 | 0.75 | Medicago truncatula | 7652 | 9264 |
| | | XP_002301996 | 255761085 | 0.7738 | Populus trichocarpa | 7653 | |
| | | NP_568605 | 145358761 | 0.7024 | Arabidopsis thaliana | 7654 | 9265 |
| | 110-129 | ACU17996 | 255635284 | 1 | Glycine max | 7655 | 9266 |
| zma-miR482-5p | 122-140 | ACU21375 | 255642220 | 1 | Glycine max | 7656 | 9267 |
| | 128-146 | XP_002314999 | 255761085 | 1 | Populus trichocarpa | 7657 | |
| | | XP_002312287 | 255761085 | 0.9432 | Populus trichocarpa | 7658 | |
| | | XP_002285502 | 225424638 | 0.8428 | Vitis vinifera | 7659 | 9268 |
| | | XP_002520520 | 255761086 | 0.8341 | Ricinus communis | 7660 | |
| | | XP_002876891 | 297853636 | 0.8035 | Arabidopsis lyrata subsp. lyrata | 7661 | |
| | | NP_178465 | 30678070 | 0.7948 | Arabidopsis thaliana | 7662 | 9269 |
| | | NP_001149451 | 226506925 | 0.7773 | Zea mays | 7663 | 9270 |
| | | XP_002875224 | 297853636 | 0.7904 | Arabidopsis lyrata subsp. lyrata | 7664 | |
| | | NP_001054237 | 115461273 | 0.7686 | Oryza sativa Japonica Group | 7665 | 9271 |
| | | CAH68184 | 90399185 | 0.7642 | Oryza sativa Indica Group | 7666 | 9272 |
| | 745-763 | NP_001235027 | 351724922 | 1 | Glycine max | 7667 | 9273 |
| | | NP_001238461 | 351728042 | 0.9389 | Glycine max | 7668 | 9274 |
| | | NP_001235888 | 351727642 | 0.9389 | Glycine max | 7669 | 9275 |
| | | NP_001235511 | 351724120 | 0.9313 | Glycine max | 7670 | 9276 |
| | | ADD11814 | 289586041 | 0.8244 | Cajanus cajan | 7671 | 9277 |
| | | AAC49369 | 1420884 | 0.7939 | Phaseolus vulgaris | 7672 | 9278 |
| | 40-58 | ACU20629 | 255640688 | 1 | Glycine max | 7673 | 9279 |
| | 27-45 | ACU20555 | 255640539 | 1 | Glycine max | 7674 | 9280 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 19-37 | ACU23548 | 255646123 | 1 | Glycine max | 7675 | 9281 |
| | | Q96452 | | 0.9922 | Glycine max | 7676 | |
| | | NP_001235679 | 351721598 | 1 | Glycine max | 7677 | 9282 |
| | | ACU19187 | 255637728 | 0.9457 | Glycine max | 7678 | 9283 |
| | | ACU17765 | 255634808 | 0.8876 | Glycine max | 7679 | 9284 |
| | | XP_002523376 | 255761086 | 0.8411 | Ricinus communis | 7680 | |
| | | ACQ45020 | 228552591 | 0.845 | Cicer arietinum | 7681 | 9285 |
| | | XP_002285427 | 225461653 | 0.8256 | Vitis vinifera | 7682 | 9286 |
| | | P42654 | | 0.8372 | Vicia faba | 7683 | |
| | | XP_002316863 | 255761085 | 0.8333 | Populus trichocarpa | 7684 | |
| | 59-77 | ACU24228 | 255647528 | 1 | Glycine max | 7685 | 9287 |
| | | ACU18882 | 255637100 | 0.7652 | Glycine max | 7686 | 9288 |
| | | XP_002276186 | 225429425 | 0.7652 | Vitis vinifera | 7687 | 9289 |
| | | XP_002516481 | 255761086 | 0.7391 | Ricinus communis | 7688 | |
| | | XP_002324746 | 255761085 | 0.7304 | Populus trichocarpa | 7689 | |
| | | NP_565612 | 145360329 | 0.7217 | Arabidopsis thaliana | 7690 | 9290 |
| | | XP_002880724 | 297853636 | 0.7275 | Arabidopsis lyrata subsp. lyrata | 7691 | |
| | | XP_002281479 | 225442372 | 0.7362 | Vitis vinifera | 7692 | 9291 |
| | | ABB86253 | 82621129 | 0.7014 | Solanum tuberosum | 7693 | 9292 |
| | | CBI35995 | 270253379 | 0.7362 | Vitis vinifera | 7694 | |
| | 296-314 | NP_001237978 | 351721473 | 1 | Glycine max | 7695 | 9293 |
| | 59-77 | ACU18882 | 255637100 | 1 | Glycine max | 7696 | 9294 |
| | | ACU24228 | 255647528 | 0.9209 | Glycine max | 7697 | 9295 |
| | | NP_001031418 | 79323070 | 0.723 | Arabidopsis thaliana | 7698 | 9296 |
| | 204-222 | ACU20859 | 255641163 | 1 | Glycine max | 7699 | 9297 |
| | 91-109 | ACU15870 | 255631011 | 1 | Glycine max | 7700 | 9298 |
| | 390-408 | CAI43251 | 57283984 | 1 | Phaseolus vulgaris var. nanus | 7701 | 9299 |
| | | ABA86966 | 77540215 | 0.937 | Glycine max | 7702 | 9300 |
| | | NP_001237472 | 351721637 | 0.937 | Glycine max | 7703 | 9301 |
| | | ACU23435 | 255645890 | 0.9213 | Glycine max | 7704 | 9302 |
| | | XP_002283671 | 225434934 | 0.8228 | Vitis vinifera | 7705 | 9303 |
| | | ACJ11723 | 211906459 | 0.8386 | Gossypium hirsutum | 7706 | 9304 |
| | | ABA46792 | 76573374 | 0.8228 | Solanum tuberosum | 7707 | 9305 |
| | | XP_002299871 | 255761085 | 0.815 | Populus trichocarpa | 7708 | |
| | | CAN67342 | 147772559 | 0.815 | Vitis vinifera | 7709 | |
| | | XP_002876302 | 297853636 | 0.811 | Arabidopsis lyrata subsp. lyrata | 7710 | |
| | 61-79 | ACU17423 | 255634119 | 1 | Glycine max | 7711 | 9306 |
| | 140-158 | ABA86966 | 77540215 | 1 | Glycine max | 7712 | 9307 |
| | | CAI43251 | 57283984 | 0.9407 | Phaseolus vulgaris var. nanus | 7713 | 9308 |
| | | XP_002283693 | 225449540 | 0.8261 | Vitis vinifera | 7714 | 9309 |
| | 309-327 | AAV87173 | 56404220 | 1 | Phaseolus vulgaris | 7715 | 9310 |
| | | BAD97829 | 63002633 | 0.7487 | Prunus persica | 7716 | 9311 |
| ptc-miRf10522-akr | 79-98 | ACU20325 | 255640067 | 1 | Glycine max | 7717 | 9312 |
| | 321-340 | ADM32504 | 304421409 | 1 | Glycine max | 7718 | 9313 |
| | | CAD12837 | 18075959 | 0.8679 | Lupinus luteus | 7719 | 9314 |
| | | CBI27290 | 270239516 | 0.7896 | Vitis vinifera | 7720 | |
| | | XP_002316086 | 255761085 | 0.7847 | Populus trichocarpa | 7721 | |
| | | XP_002512077 | 255761086 | 0.7765 | Ricinus communis | 7722 | |
| | | CAD12836 | 18075957 | 0.7471 | Lupinus luteus | 7723 | 9315 |
| | | XP_002311341 | 255761085 | 0.7553 | Populus trichocarpa | 7724 | |
| | | NP_172830 | 145335664 | 0.7259 | Arabidopsis thaliana | 7725 | 9316 |
| | | XP_002892769 | 297853636 | 0.7243 | Arabidopsis lyrata subsp. lyrata | 7726 | |
| | 1811-1830 | NP_001237605 | 351725462 | 1 | Glycine max | 7727 | 9317 |
| | | NP_001235120 | 351727636 | 0.7738 | Glycine max | 7728 | 9318 |
| osa-miRf10362-akr | 663-683 | ACU20209 | 255639831 | 1 | Glycine max | 7729 | 9319 |
| | 309-329 | XP_002531192 | 255761086 | 1 | Ricinus communis | 7730 | |
| | | XP_002298817 | 255761085 | 0.7018 | Populus trichocarpa | 7731 | |
| | 415-435 | NP_001238595 | 351724492 | 1 | Glycine max | 7732 | 9320 |
| ath-miRf10702-akr | 261-280 | ACU23703 | 255646448 | 1 | Glycine max | 7733 | 9321 |
| | 328-347 | ABD28727 | 49405947 | 1 | Medicago truncatula | 7734 | |
| | | NP_001236252 | 351723348 | 0.9592 | Glycine max | 7735 | 9322 |
| | | NP_001236882 | 351726775 | 0.9456 | Glycine max | 7736 | 9323 |
| | | CAG14986 | 45720189 | 0.9184 | Cicer arietinum | 7737 | 9324 |
| | | XP_002268544 | 225442984 | 0.8844 | Vitis vinifera | 7738 | 9325 |
| | | XP_002517623 | 255761086 | 0.8912 | Ricinus communis | 7739 | |
| | | XP_002298252 | 255761085 | 0.8707 | Populus trichocarpa | 7740 | |
| | | NP_172989 | 145335736 | 0.8639 | Arabidopsis thaliana | 7741 | 9326 |
| | | EEC76567 | 54362548 | 0.8571 | Oryza sativa Indica Group | 7742 | |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | BAJ92153 | 326514005 | 0.8435 | *Hordeum vulgare* subsp. *vulgare* | 7743 | 9327 |
| | 690-709 | ACU24052 | 255647167 | 1 | *Glycine max* | 7744 | 9328 |
| | | NP_001237955 | 351720763 | 0.8561 | *Glycine max* | 7745 | 9329 |
| ath-miRf10148-akr | 343-362 | NP_001234975 | 351723428 | 1 | *Glycine max* | 7746 | 9330 |
| | | XP_002314377 | 255761085 | 0.8174 | *Populus trichocarpa* | 7747 | |
| | | XP_002270067 | 225431754 | 0.8119 | *Vitis vinifera* | 7748 | 9331 |
| | | CBI22983 | 270234210 | 0.8119 | *Vitis vinifera* | 7749 | |
| | | XP_002328602 | 255761085 | 0.7953 | *Populus trichocarpa* | 7750 | |
| | | BAG16526 | 171854672 | 0.7898 | *Capsicum chinense* | 7751 | 9332 |
| | | Q39659 | | 0.7621 | *Cucumis sativus* | 7752 | |
| | | NP_187342 | 145338207 | 0.7759 | *Arabidopsis thaliana* | 7753 | 9333 |
| | | XP_002882497 | 297853636 | 0.7718 | *Arabidopsis lyrata* subsp. *lyrata* | 7754 | |
| | | O49809 | | 0.7552 | *Brassica napus* | 7755 | |
| | 176-195 | NP_001235442 | 351722139 | 1 | *Glycine max* | 7756 | 9334 |
| | | NP_001236219 | 351722401 | 0.9712 | *Glycine max* | 7757 | 9335 |
| | | ABC46708 | 83776785 | 0.8417 | *Arachis hypogaea* | 7758 | 9336 |
| | | Q40519 | | 0.8201 | *Nicotiana tabacum* | 7759 | |
| | | NP_001234042 | 350537546 | 0.8273 | *Solanum lycopersicum* | 7760 | 9337 |
| | | P06183 | | 0.8201 | *Solanum tuberosum* | 7761 | |
| | | ADB93062 | 284520973 | 0.8273 | *Jatropha curcas* | 7762 | 9338 |
| | | CAA27989 | 21490 | 0.8058 | *Solanum tuberosum* | 7763 | 9339 |
| | | XP_002332206 | 255761085 | 0.7914 | *Populus trichocarpa* | 7764 | |
| | | ABK96223 | 118488825 | 0.7914 | *Populus trichocarpa* × *Populus deltoides* | 7765 | 9340 |
| | 80-99 | ACJ85304 | 217073887 | 1 | *Medicago truncatula* | 7766 | 9341 |
| | | ABF66654 | 120650107 | 0.9086 | *Ammopiptanthus mongolicus* | 7767 | 9342 |
| | | ACU19677 | 255638744 | 0.9213 | *Glycine max* | 7768 | 9343 |
| | | CBI18248 | 270229319 | 0.8807 | *Vitis vinifera* | 7769 | |
| | | XP_002530504 | 255761086 | 0.8858 | *Ricinus communis* | 7770 | |
| | | XP_002308228 | 255761085 | 0.8756 | *Populus trichocarpa* | 7771 | |
| | | XP_002262986 | 225439379 | 0.8807 | *Vitis vinifera* | 7772 | 9344 |
| | | ACU23134 | 255645273 | 0.8858 | *Glycine max* | 7773 | 9345 |
| | | ABJ97690 | 116292767 | 0.8503 | *Solanum tuberosum* | 7774 | 9346 |
| | | XP_002322994 | 255761085 | 0.7995 | *Populus trichocarpa* | 7775 | |
| | 488-507 | ACU23010 | 255645020 | 1 | *Glycine max* | 7776 | 9347 |
| | 989-1008 | XP_002314377 | 255761085 | 1 | *Populus trichocarpa* | 7777 | |
| | | NP_001234975 | 351723428 | 0.814 | *Glycine max* | 7778 | 9348 |
| | 82-101 | ABF66654 | 120650107 | 1 | *Ammopiptanthus mongolicus* | 7779 | 9349 |
| | | ACJ85304 | 217073887 | 0.9266 | *Medicago truncatula* | 7780 | 9350 |
| | 91-110 | ACU22749 | 255644490 | 1 | *Glycine max* | 7781 | 9351 |
| ath-miRf10451-akr | 256-277 | NP_001238139 | 351726107 | 1 | *Glycine max* | 7782 | 9352 |
| | | NP_001237827 | 351724486 | 0.9394 | *Glycine max* | 7783 | 9353 |
| | | NP_001237200 | 351721157 | 0.8838 | *Glycine max* | 7784 | 9354 |
| | | NP_001236083 | 351725850 | 0.8333 | *Glycine max* | 7785 | 9355 |
| | 143-164 | NP_001238139 | 351726107 | 1 | *Glycine max* | 7786 | 9356 |
| ath-miRf10751-akr | 188-207 | ACU18963 | 255637265 | 1 | *Glycine max* | 7787 | 9357 |
| | | ACU21242 | 255641949 | 0.7764 | *Glycine max* | 7788 | 9358 |
| | 23-42 | ACU20965 | 255641375 | 1 | *Glycine max* | 7789 | 9359 |
| | | XP_002301406 | 255761085 | 0.8099 | *Populus trichocarpa* | 7790 | |
| | | XP_002320196 | 255761085 | 0.7851 | *Populus trichocarpa* | 7791 | |
| | | XP_002281449 | 225454509 | 0.7879 | *Vitis vinifera* | 7792 | 9360 |
| | | NP_566074 | 145361064 | 0.7245 | *Arabidopsis thaliana* | 7793 | 9361 |
| | | XP_002880239 | 297853636 | 0.7245 | *Arabidopsis lyrata* subsp. *lyrata* | 7794 | |
| | | AAU93592 | 53793715 | 0.7135 | *Solanum demissum* | 7795 | 9362 |
| | | XP_002876635 | 297853636 | 0.719 | *Arabidopsis lyrata* subsp. *lyrata* | 7796 | |
| | | NP_191729 | 145339747 | 0.7107 | *Arabidopsis thaliana* | 7797 | 9363 |
| | 1857-1876 | XP_002525341 | 255761086 | 1 | *Ricinus communis* | 7798 | |
| | | XP_002326656 | 255761085 | 0.8901 | *Populus trichocarpa* | 7799 | |
| | | CAN79431 | 147866563 | 0.8524 | *Vitis vinifera* | 7800 | |
| | | NP_001235564 | 351725644 | 0.8599 | *Glycine max* | 7801 | 9364 |
| | | ADW84019 | 321438026 | 0.8419 | *Gossypium hirsutum* | 7802 | 9365 |
| | | XP_002303363 | 255761085 | 0.8584 | *Populus trichocarpa* | 7803 | |
| | | 2FON_A | | 0.8238 | *Solanum lycopersicum* | 7804 | |
| | | NP_001234198 | 350535510 | 0.8238 | *Solanum lycopersicum* | 7805 | 9366 |
| | | AAW78691 | 58531951 | 0.8223 | *Solanum cheesmaniae* | 7806 | |
| | | XP_002868103 | 297853636 | 0.8313 | *Arabidopsis lyrata* subsp. *lyrata* | 7807 | |
| | 738-757 | CAD31838 | 21068663 | 1 | *Cicer arietinum* | 7808 | 9367 |
| | | NP_001237954 | 351720733 | 0.9412 | *Glycine max* | 7809 | 9368 |
| | | ACU19740 | 255638874 | 0.9314 | *Glycine max* | 7810 | 9369 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | NP_001237941 | 351727802 | 0.9118 | Glycine max | 7811 | 9370 |
| | | XP_002518592 | 255761086 | 0.8824 | Ricinus communis | 7812 | |
| | | XP_002534445 | 255761086 | 0.8873 | Ricinus communis | 7813 | |
| | | AAD38143 | 5031274 | 0.8676 | Prunus armeniaca | 7814 | 9371 |
| | | XP_002283286 | 225461208 | 0.8627 | Vitis vinifera | 7815 | 9372 |
| | | ABN12320 | 124488471 | 0.848 | Gossypium hirsutum | 7816 | 9373 |
| | | XP_002867516 | 297853636 | 0.8578 | Arabidopsis lyrata subsp. lyrata | 7817 | |
| | 188-207 | ACU18963 | 255637265 | 1 | Glycine max | 7818 | 9374 |
| | 87-106 | ACU21242 | 255641949 | 1 | Glycine max | 7819 | 9375 |
| | | XP_002285386 | 225430399 | 0.7263 | Vitis vinifera | 7820 | 9376 |
| | | CBI21096 | 270231236 | 0.7263 | Vitis vinifera | 7821 | |
| | 387-406 | ABP88240 | 145652370 | 1 | Glycine max | 7822 | 9377 |
| ppt-miR1220a | 182-202 | ACU23202 | 255645411 | 1 | Glycine max | 7823 | 9378 |
| | | BAG06274 | 318612463 | 0.8691 | Vigna unguiculata | 7824 | 9379 |
| | | CBI31552 | 270244444 | 0.7404 | Vitis vinifera | 7825 | |
| | | XP_002280217 | 225449239 | 0.7404 | Vitis vinifera | 7826 | 9380 |
| | | XP_002316242 | 255761085 | 0.7652 | Populus trichocarpa | 7827 | |
| | | NP_181518 | 30688068 | 0.7111 | Arabidopsis thaliana | 7828 | 9381 |
| | | XP_002879830 | 297853636 | 0.7133 | Arabidopsis lyrata subsp. lyrata | 7829 | |
| | | AAM65420 | 21406633 | 0.7088 | Arabidopsis thaliana | 7830 | 9382 |
| | | NP_191133 | 42565959 | 0.7314 | Arabidopsis thaliana | 7831 | 9383 |
| | | XP_002876330 | 297853636 | 0.7246 | Arabidopsis lyrata subsp. lyrata | 7832 | |
| | 539-559 | NP_001234951 | 351722740 | 1 | Glycine max | 7833 | 9384 |
| | 182-202 | ACU23202 | 255645411 | 1 | Glycine max | 7834 | 9385 |
| | 233-253 | ACU22926 | 255644851 | 1 | Glycine max | 7835 | 9386 |
| | | ACU23107 | 255645218 | 0.8212 | Glycine max | 7836 | 9387 |
| | | ABU93486 | 156739649 | 0.7848 | Vigna angularis | 7837 | 9388 |
| | | ABK30788 | 116871383 | 0.745 | Litchi chinensis | 7838 | 9389 |
| | | AAK51119 | 14029148 | 0.7152 | Carica papaya | 7839 | 9390 |
| | | XP_002523709 | 255761086 | 0.7053 | Ricinus communis | 7840 | |
| | | CAA48324 | 311834 | 0.7119 | Tropaeolum majus | 7841 | 9391 |
| | | XP_002275862 | 225436483 | 0.7219 | Vitis vinifera | 7842 | 9392 |
| | | BAG06274 | 318612463 | 1 | Vigna unguiculata | 7843 | 9393 |
| ath-miRf10068-akr | 125-145 17-36 | ABY78023 | 166014266 | 1 | Glycine max | 7844 | 9394 |
| | | XP_002310310 | 255761085 | 0.815 | Populus trichocarpa | 7845 | |
| | | XP_002269295 | 225467972 | 0.7974 | Vitis vinifera | 7846 | 9395 |
| | | AAX47170 | 61611670 | 0.7665 | Pisum sativum | 7847 | 9396 |
| | | ACY82403 | 267850662 | 0.793 | Petunia x hybrida | 7848 | 9397 |
| | | CAG27846 | 83999599 | 0.7665 | Antirrhinum majus | 7849 | 9398 |
| | | CAL36572 | 113207064 | 0.7621 | Misopates orontium | 7850 | 9399 |
| | | ABD66219 | 122056646 | 0.7665 | Malus x domestica | 7851 | 9400 |
| | | AAF22455 | 6652755 | 0.7709 | Paulownia kawakamii | 7852 | 9401 |
| | | AAP40641 | 30983947 | 0.7533 | Eucalyptus occidentalis | 7853 | 9402 |
| | 816-835 | AEH04452 | 334813894 | 1 | Arachis hypogaea | 7854 | 9403 |
| | | XP_002512790 | 255761086 | 0.9358 | Ricinus communis | 7855 | |
| | | ACU21011 | 255641470 | 0.9309 | Glycine max | 7856 | 9404 |
| | | NP_001238484 | 351721287 | 0.9309 | Glycine max | 7857 | 9405 |
| | | P12858 | | 0.9185 | Pisum sativum | 7858 | |
| | | CAA33264 | 20728 | 0.916 | Pisum sativum | 7859 | 9406 |
| | | ACV32597 | 256862073 | 0.9185 | Medicago sativa | 7860 | 9407 |
| | | BAJ34149 | 312282566 | 0.8938 | Thellungiella halophila | 7861 | 9408 |
| | | ACT21568 | 251831337 | 0.8963 | Bruguiera gymnorhiza | 7862 | 9409 |
| | | ADX97321 | 323650480 | 0.9185 | Mangifera indica | 7863 | 9410 |
| | 898-917 | AEH04452 | 334813894 | 1 | Arachis hypogaea | 7864 | 9411 |
| | 121-140 | ABC68403 | 85001696 | 1 | Glycine max | 7865 | 9412 |
| | | XP_002275806 | 225426452 | 0.7992 | Vitis vinifera | 7866 | 9413 |
| | | CAN80040 | 147844259 | 0.7992 | Vitis vinifera | 7867 | 9414 |
| | | XP_002509820 | 255761086 | 0.803 | Ricinus communis | 7868 | |
| | | XP_002304502 | 255761085 | 0.7765 | Populus trichocarpa | 7869 | |
| | | AAZ39642 | 71726941 | 0.7708 | Petunia x hybrida | 7870 | 9415 |
| | | XP_002320802 | 255761085 | 0.7557 | Populus trichocarpa | 7871 | |
| | | XP_002275115 | 225454267 | 0.7614 | Vitis vinifera | 7872 | 9416 |
| | | CAN80156 | 147852118 | 0.7557 | Vitis vinifera | 7873 | 9417 |
| | | XP_002882043 | 297853636 | 0.75 | Arabidopsis lyrata subsp. lyrata | 7874 | |
| | 621-640 | NP_001238484 | 351721287 | 1 | Glycine max | 7875 | 9418 |
| | | AEH04452 | 334813894 | 0.9355 | Arachis hypogaea | 7876 | 9419 |
| | | ABK96233 | 118488846 | 0.8958 | Populus trichocarpa x Populus deltoides | 7877 | 9420 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 419-438 | ACU19391 | 255638154 | 1 | Glycine max | 7878 | 9421 |
| | 511-530 | CAC80373 | 18072796 | 1 | Capsicum annuum | 7879 | 9422 |
| | | CAC80372 | 18072794 | 0.9583 | Capsicum annuum | 7880 | 9423 |
| | | P09043 | | 0.9263 | Nicotiana tabacum | 7881 | |
| osa-miRf11352-akr | 56-78 | ACU19975 | 255639357 | 1 | Glycine max | 7882 | 9424 |
| | | ACU19227 | 255637811 | 0.9593 | Glycine max | 7883 | 9425 |
| | | ACU19215 | 255637786 | 0.7647 | Glycine max | 7884 | 9426 |
| | | XP_002513621 | 255761086 | 0.7059 | Ricinus communis | 7885 | |
| | | XP_002318354 | 255761085 | 0.724 | Populus trichocarpa | 7886 | |
| ath-miRf11021-akr | 134-154 | NP_001236767 | 351723442 | 1 | Glycine max | 7887 | 9427 |
| | 18-38 | ACJ84983 | 217073247 | 1 | Medicago truncatula | 7888 | 9428 |
| | | O48905 | | 0.991 | Medicago sativa | 7889 | |
| | | CAC10208 | 10334492 | 0.9639 | Cicer arietinum | 7890 | 9429 |
| | | NP_001236661 | 351727792 | 0.9518 | Glycine max | 7891 | 9430 |
| | | XP_002332745 | 255761085 | 0.9428 | Populus trichocarpa | 7892 | |
| | | XP_002533463 | 255761086 | 0.9398 | Ricinus communis | 7893 | |
| | | AEB60994 | 328908588 | 0.9488 | Lupinus angustifolius | 7894 | 9431 |
| | | XP_002312583 | 255761085 | 0.9367 | Populus trichocarpa | 7895 | |
| | | CAH58641 | 52851185 | 0.9247 | Plantago major | 7896 | 9432 |
| | | ABC01890 | 83283964 | 0.9337 | Solanum tuberosum | 7897 | 9433 |
| aly-miR831-5p | 234-256 | XP_002513787 | 255761086 | 1 | Ricinus communis | 7898 | |
| | | XP_002337051 | 255761085 | 0.7 | Populus trichocarpa | 7899 | |
| | | XP_002300997 | 255761085 | 0.7174 | Populus trichocarpa | 7900 | |
| far-miR1134 | 222-245 | ACF22880 | 193850552 | 1 | Glycine max | 7901 | 9434 |
| | | XP_002325840 | 255761085 | 0.7248 | Populus trichocarpa | 7902 | |
| | | XP_002281809 | 225441606 | 0.7202 | Vitis vinifera | 7903 | 9435 |
| | | ABK95741 | 118487835 | 0.7294 | Populus trichocarpa | 7904 | 9436 |
| | | XP_002319160 | 255761085 | 0.7248 | Populus trichocarpa | 7905 | |
| | | XP_002525421 | 255761086 | 0.7018 | Ricinus communis | 7906 | |
| | 48-71 | CAD31838 | 21068663 | 1 | Cicer arietinum | 7907 | 9437 |
| | | NP_001237954 | 351720733 | 0.9412 | Glycine max | 7908 | 9438 |
| | | ACU19740 | 255638874 | 0.9314 | Glycine max | 7909 | 9439 |
| | | NP_001237941 | 351727802 | 0.9118 | Glycine max | 7910 | 9440 |
| | | XP_002518592 | 255761086 | 0.8824 | Ricinus communis | 7911 | |
| | | XP_002534445 | 255761086 | 0.8873 | Ricinus communis | 7912 | |
| | | AAD38143 | 5031274 | 0.8676 | Prunus armeniaca | 7913 | 9441 |
| | | XP_002283286 | 225461208 | 0.8627 | Vitis vinifera | 7914 | 9442 |
| | | ABN12320 | 124488471 | 0.848 | Gossypium hirsutum | 7915 | 9443 |
| | | XP_002867516 | 297853636 | 0.8578 | Arabidopsis lyrata subsp. lyrata | 7916 | |
| | 39-62 | AAD49742 | 5733805 | 1 | Pisum sativum | 7917 | 9444 |
| | | AAM97354 | 22476945 | 0.9894 | Pisum sativum | 7918 | 9445 |
| | | AAD33959 | 4929351 | 0.9814 | Pisum sativum | 7919 | 9446 |
| | | ACU21225 | 255641912 | 0.9204 | Glycine max | 7920 | 9447 |
| | | XP_002313052 | 255761085 | 0.9072 | Populus trichocarpa | 7921 | |
| | | XP_002284375 | 225428500 | 0.8992 | Vitis vinifera | 7922 | 9448 |
| | | XP_002509478 | 255761086 | 0.8992 | Ricinus communis | 7923 | |
| | | XP_002306098 | 255761085 | 0.8992 | Populus trichocarpa | 7924 | |
| | | P93563 | | 0.8674 | Solanum tuberosum | 7925 | |
| | | P93397 | | 0.87 | Nicotiana tabacum | 7926 | |
| | 180-203 | ACC85689 | 186477889 | 1 | Medicago truncatula | 7927 | 9449 |
| | | NP_001235733 | 351734425 | 0.8957 | Glycine max | 7928 | 9450 |
| | | XP_002318640 | 255761085 | 0.872 | Populus trichocarpa | 7929 | |
| | | XP_002322155 | 255761085 | 0.8768 | Populus trichocarpa | 7930 | |
| | | AEQ62558 | 352740725 | 0.8815 | Aquilaria microcarpa | 7931 | 9451 |
| | | NP_001048088 | 115448616 | 0.8483 | Oryza sativa Japonica Group | 7932 | 9452 |
| | | NP_201093 | 186532680 | 0.8531 | Arabidopsis thaliana | 7933 | 9453 |
| | | NP_566897 | 30692961 | 0.8483 | Arabidopsis thaliana | 7934 | 9454 |
| | | CAD42725 | 27527522 | 0.8436 | Nicotiana tabacum | 7935 | 9455 |
| | | XP_002511439 | 255761086 | 0.8578 | Ricinus communis | 7936 | |
| | 819-842 | NP_001235100 | 351727055 | 1 | Glycine max | 7937 | 9456 |
| | | CBZ41765 | 323669526 | 0.8864 | Glycine max | 7938 | 9457 |
| | | CCD42020 | 347630190 | 0.8701 | Glycine max | 7939 | 9458 |
| | 180-203 | ACC85689 | 186477889 | 1 | Medicago truncatula | 7940 | 9459 |
| | 429-452 | NP_001238108 | 351725208 | 1 | Glycine max | 7941 | 9460 |
| | | NP_001238275 | 351722648 | 0.9264 | Glycine max | 7942 | 9461 |
| ath-miRf10687-akr | 1224-1244 | ACO48252 | 226320261 | 1 | Arachis hypogaea | 7943 | 9462 |
| | | NP_001237378 | 351726308 | 0.889 | Glycine max | 7944 | 9463 |
| | | ABR29877 | 149789411 | 0.8301 | Ricinus communis | 7945 | 9464 |
| | | XP_002280842 | 225423836 | 0.8205 | Vitis vinifera | 7946 | 9465 |
| | | CAN62388 | 147809569 | 0.8127 | Vitis vinifera | 7947 | |
| | | XP_002893416 | 297853636 | 0.7954 | Arabidopsis lyrata subsp. lyrata | 7948 | |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002888679 | 297853636 | 0.7597 | *Arabidopsis lyrata* subsp. *lyrata* | 7949 | |
| | | NP_177043 | 42563058 | 0.7558 | *Arabidopsis thaliana* | 7950 | 9466 |
| | | ACT54615 | 254032061 | 0.779 | *Brassica napus* | 7951 | 9467 |
| | | ACN39927 | 224284384 | 0.7413 | *Picea sitchensis* | 7952 | 9468 |
| | 735-755 | ACU24612 | 255648320 | 1 | *Glycine max* | 7953 | 9469 |
| | | ACU19270 | 255637904 | 0.771 | *Glycine max* | 7954 | 9470 |
| | | XP_002311695 | 255761085 | 0.7252 | *Populus trichocarpa* | 7955 | |
| | 585-605 | ACU18495 | 255636311 | 1 | *Glycine max* | 7956 | 9471 |
| | 1116-1136 | ACJ85683 | 217074645 | 1 | *Medicago truncatula* | 7957 | 9472 |
| | | NP_001235116 | 351727520 | 0.8244 | *Glycine max* | 7958 | 9473 |
| | | BAD81043 | 56744206 | 0.8189 | *Glycine max* | 7959 | 9474 |
| | | O82709 | | 0.8743 | *Pisum sativum* | 7960 | |
| | | AAK84429 | 31321895 | 0.7301 | *Brassica napus* | 7961 | 9475 |
| | | XP_002866454 | 297853636 | 0.7227 | *Arabidopsis lyrata* subsp. *lyrata* | 7962 | |
| | | NP_200987 | 145359541 | 0.7246 | *Arabidopsis thaliana* | 7963 | 9476 |
| | | XP_002511066 | 255761086 | 0.7301 | *Ricinus communis* | 7964 | |
| | | XP_002277666 | 225447724 | 0.7227 | *Vitis vinifera* | 7965 | 9477 |
| | | CAN83091 | 147858622 | 0.7227 | *Vitis vinifera* | 7966 | 9478 |
| | 363-383 | NP_001238368 | 351734499 | 1 | *Glycine max* | 7967 | 9479 |
| | 291-311 | NP_001237352 | 351734505 | 1 | *Glycine max* | 7968 | 9480 |
| | | AAC32262 | 3426303 | 0.7348 | *Pisum sativum* | 7969 | 9481 |
| | | NP_001238058 | 351723760 | 0.7652 | *Glycine max* | 7970 | 9482 |
| | | AAV28488 | 54042994 | 0.7099 | *Populus tremula* x *Populus alba* | 7971 | 9483 |
| | | XP_002518420 | 255761086 | 0.7155 | *Ricinus communis* | 7972 | |
| | | AAV49801 | 55276119 | 0.7127 | *Populus trichocarpa* x *Populus deltoides* | 7973 | 9484 |
| | | ABO33478 | 132424650 | 0.732 | *Medicago truncatula* | 7974 | 9485 |
| | | ADC35600 | 285804238 | 0.7155 | *Prunus persica* | 7975 | 9486 |
| | | AAG27464 | 11037019 | 0.7293 | *Medicago truncatula* | 7976 | 9487 |
| | | XP_002271944 | 225444459 | 0.7182 | *Vitis vinifera* | 7977 | 9488 |
| | 24-44 | XP_002509851 | 255761086 | 1 | *Ricinus communis* | 7978 | |
| | | XP_002304516 | 255761085 | 0.863 | *Populus trichocarpa* | 7979 | |
| | | XP_002298015 | 255761085 | 0.8527 | *Populus trichocarpa* | 7980 | |
| | | XP_002278860 | 225426165 | 0.8424 | *Vitis vinifera* | 7981 | 9489 |
| | | AAN65180 | 25052803 | 0.8346 | *Petroselinum crispum* | 7982 | 9490 |
| | | XP_002302599 | 255761085 | 0.832 | *Populus trichocarpa* | 7983 | |
| | | XP_002277669 | 225454333 | 0.8269 | *Vitis vinifera* | 7984 | 9491 |
| | | XP_002511904 | 255761086 | 0.8217 | *Ricinus communis* | 7985 | |
| | | ACU20804 | 255641048 | 0.8191 | *Glycine max* | 7986 | 9492 |
| | | Q40353 | | 0.801 | *Medicago sativa* | 7987 | |
| ath-miRf11037-akr | 93-113 | AEA92304 | 327505552 | 1 | *Hevea brasiliensis* | 7988 | 9493 |
| | | ADL59582 | 302595186 | 0.9815 | *Hevea brasiliensis* | 7989 | 9494 |
| | | XP_002284365 | 225435057 | 0.9213 | *Vitis vinifera* | 7990 | 9495 |
| | | CAN64127 | 147783306 | 0.9213 | *Vitis vinifera* | 7991 | 9496 |
| | | XP_002534292 | 255761086 | 0.9259 | *Ricinus communis* | 7992 | |
| | | BAB84326 | 18447920 | 0.9491 | *Nicotiana tabacum* | 7993 | 9497 |
| | | AEA92307 | 327505558 | 0.9213 | *Hevea brasiliensis* | 7994 | 9498 |
| | | BAB84324 | 18447916 | 0.912 | *Nicotiana tabacum* | 7995 | 9499 |
| | | XP_002284071 | 225449602 | 0.9167 | *Vitis vinifera* | 7996 | 9500 |
| | | ACU20932 | 255641309 | 0.9213 | *Glycine max* | 7997 | 9501 |
| mtr-miR2119 | 498-518 | ACJ84572 | 217072423 | 1 | *Medicago truncatula* | 7998 | 9502 |
| | | ACU20200 | 255639813 | 0.8895 | *Glycine max* | 7999 | 9503 |
| | | XP_002520842 | 255761086 | 0.8226 | *Ricinus communis* | 8000 | |
| | | CBI25388 | 270236032 | 0.8072 | *Vitis vinifera* | 8001 | 9504 |
| | | XP_002325811 | 255761085 | 0.8046 | *Populus trichocarpa* | 8002 | |
| | | Q42967 | | 0.7841 | *Nicotiana tabacum* | 8003 | |
| | | 1J93_A | | 0.7738 | *Nicotiana tabacum* | 8004 | |
| | | XP_002274385 | 225448634 | 0.7584 | *Vitis vinifera* | 8005 | 9505 |
| | | XP_002879873 | 297853636 | 0.7661 | *Arabidopsis lyrata* subsp. *lyrata* | 8006 | |
| | | NP_001050049 | 115452896 | 0.7506 | *Oryza sativa* Japonica Group | 8007 | 9506 |
| | 153-173 | CAA80691 | 452768 | 1 | *Phaseolus acutifolius* | 8008 | 9507 |
| | | CAA80692 | 452766 | 0.9974 | *Phaseolus acutifolius* | 8009 | 9508 |
| | | AAO72531 | 29373060 | 0.9421 | *Lotus corniculatus* | 8010 | 9509 |
| | | CAG30579 | 51587337 | 0.9395 | *Lotus japonicus* | 8011 | 9510 |
| | | P13603 | | 0.9237 | *Trifolium repens* | 8012 | |
| | | P12886 | | 0.9184 | *Pisum sativum* | 8013 | |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002309899 | 255761085 | 0.8868 | Populus trichocarpa | 8014 | |
| | | XP_002328464 | 255761085 | 0.8737 | Populus trichocarpa | 8015 | |
| | | ABK95643 | 118487635 | 0.8789 | Populus trichocarpa | 8016 | 9511 |
| | | XP_002309900 | 255761085 | 0.8763 | Populus trichocarpa | 8017 | |
| osa-miR2055 | 514-534 | ACU20018 | 255639446 | 1 | Glycine max | 8018 | 9512 |
| ptc-miRf10132-akr | 129-151 | XP_003527653 | 356517960 | 1 | Glycine max | 8019 | 9513 |
| | | XP_003523542 | 356509614 | 0.7828 | Glycine max | 8020 | 9514 |
| tae-miR2003 | 89-110 | ABC47858 | 83853825 | 1 | Glycine max | 8021 | 9515 |
| | 1828-1849 | ABC47841 | 83853806 | 1 | Glycine max | 8022 | 9516 |
| | | XP_002283105 | 225438780 | 0.7143 | Vitis vinifera | 8023 | 9517 |
| | | BAJ53195 | 317106690 | 0.7032 | Jatropha curcas | 8024 | |
| | | XP_002284923 | 225458677 | 0.746 | Vitis vinifera | 8025 | 9518 |
| | | BAJ53194 | 317106690 | 0.7095 | Jatropha curcas | 8026 | |
| | | XP_002301171 | 255761085 | 0.7524 | Populus trichocarpa | 8027 | |
| | | XP_002327166 | 255761085 | 0.746 | Populus trichocarpa | 8028 | |
| | | CBI19489 | 270252251 | 0.7397 | Vitis vinifera | 8029 | |
| | | XP_002510185 | 255761086 | 0.7111 | Ricinus communis | 8030 | |
| | | AAK30205 | 13560782 | 0.7016 | Daucus carota | 8031 | 9519 |
| osa-miRf11829-akr | 166-186 | AAA74456 | 500752 | 1 | Phaseolus vulgaris | 8032 | 9520 |
| | | XP_003529397 | 356521507 | 0.933 | Glycine max | 8033 | 9521 |
| | | XP_003518837 | 356500028 | 0.9175 | Glycine max | 8034 | 9522 |
| | | XP_003607969 | 357475366 | 0.8763 | Medicago truncatula | 8035 | 9523 |
| | | AAB50233 | 1906001 | 0.9021 | Glycine max | 8036 | 9524 |
| | | CAC06095 | 9968472 | 0.8797 | Lotus japonicus | 8037 | 9525 |
| | | ADJ68001 | 300119951 | 0.8488 | Gossypium hirsutum | 8038 | 9526 |
| | | XP_002518763 | 255761086 | 0.8265 | Ricinus communis | 8039 | |
| | | XP_002330328 | 255761085 | 0.8196 | Populus trichocarpa | 8040 | |
| | | ABK95605 | 118487556 | 0.8179 | Populus trichocarpa | 8041 | 9527 |
| | 134-154 | CBI32147 | 270260094 | 1 | Vitis vinifera | 8042 | 9528 |
| | | XP_002315592 | 255761085 | 0.8512 | Populus trichocarpa | 8043 | |
| | | XP_003556331 | 356576422 | 0.8095 | Glycine max | 8044 | 9529 |
| | | XP_002262666 | 225424668 | 0.9683 | Vitis vinifera | 8045 | 9530 |
| | | XP_002312609 | 255761085 | 0.8333 | Populus trichocarpa | 8046 | |
| | | XP_003536266 | 356535465 | 0.8036 | Glycine max | 8047 | 9531 |
| | | XP_003590703 | 357440850 | 0.8472 | Medicago truncatula | 8048 | 9532 |
| | | ADN33838 | 307135962 | 0.871 | Cucumis melo subsp. melo | 8049 | 9533 |
| | | ACF86937 | 194705705 | 0.756 | Zea mays | 8050 | 9534 |
| | | NP_001152185 | 226494944 | 0.7421 | Zea mays | 8051 | 9535 |
| | 345-365 | XP_003522862 | 356508229 | 1 | Glycine max | 8052 | 9536 |
| | | XP_003533465 | 356529778 | 0.9262 | Glycine max | 8053 | 9537 |
| | 302-322 | XP_003546711 | 356556804 | 1 | Glycine max | 8054 | 9538 |
| | | XP_003542817 | 356548860 | 0.9169 | Glycine max | 8055 | 9539 |
| | | XP_003627885 | 357515192 | 0.7569 | Medicago truncatula | 8056 | 9540 |
| | 236-256 | XP_003526444 | 356515512 | 1 | Glycine max | 8057 | |
| | | CBI20954 | 270231236 | 0.7572 | Vitis vinifera | 8058 | |
| | | XP_003603503 | 357466436 | 0.758 | Medicago truncatula | 8059 | |
| | | XP_002516594 | 255761086 | 0.7337 | Ricinus communis | 8060 | |
| | | XP_002308627 | 255761085 | 0.7281 | Populus trichocarpa | 8061 | |
| | | XP_002282016 | 225430126 | 0.756 | Vitis vinifera | 8062 | |
| | 564-584 | XP_002509464 | 255761086 | 1 | Ricinus communis | 8063 | |
| | | XP_002329785 | 255761085 | 0.8641 | Populus trichocarpa | 8064 | |
| | | XP_003543041 | 356549318 | 0.8345 | Glycine max | 8065 | 9541 |
| | | XP_002305792 | 255761085 | 0.8746 | Populus trichocarpa | 8066 | |
| | | XP_003545990 | 356555337 | 0.8537 | Glycine max | 8067 | 9542 |
| | | NP_193830 | 30685267 | 0.8084 | Arabidopsis thaliana | 8068 | 9543 |
| | | AAL38704 | 17528987 | 0.8066 | Arabidopsis thaliana | 8069 | 9544 |
| | | XP_002869916 | 297853636 | 0.8049 | Arabidopsis lyrata subsp. lyrata | 8070 | |
| | | ABF69959 | 102139737 | 0.7787 | Musa acuminata | 8071 | 9545 |
| | | XP_002863589 | 297853636 | 0.7805 | Arabidopsis lyrata subsp. lyrata | 8072 | |
| | 92-112 | AAT35563 | 47558925 | 1 | Phaseolus vulgaris | 8073 | 9546 |
| | | NP_001237920 | 351727189 | 0.8889 | Glycine max | 8074 | 9547 |
| | | XP_003556188 | 356576132 | 0.8468 | Glycine max | 8075 | 9548 |
| | | CAA06615 | 3413499 | 0.7387 | Pisum sativum | 8076 | 9549 |
| | 30-50 | XP_003530858 | 356524482 | 1 | Glycine max | 8077 | 9550 |
| | 123-143 | XP_003629209 | 357517840 | 1 | Medicago truncatula | 8078 | 9551 |
| | | XP_003520082 | 356502550 | 0.8531 | Glycine max | 8079 | 9552 |
| | | XP_003547906 | 356559235 | 0.8431 | Glycine max | 8080 | 9553 |
| | | CBI20672 | 270231236 | 0.7496 | Vitis vinifera | 8081 | |
| | | XP_002279909 | 225429561 | 0.7613 | Vitis vinifera | 8082 | 9554 |

TABLE 9-continued

Target Genes of upregulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002516094 | 255761086 | 0.7963 | Ricinus communis | 8083 | |
| | | BAK61816 | 343887266 | 0.7947 | Citrus unshiu | 8084 | 9555 |
| | | XP_002308543 | 255761085 | 0.7813 | Populus trichocarpa | 8085 | |
| | | XP_002873542 | 297853636 | 0.7496 | Arabidopsis lyrata subsp. lyrata | 8086 | |
| | | NP_568256 | 18416731 | 0.7379 | Arabidopsis thaliana | 8087 | 9556 |
| | 427-447 | ACI23460 | 207113464 | 1 | Glycine soja | 8088 | 9557 |
| | | XP_003544485 | 356552257 | 0.9828 | Glycine max | 8089 | 9558 |
| | | NP_001235613 | 351727089 | 0.8798 | Glycine max | 8090 | 9559 |
| | | ACU20715 | 255640864 | 0.8197 | Glycine max | 8091 | 9560 |
| | 212-232 | NP_001236871 | 351726450 | 1 | Glycine max | 8092 | 9561 |
| | | XP_003523441 | 356509406 | 0.9197 | Glycine max | 8093 | 9562 |
| | | ACS94038 | 242877144 | 0.8294 | Cicer arietinum | 8094 | 9563 |
| | | XP_003602038 | 357463512 | 0.8261 | Medicago truncatula | 8095 | 9564 |
| | | ACD39411 | 187940570 | 0.7759 | Arachis hypogaea | 8096 | 9565 |
| | | AER45736 | 354992034 | 0.786 | Medicago sativa | 8097 | 9566 |
| | | XP_002520341 | 255761086 | 0.7425 | Ricinus communis | 8098 | |
| | | AEF80001 | 333696915 | 0.7258 | Corylus heterophylla | 8099 | 9567 |
| | | ACI15342 | 206584338 | 0.7324 | Gossypium hirsutum | 8100 | 9568 |
| | | ADL36795 | 302399000 | 0.7492 | Malus x domestica | 8101 | 9569 |
| | 616-636 | XP_003534059 | 356530984 | 1 | Glycine max | 8102 | 9570 |
| | | XP_003548267 | 356559966 | 0.8665 | Glycine max | 8103 | 9571 |
| | | XP_003619718 | 357498858 | 0.7211 | Medicago truncatula | 8104 | 9572 |
| | 118-138 | XP_003589961 | 357439368 | 1 | Medicago truncatula | 8105 | 9573 |
| | | XP_003535239 | 356533372 | 0.8081 | Glycine max | 8106 | 9574 |
| | | XP_003519713 | 356501802 | 0.8046 | Glycine max | 8107 | 9575 |
| | | XP_002514955 | 255761086 | 0.7729 | Ricinus communis | 8108 | |
| | | XP_002315622 | 255761085 | 0.7817 | Populus trichocarpa | 8109 | |
| | | CAA58823 | 639833 | 0.7676 | Solanum tuberosum | 8110 | 9576 |
| | | NP_001148767 | 226532264 | 0.7588 | Zea mays | 8111 | 9577 |
| | | XP_003557368 | 357111130 | 0.7588 | Brachypodium distachyon | 8112 | 9578 |
| | | BAJ94094 | 326490040 | 0.7711 | Hordeum vulgare subsp. vulgare | 8113 | 9579 |
| | | NP_196470 | 145357793 | 0.7835 | Arabidopsis thaliana | 8114 | 9580 |
| | 92-112 | XP_003597553 | 357454544 | 1 | Medicago truncatula | 8115 | 9581 |
| | | XP_003542066 | 356547327 | 0.8553 | Glycine max | 8116 | 9582 |
| | | XP_003546745 | 356556873 | 0.8496 | Glycine max | 8117 | 9583 |
| | | XP_002514088 | 255761086 | 0.8177 | Ricinus communis | 8118 | |
| | | Q9MT28 | | 0.7857 | Solanum tuberosum | 8119 | |
| | | XP_002285366 | 225430389 | 0.8233 | Vitis vinifera | 8120 | 9584 |
| | | NP_194713 | 145349228 | 0.7989 | Arabidopsis thaliana | 8121 | 9585 |
| | | AAB04607 | 1448916 | 0.7989 | Arabidopsis thaliana | 8122 | 9586 |
| | | XP_002867385 | 297853636 | 0.7989 | Arabidopsis lyrata subsp. lyrata | 8123 | |
| | | 2C2B_A | | 0.7763 | Arabidopsis thaliana | 8124 | |
| | 135-155 | XP_003541398 | 356545954 | 1 | Glycine max | 8125 | 9587 |
| | 142-162 | AAB50233 | 1906001 | 1 | Glycine max | 8126 | 9588 |
| | | P38500 | | 0.8037 | Betula pendula | 8127 | |
| | 123-143 | XP_003547906 | 356559235 | 1 | Glycine max | 8128 | 9589 |
| | | XP_003629209 | 357517840 | 0.8837 | Medicago truncatula | 8129 | 9590 |

TABLE 10

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| aly-miR160c-3p | 116-136 | XP_003531153 | 356525075 | 1 | Glycine max | 9591 | 10365 |
| | | XP_003524859 | 356512301 | 0.936170213 | Glycine max | 9592 | 10366 |
| | | ABO61516 | 134142361 | 0.932301741 | Glycine max | 9593 | 10367 |
| | | BAF62636 | 148189857 | 0.868471954 | Phaseolus vulgaris | 9594 | 10368 |
| | | ABI34432 | 113206403 | 0.785299807 | Pisum sativum | 9595 | 10369 |
| | | XP_002312450 | 255761085 | 0.767891683 | Populus trichocarpa | 9596 | |
| | | XP_002284648 | 225424290 | 0.735009671 | Vitis vinifera | 9597 | 10370 |
| | | BAG16374 | 171702836 | 0.721470019 | Brassica oleracea var. italica | 9598 | 10371 |
| | | AEK06229 | 339779228 | 0.733075435 | Vitis vinifera | 9599 | 10372 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| bdi-miR2508 | 699-720 | XP_003600994 | 357461424 | 1 | Medicago truncatula | 9600 | 10373 |
| | | XP_003538485 | 356540010 | 0.862608696 | Glycine max | 9601 | 10374 |
| | | NP_001236616 | 351726477 | 0.850434783 | Glycine max | 9602 | 10375 |
| | | XP_003519418 | 356501206 | 0.810434783 | Glycine max | 9603 | 10376 |
| | | XP_003544045 | 356551362 | 0.812173913 | Glycine max | 9604 | 10377 |
| | | XP_003616702 | 357492826 | 0.803478261 | Medicago truncatula | 9605 | 10378 |
| | | XP_002520796 | 255761086 | 0.76 | Ricinus communis | 9606 | |
| | | XP_002315131 | 255761085 | 0.766956522 | Populus trichocarpa | 9607 | |
| | | ABK92474 | 118481040 | 0.768695652 | Populus trichocarpa | 9608 | 10379 |
| | | XP_002312186 | 255761085 | 0.765217391 | Populus trichocarpa | 9609 | |
| | 719-740 | XP_003520941 | 356504312 | 1 | Glycine max | 9610 | 10380 |
| | | XP_003520942 | 356504314 | 0.820557491 | Glycine max | 9611 | 10381 |
| | | XP_003516921 | 356496125 | 0.740418118 | Glycine max | 9612 | 10382 |
| | 73-94 | XP_003540719 | 356544563 | 1 | Glycine max | 9613 | 10383 |
| | | XP_003539077 | 356541217 | 0.940068493 | Glycine max | 9614 | 10384 |
| | | XP_003606701 | 357472832 | 0.821917808 | Medicago truncatula | 9615 | 10385 |
| | | CBI16224 | 270227042 | 0.741438356 | Vitis vinifera | 9616 | |
| | | CAN60348 | 147789065 | 0.731164384 | Vitis vinifera | 9617 | 10386 |
| | | XP_003313424 | 255761085 | 0.75 | Populus trichocarpa | 9618 | |
| | | XP_002284473 | 225435091 | 0.729452055 | Vitis vinifera | 9619 | 10387 |
| | | XP_002278215 | 225449449 | 0.731164384 | Vitis vinifera | 9620 | 10388 |
| | | CBI16199 | 270227042 | 0.724315068 | Vitis vinifera | 9621 | |
| | 651-672 | XP_003516921 | 356496125 | 1 | Glycine max | 9622 | 10389 |
| | | XP_003520941 | 356504312 | 0.75308642 | Glycine max | 9623 | 10390 |
| | 77-98 | XP_003522150 | 356506771 | 1 | Glycine max | 9624 | 10391 |
| | | XP_003516941 | 356496165 | 0.967684022 | Glycine max | 9625 | 10392 |
| | | XP_003604619 | 357468668 | 0.845601436 | Medicago truncatula | 9626 | 10393 |
| | | XP_002322961 | 255761085 | 0.782764811 | Populus trichocarpa | 9627 | |
| | | XP_002533894 | 255761086 | 0.763016158 | Ricinus communis | 9628 | |
| | | XP_002278638 | 225440625 | 0.782764811 | Vitis vinifera | 9629 | 10394 |
| | | XP_002322962 | 255761085 | 0.777378815 | Populus trichocarpa | 9630 | |
| | | XP_002308209 | 255761085 | 0.771992819 | Populus trichocarpa | 9631 | |
| | | XP_003552227 | 356568050 | 0.822262118 | Glycine max | 9632 | 10395 |
| | | AAC49536 | 1685086 | 0.755834829 | Nicotiana tabacum | 9633 | 10396 |
| | 86-107 | CAN73336 | 147800866 | 1 | Vitis vinifera | 9634 | |
| | | XP_002282815 | 225449411 | 0.990859232 | Vitis vinifera | 9635 | 10397 |
| | | XP_002282823 | 225449413 | 0.946983547 | Vitis vinifera | 9636 | 10398 |
| | | XP_002278232 | 225449451 | 0.936014625 | Vitis vinifera | 9637 | 10399 |
| | | CAN60069 | 147779995 | 0.92321755 | Vitis vinifera | 9638 | |
| | | CAN72263 | 147821463 | 0.92321755 | Vitis vinifera | 9639 | 10400 |
| | | XP_002278275 | 225449453 | 0.91773309 | Vitis vinifera | 9640 | 10401 |
| | 585-606 | XP_003516921 | 356496125 | 1 | Glycine max | 9641 | 10402 |
| | 549-570 | XP_003606701 | 357472832 | 1 | Medicago truncatula | 9642 | 10403 |
| | | XP_003540719 | 356544563 | 0.839316239 | Glycine max | 9643 | 10404 |
| | | XP_003623041 | 357505504 | 0.733333333 | Medicago truncatula | 9644 | 10405 |
| | | XP_003551448 | 356566457 | 0.714529915 | Glycine max | 9645 | 10406 |
| | | XP_003532315 | 356527432 | 0.712820513 | Glycine max | 9646 | 10407 |
| | 164-185 | XP_003529133 | 356520972 | 1 | Glycine max | 9647 | 10408 |
| | | XP_003552215 | 356568025 | 0.954385965 | Glycine max | 9648 | 10409 |
| | | XP_003529131 | 356520968 | 0.722807018 | Glycine max | 9649 | 10410 |
| | | ABC59623 | 84626065 | 0.721052632 | Pisum sativum | 9650 | 10411 |
| | 3846-3867 | XP_003551446 | 356566453 | 1 | Glycine max | 9651 | |
| | 699-720 | XP_003600994 | 357461424 | 1 | Medicago truncatula | 9652 | 10412 |
| | 261-282 | XP_003520941 | 356504312 | 1 | Glycine max | 9653 | 10413 |
| | 576-597 | XP_003604619 | 357468668 | 1 | Medicago truncatula | 9654 | 10414 |
| | | XP_003522150 | 356506771 | 0.845601436 | Glycine max | 9655 | 10415 |
| | | XP_002308208 | 255761085 | 0.777378815 | Populus trichocarpa | 9656 | |
| | 0-21 | XP_003516941 | 356496165 | 1 | Glycine max | 9657 | 10416 |
| | 645-666 | CBI16199 | 270227042 | 1 | Vitis vinifera | 9658 | |
| | | CAN80346 | 147858024 | 0.924028269 | Vitis vinifera | 9659 | 10417 |
| | | XP_003552160 | 356567914 | 0.85335689 | Glycine max | 9660 | 10418 |
| | | XP_002329138 | 255761085 | 0.846289753 | Populus trichocarpa | 9661 | |
| | | XP_002299296 | 255761085 | 0.85335689 | Populus trichocarpa | 9662 | |
| | | XP_002531824 | 255761086 | 0.848056537 | Ricinus communis | 9663 | |
| | 690-711 | XP_003530212 | 356523164 | 1 | Glycine max | 9664 | 10419 |
| | | XP_003551482 | 356566526 | 0.955094991 | Glycine max | 9665 | 10420 |
| | | XP_002308164 | 255761085 | 0.778929188 | Populus trichocarpa | 9666 | |
| | | XP_002531565 | 255761086 | 0.772020725 | Ricinus communis | 9667 | |
| | | CAA74105 | 3805963 | 0.773747841 | Populus trichocarpa | 9668 | 10421 |
| | | XP_002300066 | 255761085 | 0.730569948 | Populus trichocarpa | 9669 | |
| | 681-702 | XP_003530213 | 356523166 | 1 | Glycine max | 9670 | 10422 |
| | | XP_003552179 | 356567952 | 0.915447154 | Glycine max | 9671 | 10423 |
| | | XP_003532290 | 356527381 | 0.765853659 | Glycine max | 9672 | 10424 |
| | | XP_002309069 | 255761085 | 0.733333333 | Populus trichocarpa | 9673 | |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002531562 | 255761086 | 0.726829268 | Ricinus communis | 9674 | |
| | | XP_002271006 | 225440401 | 0.713821138 | Vitis vinifera | 9675 | 10425 |
| | | XP_002268628 | 225440403 | 0.713821138 | Vitis vinifera | 9676 | 10426 |
| | | XP_002269038 | 225440405 | 0.707317073 | Vitis vinifera | 9677 | 10427 |
| | | CBI30529 | 270242856 | 0.704065041 | Vitis vinifera | 9678 | |
| | 651-672 | XP_003551482 | 356566526 | 1 | Glycine max | 9679 | 10428 |
| | | XP_003530212 | 356523164 | 0.960069444 | Glycine max | 9680 | 10429 |
| | 666-687 | XP_003539958 | 356543013 | 1 | Glycine max | 9681 | 10430 |
| | | XP_003551299 | 356566152 | 0.941605839 | Glycine max | 9682 | 10431 |
| | | XP_003518300 | 356498931 | 0.879562044 | Glycine max | 9683 | 10432 |
| | | XP_003544873 | 356553053 | 0.881386861 | Glycine max | 9684 | 10433 |
| | | XP_003615575 | 357490574 | 0.855839416 | Medicago truncatula | 9685 | 10434 |
| | | XP_002520425 | 255761086 | 0.822992701 | Ricinus communis | 9686 | |
| | | XP_002314124 | 255761085 | 0.812043796 | Populus trichocarpa | 9687 | |
| | | XP_002299828 | 255761085 | 0.813868613 | Populus trichocarpa | 9688 | |
| | | XP_002280416 | 225434677 | 0.79379562 | Vitis vinifera | 9689 | 10435 |
| | 86-107 | CAN73336 | 147800866 | 1 | Vitis vinifera | 9690 | |
| | 121-142 | XP_003615575 | 357490574 | 1 | Medicago truncatula | 9691 | 10436 |
| | | XP_003539958 | 356543013 | 0.777403035 | Glycine max | 9692 | 10437 |
| | 1113-1134 | XP_003548937 | 356561332 | 1 | Glycine max | 9693 | 10438 |
| | | XP_003519950 | 356502284 | 0.814741036 | Glycine max | 9694 | 10439 |
| | | XP_002319173 | 255761085 | 0.802788845 | Populus trichocarpa | 9695 | |
| | | XP_002325825 | 255761085 | 0.794820717 | Populus trichocarpa | 9696 | |
| | | CAN70030 | 147821579 | 0.790836653 | Vitis vinifera | 9697 | 10440 |
| | | XP_002525455 | 255761086 | 0.778884462 | Ricinus communis | 9698 | |
| | | XP_002304847 | 255761085 | 0.780876494 | Populus trichocarpa | 9699 | |
| | | XP_003625586 | 357510594 | 0.784860558 | Medicago truncatula | 9700 | 10441 |
| | | XP_003607828 | 357475084 | 0.778884462 | Medicago truncatula | 9701 | 10442 |
| | | XP_002523396 | 255761086 | 0.782868526 | Ricinus communis | 9702 | |
| | 633-654 | XP_003551299 | 356566152 | 1 | Glycine max | 9703 | 10443 |
| | 1051-1072 | XP_003520176 | 356502743 | 1 | Glycine max | 9704 | 10444 |
| | | XP_003528495 | 356519673 | 0.93444227 | Glycine max | 9705 | 10445 |
| | | XP_003608057 | 357475542 | 0.777886497 | Medicago truncatula | 9706 | 10446 |
| | 636-657 | XP_003552213 | 356568021 | 1 | Glycine max | 9707 | 10447 |
| | | XP_003529132 | 356520970 | 0.732517483 | Glycine max | 9708 | 10448 |
| | | XP_003552214 | 356568023 | 0.723776224 | Glycine max | 9709 | 10449 |
| | | XP_003529133 | 356520972 | 0.708041958 | Glycine max | 9710 | 10450 |
| | 666-687 | XP_003544873 | 356553053 | 1 | Glycine max | 9711 | 10451 |
| | 666-687 | XP_003552227 | 356568050 | 1 | Glycine max | 9712 | 10452 |
| | 777-798 | XP_003529132 | 356520970 | 1 | Glycine max | 9713 | 10453 |
| | | XP_003552213 | 356568021 | 0.708551483 | Glycine max | 9714 | 10454 |
| | 654-675 | XP_003552215 | 356568025 | 1 | Glycine max | 9715 | 10455 |
| | 660-681 | XP_003529131 | 356520968 | 1 | Glycine max | 9716 | 10456 |
| | 636-657 | XP_003539077 | 356541217 | 1 | Glycine max | 9717 | 10457 |
| | | XP_003551449 | 356566459 | 0.712328767 | Glycine max | 9718 | 10458 |
| | 693-714 | XP_003538485 | 356540010 | 1 | Glycine max | 9719 | 10459 |
| | | CBI25418 | 270236032 | 0.785349233 | Vitis vinifera | 9720 | 10460 |
| | 567-588 | XP_003552179 | 356567952 | 1 | Glycine max | 9721 | 10461 |
| | | XP_003530213 | 356523166 | 0.964041096 | Glycine max | 9722 | 10462 |
| gma-miR2119 | 138-158 | XP_003527195 | 356517033 | 1 | Glycine max | 9723 | 10463 |
| | | XP_003527162 | 356516966 | 0.885620915 | Glycine max | 9724 | 10464 |
| | | XP_003527196 | 356517035 | 0.866013072 | Glycine max | 9725 | 10465 |
| | | XP_003522929 | 356508367 | 0.81372549 | Glycine max | 9726 | 10466 |
| | | XP_003522930 | 356508369 | 0.839869281 | Glycine max | 9727 | 10467 |
| | | ACU24029 | 255647121 | 0.833333333 | Glycine max | 9728 | 10468 |
| | 157-177 | XP_003542005 | 356547201 | 1 | Glycine max | 9729 | 10469 |
| | | ACU18712 | 255636755 | 0.994722955 | Glycine max | 9730 | 10470 |
| | | XP_003545664 | 356554663 | 0.939313984 | Glycine max | 9731 | 10471 |
| | | AAN03476 | 22597177 | 0.936675462 | Glycine max | 9732 | 10472 |
| | | XP_003544738 | 356552774 | 0.802110818 | Glycine max | 9733 | 10473 |
| | | AAO72531 | 29373060 | 0.807387863 | Lotus corniculatus | 9734 | 10474 |
| | | CAA80691 | 452768 | 0.799472296 | Phaseolus acutifolius | 9735 | 10475 |
| | | CAG30579 | 51587337 | 0.80474934 | Lotus japonicus | 9736 | 10476 |
| | | AET21261 | 356582741 | 0.802110818 | Lotus japonicus | 9737 | 10477 |
| | | P13603 | | 0.799472296 | Trifolium repens | 9738 | |
| | 526-546 | XP_003521584 | 356505611 | 1 | Glycine max | 9739 | 10478 |
| | | XP_003554536 | 356572764 | 0.971098266 | Glycine max | 9740 | 10479 |
| | | XP_003536003 | 356534928 | 0.809248555 | Glycine max | 9741 | 10480 |
| | | XP_003518934 | 356500225 | 0.800578035 | Glycine max | 9742 | 10481 |
| | | XP_002302739 | 255761085 | 0.789017341 | Populus trichocarpa | 9743 | |
| | | XP_002320324 | 255761085 | 0.777456647 | Populus trichocarpa | 9744 | |
| | | NP_191825 | 145339785 | 0.757225434 | Arabidopsis thaliana | 9745 | 10482 |
| | | XP_002876684 | 297853636 | 0.757225434 | Arabidopsis lyrata subsp. lyrata | 9746 | |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002872855 | 297853636 | 0.760115607 | Arabidopsis lyrata subsp. lyrata | 9747 | |
| | | CAB83116 | 7362737 | 0.748554913 | Arabidopsis thaliana | 9748 | 10483 |
| | 2061-2081 | XP_003524240 | 356511040 | 1 | Glycine max | 9749 | 10484 |
| | | XP_003532800 | 356528417 | 0.955097087 | Glycine max | 9750 | 10485 |
| | | XP_003630005 | 357519432 | 0.82038835 | Medicago truncatula | 9751 | 10486 |
| | | XP_002317684 | 255761085 | 0.770631068 | Populus trichocarpa | 9752 | |
| | | XP_002332198 | 255761085 | 0.766990291 | Populus trichocarpa | 9753 | |
| | | XP_003533825 | 356530512 | 0.769417476 | Glycine max | 9754 | 10487 |
| | | XP_003547559 | 356558531 | 0.764563107 | Glycine max | 9755 | 10488 |
| | | XP_002271023 | 225444212 | 0.751213592 | Vitis vinifera | 9756 | 10489 |
| | 399-419 | XP_003539263 | 356541601 | 1 | Glycine max | 9757 | 10490 |
| | | XP_003517354 | 356497002 | 0.913716814 | Glycine max | 9758 | 10491 |
| | | XP_003611556 | 357482538 | 0.767699115 | Medicago truncatula | 9759 | 10492 |
| | | CAI79403 | 62700758 | 0.71460177 | Senna occidentalis | 9760 | 10493 |
| | 265-285 | XP_003554536 | 356572764 | 1 | Glycine max | 9761 | 10494 |
| | | XP_003521584 | 356505611 | 0.971098266 | Glycine max | 9762 | 10495 |
| | | XP_003625940 | 357511302 | 0.75433526 | Medicago truncatula | 9763 | 10496 |
| | 159-179 | XP_003545664 | 356554663 | 1 | Glycine max | 9764 | 10497 |
| | | XP_003542005 | 356547201 | 0.959568733 | Glycine max | 9765 | 10498 |
| | | P12886 | | 0.789757412 | Pisum sativum | 9766 | |
| | 360-380 | AAO83155 | 29365515 | 1 | Phaseolus vulgaris | 9767 | 10499 |
| | | XP_003534097 | 356531061 | 0.870201097 | Glycine max | 9768 | 10500 |
| | | XP_003548308 | 356560048 | 0.886654479 | Glycine max | 9769 | 10501 |
| | 2055-2075 | XP_003532800 | 356528417 | 1 | Glycine max | 9770 | 10502 |
| | | XP_003524240 | 356511040 | 0.955097087 | Glycine max | 9771 | 10503 |
| | 2157-2177 | XP_003547559 | 356558531 | 1 | Glycine max | 9772 | 10504 |
| | 174-194 | XP_003517354 | 356497002 | 1 | Glycine max | 9773 | 10505 |
| | | XP_003539263 | 356541601 | 0.919821826 | Glycine max | 9774 | 10506 |
| gso-miR482a | 22-42 | AAU95080 | 53830374 | 1 | Glycine max | 9775 | 10507 |
| | 22-42 | AAF44087 | 7263110 | 1 | Glycine max | 9776 | 10508 |
| | | AAX81296 | 62361234 | 0.714285714 | Arachis hypogaea | 9777 | 10509 |
| | 1195-1215 | NP_001237600 | 351725318 | 1 | Glycine max | 9778 | 10510 |
| | | XP_003556265 | 356576288 | 0.891737892 | Glycine max | 9779 | 10511 |
| | | XP_003591822 | 357443088 | 0.811965812 | Medicago truncatula | 9780 | 10512 |
| | | ACI46678 | 209419748 | 0.811965812 | Galega orientalis | 9781 | 10513 |
| | | XP_003518682 | 356499714 | 0.740740741 | Glycine max | 9782 | 10514 |
| | | XP_003516851 | 356495985 | 0.752136752 | Glycine max | 9783 | 10515 |
| | | XP_003614455 | 357488334 | 0.732193732 | Medicago truncatula | 9784 | 10516 |
| | 503-523 | XP_003533606 | 356530067 | 1 | Glycine max | 9785 | 10517 |
| | 59-79 | XP_003518623 | 356499593 | 1 | Glycine max | 9786 | 10518 |
| | | XP_003591325 | 357442094 | 0.832673267 | Medicago truncatula | 9787 | 10519 |
| | | XP_003626036 | 357511494 | 0.751485149 | Medicago truncatula | 9788 | 10520 |
| | | XP_002515202 | 255761086 | 0.7 | Ricinus communis | 9789 | |
| | 22-42 | AAF44087 | 7263110 | 1 | Glycine max | 9790 | 10521 |
| osa-miR162a | 342-362 | XP_003590416 | 357440276 | 1 | Medicago truncatula | 9791 | 10522 |
| | | XP_003554409 | 356572505 | 0.775075988 | Glycine max | 9792 | 10523 |
| | | XP_003521428 | 356505296 | 0.767477204 | Glycine max | 9793 | 10524 |
| | | XP_003625731 | 357510884 | 0.770516717 | Medicago truncatula | 9794 | 10525 |
| | | XP_002264567 | 225441081 | 0.734042553 | Vitis vinifera | 9795 | 10526 |
| | | XP_003541439 | 356546037 | 0.759878419 | Glycine max | 9796 | 10527 |
| | | CAN74141 | 147838148 | 0.705167173 | Vitis vinifera | 9797 | |
| | | XP_002519415 | 255761086 | 0.703647416 | Ricinus communis | 9798 | |
| | 619-639 | XP_003528812 | 356520321 | 1 | Glycine max | 9799 | 10528 |
| | | XP_003528810 | 356520317 | 0.979865772 | Glycine max | 9800 | 10529 |
| | | XP_003548576 | 356560594 | 0.976510067 | Glycine max | 9801 | 10530 |
| | | XP_003543259 | 356549760 | 0.963087248 | Glycine max | 9802 | 10531 |
| | | XP_003543258 | 356549758 | 0.959731544 | Glycine max | 9803 | 10532 |
| | | ACU23594 | 255646218 | 0.966442953 | Glycine max | 9804 | 10533 |
| | | ACJ85054 | 217073389 | 0.89261745 | Medicago truncatula | 9805 | 10534 |
| | | XP_002329431 | 255761085 | 0.879194631 | Populus trichocarpa | 9806 | |
| | | XP_003604056 | 357467542 | 0.848993289 | Medicago truncatula | 9807 | 10535 |
| | | XP_002524558 | 255761086 | 0.82885906 | Ricinus communis | 9808 | |
| | 585-605 | XP_003543259 | 356549760 | 1 | Glycine max | 9809 | 10536 |
| | | XP_003528812 | 356520321 | 0.963087248 | Glycine max | 9810 | 10537 |
| | | XP_002330691 | 255761085 | 0.859060403 | Populus trichocarpa | 9811 | |
| | 1037-1057 | XP_002311013 | 255761085 | 1 | Populus trichocarpa | 9812 | |
| | | XP_002315438 | 255761085 | 0.935779817 | Populus trichocarpa | 9813 | |
| | | XP_002521182 | 255761086 | 0.862385321 | Ricinus communis | 9814 | |
| | | XP_003536707 | 356536360 | 0.834862385 | Glycine max | 9815 | 10538 |
| | | XP_003555872 | 356575487 | 0.830275229 | Glycine max | 9816 | 10539 |
| | | XP_002268975 | 225450253 | 0.811926606 | Vitis vinifera | 9817 | 10540 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 144-164 | XP_003548576 | 356560594 | 1 | *Glycine max* | 9818 | 10541 |
| | 63-83 | XP_003528812 | 356520321 | 1 | *Glycine max* | 9819 | 10542 |
| | 217-237 | NP_001237819 | 351724250 | 1 | *Glycine max* | 9820 | 10543 |
| | | NP_001238239 | 351721616 | 0.964285714 | *Glycine max* | 9821 | 10544 |
| | | ACF06595 | 192912973 | 0.898809524 | *Elaeis guineensis* | 9822 | 10545 |
| | | Q5J907 | | 0.892857143 | *Elaeis guineensis* | 9823 | |
| | | ACF06596 | 192912975 | 0.904761905 | *Elaeis guineensis* | 9824 | 10546 |
| | | ACF06557 | 192910897 | 0.875 | *Elaeis guineensis* | 9825 | 10547 |
| | | XP_003577266 | 357155873 | 0.845238095 | *Brachypodium distachyon* | 9826 | 10548 |
| | | XP_002516930 | 255761086 | 0.857142857 | *Ricinus communis* | 9827 | |
| | | AEH05972 | 334854631 | 0.863095238 | *Hevea brasiliensis* | 9828 | 10549 |
| | | NP_001235906 | 351720717 | 0.851190476 | *Glycine max* | 9829 | 10550 |
| osa-miR1846e | 615-634 | XP_003531377 | 356525528 | 1 | *Glycine max* | 9830 | 10551 |
| | | XP_003525073 | 356512737 | 0.958823529 | *Glycine max* | 9831 | 10552 |
| | | XP_002310600 | 255761085 | 0.785294118 | *Populus trichocarpa* | 9832 | |
| | | XP_002307126 | 255761085 | 0.8 | *Populus trichocarpa* | 9833 | |
| | | XP_002280295 | 225438578 | 0.808823529 | *Vitis vinifera* | 9834 | 10553 |
| | | XP_003523264 | 356509047 | 0.826470588 | *Glycine max* | 9835 | 10554 |
| | | AAZ66923 | 37694873 | 0.708823529 | *Brassica rapa* | 9836 | 10555 |
| | | ACK44524 | 217426787 | 0.708823529 | *Arabidopsis arenosa* | 9837 | 10556 |
| | | XP_002871399 | 297853636 | 0.7 | *Arabidopsis lyrata* subsp. *lyrata* | 9838 | |
| | | NP_196563 | 145357839 | 0.702941176 | *Arabidopsis thaliana* | 9839 | 10557 |
| | 379-398 | XP_003531668 | 356526120 | 1 | *Glycine max* | 9840 | 10558 |
| | | XP_003529761 | 356522251 | 0.915980231 | *Glycine max* | 9841 | 10559 |
| | | XP_003530142 | 356523023 | 0.756177924 | *Glycine max* | 9842 | 10560 |
| | | XP_003546477 | 356556325 | 0.73476112 | *Glycine max* | 9843 | 10561 |
| | | XP_003531667 | 356526118 | 0.731466227 | *Glycine max* | 9844 | 10562 |
| | 114-133 | XP_003529761 | 356522251 | 1 | *Glycine max* | 9845 | 10563 |
| | | XP_003531668 | 356526120 | 0.917491749 | *Glycine max* | 9846 | 10564 |
| | | XP_003597728 | 357454894 | 0.724422442 | *Medicago truncatula* | 9847 | 10565 |
| | 367-386 | XP_003530142 | 356523023 | 1 | *Glycine max* | 9848 | 10566 |
| | | XP_003597726 | 357454890 | 0.700490998 | *Medicago truncatula* | 9849 | 10567 |
| osa-miR2104 | 256-277 | NP_001105847 | 162464254 | 1 | *Zea mays* | 9850 | |
| | | ABA42672 | 76443928 | 0.881188119 | *Zea mays* | 9851 | |
| | | Q2N2K2 | | 0.927392739 | *Glycine max* | 9852 | |
| | | XP_002447301 | 255761094 | 0.907590759 | *Sorghum bicolor* | 9853 | |
| | | ACG23902 | 195604143 | 0.811881188 | *Zea mays* | 9854 | 10568 |
| | 256-277 | NP_001105847 | 162464254 | 1 | *Zea mays* | 9855 | 10569 |
| osa-miRf11415-akr | 103-122 | ABU94631 | 156754274 | 1 | *Phaseolus vulgaris* | 9856 | 10570 |
| | | XP_003536353 | 356535640 | 0.944250871 | *Glycine max* | 9857 | 10571 |
| | | XP_003556232 | 356576220 | 0.951219512 | *Glycine max* | 9858 | 10572 |
| | | ACU24483 | 255648054 | 0.947735192 | *Glycine max* | 9859 | 10573 |
| | | AAC17529 | 3158475 | 0.919860627 | *Samanea saman* | 9860 | 10574 |
| | | ACJ85173 | 217073625 | 0.905923345 | *Medicago truncatula* | 9861 | 10575 |
| | | XP_003548070 | 356559566 | 0.891986063 | *Glycine max* | 9862 | 10576 |
| | | BAB40143 | 13486941 | 0.888501742 | *Pyrus communis* | 9863 | 10577 |
| | | ACU20229 | 255639872 | 0.891986063 | *Glycine max* | 9864 | 10578 |
| | | BAD90699 | 60498688 | 0.898954704 | *Mimosa pudica* | 9865 | 10579 |
| ctr-miR171 | 477-497 | XP_003538071 | 356539165 | 1 | *Glycine max* | 9866 | 10580 |
| | | XP_003517966 | 356498249 | 0.849056604 | *Glycine max* | 9867 | 10581 |
| pta-miR166c | 17-37 | XP_003627005 | 357513432 | 1 | *Medicago truncatula* | 9868 | 10582 |
| | | XP_003531652 | 356526088 | 0.921875 | *Glycine max* | 9869 | 10583 |
| | | XP_003530109 | 356522957 | 0.923076923 | *Glycine max* | 9870 | 10584 |
| | | XP_003530112 | 356522963 | 0.913461538 | *Glycine max* | 9871 | 10585 |
| | | ACI13685 | 206572104 | 0.889423077 | *Malus × domestica* | 9872 | 10586 |
| | | XP_003597690 | 357454818 | 0.894230769 | *Medicago truncatula* | 9873 | 10587 |
| | | XP_002515977 | 255761086 | 0.887019231 | *Ricinus communis* | 9874 | |
| | | XP_002284003 | 225442500 | 0.890625 | *Vitis vinifera* | 9875 | 10588 |
| | | CBI36079 | 270253379 | 0.890625 | *Vitis vinifera* | 9876 | |
| | | XP_003531653 | 356526090 | 0.900240385 | *Glycine max* | 9877 | 10589 |
| | 87-107 | CAN73584 | 147820217 | 1 | *Vitis vinifera* | 9878 | |
| | | XP_002281868 | 225444032 | 1 | *Vitis vinifera* | 9879 | 10590 |
| | | XP_002298892 | 255761085 | 0.918343195 | *Populus trichocarpa* | 9880 | |
| | | XP_002332526 | 255761085 | 0.90887574 | *Populus trichocarpa* | 9881 | |
| | | XP_003535078 | 356533042 | 0.880473373 | *Glycine max* | 9882 | 10591 |
| | | XP_003546255 | 356555874 | 0.882840237 | *Glycine max* | 9883 | 10592 |
| | | AAS66760 | 45479745 | 0.878106509 | *Nicotiana sylvestris* | 9884 | 10593 |
| | | XP_003532788 | 356528393 | 0.852071006 | *Glycine max* | 9885 | 10594 |
| | | XP_003524993 | 356512573 | 0.840236686 | *Glycine max* | 9886 | 10595 |
| | | ACI13683 | 206572100 | 0.820118343 | *Malus × domestica* | 9887 | 10596 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 40-60 | AAS10176 | 41745611 | 1 | Antirrhinum majus | 9888 | 10597 |
| | 1228-1248 | XP_002285176 | 225435326 | 1 | Vitis vinifera | 9889 | 10598 |
| | | CAN61612 | 147783603 | 0.981042654 | Vitis vinifera | 9890 | |
| | | XP_002529946 | 255761086 | 0.918246445 | Ricinus communis | 9891 | |
| | | XP_003538150 | 356539326 | 0.892180095 | Glycine max | 9892 | 10599 |
| | | XP_003539764 | 356542618 | 0.895734597 | Glycine max | 9893 | 10600 |
| | | ACI13684 | 206572102 | 0.888625592 | Malus × domestica | 9894 | 10601 |
| | | XP_003539765 | 356542620 | 0.890995261 | Glycine max | 9895 | 10602 |
| | | AAX19050 | 60327620 | 0.881516588 | Populus trichocarpa | 9896 | 10603 |
| | | DAA05766 | 109729904 | 0.853080569 | Lotus japonicus | 9897 | |
| | | AAY33856 | 63115353 | 0.8507109 | Gossypium barbadense | 9898 | 10604 |
| | 557-577 | XP_002298892 | 255761085 | 1 | Populus trichocarpa | 9899 | |
| | | CAN73584 | 147820217 | 0.91943128 | Vitis vinifera | 9900 | |
| | 515-535 | XP_003597690 | 357454818 | 1 | Medicago truncatula | 9901 | 10605 |
| | | XP_002284014 | 225442502 | 0.897129187 | Vitis vinifera | 9902 | 10606 |
| | | XP_002304217 | 255761085 | 0.888755981 | Populus trichocarpa | 9903 | |
| | 560-580 | XP_002285176 | 225435326 | 1 | Vitis vinifera | 9904 | 10607 |
| | 554-574 | XP_003603630 | 357466690 | 1 | Medicago truncatula | 9905 | 10608 |
| | | XP_003522716 | 356507930 | 0.943645084 | Glycine max | 9906 | 10609 |
| | | XP_003526496 | 356515618 | 0.940047962 | Glycine max | 9907 | 10610 |
| | | ACI13686 | 206572106 | 0.872901679 | Malus × domestica | 9908 | 10611 |
| | | ADL36609 | 302398628 | 0.863309353 | Malus × domestica | 9909 | 10612 |
| | | CBI20838 | 270231236 | 0.862110312 | Vitis vinifera | 9910 | |
| | | XP_002283717 | 225429913 | 0.862110312 | Vitis vinifera | 9911 | 10613 |
| | | ACL51017 | 219879369 | 0.858513189 | Citrus trifoliata | 9912 | 10614 |
| | | XP_002309538 | 255761085 | 0.868105516 | Populus trichocarpa | 9913 | |
| | | XP_002324794 | 255761085 | 0.857314149 | Populus trichocarpa | 9914 | |
| | 40-60 | AAS10176 | 41745611 | 1 | Antirrhinum majus | 9915 | 10615 |
| | 554-574 | XP_003530109 | 356522957 | 1 | Glycine max | 9916 | 10616 |
| | 590-610 | XP_003524993 | 356512573 | 1 | Glycine max | 9917 | 10617 |
| | | XP_003594520 | 357448488 | 0.781946073 | Medicago truncatula | 9918 | 10618 |
| | 25-45 | XP_003522716 | 356507930 | 1 | Glycine max | 9919 | 10619 |
| | | XP_003603630 | 357466690 | 0.932464455 | Medicago truncatula | 9920 | 10620 |
| | 560-580 | XP_003530112 | 356522963 | 1 | Glycine max | 9921 | 10621 |
| | 530-550 | XP_003532788 | 356528393 | 1 | Glycine max | 9922 | 10622 |
| | 87-107 | CAN73584 | 147820217 | 1 | Vitis vinifera | 9923 | |
| | 566-586 | XP_003531653 | 356526090 | 1 | Glycine max | 9924 | 10623 |
| | 560-580 | XP_003539764 | 356542618 | 1 | Glycine max | 9925 | 10624 |
| | | XP_002285176 | 225435326 | 0.894674556 | Vitis vinifera | 9926 | 10625 |
| | | CAC84906 | 18076735 | 0.829585799 | Zinnia violacea | 9927 | 10626 |
| | 828-848 | XP_003539765 | 356542620 | 1 | Glycine max | 9928 | 10627 |
| ptc-miRf10976-akr | 81-100 | XP_003548151 | 356559731 | 1 | Glycine max | 9929 | 10628 |
| | | XP_003529873 | 356522477 | 0.888 | Glycine max | 9930 | 10629 |
| | | XP_003548400 | 356560236 | 0.849333333 | Glycine max | 9931 | 10630 |
| | 249-268 | NP_001238468 | 351720798 | 1 | Glycine max | 9932 | 10631 |
| | 242-261 | XP_003520705 | 356503828 | 1 | Glycine max | 9933 | 10632 |
| | | XP_003553607 | 356570870 | 0.874626866 | Glycine max | 9934 | 10633 |
| | 295-314 | XP_003533044 | 356528917 | 1 | Glycine max | 9935 | 10634 |
| | | XP_003529756 | 356522241 | 0.905759162 | Glycine max | 9936 | 10635 |
| | | XP_003543627 | 356550505 | 0.732984293 | Glycine max | 9937 | 10636 |
| | | XP_003546548 | 356556469 | 0.722513089 | Glycine max | 9938 | 10637 |
| | | XP_003597684 | 357454806 | 0.712041885 | Medicago truncatula | 9939 | 10638 |
| | | XP_003597685 | 357454808 | 0.701570681 | Medicago truncatula | 9940 | 10639 |
| | 268-287 | XP_003528486 | 356519654 | 1 | Glycine max | 9941 | 10640 |
| | | XP_003520183 | 356502757 | 0.899071926 | Glycine max | 9942 | 10641 |
| ptc-miRf11018-akr | 66-85 | XP_003524954 | 356512494 | 1 | Glycine max | 9943 | 10642 |
| | | XP_003531241 | 356525252 | 0.920604915 | Glycine max | 9944 | 10643 |
| | | AET04202 | 357518874 | 0.797731569 | Medicago truncatula | 9945 | 10644 |
| | | AET04197 | 357518864 | 0.752362949 | Medicago truncatula | 9946 | 10645 |
| | | AET04200 | 357518870 | 0.756143667 | Medicago truncatula | 9947 | 10646 |
| ptc-miRf11669-akr | 1236-1255 | XP_002275990 | 225451234 | 1 | Vitis vinifera | 9948 | 10647 |
| | | XP_002512253 | 255761086 | 0.916923077 | Ricinus communis | 9949 | |
| | | XP_003554689 | 356573071 | 0.895384615 | Glycine max | 9950 | 10648 |
| | | XP_002319618 | 255761085 | 0.916923077 | Populus trichocarpa | 9951 | |
| | | XP_002336146 | 255761085 | 0.895384615 | Populus trichocarpa | 9952 | |
| | | XP_002328363 | 255761085 | 0.895384615 | Populus trichocarpa | 9953 | |
| | | ACU22789 | 255644572 | 0.886153846 | Glycine max | 9954 | 10649 |
| | | ADN33908 | 307136046 | 0.898461538 | Cucumis melo subsp. melo | 9955 | 10650 |
| | | Q43317 | | 0.898461538 | Citrullus lanatus subsp. vulgaris | 9956 | |
| | | XP_002311629 | 255761085 | 0.901538462 | Populus trichocarpa | 9957 | |
| | 259-278 | XP_003624868 | 357509158 | 1 | Medicago truncatula | 9958 | 10651 |
| | | ACJ85972 | 217075223 | 0.995098039 | Medicago truncatula | 9959 | 10652 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_003608106 | 357475640 | 0.965686275 | Medicago truncatula | 9960 | 10653 |
| | | NP_001237278 | 351723416 | 0.965686275 | Glycine max | 9961 | 10654 |
| | | NP_564149 | 30687501 | 0.931372549 | Arabidopsis thaliana | 9962 | 10655 |
| | | NP_001237990 | 351721817 | 0.941176471 | Glycine max | 9963 | 10656 |
| | | XP_002890456 | 297853636 | 0.926470588 | Arabidopsis lyrata subsp. lyrata | 9964 | |
| | | NP_565156 | 186496015 | 0.93627451 | Arabidopsis thaliana | 9965 | 10657 |
| | | XP_002887683 | 297853636 | 0.931372549 | Arabidopsis lyrata subsp. lyrata | 9966 | |
| | | AAM62756 | 21404242 | 0.926470588 | Arabidopsis thaliana | 9967 | 10658 |
| | 170-189 | XP_003535921 | 356534761 | 1 | Glycine max | 9968 | 10659 |
| | | XP_003519071 | 356500502 | 0.968379447 | Glycine max | 9969 | 10660 |
| | | XP_002284060 | 225441833 | 0.773386034 | Vitis vinifera | 9970 | 10661 |
| | | CAN82225 | 147852313 | 0.770750988 | Vitis vinifera | 9971 | 10662 |
| | | XP_002532077 | 255761086 | 0.744400527 | Ricinus communis | 9972 | |
| | | XP_002323318 | 255761085 | 0.737812912 | Populus trichocarpa | 9973 | |
| | | XP_002308029 | 255761085 | 0.749670619 | Populus trichocarpa | 9974 | |
| | | CBI29841 | 270242856 | 0.753623188 | Vitis vinifera | 9975 | 10663 |
| | | NP_565960 | 18405800 | 0.723320158 | Arabidopsis thaliana | 9976 | 10664 |
| | | XP_002878149 | 297853636 | 0.72859025 | Arabidopsis lyrata subsp. lyrata | 9977 | |
| | 120-139 | AAQ57205 | 34099832 | 1 | Populus tremula × Populus alba | 9978 | 10665 |
| | 877-896 | XP_003526542 | 356515711 | 1 | Glycine max | 9979 | 10666 |
| | | XP_003523783 | 356510109 | 0.846153846 | Glycine max | 9980 | 10667 |
| | 588-607 | XP_002264051 | 225429233 | 1 | Vitis vinifera | 9981 | 10668 |
| | | CAN64867 | 123673833 | 0.996763754 | Vitis vinifera | 9982 | |
| | | XP_002513130 | 255761086 | 0.877022654 | Ricinus communis | 9983 | |
| | | XP_003525216 | 356513027 | 0.83171521 | Glycine max | 9984 | 10669 |
| | | XP_003530931 | 356524629 | 0.828478964 | Glycine max | 9985 | 10670 |
| | | ACU18834 | 255637002 | 0.828478964 | Glycine max | 9986 | 10671 |
| | | XP_002319995 | 255761085 | 0.834951456 | Populus trichocarpa | 9987 | |
| | | BAH79622 | 240846167 | 0.822006472 | Glycine max | 9988 | |
| | | XP_002310364 | 255761085 | 0.805825243 | Populus trichocarpa | 9989 | |
| | | XP_003631000 | 357521422 | 0.812297735 | Medicago truncatula | 9990 | 10672 |
| | 917-936 | XP_003548812 | 356561077 | 1 | Glycine max | 9991 | 10673 |
| | | XP_003525850 | 356514311 | 0.700787402 | Glycine max | 9992 | 10674 |
| | 1246-1265 | XP_003555457 | 356574646 | 1 | Glycine max | 9993 | 10675 |
| | | XP_003543286 | 356549814 | 0.955497382 | Glycine max | 9994 | 10676 |
| | | XP_003617150 | 357493722 | 0.756544503 | Medicago truncatula | 9995 | 10677 |
| | | XP_002272310 | 225435984 | 0.712041885 | Vitis vinifera | 9996 | 10678 |
| | | CBI24343 | 270235077 | 0.712041885 | Vitis vinifera | 9997 | |
| | 1320-1339 | XP_003519686 | 356501748 | 1 | Glycine max | 9998 | 10679 |
| | | XP_003547896 | 356559215 | 0.95412844 | Glycine max | 9999 | 10680 |
| | | XP_003547897 | 356559217 | 0.95412844 | Glycine max | 10000 | 10681 |
| | | XP_003517138 | 356496566 | 0.812844037 | Glycine max | 10001 | 10682 |
| | | XP_003612325 | 357484076 | 0.783486239 | Medicago truncatula | 10002 | 10683 |
| | | XP_003629155 | 357517732 | 0.798165138 | Medicago truncatula | 10003 | 10684 |
| | | XP_003537681 | 356538378 | 0.8 | Glycine max | 10004 | 10685 |
| | 602-621 | XP_003520116 | 356502619 | 1 | Glycine max | 10005 | 10686 |
| | | XP_002280702 | 225438602 | 0.856050955 | Vitis vinifera | 10006 | 10687 |
| | | EAZ28751 | 54398660 | 0.829299363 | Oryza sativa Japonica Group | 10007 | |
| | 214-233 | XP_003554103 | 356571887 | 1 | Glycine max | 10008 | 10688 |
| | | XP_003521108 | 356504648 | 0.923076923 | Glycine max | 10009 | 10689 |
| | | ACU18694 | 255636716 | 0.919230769 | Glycine max | 10010 | 10690 |
| | | XP_003624904 | 357509230 | 0.807692308 | Medicago truncatula | 10011 | 10691 |
| | | XP_002526199 | 255761086 | 0.734615385 | Ricinus communis | 10012 | |
| | | XP_002283307 | 225440154 | 0.761538462 | Vitis vinifera | 10013 | 10692 |
| | | XP_002307956 | 255761085 | 0.726923077 | Populus trichocarpa | 10014 | |
| | | XP_002876377 | 297853636 | 0.703846154 | Arabidopsis lyrata subsp. lyrata | 10015 | |
| | 329-348 | XP_003547896 | 356559215 | 1 | Glycine max | 10016 | 10693 |
| | | XP_003519686 | 356501748 | 0.961182994 | Glycine max | 10017 | 10694 |
| | | XP_002521706 | 255761086 | 0.715341959 | Ricinus communis | 10018 | |
| | | XP_002306425 | 255761085 | 0.71349353 | Populus trichocarpa | 10019 | |
| vvi-miR394b | 209-228 | XP_003601765 | 357462966 | 1 | Medicago truncatula | 10020 | 10695 |
| | | XP_003538543 | 356540129 | 0.843010753 | Glycine max | 10021 | 10696 |
| | | XP_003551172 | 356565895 | 0.868817204 | Glycine max | 10022 | 10697 |
| | | ACU23751 | 255646552 | 0.864516129 | Glycine max | 10023 | 10698 |
| | | ACL51019 | 219879373 | 0.767741935 | Citrus trifoliata | 10024 | 10699 |
| | | ACI13687 | 206572108 | 0.761290323 | Malus × domestica | 10025 | 10700 |
| | | XP_002514903 | 255761086 | 0.746236559 | Ricinus communis | 10026 | |
| | | XP_002271194 | 225425399 | 0.739784946 | Vitis vinifera | 10027 | 10701 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002297845 | 255761085 | 0.750537634 | Populus trichocarpa | 10028 | |
| | | XP_003531199 | 356525167 | 0.735483871 | Glycine max | 10029 | 10702 |
| | 1188-1207 | XP_003551172 | 356565895 | 1 | Glycine max | 10030 | 10703 |
| | 256-275 | XP_003593155 | 357445754 | 1 | Medicago truncatula | 10031 | 10704 |
| | | XP_003547599 | 356558613 | 0.890145396 | Glycine max | 10032 | 10705 |
| | | XP_003547600 | 356558615 | 0.890145396 | Glycine max | 10033 | 10706 |
| | | XP_003593158 | 357445760 | 0.843295638 | Medicago truncatula | 10034 | 10707 |
| | | NP_567920 | 186515898 | 0.81098546 | Arabidopsis thaliana | 10035 | 10708 |
| | | AEG25668 | 333952413 | 0.814216478 | Gossypium hirsutum | 10036 | 10709 |
| | | AAK68074 | 14573458 | 0.809369952 | Arabidopsis thaliana | 10037 | 10710 |
| | | ADE22249 | 292385867 | 0.822294023 | Ageratina adenophora | 10038 | 10711 |
| | | XP_002867182 | 297853636 | 0.809369952 | Arabidopsis lyrata subsp. lyrata | 10039 | |
| | | AEA76434 | 327422166 | 0.81098546 | Gossypium hirsutum | 10040 | 10712 |
| | 268-287 | XP_003524786 | 356512154 | 1 | Glycine max | 10041 | 10713 |
| | | XP_002331852 | 255761085 | 0.762032086 | Populus trichocarpa | 10042 | |
| | | XP_002316738 | 255761085 | 0.751336898 | Populus trichocarpa | 10043 | |
| | | XP_002519740 | 255761086 | 0.748663102 | Ricinus communis | 10044 | |
| | | XP_003532647 | 356528107 | 0.71657754 | Glycine max | 10045 | 10714 |
| | | CAN63784 | 147790991 | 0.703208556 | Vitis vinifera | 10046 | 10715 |
| | | XP_002273992 | 225463405 | 0.703208556 | Vitis vinifera | 10047 | 10716 |
| | 435-454 | XP_003556143 | 356576040 | 1 | Glycine max | 10048 | 10717 |
| | | XP_003556144 | 356576042 | 0.964285714 | Glycine max | 10049 | 10718 |
| | | XP_003536435 | 356535807 | 0.932539683 | Glycine max | 10050 | 10719 |
| | | XP_003536434 | 356535805 | 0.924603175 | Glycine max | 10051 | 10720 |
| | | ACU19073 | 255637492 | 0.920634921 | Glycine max | 10052 | 10721 |
| | | XP_003556145 | 356576044 | 0.94047619 | Glycine max | 10053 | 10722 |
| | | XP_003536436 | 356535809 | 0.900793651 | Glycine max | 10054 | 10723 |
| | | XP_003556146 | 356576046 | 0.912698413 | Glycine max | 10055 | 10724 |
| | | XP_003592142 | 357443728 | 0.793650794 | Medicago truncatula | 10056 | 10725 |
| | | ACU23298 | 255645607 | 0.777777778 | Glycine max | 10057 | 10726 |
| | 475-494 | XP_003531199 | 356525167 | 1 | Glycine max | 10058 | 10727 |
| | | XP_003524898 | 356512380 | 0.911699779 | Glycine max | 10059 | 10728 |
| | | ACU17886 | 255635055 | 0.905077263 | Glycine max | 10060 | 10729 |
| | 1104-1123 | XP_003538543 | 356540129 | 1 | Glycine max | 10061 | 10730 |
| | 123-142 | XP_003553643 | 356570944 | 1 | Glycine max | 10062 | 10731 |
| | | XP_003521540 | 356505523 | 0.763779528 | Glycine max | 10063 | 10732 |
| | 29-48 | NP_001058751 | 115470304 | 1 | Oryza sativa Japonica Group | 10064 | 10733 |
| | | EAZ02551 | 54362548 | 0.987012987 | Oryza sativa Indica Group | 10065 | |
| | | ACG30543 | 195617425 | 0.896103896 | Zea mays | 10066 | 10734 |
| | | BAJ93722 | 326533897 | 0.896103896 | Hordeum vulgare subsp. vulgare | 10067 | 10735 |
| | | XP_002459234 | 255761094 | 0.883116883 | Sorghum bicolor | 10068 | |
| | | XP_003557668 | 357111736 | 0.896103896 | Brachypodium distachyon | 10069 | 10736 |
| | | ACG28009 | 195612357 | 0.883116883 | Zea mays | 10070 | 10737 |
| | | ACG24589 | 195605517 | 0.844155844 | Zea mays | 10071 | 10738 |
| | | XP_003555981 | 356575711 | 0.87012987 | Glycine max | 10072 | 10739 |
| | | XP_002284176 | 225438945 | 0.87012987 | Vitis vinifera | 10073 | 10740 |
| | 1029-1048 | XP_003524898 | 356512380 | 1 | Glycine max | 10074 | 10741 |
| | 1245-1264 | XP_003601765 | 357462966 | 1 | Medicago truncatula | 10075 | 10742 |
| zma-miR167u | 68-87 | XP_002519732 | 255761086 | 1 | Ricinus communis | 10076 | |
| | | XP_002298511 | 255761085 | 0.8183391 | Populus trichocarpa | 10077 | |
| | | XP_002317300 | 255761085 | 0.801038062 | Populus trichocarpa | 10078 | |
| | | XP_002272126 | 225463413 | 0.788927336 | Vitis vinifera | 10079 | 10743 |
| | | XP_003524790 | 356512162 | 0.780276817 | Glycine max | 10080 | 10744 |
| | | NP_180988 | 145360605 | 0.761245675 | Arabidopsis thaliana | 10081 | 10745 |
| | | XP_003532649 | 356528111 | 0.780276817 | Glycine max | 10082 | 10746 |
| | | XP_002879497 | 297853636 | 0.757785467 | Arabidopsis lyrata subsp. lyrata | 10083 | |
| | | NP_568662 | 30694937 | 0.742214533 | Arabidopsis thaliana | 10084 | 10747 |
| | | AAL11600 | 15983463 | 0.740484429 | Arabidopsis thaliana | 10085 | 10748 |
| | 503-522 | XP_003556422 | 356576607 | 1 | Glycine max | 10086 | 10749 |
| | | XP_003556421 | 356576605 | 1 | Glycine max | 10087 | 10750 |
| | | XP_003536179 | 356535285 | 0.754266212 | Glycine max | 10088 | 10751 |
| | 109-128 | XP_003533248 | 356529329 | 1 | Glycine max | 10089 | 10752 |
| | | XP_003547372 | 356558152 | 0.944690265 | Glycine max | 10090 | 10753 |
| | | XP_003550546 | 356564612 | 0.778761062 | Glycine max | 10091 | 10754 |
| | | XP_003528627 | 356519941 | 0.783185841 | Glycine max | 10092 | 10755 |
| | | XP_003609706 | 357478840 | 0.765486726 | Medicago truncatula | 10093 | 10756 |
| | | XP_002273305 | 225431819 | 0.727876106 | Vitis vinifera | 10094 | 10757 |
| | | CBI22951 | 270234210 | 0.727876106 | Vitis vinifera | 10095 | |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | 1585-1604 | XP_003550723 | 356564979 | 1 | Glycine max | 10096 | 10758 |
| | | XP_003550724 | 356564981 | 0.985380117 | Glycine max | 10097 | 10759 |
| | | XP_003529499 | 356521718 | 0.956140351 | Glycine max | 10098 | 10760 |
| | | XP_003529500 | 356521720 | 0.946393762 | Glycine max | 10099 | 10761 |
| | | XP_003546300 | 356555968 | 0.819688109 | Glycine max | 10100 | 10762 |
| | | XP_002314972 | 255761085 | 0.726120858 | Populus trichocarpa | 10101 | |
| | | CBI22841 | 270234210 | 0.730994152 | Vitis vinifera | 10102 | |
| | | XP_002519280 | 255761086 | 0.717348928 | Ricinus communis | 10103 | |
| | 335-354 | XP_003516798 | 356495878 | 1 | Glycine max | 10104 | 10763 |
| | 29-48 | XP_003525532 | 356513666 | 1 | Glycine max | 10105 | 10764 |
| | 24-43 | XP_003529500 | 356521720 | 1 | Glycine max | 10106 | 10765 |
| | | XP_003550723 | 356564979 | 0.959486166 | Glycine max | 10107 | 10766 |
| | | XP_002883053 | 297853636 | 0.707509881 | Arabidopsis lyrata subsp. lyrata | 10108 | |
| | | NP_001118648 | 186510162 | 0.70256917 | Arabidopsis thaliana | 10109 | 10767 |
| | 671-690 | XP_003533338 | 356529518 | 1 | Glycine max | 10110 | 10768 |
| | 314-333 | XP_003529470 | 356521656 | 1 | Glycine max | 10111 | 10769 |
| | | XP_003556768 | 356577305 | 0.95687885 | Glycine max | 10112 | 10770 |
| | | Q43088 | | 0.80698152 | Ribulose-bisphosphate carboxylase | 10113 | |
| | | 1MLV_A | | 0.747433265 | Pisum sativum | 10114 | |
| | | 2H21_A | | 0.743326489 | Pisum sativum | 10115 | |
| zma-miR396b-3p | 330-350 | ABE91847 | 61675805 | 1 | Medicago truncatula | 10116 | 10771 |
| | 330-350 | ABE91847 | 61675805 | 1 | Medicago truncatula | 10117 | 10772 |
| aly-miR396a-3p | 330-350 | ABE91847 | 61675805 | 1 | Medicago truncatula | 10118 | 10773 |
| | 330-350 | ABE91847 | 61675805 | 1 | Medicago truncatula | 10119 | 10774 |
| gma-miR4412-3p | 224-244 | NP_001235045 | 351725442 | 1 | Glycine max | 10120 | 10775 |
| | | XP_002274402 | 225425717 | 0.733905579 | Vitis vinifera | 10121 | 10776 |
| | | XP_002315800 | 255761085 | 0.703862661 | Populus trichocarpa | 10122 | |
| | 1796-1816 | NP_001235618 | 351727227 | 1 | Glycine max | 10123 | 10777 |
| gma-miR482b-5p | 177-198 | AAX13306 | 60100357 | 1 | Lotus japonicus | 10124 | 10778 |
| | | NP_001236130 | 351727233 | 0.959641256 | Glycine max | 10125 | 10779 |
| | | AAN15183 | 23194452 | 0.865470852 | Gossypium hirsutum | 10126 | 10780 |
| | | AAY30856 | 63094568 | 0.874439462 | Prunus dulcis | 10127 | 10781 |
| | | ABV60385 | 157674586 | 0.874439462 | Carica papaya | 10128 | |
| | | ABM69043 | 122938394 | 0.860986547 | Gossypium hirsutum | 10129 | 10782 |
| | | ADD91578 | 291278193 | 0.878923767 | Prunus serrulata var. lannesiana | 10130 | 10783 |
| | | AAO20104 | 27763669 | 0.860986547 | Momordica charantia | 10131 | 10784 |
| | | AAD01742 | 4103341 | 0.869955157 | Cucumis sativus | 10132 | 10785 |
| | | ABQ85556 | 148535235 | 0.874439462 | Prunus persica | 10133 | 10786 |
| | 339-360 | BAG06679 | 166788446 | 1 | Phaseolus vulgaris | 10134 | 10787 |
| | | ACU20774 | 255640988 | 0.995575221 | Glycine max | 10135 | 10788 |
| | | ACU24523 | 255648136 | 0.977876106 | Glycine max | 10136 | 10789 |
| | | AAM91028 | 57472398 | 0.977876106 | Pisum sativum | 10137 | 10790 |
| | | XP_002272971 | 225462010 | 0.96460177 | Vitis vinifera | 10138 | 10791 |
| | | ABW06389 | 157955930 | 0.938053097 | Gossypium hirsutum | 10139 | 10792 |
| | | ABW06392 | 157955936 | 0.933628319 | Gossypium hirsutum | 10140 | 10793 |
| | | ACJ86177 | 217075633 | 0.938053097 | Medicago truncatula | 10141 | 10794 |
| | | XP_002532178 | 255761086 | 0.951327434 | Ricinus communis | 10142 | |
| | | ABW06390 | 157955932 | 0.938053097 | Gossypium hirsutum | 10143 | 10795 |
| | 35-56 | CAN81115 | 147863854 | 1 | Vitis vinifera | 10144 | 10796 |
| ptc-miRf11953-akr | 753-772 | XP_002271271 | 225468315 | 1 | Vitis vinifera | 10145 | 10797 |
| | | XP_002532424 | 255761086 | 0.945652174 | Ricinus communis | 10146 | |
| | | ACU20760 | 255640960 | 0.945652174 | Glycine max | 10147 | 10798 |
| | | XP_002877709 | 297853636 | 0.940217391 | Arabidopsis lyrata subsp. lyrata | 10148 | |
| | | NP_001235421 | 351721538 | 0.934782609 | Glycine max | 10149 | 10799 |
| | | NP_001236131 | 351727263 | 0.940217391 | Glycine max | 10150 | 10800 |
| | | NP_190556 | 145339306 | 0.934782609 | Arabidopsis thaliana | 10151 | 10801 |
| | | ACU14878 | 255629066 | 0.940217391 | Glycine max | 10152 | 10802 |
| | | XP_002866698 | 297853636 | 0.923913043 | Arabidopsis lyrata subsp. lyrata | 10153 | |
| | | NP_569051 | 186532841 | 0.918478261 | Arabidopsis thaliana | 10154 | 10803 |
| | 309-328 | ACU18943 | 255637224 | 1 | Glycine max | 10155 | 10804 |
| | | ACU23146 | 255645298 | 0.953405018 | Glycine max | 10156 | 10805 |
| | | ACJ84492 | 217072263 | 0.810035842 | Medicago truncatula | 10157 | 10806 |
| | | ABK94686 | 118485671 | 0.784946237 | Populus trichocarpa | 10158 | 10807 |
| | | XP_002528545 | 255761086 | 0.76702509 | Ricinus communis | 10159 | |
| | | XP_002326541 | 255761085 | 0.741935484 | Populus trichocarpa | 10160 | |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_002278543 | 225427135 | 0.752688172 | Vitis vinifera | 10161 | 10808 |
| | | XP_002274164 | 225454758 | 0.734767025 | Vitis vinifera | 10162 | 10809 |
| | | XP_002303431 | 255761085 | 0.749103943 | Populus trichocarpa | 10163 | |
| | 218-237 | ACU18943 | 255637224 | 1 | Glycine max | 10164 | 10810 |
| | 1421-1440 | P08926 | | 1 | Pisum sativum | 10165 | |
| | | BAE71311 | 84468455 | 0.957410562 | Trifolium pratense | 10166 | 10811 |
| | | BAE71231 | 84468295 | 0.955706985 | Trifolium pratense | 10167 | 10812 |
| | | BAE71302 | 84468437 | 0.954003407 | Trifolium pratense | 10168 | 10813 |
| | | BAE71227 | 84468287 | 0.93867121 | Trifolium pratense | 10169 | 10814 |
| | | ACJ85785 | 217074849 | 0.94548552 | Medicago truncatula | 10170 | 10815 |
| | | AEO21430 | 346229112 | 0.906303237 | Glycine max | 10171 | 10816 |
| | | XP_002313525 | 255761085 | 0.877342419 | Populus trichocarpa | 10172 | |
| | | AAC68501 | 3790440 | 0.889267462 | Canavalia lineata | 10173 | 10817 |
| | | XP_002328161 | 255761085 | 0.865417376 | Populus trichocarpa | 10174 | |
| | 165-184 | ACU23935 | 255646930 | 1 | Glycine max | 10175 | 10818 |
| | 60-79 | BAE71304 | 84468441 | 1 | Trifolium pratense | 10176 | 10819 |
| | | P08926 | | 0.947939262 | Pisum sativum | 10177 | |
| bna-miR2111b-5p | 163-183 | ACU23935 | 255646930 | 1 | Glycine max | 10178 | 10820 |
| | 1419-1439 | P08926 | | 1 | Pisum sativum | 10179 | |
| | | BAE71311 | 84468455 | 0.957410562 | Trifolium pratense | 10180 | 10821 |
| | | BAE71231 | 84468295 | 0.955706985 | Trifolium pratense | 10181 | 10822 |
| | | BAE71302 | 84468437 | 0.954003407 | Trifolium pratense | 10182 | 10823 |
| | | BAE71227 | 84468287 | 0.93867121 | Trifolium pratense | 10183 | 10824 |
| | | ACJ85785 | 217074849 | 0.94548552 | Medicago truncatula | 10184 | 10825 |
| | | AEO21430 | 346229112 | 0.906303237 | Glycine max | 10185 | 10826 |
| | | XP_002313525 | 255761085 | 0.877342419 | Populus trichocarpa | 10186 | |
| | | AAC68501 | 3790440 | 0.889267462 | Canavalia lineata | 10187 | 10827 |
| | | XP_002328161 | 255761085 | 0.865417376 | Populus trichocarpa | 10188 | |
| | 153-173 | ACU23159 | 255645324 | 1 | Glycine max | 10189 | 10828 |
| | | CAF04055 | 119391878 | 0.745098039 | Nicotiana benthamiana | 10190 | 10829 |
| | | CAF25317 | 119391874 | 0.735294118 | Capsicum annuum | 10191 | 10830 |
| | | XP_002306360 | 255761085 | 0.715686275 | Populus trichocarpa | 10192 | |
| | | XP_002279217 | 225438516 | 0.732026144 | Vitis vinifera | 10193 | 10831 |
| | | XP_002530256 | 255761086 | 0.715686275 | Ricinus communis | 10194 | |
| | | CBI22773 | 270234152 | 0.722222222 | Vitis vinifera | 10195 | |
| | | CBI21530 | 270232045 | 0.732026144 | Vitis vinifera | 10196 | |
| | 163-183 | ACU23935 | 255646930 | 1 | Glycine max | 10197 | 10832 |
| | 58-78 | BAE71304 | 84468441 | 1 | Trifolium pratense | 10198 | 10833 |
| | | P08926 | | 0.947939262 | Pisum sativum | 10199 | |
| ptc-miRf11079-akr | 720-743 | ACU24381 | 255647842 | 1 | Glycine max | 10200 | 10834 |
| | | NP_001238255 | 351722074 | 0.996688742 | Glycine max | 10201 | 10835 |
| | | NP_001235901 | 351728022 | 0.943708609 | Glycine max | 10202 | 10836 |
| | | AAK84883 | 15148911 | 0.917218543 | Phaseolus vulgaris | 10203 | 10837 |
| | | AEE99077 | 332739375 | 0.870860927 | Medicago truncatula | 10204 | 10838 |
| | | XP_002529954 | 255761086 | 0.768211921 | Ricinus communis | 10205 | |
| | | XP_002310688 | 255761085 | 0.771523179 | Populus trichocarpa | 10206 | |
| | | XP_002307195 | 255761085 | 0.741721854 | Populus trichocarpa | 10207 | |
| | 69-92 | AAK84883 | 15148911 | 1 | Phaseolus vulgaris | 10208 | 10839 |
| | 603-626 | AAK84883 | 15148911 | 1 | Phaseolus vulgaris | 10209 | 10840 |
| | 720-743 | NP_001235901 | 351728022 | 1 | Glycine max | 10210 | 10841 |
| | 721-744 | ACU24381 | 255647842 | 1 | Glycine max | 10211 | 10842 |
| bra-miR160a-3p | 989-1009 | XP_003530952 | 356524671 | 1 | Glycine max | 10212 | 10843 |
| | | XP_003525194 | 356512983 | 0.970842333 | Glycine max | 10213 | 10844 |
| | | XP_003521511 | 356505464 | 0.904967603 | Glycine max | 10214 | 10845 |
| | | XP_003592908 | 357445260 | 0.792656587 | Medicago truncatula | 10215 | 10846 |
| | | ABE91931 | 61675804 | 0.792656587 | Medicago truncatula | 10216 | 10847 |
| | | XP_003626539 | 357512500 | 0.795896328 | Medicago truncatula | 10217 | 10848 |
| | | XP_002281426 | 225441572 | 0.791576674 | Vitis vinifera | 10218 | 10849 |
| | | Q9XHM1 | | 0.789416847 | Medicago truncatula | 10219 | |
| | | XP_003589347 | 357438142 | 0.782937365 | Medicago truncatula | 10220 | 10850 |
| | | CAN81874 | 147860525 | 0.761339093 | Vitis vinifera | 10221 | 10851 |
| gma-miR1507a | 328-349 | XP_003521176 | 356504786 | 1 | Glycine max | 10222 | 10852 |
| gma-miR1524 | 507-527 | XP_003554498 | 356572687 | 1 | Glycine max | 10223 | 10853 |
| | | XP_003521507 | 356505456 | 0.941358025 | Glycine max | 10224 | 10854 |
| | | XP_003535834 | 356534585 | 0.712962963 | Glycine max | 10225 | 10855 |
| | | XP_003519022 | 356500404 | 0.712962963 | Glycine max | 10226 | 10856 |
| ppt-miR166m | 189-209 | XP_003553029 | 356569688 | 1 | Glycine max | 10227 | 10857 |
| | | XP_003537529 | 356538072 | 0.931216931 | Glycine max | 10228 | 10858 |
| | | XP_003601737 | 357462910 | 0.727513228 | Medicago truncatula | 10229 | 10859 |
| | 557-577 | XP_002298892 | 255761085 | 1 | Populus trichocarpa | 10230 | |
| | | CAN73584 | 147820217 | 0.91943128 | Vitis vinifera | 10231 | |
| | | XP_002332526 | 255761085 | 0.94549763 | Populus trichocarpa | 10232 | |
| | | XP_002281868 | 225444032 | 0.91943128 | Vitis vinifera | 10233 | 10860 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_003535078 | 356533042 | 0.892180095 | Glycine max | 10234 | 10861 |
| | | XP_003546255 | 356555874 | 0.893364929 | Glycine max | 10235 | 10862 |
| | | AAS66760 | 45479745 | 0.86492891 | Nicotiana sylvestris | 10236 | 10863 |
| | | XP_003532788 | 356528393 | 0.849526066 | Glycine max | 10237 | 10864 |
| | | XP_003524993 | 356512573 | 0.845971564 | Glycine max | 10238 | 10865 |
| | | ACI13683 | 206572100 | 0.816350711 | Malus × domestica | 10239 | 10866 |
| | 515-535 | XP_003597690 | 357454818 | 1 | Medicago truncatula | 10240 | 10867 |
| | | XP_003531652 | 356526088 | 0.918660287 | Glycine max | 10241 | 10868 |
| | | XP_003530109 | 356522957 | 0.921052632 | Glycine max | 10242 | 10869 |
| | | XP_002284003 | 225442500 | 0.897129187 | Vitis vinifera | 10243 | 10870 |
| | | CBI36079 | 270253379 | 0.897129187 | Vitis vinifera | 10244 | |
| | | XP_002515977 | 255761086 | 0.901913876 | Ricinus communis | 10245 | |
| | | XP_003530112 | 356522963 | 0.916267943 | Glycine max | 10246 | 10871 |
| | | XP_002284014 | 225442502 | 0.897129187 | Vitis vinifera | 10247 | 10872 |
| | | ACI13685 | 206572104 | 0.89354067 | Malus × domestica | 10248 | 10873 |
| | | XP_002304217 | 255761085 | 0.888755981 | Populus trichocarpa | 10249 | |
| | 560-580 | XP_002285176 | 225435326 | 1 | Vitis vinifera | 10250 | 10874 |
| | | CAN61612 | 147783603 | 0.981042654 | Vitis vinifera | 10251 | |
| | | XP_002529946 | 255761086 | 0.918246445 | Ricinus communis | 10252 | |
| | | XP_003538150 | 356539326 | 0.892180095 | Glycine max | 10253 | 10875 |
| | | XP_003539764 | 356542618 | 0.895734597 | Glycine max | 10254 | 10876 |
| | | ACI13684 | 206572102 | 0.888625592 | Malus × domestica | 10255 | 10877 |
| | | XP_003539765 | 356542620 | 0.890995261 | Glycine max | 10256 | 10878 |
| | | AAX19050 | 60327620 | 0.881516588 | Populus trichocarpa | 10257 | 10879 |
| | | DAA05766 | 109729904 | 0.853080569 | Lotus japonicus | 10258 | |
| | | AAY33856 | 63115353 | 0.8507109 | Gossypium barbadense | 10259 | 10880 |
| | 554-574 | XP_003603630 | 357466690 | 1 | Medicago truncatula | 10260 | 10881 |
| | | XP_003522716 | 356507930 | 0.943645084 | Glycine max | 10261 | 10882 |
| | | XP_003526496 | 356515618 | 0.940047962 | Glycine max | 10262 | 10883 |
| | | ACI13686 | 206572106 | 0.872901679 | Malus × domestica | 10263 | 10884 |
| | | ADL36609 | 302398628 | 0.863309353 | Malus × domestica | 10264 | 10885 |
| | | CBI20838 | 270231236 | 0.862110312 | Vitis vinifera | 10265 | |
| | | XP_002283717 | 225429913 | 0.862110312 | Vitis vinifera | 10266 | 10886 |
| | | ACL51017 | 219879369 | 0.858513189 | Citrus trifoliata | 10267 | 10887 |
| | | XP_002309538 | 255761085 | 0.868105516 | Populus trichocarpa | 10268 | |
| | | XP_002324794 | 255761085 | 0.857314149 | Populus trichocarpa | 10269 | |
| | 40-60 | AAS10176 | 41745611 | 1 | Antirrhinum majus | 10270 | 10888 |
| | 554-574 | XP_003530109 | 356522957 | 1 | Glycine max | 10271 | 10889 |
| | | XP_003531653 | 356526090 | 0.95823389 | Glycine max | 10272 | 10890 |
| | | XP_003627005 | 357513432 | 0.91646778 | Medicago truncatula | 10273 | 10891 |
| | | XP_003597690 | 357454818 | 0.918854415 | Medicago truncatula | 10274 | 10892 |
| | 590-610 | XP_003524993 | 356512573 | 1 | Glycine max | 10275 | 10893 |
| | | XP_002298892 | 255761085 | 0.832356389 | Populus trichocarpa | 10276 | |
| | | XP_003594520 | 357448488 | 0.781946073 | Medicago truncatula | 10277 | 10894 |
| | 25-45 | XP_003522716 | 356507930 | 1 | Glycine max | 10278 | 10895 |
| | | XP_003603630 | 357466690 | 0.932464455 | Medicago truncatula | 10279 | 10896 |
| | 560-580 | XP_003530112 | 356522963 | 1 | Glycine max | 10280 | 10897 |
| | 572-592 | P00965 | | 1 | Phaseolus vulgaris | 10281 | |
| | | XP_003544980 | 356553268 | 0.935393258 | Glycine max | 10282 | 10898 |
| | | XP_003519325 | 356501016 | 0.935393258 | Glycine max | 10283 | 10899 |
| | | ACU19484 | 255638343 | 0.926966292 | Glycine max | 10284 | 10900 |
| | | XP_003519326 | 356501018 | 0.935393258 | Glycine max | 10285 | 10901 |
| | | AAB61597 | 2213876 | 0.901685393 | Hevea brasiliensis | 10286 | 10902 |
| | | P32289 | | 0.901685393 | Vigna aconitifolia | 10287 | |
| | | ABW89460 | 159138920 | 0.904494382 | Gossypium herbaceum | 10288 | 10903 |
| | | P04770 | | 0.896067416 | Phaseolus vulgaris | 10289 | |
| | | ABW89461 | 159138922 | 0.901685393 | Gossypium hirsutum | 10290 | 10904 |
| | 87-107 | CAN73584 | 147820217 | 1 | Vitis vinifera | 10291 | |
| | 530-550 | XP_003532788 | 356528393 | 1 | Glycine max | 10292 | 10905 |
| | 516-536 | XP_003537529 | 356538072 | 1 | Glycine max | 10293 | 10906 |
| | 566-586 | XP_003531653 | 356526090 | 1 | Glycine max | 10294 | 10907 |
| | 560-580 | XP_003539764 | 356542618 | 1 | Glycine max | 10295 | 10908 |
| | | XP_002285176 | 225435326 | 0.894674556 | Vitis vinifera | 10296 | 10909 |
| | | CAC84906 | 18076735 | 0.829585799 | Zinnia violacea | 10297 | 10910 |
| | 828-848 | XP_003539765 | 356542620 | 1 | Glycine max | 10298 | 10911 |
| ptc-miR166p | 557-577 | XP_002298892 | 255761085 | 1 | Populus trichocarpa | 10299 | |
| | | CAN73584 | 147820217 | 0.91943128 | Vitis vinifera | 10300 | |
| | | XP_002332526 | 255761085 | 0.94549763 | Populus trichocarpa | 10301 | |
| | | XP_002281868 | 225444032 | 0.91943128 | Vitis vinifera | 10302 | 10912 |
| | | XP_003535078 | 356533042 | 0.892180095 | Glycine max | 10303 | 10913 |
| | | XP_003546255 | 356555874 | 0.893364929 | Glycine max | 10304 | 10914 |
| | | AAS66760 | 45479745 | 0.86492891 | Nicotiana sylvestris | 10305 | 10915 |

TABLE 10-continued

Target Genes of down-regulated Small RNA Molecules Associated with Abiotic Stress Tolerance in Soybean Plants.

| Mir Name | Mir Binding Position | Homolog NCBI Accession | Nucleotide NCBI GI number | Identity | Organism | Protein Seq id no: | Nucleotide Seq id no: |
|---|---|---|---|---|---|---|---|
| | | XP_003532788 | 356528393 | 0.849526066 | Glycine max | 10306 | 10916 |
| | | XP_003524993 | 356512573 | 0.845971564 | Glycine max | 10307 | 10917 |
| | | ACI13683 | 206572100 | 0.816350711 | Malus × domestica | 10308 | 10918 |
| | 515-535 | XP_003597690 | 357454818 | 1 | Medicago truncatula | 10309 | 10919 |
| | | XP_003531652 | 356526088 | 0.918660287 | Glycine max | 10310 | 10920 |
| | | XP_003530109 | 356522957 | 0.921052632 | Glycine max | 10311 | 10921 |
| | | XP_002284003 | 225442500 | 0.897129187 | Vitis vinifera | 10312 | 10922 |
| | | CBI36079 | 270253379 | 0.897129187 | Vitis vinifera | 10313 | |
| | | XP_002515977 | 255761086 | 0.901913876 | Ricinus communis | 10314 | |
| | | XP_003530112 | 356522963 | 0.916267943 | Glycine max | 10315 | 10923 |
| | | XP_002284014 | 225442502 | 0.897129187 | Vitis vinifera | 10316 | 10924 |
| | | ACI13685 | 206572104 | 0.89354067 | Malus × domestica | 10317 | 10925 |
| | | XP_002304217 | 255761085 | 0.888755981 | Populus trichocarpa | 10318 | |
| | 560-580 | XP_002285176 | 225435326 | 1 | Vitis vinifera | 10319 | 10926 |
| | | CAN61612 | 147783603 | 0.981042654 | Vitis vinifera | 10320 | |
| | | XP_002529946 | 255761086 | 0.918246445 | Ricinus communis | 10321 | |
| | | XP_003538150 | 356539326 | 0.892180095 | Glycine max | 10322 | 10927 |
| | | XP_003539764 | 356542618 | 0.895734597 | Glycine max | 10323 | 10928 |
| | | ACI13684 | 206572102 | 0.888625592 | Malus × domestica | 10324 | 10929 |
| | | XP_003539765 | 356542620 | 0.890995261 | Glycine max | 10325 | 10930 |
| | | AAX19050 | 60327620 | 0.881516588 | Populus trichocarpa | 10326 | 10931 |
| | | DAA05766 | 109729904 | 0.853080569 | Lotus japonicus | 10327 | |
| | | AAY33856 | 63115353 | 0.8507109 | Gossypium barbadense | 10328 | 10932 |
| | 554-574 | XP_003603630 | 357466690 | 1 | Medicago truncatula | 10329 | 10933 |
| | | XP_003522716 | 356507930 | 0.943645084 | Glycine max | 10330 | 10934 |
| | | XP_003526496 | 356515618 | 0.940047962 | Glycine max | 10331 | 10935 |
| | | ACI13686 | 206572106 | 0.872901679 | Malus × domestica | 10332 | 10936 |
| | | ADL36609 | 302398628 | 0.863309353 | Malus × domestica | 10333 | 10937 |
| | | CBI20838 | 270231236 | 0.862110312 | Vitis vinifera | 10334 | |
| | | XP_002283717 | 225429913 | 0.862110312 | Vitis vinifera | 10335 | 10938 |
| | | ACL51017 | 219879369 | 0.858513189 | Citrus trifoliata | 10336 | 10939 |
| | | XP_002309538 | 255761085 | 0.868105516 | Populus trichocarpa | 10337 | |
| | | XP_002324794 | 255761085 | 0.857314149 | Populus trichocarpa | 10338 | |
| | 40-60 | AAS10176 | 41745611 | 1 | Antirrhinum majus | 10339 | 10940 |
| | 554-574 | XP_003530109 | 356522957 | 1 | Glycine max | 10340 | 10941 |
| | | XP_003531653 | 356526090 | 0.95823389 | Glycine max | 10341 | 10942 |
| | | XP_003627005 | 357513432 | 0.91646778 | Medicago truncatula | 10342 | 10943 |
| | | XP_003597690 | 357454818 | 0.918854415 | Medicago truncatula | 10343 | 10944 |
| | 590-610 | XP_003524993 | 356512573 | 1 | Glycine max | 10344 | 10945 |
| | | XP_003594520 | 357448488 | 0.781946073 | Medicago truncatula | 10345 | 10946 |
| | 25-45 | XP_003522716 | 356507930 | 1 | Glycine max | 10346 | 10947 |
| | | XP_003603630 | 357466690 | 0.932464455 | Medicago truncatula | 10347 | 10948 |
| | 560-580 | XP_003530112 | 356522963 | 1 | Glycine max | 10348 | 10949 |
| | 530-550 | XP_003532788 | 356528393 | 1 | Glycine max | 10349 | 10950 |
| | 87-107 | CAN73584 | 147820217 | 1 | Vitis vinifera | 10350 | |
| | 113-133 | XP_003516553 | 356495373 | 1 | Glycine max | 10351 | 10951 |
| | | XP_003537620 | 356538255 | 0.909756098 | Glycine max | 10352 | 10952 |
| | 566-586 | XP_003531653 | 356526090 | 1 | Glycine max | 10353 | 10953 |
| | 560-580 | XP_003539764 | 356542618 | 1 | Glycine max | 10354 | 10954 |
| | | XP_002285176 | 225435326 | 0.894674556 | Vitis vinifera | 10355 | 10955 |
| | | CAC84906 | 18076735 | 0.829585799 | Zinnia violacea | 10356 | 10956 |
| | 828-848 | XP_003539765 | 356542620 | 1 | Glycine max | 10357 | 10957 |
| ptc-miRf10007-akr | 368-388 | XP_003550796 | 356565126 | 1 | Glycine max | 10358 | 10958 |
| | | XP_003528595 | 356519875 | 0.931982634 | Glycine max | 10359 | 10959 |
| | | XP_003609844 | 357479116 | 0.714905933 | Medicago truncatula | 10360 | 10960 |
| ptc-miRf11396-akr | 600-621 | XP_003520116 | 356502619 | 1 | Glycine max | 10361 | 10961 |
| | | XP_002280702 | 225438602 | 0.856050955 | Vitis vinifera | 10362 | 10962 |
| | | EAZ28751 | 54398660 | 0.829299363 | Oryza sativa Japonica Group | 10363 | |
| ptc-miRf12069-akr | 88-108 | NP_001236364 | 351726593 | 1 | Glycine max | 10364 | 10963 |

Example 4

Verification of Expression of miRNA Molecules Associated with Abiotic Stress

Following identification of small RNA molecules potentially involved in improvement of soybean abiotic stress tolerance and their target genes (mRNAs) using bioinformatics tools, as described in Example 4 above, the actual mRNA levels in an experiment are determined using reverse transcription assay followed by quantitative Real-Time PCR (qRT-PCR) analysis. RNA levels are compared between different tissues, developmental stages, growing conditions and/or genetic backgrounds incorporated in each experiment. A correlation analysis between mRNA levels in different experimental conditions/genetic backgrounds is applied and used as evidence for the role of the gene in the plant.

Methods

Root and leaf samples are freshly excised from soybean plants grown as described above on Murashige-Skoog (Duchefa). Experimental plants are grown either under optimal irrigation conditions, salt levels or temperatures to be used as a control group, or under stressful conditions of prolonged water deprivation, high salt concentrations and a heat shock treatment at a temperature higher than 34° C. to be used as stress-induced groups to assess the drought, salinity and heat shock tolerance, respectively, of control versus transgenic plants. Total RNA is extracted from the different tissues, using mirVana™ commercial kit (Ambion) following the protocol provided by the manufacturer. For measurement and verification of messenger RNA (mRNA) expression level of all genes, reverse transcription followed by quantitative real time PCR (qRT-PCR) is performed on total RNA extracted from each plant tissue (i.e., roots and leaves) from each experimental group as described above. To elaborate, reverse transcription is performed on 1 µg total RNA, using a miScript Reverse Transcriptase kit (Qiagen), following the protocol suggested by the manufacturer. Quantitative RT-PCR is performed on cDNA (0.1 ng/µl final concentration), using a miScript SYBR GREEN PCR (Qiagen) forward (based on the miR sequence itself) and reverse primers (supplied with the kit). All qRT-PCR reactions are performed in triplicates using an ABI7500 real-time PCR machine, following the recommended protocol for the machine. To normalize the expression level of miRNAs associated with enhanced abiotic stress tolerance between the different tissues and growing conditions of the soybean plants, normalizer miRNAs are selected and used for comparison. Normalizer miRNAs, which are miRNAs with unchanged expression level between tissues and growing conditions, are custom selected for each experiment. The normalization procedure consists of second-degree polynomial fitting to a reference data (which is the median vector of all the data—excluding outliers) as described by Rosenfeld et al (2008, *Nat Biotechnol*, 26(4):462-469). A summary of primers for the differential small RNA molecules that will be used in the qRT-PCR validation and analysis is presented in Table 11a below.

TABLE 11a

Primers of Differential miRNA Molecules for qRT-PCR Validation Step.

| Mir Name | Primer Sequence (SEQ ID NO:) | Primer Length | Tm |
|---|---|---|---|
| ahy-miR3514-5p | TGGCAGGATTCTGTATTAACGGTGGA (10964) | 26 | 59.6 |
| aly-miR160c-3p | GCGTACAAGGAGCCAAGCATG (10965) | 21 | 58.5 |
| aly-miR396a-3p | GGCGTTCAATAAAGCTGTGGGAAG (10966) | 24 | 58.7 |
| aly-miR396b-3p | GCGCTCAAGAAAGCTGTGGGAAA (10967) | 23 | 60.3 |
| aly-miR831-5p | GGCAGAAGAGGTACAAGGAGATGAGA (10968) | 26 | 59.2 |
| aqc-miR159 | GGCTTTGGACTGAAGGGAGCTCTA (10969) | 24 | 59.8 |
| ath-miR157a | TTTGGCTTGACAGAAGATAGAGAGCAC (10970) | 27 | 58.8 |
| ath-miR159b | GGCTTTGGATTGAAGGGAGCTCTT (10971) | 24 | 59.0 |
| ath-miR159c | GCTTTGGATTGAAGGGAGCTCCT (10972) | 23 | 58.7 |
| ath-miRf10068-akr | CACCGGTGGAGGAGTGAGAG (10973) | 20 | 58.0 |
| ath-miRf10148-akr | GGCGGTGGTGGAAAGATCAAGAT (10974) | 23 | 59.1 |
| ath-miRf10197-akr | CACTCGACCAAGGGGGTCGAGTGA (10975) | 24 | 63.6 |
| ath-miRf10209-akr | ATGGTGGTACTCGGCCAGGTGGT (10976) | 23 | 63.5 |
| ath-miRf10239-akr | GCCGCCTTGCATCAACTGAATC (10977) | 22 | 59.2 |
| ath-miRf10240-akr | GCATCGAAGGAGATGGAGGACG (10978) | 22 | 59.0 |
| ath-miRf10279-akr | ACTCAGCCTGGGGGTCGAG (10979) | 19 | 59.7 |
| ath-miRf10368-akr | GGCACTTGGGTGGTGCTGATTAT (10980) | 23 | 59.3 |
| ath-miRf10451-akr | GGCAAGAAGGAGGAACAACCTGTTG (10981) | 25 | 60.0 |
| ath-miRf10633-akr | TGGCGGTGGATACTTCTTGATCGG (10982) | 24 | 60.5 |
| ath-miRf10687-akr | GGCTTAGCTGAAGAAGCAGAGGAG (10983) | 24 | 58.9 |
| ath-miRf10701-akr | TGCAGTTCCTGGAGGTGGAGG (10984) | 21 | 60.0 |
| ath-miRf10702-akr | CGTGGGAGGACTCCAAGTGTG (10985) | 21 | 58.9 |
| ath-miRf10751-akr | GCCTTGTGGAGAGGAAGCAAGA (10986) | 22 | 58.6 |

TABLE 11a-continued

Primers of Differential miRNA Molecules for qRT-PCR Validation Step.

| Mir Name | Primer Sequence (SEQ ID NO:) | Primer Length | Tm |
|---|---|---|---|
| ath-miRf10763-akr | GCGGTGGTGAAGAAGCATGGTT (10987) | 22 | 60.1 |
| ath-miRf10924-akr | GCTGAGGCGTATCAGGAGGTAGT (10988) | 23 | 59.4 |
| ath-miRf11021-akr | GGCGAGGTTTGCGATGAGAAAGAG (10989) | 24 | 60.2 |
| ath-miRf11037-akr | GCTCATCGGAGAAACAGAGGAGC (10990) | 23 | 59.2 |
| ath-miRf11042-akr | GGAAGAGGCAGTGCATGGGTA (10991) | 21 | 58.3 |
| ath-miRf11045-akr | GGCTTTCTTGTGGAGGAAGCAAGAT (10992) | 25 | 59.3 |
| bdi-miR2508 | GCATTGAGTGCAGCGTTGATGAAC (10993) | 24 | 59.7 |
| bna-miR2111b-5p | CATTTGGCTAATCTGCATCCTGAGGTTTA (10994) | 29 | 59.1 |
| bra-miR160a-3p | CGCGTATGAGGAGCCATGCATA (10995) | 22 | 59.0 |
| csi-miR162-5p | TGGAGGCAGCGGTTCATCGATC (10996) | 22 | 61.1 |
| csi-miR3946 | GGCTTGTAGAGAAAGAGAAGAGAGCAC (10997) | 27 | 58.8 |
| csi-miR3948 | TGGAGTGGGAGTGGGAGTAGGGTG (10998) | 24 | 62.6 |
| ctr-miR171 | GCTTGAGCCGCGTCAATATCTCC (10999) | 23 | 60.1 |
| far-miR1134 | GCCGACAACAACAACAAGAAGAAGAG (11000) | 26 | 58.9 |
| ghr-miR2950 | TGGTGTGCAGGGGGTGGAATA (11001) | 21 | 59.6 |
| gma-miR1507a | TGGCTCTCATTCCATACATCGTCTGA (11002) | 26 | 59.2 |
| gma-miR1524 | CGAGTCCGAGGAAGGAACTCC (11003) | 21 | 58.2 |
| gma-miR156g | TTTGGCACAGAAGATAGAGAGCACAG (11004) | 26 | 58.7 |
| gma-miR157c | TGGCTGACAGAAGACTAGAGAGCAC (11005) | 25 | 59.6 |
| gma-miR159a-3p | TGGCTTTGGATTGAAGGGAGCTCTA (11006) | 25 | 59.5 |
| gma-miR159d | GCAGCTGCTTAGCTATGGATCCC (11007) | 23 | 59.3 |
| gma-miR2119 | GGCTCAAAGGGAGTTGTAGGGGAA (11008) | 24 | 60.0 |
| gma-miR396d | GCAAGAAAGCTGTGGGAGAATATGGC (11009) | 26 | 60.2 |
| gma-miR4371b | AAGTGATGACGTGGTAGACGGAGT (11010) | 24 | 59.3 |
| gma-miR4376-5p | TACGCAGGAGAGATGACGCTGT (11011) | 22 | 59.6 |
| gma-miR4412-3p | AGTGGCGTAGATCCCCACAAC (11012) | 21 | 58.4 |
| gma-miR4416a | ACGGGTCGCTCTCACCTAGG (11013) | 20 | 59.5 |
| gma-miR482a-3p | TCTTCCCAATTCCGCCCATTCCTA (11014) | 24 | 59.6 |
| gma-miR482b-5p | GCTATGGGGGATTGGGAAGGAAT (11015) | 24 | 59.9 |
| gso-miR169g* | TCGGCAAGTTGGCCTTGGCT (11016) | 20 | 61.5 |
| gso-miR482a | GGCTCTTCCCTACACCTCCCATAC (11017) | 24 | 59.7 |
| iba-miR157 | CATTTGGCTTGACAGAAGATAGAGAGCAT (11018) | 29 | 58.9 |
| mdm-miR482a-5p | CGGAATGGGCTGTTTGGGAACA (11019) | 22 | 59.7 |
| mtr-miR2119 | GCTCAAAGGGAGGTGTGGAGTAG (11020) | 23 | 58.5 |
| osa-miR159e | GCATTGGATTGAAGGGAGCTCCT (11021) | 23 | 58.8 |
| osa-miR159f | GGCCTTGGATTGAAGGGAGCTCTA (11022) | 24 | 59.9 |

TABLE 11a-continued

Primers of Differential miRNA Molecules for qRT-PCR Validation Step.

| Mir Name | Primer Sequence (SEQ ID NO:) | Primer Length | Tm |
|---|---|---|---|
| osa-miR162a | GGCTCGATAAACCTCTGCATCCAG (11023) | 24 | 59.3 |
| osa-miR1846e | CAACGAGGAGGCCGGGACCA (11024) | 20 | 62.8 |
| osa-miR1850.1 | GCTGGAAAGTTGGGAGATTGGGG (11025) | 23 | 59.6 |
| osa-miR1858a | GAGAGGAGGACGGAGTGGGGC (11026) | 21 | 62.2 |
| osa-miR1869 | GCTGAGAACAATAGGCATGGAGGTA (11027) | 26 | 60.0 |
| osa-miR1874-3p | GCTATGGATGGAGGTGTAACCCGATG (11028) | 26 | 60.6 |
| osa-miR1879 | CGTGTTTGGTTTAGGGATGAGGTGG (11029) | 25 | 59.6 |
| osa-miR1881 | GCAATGTTATTGTAGCGTGGTGGTGT (11030) | 26 | 60.1 |
| osa-miR2055 | GGCTTTCCTTGGGAAGGTGGTTTC (11031) | 24 | 60.0 |
| osa-miR2104 | GCGGCGAGGGGATGCGAGCG (11032) | 20 | 67.4 |
| osa-miRf10105-akr | TTGGCCTCGTCGAAGAAGGAGA (11033) | 22 | 59.5 |
| osa-miRf10151-akr | GGCTGGCTATATTTTGGGACGGAG (11034) | 24 | 59.3 |
| osa-miRf10362-akr | GCTGGAGGATGCGACGGTGCT (11035) | 21 | 63.6 |
| osa-miRf10839-akr | CCCTGTGACGTTGGTGAAGGTG (11036) | 22 | 59.7 |
| osa-miRf10849-akr | TGGACTGTTTGGGGGAGCTTCT (11037) | 22 | 59.6 |
| osa-miRf11013-akr | GGTTTGCCGGAGTTGGAGGAGA (11038) | 22 | 60.6 |
| osa-miRf11341-akr | CGCGCCGACGATGACGGTGGAGT (11039) | 23 | 67.4 |
| osa-miRf11352-akr | GCAGGGATTTTGGAAGGAGGTGACA (11040) | 25 | 60.8 |
| osa-miRf11355-akr | GGTGGAGGTGGAGCTGTGCCAAA (11041) | 23 | 63.2 |
| osa-miRf11415-akr | GAGAGCAGGATGCAGCCAAGG (11042) | 21 | 59.6 |
| osa-miRf11595-akr | CCATCGGTGTTGGAGGTGGC (11043) | 20 | 59.8 |
| osa-miRf11649-akr | AAACCGTGCAAAGGAGGTCCC (11044) | 21 | 59.4 |
| osa-miRf11829-akr | ACGCGGAGGAGGTGGTGTTCT (11045) | 21 | 62.0 |
| osa-miRf11996-akr | GCGTCTTATAACCTGAAACGGGGG (11046) | 24 | 59.5 |
| pab-miR3711 | TGGCGCTAGAAGGAGGGCCT (11047) | 20 | 61.6 |
| ppt-miR1220a | GCTTCCGGTGGTGAGGAAGATAG (11048) | 23 | 58.6 |
| ppt-miR166m | GCTCGGACCAGGCATCATTCCTT (11049) | 23 | 61.0 |
| ppt-miR533b-5p | GAGCTGTCCAGGCTGTGAGGG (11050) | 21 | 61.0 |
| ppt-miR895 | GCGTAGCTTAGCGAGGTGTTGGTA (11051) | 24 | 60.7 |
| psi-miR159 | GCCTTGGATTGAAGGGAGCTCCA (11052) | 23 | 60.6 |
| pta-miR156a | TTTGGCCAGAAGATAGAGAGCACATC (11053) | 26 | 58.5 |
| pta-miR156b | TTGCCAGAAGATAGAGAGCACAAC (11054) | 25 | 58.6 |
| pta-miR166c | CCGGACCAGGCTTCATCCCAG (11055) | 21 | 61.1 |
| ptc-miR166p | TCGGACCAGGCTCCATTCCTT (11056) | 21 | 59.4 |
| ptc-miRf10007-akr | GCCATTGACAGGGAAACTCACCA (11057) | 23 | 59.2 |
| ptc-miRf10132-akr | TTGGCGGTGATTGAACGGAGGGT (11058) | 23 | 62.7 |
| ptc-miRf10148-akr | TGGTGCACCTGGTGGTGGAG (11059) | 20 | 60.8 |

TABLE 11a-continued

Primers of Differential miRNA Molecules for qRT-PCR Validation Step.

| Mir Name | Primer Sequence (SEQ ID NO:) | Primer Length | Tm |
|---|---|---|---|
| ptc-miRf10226-akr | TCCTTTGGGGAGATGGAGAGCTT (11060) | 23 | 58.9 |
| ptc-miRf10271-akr | TGGCTTGGATTGAAGGGAGCTCTAA (11061) | 25 | 59.5 |
| ptc-miRf10300-akr | GGCTTTGGAAAGCAAGTGAGGTG (11062) | 23 | 58.7 |
| ptc-miRf10522-akr | TTGGGGAGCTGGACTCTGGA (11063) | 20 | 58.6 |
| ptc-miRf10619-akr | GTTGGGCTTGCTGCTGGAGGA (11064) | 21 | 61.5 |
| ptc-miRf10734-akr | GCCATCTAGGTGGTGGTCCAGTG (11065) | 23 | 60.7 |
| ptc-miRf10976-akr | TGGGAACGTGGCTGTGGCTA (11066) | 20 | 60.3 |
| ptc-miRf10985-akr | TGGCCAGAAGATAGAGAGCACTGA (11067) | 24 | 58.8 |
| ptc-miRf11018-akr | CCTGCAAACCTAAGGGAGCGG (11068) | 21 | 59.6 |
| ptc-miRf11079-akr | AAGATGGAGAAGCAGGGCACGTGC (11069) | 24 | 63.4 |
| ptc-miRf11315-akr | GCCAACTTAGAGTTGGGGGTGG (11070) | 22 | 59.2 |
| ptc-miRf11324-akr | CTTGTCGCAGGAGAGATGGCGCT (11071) | 23 | 63.1 |
| ptc-miRf11396-akr | GCCAAGGCTCTGATACCATGTCAA (11072) | 24 | 58.9 |
| ptc-miRf11669-akr | GGCCAAGGCTCTGATACCATGTT (11073) | 23 | 58.8 |
| ptc-miRf11757-akr | CCTTGGTGAATGGTTGGGAGGAAT (11074) | 24 | 58.7 |
| ptc-miRf11844-akr | CCCAACTTGGAGGTGGGTGTGG (11075) | 22 | 61.4 |
| ptc-miRf11847-akr | GCGAAAGTGTGGAGAAGGTTGCC (11076) | 23 | 60.6 |
| ptc-miRf11855-akr | GGCAGAGCATGGATGGAGCTA (11077) | 21 | 58.2 |
| ptc-miRf11953-akr | GGCGTAATCTGCATCCTGAGGTT (11078) | 23 | 58.9 |
| ptc-miRf12069-akr | GGAGGGGCTGCAAGACCCAAG (11079) | 21 | 61.5 |
| ptc-miRf12389-akr | GTCGACCTGGCGAGTCAACCGGG (11080) | 23 | 65.3 |
| sbi-miR159a | GGCTTTGGATTGAAGGGAGCTCTG (11081) | 24 | 59.6 |
| smo-miR1103-3p | GCTGGAAAAAGGAGGTGCATTCTTGT (11082) | 26 | 60.0 |
| smo-miR156b | TGGCCTGACAGAAGATAGAGAGCAC (11083) | 25 | 59.7 |
| tae-miR2003 | CGGTTGGGCTGTATGATGGCGA (11084) | 22 | 61.3 |
| vvi-miR2111-5p | TGGCTAATCTGCATCCTGAGGTCTA (11085) | 25 | 58.7 |
| vvi-miR394b | GCTTGGCATTCTGTCCACCTCC (11086) | 22 | 59.9 |
| zma-miR167u | GGCTGAAGCTGCCACATGATCTG (11087) | 23 | 60.2 |
| zma-miR396b-3p | GGCTTCCACAGCTTTCTTGAACTG (11088) | 24 | 58.5 |
| zma-miR398a-5p | TGTGTTCTCAGGTCGCCCCCG (11089) | 21 | 62.9 |
| zma-miR482-5p | TGGCTCTTCCTTGTTCCTCCCATT (11090) | 24 | 59.7 |

Alternative RT-PCR Validation Method of Selected microRNAs of the Invention

A novel microRNA quantification method has been applied using stem-loop RT followed by PCR analysis (Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J. 2005, Nucleic Acids Res 33(20):e179; Varkonyi-Gasic E, Wu R, Wood M, Walton E F, Hellens R P. 2007, Plant Methods 3:12). This highly accurate method allows the detection of less abundant miRNAs. In this method, stem-loop RT primers are used, which provide higher specificity and efficiency to the reverse transcription process. While the conventional method relies on polyadenylated (poly (A)) tail and thus becomes sensitive to methylation because of the susceptibility of the enzymes involved, in this novel method the reverse transcription step is transcript-specific and insensitive to methylation. Reverse transcriptase reactions contained RNA samples including purified total RNA, 50 nM stem-loop RT primer (50-51 nucleotide long, see Table 11b, synthesized by Sigma), and using the SuperScript II reverse transcriptase (Invitrogen). A mix of up to 12 stem-loop RT primers may be used in each reaction, and the forward primers are such that the last 6 nucleotides are replaced with a GC rich sequence. For the PCR step, each miRNA has a custom forward primer (18-24 nucleotide long) and a universal stem loop reverse primer (5'-GTGCAGGGTCCGAGGT-3'-SEQ ID NO: 11617). Table 11b below lists the primers used for PCR validation using this method. Note, SL-RT stands for stem loop reverse transcription primer, and SL-F stands for stem loop forward primer.

TABLE 11b

Stem Loop Reverse Transcriptase Primers for RT-PCR Validation of Differential Mirs under Abiotic Stress.

| Mir Name | Stem Loop Primer (SEQ ID NO:) | Forward Primer (SEQ ID NO:) | Forward Primer Length |
|---|---|---|---|
| ahy-miR3514-5p | GTCGTATCCAGTGCAGGGTCCGAGGTATTC GCACTGGATACGACTCCACC (11618) | CGGCGGAGGATTCTGTAT TAAC (11619) | 22 |
| aly-miR396a-3p | GTCGTATCCAGTGCAGGGTCCGAGGTATTC GCACTGGATACGACCTTCCC (11620) | CGGCGGGTTCAATAAAG CTGT (11621) | 21 |
| aly-miR396b-3p | GTCGTATCCAGTGCAGGGTCCGAGGTATTC GCACTGGATACGACTTTCCC (11622) | CGGCGGGCTCAAGAAAG CTGT (11623) | 21 |
| aly-miR831-5p | GTCGTATCCAGTGCAGGGTCCGAGGTATTC GCACTGGATACGACTCTCAT (11624) | CGGCGGAGAAGAGGTAC AAGGAG (11625) | 23 |
| ath-miRf10197-akr | GTCGTATCCAGTGCAGGGTCCGAGGTATTC GCACTGGATACGACTCACTCG (11626) | CGCTCACTCGACCAAGG GGGT (11627) | 21 |
| ath-miRf10279-akr | GTCGTATCCAGTGCAGGGTCCGAGGTATTC GCACTGGATACGACATCACT (11628) | TTCCACTCAGCCTGGGGG TCG (11629) | 21 |
| ath-miRf10687-akr | GTCGTATCCAGTGCAGGGTCCGAGGTATTC GCACTGGATACGACCTCCTC (11630) | CGGCGGTTAGCTGAAGA AGCA (11631) | 21 |
| gma-miRf10687-akr-homolog | GTCGTATCCAGTGCAGGGTCCGAGGTATTC GCACTGGATACGACCTCCTC (11632) | GAGCTTAGCCGCAGAGG CA (11633) | 19 |
| ath-miRf11021-akr | GTCGTATCCAGTGCAGGGTCCGAGGTATTC GCACTGGATACGACCTCTTT (11634) | CGGCGAGGTTTGCGATG AG (11635) | 19 |
| ath-miRf11045-akr | GTCGTATCCAGTGCAGGGTCCGAGGTATTC GCACTGGATACGACATCTTG (11636) | CGGCGGTTTCTTGTGGAG GAAG (11637) | 22 |
| csi-miR162-5p | GTCGTATCCAGTGCAGGGTCCGAGGTATTC GCACTGGATACGACGATCGA (11638) | CGTCTGGAGGCAGCGGTT CA (11639) | 20 |
| far-miR1134 | GTCGTATCCAGTGCAGGGTCCGAGGTATTC GCACTGGATACGACCTCTTC (11640) | CGCGCCGACAACAACAA CAAGAA (11641) | 23 |
| gma-miR159d | GTCGTATCCAGTGCAGGGTCCGAGGTATTC GCACTGGATACGACGGGATC (11642) | CGGCGGAGCTGCTTAGCT ATG (11643) | 21 |
| gma-miR396d | GTCGTATCCAGTGCAGGGTCCGAGGTATTC GCACTGGATACGACGCCATA (11644) | CGCGCAAGAAAGCTGTG GGAGAA (11645) | 23 |
| gma-miR4376-5p | GTCGTATCCAGTGCAGGGTCCGAGGTATTC GCACTGGATACGACACAGCG (11646) | GGCCGGTACGCAGGAGA GATGA (11647) | 22 |
| gma-miR4412-3p | GTCGTATCCAGTGCAGGGTCCGAGGTATTC GCACTGGATACGACGTTGTG (11648) | TTCCAGTGGCGTAGATCC C (11649) | 19 |
| gma-miR4416a | GTCGTATCCAGTGCAGGGTCCGAGGTATTC GCACTGGATACGACCCTAGG (11650) | CGGCACGGGTCGCTCTCA (11651) | 18 |
| gma-miR482a-3p | GTCGTATCCAGTGCAGGGTCCGAGGTATTC GCACTGGATACGACTAGGAA (11652) | CGTCTCTTCCCAATTCCG CCCA (11653) | 22 |
| gso-miR169g* | GTCGTATCCAGTGCAGGGTCCGAGGTATTC GCACTGGATACGACAGCCAAG (11654) | GTTACTCGGCAAGTTGGC (11655) | 18 |
| mtr-miR2119 | GTCGTATCCAGTGCAGGGTCCGAGGTATTC GCACTGGATACGACCTACTC (11656) | CGGCGGTCAAAGGGAGG TGTG (11657) | 21 |
| osa-miR1874-3p | GTCGTATCCAGTGCAGGGTCCGAGGTATTC GCACTGGATACGACCATCGG (11658) | CGGCGGTATGGATGGAG GTGTAAC (11659) | 24 |

TABLE 11b-continued

Stem Loop Reverse Transcriptase Primers for RT-PCR Validation of Differential Mirs under Abiotic Stress.

| Mir Name | Stem Loop Primer (SEQ ID NO:) | Forward Primer (SEQ ID NO:) | Forward Primer Length |
|---|---|---|---|
| osa-miRf10105-akr | GTCGTATCCAGTGCAGGGTCCGAGGTATTCGCACTGGATACGACTCTCCT (11660) | CCGGTTGGCCTCGTCGAAGA (11661) | 20 |
| osa-miRf10151-akr | GTCGTATCCAGTGCAGGGTCCGAGGTATTCGCACTGGATACGACCTCCGT (11662) | CGGCGGTGGCTATATTTTGGG (11663) | 21 |
| osa-miRf10362-akr | GTCGTATCCAGTGCAGGGTCCGAGGTATTCGCACTGGATACGACAGCACC (11664) | CGATGCTGGAGGATGCGAC (11665) | 19 |
| osa-miRf10839-akr | GTCGTATCCAGTGCAGGGTCCGAGGTATTCGCACTGGATACGACCACCTT (11666) | CGGCCCTGTGACGTTGTG (11667) | 19 |
| osa-miRf11649-akr | GTCGTATCCAGTGCAGGGTCCGAGGTATTCGCACTGGATACGACGGGACC (11668) | GCGCAAACCGTGCAAAGGA (11669) | 19 |
| pab-miR3711 | GTCGTATCCAGTGCAGGGTCCGAGGTATTCGCACTGGATACGACAGGCCC (11670) | GGCCCTGGCGCTAGAAGGA (11671) | 19 |
| ppt-miR533b-5p | GTCGTATCCAGTGCAGGGTCCGAGGTATTCGCACTGGATACGACCCCTCA (11672) | CGGCGAGCTGTCCAGGCTG (11673) | 19 |
| ppt-miR895 | GTCGTATCCAGTGCAGGGTCCGAGGTATTCGCACTGGATACGACTACCAA (11674) | CGGCGGGTAGCTTAGCGAGGTG (11675) | 22 |
| ptc-miRf10300-akr | GTCGTATCCAGTGCAGGGTCCGAGGTATTCGCACTGGATACGACCACCTC (11676) | CGGCGGTTTGGAAAGCAAGT (11677) | 20 |
| ptc-miRf10522-akr | GTCGTATCCAGTGCAGGGTCCGAGGTATTCGCACTGGATACGACTCCAGA (11678) | CGCGCTTGGGGAGCTGGAC (11679) | 19 |
| ptc-miRf10619-akr | GTCGTATCCAGTGCAGGGTCCGAGGTATTCGCACTGGATACGACTCCTCC (11680) | CGGCGTTGGGCTTGCTGCT (11681) | 19 |
| ptc-miRf11855-akr | GTCGTATCCAGTGCAGGGTCCGAGGTATTCGCACTGGATACGACTAGCTC (11682) | CGGCGGCAGAGCATGGATG (11683) | 19 |
| ptc-miRf12069-akr | GTCGTATCCAGTGCAGGGTCCGAGGTATTCGCACTGGATACGACCTTGGG (11684) | CGTCGGAGGGGCTGCAAGA (11685) | 19 |
| smo-miR1103-3p | GTCGTATCCAGTGCAGGGTCCGAGGTATTCGCACTGGATACGACACAAGA (11686) | CGGCTGGAAAAAGGAGGTGCAT (11687) | 22 |
| zma-miR396b-3p | GTCGTATCCAGTGCAGGGTCCGAGGTATTCGCACTGGATACGACTTTCCC (11688) | CGGCGGGTTCAATAAAGCTGT (11689) | 21 |
| zma-miR482-5p | GTCGTATCCAGTGCAGGGTCCGAGGTATTCGCACTGGATACGACAAGGCT (11690) | CGGCGGTGGGAGATGAAGG (11691) | 19 |
| aly-miR160c-3p | GTCGTATCCAGTGCAGGGTCCGAGGTATTCGCACTGGATACGACCATGCT (11692) | GAATCGCGTACAAGGAGCCA (11693) | 20 |
| aqc-miR159 | GTCGTATCCAGTGCAGGGTCCGAGGTATTCGCACTGGATACGACTAGAGC (11694) | CGGCGGTTTGGACTGAAGGGA (11695) | 21 |
| ath-miR157a | GTCGTATCCAGTGCAGGGTCCGAGGTATTCGCACTGGATACGACGTGCTC (11696) | CGGCGGTTGACAGAAGATAGA (11697) | 21 |
| ath-miR159b | GTCGTATCCAGTGCAGGGTCCGAGGTATTCGCACTGGATACGACAAGAGC (11698) | CGGCGGTTTGGATTGAAGGGA (11699) | 21 |
| ath-miR159c | GTCGTATCCAGTGCAGGGTCCGAGGTATTCGCACTGGATACGACAGGAGC (11700) | CGGCGGTTTGGATTGAAGGGA (11701) | 21 |
| ath-miRf10068-akr | GTCGTATCCAGTGCAGGGTCCGAGGTATTCGCACTGGATACGACCTCTCA (11702) | GGCCCACCGGTGGAGGAG (11703) | 18 |
| ath-miRf10148-akr | GTCGTATCCAGTGCAGGGTCCGAGGTATTCGCACTGGATACGACATCTTG (11704) | CGGCGGGGTGGTGGAAAGAT (11705) | 20 |
| ath-miRf10209-akr | GTCGTATCCAGTGCAGGGTCCGAGGTATTCGCACTGGATACGACACCACC (11706) | CGTCATGGTGGTACTCGGCCA (11707) | 21 |

TABLE 11b-continued

Stem Loop Reverse Transcriptase Primers for RT-PCR Validation of Differential Mirs under Abiotic Stress.

| Mir Name | Stem Loop Primer (SEQ ID NO:) | Forward Primer (SEQ ID NO:) | Forward Primer Length |
|---|---|---|---|
| ath-miRf10239-akr | GTCGTATCCAGTGCAGGGTCCGAGGTATTCGCACTGGATACGACGATTCA (11708) | CGGCCGCCTTGCATCAAC (11709) | 18 |
| ath-miRf10240-akr | GTCGTATCCAGTGCAGGGTCCGAGGTATTCGCACTGGATACGACCGTCCT (11710) | CGGCGGATCGAAGGAGATGG (11711) | 20 |
| ath-miRf10368-akr | GTCGTATCCAGTGCAGGGTCCGAGGTATTCGCACTGGATACGACATAATC (11712) | AAGGCCTACTTGGGTGGTGCT (11713) | 21 |
| ath-miRf10451-akr | GTCGTATCCAGTGCAGGGTCCGAGGTATTCGCACTGGATACGACCAACAG (11714) | CGGCGGAAGAAGGAGAACAAC (11715) | 22 |
| ath-miRf10633-akr | GTCGTATCCAGTGCAGGGTCCGAGGTATTCGCACTGGATACGACCCGATC (11716) | CGGCTGGCGGTGGATACTTCTT (11717) | 22 |
| ath-miRf10701-akr | GTCGTATCCAGTGCAGGGTCCGAGGTATTCGCACTGGATACGACTCCTCC (11718) | CGCGCTGCAGTTCCTGGAGGT (11719) | 21 |
| ath-miRf10702-akr | GTCGTATCCAGTGCAGGGTCCGAGGTATTCGCACTGGATACGACCACACT (11720) | CGGCGTGGGAGGACTCCA (11721) | 18 |
| ath-miRf10751-akr | GTCGTATCCAGTGCAGGGTCCGAGGTATTCGCACTGGATACGACTCTTGC (11722) | CGGCGGCTTGTGGAGAGGAA (11723) | 20 |
| ath-miRf10763-akr | GTCGTATCCAGTGCAGGGTCCGAGGTATTCGCACTGGATACGACAACCAT (11724) | CGCGCGGTGGTGAAGAAGC (11725) | 19 |
| ath-miRf10924-akr | GTCGTATCCAGTGCAGGGTCCGAGGTATTCGCACTGGATACGACACTACC (11726) | CGTAGGTGAGGCGTATCAGGA (11727) | 21 |
| ath-miRf11037-akr | GTCGTATCCAGTGCAGGGTCCGAGGTATTCGCACTGGATACGACGCTCCT (11728) | CGGCGGTCATCGGAGAAACAG (11729) | 21 |
| ath-miRf11042-akr | GTCGTATCCAGTGCAGGGTCCGAGGTATTCGCACTGGATACGACTACCCAT (11730) | AATCCTGGAAGAGGCAGTGC (11731) | 20 |
| bdi-miR2508 | GTCGTATCCAGTGCAGGGTCCGAGGTATTCGCACTGGATACGACGTTCAT (11732) | CGGCATTGAGTGCAGCGTTG (11733) | 20 |
| bna-miR2111b-5p | GTCGTATCCAGTGCAGGGTCCGAGGTATTCGCACTGGATACGACTAAACC (11734) | CGGCGGTAATCTGCATCCTGA (11735) | 21 |
| bra-miR160a-3p | GTCGTATCCAGTGCAGGGTCCGAGGTATTCGCACTGGATACGACTATGCA (11736) | GAATCGCGTATGAGGAGCCA (11737) | 20 |
| csi-miR3946 | GTCGTATCCAGTGCAGGGTCCGAGGTATTCGCACTGGATACGACGTGCTC (11738) | CGGCGGTTGTAGAGAAAGAGAAGA (11739) | 24 |
| csi-miR3948 | GTCGTATCCAGTGCAGGGTCCGAGGTATTCGCACTGGATACGACCACCCT (11740) | CGGCTGGAGTGGGAGTGGGAGT (11741) | 22 |
| ctr-miR171 | GTCGTATCCAGTGCAGGGTCCGAGGTATTCGCACTGGATACGACGGAGAT (11742) | AATCCTTTGAGCCGCGTCAAT (11743) | 21 |
| ghr-miR2950 | GTCGTATCCAGTGCAGGGTCCGAGGTATTCGCACTGGATACGACTATTCC (11744) | CGTCTGGTGTGCAGGGGGT (11745) | 19 |
| gma-miR1507a | GTCGTATCCAGTGCAGGGTCCGAGGTATTCGCACTGGATACGACTCAGAC (11746) | CGGCGGTCTCATTCCATACATC (11747) | 22 |
| gma-miR1524 | GTCGTATCCAGTGCAGGGTCCGAGGTATTCGCACTGGATACGACGGAGTT (11748) | GCGCCGAGTCCGAGGAAGG (11749) | 19 |
| gma-miR156g | GTCGTATCCAGTGCAGGGTCCGAGGTATTCGCACTGGATACGACCTGTGC (11750) | GCGGCGGACAGAAGATAGAGA (11751) | 21 |
| gma-miR157c | GTCGTATCCAGTGCAGGGTCCGAGGTATTCGCACTGGATACGACGTGCTC (11752) | CGGCGGTGACAGAAGACTAGA (11753) | 21 |
| gma-miR159a-3p | GTCGTATCCAGTGCAGGGTCCGAGGTATTCGCACTGGATACGACTAGAGC (11754) | CGGCGGTTTGGATTGAAGGGA (11755) | 21 |

TABLE 11b-continued

Stem Loop Reverse Transcriptase Primers for RT-PCR Validation of Differential Mirs under Abiotic Stress.

| Mir Name | Stem Loop Primer (SEQ ID NO:) | Forward Primer (SEQ ID NO:) | Forward Primer Length |
|---|---|---|---|
| gma-miR2119 | GTCGTATCCAGTGCAGGGTCCGAGGTATTCGCACTGGATACGACTTCCCC (11756) | CGGCGGTCAAAGGGAGTTGTA (11757) | 21 |
| gma-miR4371b | GTCGTATCCAGTGCAGGGTCCGAGGTATTCGCACTGGATACGACACTCCG (11758) | CGGCGGAAGTGATGACGTGGTAGA (11759) | 24 |
| gma-miR482b-5p | GTCGTATCCAGTGCAGGGTCCGAGGTATTCGCACTGGATACGACATTCCT (11760) | CGGCTATGGGGGATTGGGA (11761) | 20 |
| gso-miR482a | GTCGTATCCAGTGCAGGGTCCGAGGTATTCGCACTGGATACGACGTATGG (11762) | CGGCGGTCTTCCCTACACCTC (11763) | 21 |
| iba-miR157 | GTCGTATCCAGTGCAGGGTCCGAGGTATTCGCACTGGATACGACATGCTC (11764) | CGGCGGTTGACAGAAGATAGA (11765) | 21 |
| mdm-miR482a-5p | GTCGTATCCAGTGCAGGGTCCGAGGTATTCGCACTGGATACGACTGTTCC (11766) | CGGCGGAATGGGCTGTTTG (11767) | 19 |
| osa-miR159e | GTCGTATCCAGTGCAGGGTCCGAGGTATTCGCACTGGATACGACAGGAGC (11768) | CGGCGGATTGGATTGAAGGGA (11769) | 21 |
| osa-miR159f | GTCGTATCCAGTGCAGGGTCCGAGGTATTCGCACTGGATACGACTAGAGC (11770) | AAGGCCTCTTGGATTGAAGGGA (11771) | 22 |
| osa-miR162a | GTCGTATCCAGTGCAGGGTCCGAGGTATTCGCACTGGATACGACCTGGAT (11772) | CGGCGGTCGATAAACCTCTGC (11773) | 21 |
| osa-miR1846e | GTCGTATCCAGTGCAGGGTCCGAGGTATTCGCACTGGATACGACTGGTCC (11774) | CGTCCAACGAGGAGGCCG (11775) | 18 |
| osa-miR1850.1 | GTCGTATCCAGTGCAGGGTCCGAGGTATTCGCACTGGATACGACCCCCAA (11776) | CGGCGGTGGAAAGTTGGGAGA (11777) | 21 |
| osa-miR1858a | GTCGTATCCAGTGCAGGGTCCGAGGTATTCGCACTGGATACGACGCCCCA (11778) | CGGCGAGAGGAGGACGGAG (11779) | 19 |
| osa-miR1869 | GTCGTATCCAGTGCAGGGTCCGAGGTATTCGCACTGGATACGACTACCTC (11780) | CGCGCTGAGAACAATAGGCATGG (11781) | 23 |
| osa-miR1879 | GTCGTATCCAGTGCAGGGTCCGAGGTATTCGCACTGGATACGACCCACCT (11782) | CGCGCGTGTTTGGTTTAGGGATG (11783) | 23 |
| osa-miR1881 | GTCGTATCCAGTGCAGGGTCCGAGGTATTCGCACTGGATACGACACACCA (11784) | CGGCGGAATGTTATTGTAGCGTGG (11785) | 24 |
| osa-miR2055 | GTCGTATCCAGTGCAGGGTCCGAGGTATTCGCACTGGATACGACGAAACC (11786) | AAGGCCTTTTCCTTGGGAAGGT (11787) | 22 |
| osa-miR2104 | GTCGTATCCAGTGCAGGGTCCGAGGTATTCGCACTGGATACGACCACGCT (11788) | TTAGCGGCGAGGGGATGCG (11789) | 19 |
| osa-miRf10849-akr | GTCGTATCCAGTGCAGGGTCCGAGGTATTCGCACTGGATACGACAGAAGC (11790) | CGGCTGGACTGTTTGGGGGA (11791) | 20 |
| osa-miRf11013-akr | GTCGTATCCAGTGCAGGGTCCGAGGTATTCGCACTGGATACGACTCTCCT (11792) | TAGGGTTTGCCGGAGTTGG (11793) | 19 |
| osa-miRf11341-akr | GTCGTATCCAGTGCAGGGTCCGAGGTATTCGCACTGGATACGACACTCCAC (11794) | TAGCGCGCCGACGATGACG (11795) | 19 |
| osa-miRf11352-akr | GTCGTATCCAGTGCAGGGTCCGAGGTATTCGCACTGGATACGACTGTCAC (11796) | CGCGCAGGGATTTTGAAGGAG (11797) | 22 |
| osa-miRf11355-akr | GTCGTATCCAGTGCAGGGTCCGAGGTATTCGCACTGGATACGACTTTGGC (11798) | CGTCGGTGGAGGTGGAGCTGT (11799) | 21 |
| osa-miRf11415-akr | GTCGTATCCAGTGCAGGGTCCGAGGTATTCGCACTGGATACGACCCTTGG (11800) | CGGCGAGAGCAGGATGCAG (11801) | 19 |
| osa-miRf11595-akr | GTCGTATCCAGTGCAGGGTCCGAGGTATTCGCACTGGATACGACGCCACC (11802) | CGCGCCATCGGTGTTGGA (11803) | 18 |

TABLE 11b-continued

Stem Loop Reverse Transcriptase Primers for RT-PCR Validation of
Differential Mirs under Abiotic Stress.

| Mir Name | Stem Loop Primer (SEQ ID NO:) | Forward Primer (SEQ ID NO:) | Forward Primer Length |
|---|---|---|---|
| osa-miRf11829-akr | GTCGTATCCAGTGCAGGGTCCGAGGTATTC GCACTGGATACGACAGAACA (11804) | CGTCACGCGGAGGAGGT GG (11805) | 19 |
| osa-miRf11996-akr | GTCGTATCCAGTGCAGGGTCCGAGGTATTC GCACTGGATACGACCCCCCG (11806) | CGGCGGGTCTTATAACCT GAAA (11807) | 22 |
| ppt-miR1220a | GTCGTATCCAGTGCAGGGTCCGAGGTATTC GCACTGGATACGACCTATCT (11808) | GCGCTTCCGGTGGTGAGG A (11809) | 19 |
| ppt-miR166m | GTCGTATCCAGTGCAGGGTCCGAGGTATTC GCACTGGATACGACAAGGAA (11810) | CGGCTCGGACCAGGCAT CA (11811) | 19 |
| psi-miR159 | GTCGTATCCAGTGCAGGGTCCGAGGTATTC GCACTGGATACGACTGGAGC (11812) | AAGGCCTCTTGGATTGAA GGGA (11813) | 22 |
| pta-miR156a | GTCGTATCCAGTGCAGGGTCCGAGGTATTC GCACTGGATACGACGATGTG (11814) | CGGCGGCAGAAGATAGA GAG (11815) | 20 |
| pta-miR156b | GTCGTATCCAGTGCAGGGTCCGAGGTATTC GCACTGGATACGACGTTGTG (11816) | CGGCGGCAGAAGATAGA GAG (11817) | 20 |
| pta-miR166c | GTCGTATCCAGTGCAGGGTCCGAGGTATTC GCACTGGATACGACCTGGGA (11818) | CGTCCCGGACCAGGCTTC A (11819) | 19 |
| ptc-miR166p | GTCGTATCCAGTGCAGGGTCCGAGGTATTC GCACTGGATACGACAAGGAA (11820) | CGTCTCGGACCAGGCTCC A (11821) | 19 |
| ptc-miRf10007-akr | GTCGTATCCAGTGCAGGGTCCGAGGTATTC GCACTGGATACGACTGGTGA (11822) | CGGCGGCATTGACAGGG AAAC (11823) | 21 |
| ptc-miRf10132-akr | GTCGTATCCAGTGCAGGGTCCGAGGTATTC GCACTGGATACGACACCCTC (11824) | CGTCTTGGCGGTGATTGA ACG (11825) | 21 |
| ptc-miRf10148-akr | GTCGTATCCAGTGCAGGGTCCGAGGTATTC GCACTGGATACGACCTCCAC (11826) | CGGCTGGTGCACCTGGTG (11827) | 18 |
| ptc-miRf10226-akr | GTCGTATCCAGTGCAGGGTCCGAGGTATTC GCACTGGATACGACAAGCTC (11828) | AATCCTTCCTTTGGGGAG ATGGA (11829) | 23 |
| ptc-miRf10271-akr | GTCGTATCCAGTGCAGGGTCCGAGGTATTC GCACTGGATACGACTTAGAG (11830) | CGGCGGTTGGATTGAAG GGAG (11831) | 21 |
| ptc-miRf10734-akr | GTCGTATCCAGTGCAGGGTCCGAGGTATTC GCACTGGATACGACCACTGG (11832) | CGGCGGCATCTAGGTGGT GGT (11833) | 21 |
| ptc-miRf10976-akr | GTCGTATCCAGTGCAGGGTCCGAGGTATTC GCACTGGATACGACTAGCCA (11834) | CGGCTGGGAACGTGGCT G (11835) | 18 |
| ptc-miRf10985-akr | GTCGTATCCAGTGCAGGGTCCGAGGTATTC GCACTGGATACGACTCAGTG (11836) | CGGCGGCAGAAGATAGA GAG (11837) | 20 |
| ptc-miRf11018-akr | GTCGTATCCAGTGCAGGGTCCGAGGTATTC GCACTGGATACGACCCGCTC (11838) | CGGCGGCTGCAAACCTA AGG (11839) | 20 |
| ptc-miRf11079-akr | GTCGTATCCAGTGCAGGGTCCGAGGTATTC GCACTGGATACGACGCACGT (11840) | CGGCAAGATGGAGAAGC AGGGC (11841) | 22 |
| ptc-miRf11315-akr | GTCGTATCCAGTGCAGGGTCCGAGGTATTC GCACTGGATACGACCCACCC (11842) | CGCCGATCAACTTAGAGT TGG (11843) | 21 |
| ptc-miRf11324-akr | GTCGTATCCAGTGCAGGGTCCGAGGTATTC GCACTGGATACGACAGCGCC (11844) | CGGCCTTGTCGCAGGAG AGAT (11845) | 21 |
| ptc-miRf11396-akr | GTCGTATCCAGTGCAGGGTCCGAGGTATTC GCACTGGATACGACTTGACA (11846) | CGCGCCAAGGCTCTGATA CCA (11847) | 21 |
| ptc-miRf11669-akr | GTCGTATCCAGTGCAGGGTCCGAGGTATTC GCACTGGATACGACAACATG (11848) | CGGCGGCAAGGCTCTGA TAC (11849) | 20 |
| ptc-miRf11757-akr | GTCGTATCCAGTGCAGGGTCCGAGGTATTC GCACTGGATACGACATTCCT (11850) | CGGCCTTGGTGAATGGTT GGG (11851) | 21 |

TABLE 11b-continued

Stem Loop Reverse Transcriptase Primers for RT-PCR Validation of Differential Mirs under Abiotic Stress.

| Mir Name | Stem Loop Primer (SEQ ID NO:) | Forward Primer (SEQ ID NO:) | Forward Primer Length |
|---|---|---|---|
| ptc-miRf11844-akr | GTCGTATCCAGTGCAGGGTCCGAGGTATTCGCACTGGATACGACCCACAC (11852) | CGGCCCCAACTTGGAGGTGG (11853) | 20 |
| ptc-miRf11847-akr | GTCGTATCCAGTGCAGGGTCCGAGGTATTCGCACTGGATACGACGGCAAC (11854) | CGGCGGGAAAGTGTGGAGAAG (11855) | 21 |
| ptc-miRf11953-akr | GTCGTATCCAGTGCAGGGTCCGAGGTATTCGCACTGGATACGACAACCTC (11856) | CGGCGGGTAATCTGCATCCT (11857) | 20 |
| ptc-miRf12389-akr | GTCGTATCCAGTGCAGGGTCCGAGGTATTCGCACTGGATACGACCCCGGT (11858) | TTCCGTCGACCTGGCGAGTCA (11859) | 21 |
| sbi-miR159a | GTCGTATCCAGTGCAGGGTCCGAGGTATTCGCACTGGATACGACCAGAGC (11860) | CGGCGGTTTGGATTGAAGGGA (11861) | 21 |
| smo-miR156b | GTCGTATCCAGTGCAGGGTCCGAGGTATTCGCACTGGATACGACGTGCTC (11862) | CGGCGGCTGACAGAAGATAGA (11863) | 21 |
| tae-miR2003 | GTCGTATCCAGTGCAGGGTCCGAGGTATTCGCACTGGATACGACTCGCCA (11864) | AACCGGTTGGGCTGTATGA (11865) | 19 |
| vvi-miR2111-5p | GTCGTATCCAGTGCAGGGTCCGAGGTATTCGCACTGGATACGACTAGACC (11866) | CGGCGGTAATCTGCATCCTGA (11867) | 21 |
| vvi-miR394b | GTCGTATCCAGTGCAGGGTCCGAGGTATTCGCACTGGATACGACGGAGGT (11868) | CGGCGGTTGGCATTCTGTCC (11869) | 20 |
| zma-miR167u | GTCGTATCCAGTGCAGGGTCCGAGGTATTCGCACTGGATACGACCAGATC (11870) | CCGGGGTGAAGCTGCCACAT (11871) | 20 |
| zma-miR398a-5p | GTCGTATCCAGTGCAGGGTCCGAGGTATTCGCACTGGATACGACCATGTG (11872) | CGGCGGGCGAACTGAGAA (11873) | 19 |

Example 5

Results of RT-PCR Validation of Selected miRNAs of the Invention

An RT-PCR analysis was run on selected microRNAs of the invention, using the stem-loop RT primers as described in Table 11b in Example 4 above. Total RNA was extracted from leaf tissues of soybean plants grown as described above, and was used as a template for RT-PCR analysis. Expression level and directionality of several up-regulated and down-regulated microRNAs that were found to be differential on the microarray analysis were verified. Results are summarized in Table 12 below.

TABLE 12

Summary of RT-PCR Verification Results on Selected miRNAs using Stem Loop RT (Alternative) Method

| Trait | Mir Name | p-Value | Fold Change |
|---|---|---|---|
| Drought | gma-miR4376-5p | 8.50E−03 | 2.38 (−) |
|  | zma-miR396b-3p | 4.60E−03 | 1.41 (−) |
|  | aly-miR396b-3p | 3.80E−06 | 3.48 (−) |
|  | gma-miR156g | 5.40E−02 | 1.48 (+) |
|  | gma-miRf10687-akr-homolog | 7.80E−02 | 1.95 (+) |
| Salt | gma-miR159d | 5.60E−05 | 3.35 (−) |
|  | aly-miR396b-3p | 3.80E−07 | 5.45 (−) |
|  | gma-miR4416a | 5.20E−04 | 2.58 (−) |
|  | aly-miR396a-3p | 1.20E−08 | 13.50 (−) |
|  | zma-miR396b-3p | 4.90E−05 | 9.58 (−) |
| Heat Shock | gma-miR4412-3p | 1.50E−03 | 2.31 (−) |
|  | csi-miR162-5p | 2.60E−03 | 1.86 (−) |
|  | ath-miRf10279-akr | 2.40E−02 | 1.40 (−) |

Example 6

Generation of Transgenic Plants

Gene Cloning Strategies for miRNA Molecules and Creation of Binary Vectors for Expression in Plants The best validated miRNA sequences are cloned into pORE-E1 binary vectors (FIG. 1) for the generation of transgenic plants. The full-length precursor sequence comprising of the hairpin sequence of each selected miRNA, is synthesized by Genscript (USA). The resulting clone is digested with appropriate restriction enzymes and inserted into the Multi Cloning Site (MCS) of a similarly digested binary vector through ligation using T4 DNA ligase enzyme (Promega, Madison, Wis., USA).

Example 7

Generation of Transgenic Model Plants Expressing Abiotic Stress Associated miRNAs

*Arabidopsis thaliana* Transformation Protocol

Figure 3:
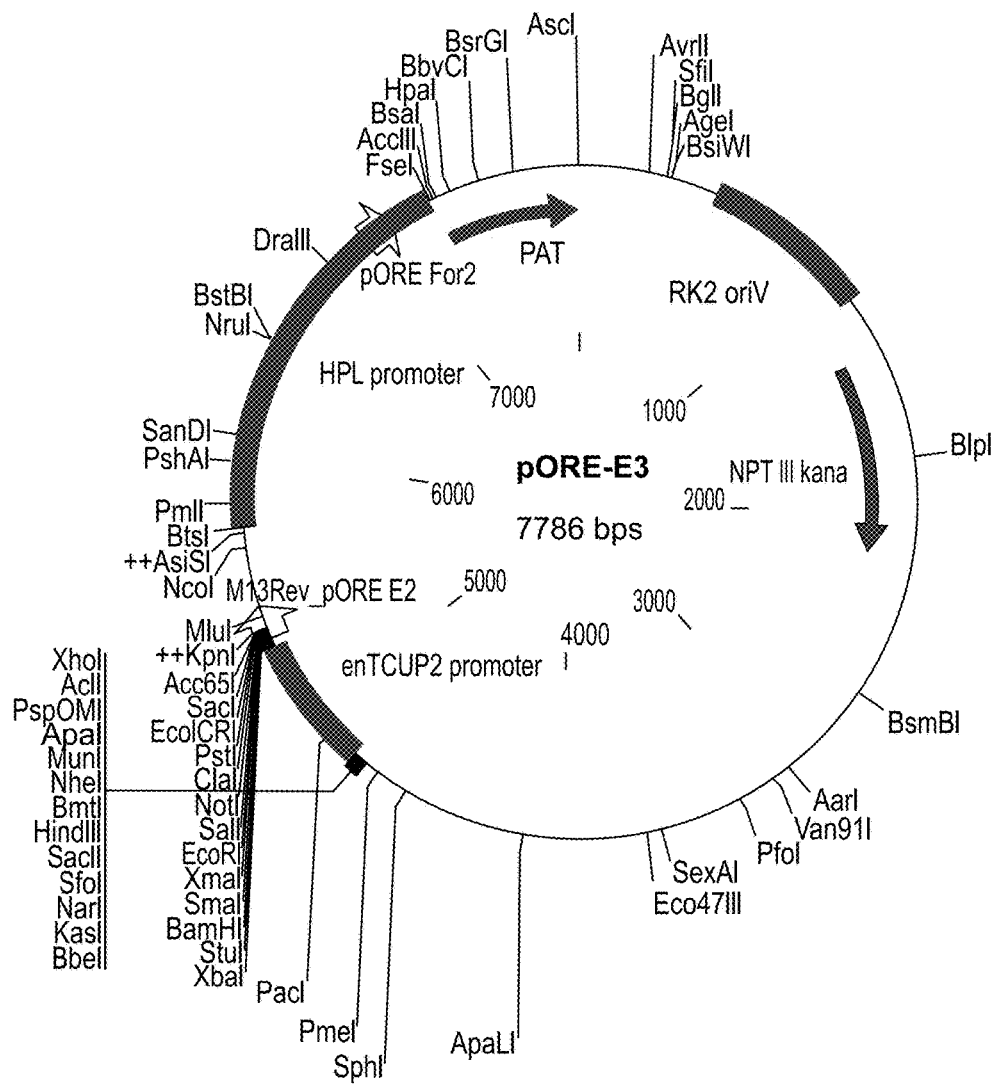
FIG. 3 is a schematic illustration of a plasmid map of the binary vector pORE-E3 used for plant transformation according to some embodiments of the invention.

*Araboposis thaliana* transformation is performed using the floral dip procedure following a slightly modified version of the published protocol (Clough and Bent, 1998, *Plant J* 16(6): 735-43; and Desfeux et al., 2000, *Plant Physiol* 123(3): 895-904). Briefly, T0 Plants are planted in small pots filled with soil. The pots are covered with aluminum foil and a plastic dome, kept at 4° C. for 3-4 days, then uncovered and incubated in a growth chamber at 24° C. under 16 hr light:8 hr dark cycles. A week prior to transformation all individual flowering stems are removed to allow for growth of multiple flowering stems instead. A single colony of *Agrobacterium* (GV3101) carrying the binary vectors (pORE-E1 or pORE-E3, see FIGS. 1 and 3, respectively), harboring the selected miRNA hairpin sequences with additional flanking sequences both upstream and downstream of it, is cultured in LB medium supplemented with kanamycin (50 mg/L) and gentamycin (25 mg/L). Three days prior to transformation, each culture is incubated at 28° C. for 48 hrs, shaking at 180 rpm. The starter culture is split the day before transformation into two cultures, which are allowed to grow further at 28° C. for 24 hours at 180 rpm. Pellets containing the *agrobacterium* cells are obtained by centrifugation of the cultures at 5000 rpm for 15 minutes. The pellets are re-suspended in an infiltration medium (10 mM $MgCl_2$, 5% sucrose, 0.044 µM BAP (Sigma) and 0.03% Tween 20) prepared with double-distilled water.

Transformation of T0 plants is performed by inverting each plant into the *agrobacterium* suspension, keeping the flowering stem submerged for 5 minutes. Following inoculation, each plant is blotted dry for 5 minutes on both sides, and placed sideways on a fresh covered tray for 24 hours at 22° C. Transformed (transgenic) plants are then uncovered and transferred to a greenhouse for recovery and maturation. The transgenic T0 plants are grown in the greenhouse for 3-5 weeks until the seeds are ready, which are then harvested from plants and kept at room temperature until sowing.

Tomato (*Solanum lycopersicum*) Transformation Protocol

Figure 2:
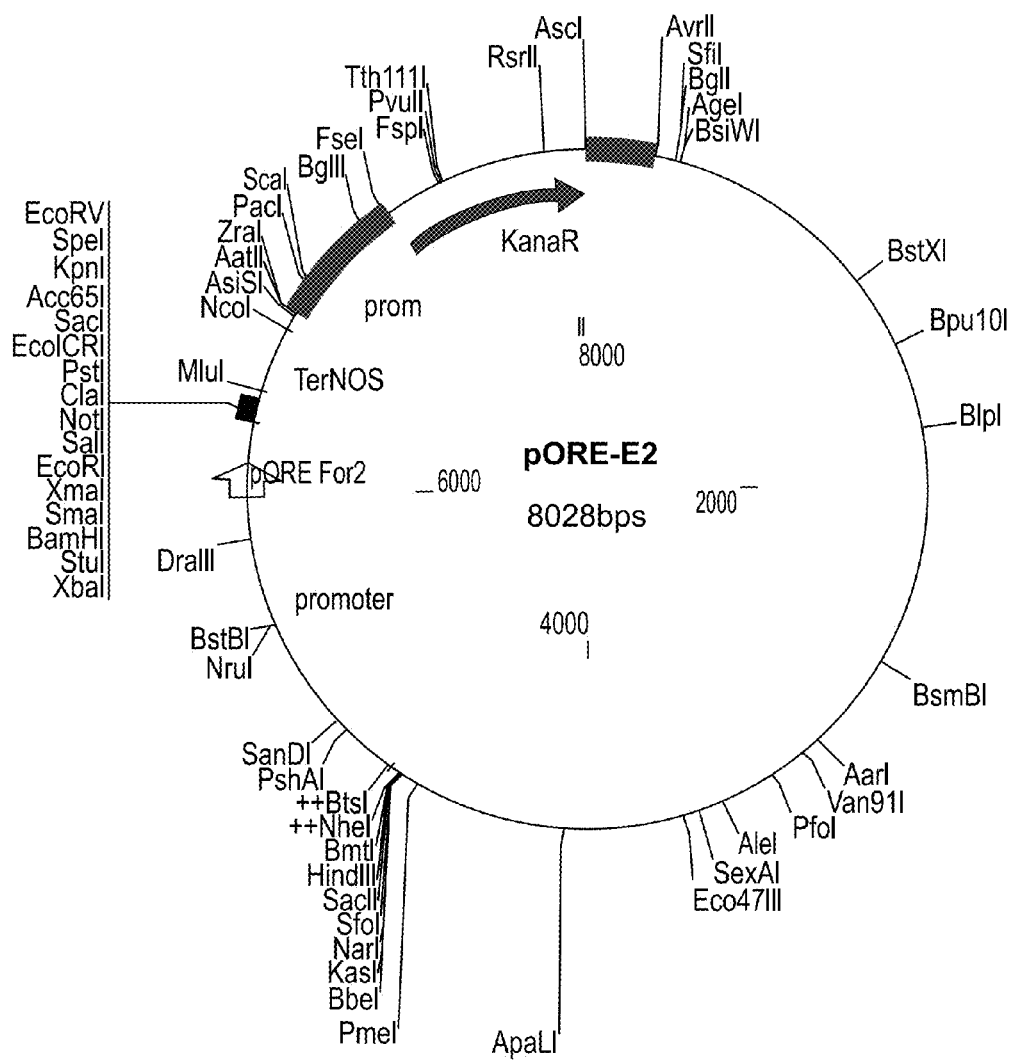
FIG. 2 is a schematic illustration of a plasmid map of the binary vector pORE-E2 used for plant transformation according to some embodiments of the invention.

M82 tomato (*Solanum lycopersicum*) transformation is performed using a slightly modified protocol described previously (McCormick 1991, Plant Tissue Culture Manual, Vol. B6, Lindsey, K., ed. Dordrecht, The Netherlands: Kluwer Academic Publishers, pp. 1-9). Briefly, seeds are surface-sterilized 10 days prior to transformation by soaking and shaking in 70% ethanol followed by a 3% bleach solution. After washing, seeds are sown and allowed to grow into seedlings. Cotyledons are cut and treated with an *agrobacterium* (GV3101, carrying the binary vector pORE-E2, see FIG. 2) solution using a gentle agitation, dried and left on feeder medium for two days in the dark. Then, cotyledons are transferred to a first selection medium (Jones I) for two weeks, followed by a two-week incubation in a second selection medium (Jones II) for callus initiation. Cotyledons are transferred every two weeks to a fresh selection medium (Jones II) until plantlet forms. Plantlets with active meristems are separated from the callus and transferred to a third selection medium (Jones III), and transferred into a rooting medium. Once roots form, the plantlets are planted in soil.

Transgenic *Arabidopsis* Plants Over-Expressing Selected microRNA Sequences

Several microRNAs of the invention were selected for over-expression in both *Arabidopsis*. Transformation protocols are followed as described above for each plant, and *agrobacterium* is utilized, carrying one of three binary vectors: pORE-E1, pORE-E2, or pORE-E3.

*Arabidopsis* transgenic plants were created with osa-miRf11996-akr of the invention. This miRNA was down-regulated under drought and salinity stresses compared to optimal conditions. Thus, the researchers tested the effects of modifying its expression level in model *Arabidopsis* plants. Four transgenic plants over-expressing osa-miRf11996-akr (in binary vector pORE-E3) were created and compared to control Columbia plants. Transgenic and control plants were grown under 16 h light:8 h dark regime at 22° C. in controlled growth rooms until seedlings were four weeks old. Next, plants were divided into two groups: control plants were irrigated with tap water twice a week and treated plants were either subjected to drought and received no irrigation for 5 days, or irrigated with 300 mM NaCl solution for 10 days for salinity stress induction. At the end of each treatment, plants were harvested and dry weight was recorded.

An ANOVA test was applied for statistical analysis of the data and results are summarized in Table 13 below. Control plants' dry weight was averaged and recorded as 100%, to be used as a reference for comparison to the average of each treated strain for each condition. Interestingly, the dry weight of all transgenic strains over-expressing osa-miRf11996-akr was significantly ($p<1.0E-6$) decreased compared to wild type control plants under all conditions. These results correlate with the fact that osa-miRf11996-akr was shown to be down-regulated under various abiotic stresses (e.g., Tables 2 and 4), thus indicating that its expression level needs to be decreased to improve a plant's tolerance to abiotic stress. Accordingly, the researchers also down-regulate osa-miRf11996-akr in *Arabidopsis* plants by using target mimic, as described and explained in Example 12 below.

TABLE 13

Dry Weight Results of Control and Transgenic (Over-expressing osa-miRf11996-akr) *Arabidopsis* Plants.

| Treatment | Strain | Dry weight +− SD | Number of Plants | Dry Weight % of Control |
|---|---|---|---|---|
| No treatment | Control | 483.353 +− 113.070 | 17 | |
| | 11996-2 | 305.909 +− 88.033 | 22 | 63.29% |
| | 11996-3 | 231.500 +− 72.002 | 26 | 47.90% |
| | 11996-5 | 179.194 +− 71.185 | 31 | 37.07% |
| | 11996-7 | 285.158 +− 101.236 | 19 | 59.00% |
| Drought | Control | 225.478 +− 99.687 | 23 | |
| | 11996-2 | 170.000 +− 60.393 | 21 | 75.40% |
| | 11996-3 | 157.269 +− 63.415 | 26 | 69.75% |
| | 11996-5 | 186.353 +− 92.723 | 20 | 82.65% |
| | 11996-7 | 179.818 +− 68.019 | 22 | 79.75% |
| Salinity | Control | 210.895 +− 76.991 | 19 | |
| | 11996-2 | 77.143 +− 41.214 | 21 | 36.58% |
| | 11996-3 | 109.130 +− 60.144 | 23 | 51.75% |
| | 11996-5 | 103.480 +− 44.930 | 25 | 49.07% |
| | 11996-7 | 116.789 +− 64.514 | 19 | 55.38% |

Example 8

Selection of Transgenic *Arabidopsis* Plants Expressing Abiotic Stress Genes According to Expression Level

*Arabidopsis* seeds are sown and Basta is sprayed for the first time on 1-2 weeks old seedlings, at least twice every few days. Only resistant plants, which are heterozygous for the transgene, survive. PCR on the genomic gene sequence is performed on the surviving seedlings using primers pORE-F2 (fwd, 5'-TTTAGCGATGAACTTCACTC-3', SEQ ID NO: 11614) and a custom designed reverse primer based on each small RNA sequence.

Example 9

Evaluating Changes in Root Architecture of Transgenic Plants

Many key traits in modern agriculture can be explained by changes in the root architecture of the plant. Root size and depth have been shown to logically correlate with drought tolerance and fertilizer use efficiency, since deeper and more branched root systems provide better coverage of the soil and can access water and nutrients stored in deeper soil layers.

To test whether the transgenic plants produce a modified root structure, plants can be grown in agar plates placed vertically. A digital picture of the plates is taken every few days and the maximal length and total area covered by the plant roots are assessed. From every construct created, several independent transformation events are checked in replicates. To assess significant differences between root features, statistical test, such as a Student's t-test, is employed in order to identify enhanced root features and to provide a statistical value to the findings.

Example 10

Abiotic Stress Tolerance Assessments of Control and Transgenic Plants

Transgenic plants expressing the polynucleotides of some embodiments of the invention exhibit tolerance to abiotic stress in the form of extreme deficiency in water, high salt concentrations, or heat shock and exhibit better overall survival and growth compared to control non-transgenic plants.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Under normal conditions (non-stress, optimal growth conditions), transgenic plants exhibit a phenotype equivalent or superior to that of the wild type plants. Following stress induction, transformed plants not exhibiting substantial physiological and/or morphological effects, or exhibiting higher biomass than wild-type plants, are identified as abiotic stress tolerant plants. Following are a number of screens aimed at identifying the transgenic plants which exhibit abiotic stress tolerance according to some embodiments of the invention.

Soil-Based Drought Tolerance Assay

Screens are performed with plants over-expressing the differential small RNAs detailed above. Briefly, seeds from control *Arabidopsis* plants, or other transgenic plants over-expressing the small RNA molecule of the invention are germinated and transferred to pots. Drought stress is obtained when irrigation is ceased and the two plant types (transgenic and control plants) are compared when most control plants develop severe wilting, at which point rehydration of the plants is initiated. Transgenic plants are ranked on two levels compared to controls: (1) tolerance to drought conditions, and (2) recovery (survival) following re-watering.

To illustrate and elaborate on the above drought tolerance assays of any given wild type plant compared to a corresponding transgenic plant (in which a drought-associated miRNA has been over-expressed), two different approaches are taken as follows:

Lethal drought stress—whereby wild type (used as a control) and transgenic plants (1-3 weeks old) are grown under prolonged extreme drought conditions (duration varies in accordance with plant species). Next, a recovery attempt is implemented during which plants are regularly irrigated and survival level is estimated in the two plant groups 1-2 days post irrigation initiation. While the control (wild type) plant is not expected to survive this extreme stress, the transgenic plant is expected to demonstrate some improved drought tolerance, usually within hours of re-hydration.

Non-lethal drought stress—whereby wild type (used as a control) and transgenic plants (1-3 weeks old) are grown under regular short-term cycles of drought and re-hydration steps, such that re-hydration is applied when general visible drought symptoms (e.g., evident decrease in turgor pressure of lower leaves) emerge in the experimental plants. This drought/irrigation alternating treatment continues until the flowering stage of the plants is reached, followed by an evaluation of dry matter weight. Both wild type and transgenic plants are expected to survive this non-lethal stress, however, measurable differences in drought tolerance are demonstrated by increased yield of the transgenic compared with the wild type plants.

Drought Tolerance Assay Using Sorbitol

Another assay designed to assess whether transgenic plants are more tolerant to drought or severe water deprivation compared to control plants, involves induction of an osmotic stress by the non-ionic osmolyte sorbitol. Control and transgenic plants are germinated and grown in plant-agar plates for 4 days, after which they are transferred to plates containing 500 mM sorbitol, to cause delayed growth. Following the stress treatment, control and transgenic plants are compared by measuring plant weight (wet and dry), yield, and growth rate measured as time to flowering.

Methods for Salinity Tolerance Assessment

Osmotic stress assays, such as chloride and mannitol assays, are aimed to determine whether an osmotic stress phenotype is sodium chloride-specific or a result of a general osmotic stress. Plants which are tolerant to osmotic stress may also exhibit tolerance to drought and/or freezing. For salt and osmotic stress germination experiments, the medium is supplemented with 50, 100, or 200 mM NaCl or 100 mM, 200 mM NaCl, 400 mM mannitol.

Methods for Heat Stress Tolerance Assessment

Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold nor heat stress.

Methods for Cold Stress Tolerance Assessment

To analyze cold stress, mature (25 day old) plants are transferred to 4° C. chambers for 1 or 2 weeks, with constitutive light. Next, plants are moved back to the greenhouse for 2 weeks to recover. Following the recovery period, chilling damages such as growth retardation are determined based on measurements of plant weight (wet and dry) and growth rates (e.g. time to flowering, plant size, yield, etc) taken on control and transgenic plants.

Example 11

Testing Morphologic Parameters in Transgenic Plants

To analyze whether the transgenic *Arabidopsis* plants are more tolerant to abiotic stresses, plants are grown under optimal versus stress conditions, i.e either drought for five days without irrigation, or high salt conditions for ten days, or a one-hour heat shock. Plants are allowed to grow until seed production, followed by an analysis of their overall size, time to flowering, yield, and protein content of shoot and/or grain. Additional parameters checked can be the overall size of the plant, wet and dry weight, the weight of the seeds yielded, the average seed size and the number of seeds produced per plant. Transformed plants not exhibiting substantial physiological and/or morphological effects, or exhibiting higher measured parameters levels compared to wild-type plants, are identified as abiotic stress tolerant plants.

Example 12

Method for Generating Transgenic Plants with Enhanced or Reduced miRNA Regulation of Target Genes Target prediction enables two contrasting strategies; an enhancement (positive) or a reduction (negative) of small RNA regulation. Both these strategies have been used in plants and have resulted in significant phenotype alterations. For complete in-vivo assessment of the phenotypic effects of the differential small RNAs of this invention, the inventors plan to implement both over-expression and down-regulation methods on the small RNA molecules found to associate with abiotic stress tolerance as listed in Tables 1-6. In the case of small RNAs that were up-regulated under abiotic stress conditions, an enhancement in abiotic stress tolerance can theoretically be achieved by maintaining their directionality, i.e. over-expressing them. Conversely, in the case of small RNAs that were down-regulated under abiotic stress conditions, enhancement in tolerance can be achieved by reducing their regulation. Regulation reduction of small RNA target genes can be accomplished in one of two approaches:

Expressing a miRNA-Resistant Target

In this method, silent mutations are introduced in the miRNA binding site of the target gene so that the DNA and resulting RNA sequences are changed to prevent miRNA binding, but the amino acid sequence of the protein is unchanged.

For design of miRNA-resistant target sequences for the small RNA molecules of the invention, optimization of the nucleic acid sequence in accordance with the preferred codon usage for a particular plant species is required. Tables such as those provided on-line at the Codon Usage Database through the NCBI (National Center for Biotechnology Information) webpage (Hypertext Transfer Protocol://World Wide Web (dot) ncbi (dot) nlm (dot) nih (dot) gov/Taxonomy/Utils/wprintgc (dot) cgi) were used. The Genbank database contains codon usage tables for a number of different species, with its Table 11 (The Bacterial, Archaeal and Plant Plastid Code) being the most relevant for plant species of this invention. Mir-resistant target examples for unregulated and downregulated miRs of the invention are presented in Tables 14-15 below.

TABLE 14 miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| aqc-miR159 | XP_003543825 | | 0 |
| | | 958-978 | 11091 |
| | | 958-978 | 11092 |
| | XP_003541563 | | 0 |
| | | 1111-1131 | 11093 |
| | | 1111-1131 | 11094 |
| | XP_003556814 | | 0 |
| | | 952-972 | 11095 |
| | | 952-972 | 11096 |
| | XP_003526354 | | 0 |
| | | 928-948 | 11097 |
| | | 928-948 | 11098 |
| | XP_003523913 | | 0 |
| | | 931-951 | 11099 |
| | | 931-951 | 11100 |
| | XP_003545791 | | 0 |
| | | 934-954 | 11101 |
| | | 934-954 | 11102 |
| ath-miR159b | XP_003542140 | | 0 |
| | | 404-424 | 11103 |
| | | 404-424 | 11104 |

TABLE 14-continued miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| ath-miR159c | XP_003519140 | | 0 |
| | | 143-163 | 11105 |
| | | 143-163 | 11106 |
| | XP_003531162 | | 0 |
| | | 2030-2050 | 11107 |
| | | 2030-2050 | 11108 |
| | XP_003524148 | | 0 |
| | | 1188-1208 | 11109 |
| | | 1188-1208 | 11110 |
| | XP_003547199 | | 0 |
| | | 1263-1283 | 11111 |
| | | 1263-1283 | 11112 |
| | XP_003541668 | | 0 |
| | | 1329-1349 | 11113 |
| | | 1329-1349 | 11114 |
| ath-miRf10240-akr | XP_003525932 | | 0 |
| | | 357-376 | 11115 |
| | | 357-376 | 11116 |
| | XP_003523287 | | 0 |
| | | 864-883 | 11117 |
| | | 864-883 | 11118 |
| | XP_003547951 | | 0 |
| | | 1451-1470 | 11119 |
| | | 1451-1470 | 11120 |
| | XP_003629354 | | 0 |
| | | 1224-1243 | 11121 |
| | | 1224-1243 | 11122 |
| ath-miRf10368-akr | XP_003543893 | | 0 |
| | | 584-603 | 11123 |
| | | 584-603 | 11124 |
| | XP_003539013 | | 0 |
| | | 599-618 | 11125 |
| | | 599-618 | 11126 |
| | XP_003556840 | | 0 |
| | | 727-746 | 11127 |
| | | 727-746 | 11128 |
| | XP_003538207 | | 0 |
| | | 1733-1752 | 11129 |
| | | 1733-1752 | 11130 |
| ath-miRf10763-akr | XP_003520499 | | 0 |
| | | 245-264 | 11131 |
| | | 245-264 | 11132 |
| | XP_003519685 | | 0 |
| | | 240-259 | 11133 |
| | | 240-259 | 11134 |
| | ACU17625 | | 0 |
| | | 176-195 | 11135 |
| | | 176-195 | 11136 |
| | XP_003527981 | | 0 |
| | | 558-577 | 11137 |
| | | 558-577 | 11138 |
| | XP_003547100 | | 0 |
| | | 1686-1705 | 11139 |
| | | 1686-1705 | 11140 |
| | XP_003524815 | | 0 |
| | | 524-543 | 11141 |
| | | 524-543 | 11142 |
| csi-miR3948 | XP_003547789 | | 0 |
| | | 31-54 | 11143 |
| | | 31-54 | 11144 |
| | XP_003527776 | | 0 |
| | | 46-69 | 11145 |
| | | 46-69 | 11146 |

TABLE 14-continued miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| | XP_003550061 | | 0 |
| | | 178-201 | 11147 |
| | | 178-201 | 11148 |
| | XP_003525811 | | 0 |
| | | 178-201 | 11149 |
| | | 178-201 | 11150 |
| | XP_003539180 | | 0 |
| | | 283-306 | 11151 |
| | | 283-306 | 11152 |
| | BAD18437 | | 0 |
| | | 278-301 | 11153 |
| | | 278-301 | 11154 |
| ghr-miR2950 | XP_003529456 | | 0 |
| | | 1017-1037 | 11155 |
| | | 1017-1037 | 11156 |
| | XP_003554852 | | 0 |
| | | 380-400 | 11157 |
| | | 380-400 | 11158 |
| gma-miR156g | XP_003520455 | | 0 |
| | | 737-756 | 11159 |
| | | 737-756 | 11160 |
| | XP_003553428 | | 0 |
| | | 734-753 | 11161 |
| | | 734-753 | 11162 |
| | XP_003520534 | | 0 |
| | | 734-753 | 11163 |
| | | 734-753 | 11164 |
| | XP_003553944 | | 0 |
| | | 1089-1108 | 11165 |
| | | 1089-1108 | 11166 |
| | XP_003551188 | | 0 |
| | | 1046-1065 | 11167 |
| | | 1046-1065 | 11168 |
| | XP_003532399 | | 0 |
| | | 941-960 | 11169 |
| | | 941-960 | 11170 |
| | XP_003549130 | | 0 |
| | | 1034-1053 | 11171 |
| | | 1034-1053 | 11172 |
| | XP_003550514 | | 0 |
| | | 706-725 | 11173 |
| | | 706-725 | 11174 |
| | XP_003525415 | | 0 |
| | | 1214-1233 | 11175 |
| | | 1214-1233 | 11176 |
| | XP_003538544 | | 0 |
| | | 1269-1288 | 11177 |
| | | 1269-1288 | 11178 |
| | XP_003525436 | | 0 |
| | | 1333-1352 | 11179 |
| | | 1333-1352 | 11180 |
| | XP_003550708 | | 0 |
| | | 1184-1203 | 11181 |
| | | 1184-1203 | 11182 |
| | XP_003520128 | | 0 |
| | | 1007-1026 | 11183 |
| | | 1007-1026 | 11184 |
| | XP_003523155 | | 0 |
| | | 959-978 | 11185 |
| | | 959-978 | 11186 |
| | XP_003551421 | | 0 |
| | | 758-777 | 11187 |
| | | 758-777 | 11188 |
| | XP_003522278 | | 0 |
| | | 1262-1281 | 11189 |
| | | 1262-1281 | 11190 |

TABLE 14-continued miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| gma-miR157c | Redundant target XP_003549130 | | 0 |
| gma-miR159a-3p | Redundant targets: XP_003542140, XP_003543825, XP_003526354, XP_003541563, XP_003556814, XP_003545791, XP_003523913. | | |
| iba-miR157 | Redundant targets: XP_003520455, XP_003553428, XP_003520534, XP_003553944, XP_003551188, XP_003532399, XP_003549130, XP_003525415, XP_003538544, XP_003525436, XP_003520128, XP_003551421, XP_003523155, XP_003550708, XP_003522278 | | |
| mdm-miR482a-5p | XP_003528897 | | |
| | | 940-960 | 11191 |
| | | 940-960 | 11192 |
| | | 940-960 | 11193 |
| | | 940-960 | 11194 |
| osa-miR159e | Redundant targets: XP_003543825, XP_003531162, XP_003526354, XP_003524148, XP_003547199, XP_003541563, XP_003556814, XP_003541668, XP_003523913, XP_003545791. | | |
| osa-miR159f | Redundant targets: XP_003543825, XP_003526354, XP_003541563, XP_003556814, XP_003523913, XP_003545791. | | |
| osa-miR1850.1 | XP_003555849 | | |
| | | 147-167 | 11195 |
| | | 147-167 | 11196 |
| | XP_003534041 | | 0 |
| | | 29-49 | 11197 |
| | | 29-49 | 11198 |
| | XP_003548988 | | 0 |
| | | 451-471 | 11199 |
| | | 451-471 | 11200 |
| osa-miR1858a | XP_003521247 | | 0 |
| | | 287-307 | 11201 |
| | | 287-307 | 11202 |
| | NP_001235053 | | 0 |
| | | 281-301 | 11203 |
| | | 281-301 | 11204 |
| | XP_003530234 | | 0 |
| | | 368-388 | 11205 |
| | | 368-388 | 11206 |
| | XP_003551508 | | 0 |
| | | 377-397 | 11207 |
| | | 377-397 | 11208 |
| | XP_003528545 | | 0 |
| | | 131-151 | 11209 |
| | | 131-151 | 11210 |
| | XP_003547641 | | 0 |
| | | 155-175 | 11211 |
| | | 155-175 | 11212 |
| | XP_003543554 | | 0 |
| | | 185-205 | 11213 |
| | | 185-205 | 11214 |
| | XP_003556667 | | 0 |
| | | 131-151 | 11215 |
| | | 131-151 | 11216 |
| osa-miRf11829-akr | XP_003546711 | | 0 |
| | | 346-366 | 11217 |
| | | 346-366 | 11218 |
| | ACI23460 | | 0 |
| | | 334-354 | 11219 |
| | | 334-354 | 11220 |
| | XP_003541398 | | 0 |
| | | 365-385 | 11221 |
| | | 365-385 | 11222 |

TABLE 14-continued miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| psi-miR159 | Redundant targets: XP_003543825, XP_003526354, XP_003541563, XP_003556814, XP_003545791, XP_003523913. | | |
| pta-miR156a | Redundant targets: XP_003549130, XP_003553428, XP_003553944, XP_003525436, XP_003520455, XP_003520128, XP_003550708, XP_003523155, XP_003551421, XP_003522278. | | |
| pta-miR156b | XP_003551276 | | |
| | | 202-221 | 11223 |
| | | 202-221 | 11224 |
| | | 202-221 | 11225 |
| | | 202-221 | 11226 |
| ptc-miRf10132-akr | XP_003527653 | | |
| | | 128-150 | 11227 |
| | | 128-150 | 11228 |
| | | 128-150 | 11229 |
| ptc-miRf10226-akr | XP_003549610 | | 0 |
| | | 123-145 | 11230 |
| | | 123-145 | 11231 |
| | XP_003525906 | | 0 |
| | | 174-196 | 11232 |
| | | 174-196 | 11233 |
| | XP_003547131 | | 0 |
| | | 2282-2304 | 11234 |
| | | 2282-2304 | 11235 |
| | XP_003542817 | | 0 |
| | | 240-262 | 11236 |
| | | 240-262 | 11237 |
| ptc-miRf10271-akr | Redundant targets: XP_003543825, XP_003526354, XP_003541563, XP_003556814, XP_003523913, XP_003545791. | | |
| ptc-miRf10734-akr | XP_003520774 | | 0 |
| | | 1439-1459 | 11238 |
| | | 1439-1459 | 11239 |
| | XP_003538849 | | 0 |
| | | 1187-1207 | 11240 |
| | | 1187-1207 | 11241 |
| ptc-miRf10985-akr | XP_003546504 | | 0 |
| | | 1472-1491 | 11242 |
| | | 1472-1491 | 11243 |
| | XP_003545057 | | 0 |
| | | 3399-3418 | 11244 |
| | | 3399-3418 | 11245 |
| ptc-miRf11315-akr | XP_003550774 | | 0 |
| | | 311-330 | 11246 |
| | | 311-330 | 11247 |
| | XP_003518840 | | 0 |
| | | 255-274 | 11248 |
| | | 255-274 | 11249 |
| ptc-miRf11757-akr | XP_003612685 | | 0 |
| | | 388-410 | 11250 |
| | | 388-410 | 11251 |
| | | 388-410 | 11252 |
| | | 388-410 | 11253 |

TABLE 14-continued miRNA-Resistant Target Examples for Selected upregulated miRNAs of the Invention.

| Mir name | Homolog NCBI Accession | NCBI Mir Binding Site | mutated nucleotide sequence/SEQ ID NO: |
|---|---|---|---|
| ath-miR157a | Redundant targets: XP_003525415, XP_003553428, XP_003538544, XP_003553944, XP_003551188, XP_003525436, XP_003520455, XP_003523155, XP_003551421, XP_003549130, XP_003522278. | | |
| sbi-miR159a | Redundant targets: XP_003543825, XP_003526354, XP_003541563, XP_003556814. | | |
| smo-miR156b | XP_003528960 | | |
| | | 462-482 | 11254 |
| | | 462-482 | 11255 |
| | | 462-482 | 11256 |
| | | 462-482 | 11257 |

TABLE 15 miRNA-Resistant Target Examples for Selected down-regulated miRNAs of the Invention.

| Mir name | Homolog NCBI Accession | NCBI Mir Binding Site | Mutated Nucleotide Sequence/SEQ ID NO: |
|---|---|---|---|
| bdi-miR2508 | XP_003530212 | | |
| | | 689-710 | 11258 |
| | | 689-710 | 11259 |
| | XP_003530213 | | 0 |
| | | 794-815 | 11260 |
| | | 794-815 | 11261 |
| | XP_003551482 | | 0 |
| | | 689-710 | 11262 |
| | | 689-710 | 11263 |
| | XP_003548937 | | 0 |
| | | 1148-1169 | 11264 |
| | | 1148-1169 | 11265 |
| | XP_003551299 | | 0 |
| | | 733-754 | 11266 |
| | | 733-754 | 11267 |
| | XP_003520176 | | 0 |
| | | 2159-2180 | 11268 |
| | | 2159-2180 | 11269 |
| | XP_003544873 | | 0 |
| | | 656-677 | 11270 |
| | | 656-677 | 11271 |
| | XP_003552227 | | 0 |
| | | 665-686 | 11272 |
| | | 665-686 | 11273 |
| | XP_003539077 | | 0 |
| | | 713-734 | 11274 |
| | | 713-734 | 11275 |
| | XP_003552179 | | 0 |
| | | 701-722 | 11276 |
| | | 701-722 | 11277 |
| | NP_001236616 | | 0 |
| | | 698-719 | 11278 |
| | | 698-719 | 11279 |
| | XP_003540719 | | 0 |
| | | 707-728 | 11280 |
| | | 707-728 | 11281 |
| | XP_003522150 | | 0 |
| | | 662-683 | 11282 |
| | | 662-683 | 11283 |
| bra-miR160a-3p | XP_003530952 | | 0 |
| | | 1283-1303 | 11284 |
| | | 1283-1303 | 11285 |
| gma-miR2119 | XP_003542005 | | 0 |
| | | 212-232 | 11286 |
| | | 212-232 | 11287 |
| | XP_003521584 | | 0 |
| | | 421-441 | 11288 |
| | | 421-441 | 11289 |
| | XP_003524240 | | 0 |
| | | 1982-2002 | 11290 |
| | | 1982-2002 | 11291 |
| | XP_003545664 | | 0 |
| | | 96-116 | 11292 |
| | | 96-116 | 11293 |
| | XP_003532800 | | 0 |
| | | 1982-2002 | 11294 |
| | | 1982-2002 | 11295 |
| | XP_003547559 | | 0 |
| | | 2084-2104 | 11296 |
| | | 2084-2104 | 11297 |
| gso-miR482a | NP_001237600 | | 0 |
| | | 1153-1173 | 11298 |
| | | 1153-1173 | 11299 |
| | XP_003533606 | | 0 |
| | | 523-543 | 11300 |
| | | 523-543 | 11301 |
| | XP_003518623 | | 0 |
| | | 444-464 | 11302 |
| | | 444-464 | 11303 |
| | AAF44087 | | 0 |
| | | Jan-21 | 11304 |
| | | Jan-21 | 11305 |
| osa-miR162a | XP_003528812 | | |
| | | 612-632 | 11306 |
| | | 612-632 | 11307 |
| | | 612-632 | 11308 |
| | | 612-632 | 11309 |
| osa-miR1846e | XP_003531668 | | 0 |
| | | 471-490 | 11310 |
| | | 471-490 | 11311 |
| | XP_003529761 | | 0 |
| | | 363-382 | 11312 |
| | | 363-382 | 11313 |
| | XP_003530142 | | 0 |
| | | 366-385 | 11314 |
| | | 366-385 | 11315 |
| ppt-miR166m | XP_003553029 | | 0 |
| | | 530-550 | 11316 |
| | | 530-550 | 11317 |
| | XP_003597690 | | 0 |
| | | 875-895 | 11318 |
| | | 875-895 | 11319 |

TABLE 15-continued miRNA-Resistant Target Examples for Selected down-regulated miRNAs of the Invention.

| Mir name | Homolog NCBI Accession | NCBI Mir Binding Site | Mutated Nucleotide Sequence/ SEQ ID NO: |
|---|---|---|---|
| | XP_002285176 | | 0 |
| | | 562-582 | 11320 |
| | | 562-582 | 11321 |
| | XP_003530109 | | 0 |
| | | 906-926 | 11322 |
| | | 906-926 | 11323 |
| | XP_003524993 | | 0 |
| | | 1030-1050 | 11324 |
| | | 1030-1050 | 11325 |
| | XP_003522716 | | 0 |
| | | 825-845 | 11326 |
| | | 825-845 | 11327 |
| | XP_003530112 | | 0 |
| | | 606-626 | 11328 |
| | | 606-626 | 11329 |
| | XP_003532788 | | 0 |
| | | 577-597 | 11330 |
| | | 577-597 | 11331 |
| | XP_003537529 | | 0 |
| | | 515-535 | 11332 |
| | | 515-535 | 11333 |
| | XP_003531653 | | 0 |
| | | 777-797 | 11334 |
| | | 777-797 | 11335 |
| | XP_003539764 | | 0 |
| | | 1227-1247 | 11336 |
| | | 1227-1247 | 11337 |
| | XP_003539765 | | 0 |
| | | 1227-1247 | 11338 |
| | | 1227-1247 | 11339 |
| ptc-miRf10007-akr | XP_003550796 | | |
| | | 1378-1398 | 11340 |
| | | 1378-1398 | 11341 |
| | | 1378-1398 | 11342 |
| | | 1378-1398 | 11343 |
| ptc-miRf10976-akr | XP_003533044 | | 0 |
| | | 318-337 | 11344 |
| | | 318-337 | 11345 |
| | XP_003528486 | | 0 |
| | | 267-286 | 11346 |
| | | 267-286 | 11347 |
| | XP_003548151 | | 0 |
| | | 885-904 | 11348 |
| | | 885-904 | 11349 |
| | NP_001238468 | | 0 |
| | | 245-264 | 11350 |
| | | 245-264 | 11351 |
| ptc-miRf11396-akr | XP_003520116 | | |
| | | 764-785 | 11352 |
| | | 764-785 | 11353 |
| | | 764-785 | 11354 |
| | | 764-785 | 11355 |
| ptc-miRf11669-akr | XP_003554103 | | |
| | | 208-227 | 11356 |
| | | 208-227 | 11357 |
| | | 208-227 | 11358 |
| | | 208-227 | 11359 |

Expressing a Target-Mimic Sequence

Plant miRNAs usually lead to cleavage of their targeted gene, with this cleavage typically occurring between bases 10 and 11 of the miRNA. This position is therefore especially sensitive to mismatches between the miRNA and the target. It was found that expressing a DNA sequence that could potentially be targeted by a miRNA, but contains three extra nucleotides (ATC), and thus creating a bulge in a key position (between the two nucleotides that are predicted to hybridize with bases 10-11 of the miRNA), can inhibit the regulation of that miRNA on its native targets (Franco-Zorilla et al., 2007, Nat Genet 39(8):1033-1037).

This type of sequence is referred to as a "target-mimic". Inhibition of the miRNA regulation is presumed to occur through physically capturing the miRNA by the target-mimic sequence and titering-out the miRNA, thereby reducing its abundance. This method was used to reduce the amount and, consequentially, the regulation of miRNA 399 in *Arabidopsis*. Target mimic examples for upregulated and downregulated miRs of the invention are presented in Tables 16-17 below.

TABLE 16

Target Mimic Examples for Selected upregulated miRNAs of the Invention.

| Mir Name | Mimic Reverse Complement Mir/SEQ ID NO: | Full Target Mimic Nucleotide Sequence/ SEQ ID NO: |
|---|---|---|
| ahy-miR3514-5p | 11360 | 11437 |
| aly-miR831-5p | 11361 | 11438 |
| aqc-miR159 | 11362 | 11439 |
| ath-miR157a | 11363 | 11440 |
| ath-miR159b | 11364 | 11441 |
| ath-miR159c | 11365 | 11442 |
| ath-miRf10068-akr | 11366 | 11443 |
| ath-miRf10148-akr | 11367 | 11444 |
| ath-miRf10209-akr | 11368 | 11445 |
| ath-miRf10240-akr | 11369 | 11446 |
| ath-miRf10368-akr | 11370 | 11447 |
| ath-miRf10451-akr | 11371 | 11448 |
| ath-miRf10633-akr | 11372 | 11449 |
| ath-miRf10687-akr | 11373 | 11450 |
| ath-miRf10701-akr | 11374 | 11451 |
| ath-miRf10702-akr | 11375 | 11452 |
| ath-miRf10751-akr | 11376 | 11453 |
| ath-miRf10763-akr | 11377 | 11454 |
| ath-miRf10924-akr | 11378 | 11455 |
| ath-miRf11021-akr | 11379 | 11456 |
| ath-miRf11037-akr | 11380 | 11457 |
| ath-miRf11042-akr | 11381 | 11458 |
| ath-miRf11045-akr | 11382 | 11459 |
| csi-miR3946 | 11383 | 11460 |
| csi-miR3948 | 11384 | 11461 |

TABLE 16-continued

Target Mimic Examples for Selected upregulated miRNAs of the Invention.

| Mir Name | Mimic Reverse Complement Mir/SEQ ID NO: | Full Target Mimic Nucleotide Sequence/ SEQ ID NO: |
|---|---|---|
| far-miR1134 | 11385 | 11462 |
| ghr-miR2950 | 11386 | 11463 |
| gma-miR156g | 11387 | 11464 |
| gma-miR157c | 11388 | 11465 |
| gma-miR159a-3p | 11389 | 11466 |
| iba-miR157 | 11390 | 11467 |
| mdm-miR482a-5p | 11391 | 11468 |
| mtr-miR2119 | 11392 | 11469 |
| osa-miR159e | 11393 | 11470 |
| osa-miR159f | 11394 | 11471 |
| osa-miR1850.1 | 11395 | 11472 |
| osa-miR1858a | 11396 | 11473 |
| osa-miR1869 | 11397 | 11474 |
| osa-miR1874-3p | 11398 | 11475 |
| osa-miR1879 | 11399 | 11476 |
| osa-miR1881 | 11400 | 11477 |
| osa-miR2055 | 11401 | 11478 |
| osa-miRf10105-akr | 11402 | 11479 |
| osa-miRf10362-akr | 11403 | 11480 |
| osa-miRf10839-akr | 11404 | 11481 |
| osa-miRf11013-akr | 11405 | 11482 |
| osa-miRf11341-akr | 11406 | 11483 |
| osa-miRf11352-akr | 11407 | 11484 |
| osa-miRf11355-akr | 11408 | 11485 |
| osa-miRf11595-akr | 11409 | 11486 |
| osa-miRf11649-akr | 11410 | 11487 |
| osa-miRf11829-akr | 11411 | 11488 |
| pab-miR3711 | 11412 | 11489 |
| ppt-miR1220a | 11413 | 11490 |
| ppt-miR895 | 11414 | 11491 |
| psi-miR159 | 11415 | 11492 |
| pta-miR156a | 11416 | 11493 |
| pta-miR156b | 11417 | 11494 |
| ptc-miRf10132-akr | 11418 | 11495 |
| ptc-miRf10148-akr | 11419 | 11496 |
| ptc-miRf10226-akr | 11420 | 11497 |
| ptc-miRf10271-akr | 11421 | 11498 |
| ptc-miRf10300-akr | 11422 | 11499 |
| ptc-miRf10522-akr | 11423 | 11500 |
| ptc-miRf10619-akr | 11424 | 11501 |
| ptc-miRf10734-akr | 11425 | 11502 |
| ptc-miRf10985-akr | 11426 | 11503 |
| ptc-miRf11315-akr | 11427 | 11504 |
| ptc-miRf11757-akr | 11428 | 11505 |
| ptc-miRf11844-akr | 11429 | 11506 |
| ptc-miRf11847-akr | 11430 | 11507 |
| ptc-miRf11855-akr | 11431 | 11508 |
| sbi-miR159a | 11432 | 11509 |
| smo-miR1103-3p | 11433 | 11510 |
| smo-miR156b | 11434 | 11511 |
| tae-miR2003 | 11435 | 11512 |
| zma-miR482-5p | 11436 | 11513 |

TABLE 17

Target Mimic Examples for Selected downregulated miRNAs of the Invention.

| Mir Name | Mimic Reverse Complement Mir/SEQ ID NO: | Full Target Mimic Nucleotide Sequence/SEQ ID NO: |
|---|---|---|
| aly-miR160c-3p | 11514 | 11564 |
| aly-miR396a-3p | 11515 | 11565 |
| aly-miR396b-3p | 11516 | 11566 |
| ath-miRf10197-akr | 11517 | 11567 |
| ath-miRf10239-akr | 11518 | 11568 |
| ath-miRf10279-akr | 11519 | 11569 |
| bdi-miR2508 | 11520 | 11570 |
| bna-miR2111b-5p | 11521 | 11571 |
| bra-miR160a-3p | 11522 | 11572 |
| csi-miR162-5p | 11523 | 11573 |
| ctr-miR171 | 11524 | 11574 |
| gma-miR1507a | 11525 | 11575 |
| gma-miR1524 | 11526 | 11576 |

TABLE 17-continued

Target Mimic Examples for Selected downregulated miRNAs of the Invention.

| Mir Name | Mimic Reverse Complement Mir/SEQ ID NO: | Full Target Mimic Nucleotide Sequence/SEQ ID NO: |
|---|---|---|
| gma-miR159d | 11527 | 11577 |
| gma-miR2119 | 11528 | 11578 |
| gma-miR396d | 11529 | 11579 |
| gma-miR4371b | 11530 | 11580 |
| gma-miR4376-5p | 11531 | 11581 |
| gma-miR4412-3p | 11532 | 11582 |
| gma-miR4416a | 11533 | 11583 |
| gma-miR482a-3p | 11534 | 11584 |
| gma-miR482b-5p | 11535 | 11585 |
| gso-miR169g* | 11536 | 11586 |
| gso-miR482a | 11537 | 11587 |
| osa-miR162a | 11538 | 11588 |
| osa-miR1846e | 11539 | 11589 |
| osa-miR2104 | 11540 | 11590 |
| osa-miRf10151-akr | 11541 | 11591 |
| osa-miRf10849-akr | 11542 | 11592 |
| osa-miRf11415-akr | 11543 | 11593 |
| osa-miRf11996-akr | 11544 | 11594 |
| ppt-miR166m | 11545 | 11595 |
| ppt-miR533b-5p | 11546 | 11596 |
| pta-miR166c | 11547 | 11597 |
| ptc-miR166p | 11548 | 11598 |
| ptc-miRf10007-akr | 11549 | 11599 |
| ptc-miRf10976-akr | 11550 | 11600 |
| ptc-miRf11018-akr | 11551 | 11601 |
| ptc-miRf11079-akr | 11552 | 11602 |
| ptc-miRf11324-akr | 11553 | 11603 |
| ptc-miRf11396-akr | 11554 | 11604 |
| ptc-miRf11669-akr | 11555 | 11605 |
| ptc-miRf11953-akr | 11556 | 11606 |
| ptc-miRf12069-akr | 11557 | 11607 |
| ptc-miRf12389-akr | 11558 | 11608 |
| vvi-miR2111-5p | 11559 | 11609 |
| vvi-miR394b | 11560 | 11610 |
| zma-miR167u | 11561 | 11611 |
| zma-miR396b-3p | 11562 | 11612 |
| zma-miR398a-5p | 11563 | 11613 |

TABLE 18

Abbreviations of plant species

| Common Name | Organism Name | Abbreviation |
|---|---|---|
| Peanut | Arachis hypogaea | ahy |
| Arabidopsis lyrata | Arabidopsis lyrata | aly |
| Rocky Mountain Columbine | Aquilegia coerulea | aqc |
| Tausch's goatgrass | Aegilops taushii | ata |
| Arabidopsis thaliana | Arabidopsis thaliana | ath |
| Grass | Brachypodium distachyon | bdi |
| Brassica napus canola ("liftit") | Brassica napus | bna |
| Brassica oleracea wild cabbage | Brassica oleracea | bol |
| Brassica rapa yellow mustard | Brassica rapa | bra |
| Clementine | Citrus clementine | ccl |
| Orange | Citrus sinensis | csi |
| Trifoliate orange | Citrus trifoliata | ctr |
| Glycine max | Glycine max | gma |
| Wild soybean | Glycine soja | gso |
| Barley | Hordeum vulgare | hvu |
| Lotus japonicus | Lotus japonicus | lja |
| Medicago truncatula - Barrel Clover ("tiltan") | Medicago truncatula | mtr |
| Oryza sativa | Oryza sativa | osa |
| European spruce | Picea abies | pab |
| Physcomitrella patens (moss) | Physcomitrella patens | ppt |
| Pinus taeda - Loblolly Pine | Pinus taeda | pta |
| Populus trichocarpa - black cotton wood | Populus trichocarpa | ptc |
| Castor bean ("kikayon") | Ricinus communis | rco |
| Sorghum bicolor Dura | Sorghum bicolor | sbi |
| tomato microtom | Solanum lycopersicum | sly |
| Selaginella moellendorffii | Selaginella moellendorffii | smo |
| Sugarcane | Saccharum officinarum | sof |
| Sugarcane | Saccharum spp | ssp |
| Triticum aestivum | Triticum aestivum | tae |
| cacao tree and cocoa tree | Theobroma cacao | tcc |
| Vitis vinifera Grapes | Vitis vinifera | vvi |
| corn | Zea mays | zma |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10184131B2). An electronic copy of the "Sequence Listing" will also be available from the USPTO upon request and payment of the fee set forth in 37 CFR 1.19(b)(3).

What is claimed is:

1. A method of improving drought or salt tolerance of a soybean plant, the method comprising:

transforming a soybean plant with an exogenous DNA construct comprising a plant-expressible promoter operably linked to the miRNA precursor polynucleotide having the nucleic acid sequence as set forth in SEQ ID NO: 11889 which encodes the mature miRNA sequence as set forth in SEQ ID NO: 33, growing the transformed plant under drought or salt stress conditions, and wherein over-expression of said miRNA precursor polynucleotide encoding said miRNA sequence in said transformed soybean plant improves drought or salt tolerance of the transformed soybean plant as compared to a control soybean plant lacking said exogenous DNA construct and grown under the same growth and said stress conditions.

* * * * *